US012467880B2

(12) United States Patent
Mihota et al.

(10) Patent No.: US 12,467,880 B2
(45) Date of Patent: Nov. 11, 2025

(54) SENSOR DEVICE

(71) Applicants: SONY GROUP CORPORATION, Tokyo (JP); SONY SEMICONDUCTOR SOLUTIONS CORPORATION, Kanagawa (JP)

(72) Inventors: Norihito Mihota, Saitama (JP); Takuya Ichihara, Tokyo (JP); Atsushi Yamada, Kanagawa (JP); Sachio Iida, Chiba (JP); Takahiro Oishi, Kanagawa (JP); Minoru Ishida, Tokyo (JP)

(73) Assignees: Sony Group Corporation, Tokyo (JP); Sony Semiconductor Solutions Corporation, Kanagawa (JP)

( * ) Notice: Subject to any disclaimer, the term of this patent is extended or adjusted under 35 U.S.C. 154(b) by 275 days.

(21) Appl. No.: 18/251,908

(22) PCT Filed: Nov. 8, 2021

(86) PCT No.: PCT/JP2021/040983
§ 371 (c)(1),
(2) Date: May 5, 2023

(87) PCT Pub. No.: WO2022/102572
PCT Pub. Date: May 19, 2022

(65) Prior Publication Data

US 2024/0019383 A1 Jan. 18, 2024

(30) Foreign Application Priority Data

Nov. 12, 2020 (JP) ................................ 2020-188921
Nov. 1, 2021 (JP) ................................ 2021-178678

(51) Int. Cl.
*G01N 22/04* (2006.01)
*G01N 33/24* (2006.01)
(Continued)

(52) U.S. Cl.
CPC ........... *G01N 22/04* (2013.01); *G01N 33/246* (2013.01); *H01Q 17/00* (2013.01); *G01N 33/245* (2024.05); *H01Q 1/225* (2013.01)

(58) Field of Classification Search
CPC ........ G01N 22/00; G01N 22/02; G01N 22/04; G01N 33/00; G01N 33/24; G01N 33/245;
(Continued)

(56) References Cited

U.S. PATENT DOCUMENTS 7,343,261 B1 * 3/2008 Kell .......................... G01P 5/07 43/17
10,524,430 B1 * 1/2020 Nervino ............... A01G 25/167
(Continued)

FOREIGN PATENT DOCUMENTS

CA 2598487 A1 * 8/2006 ............... G01V 3/30
CN 114599964 A * 6/2022 ........... G01R 27/267
(Continued)

OTHER PUBLICATIONS

International Search Report and Written Opinion prepared by the Japan Patent Office on Dec. 14, 2021, for International Application No. PCT/JP2021/040983, 2 pgs.

*Primary Examiner* — Hoai-An D. Nguyen
(74) *Attorney, Agent, or Firm* — Sheridan Ross PC

(57) ABSTRACT

A sensor device is disclosed for measuring an amount of moisture in a medium that includes: a transmission antenna; a reception antenna to receive electromagnetic waves transmitted from the transmission antenna and through a medium; a measurement unit to measure the electromagnetic waves propagating to the reception antenna; and a sensor casing and further includes a transmission substrate including a plurality of wiring layers and a reception substrate including a plurality of wiring layers, and a measurement unit substrate including a plurality of wiring layers and includes the measurement unit or a first coating layer that, in
(Continued)

a part of the transmission substrate, coats an outer circumference of the substrate and is formed from an electromagnetic wave absorbent material and a second coating layer that, in a part of the reception substrate, coats an outer circumference of the substrate and is formed from an electromagnetic wave absorbent material.

17 Claims, 368 Drawing Sheets

(51) Int. Cl.
*H01Q 1/22* (2006.01)
*H01Q 17/00* (2006.01)

(58) Field of Classification Search
CPC .......... G01N 33/246; H01Q 1/00; H01Q 1/12; H01Q 1/22; H01Q 1/225; H01Q 13/00; H01Q 1/38; H01Q 13/10; H01Q 17/00; H01Q 23/00
USPC ......................... 324/600, 629, 637, 639, 640
See application file for complete search history.

(56) References Cited

U.S. PATENT DOCUMENTS

| | | | | |
|---|---|---|---|---|
| 12,306,115 | B2 * | 5/2025 | Yamada | G01N 22/00 |
| 2002/0075189 | A1 * | 6/2002 | Carillo, Jr. | H01Q 9/285 343/702 |
| 2018/0224382 | A1 | 8/2018 | Golombek et al. | |
| 2020/0182906 | A1 | 6/2020 | Yamada et al. | |

FOREIGN PATENT DOCUMENTS

| | | | | |
|---|---|---|---|---|
| JP | H01-285843 | | 11/1989 | |
| JP | H02-045740 | | 2/1990 | |
| JP | H06-129999 | | 5/1994 | |
| JP | 2023076774 A | * | 6/2023 | G01N 22/04 |
| WO | WO 2018/221051 | | 12/2018 | |

* cited by examiner

Fig. 4
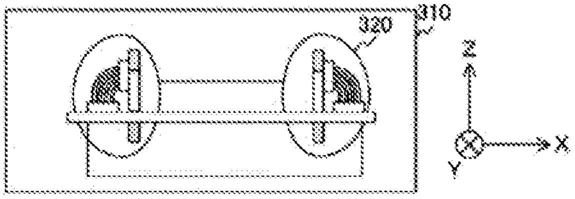
a
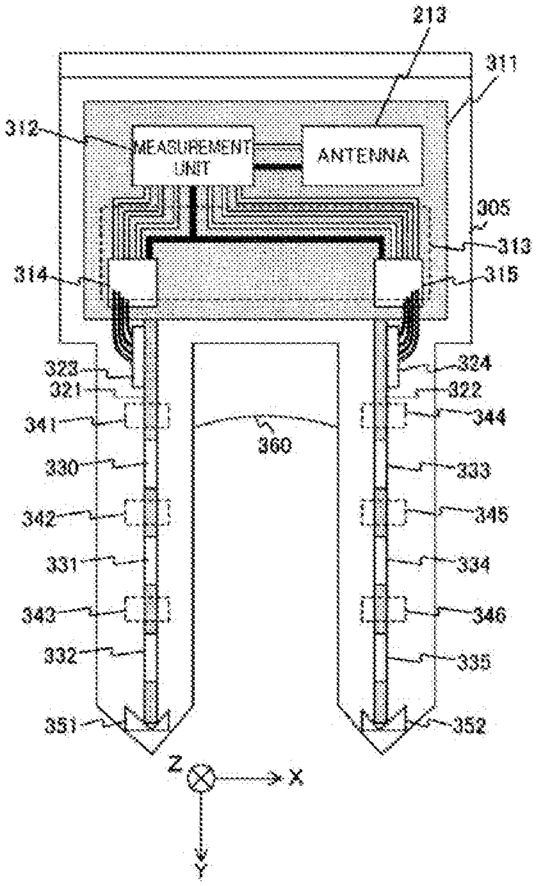
b
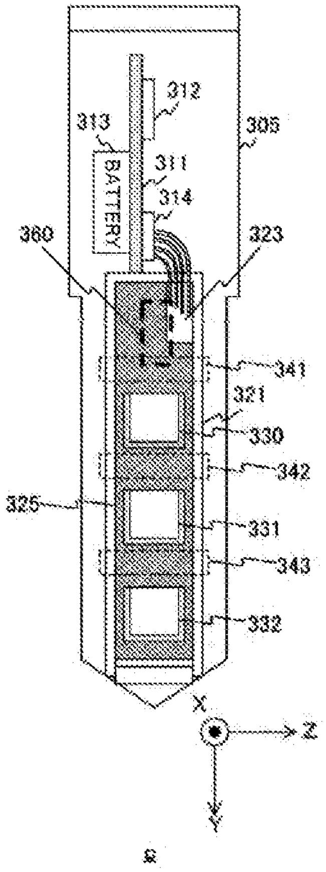
c

Fig. 11
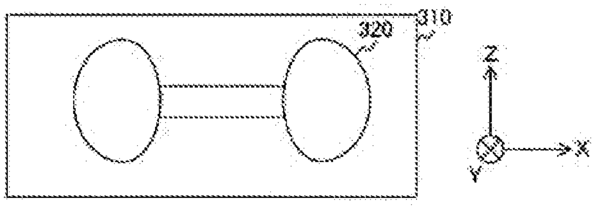
a
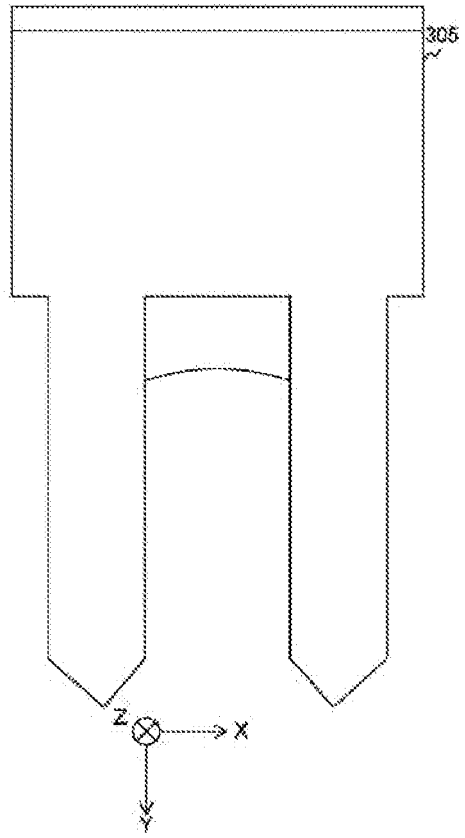
b
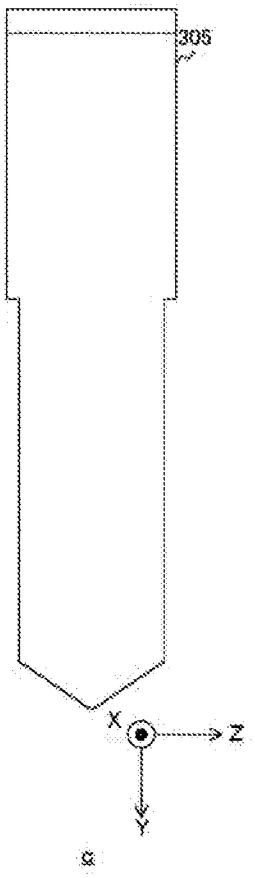
c

Fig. 14
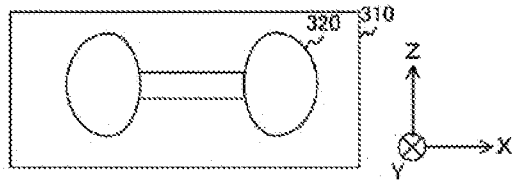
a
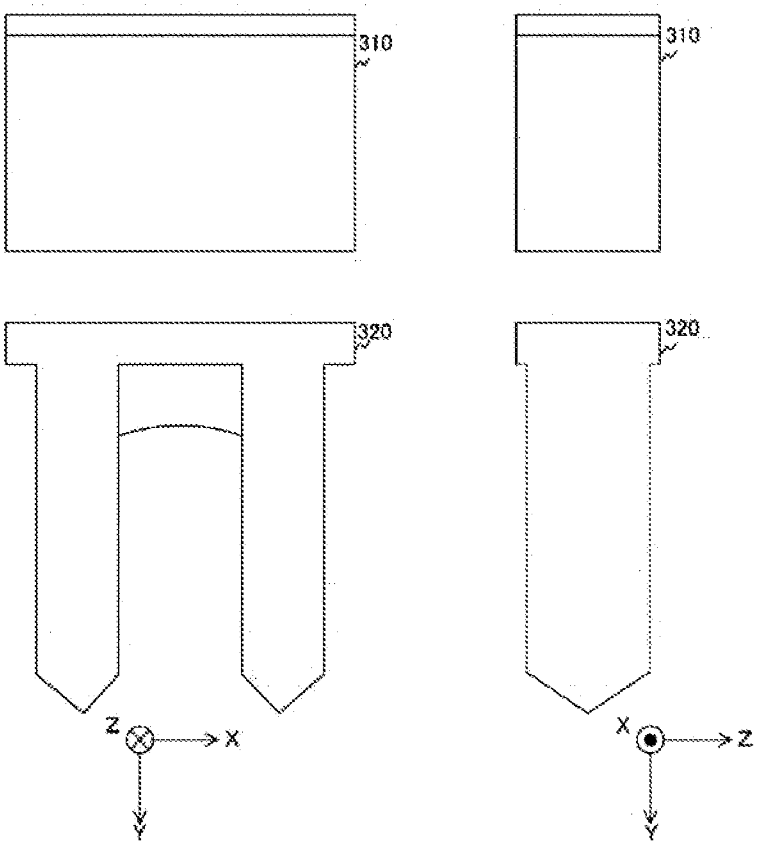
b c a b a b

Fig. 75
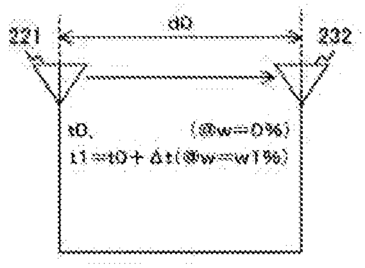
a
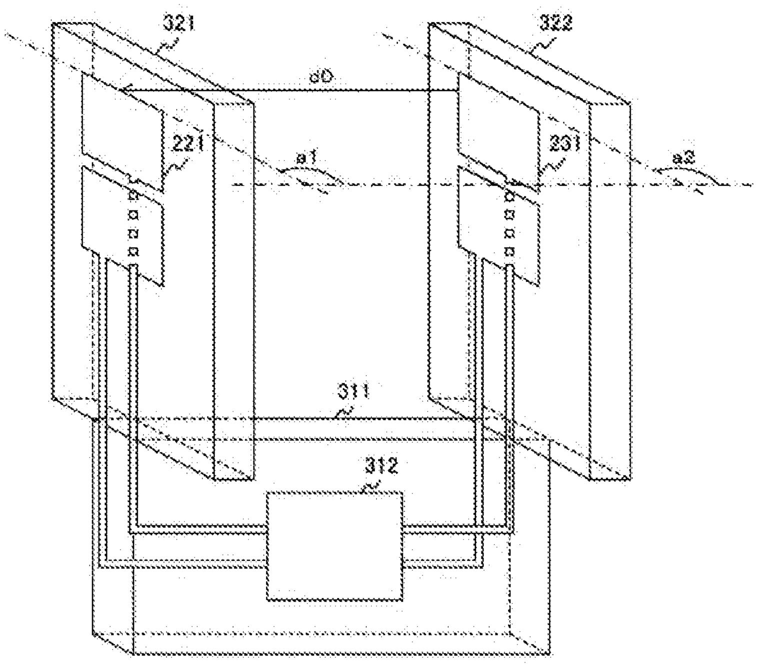
b

Fig. 76
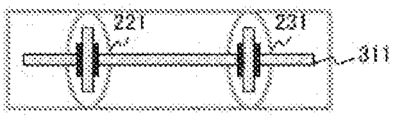
a
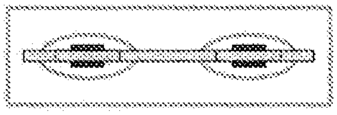
b
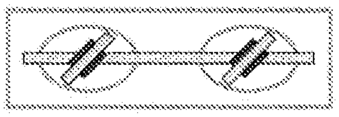
c
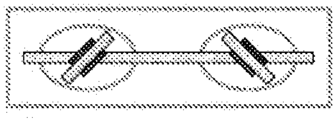
d
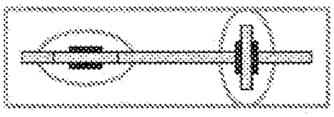
e
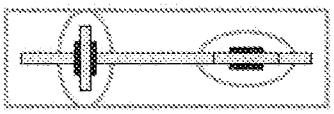
f Fig. 109
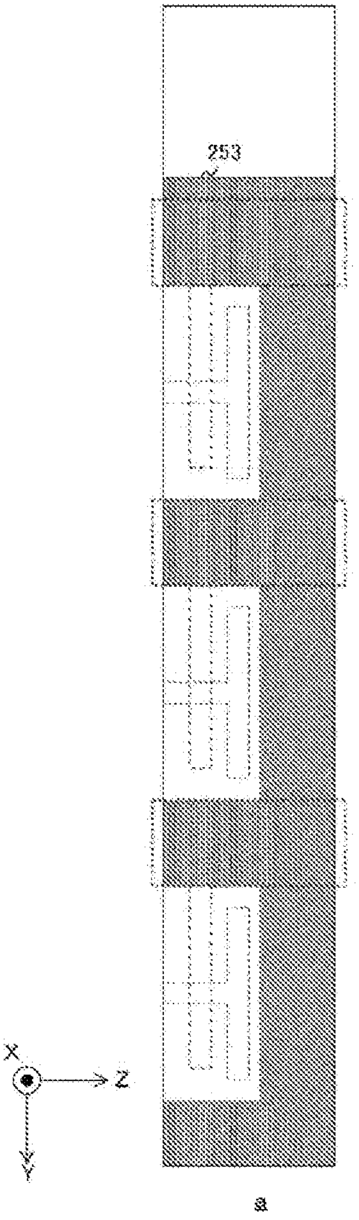
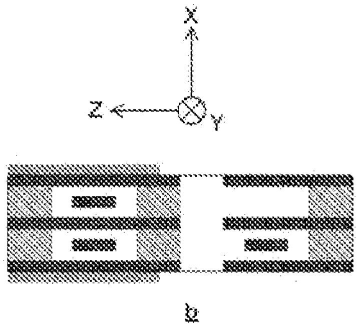

Fig. 119
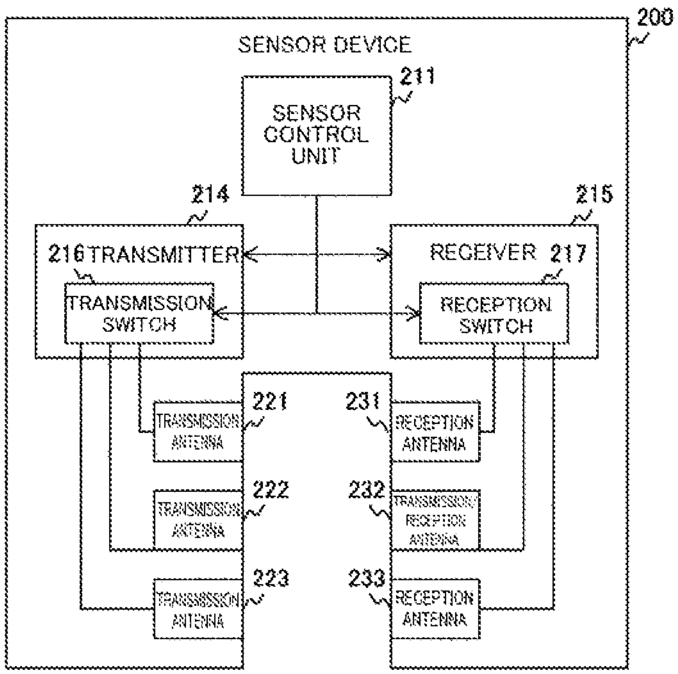
a
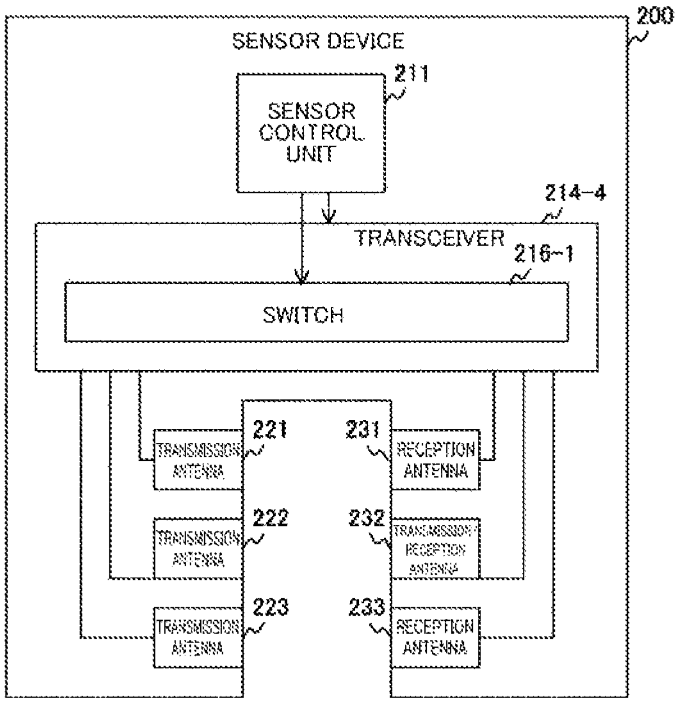
b

Fig. 120
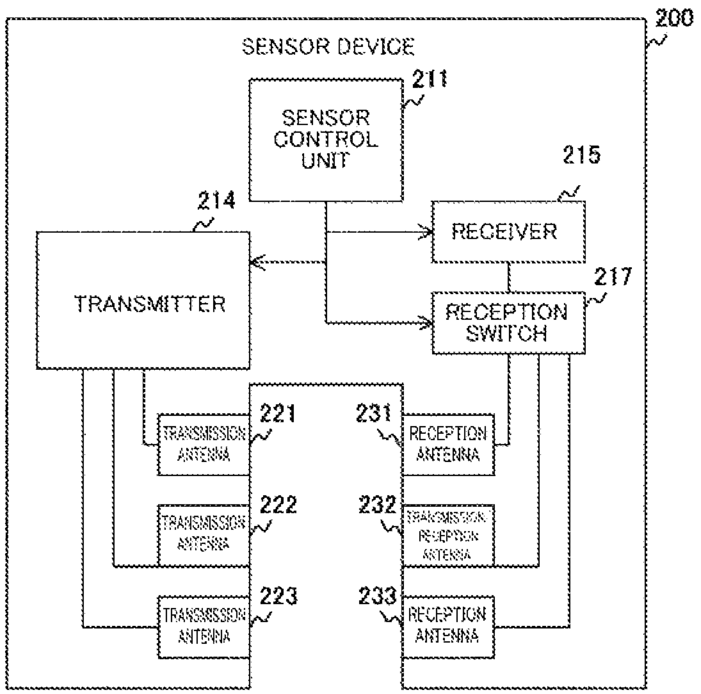
a
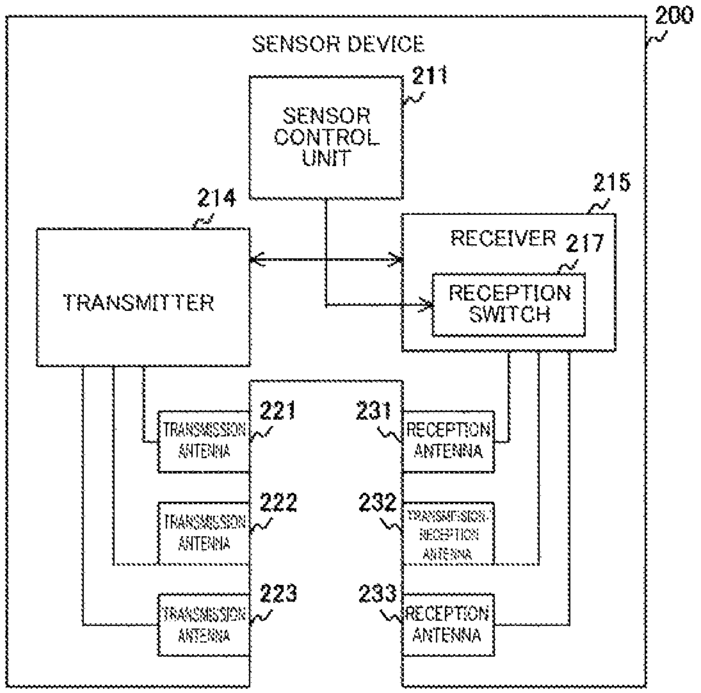
b

Fig. 147
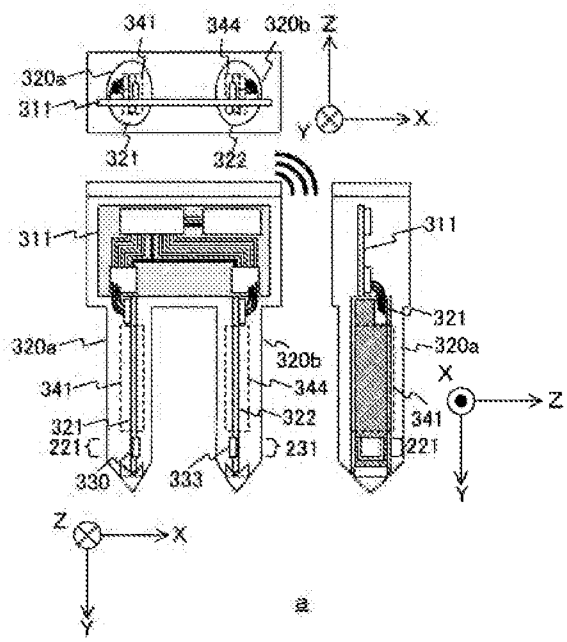
a
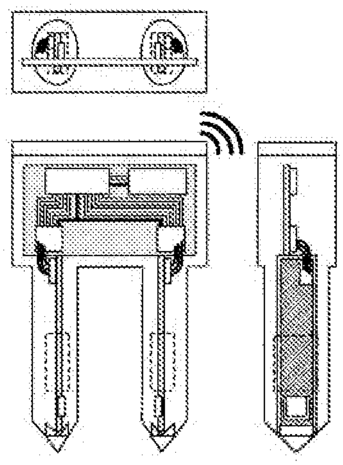
b
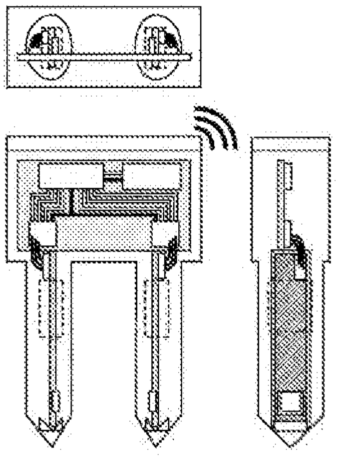
c

Fig. 149
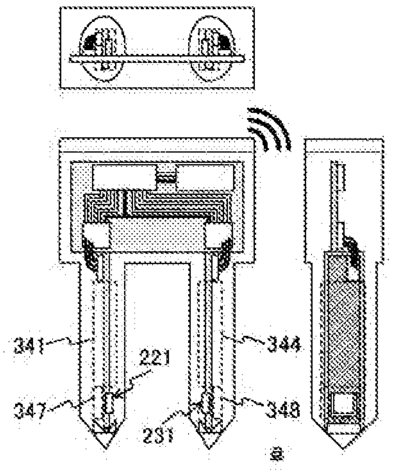
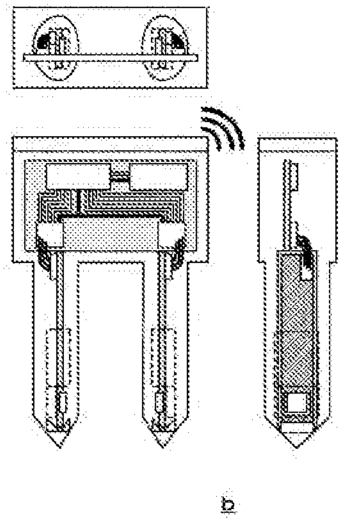
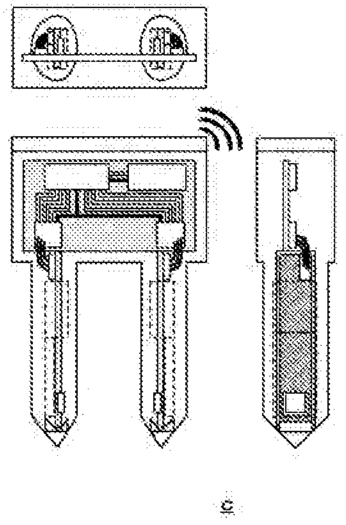

Fig. 154
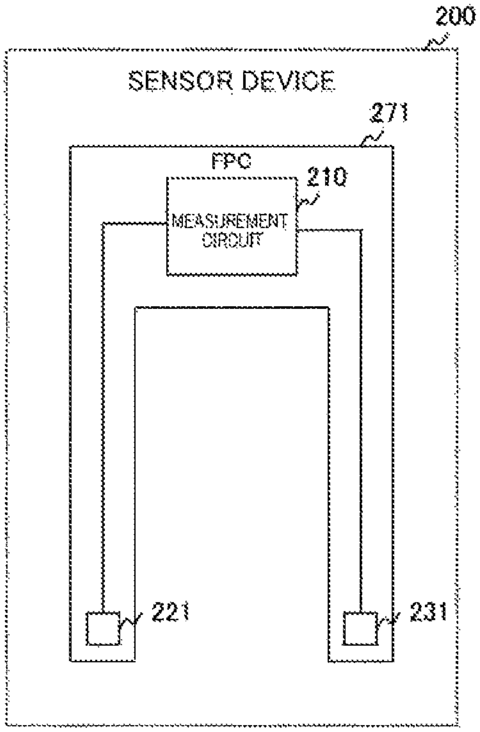
a
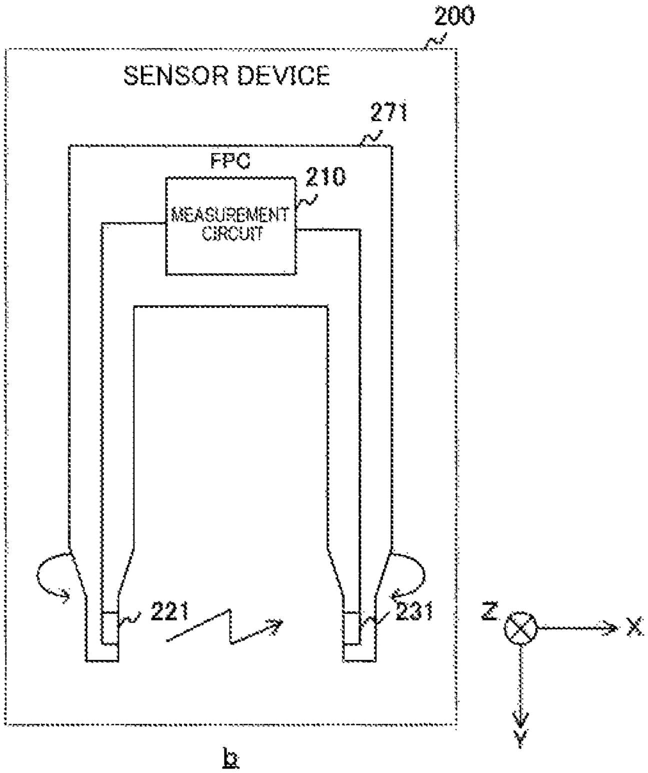
b

Fig. 155
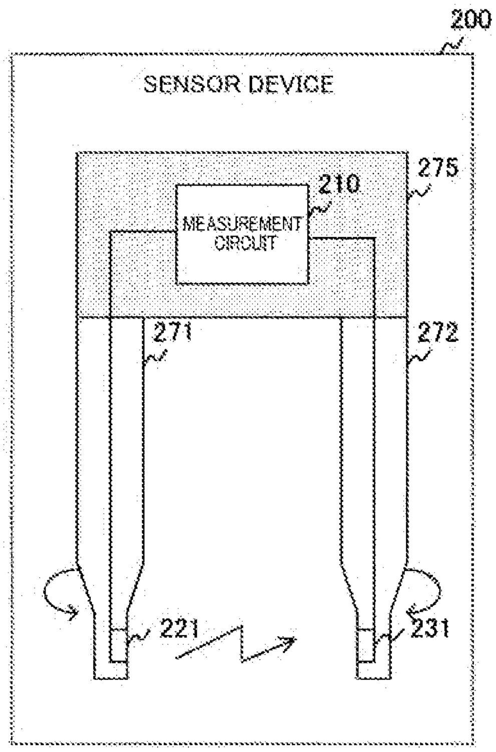
a
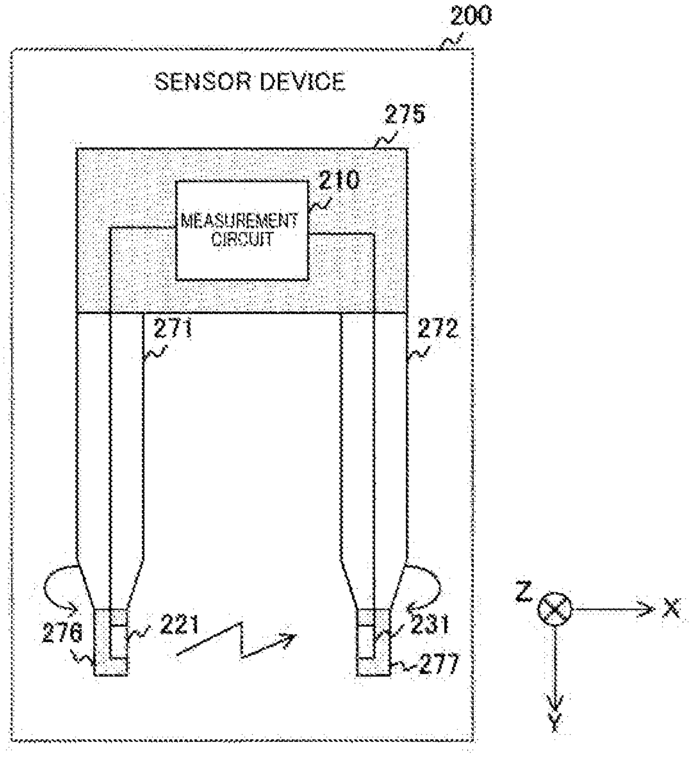
b

Fig. 156
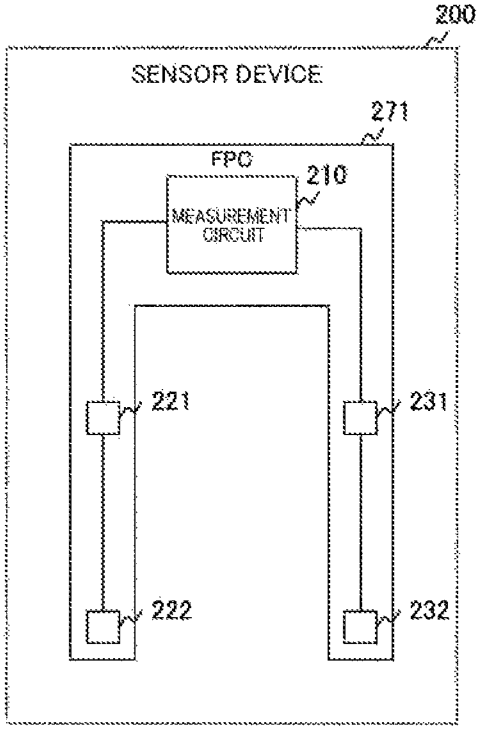
a
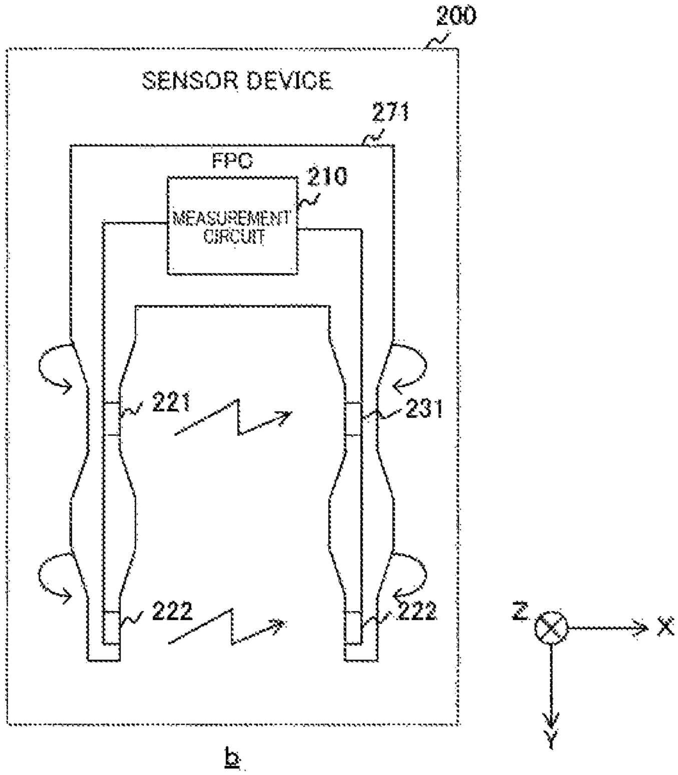
b

Fig. 157
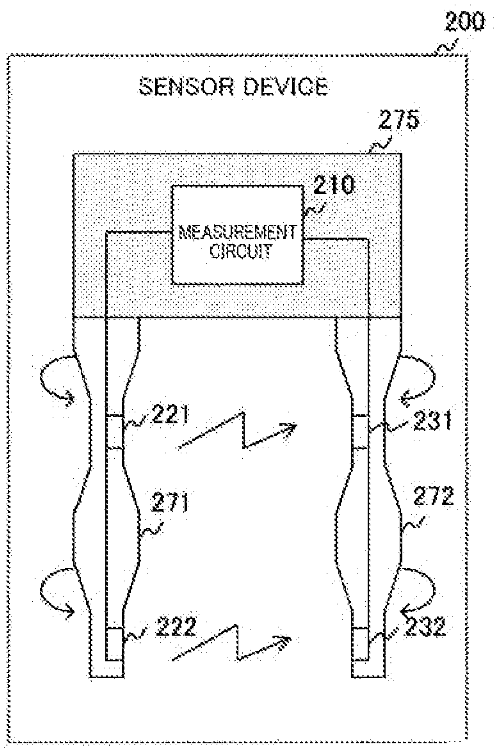
a
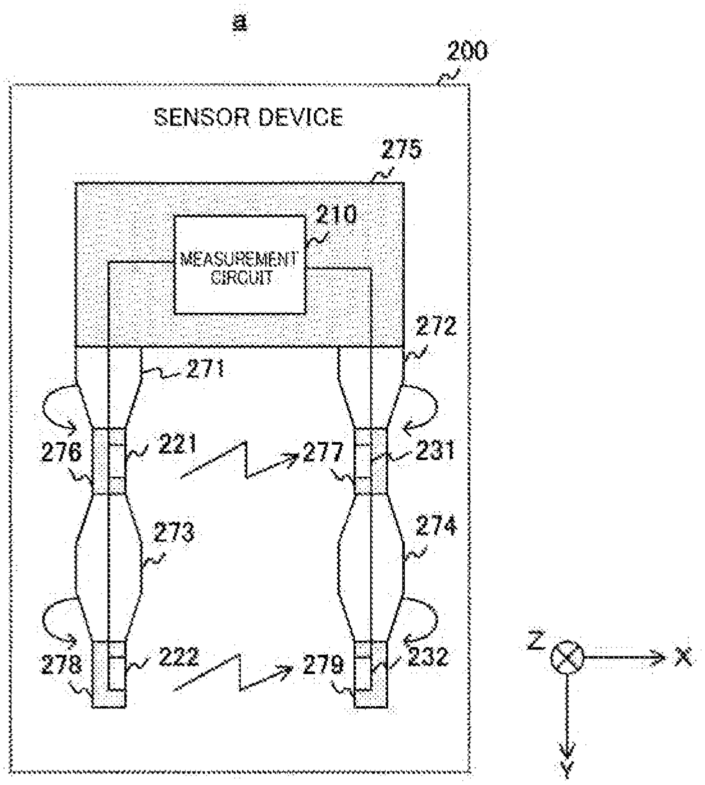
b

Fig. 158
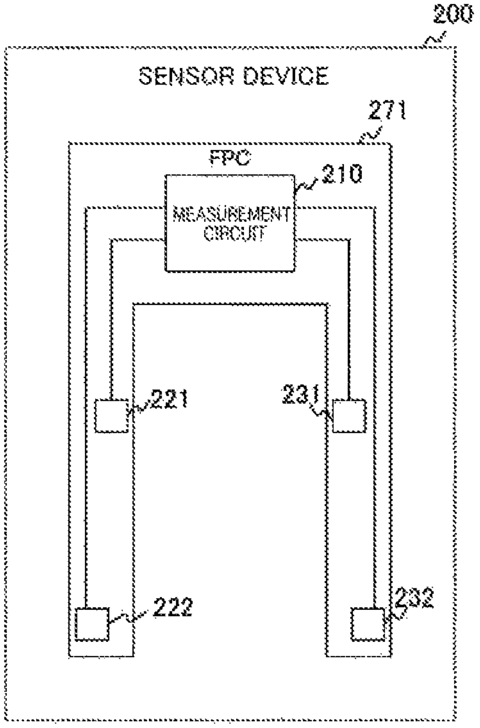
a
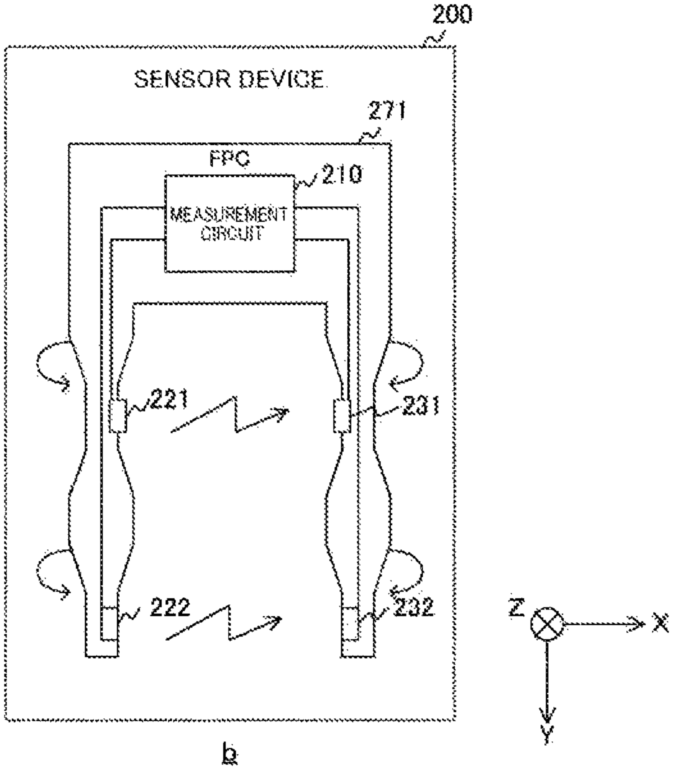
b

Fig. 159
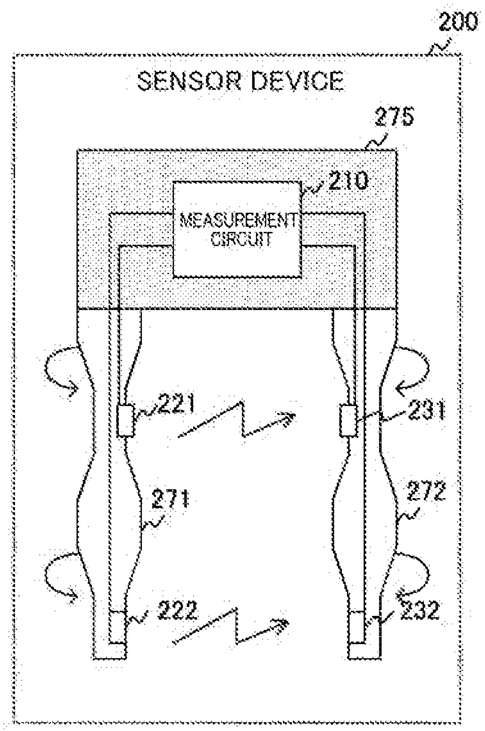
a
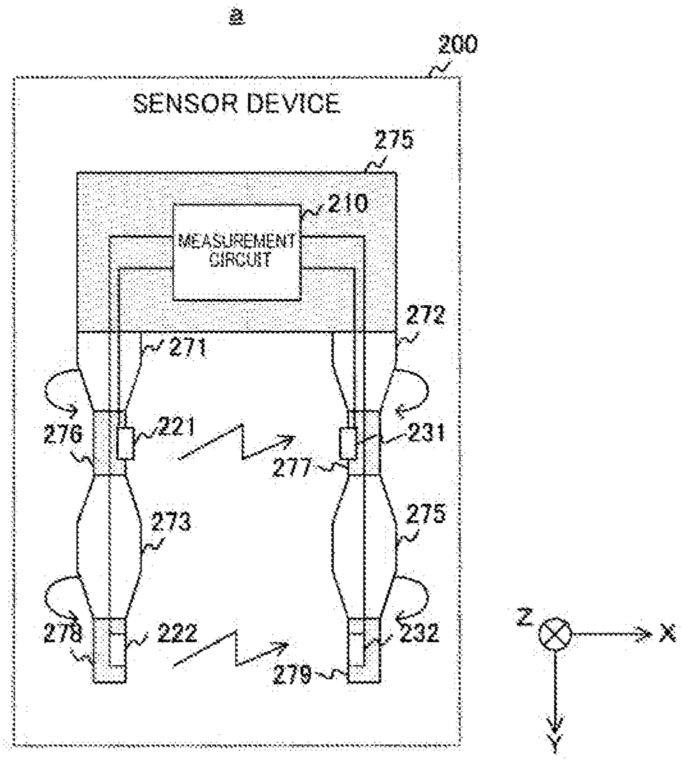
b

Fig. 161
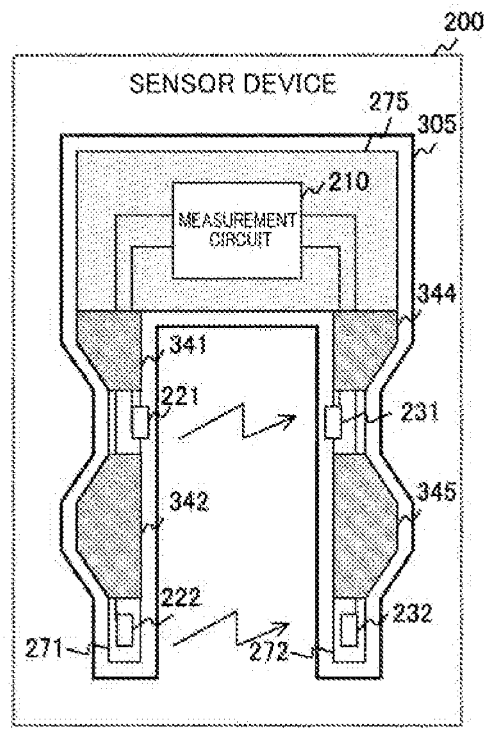
a
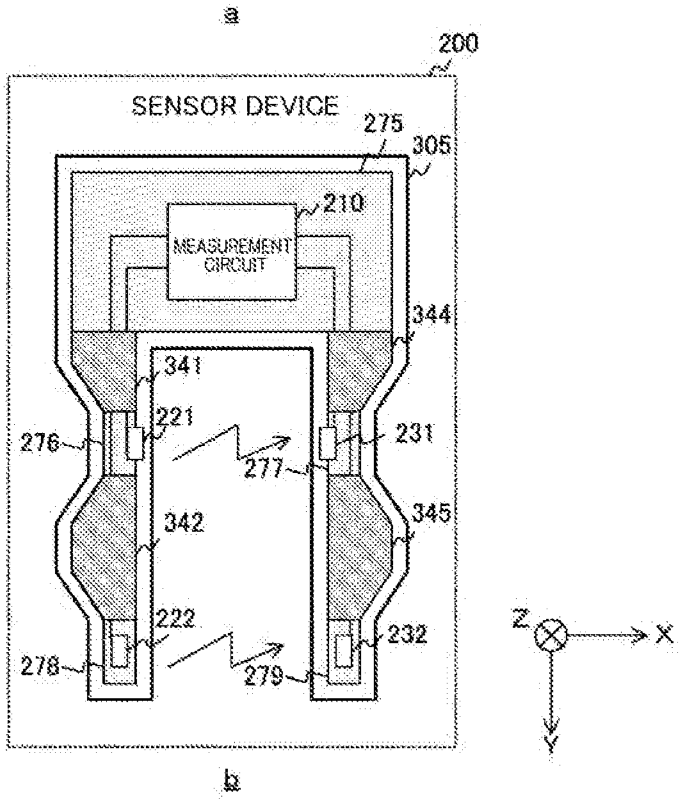
b

Fig. 162
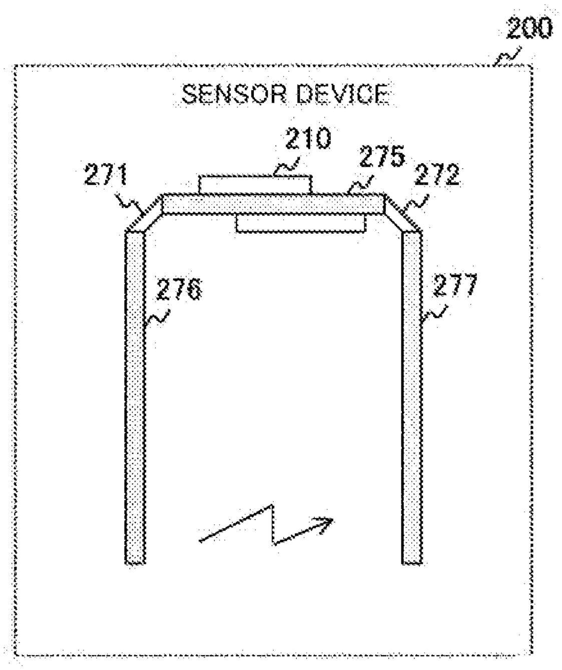
a
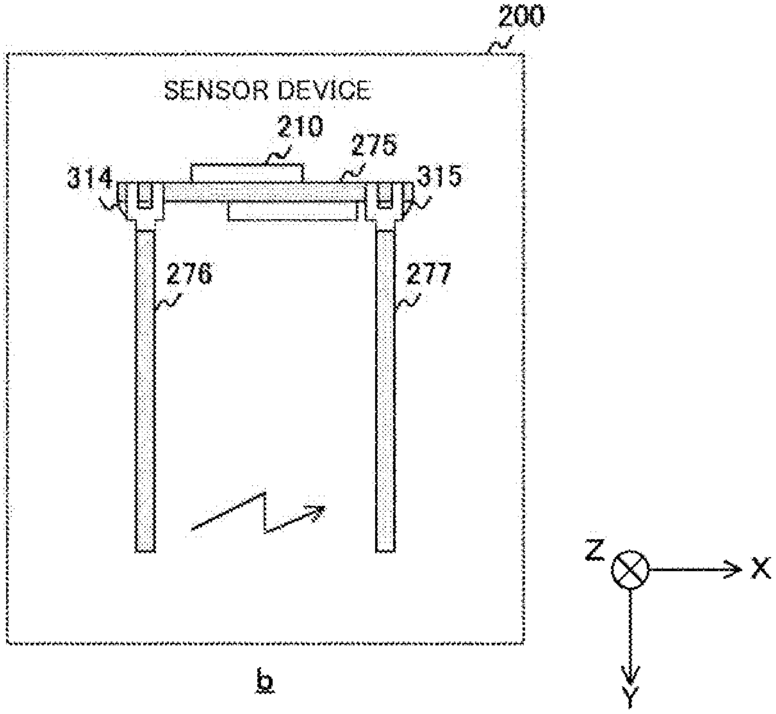
b

Fig. 164
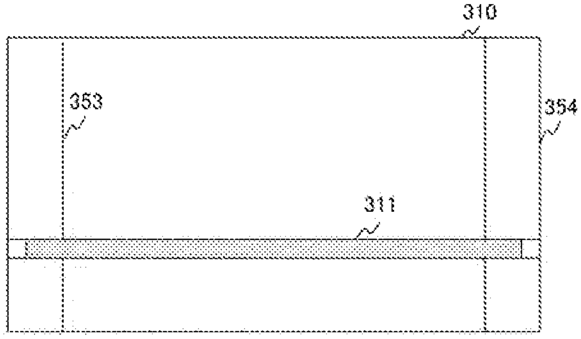
a
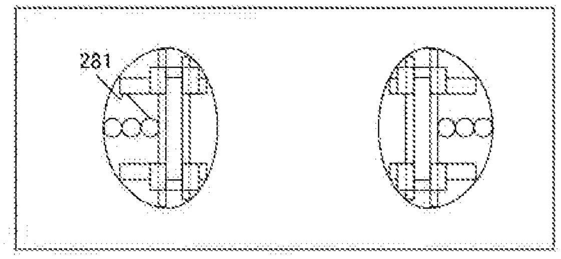
b
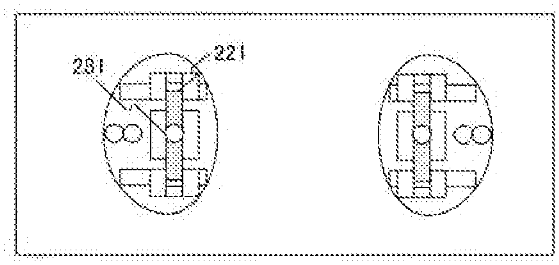
c

Fig. 168
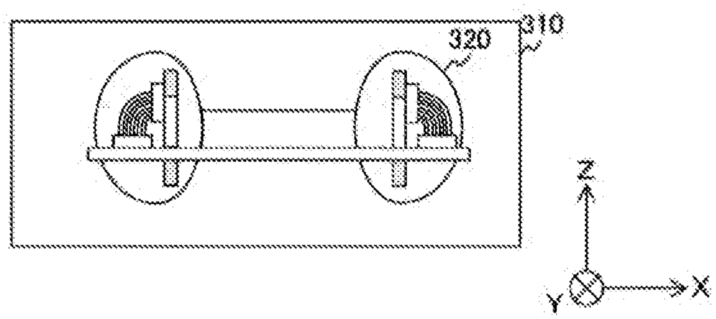
a
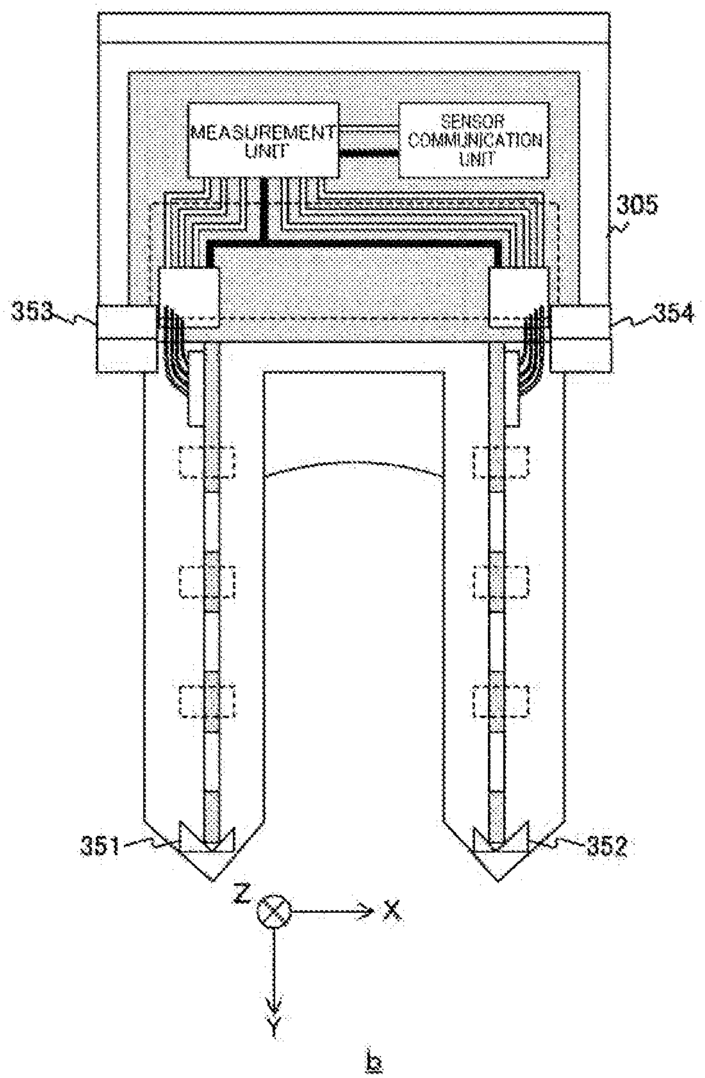
b
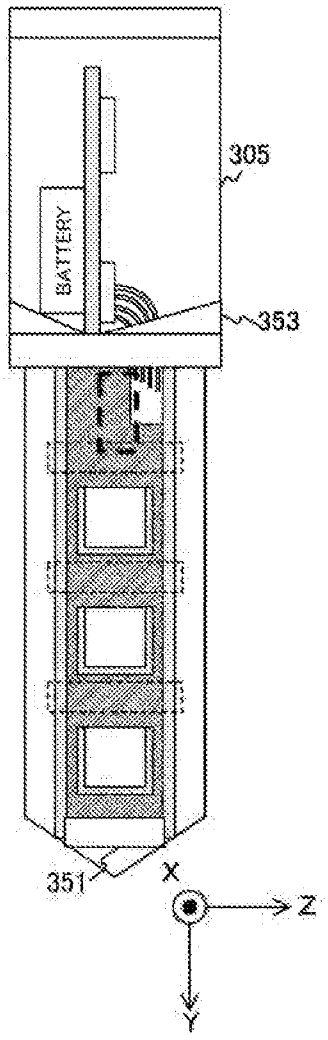
c

Fig. 169
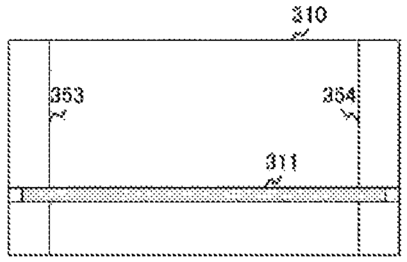
a
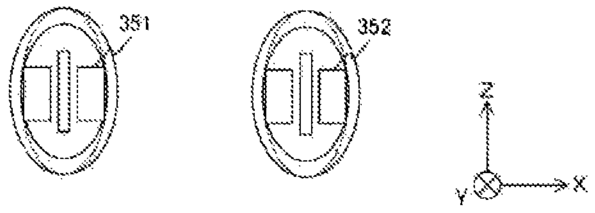
b

Fig. 180
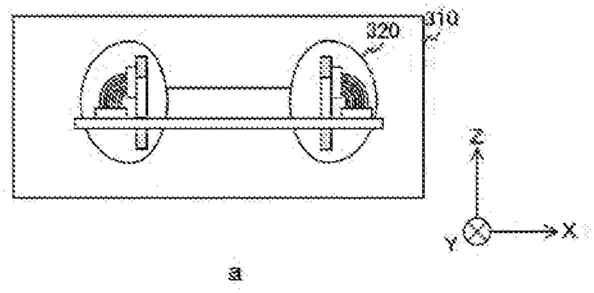
a
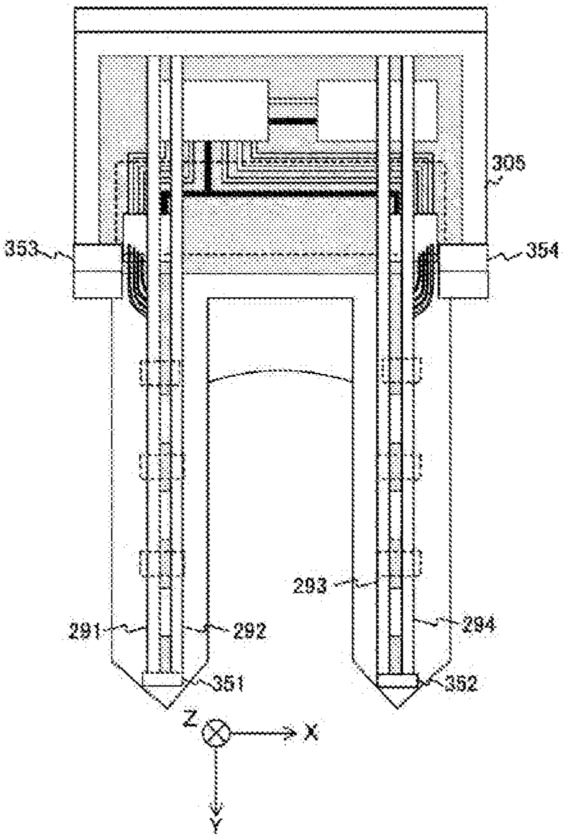
b
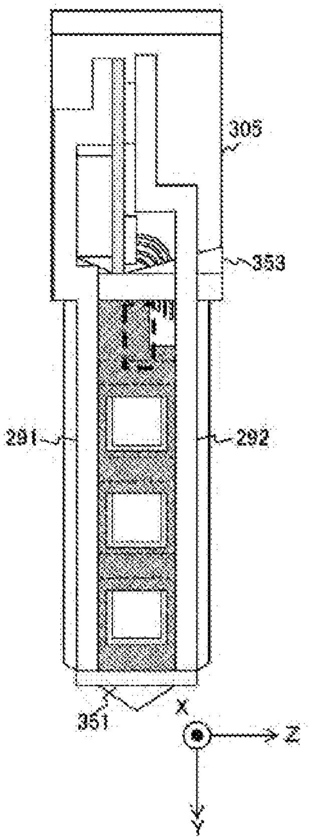
c

Fig. 182
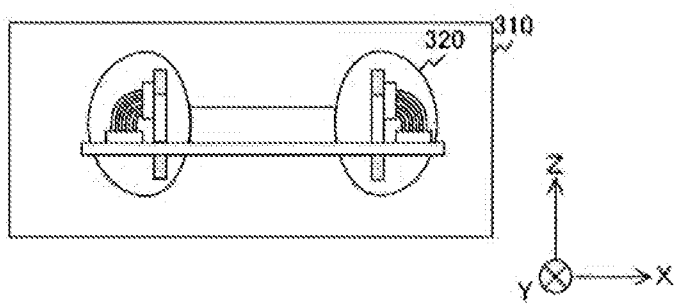
a
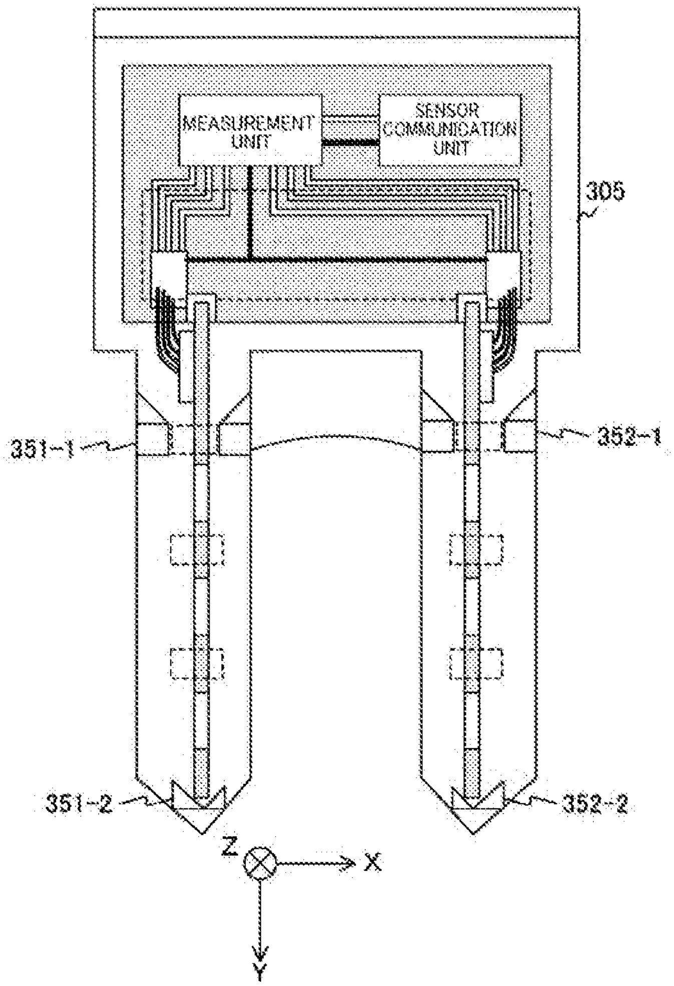
b
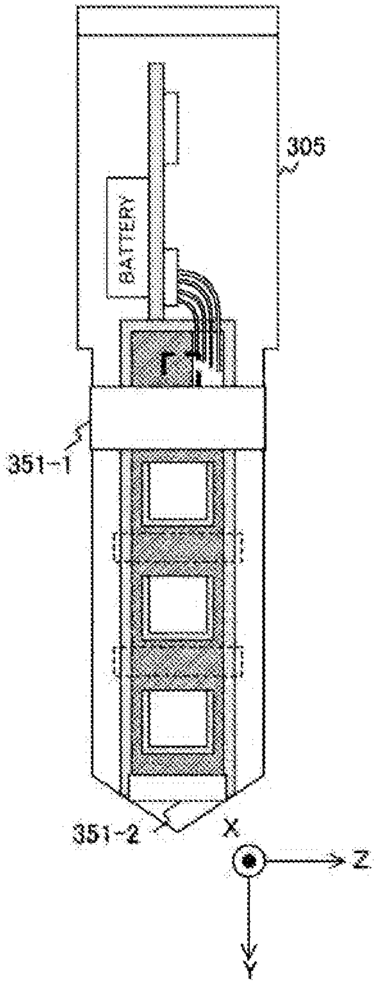
c

Fig. 189
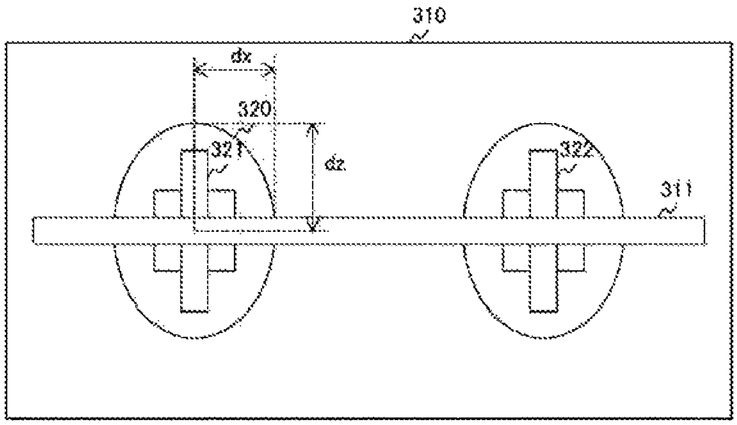
a
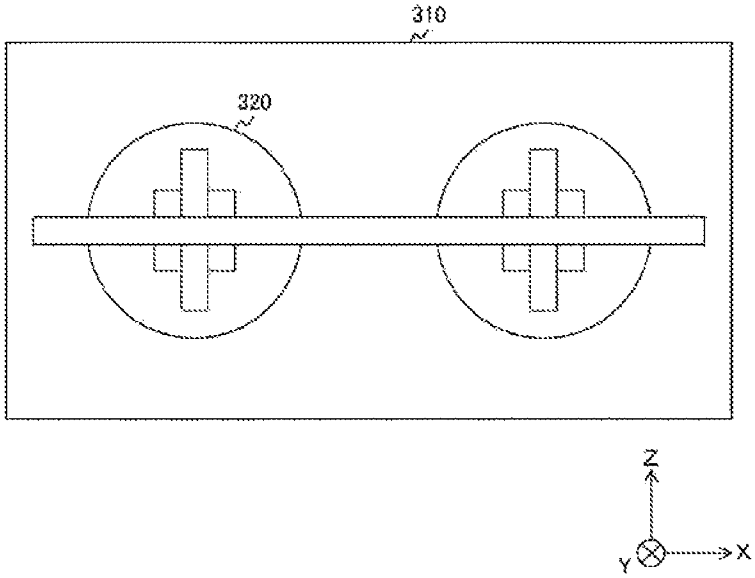
b

Fig. 190
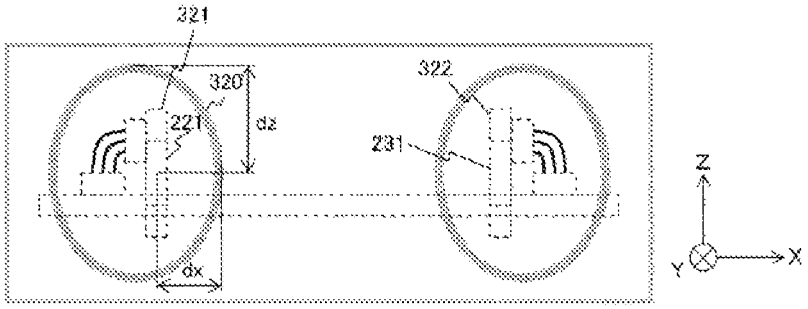
a
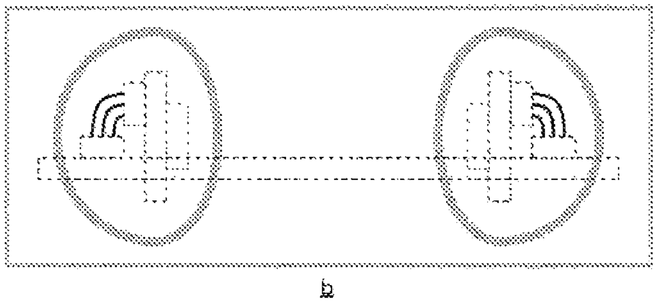
b
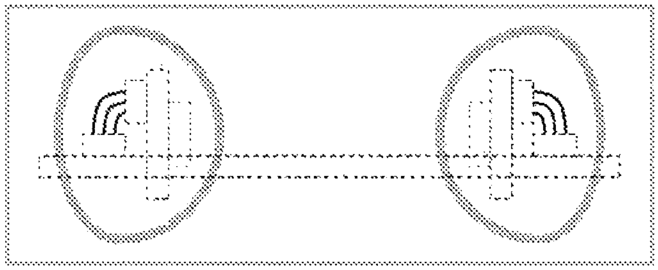
c
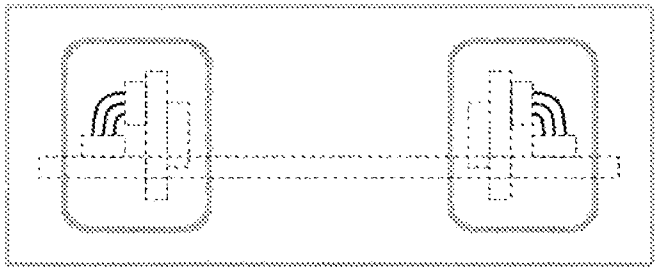
d

Fig. 191
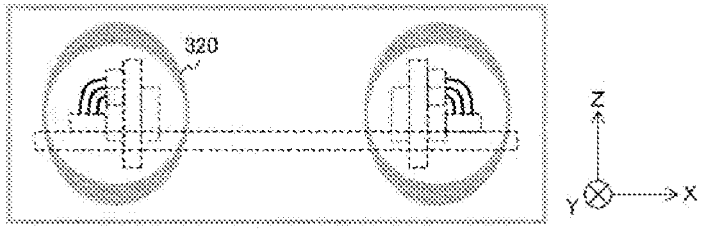
a
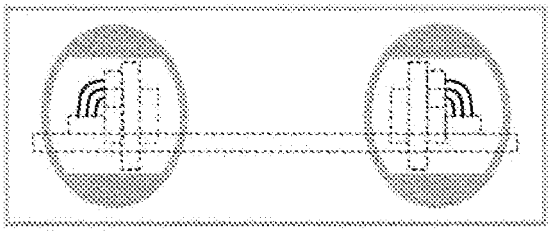
b
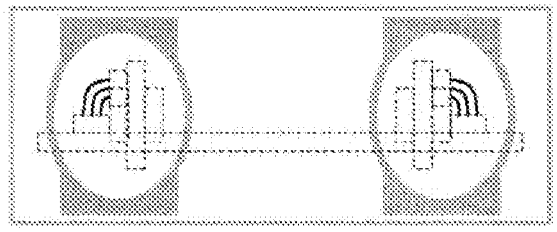
c
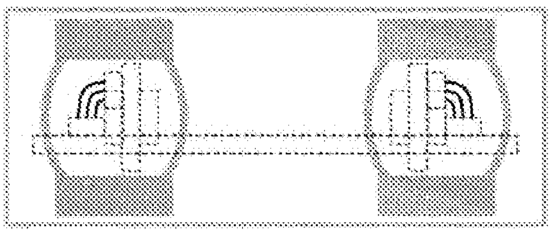
d

Fig. 193
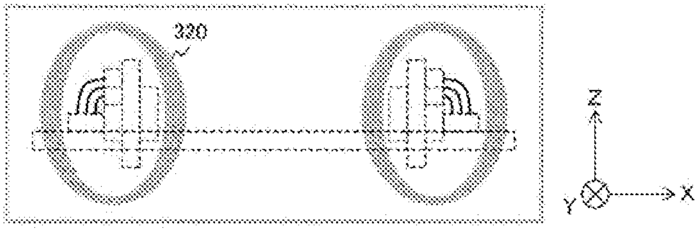
a
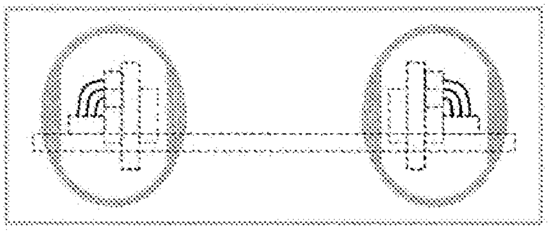
b
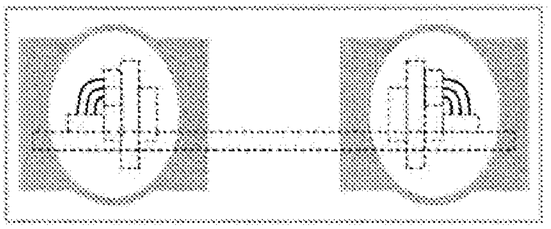
c
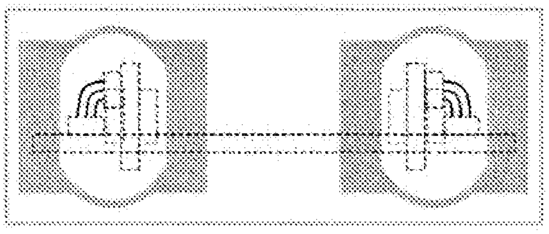
d

Fig. 194
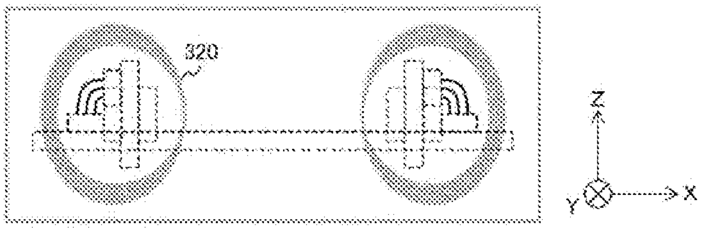
a
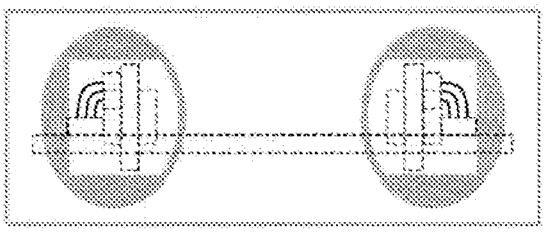
b
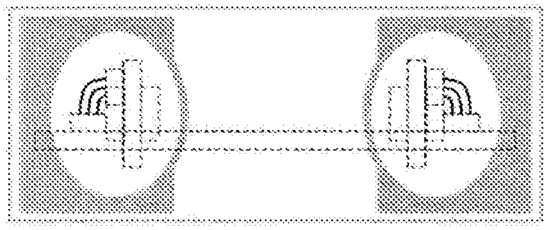
c
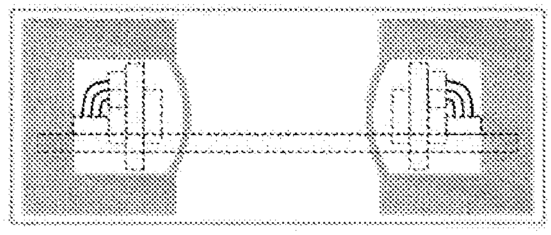
d

Fig. 199
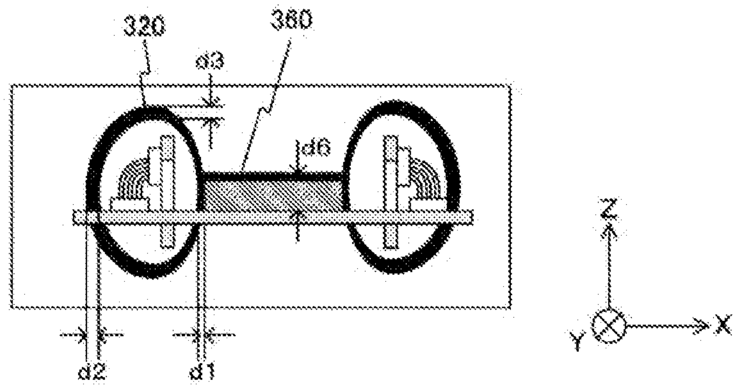
a
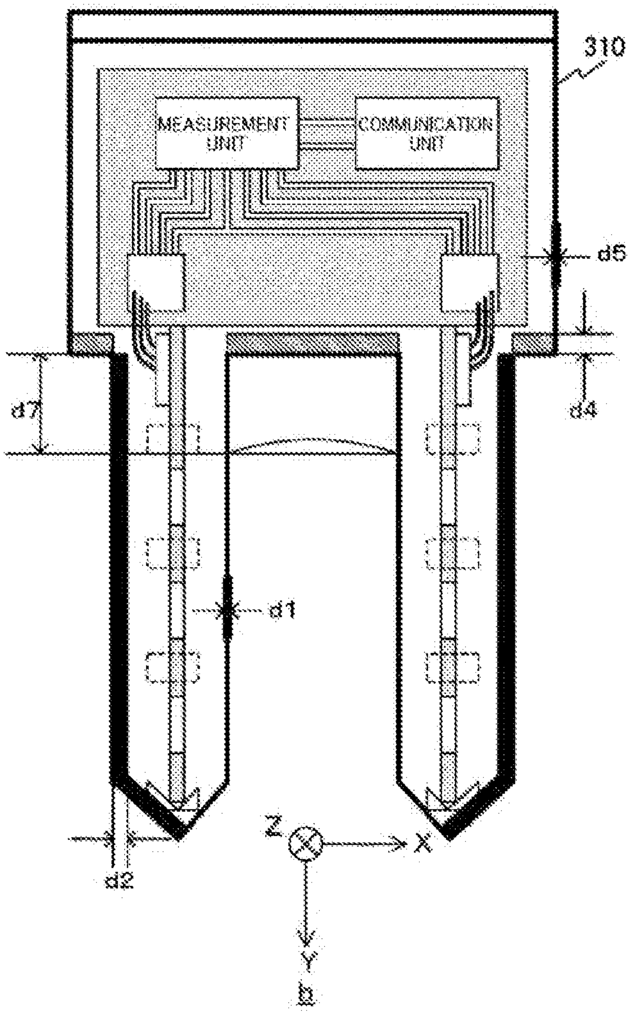
b
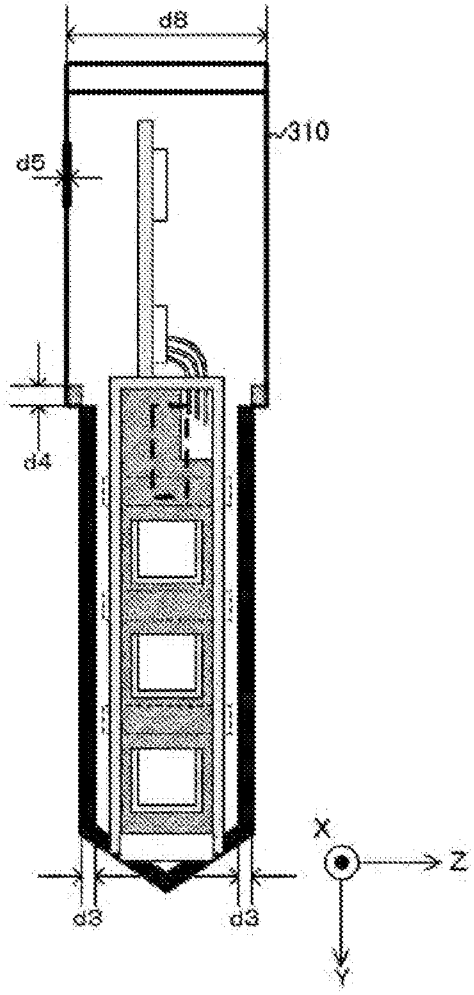
c

Fig. 209
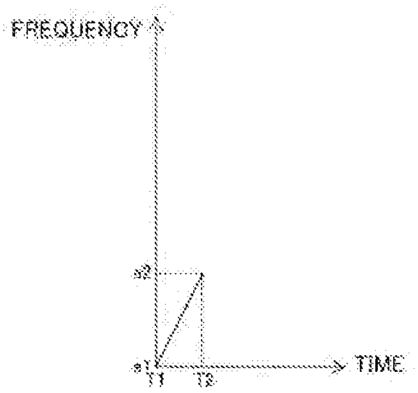
a
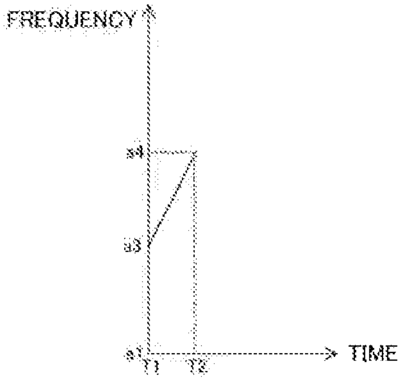
b
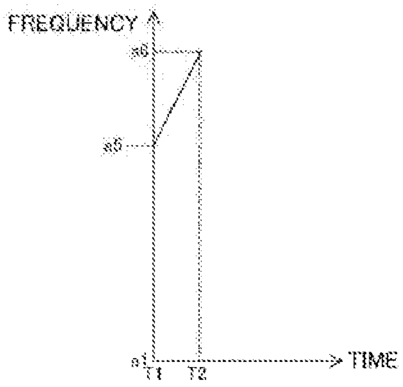
c

Fig. 224
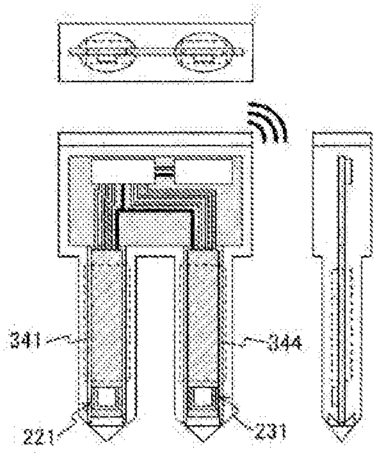
a
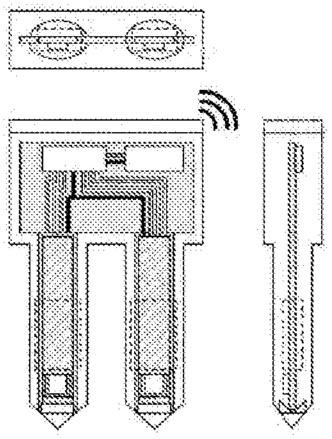
b
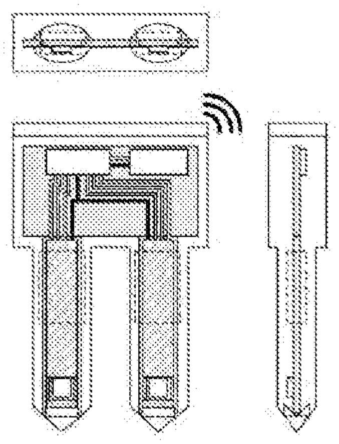
c

Fig. 229
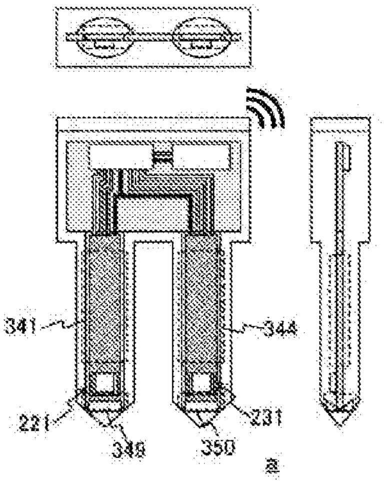
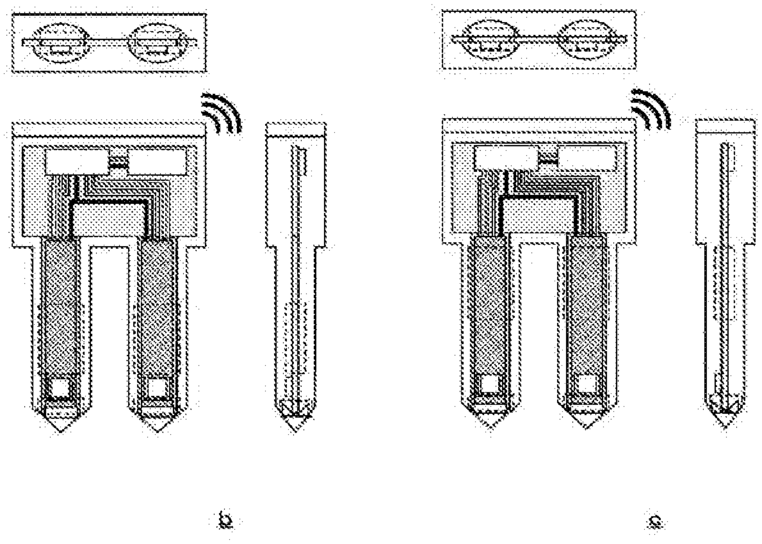

Fig. 232
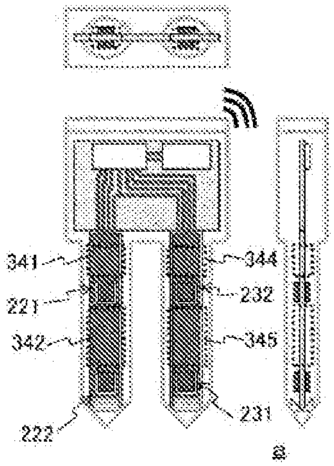
a
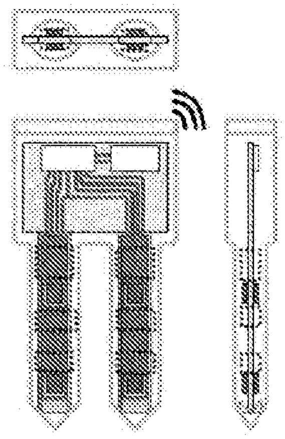
b
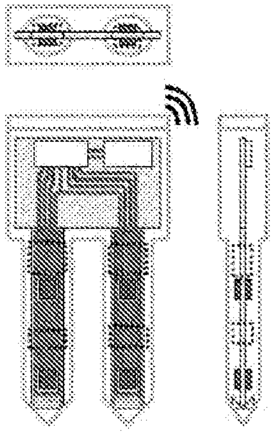
c

Fig. 233
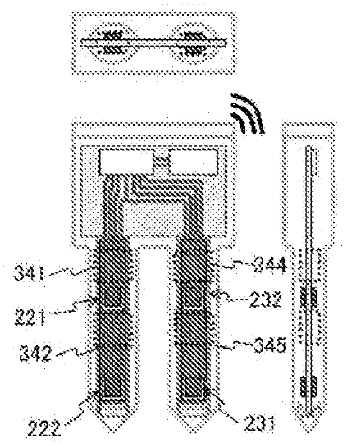
a
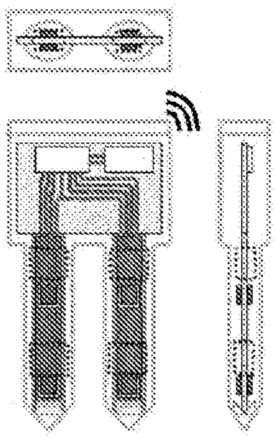
b

Fig. 234
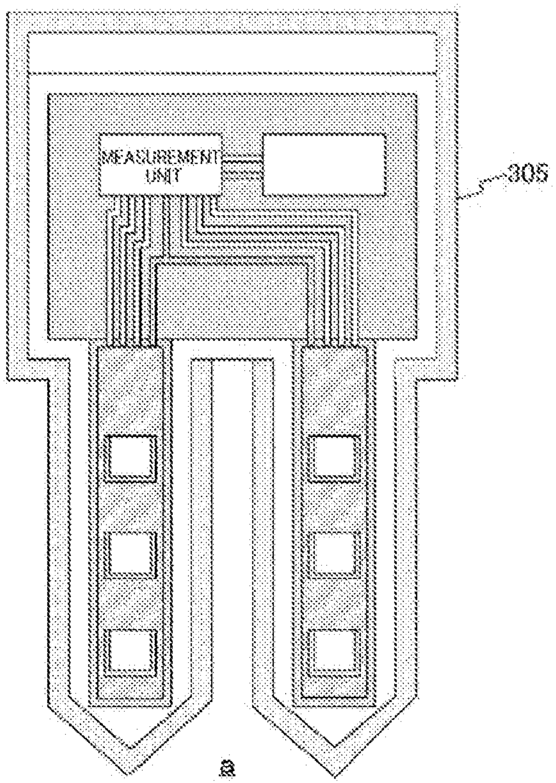
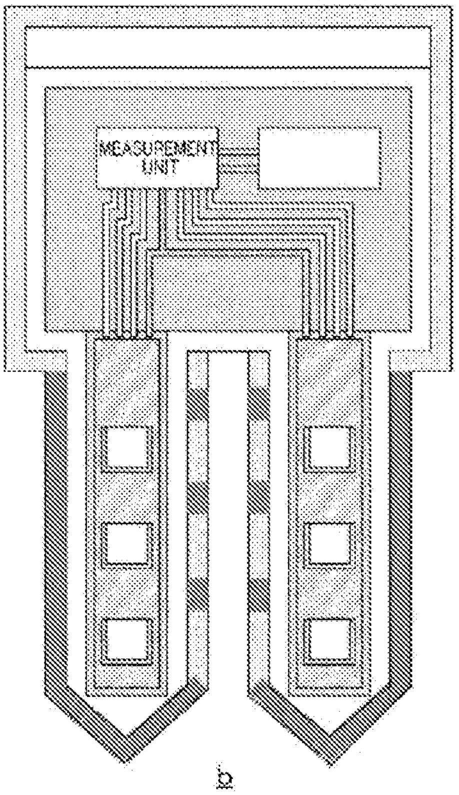
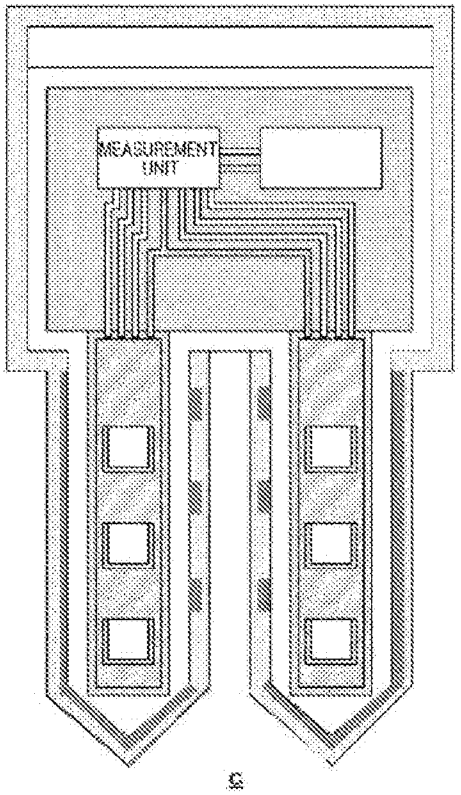

a b

Fig. 258
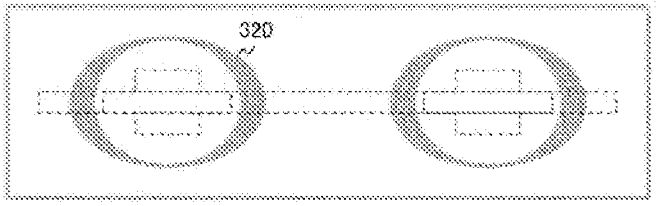
a
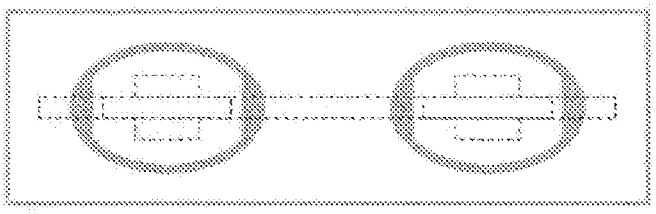
b
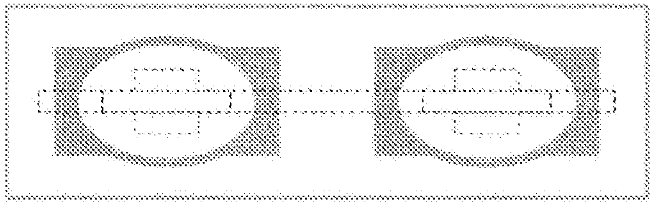
c
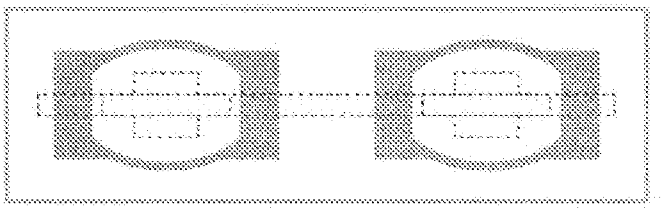
d

Fig. 259
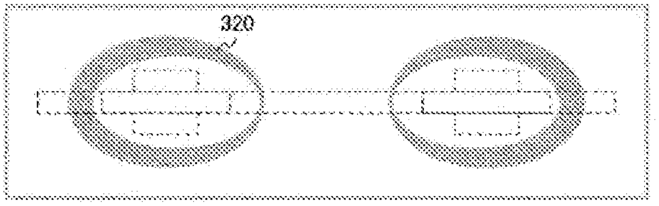
a
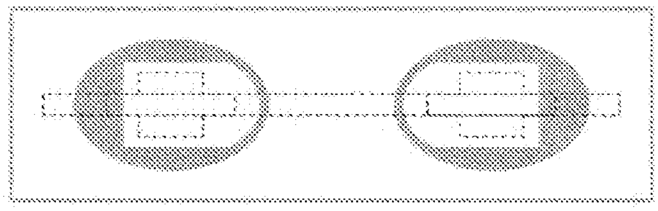
b
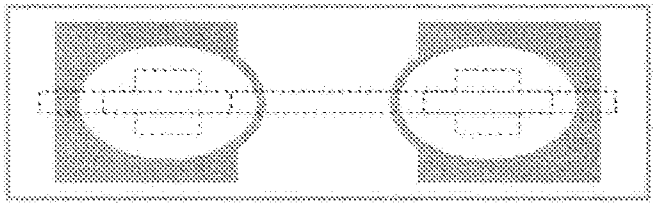
c
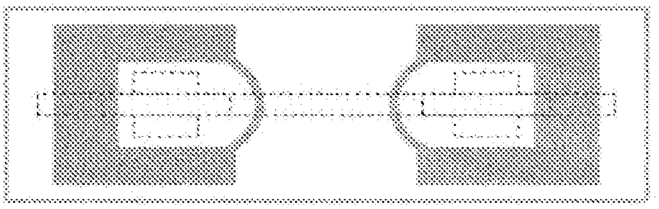
d

Fig. 260
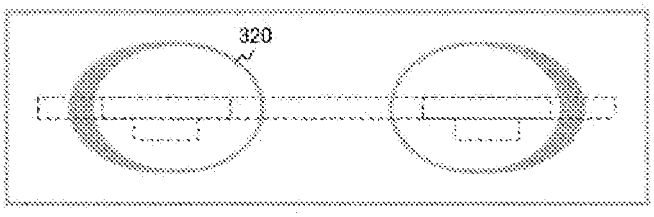
a
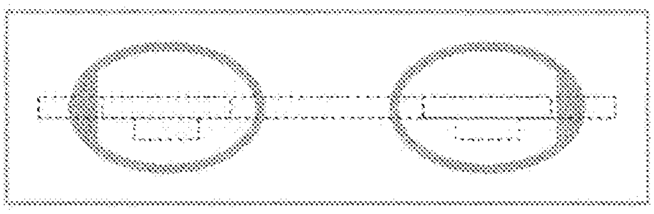
b
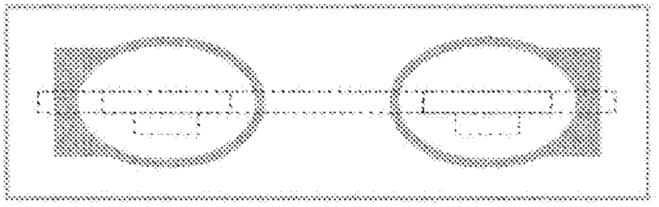
c
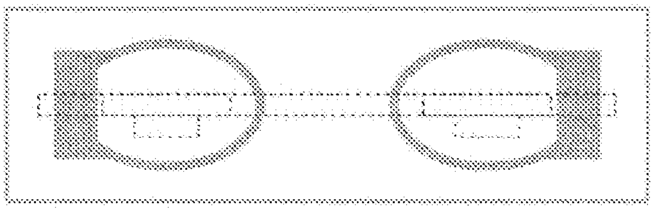
d

Fig. 261
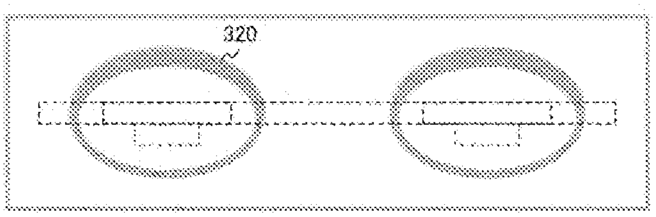
a
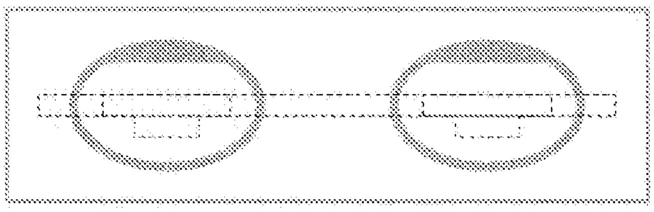
b
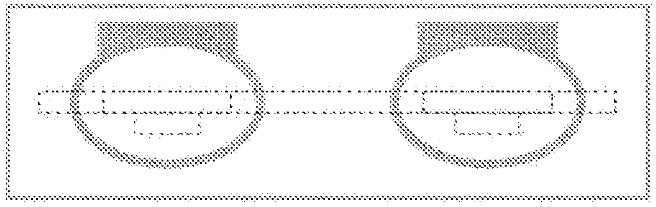
c
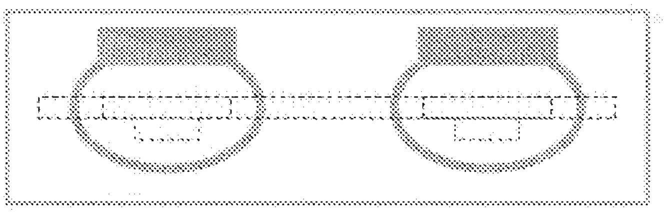
d

Fig. 263
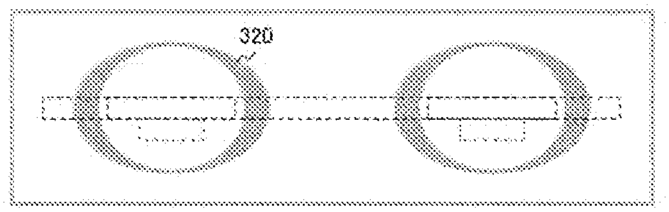
a
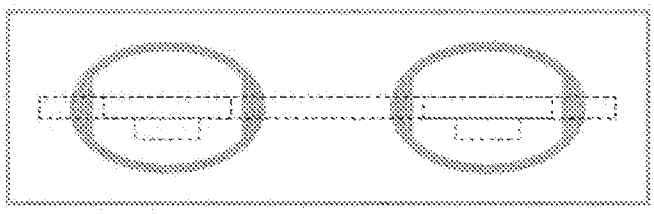
b
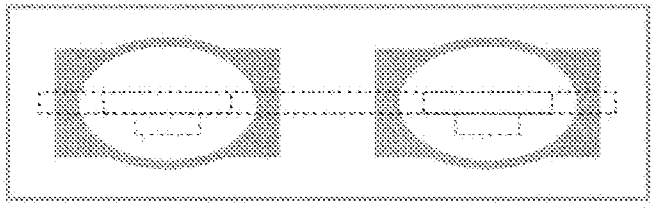
c
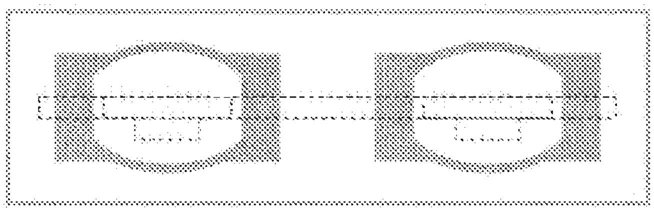
d a b c d

Fig. 267
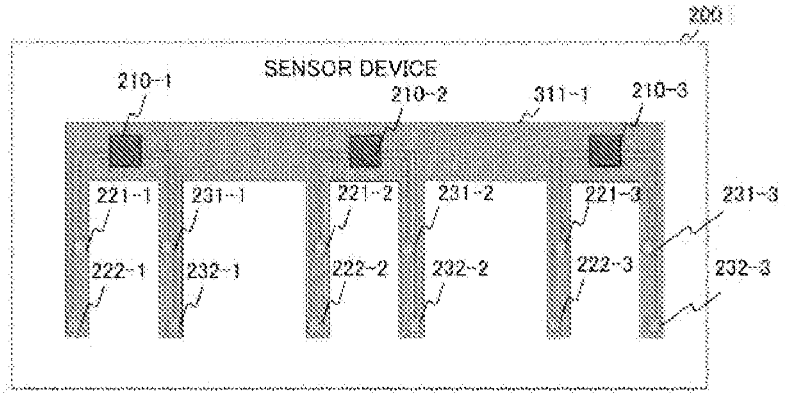
a
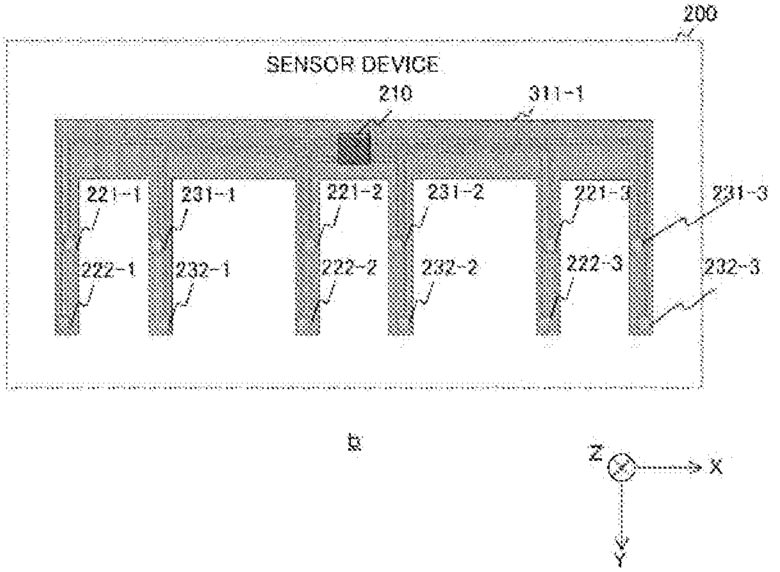
b

Fig. 268
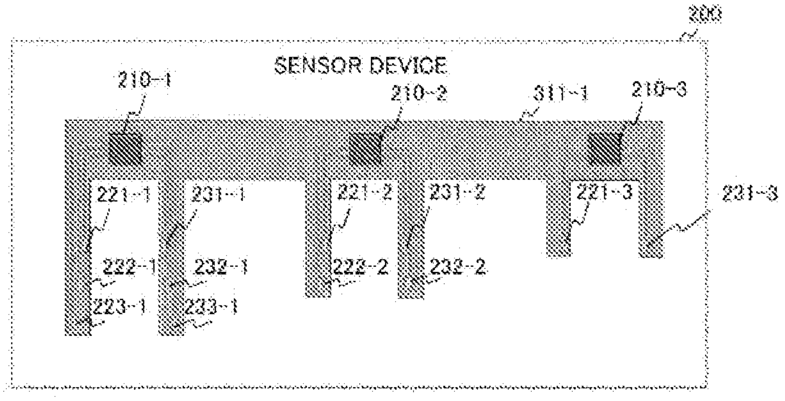
a
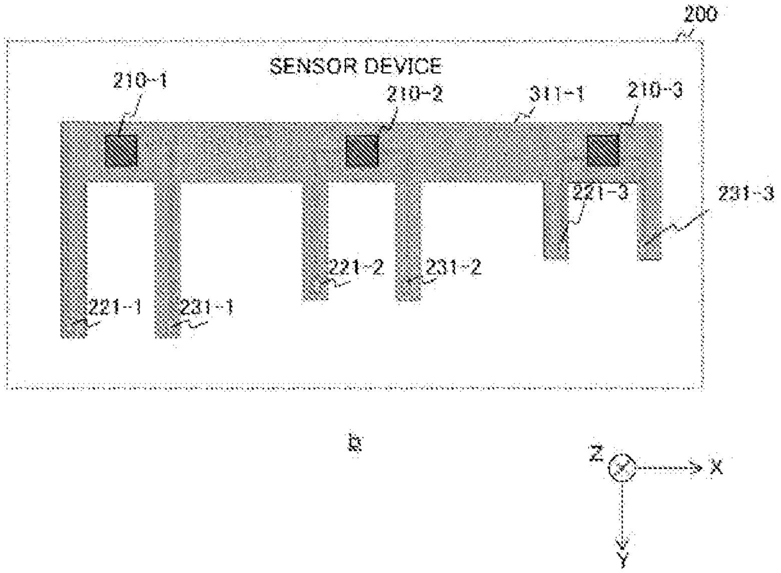
b

Fig. 269
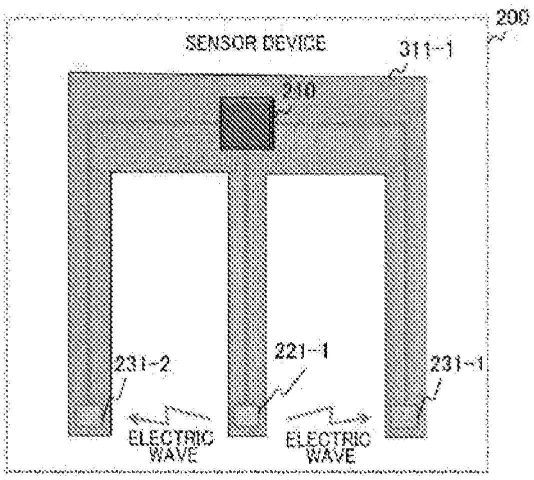
a
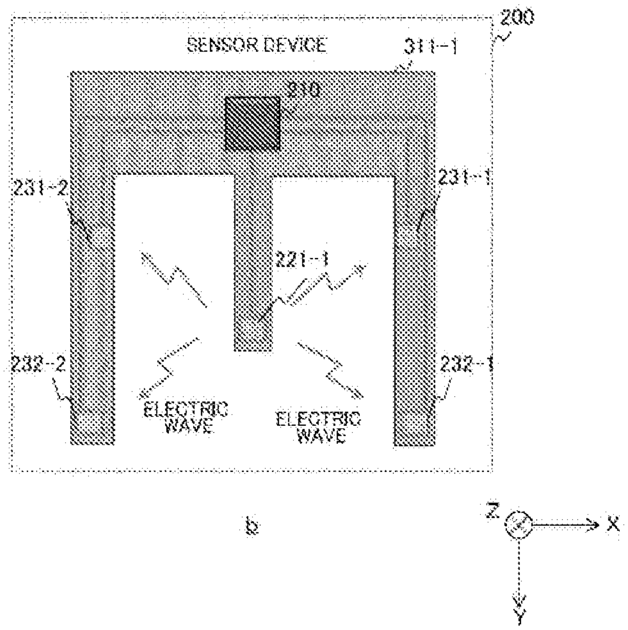
b

Fig. 273
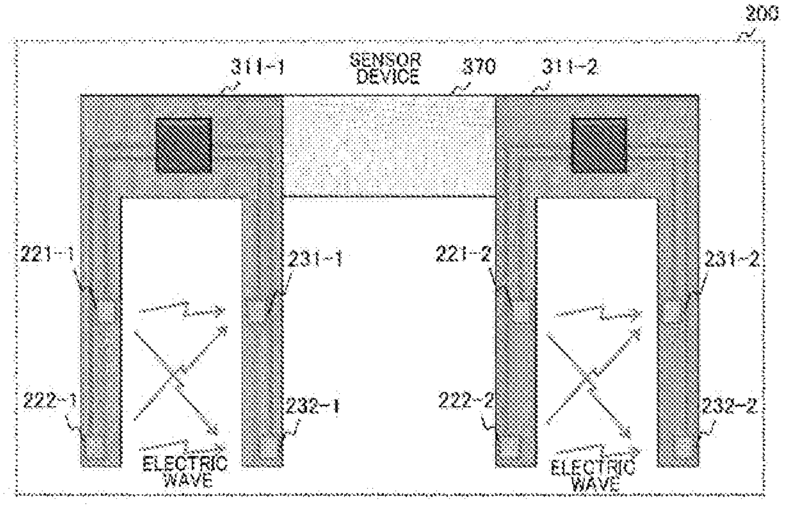
a
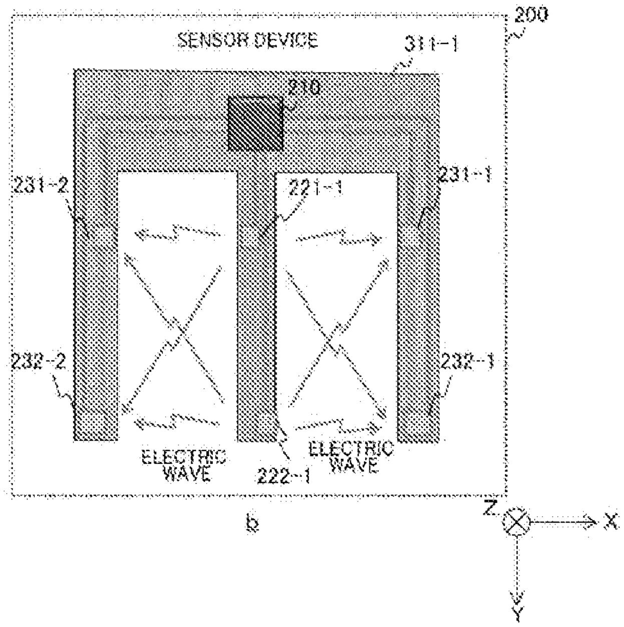
b

Fig. 285
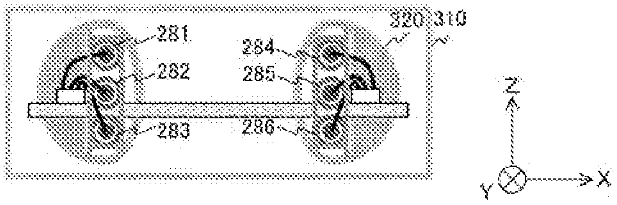
a
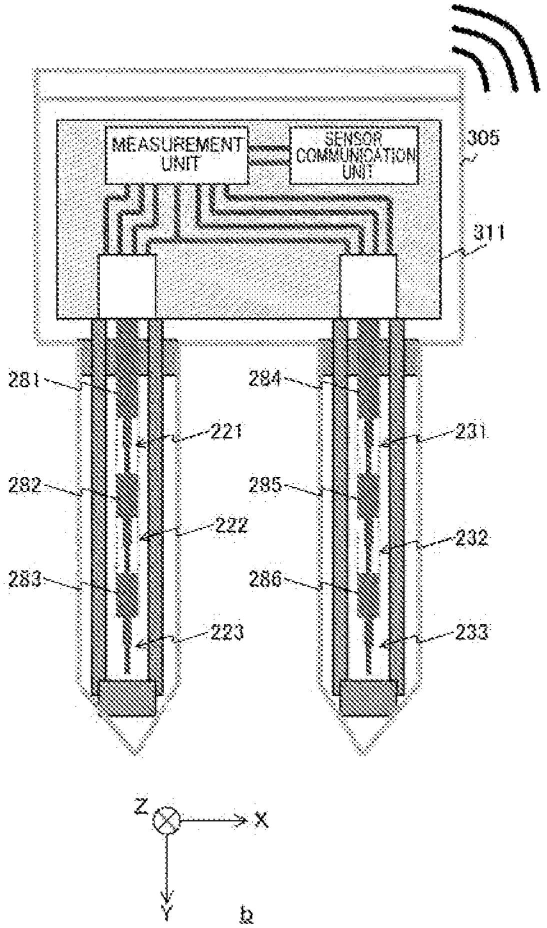
b
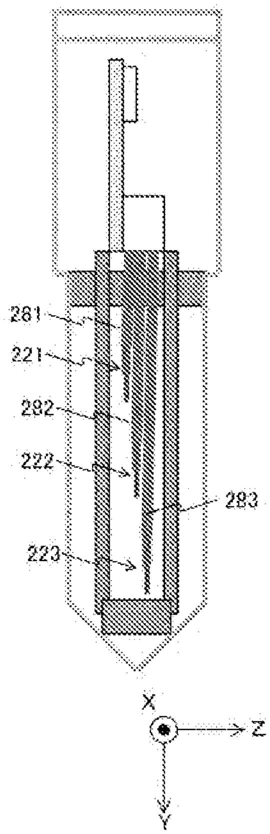
c

Fig. 287
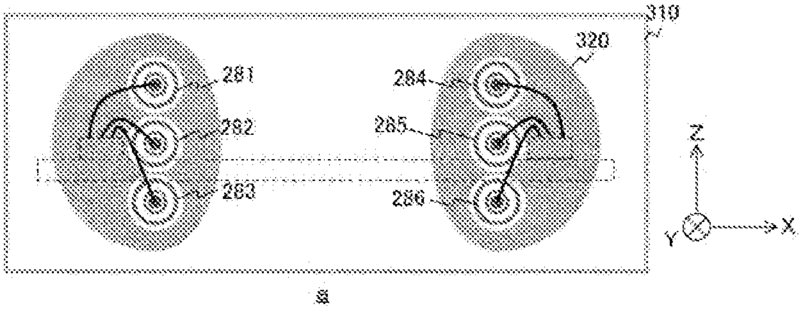
a
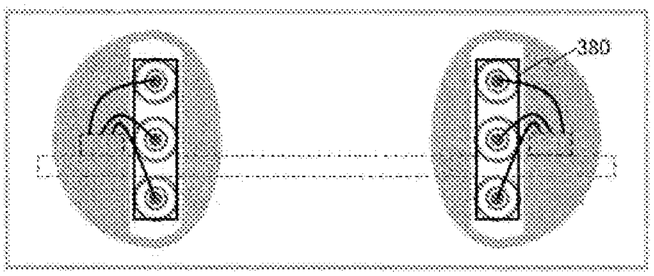
b
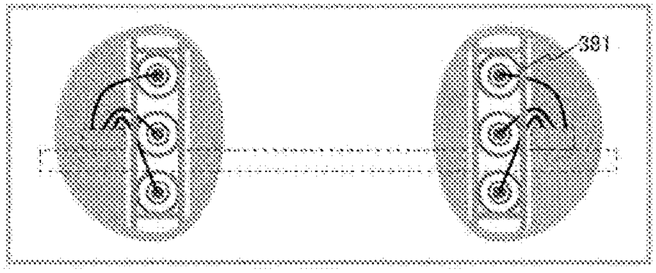
c
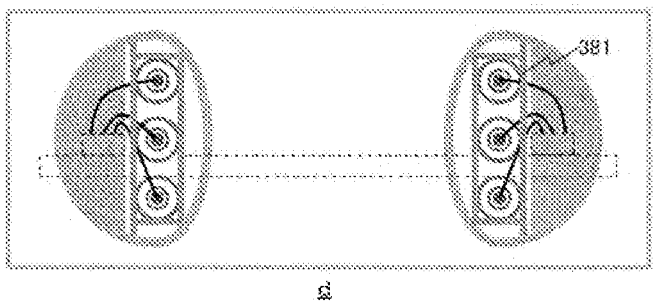
d

Fig. 288
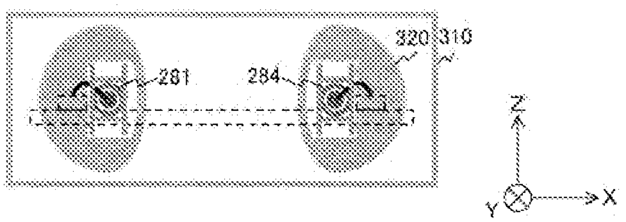
a
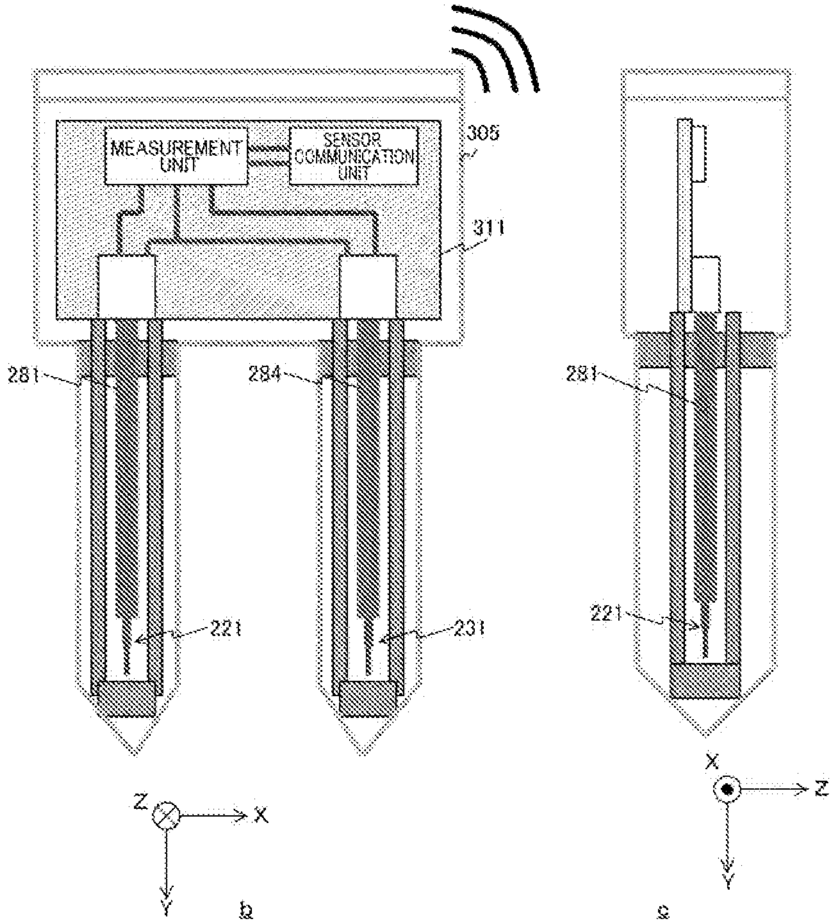
b
c

Fig. 292
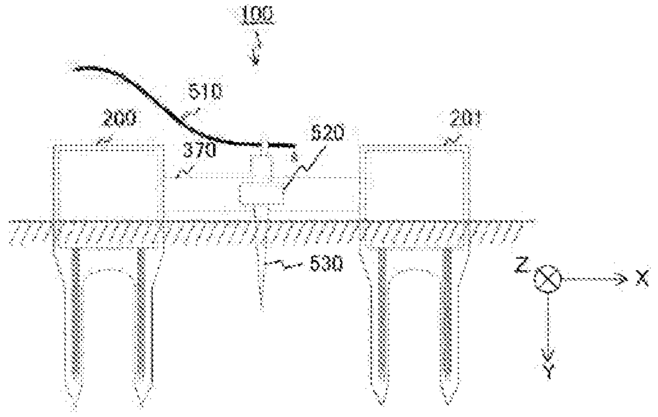
a
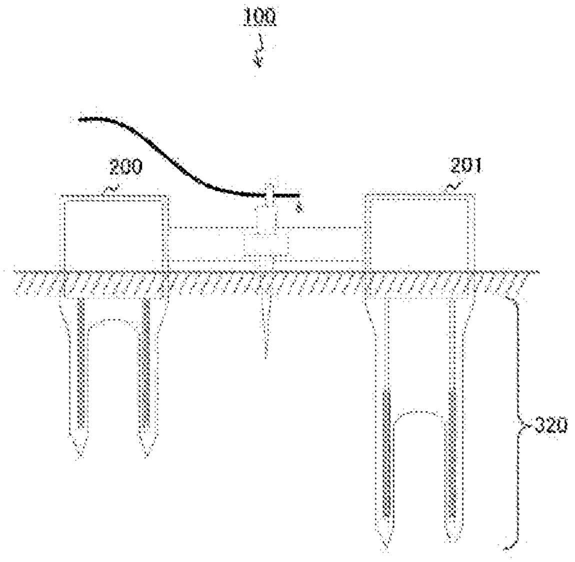
b

Fig. 294
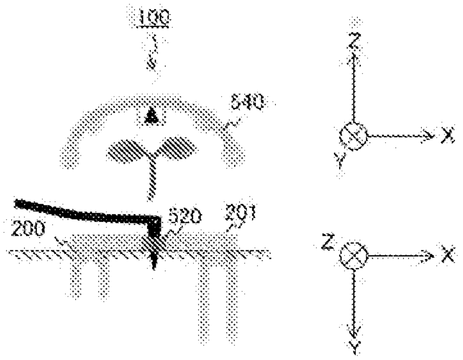
a
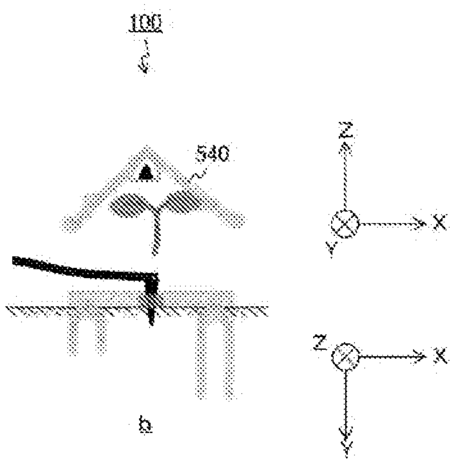
b

Fig. 297
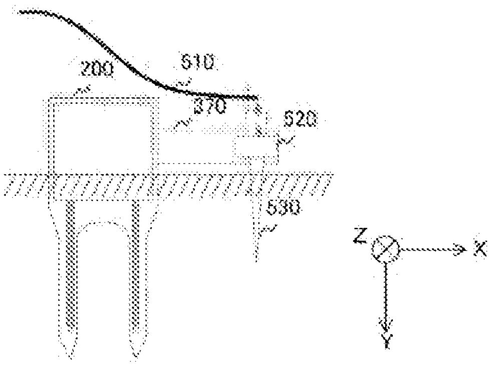
a
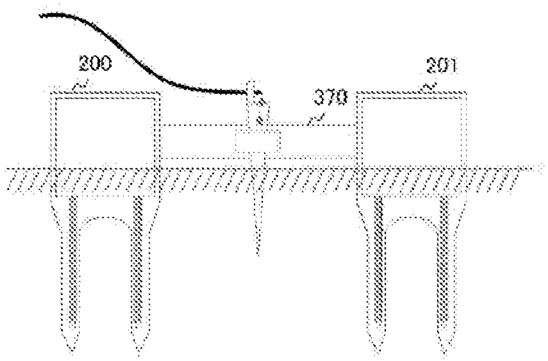
b
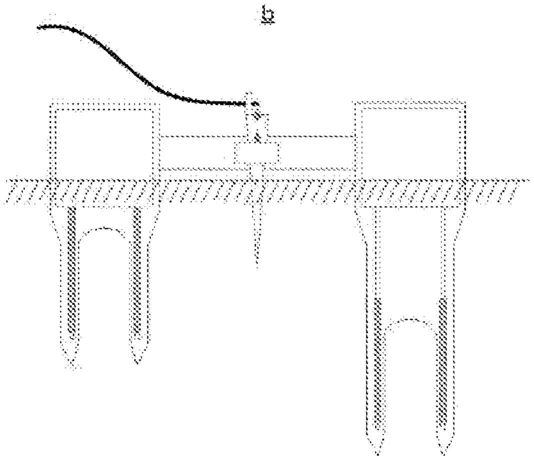
c

Fig. 298
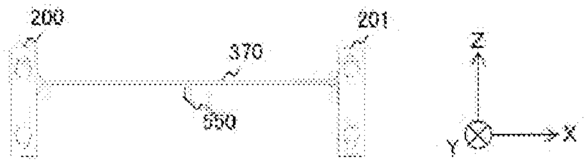
a
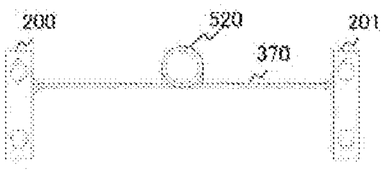
b

Fig. 323
a
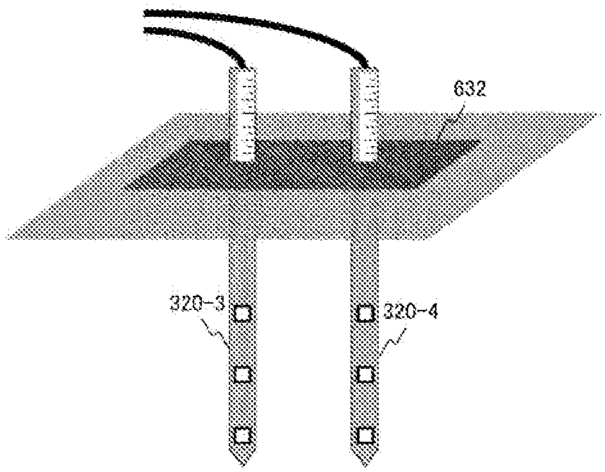
b
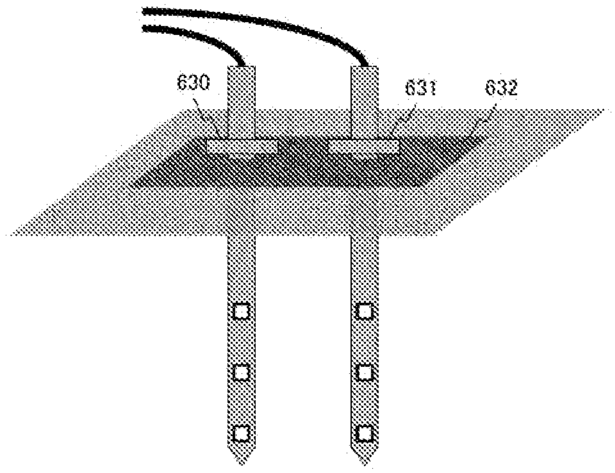
c

Fig. 326
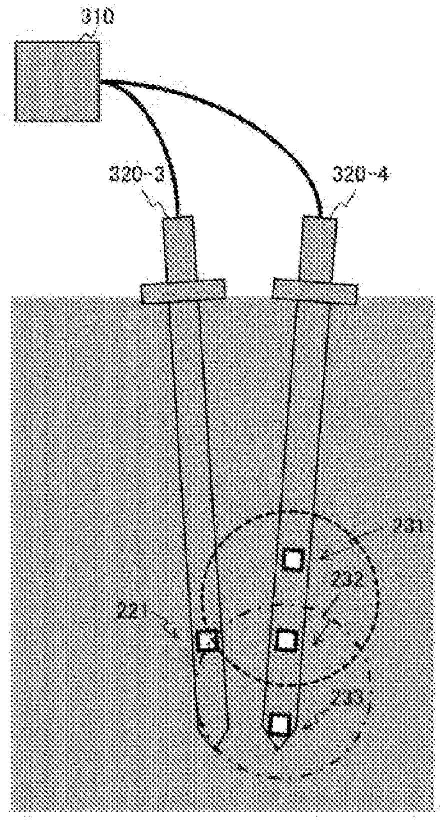
a
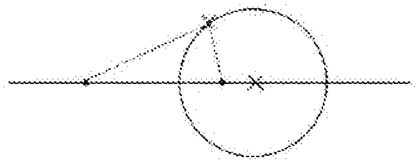
b

Fig. 329
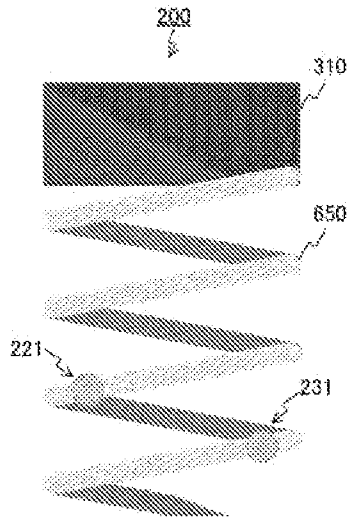
a
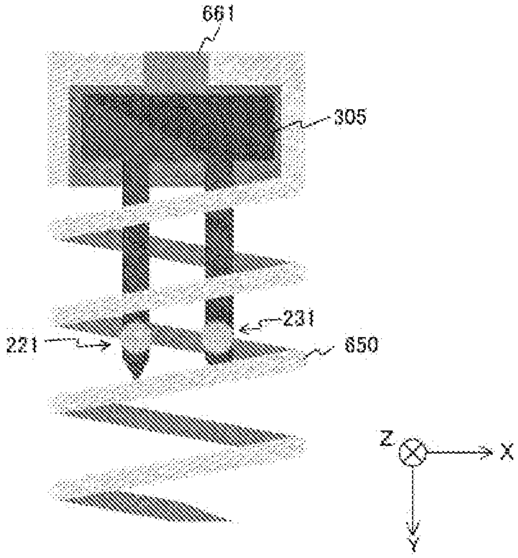
b

Fig. 330
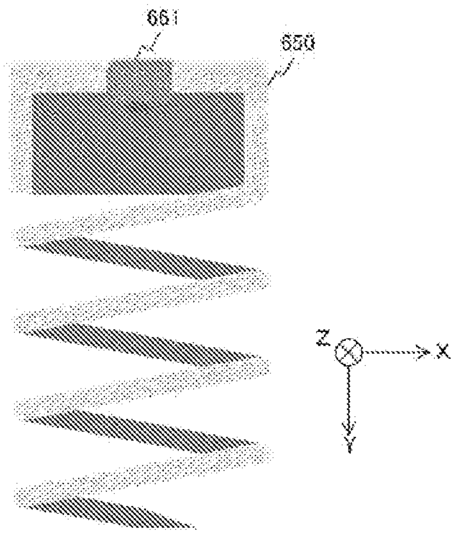
a
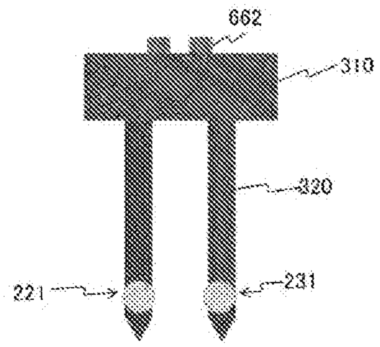
b

Fig. 341
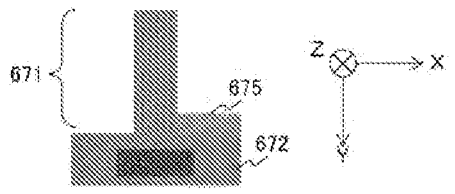
a
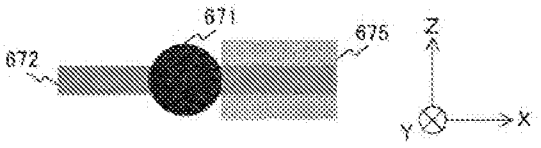
b

Fig. 342
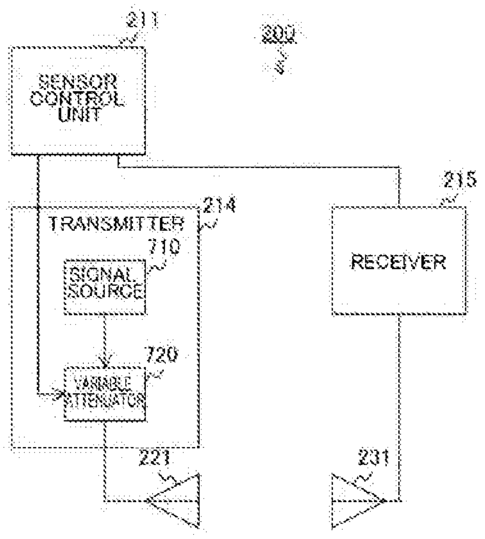
a
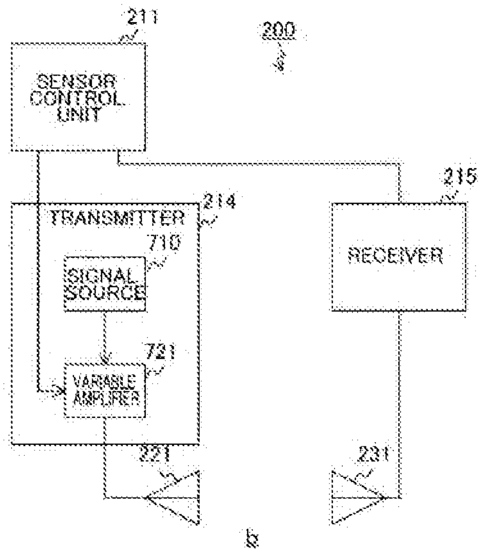
b

Fig. 347
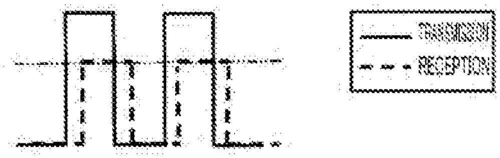
a
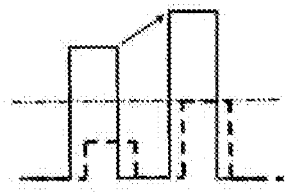
b

Fig. 353
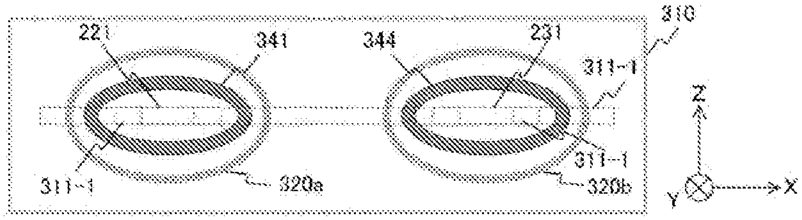
a
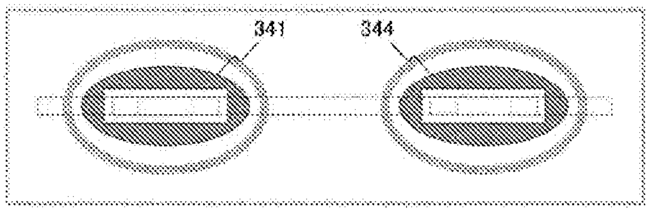
b
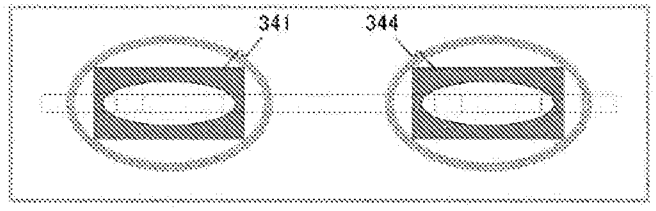
c
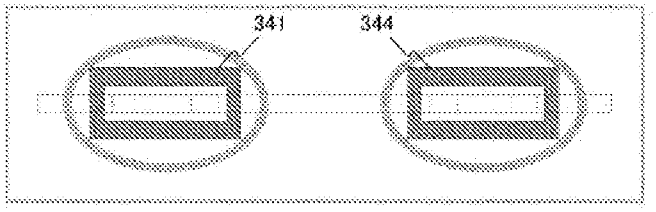
d

Fig. 355
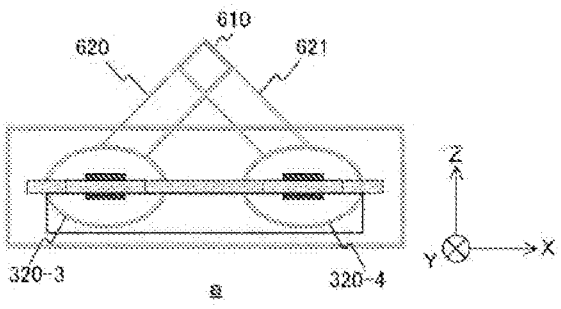
a
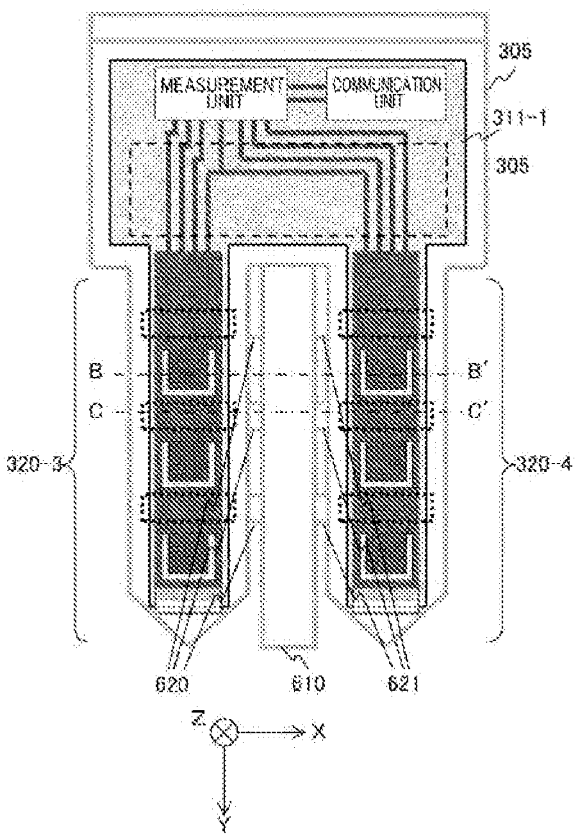
b
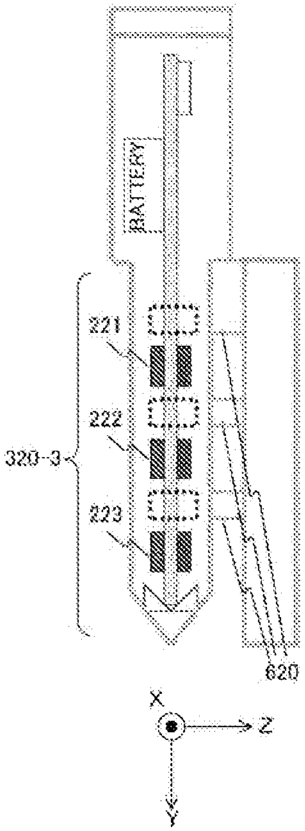
c

SENSOR DEVICE

CROSS REFERENCE TO RELATED APPLICATIONS

This application is a national stage application under 35 U.S.C. 371 and claims the benefit of PCT Application No. PCT/JP2021/040983, having an international filing date of 8 Nov. 2021, which designated the United States, which PCT application claimed the benefit of Japanese Patent Application Nos. 2020-188921, filed 12 Nov. 2020, and 2021-178678, filed 1 Nov. 2021, the entire disclosures of each of which are incorporated herein by reference.

TECHNICAL FIELD

The present technology relates to a sensor device. In details, the present technology relates to a sensor device in which one pair of probes are disposed.

BACKGROUND ART

Conventionally, devices and instruments measuring amounts of moisture in media such as a soil and the like are widely used in the fields of agriculture, environmental researches, and the like. For example, a sensor device measuring an amount of moisture in a medium on the basis of results of transmission/reception of electromagnetic waves that have propagated through a medium between one pair of probes has been proposed (for example, see PTL 1). In this way, a system using electromagnetic waves for measurement of an amount of moisture is called a microwave type. On the other hand, a system in which a value of an electric resistance or an electric capacity is substituted with an amount of moisture is called an electric resistance type or an electric capacity type.

CITATION LIST

Patent Literature

[PTL 1]
Specification of US 2018/0224382 A1

SUMMARY

Technical Problem

In the sensor device described above, by using the microwave type, compared to the electric resistance type and the electric capacity type, high speed measurement is achieved. However, according to the influence of noises and the like occurring in an electromagnetic wave, there is concern that the performance of the device such as measurement accuracy of an amount of moisture and the like may be degraded.

The present technology is in view of such situations, and an object thereof is to improve performance of a device that measures an amount of moisture in a medium.

Solution to Problem

The present technology is for solving the problem described above.

According to a first aspect, there is provided a sensor device including: a transmission antenna configured to transmit a signal as electromagnetic waves; a reception antenna configured to receive the electromagnetic waves transmitted from the transmission antenna and transmitted through a medium; and a measurement unit configured to measure the electromagnetic waves propagating to the reception antenna, and a sensor casing, further including a transmission substrate that is an electronic substrate including a plurality of wiring layers, a reception substrate that is an electronic substrate including a plurality of wiring layers, and a measurement unit substrate including a plurality of wiring layers or including a first coating layer coating an outer circumference of the substrate in a part of the transmission substrate and is formed using an electromagnetic absorbent material and a second coating layer coating an outer circumference of the substrate in a part of the reception substrate and is formed using an electromagnetic absorbent material, in which the sensor casing includes a transmission probe casing that is a part of the sensor casing and houses the transmission substrate and a reception probe casing that is another part of the sensor casing and houses the reception substrate, the transmission substrate includes a transmission line for transmission and a transmission slot antenna, the transmission line for transmission is formed using a wiring layer included in the transmission substrate, includes a first shield layer and a first signal line with being superimposed together, and is electrically connected to the measurement unit, the transmission slot antenna includes a radiation element having a slot and a transmission slot signal line part that is electrically connected to the first signal line and intersects with the slot, the radiation element is a conductor electrically connected to the first shield layer, the transmission slot antenna is connected to the transmission line for transmission, the reception substrate includes a transmission line for reception and a reception slot antenna, the transmission line of reception is formed using a wiring layer included in the reception substrate, includes a second shield layer and a second signal line with being superimposed together, and is electrically connected to the measurement unit, the reception slot antenna includes a reception element having a slot and a reception slot signal line part that is electrically connected to the second signal line and intersects with the slot, the reception element is a conductor electrically connected to the second shield layer, the reception slot antenna is connected to the transmission line for reception, each of the radiation element having the transmission slot and the reception element having the reception slot has both a size of a second direction that is a direction orthogonal to the first direction and is parallel to an extending direction of the transmission line and a size of a third direction that is orthogonal to first and second directions to be larger than a size of the first direction that is a superimposition direction, the transmission line for transmission and the radiation element that are formed using a wiring layer extending in parallel with a plane set by the second direction and the third direction and included in the transmission substrate and the transmission line for reception and the reception element that are formed using a wiring layer included in the reception substrate are arranged such that the plane of the radiation element and the plane of the reception element are on the same plane, and are disposed at positions separate away from each other by a predetermined distance, and have fixed extending directions and positions inside the sensor casing. From this, an effect of improving accuracy of measurement of the amount of moisture is acquired.

In addition, in this first aspect, the slot included in the transmission slot antenna may extend to an outer edge of the transmission substrate and include an opening part on the outer edge of the transmission substrate, and the slot included in the reception slot antenna may extend to an outer edge of the reception substrate and include an opening part on the outer edge of the reception substrate. From this, an effect of improving accuracy of measurement of the amount of moisture is acquired.

In addition, in this first aspect, a width of the transmission substrate in a direction orthogonal to an extending direction of the substrate may be equal to or smaller than ⅕ of a wavelength of the electromagnetic waves transmitted from the transmission antenna, and a width of the reception substrate in a direction orthogonal to the extending direction of the substrate may be equal to or smaller than ⅕ of the wavelength of the electromagnetic waves transmitted from the transmission antenna. From this, an effect of improving accuracy of measurement of the amount of moisture is acquired.

In addition, in this first aspect, the measurement unit may perform control of transmitting electromagnetic waves of different frequencies at different times from the transmission antenna, a width of the transmission substrate in a direction orthogonal to an extending direction of the substrate may be equal to or smaller than ⅕ of a wavelength of an electromagnetic wave having a center frequency among the electromagnetic waves transmitted from the transmission antenna, and a width of the reception substrate in a direction orthogonal to the extending direction of the substrate may be equal to or smaller than ⅕ of a wavelength of an electromagnetic wave having a center frequency among the electromagnetic waves transmitted from the transmission antenna. From this, an effect of improving accuracy of measurement of the amount of moisture is acquired.

In addition, in this first aspect, a positioning part used for fixing the extending direction and the position for each of the transmission substrate and the reception substrate may be further included. From this, an effect of being able to fix the position of the electronic substrate is acquired.

In addition, in this first aspect, the positioning part may be fixed to the sensor casing and is integrated with the sensor casing. From this, an effect of being able to fix the position of the electronic substrate is acquired.

In addition, in this first aspect, the sensor casing may have a structure including the positioning part. From this, an effect of being able to fix the position of the electronic substrate is acquired.

In addition, in this first aspect, the extending direction and the position for each of the transmission substrate and the reception substrate may be fixed by butting each of the transmission substrate and the reception substrate against the sensor casing at least at two or more points. From this, an effect of being able to fix the position of the electronic substrate is acquired.

In addition, in this first aspect, a structure acquired by hardening a periphery of each of the transmission substrate and the reception substrate using a resin may be included, and a strength of the structure acquired by hardening the periphery of the transmission substrate using the resin may be twice that of the transmission substrate or more, and a strength of the structure acquired by hardening the periphery of the reception substrate using the resin may be twice that of the reception substrate or more. From this, an effect of preventing deformation of the substrate is acquired.

In addition, in this first aspect, the transmission probe casing may be formed using an electromagnetic wave transmissive material such that a strength of the casing is higher than a strength of the transmission substrate, and the reception probe casing may be formed using an electromagnetic wave transmissive material such that a strength of the casing is higher than a strength of the reception substrate. Accordingly, noise is reduced.

In addition, in this first aspect, a thickness of a part of the transmission probe casing may be larger than a thickness of the other part in a cross-section orthogonal to an extending direction of the casing, and a thickness of a part of the reception probe casing may be larger than a thickness of the other part in a cross-section orthogonal to an extending direction of the casing. From this, an effect of setting the thickness to an appropriate value is acquired.

In addition, in this first aspect, in a cross-section orthogonal to the extending direction of the transmission probe casing, a thickness of the transmission probe casing that is positioned in a direction parallel to the substrate from a center of the transmission substrate may be larger than a thickness of the transmission probe casing that is positioned in a direction orthogonal to the substrate from the center of the transmission substrate, and, in a cross-section orthogonal to the extending direction of the reception probe casing, a thickness of the reception probe casing that is positioned in a direction parallel to the substrate from a center of the reception substrate may be larger than a thickness of the reception probe casing that is positioned in a direction orthogonal to the substrate from the center of the reception substrate. From this, an effect of setting the thickness to an appropriate value is acquired.

In addition, in this first aspect, in a cross-section orthogonal to the extending direction of the transmission probe casing, in a thickness of the transmission probe casing that is positioned in a direction orthogonal to the substrate from a center of the transmission substrate, the thickness of the casing that is positioned on a side far from the reception substrate may be larger than the thickness of the casing that is positioned on a side close to the reception substrate, and, in a cross-section orthogonal to the extending direction of the reception probe casing, in a thickness of the reception probe casing that is positioned in a direction orthogonal to the substrate from a center of the reception substrate, the thickness of the casing that is positioned on a side far from the transmission substrate may be larger than the thickness of the casing that is positioned on a side close to the transmission substrate. From this, an effect of setting the thickness to an appropriate value is acquired.

In addition, in this first aspect, in the transmission substrate, a plurality of vias connected to the first shield layer may be included, and a shield structure according to a column of the plurality of vias may be included on a lateral side of the first signal line, and, in the reception substrate, a plurality of vias connected to the second shield layer may be included, and a shield structure according to a column of the plurality of vias may be included on a lateral side of the second signal line. Accordingly, noise is reduced.

In addition, in this first aspect, the transmission substrate may include a plurality of transmission antennas, and the reception substrate may include a plurality of reception antennas. From this, an effect of sequentially measuring amounts of moisture for a plurality of depths is acquired.

In addition, in this first aspect, in the transmission substrate, the transmission line for transmission connected to the plurality of transmission antennas may be disposed independently for each of the plurality of antennas, and, in the reception substrate, the transmission line for reception connected to the plurality of reception antennas may be disposed independently for each of the plurality of antennas.

In addition, in this first aspect, the measurement unit may perform control of transmitting electromagnetic waves by selecting the transmission antenna one at each time among the plurality of transmission antennas in an order set in advance.

BRIEF DESCRIPTION OF DRAWINGS

FIG. 4 is an example of a whole view of the sensor device according to the first embodiment of the present technology.

FIG. 11 is an example of a whole view of a sensor casing in which the number of antennas is decreased in the first embodiment of the present technology.

FIG. 14 is an example of a whole view of a sensor casing in which a casing in the first embodiment of the present technology is divided.

FIG. 75 is a diagram illustrating an operation principle of the sensor device according to the first embodiment of the present technology.

FIG. 76 is a diagram illustrating an example of an angle formed between an antenna plane and a measurement unit substrate according to the first embodiment of the present technology.

FIG. 109 is an example of a cross-sectional view of a seventh layer of the inside of an in-probe substrate in which a slot is formed and substrates in the first embodiment of the present technology.

FIG. 119 is a block diagram illustrating one configuration example of a sensor device in which a transmission switch and a reception switch are built in a transmitter and a receiver in the first embodiment of the present technology.

FIG. 120 is a block diagram illustrating one configuration example of a sensor device 2 in which a switch is disposed only on a reception side in the first embodiment of the present technology.

FIG. 121 is an example of a timing diagram of time-divisional driving according to the first embodiment of the present technology.

FIG. 122 is an example of a timing diagram illustrating operations of respective units disposed inside the sensor device according to the first embodiment of the present technology.

FIG. 123 is an example of a timing diagram of time-divisional driving acquired when timings of signal processing are changed in the first embodiment of the present technology.

FIG. 124 is an example of a timing diagram illustrating operations of respective units disposed inside the sensor device acquired when timings of signal processing are changed in the first embodiment of the present technology.

FIG. 125 is an example of a timing diagram of time-divisional driving acquired when timings of signal processing and data transmission are changed in the first embodiment of the present technology.

FIG. 126 is an example of a timing diagram illustrating operations of respective units disposed inside the sensor device acquired when timings of signal processing and data transmission are changed in the first embodiment of the present technology.

FIG. 127 is an example of a timing diagram of time-divisional driving acquired when a sequence of a transmission, reception, and wave detecting operation is changed in the first embodiment of the present technology.

FIG. 128 is an example of a timing diagram illustrating operations of respective units disposed inside the sensor device acquired when a sequence of a transmission, reception, and wave detecting operation is changed in the first embodiment of the present technology.

FIG. 129 is a diagram illustrating examples of a transmission signal of each antenna of control examples a, b, and c in the first embodiment of the present technology.

FIG. 130 is a diagram illustrating examples of a transmission signal of each antenna of control example d in the first embodiment of the present technology.

FIG. 131 is a diagram illustrating an example of a sensor device in which a measurement unit casing is thinned in the first embodiment of the present technology.

FIG. 132 is a diagram illustrating an example of a sensor device in which a measurement unit casing is thickened in the first embodiment of the present technology.

Figure 133:
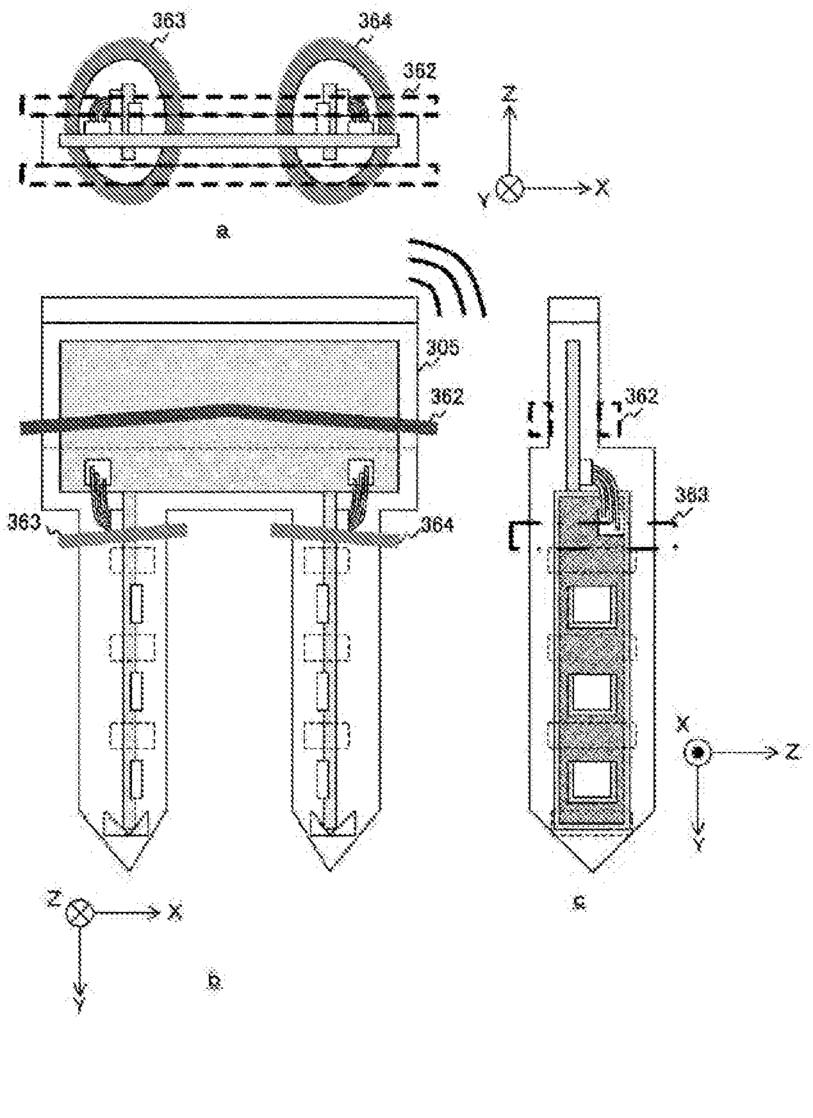

FIG. 133 is a diagram illustrating an example of a sensor device in which the measurement unit casing is thinned, and a rain gutter is added in the first embodiment of the present technology.

Figure 134:
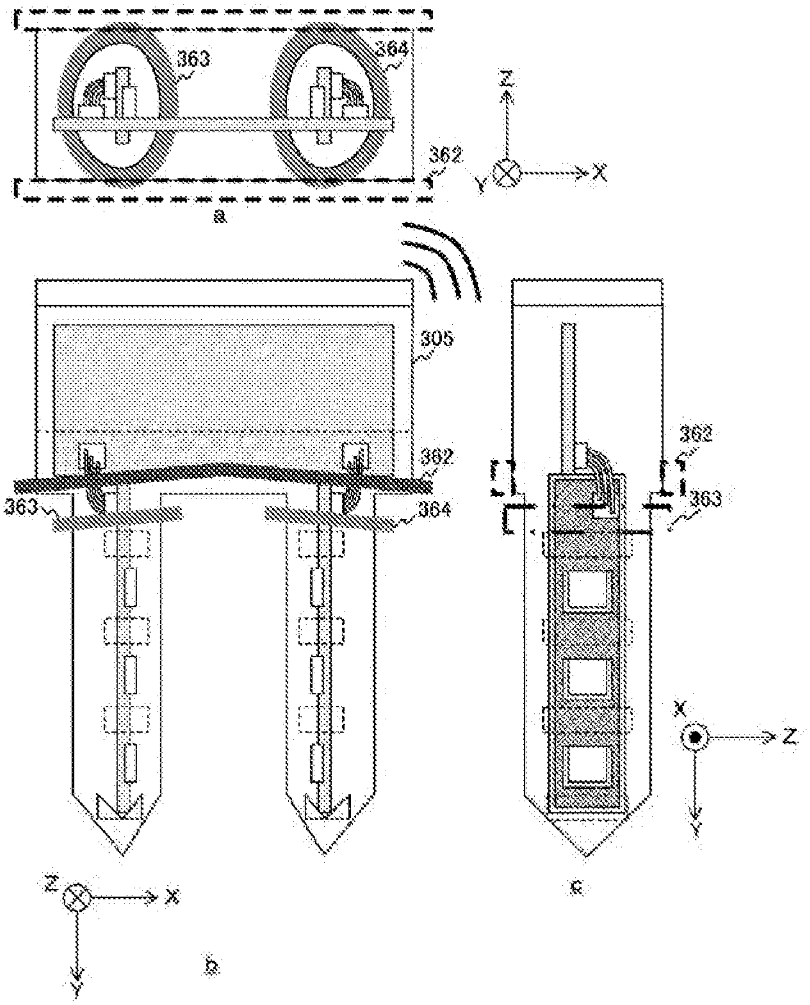

FIG. 134 is a diagram illustrating an example of a sensor device in which the measurement unit casing is thickened, and a rain gutter is added in the first embodiment of the present technology.

Figure 135:
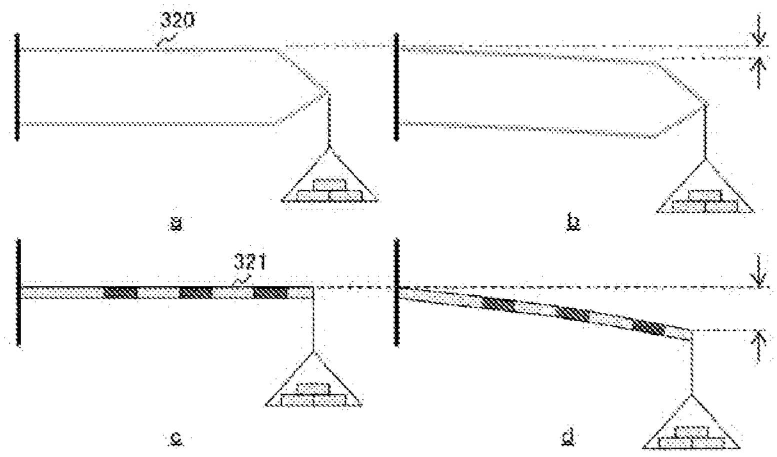

FIG. 135 is a diagram illustrating a strength of a probe casing in the first embodiment of the present technology.

Figure 136:
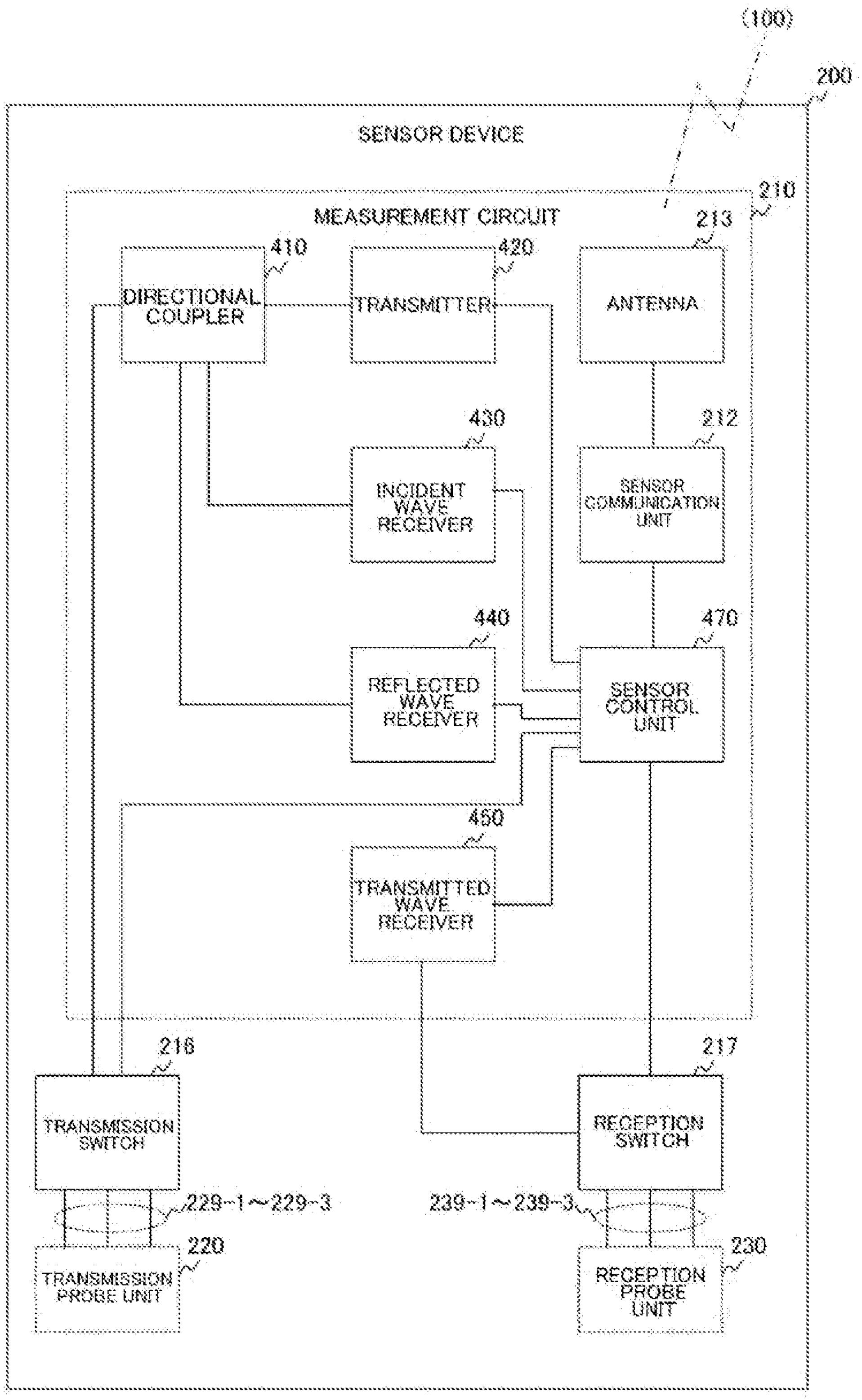

FIG. 136 is a block diagram illustrating one configuration example of a measurement circuit in the first embodiment of the present technology.

Figure 137:
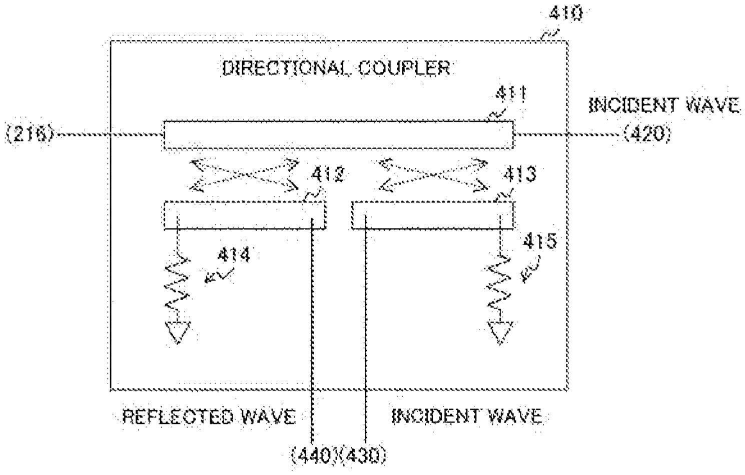

FIG. 137 is a diagram illustrating one configuration example of a directional coupler in the first embodiment of the present technology.

Figure 138:
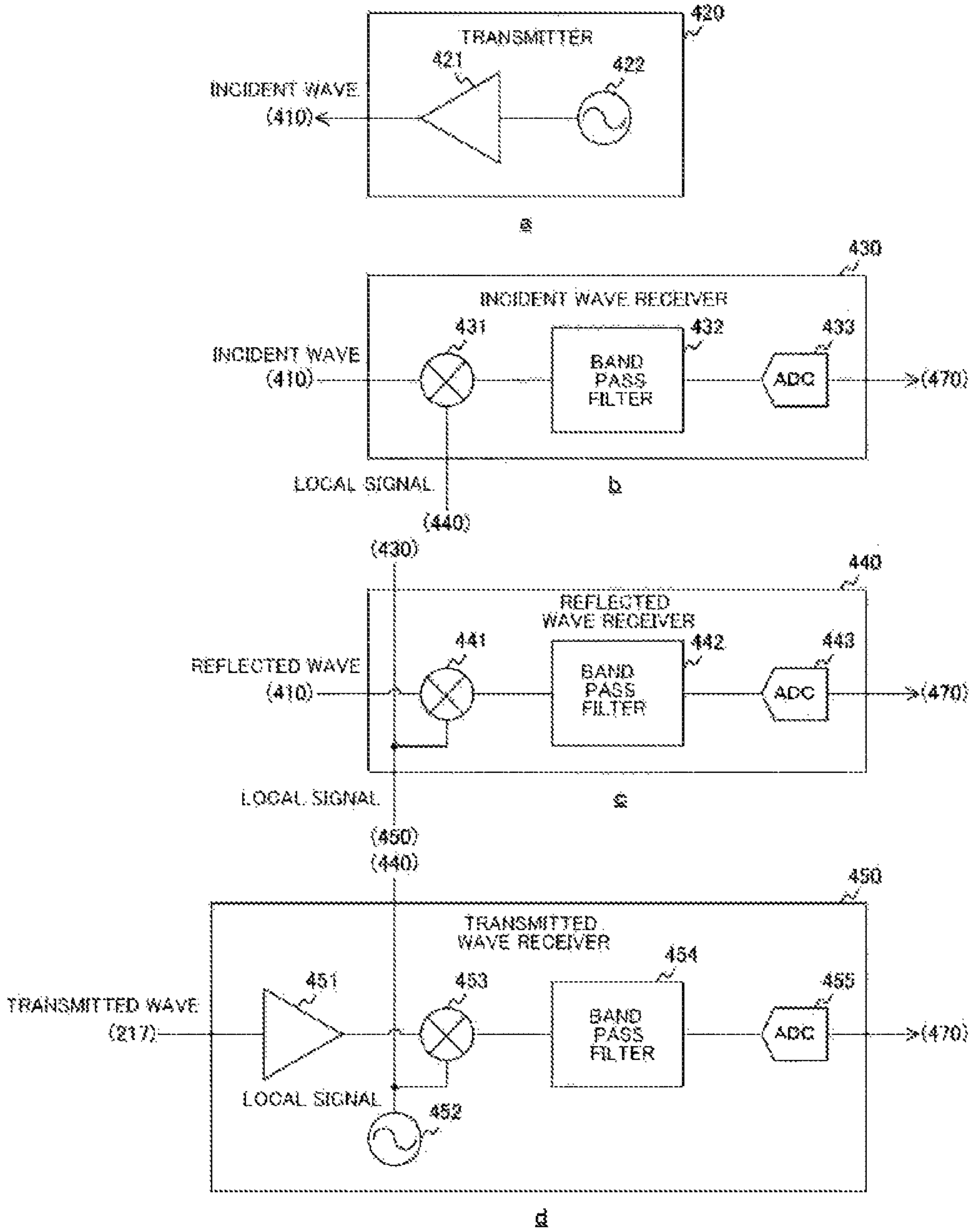

FIG. 138 is a circuit diagram illustrating one configuration example of a transmitter and a receiver in the first embodiment of the present technology.

Figure 139:
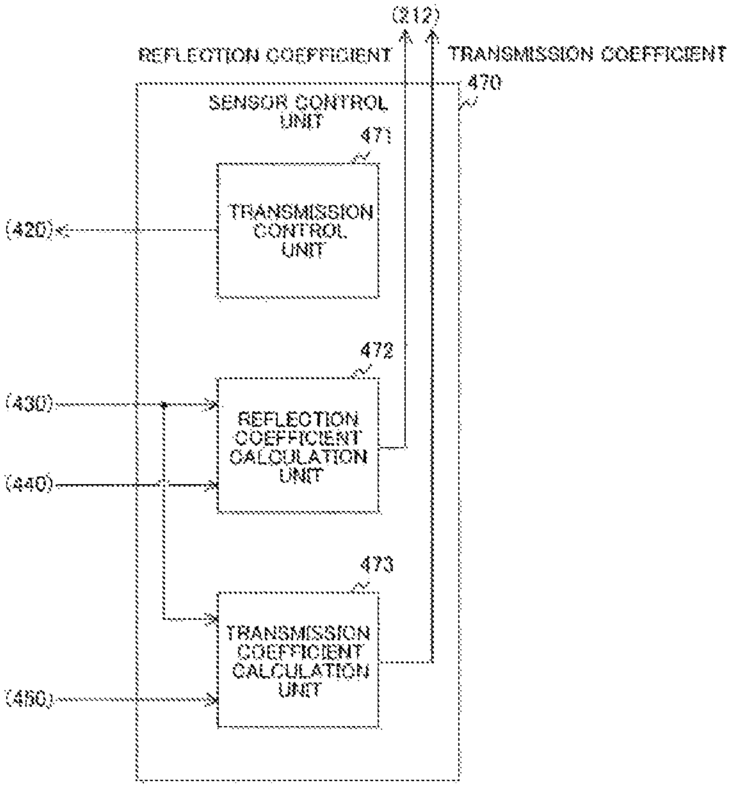

FIG. 139 is a block diagram illustrating one configuration example of a sensor control unit in the first embodiment of the present technology.

Figure 140:
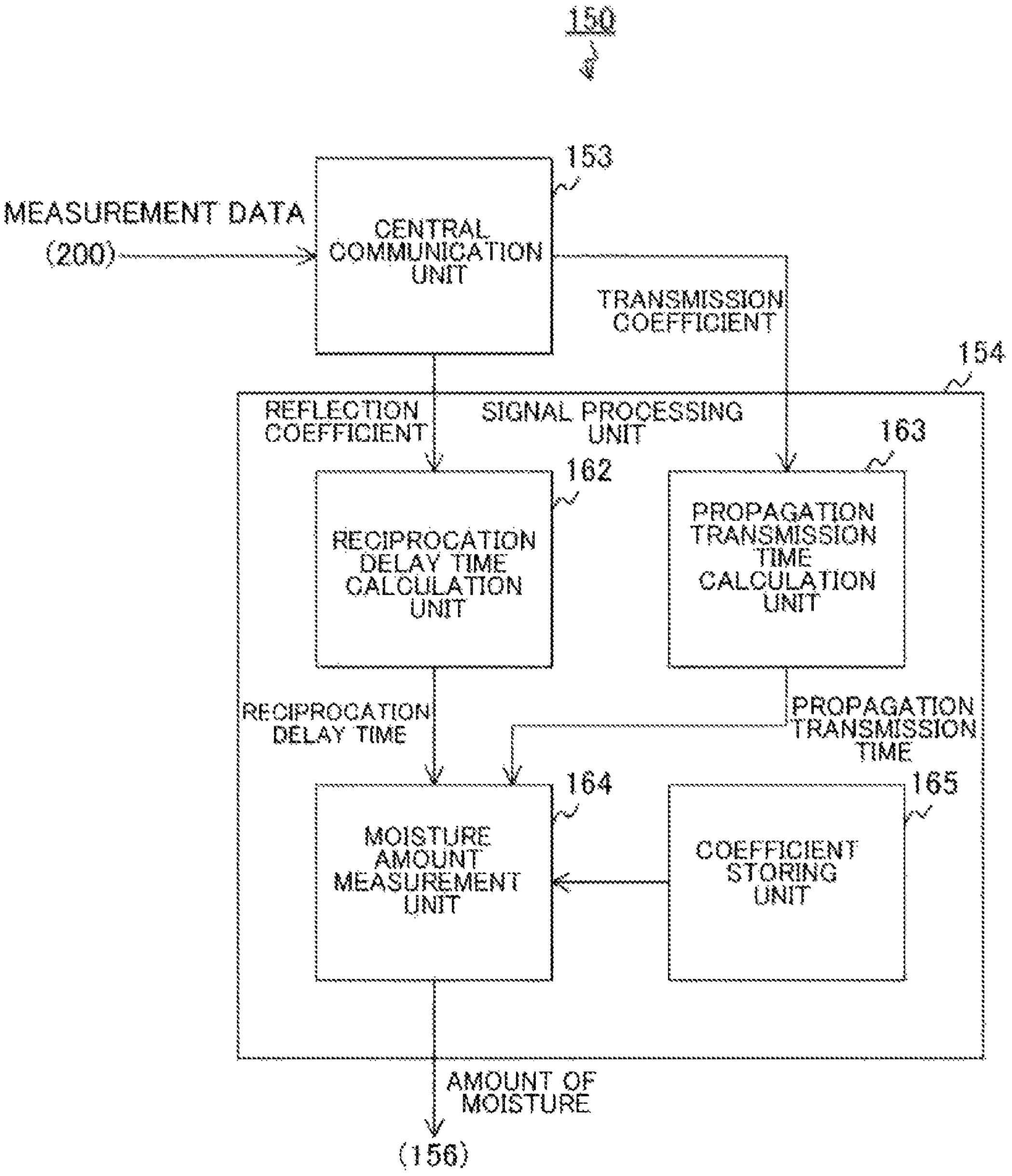

FIG. 140 is a block diagram illustrating one configuration example of a signal processing unit disposed inside the central processing device in the first embodiment of the present technology.

Figure 141:
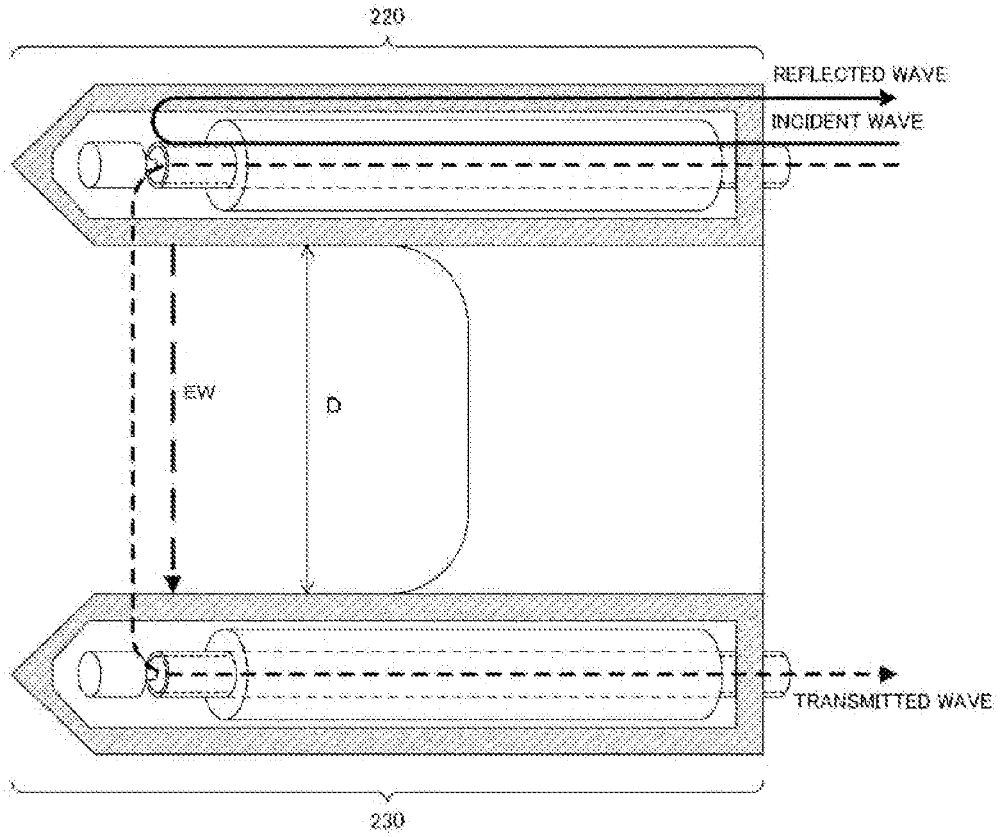

FIG. 141 is a diagram for describing a propagation path and a transmission path of electromagnetic waves and an electrical signal in the first embodiment of the present technology.

Figure 142:
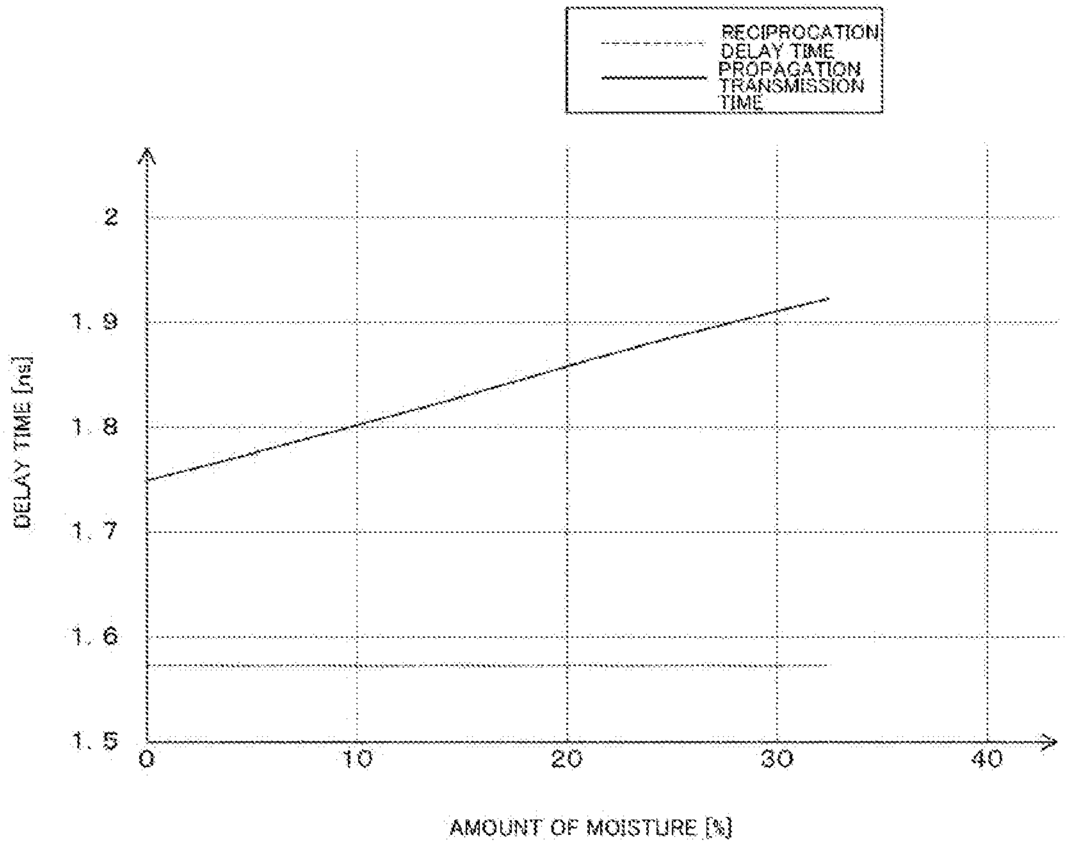

FIG. 142 is a graph showing an example of a relationship between a reciprocating delay time and a propagation transmission time and an amount of moisture in the first embodiment of the present technology.

Figure 143:
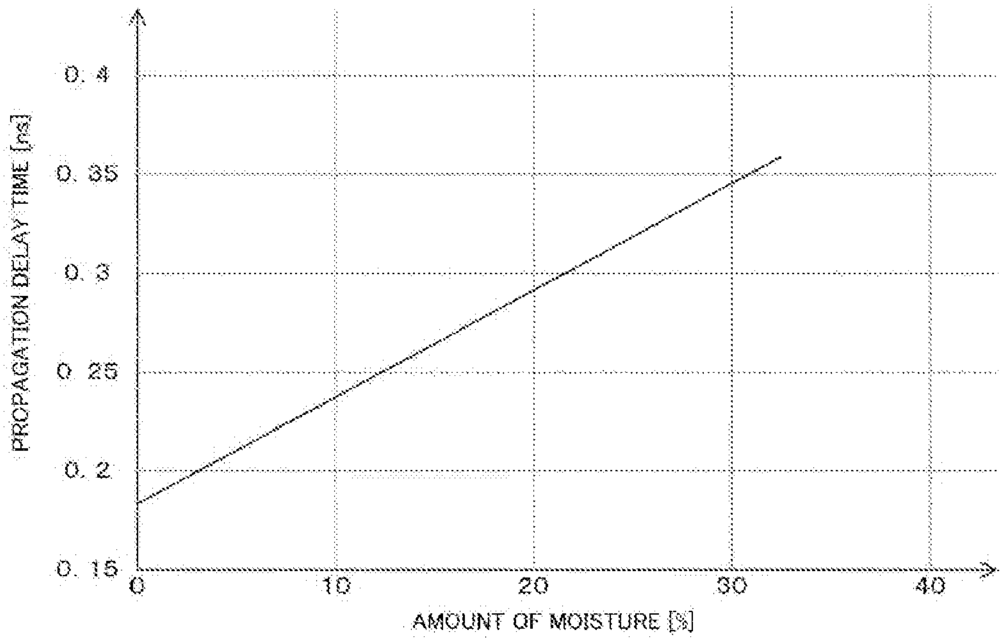

FIG. 143 is a graph showing an example of a relationship between a propagation delay time and an amount of moisture in the first embodiment of the present technology.

Figure 144:
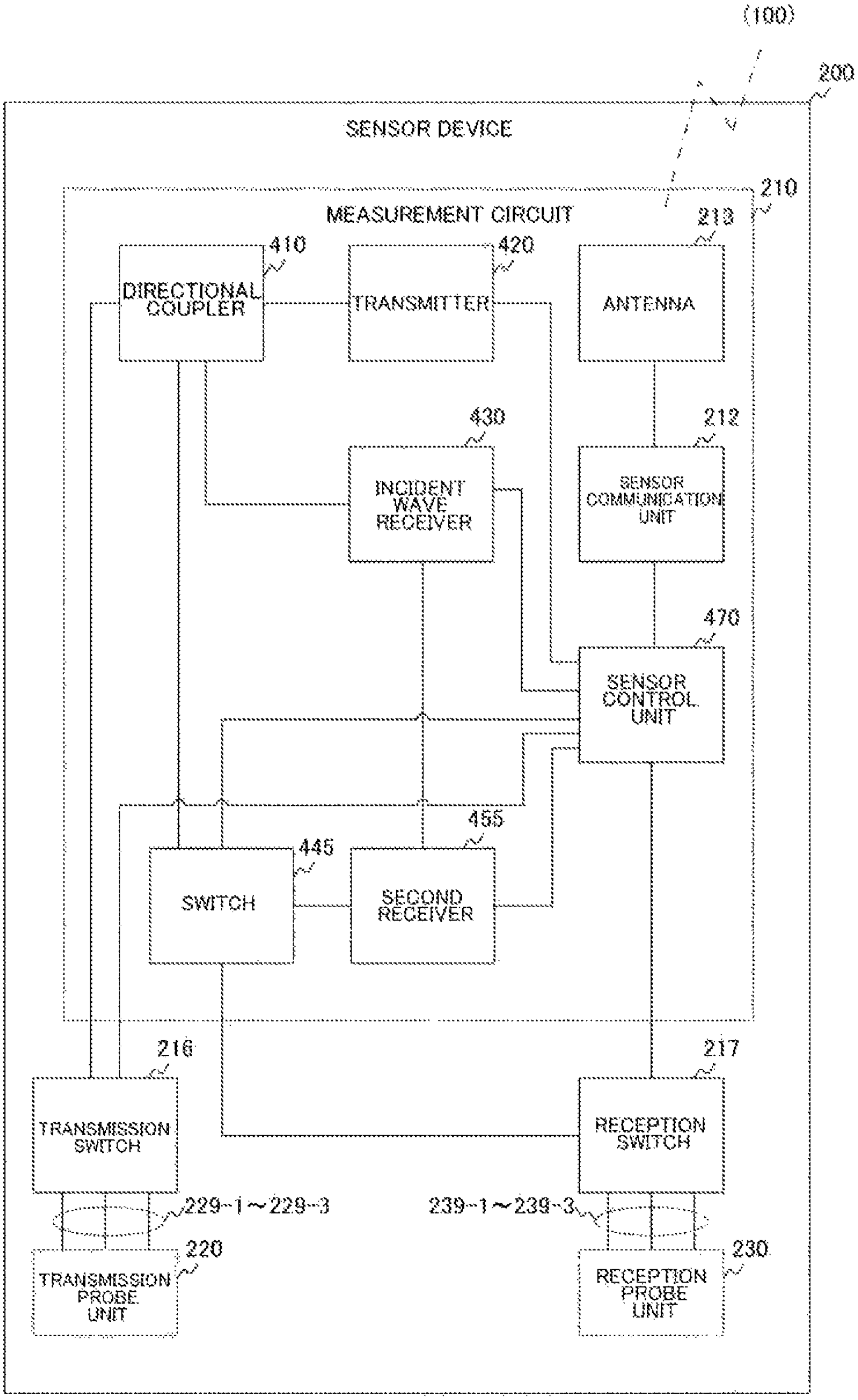

FIG. 144 is a block diagram illustrating another configuration example of a measurement circuit in the first embodiment of the present technology.

Figure 145:
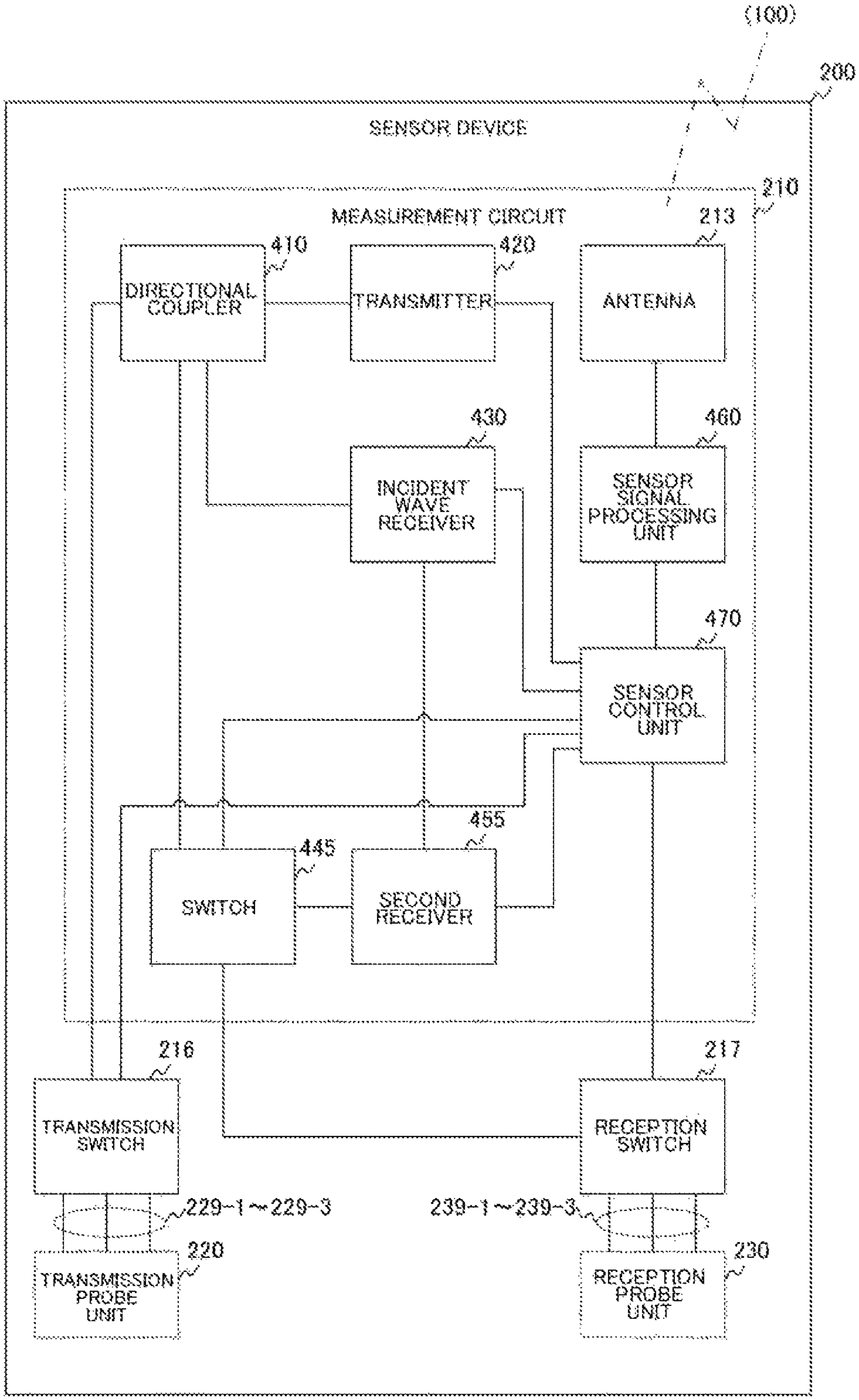

FIG. 145 is a block diagram illustrating another configuration example of a sensor device in the first embodiment of the present technology.

Figure 146:
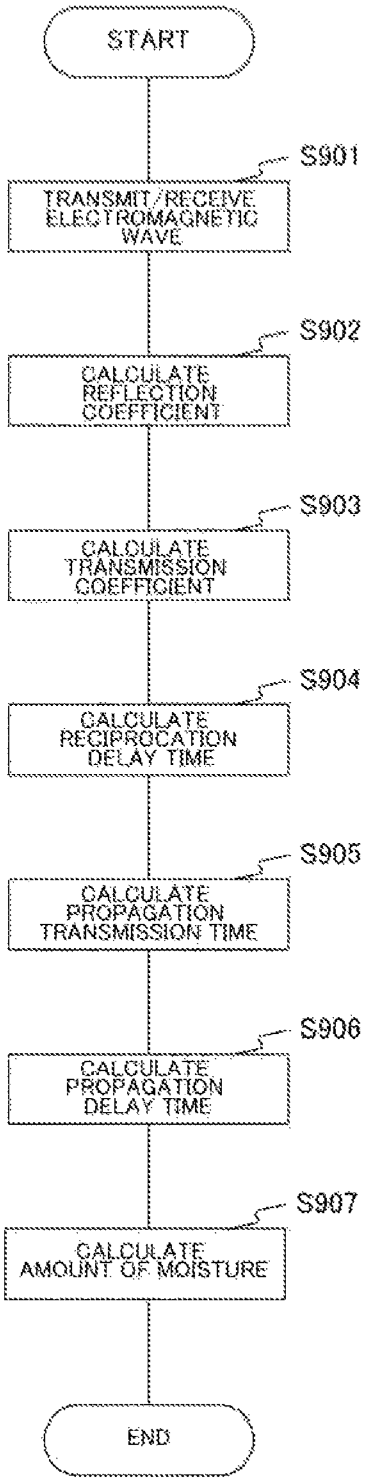

FIG. 146 is a flowchart illustrating an example of operations of a moisture measuring system according to the first embodiment of the present technology.

FIG. 147 is a diagram illustrating an example of coating portions of an electric wave absorbing unit in the first embodiment of the present technology.

Figure 148:
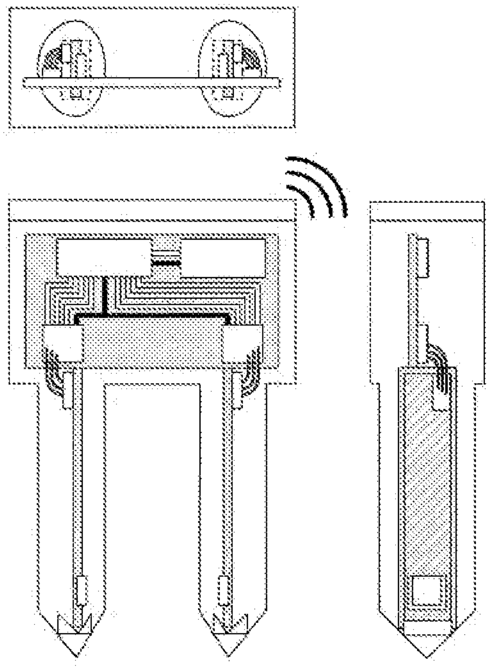

FIG. 148 is a diagram illustrating a comparative example in which coating is not performed by an electric wave absorbing unit.

FIG. 149 is a diagram illustrating an example in which one face of an in-probe substrate is coated in the first embodiment of the present technology.

Figure 150:
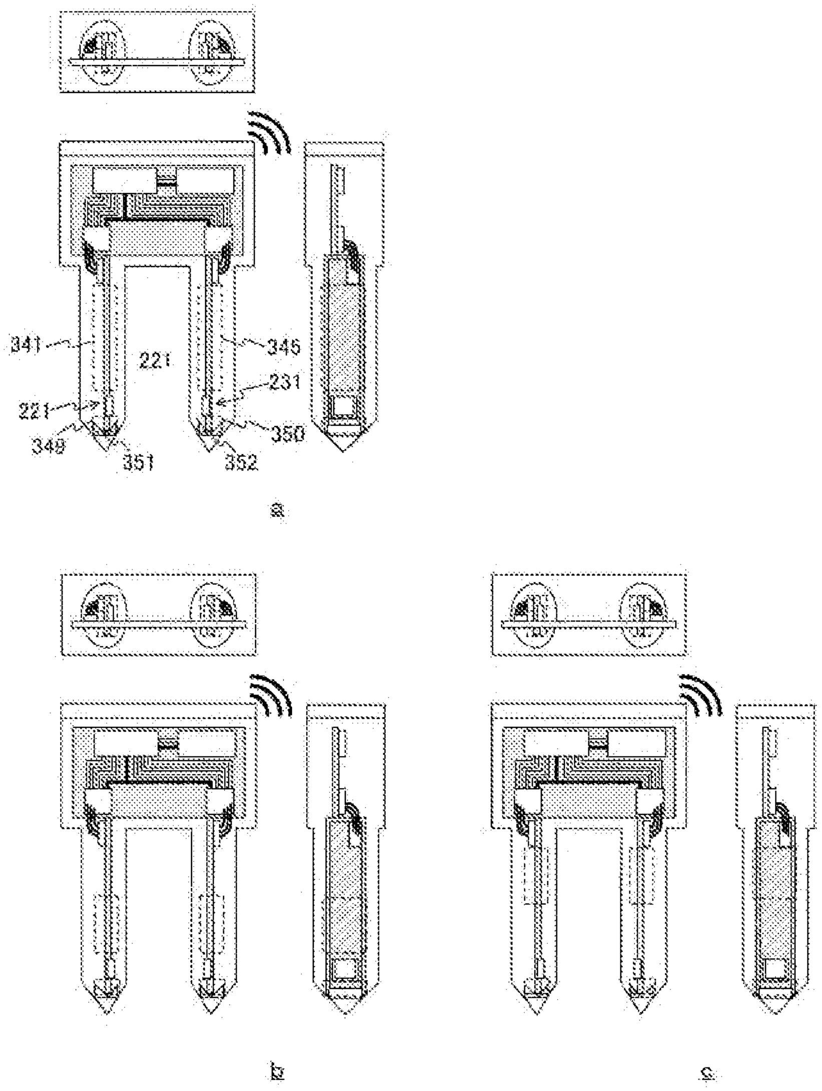

FIG. 150 is a diagram illustrating an example in which a tip end of a probe is further coated in the first embodiment of the present technology.

Figure 151:
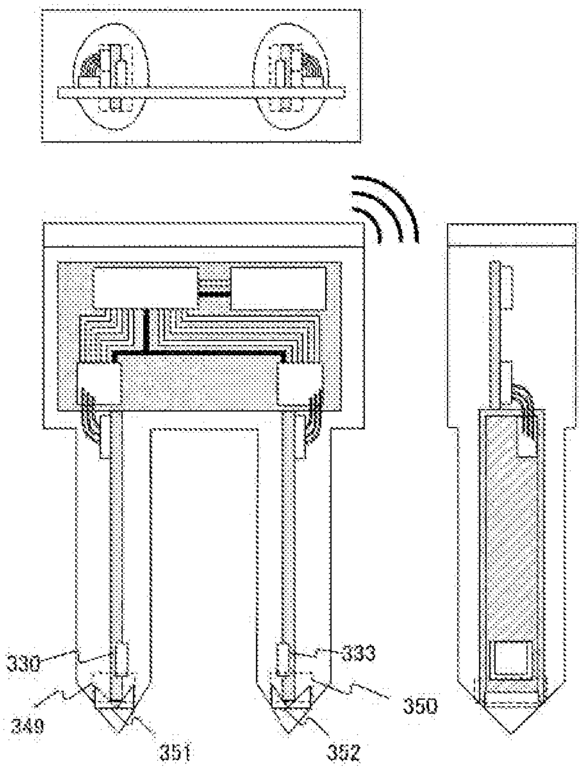

FIG. 151 is a diagram illustrating an example in which only a tip end is coated in the first embodiment of the present technology.

Figure 152:
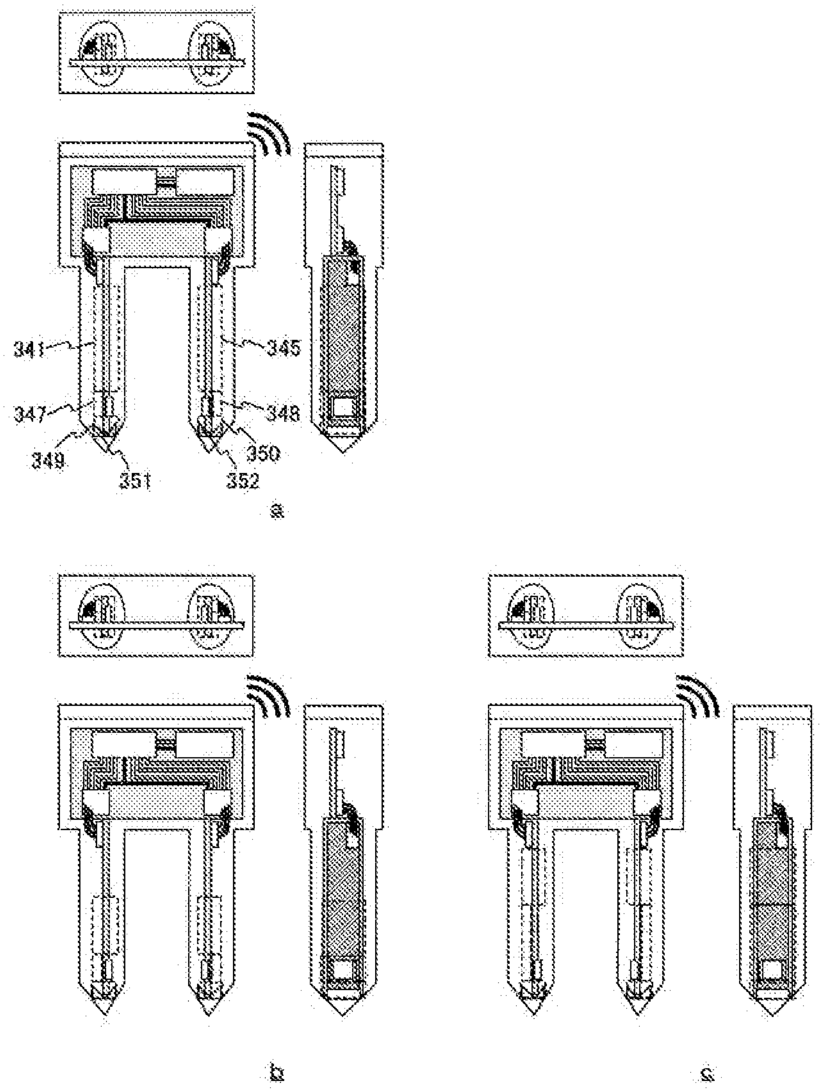

FIG. 152 is a diagram illustrating an example in which one face and a tip end of an in-probe substrate are coated in the first embodiment of the present technology.

Figure 153:
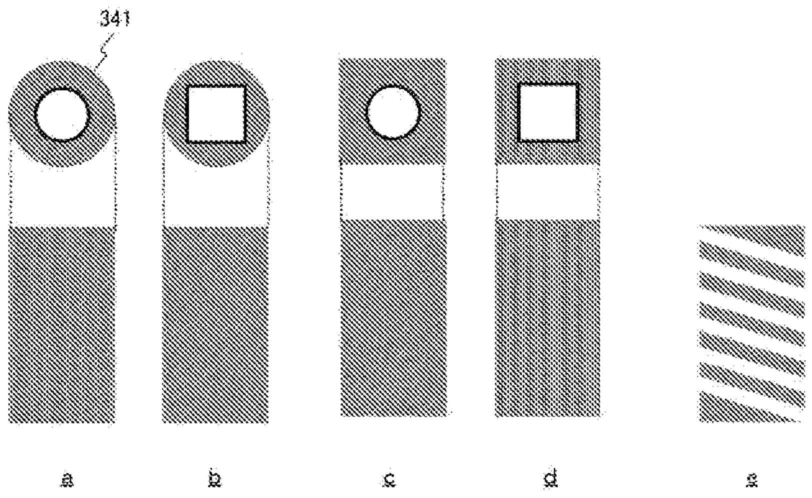

FIG. 153 is a diagram illustrating an example of a shape of an electric wave absorbing unit in the first embodiment of the present technology.

FIG. 154 is a diagram illustrating an example of a sensor device using a flexible substrate according to a first modification example of the first embodiment of the present technology.

FIG. 155 is a diagram illustrating an example of a sensor device using a flexible substrate and a rigid substrate in the first modification example of the first embodiment of the present technology.

FIG. 156 is a diagram illustrating an example of a sensor device acquired when the number of antennas is increased in the first modification example of the first embodiment of the present technology.

FIG. 157 is a diagram illustrating an example of a sensor device using a flexible substrate and a rigid substrate acquired when the number of antennas is increased in the first modification example of the first embodiment of the present technology.

FIG. 158 is a diagram illustrating an example of a sensor device in which a transmission line is wired for each antenna in the first modification example of the first embodiment of the present technology.

FIG. 159 is a diagram illustrating an example of a sensor device using a flexible substrate and a rigid substrate in which a transmission line is wired for each antenna in the first modification example of the first embodiment of the present technology.

Figure 160:
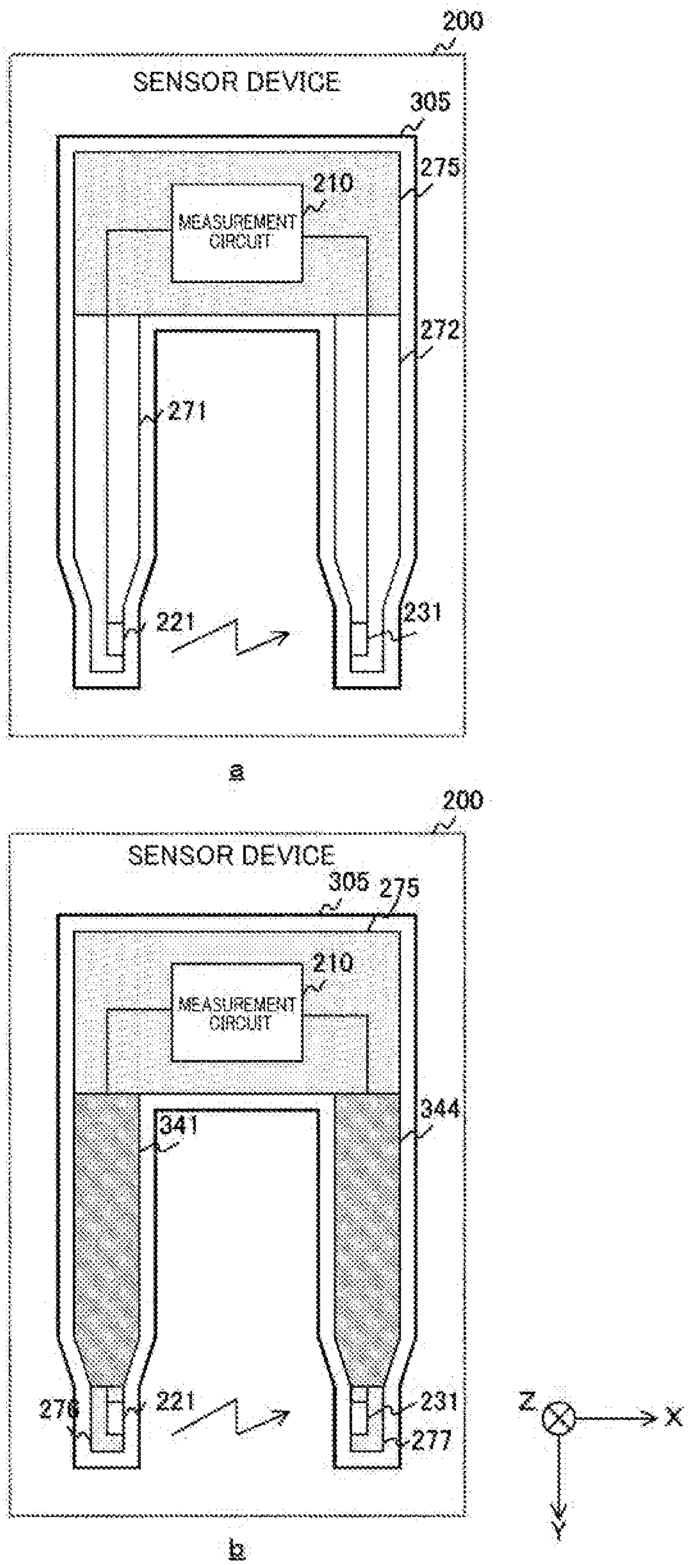

FIG. 160 is a diagram illustrating an example of a sensor device in which substrates are disposed inside a sensor casing of a hard shell in the first modification example of the first embodiment of the present technology.

FIG. 161 is a diagram illustrating an example of a sensor device in which the number of antennas is increased, and substrates are disposed inside a sensor casing of a hard shell in the first modification example of the first embodiment of the present technology.

FIG. 162 is a diagram illustrating an example of a sensor device and a comparative example in the first modification example of the first embodiment of the present technology.

Figure 163:
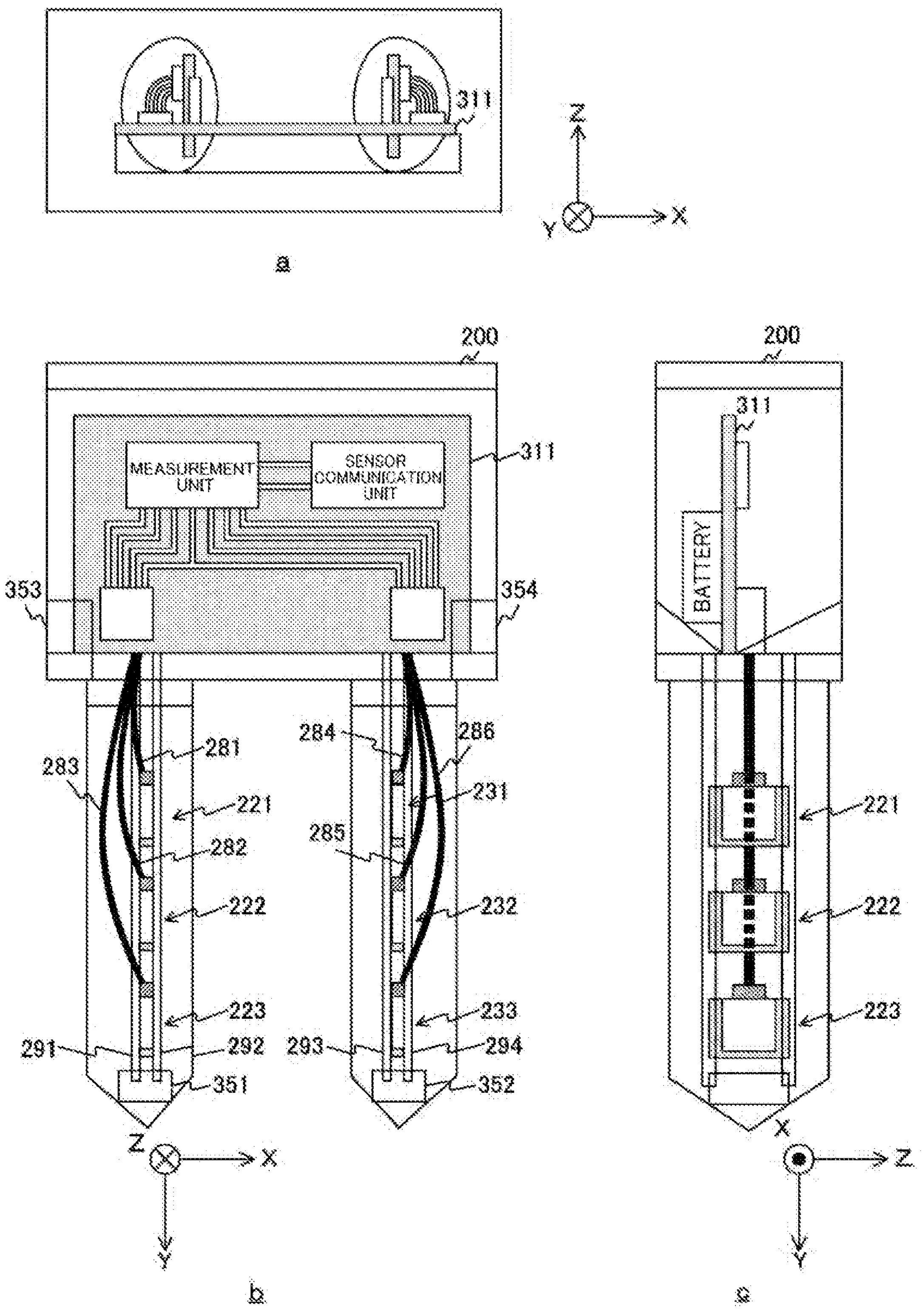

FIG. 163 is a diagram illustrating an example of a sensor device according to a third modification example of the first embodiment of the present technology.

FIG. 164 is a diagram illustrating an example of a top view and a cross-sectional view of the sensor device according to the third modification example of the first embodiment of the present technology.

Figure 165:
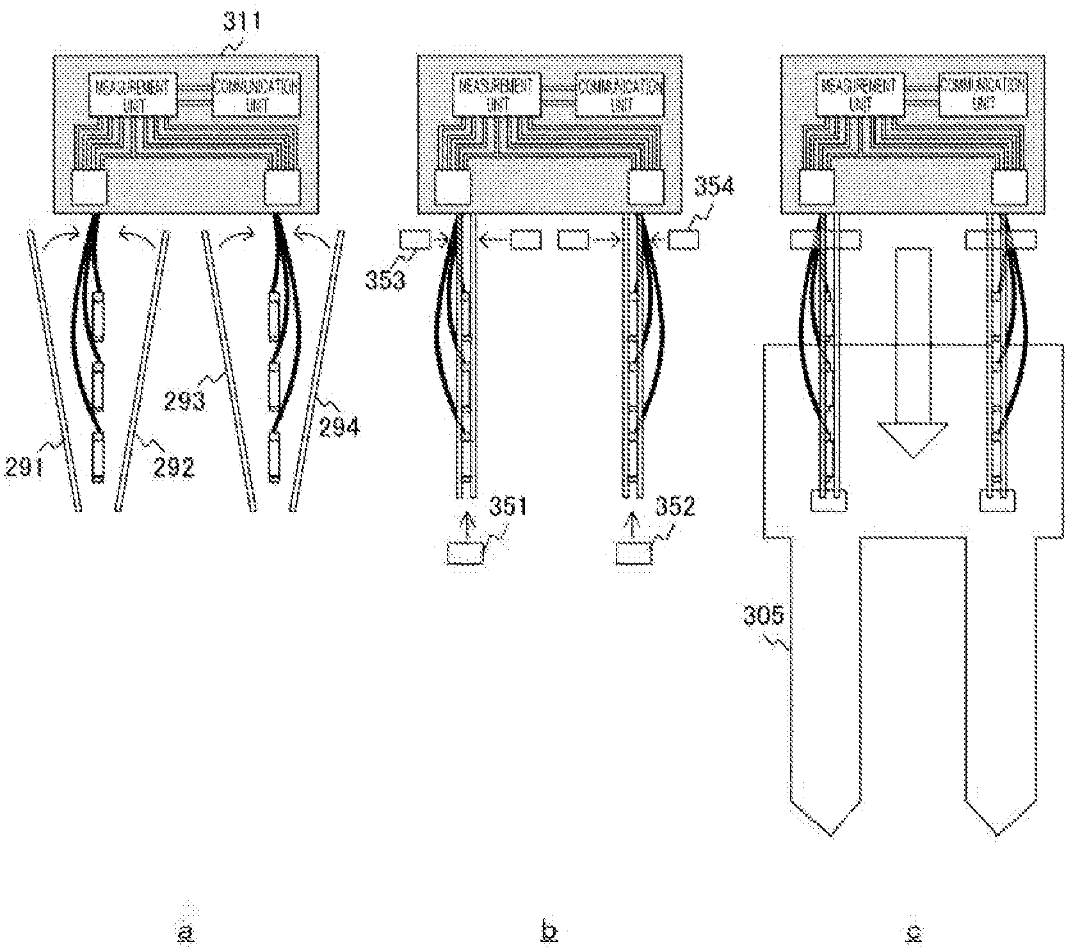

FIG. 165 is a diagram illustrating a method of housing substrates in the third modification example of the first embodiment of the present technology.

Figure 166:
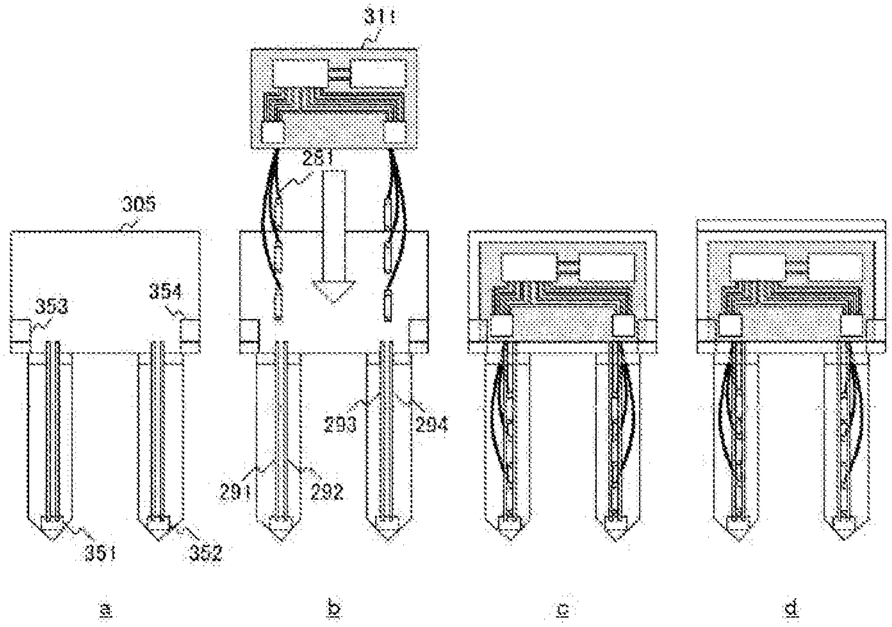

FIG. 166 is a diagram illustrating another example of a method of housing substrates in the third modification example of the first embodiment of the present technology.

Figure 167:
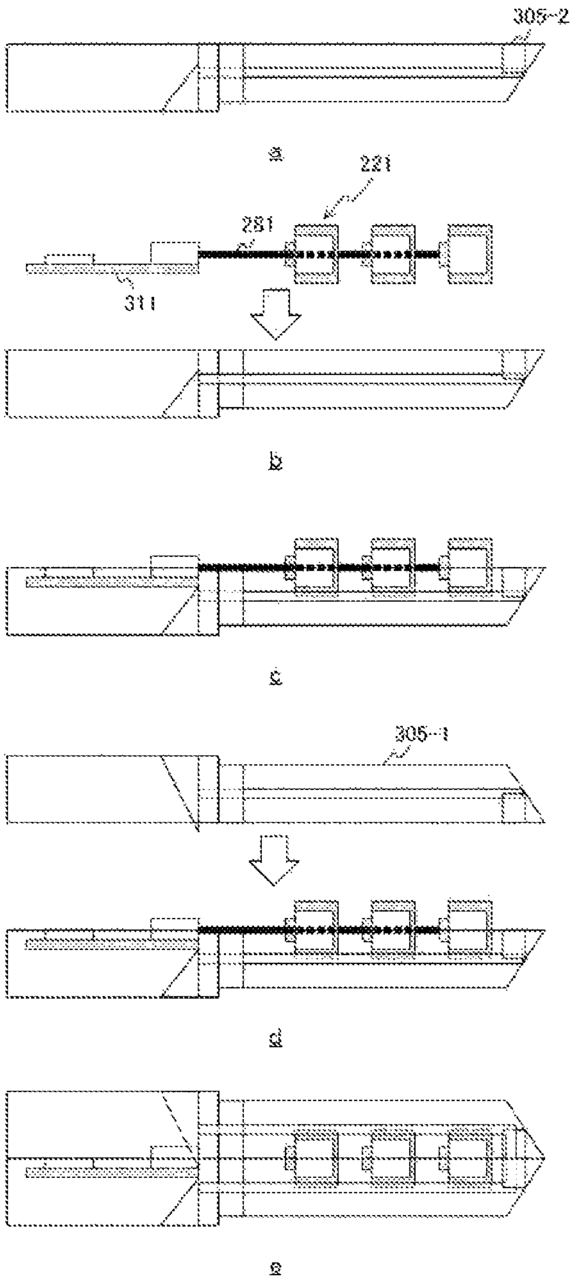

FIG. 167 is a diagram illustrating another example of a method of housing substrates in the third modification example of the first embodiment of the present technology.

FIG. 168 is a diagram illustrating an example of a sensor device according to a fourth modification example of the first embodiment of the present technology.

FIG. 169 is a diagram illustrating an example of a top view and a cross-sectional view of the sensor device according to the fourth modification example of the first embodiment of the present technology.

Figure 170:
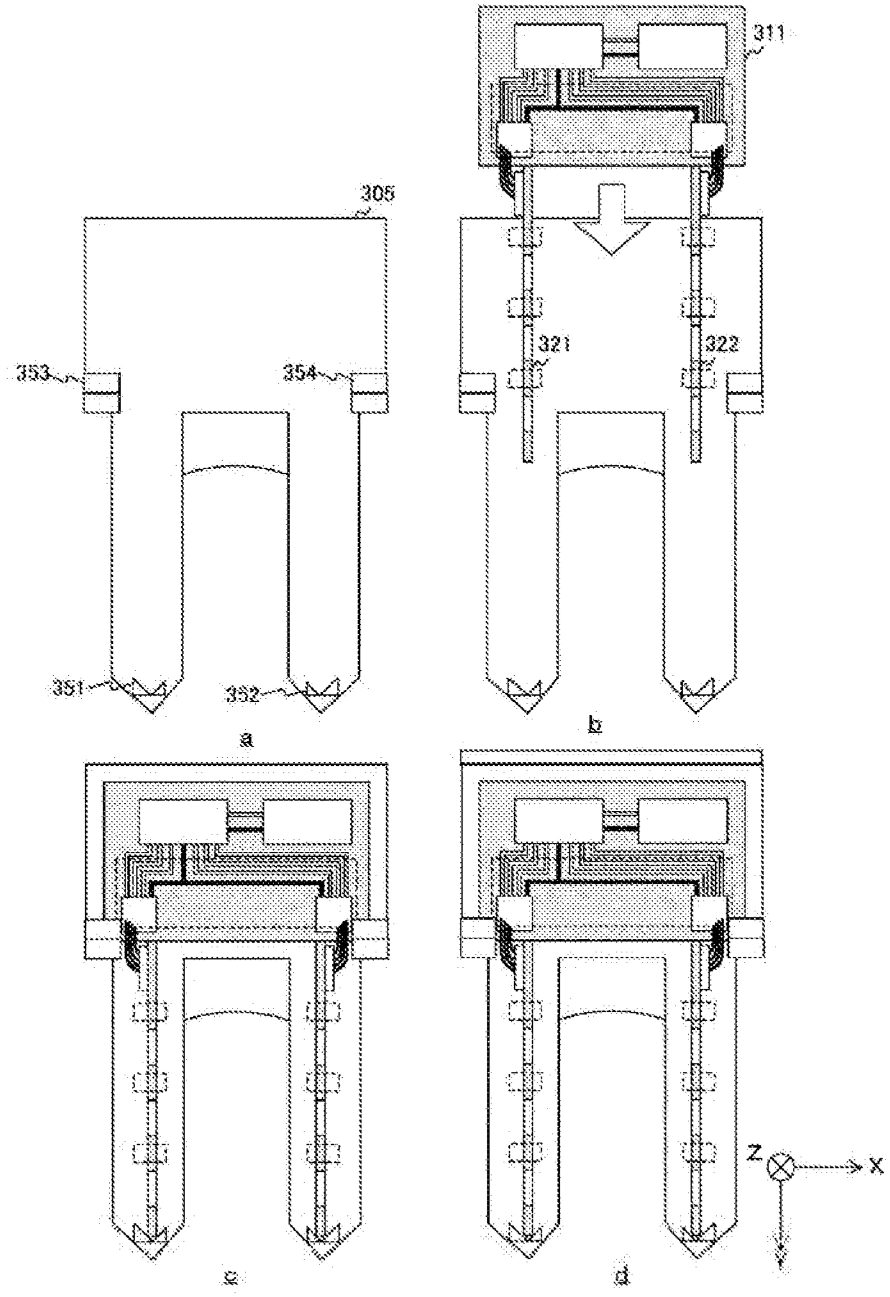

FIG. 170 is a diagram illustrating a method of housing substrates in the fourth modification example of the first embodiment of the present technology.

Figure 171:
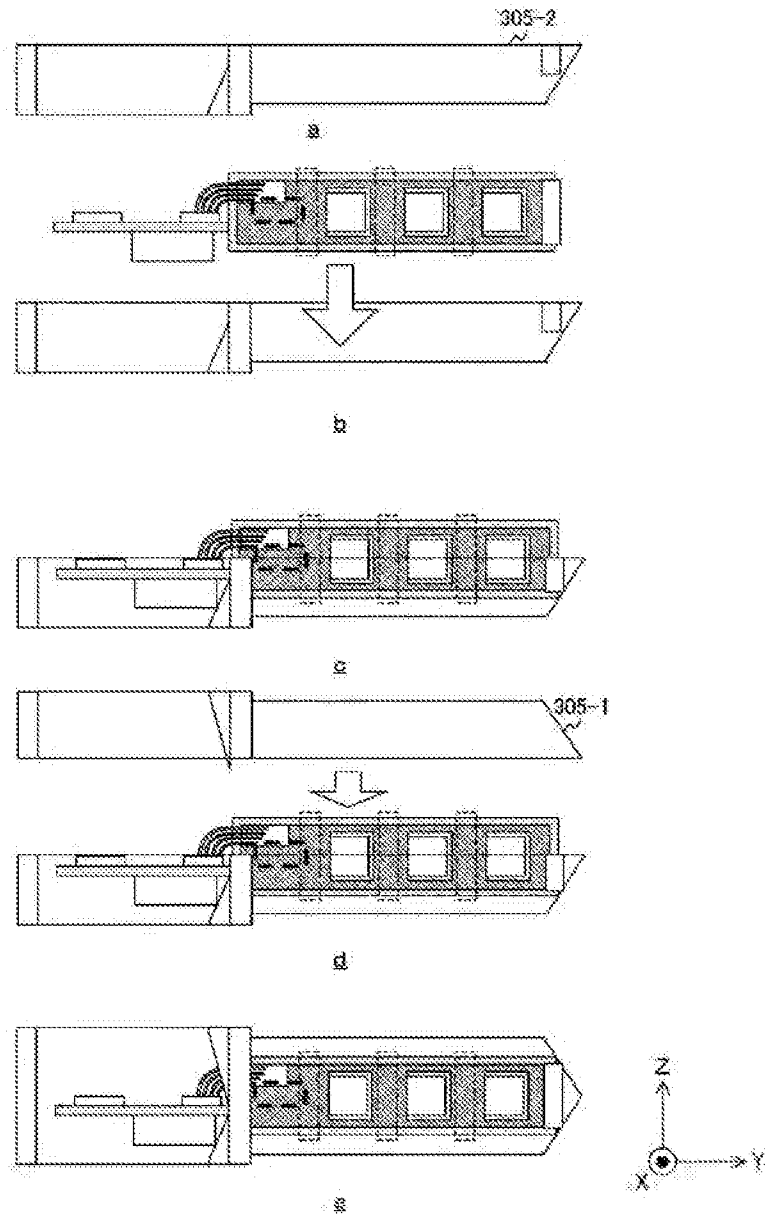

FIG. 171 is a diagram illustrating another example of a method of housing substrates in the fourth modification example of the first embodiment of the present technology.

Figure 172:
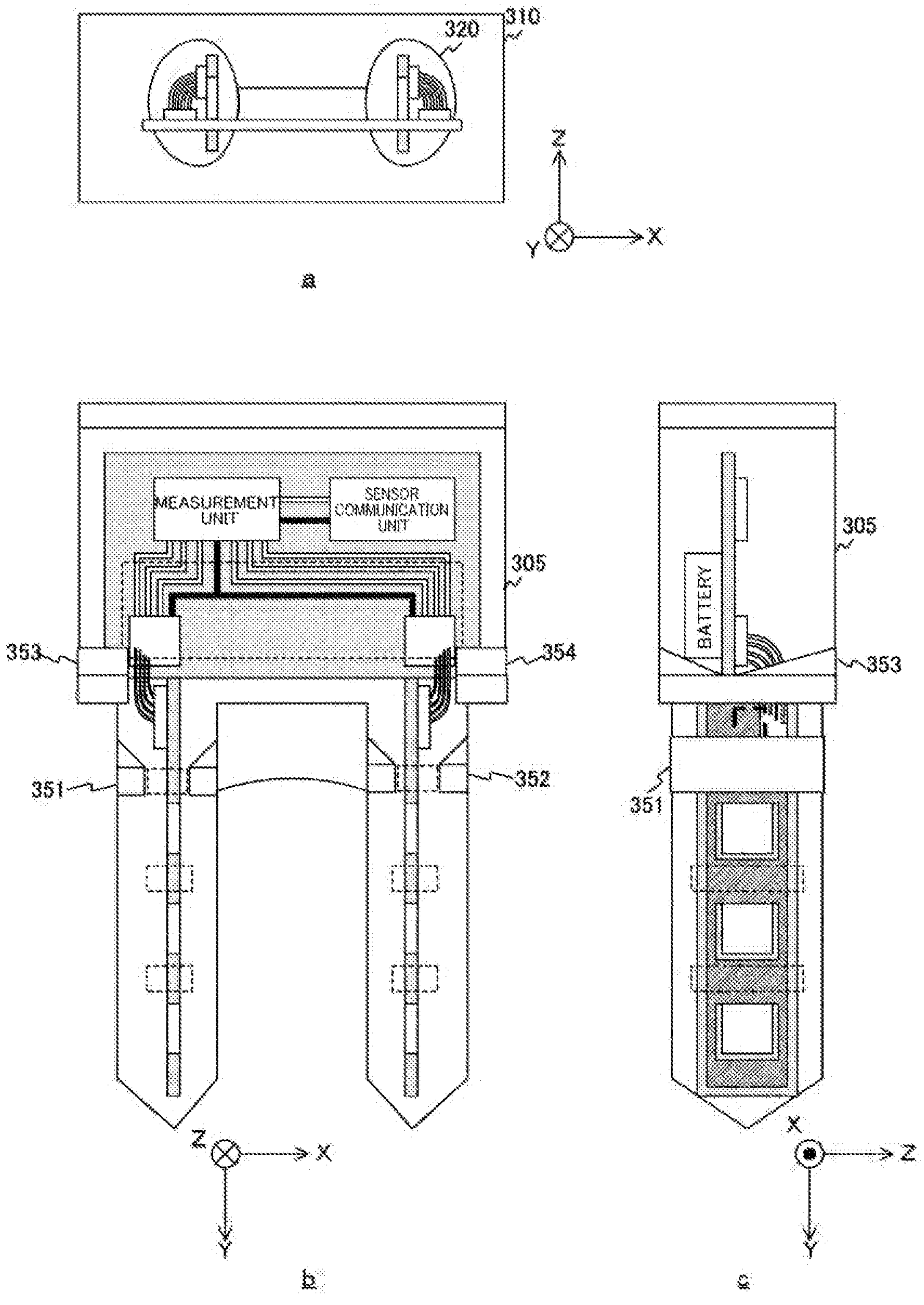

FIG. 172 is a diagram illustrating an example of a sensor device in which positions of positioning parts are changed in the fourth modification example of the first embodiment of the present technology.

Figure 173:
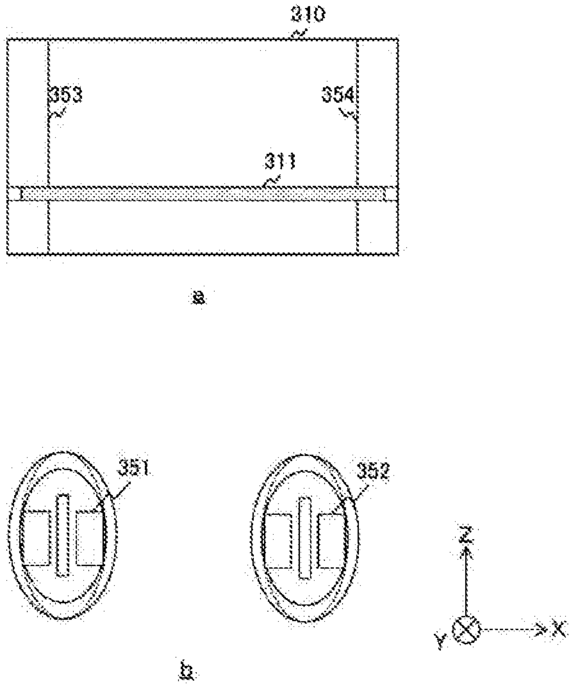

FIG. 173 is a diagram illustrating an example of a top view and a cross-sectional view of a sensor device in which positions of positioning parts are changed in the fourth modification example of the first embodiment of the present technology.

Figure 174:
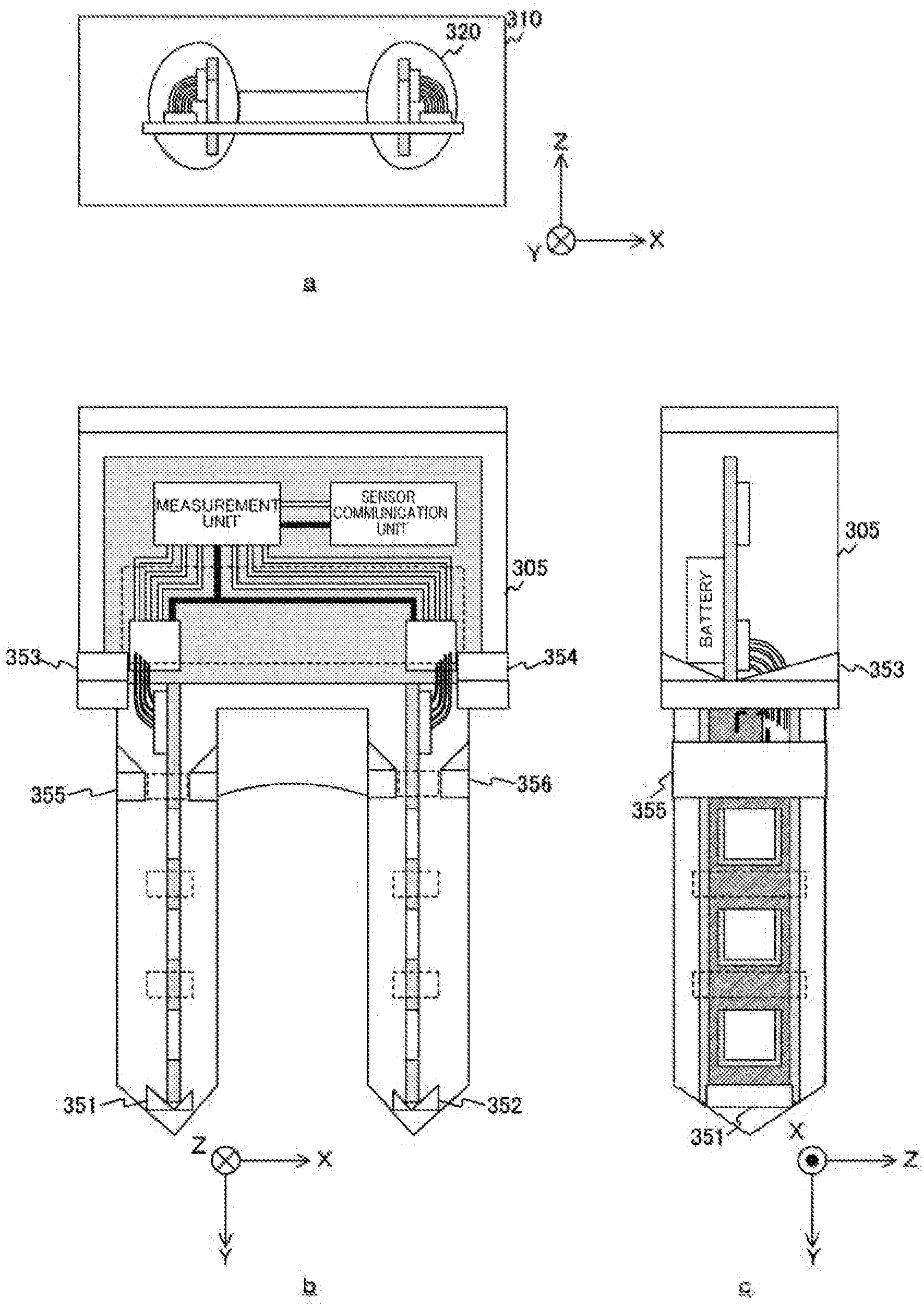

FIG. 174 is a diagram illustrating an example of a sensor device in which positioning parts are added in the fourth modification example of the first embodiment of the present technology.

Figure 175:
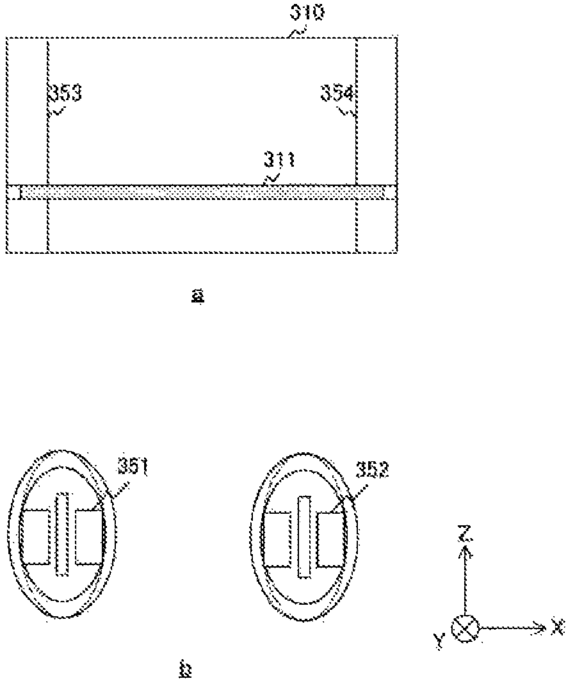

FIG. 175 is a diagram illustrating an example of a top view and a cross-sectional view of a sensor device in which positioning parts are added in the fourth modification example of the first embodiment of the present technology.

Figure 176:
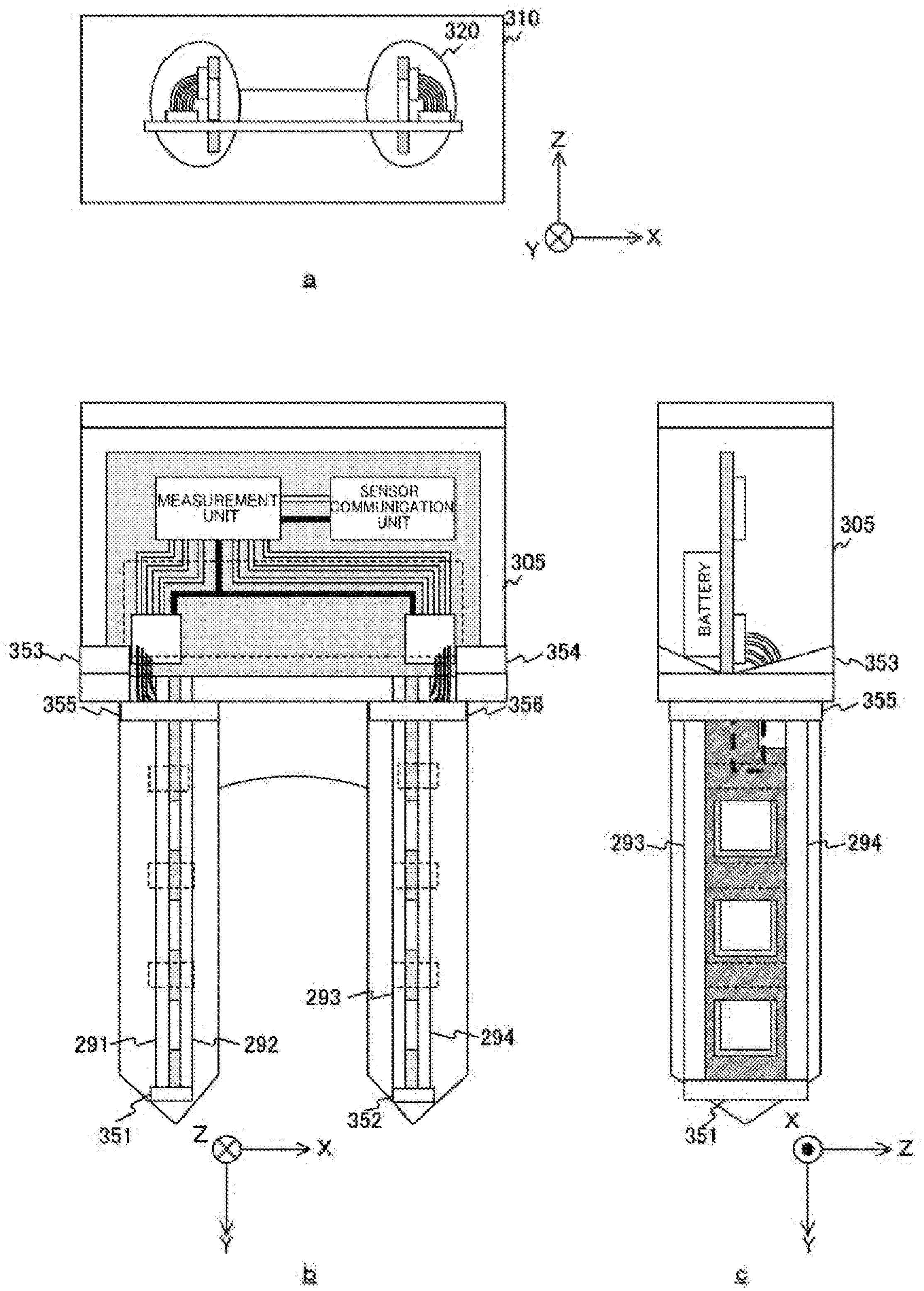

FIG. 176 is a diagram illustrating an example of a sensor device in which a shape of positioning parts is different in the fourth modification example of the first embodiment of the present technology.

Figure 177:
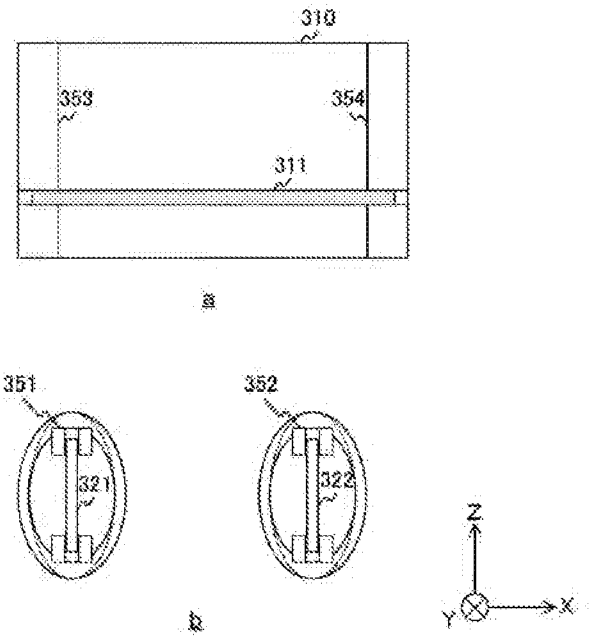

FIG. 177 is a diagram illustrating an example of a top view and a cross-sectional view of a sensor device in which a shape of positioning parts is different in the fourth modification example of the first embodiment of the present technology.

Figure 178:
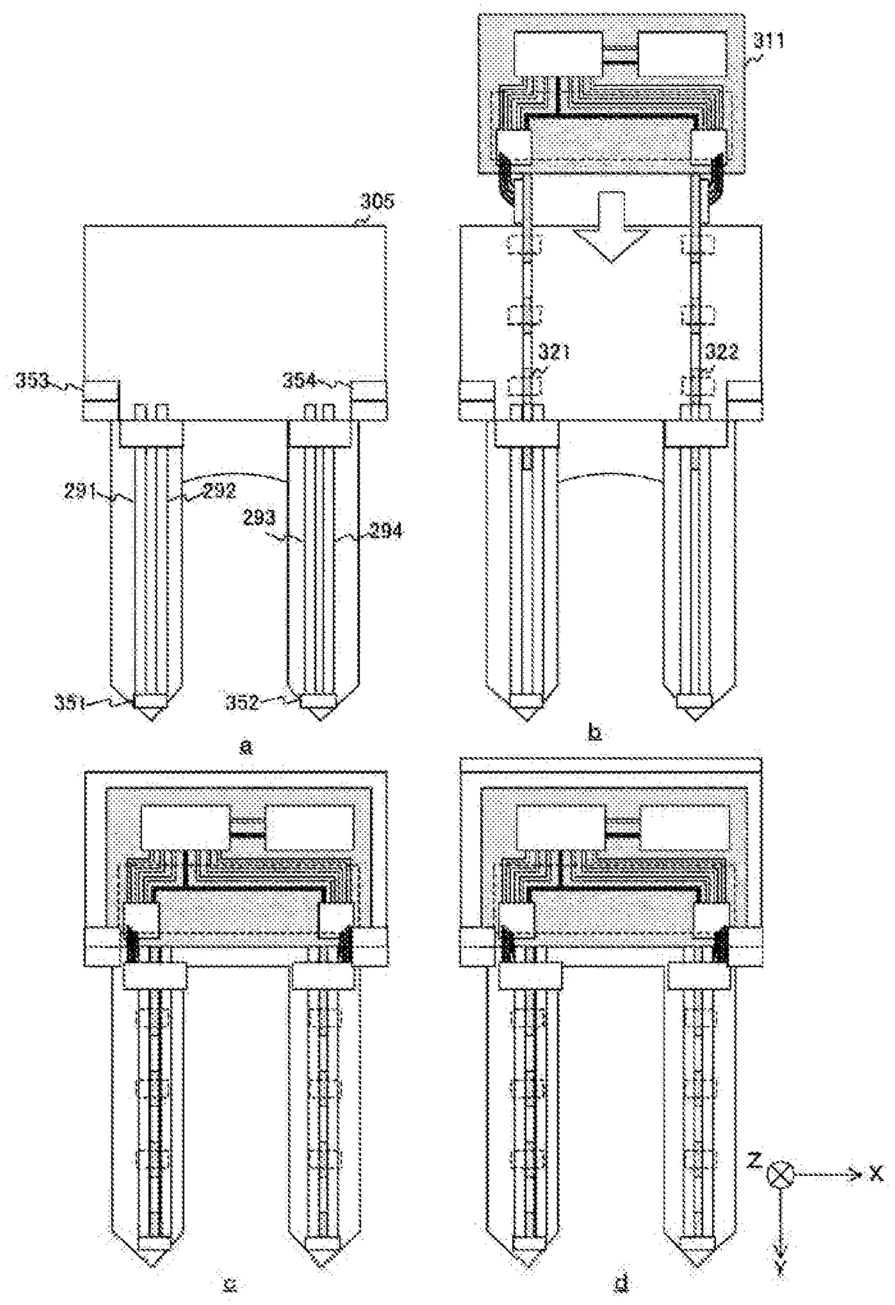

FIG. 178 is a diagram illustrating a method of housing substrates in a case in which the shape of positioning parts is different in the fourth modification example of the first embodiment of the present technology.

Figure 179:
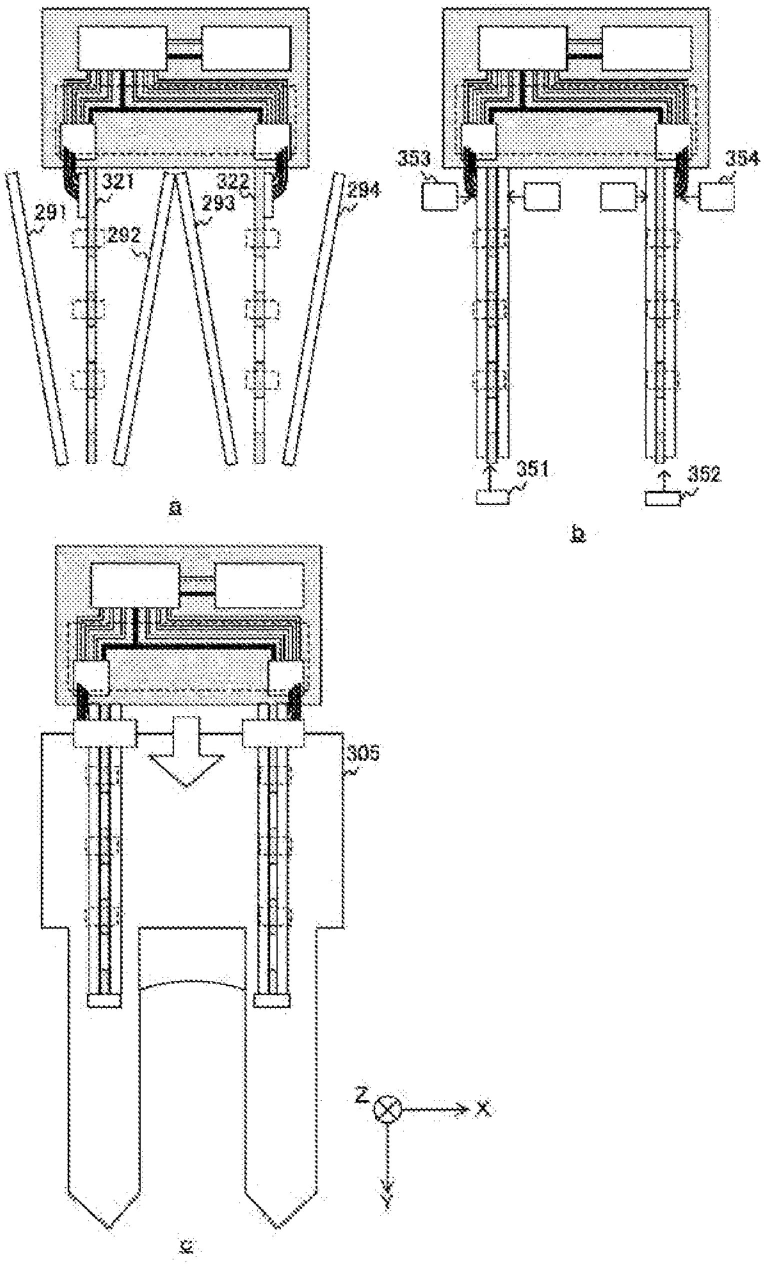

FIG. 179 is a diagram illustrating another example of a method of housing substrates in a case in which the shape of positioning parts is different in the fourth modification example of the first embodiment of the present technology.

FIG. 180 is a diagram illustrating an example of a sensor device in which the frames are extended in the fourth modification example of the first embodiment of the present technology.

Figure 181:
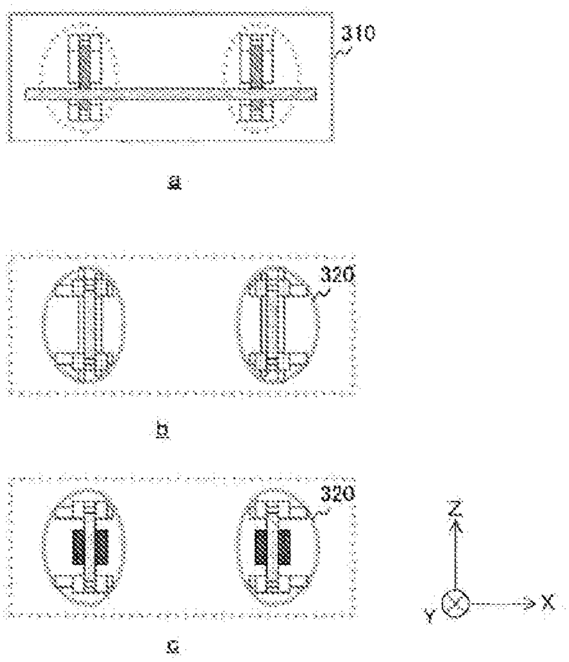

FIG. 181 is a diagram illustrating an example of a top view and a cross-sectional view of a sensor device in which the frames are extended in the fourth modification example of the first embodiment of the present technology.

FIG. 182 is a diagram illustrating an example of a sensor device in which positioning parts disposed inside the measurement unit casing are reduced in the fourth modification example of the first embodiment of the present technology.

Figure 183:
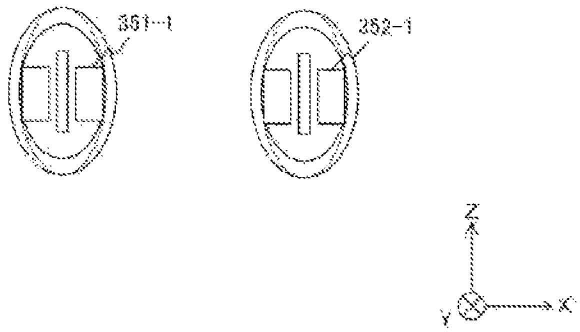

FIG. 183 is a diagram illustrating an example of a cross-sectional view of a sensor device in which positioning parts disposed inside the measurement unit casing are reduced in the fourth modification example of the first embodiment of the present technology.

Figure 184:
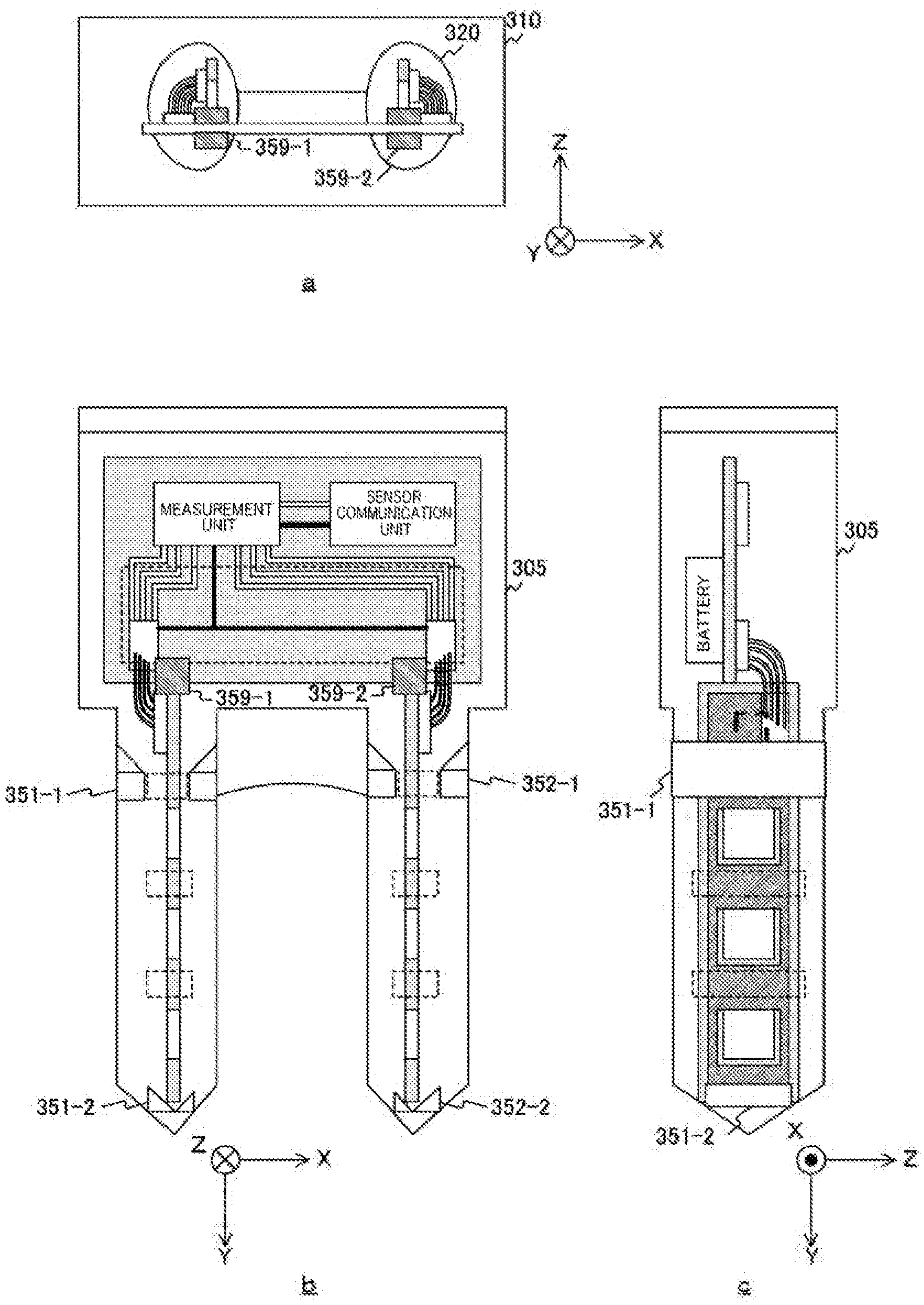

FIG. 184 is a diagram illustrating an example of a sensor device in which a jig is added in the fourth modification example of the first embodiment of the present technology.

Figure 185:
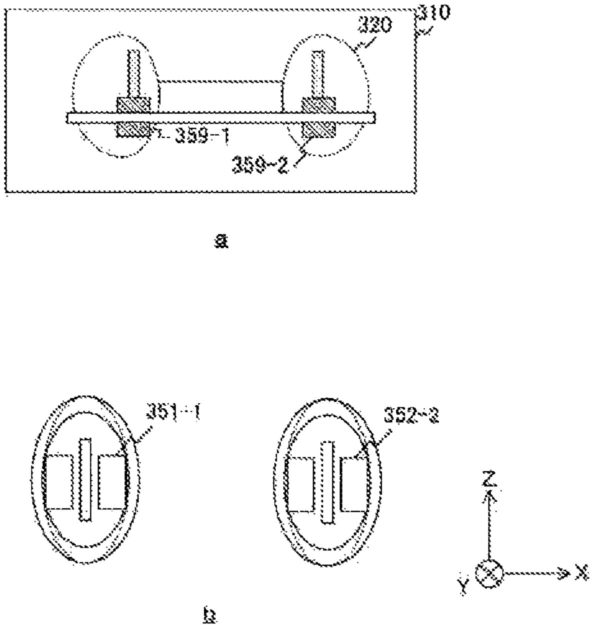

FIG. 185 is a diagram illustrating an example of a top view and a cross-sectional view of a sensor device in which a jig is added in the fourth modification example of the first embodiment of the present technology.

Figure 186:
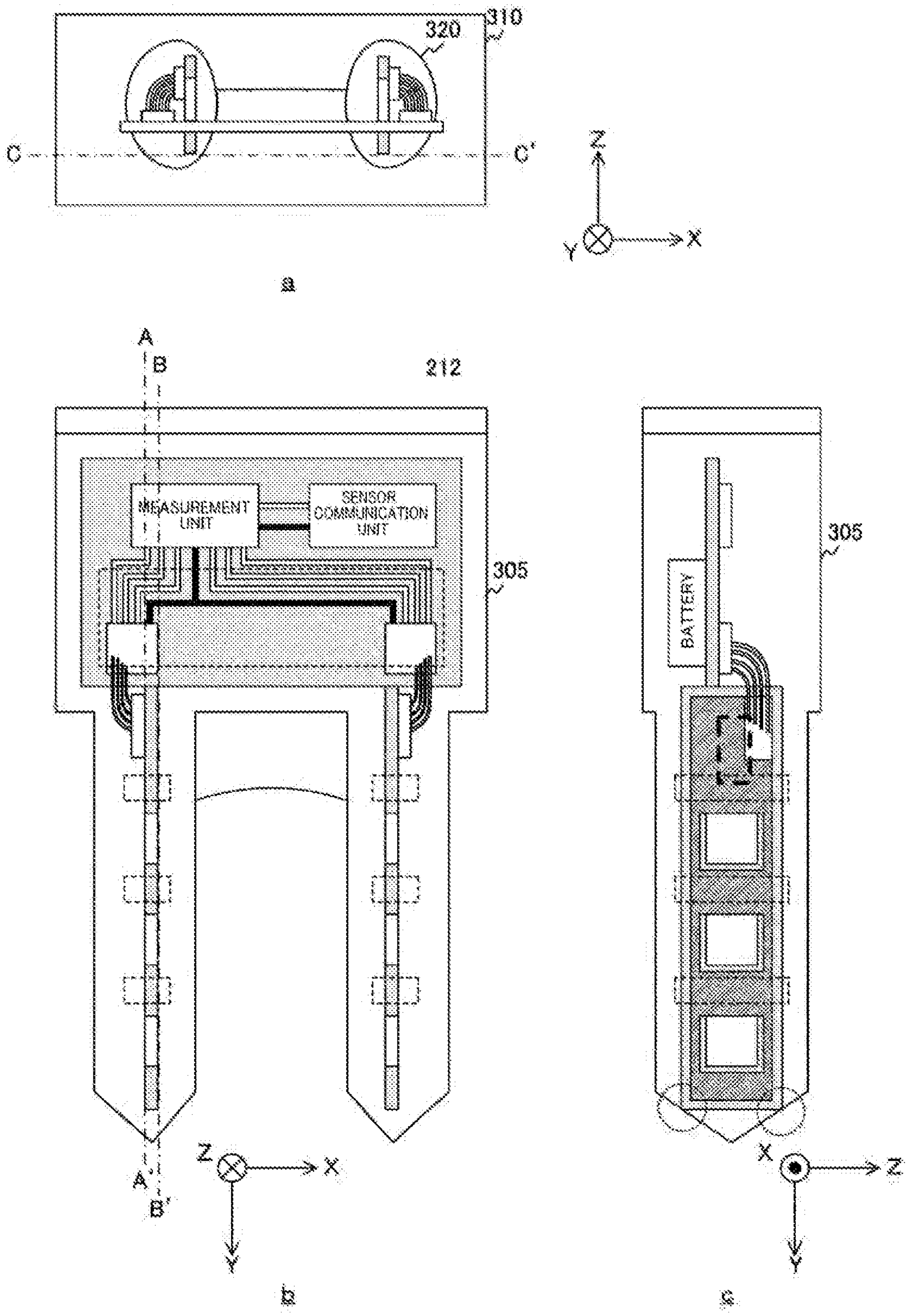

FIG. 186 is a diagram illustrating an example of a sensor device in which an in-probe substrate is butted against a sensor casing in the fourth modification example of the first embodiment of the present technology.

Figure 187:
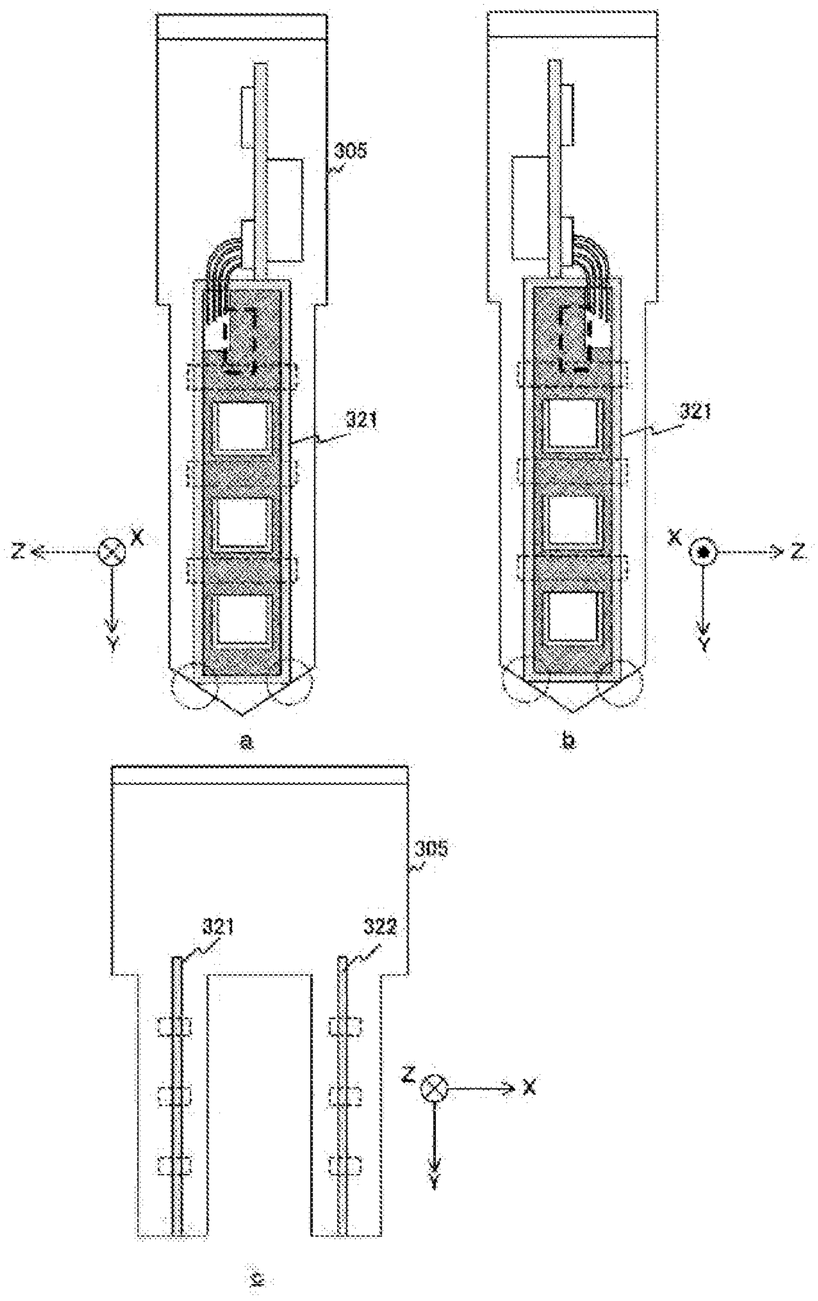

FIG. 187 is an example of a cross-sectional view of a sensor casing in the fourth modification example of the first embodiment of the present technology.

Figure 188:
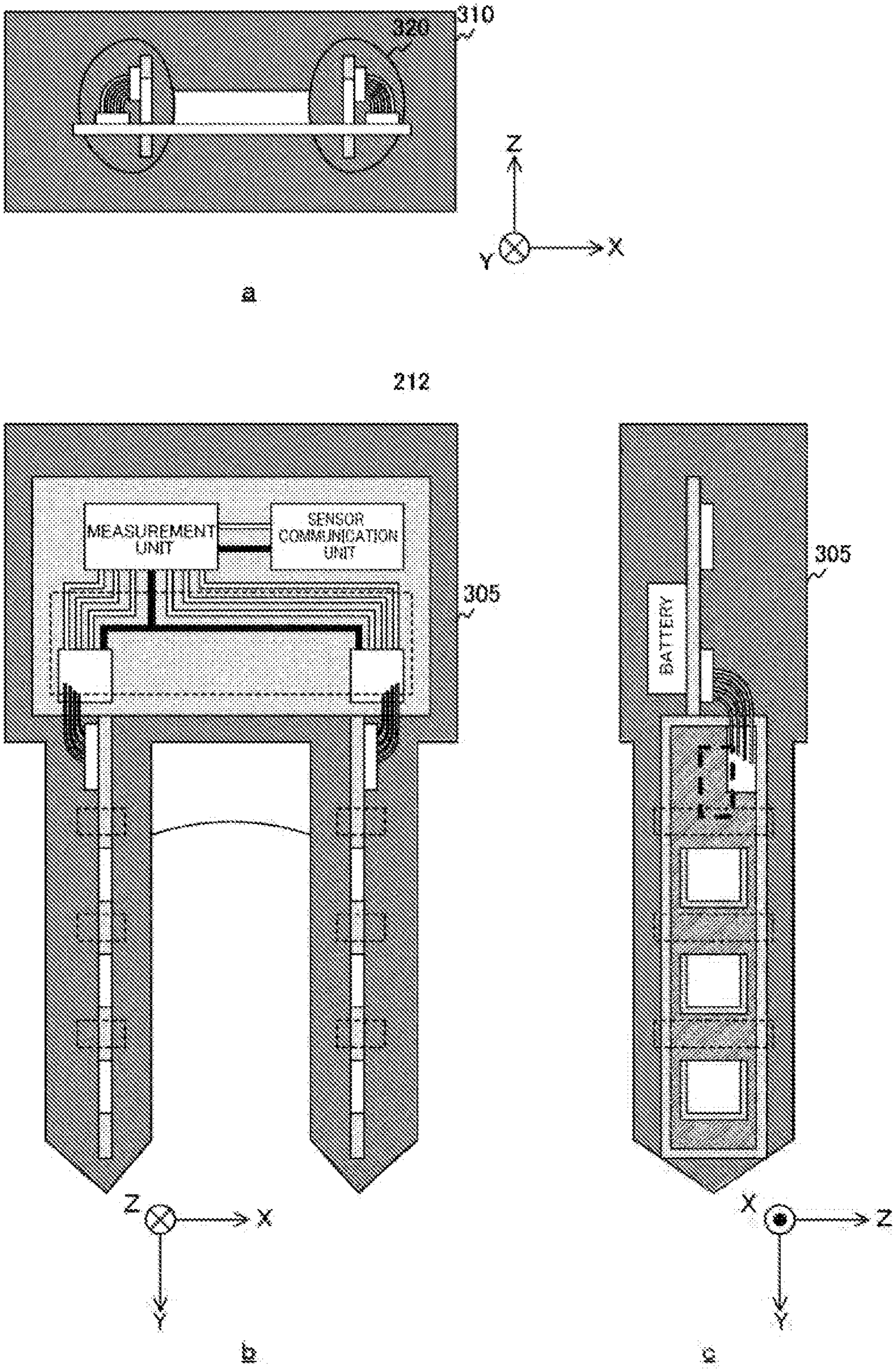

FIG. 188 is a diagram illustrating an example of a sensor device filled with a resin in the fourth modification example of the first embodiment of the present technology.

FIG. 189 is an example of cross-sectional views of a probe casing 320 acquired when seen from above in the fourth modification example of the first embodiment of the present technology and a comparative example.

FIG. 190 is an example of a cross-sectional view of a probe casing acquired when seen from above in a fifth modification example of the first embodiment of the present technology.

FIG. 191 is an example of a cross-sectional view of a probe casing of which a thickness in a direction parallel to an in-probe substrate is thickened in two-sides radiation in the fifth modification example of the first embodiment of the present technology.

Figure 192:
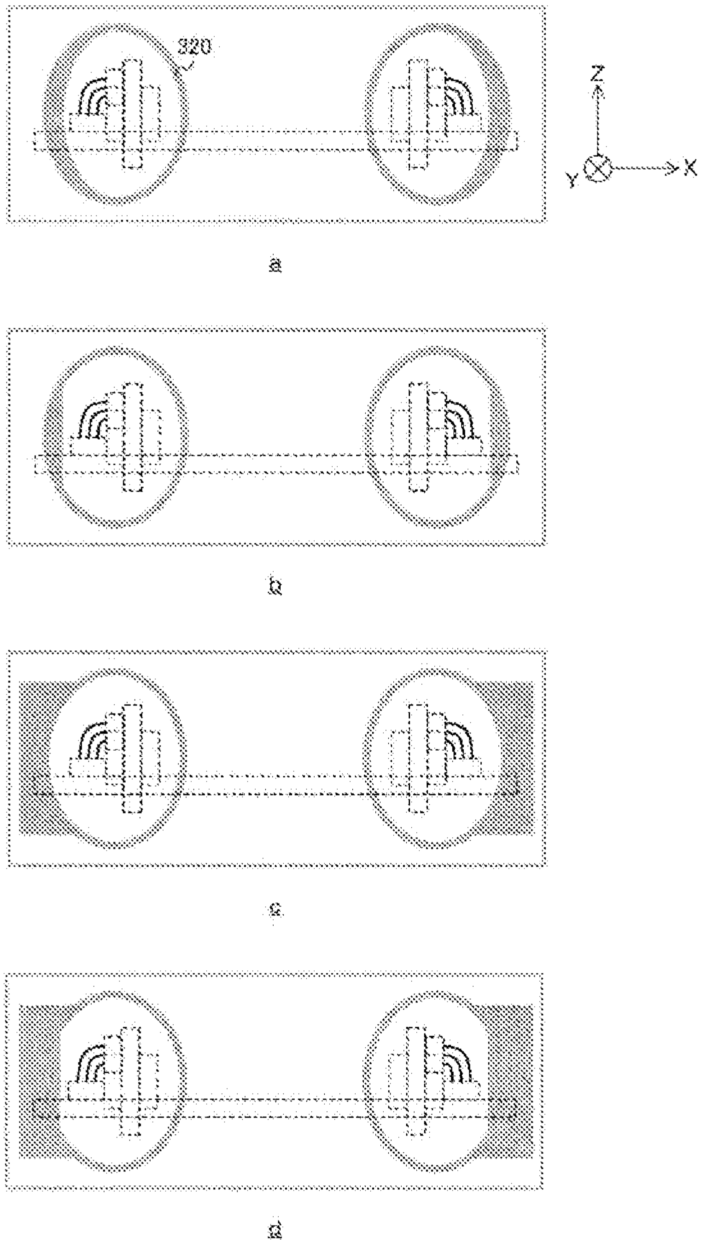

FIG. 192 is an example of a cross-sectional view of a probe casing of which a thickness in a direction perpendicular to an in-probe substrate is thickened in two-sides radiation in the fifth modification example of the first embodiment of the present technology.

FIG. 193 is another example of a cross-sectional view of a probe casing of which a thickness in a direction perpendicular to the in-probe substrate is thickened in two-sides radiation in the fifth modification example of the first embodiment of the present technology.

FIG. 194 is an example of a cross-sectional view of a probe casing of which a thickness in a direction perpendicular to an in-probe substrate and an outer side is thickened in two-sides radiation in the fifth modification example of the first embodiment of the present technology.

Figure 195:
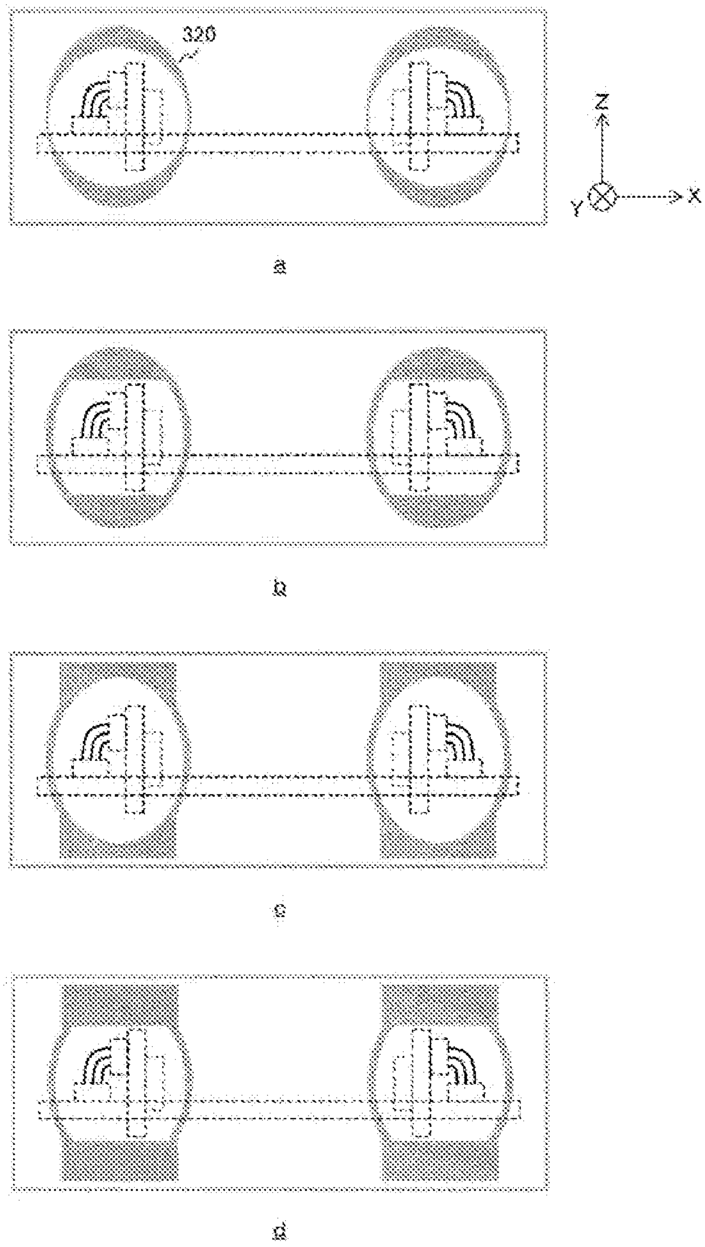

FIG. 195 is an example of a cross-sectional view of a probe casing of which a thickness in a direction parallel to an in-probe substrate is thickened in one-side radiation in the fifth modification example of the first embodiment of the present technology.

Figure 196:
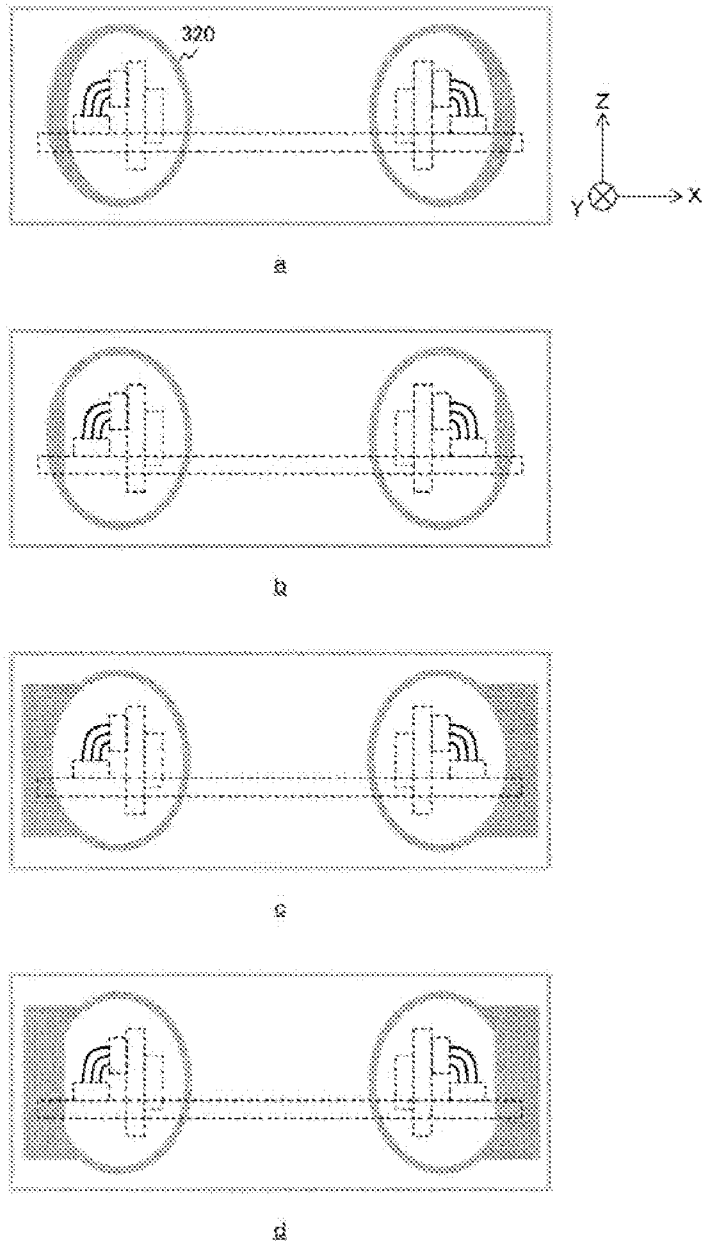

FIG. 196 is an example of a cross-sectional view of a probe casing of which a thickness in a direction perpendicular to an in-probe substrate is thickened in one-side radiation in the fifth modification example of the first embodiment of the present technology.

Figure 197:
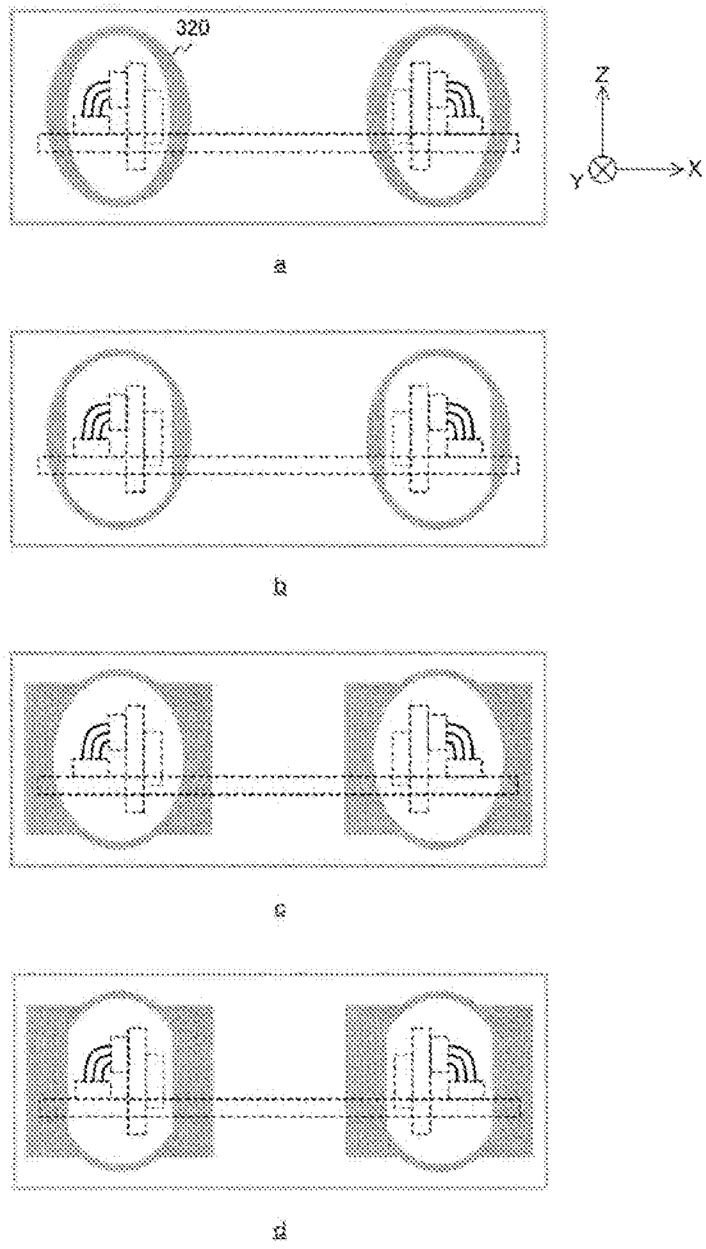

FIG. 197 is another example of a cross-sectional view of a probe casing of which a thickness in a direction perpendicular to an in-probe substrate is thickened in one-side radiation in the fifth modification example of the first embodiment of the present technology.

Figure 198:
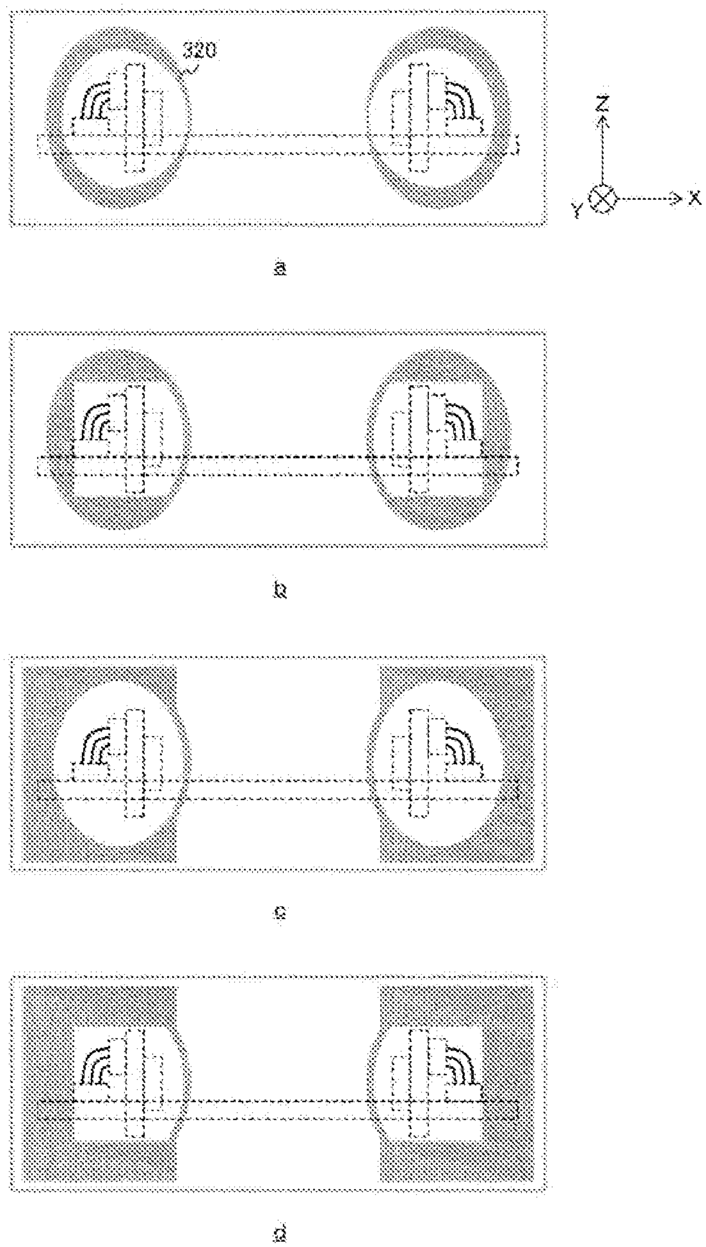

FIG. 198 is an example of a cross-sectional view of a probe casing of which a thickness in a direction perpendicular to an in-probe substrate and on an outer side is thickened in one-side radiation in the fifth modification example of the first embodiment of the present technology.

FIG. 199 is a diagram illustrating an example of setting a thickness of a sensor casing in the fifth modification example of the first embodiment of the present technology.

Figure 200:
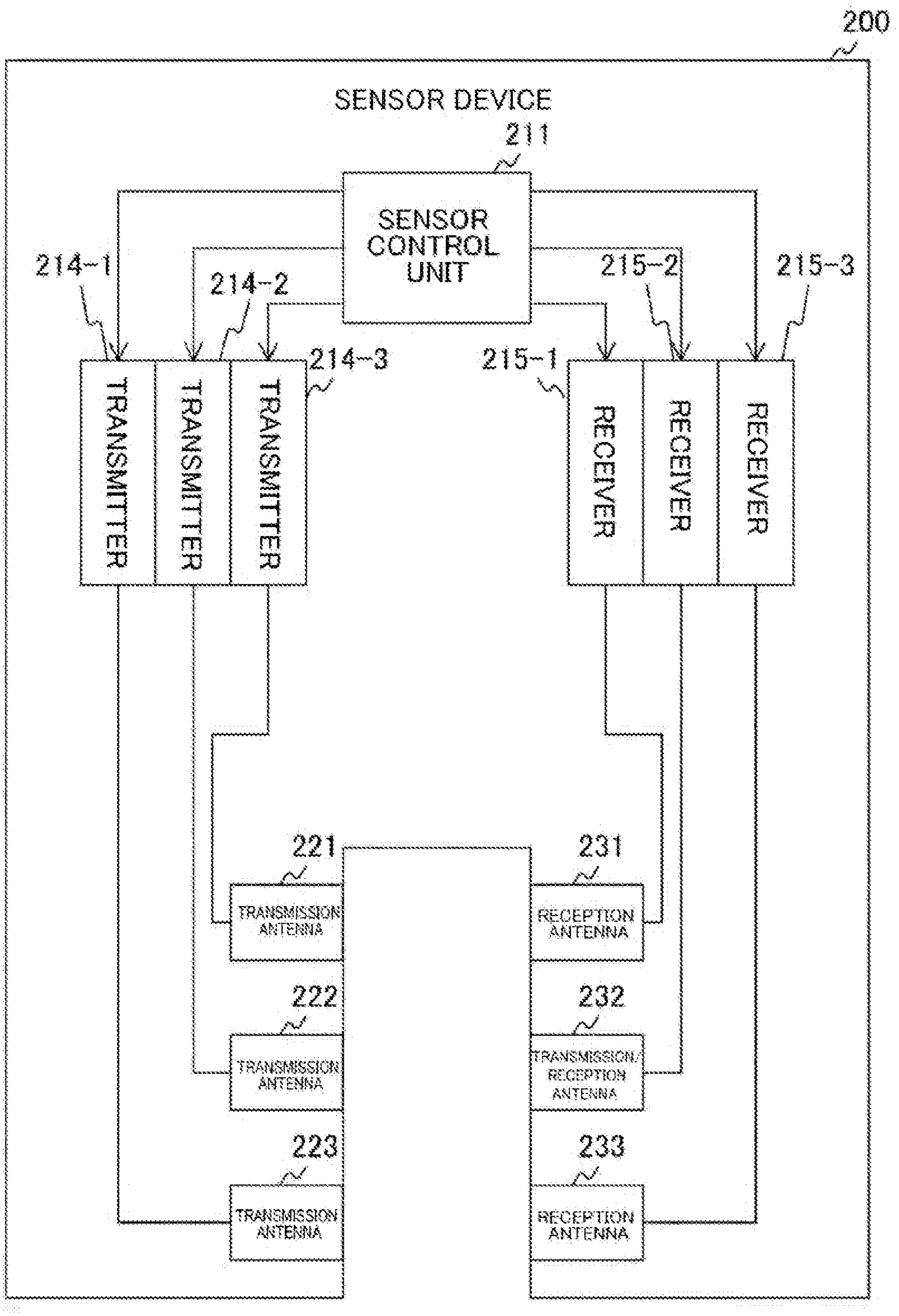

FIG. 200 is a diagram illustrating one configuration example of a sensor device in which a transceiver is disposed for each antenna in a sixth modification example of the first embodiment of the present technology.

Figure 201:
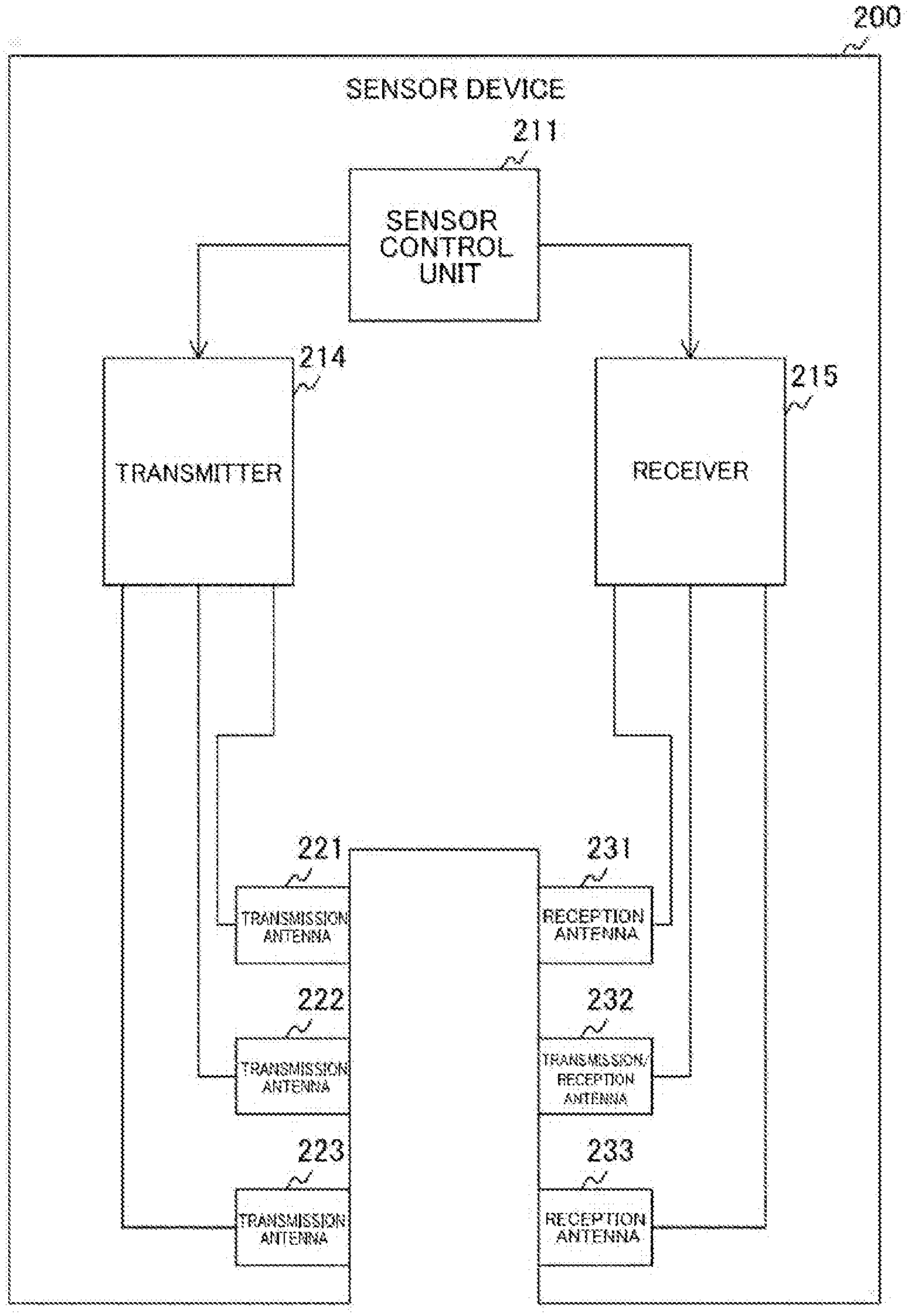

FIG. 201 is a diagram illustrating one configuration example of a sensor device including one transmitter and one receiver in the sixth modification example of the first embodiment of the present technology.

Figure 202:
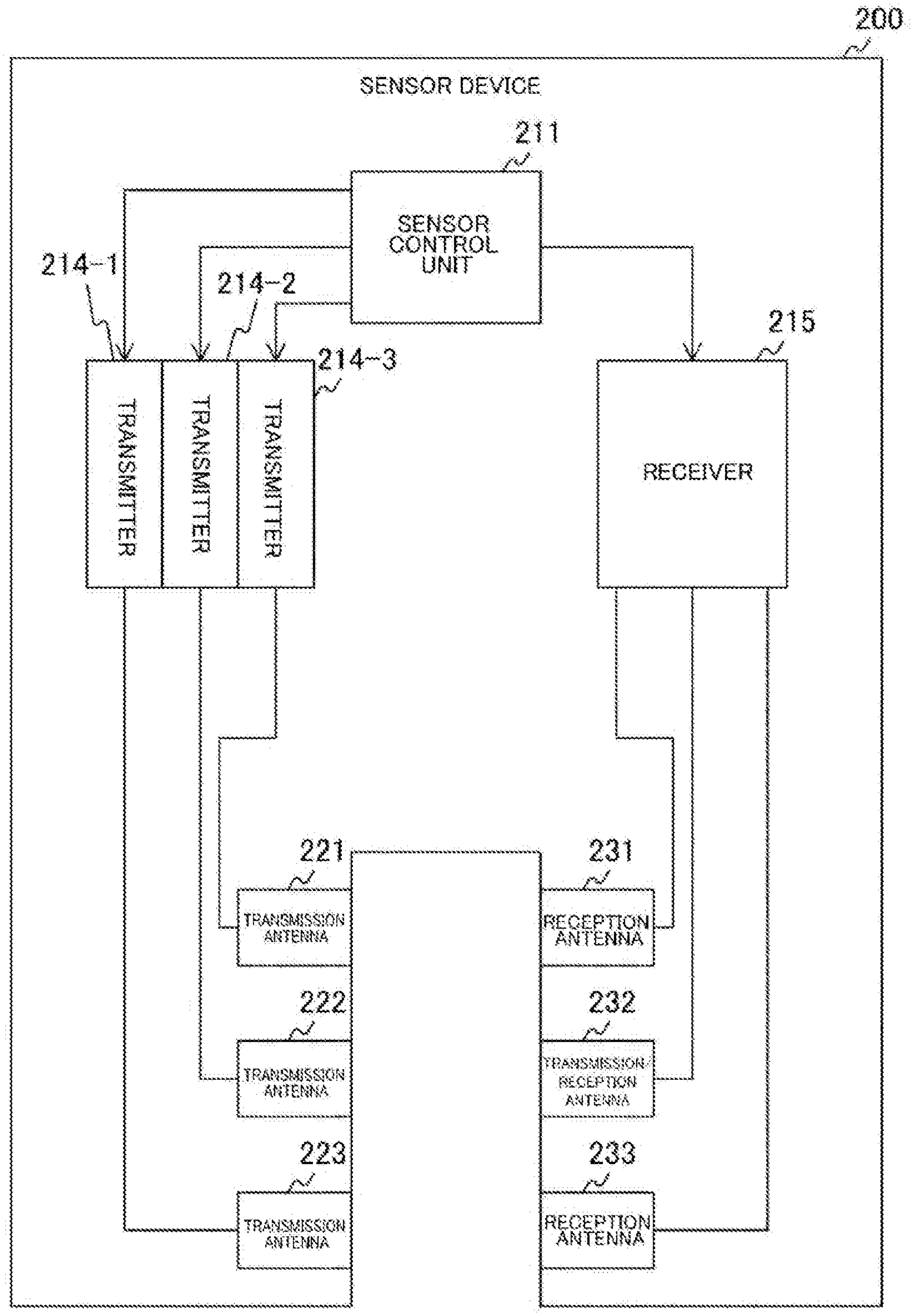

FIG. 202 is a diagram illustrating one configuration example of a sensor device having one receiver in the sixth modification example of the first embodiment of the present technology.

Figure 203:
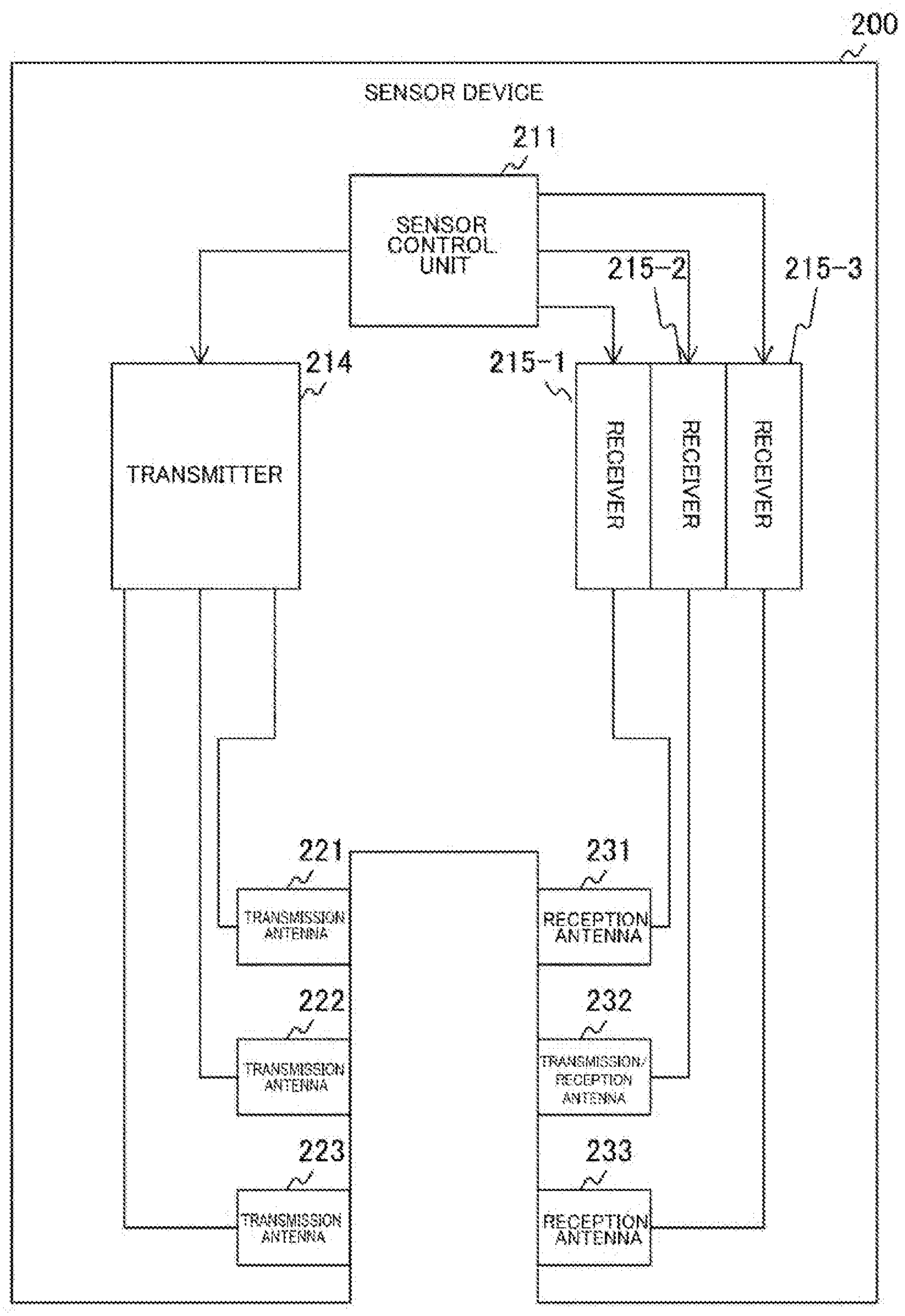

FIG. 203 is a diagram illustrating one configuration example of a sensor device having one transmitter in the sixth modification example of the first embodiment of the present technology.

Figure 204:
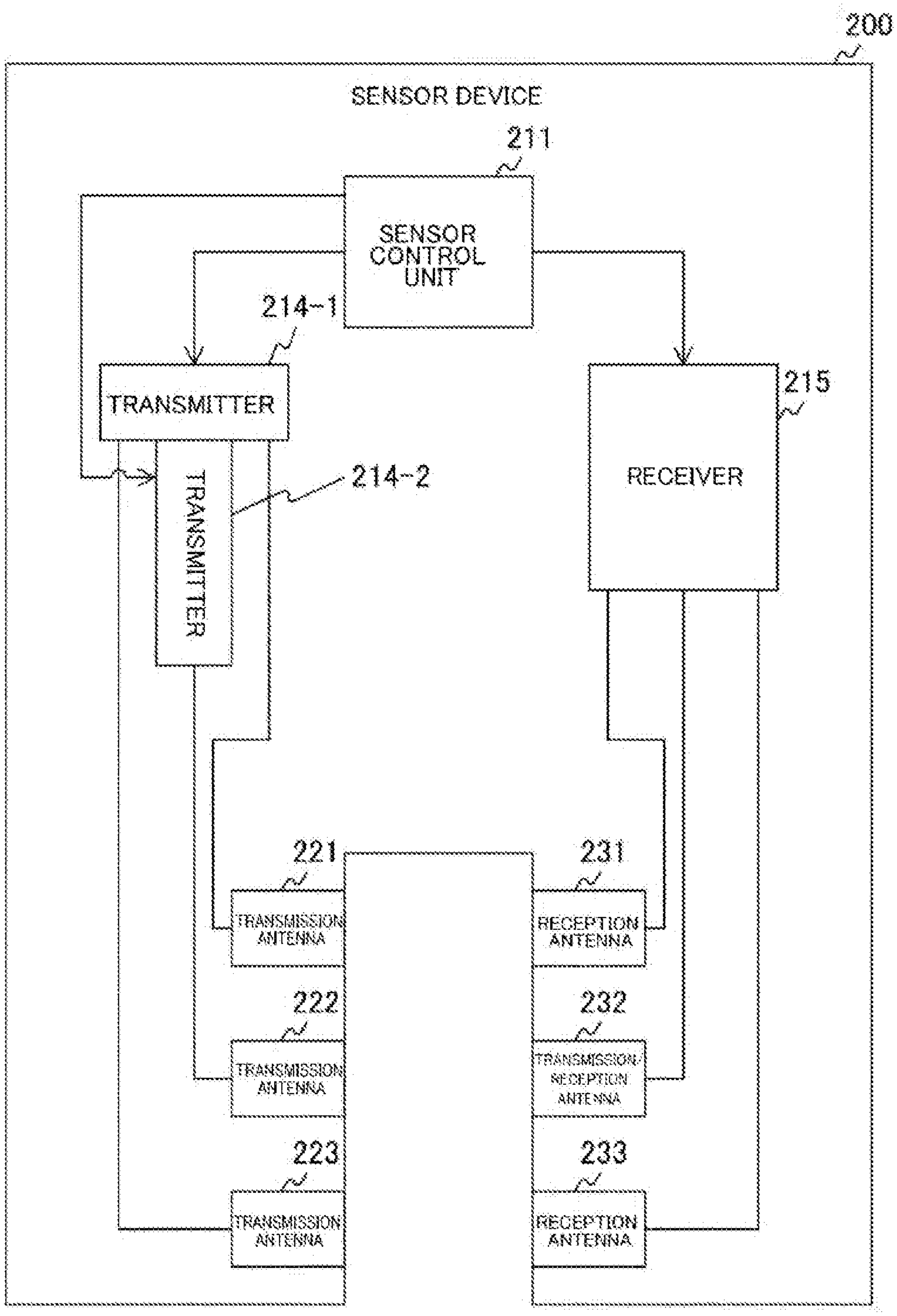

FIG. 204 is a diagram illustrating another example of a sensor device having a plurality of transmitters in the sixth modification example of the first embodiment of the present technology.

Figure 205:
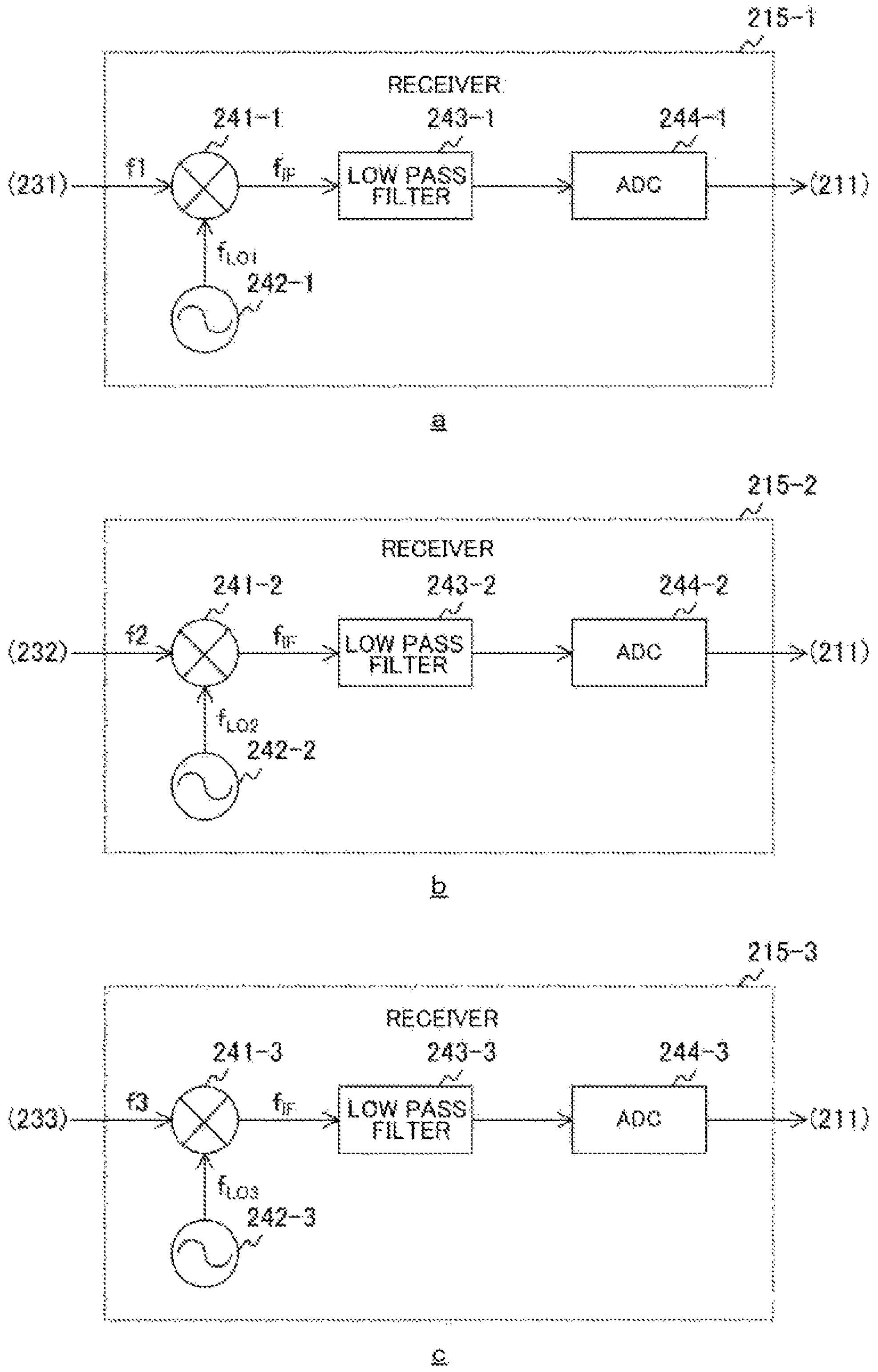

FIG. 205 is a block diagram illustrating one configuration example of a receiver in the sixth modification example of the first embodiment of the present technology.

Figure 206:
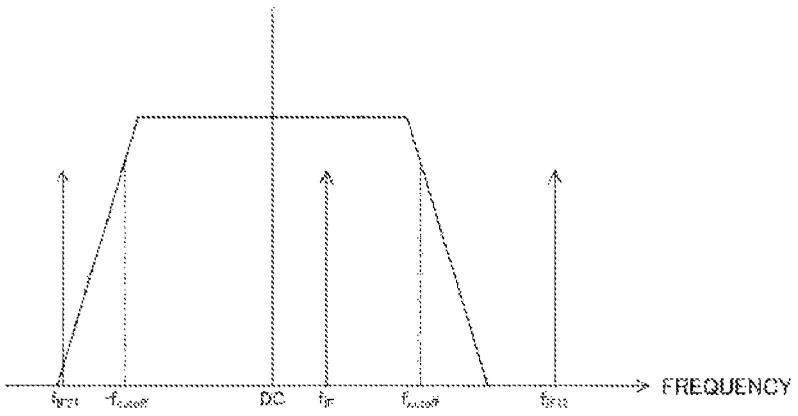

FIG. 206 is a diagram illustrating an example of a frequency characteristics of a reception signal in the sixth modification example of the first embodiment of the present technology.

Figure 207:
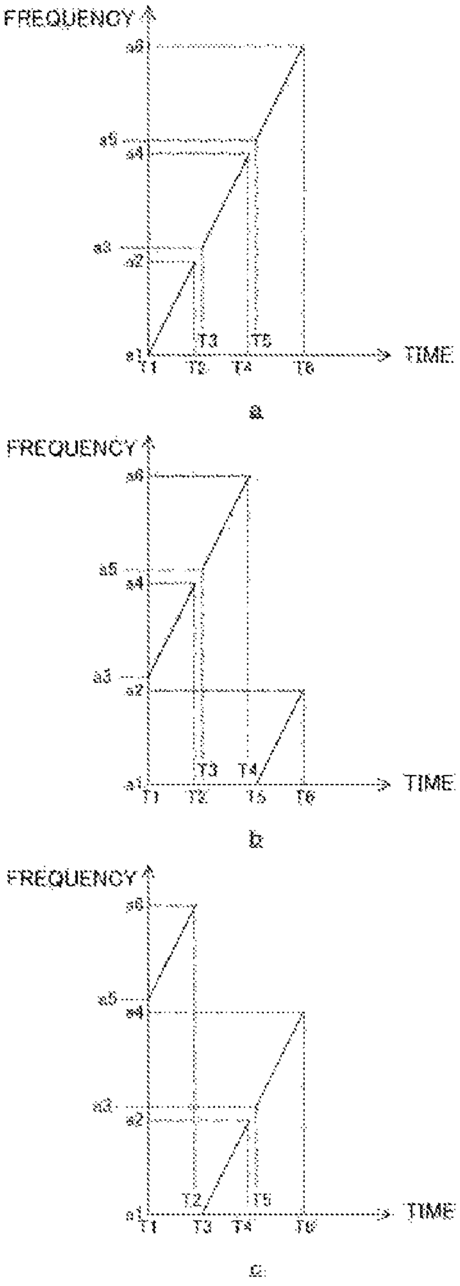

FIG. 207 is an example of a timing diagram of frequency divisional driving in the sixth modification example of the first embodiment of the present technology.

Figure 208:
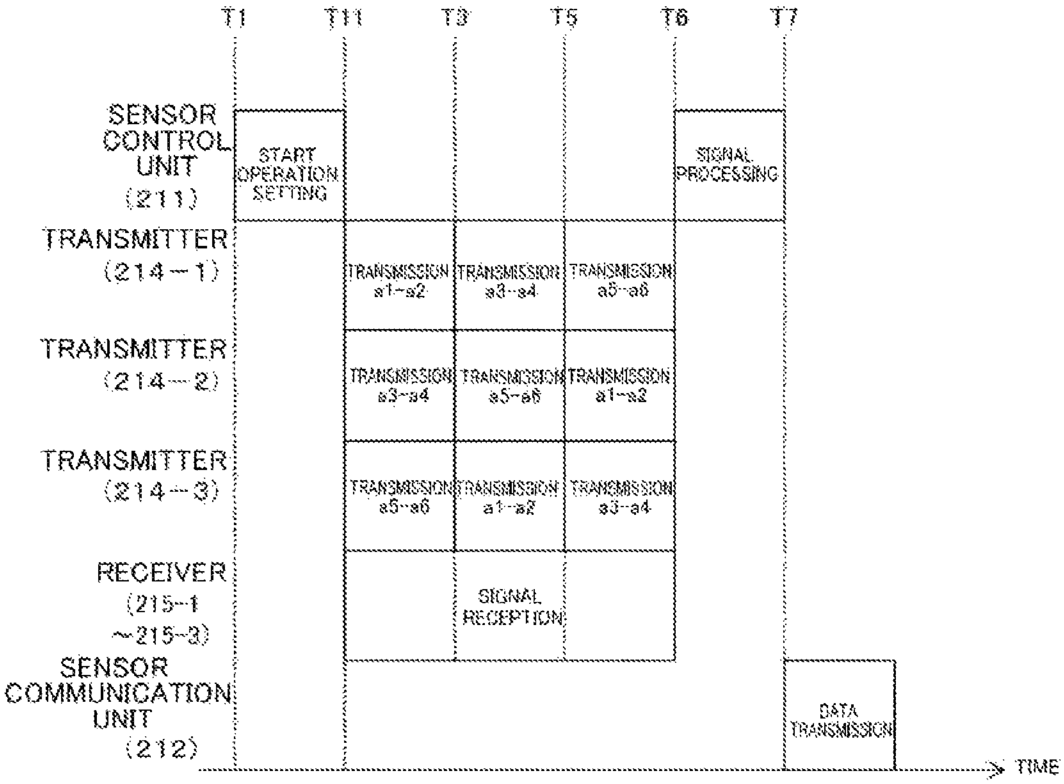

FIG. 208 is an example of a timing diagram illustrating operations of respective units disposed inside of the sensor device in the sixth modification example of the first embodiment of the present technology.

FIG. 209 is an example of a timing diagram of frequency divisional driving acquired when a sweeping period is shortened in the sixth modification example of the first embodiment of the present technology.

Figure 210:
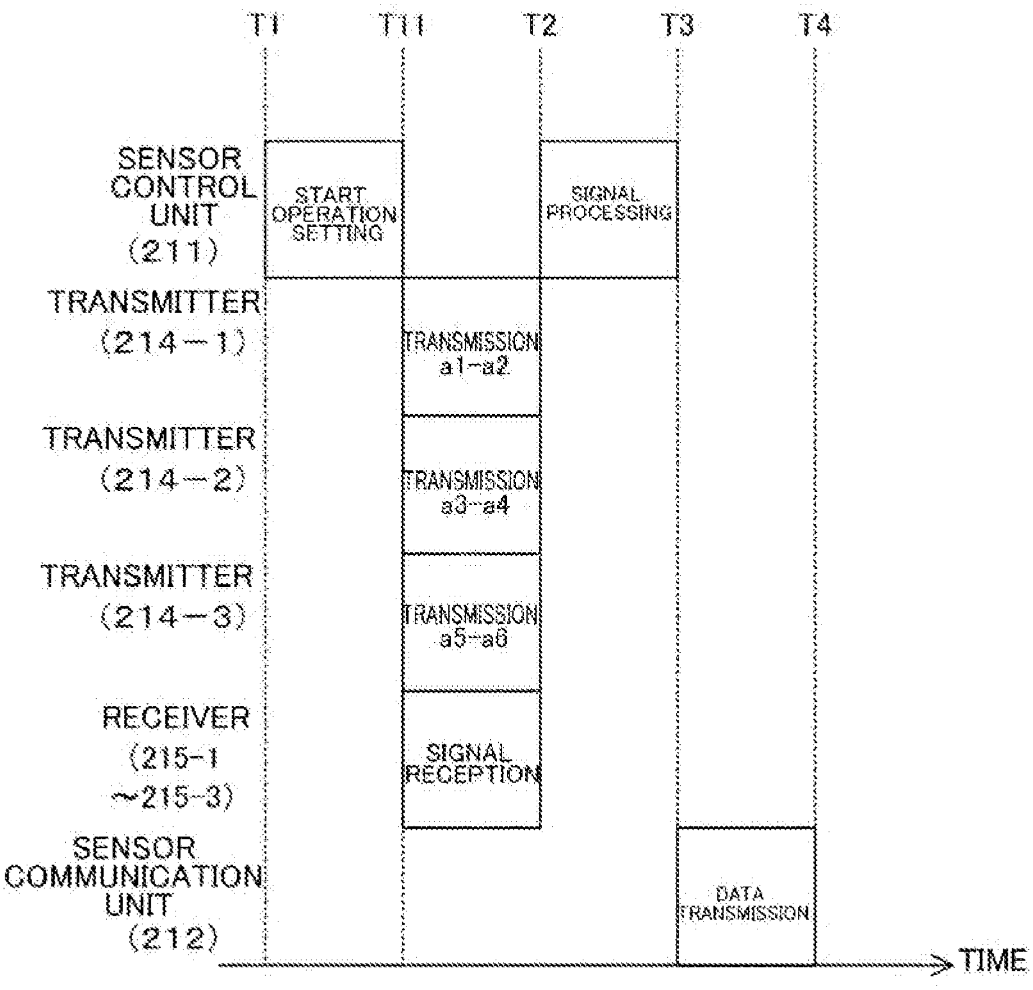

FIG. 210 is an example of a timing diagram illustrating operations of respective units disposed inside the sensor device acquired when a sweeping period is shortened in the sixth modification example of the first embodiment of the present technology.

Figure 211:
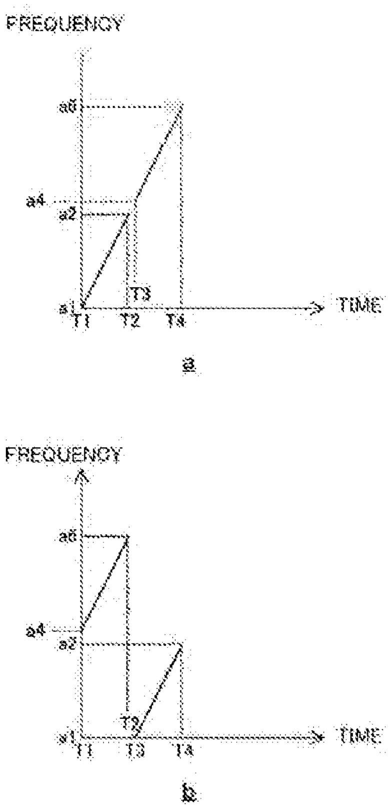

FIG. 211 is an example of a timing diagram of frequency divisional driving in which frequencies of two antennas are the same in the sixth modification example of the first embodiment of the present technology.

Figure 212:
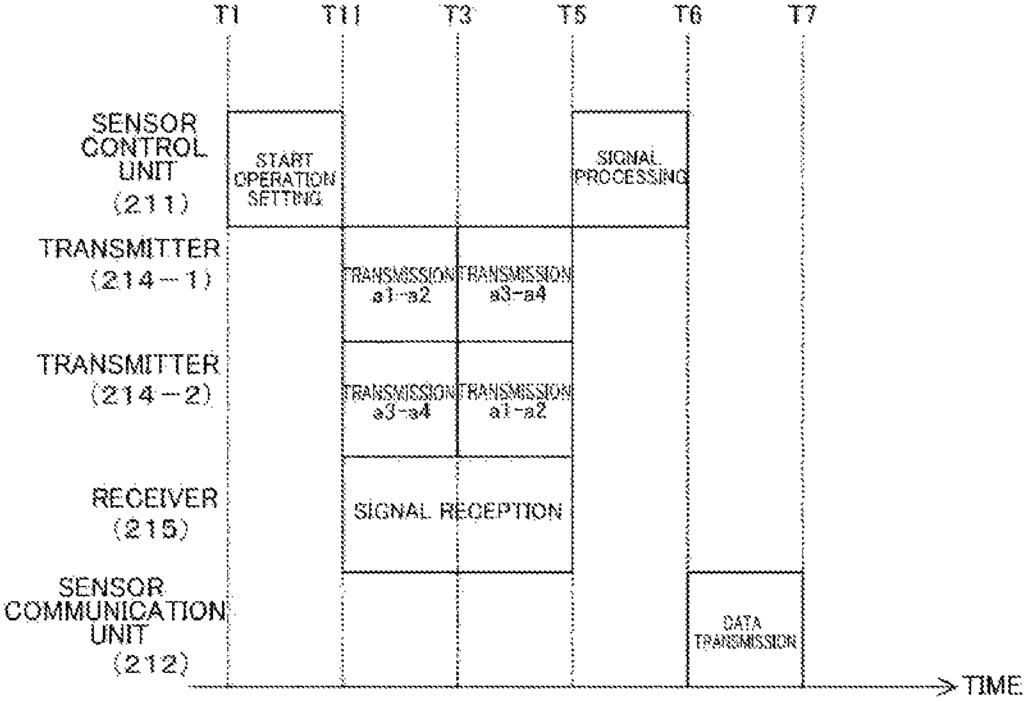

FIG. 212 is an example of a timing diagram illustrating operations of respective units disposed inside the sensor device in which frequencies of two antennas are the same in the sixth modification example of the first embodiment of the present technology.

Figure 213:
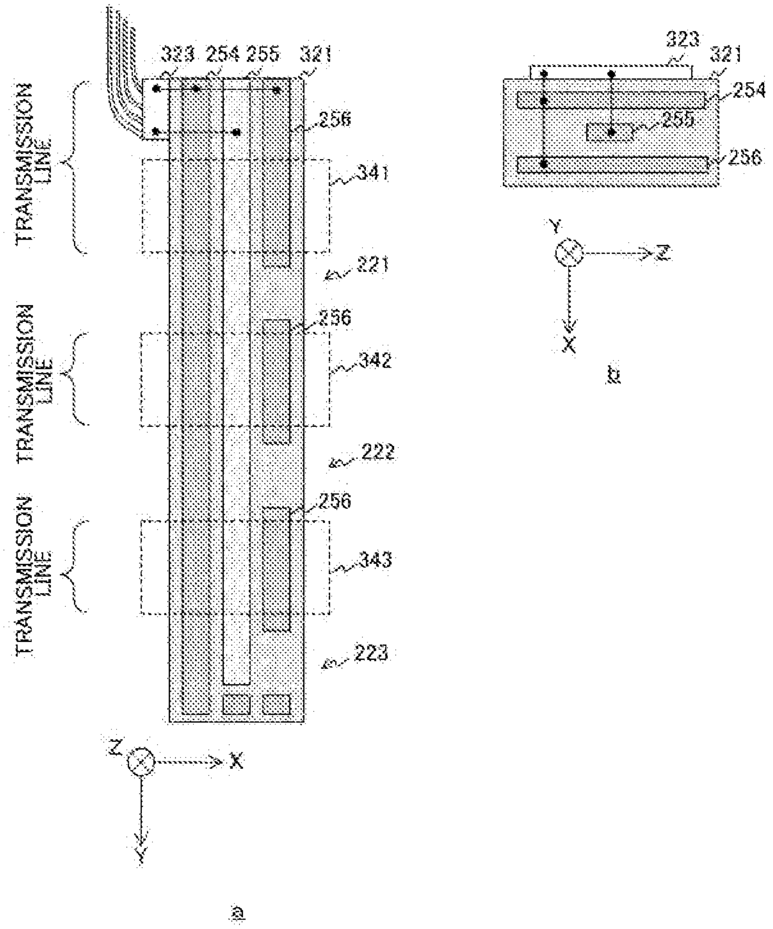

FIG. 213 is a diagram illustrating an example of a cross-sectional view of an in-probe substrate in a seventh modification example of the first embodiment of the present technology.

Figure 214:
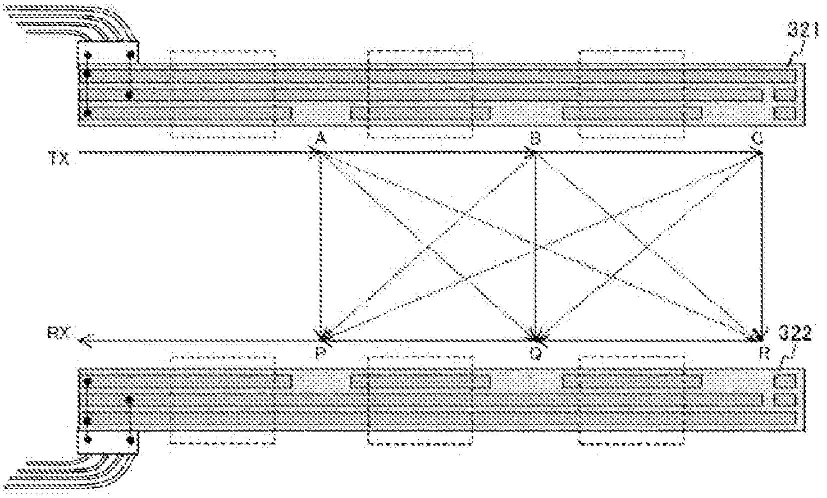

FIG. 214 is a diagram illustrating a transmission path of a signal for each antenna in the seventh modification example of the first embodiment of the present technology.

Figure 215:
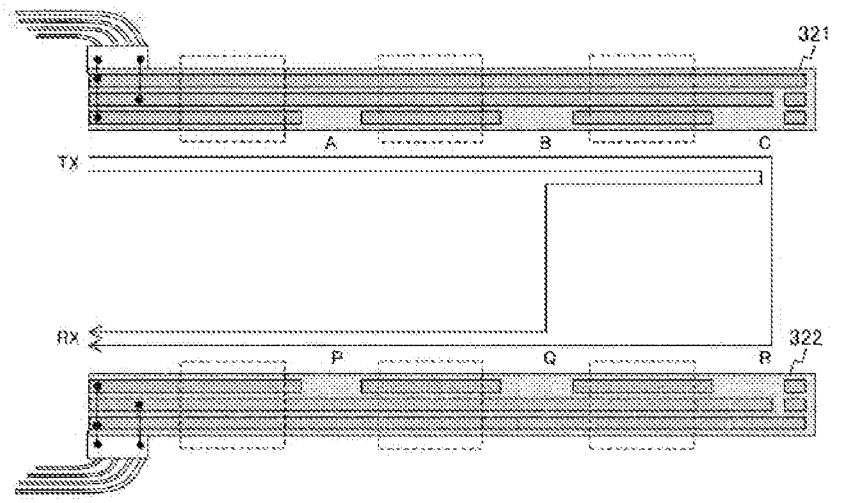

FIG. 215 is a diagram illustrating transmission paths of signals of two systems in the seventh modification example of the first embodiment of the present technology.

Figure 216:
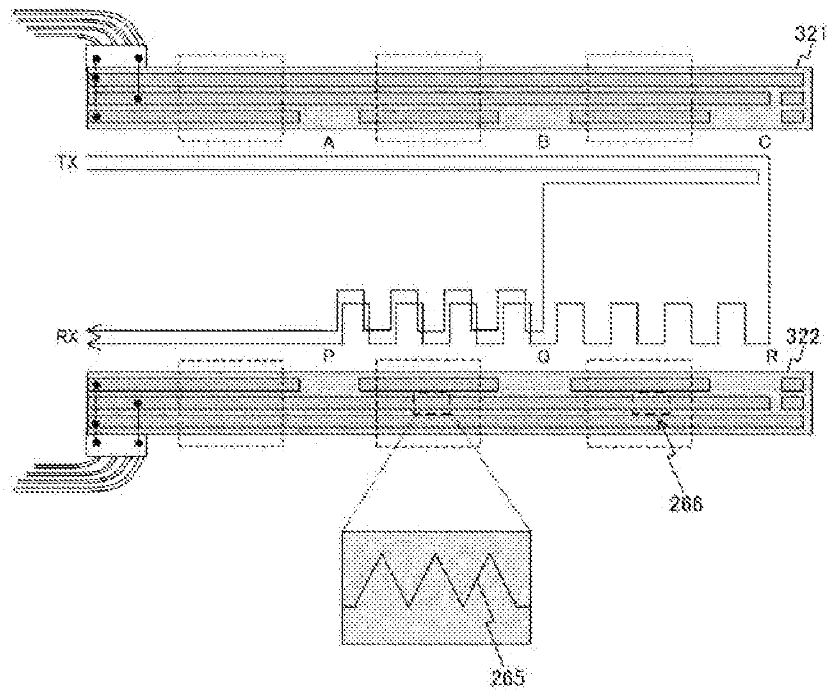

FIG. 216 is a diagram illustrating an example of a sensor device in which a delay line is disposed in the seventh modification example of the first embodiment of the present technology.

Figure 217:
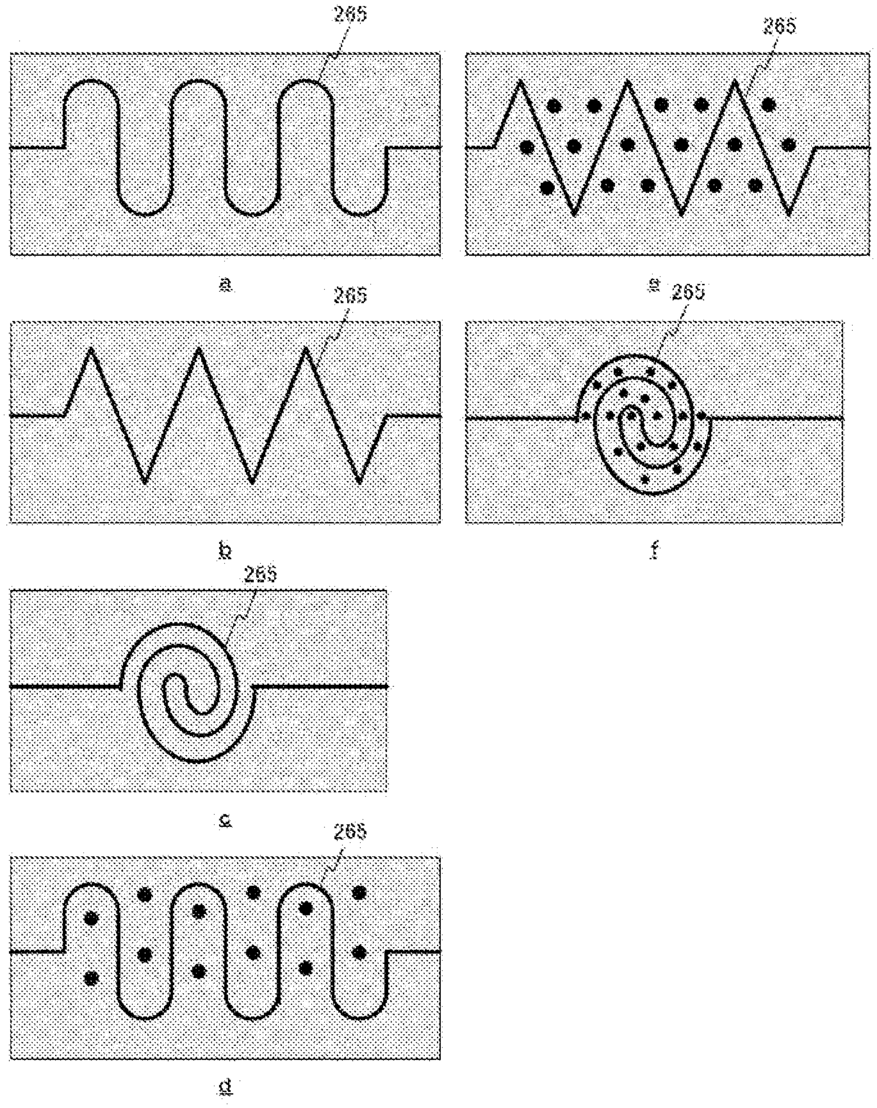

FIG. 217 is a diagram illustrating an example of a shape of a delay line in the seventh modification example of the first embodiment of the present technology.

Figure 218:
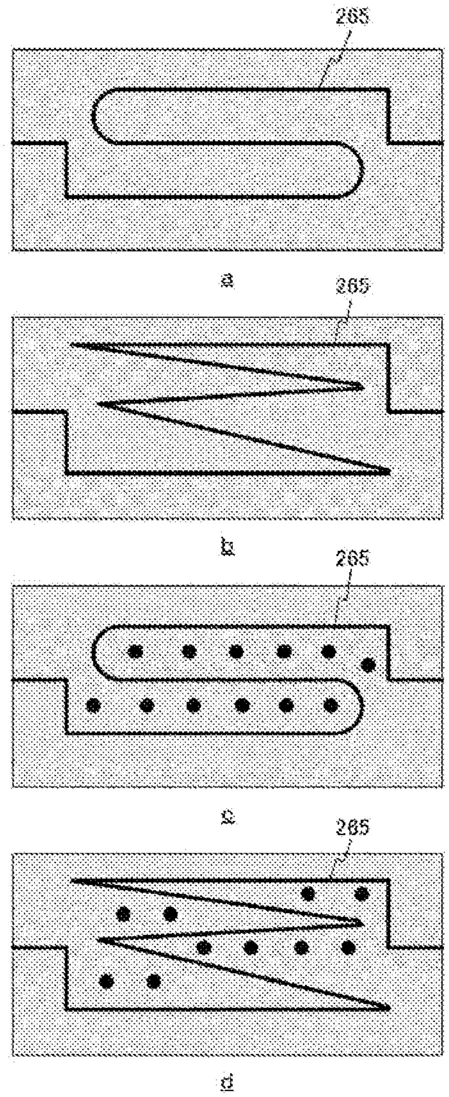

FIG. 218 is a diagram illustrating another example of a shape of a delay line in the seventh modification example of the first embodiment of the present technology.

Figure 219:
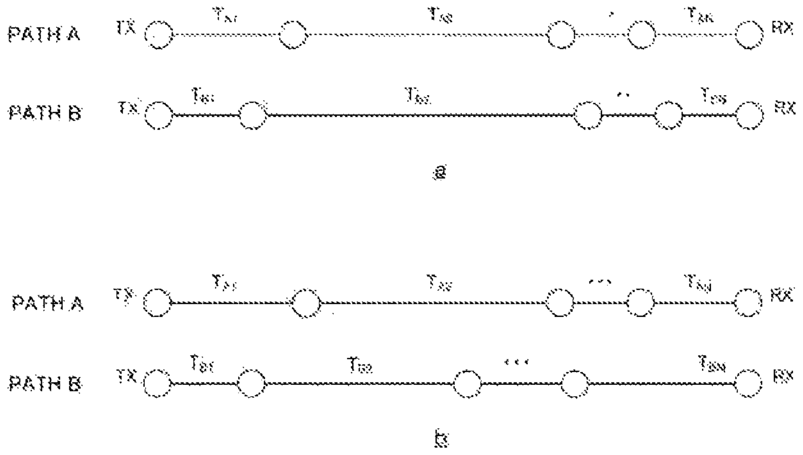

FIG. 219 is a diagram illustrating a method of setting a delay amount of a delay line in the seventh modification example of the first embodiment of the present technology.

Figure 220:
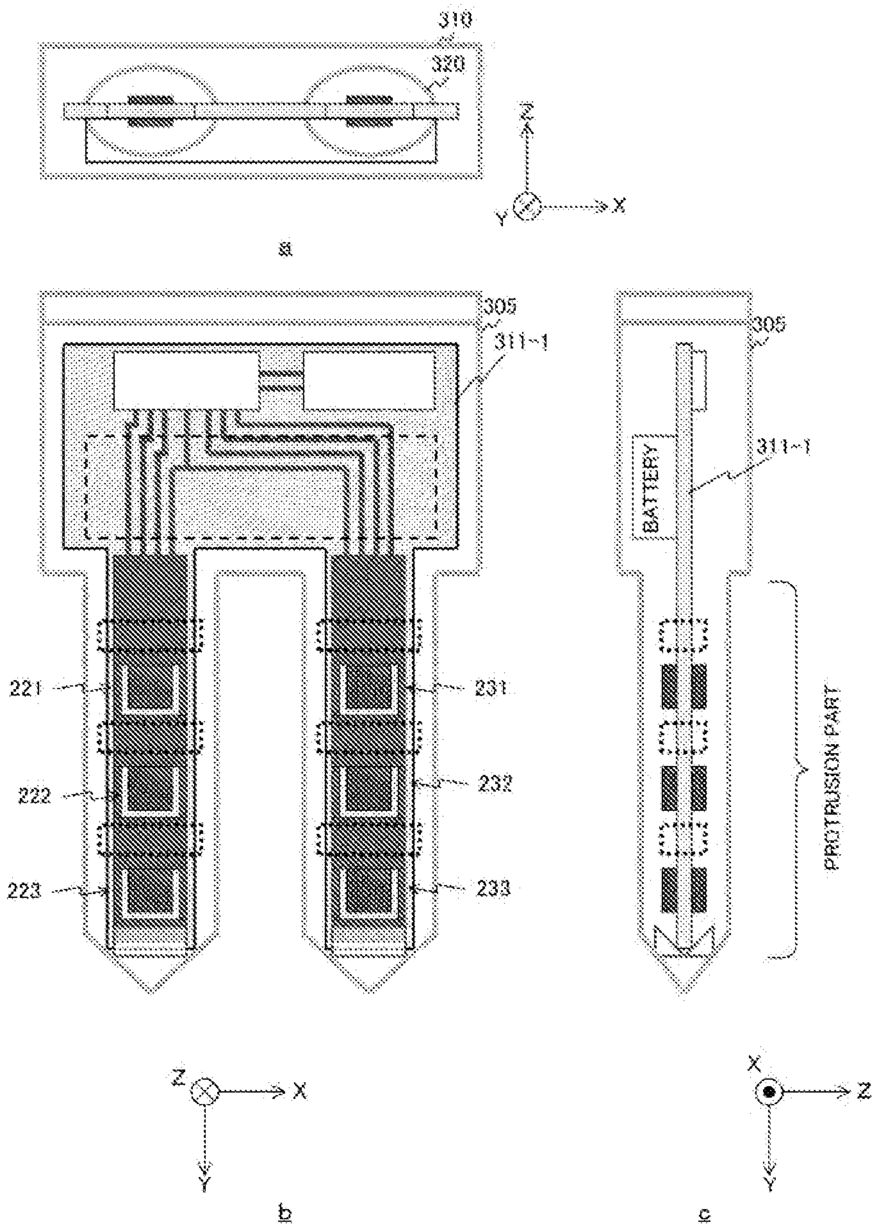

FIG. 220 is a diagram illustrating an example of a sensor device according to a second embodiment of the present technology.

Figure 221:
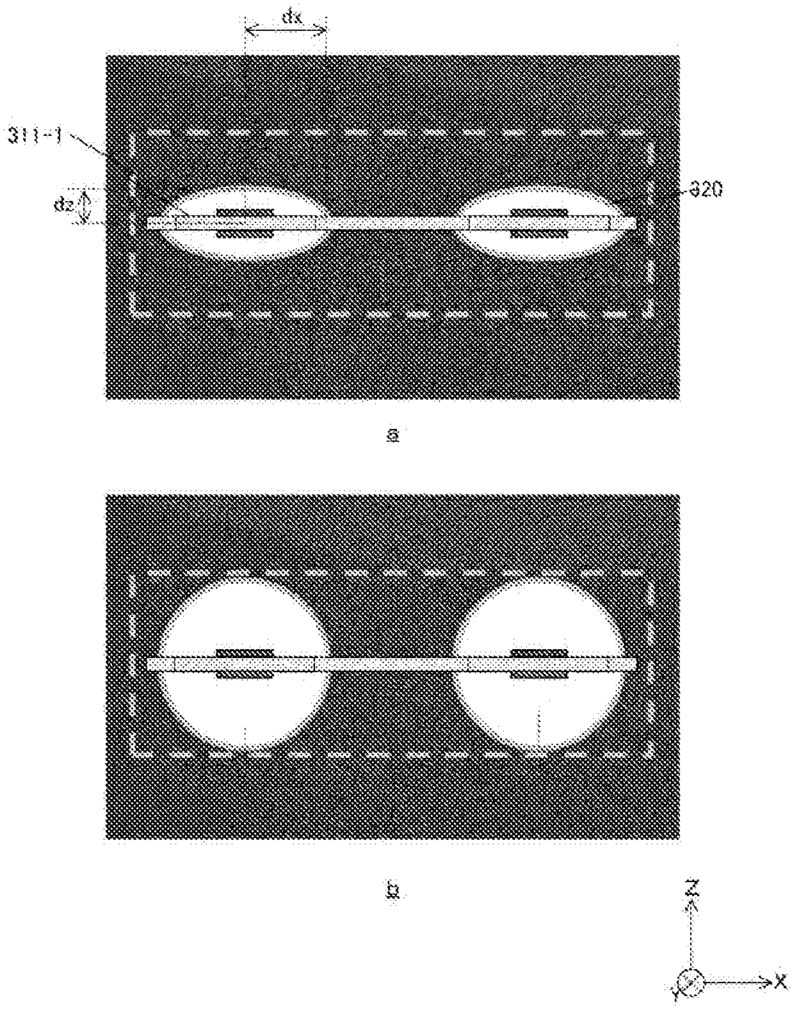

FIG. 221 is an example of a cross-sectional view of a sensor device acquired when seen from above in the second embodiment of the present technology and a comparative example.

Figure 222:
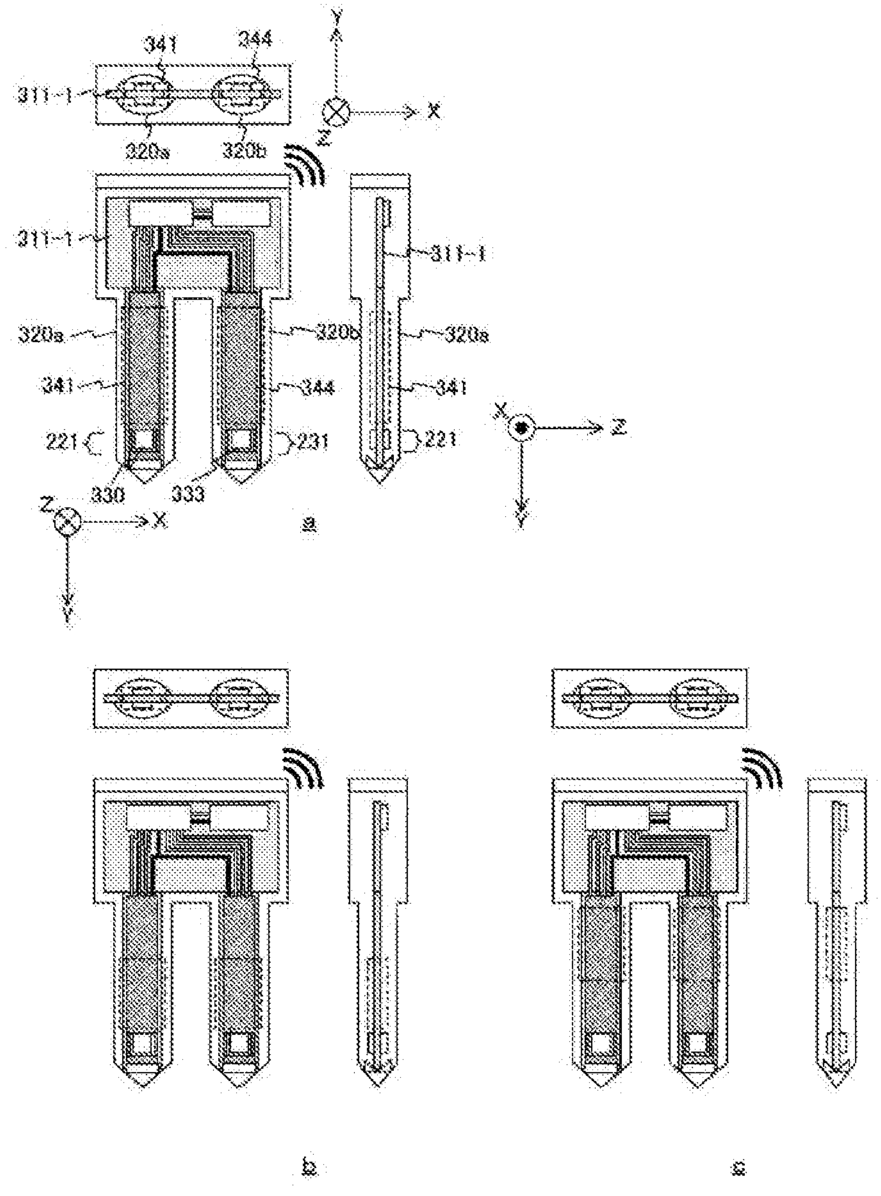

FIG. 222 is a diagram illustrating an example of coating portions of an electric wave absorbing unit at the time of two-sides radiation in the second embodiment of the present technology.

Figure 223:
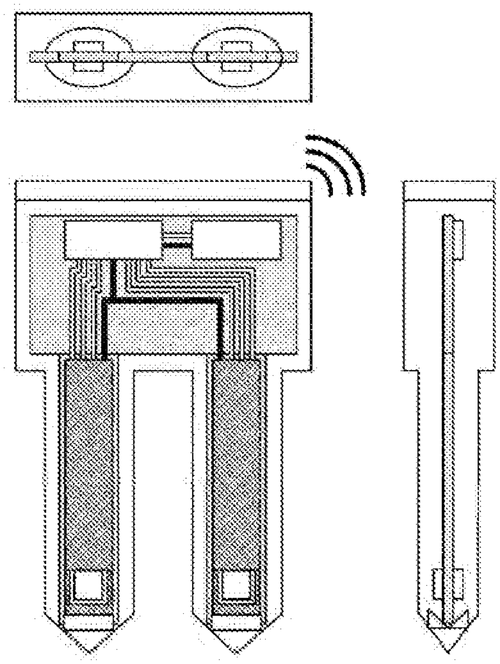

FIG. 223 is a diagram illustrating an example in which coating is not performed by an electric wave absorbing unit at the time of two-sides radiation in the second embodiment of the present technology.

FIG. 224 is a diagram illustrating an example of coating portions of an electric wave absorbing unit at the time of one-side radiation in the second embodiment of the present technology.

Figure 225:
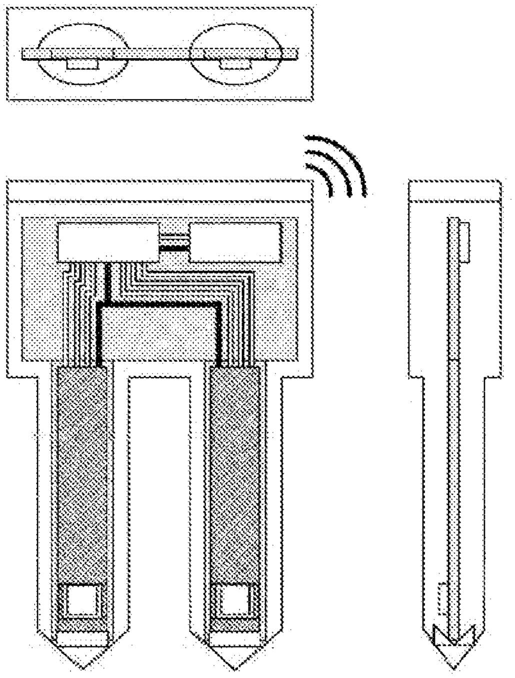

FIG. 225 is a diagram illustrating an example in which coating is not performed by an electric wave absorbing unit at the time of one-side radiation in the second embodiment of the present technology.

Figure 226:
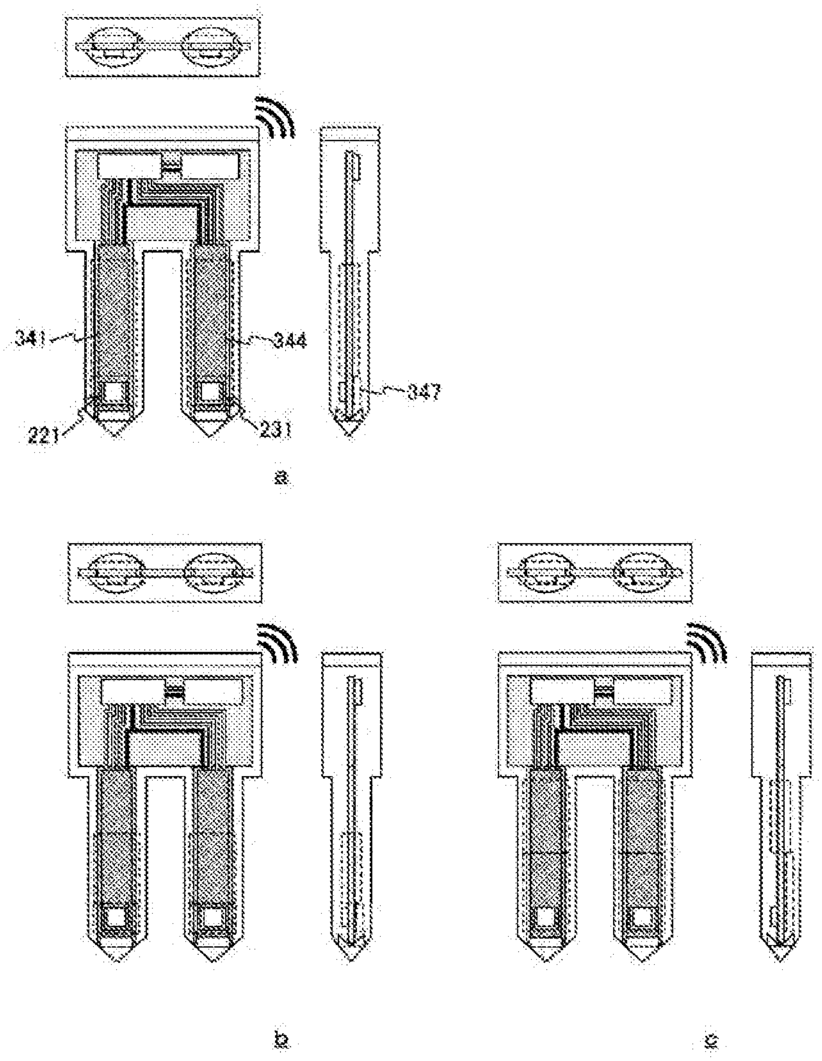

FIG. 226 is a diagram illustrating an example in which one face is coated at the time of one-side radiation in the second embodiment of the present technology.

Figure 227:
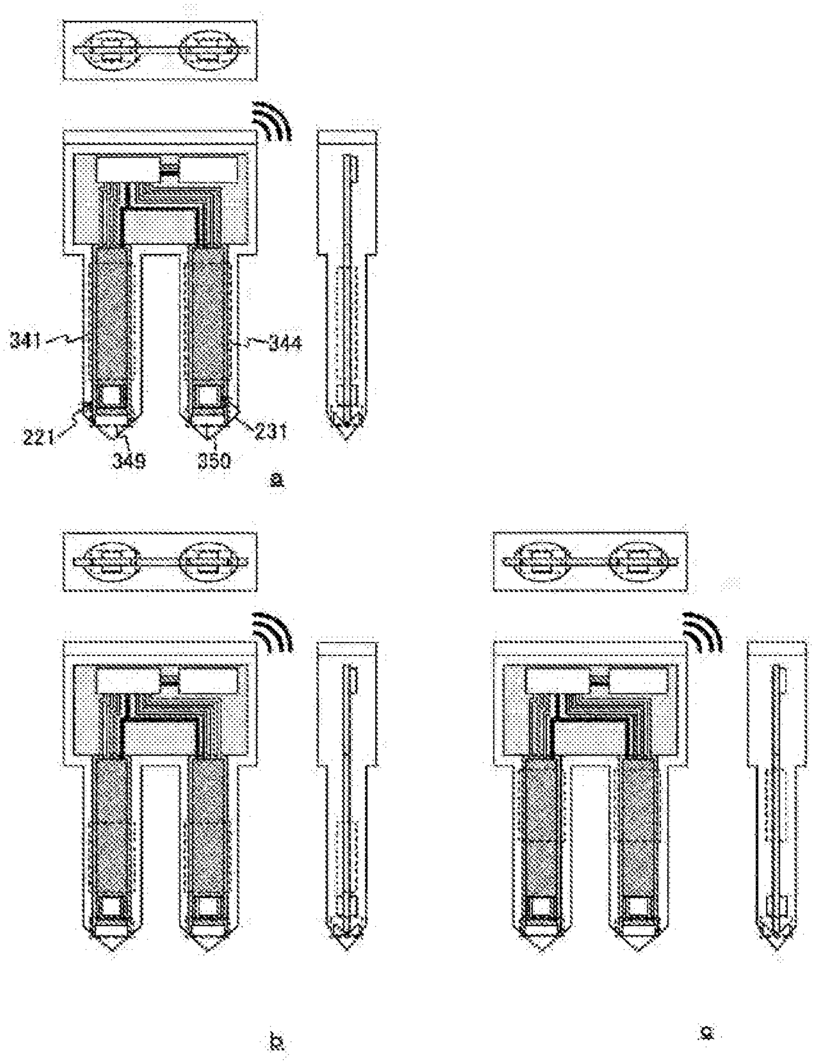

FIG. 227 is a diagram illustrating an example in which a transmission line and a tip end are coated at the time of two-sides radiation in the second embodiment of the present technology.

Figure 228:
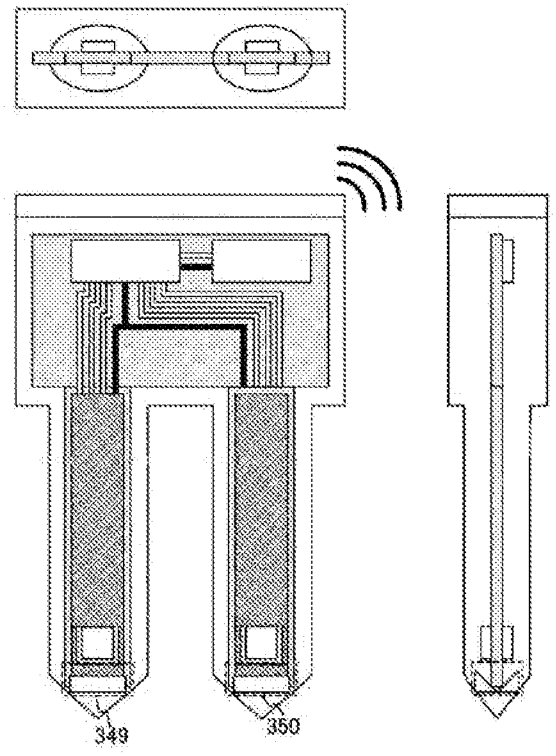

FIG. 228 is a diagram illustrating an example in which only a tip end is coated at the time of two-sides radiation in the second embodiment of the present technology.

FIG. 229 is a diagram illustrating an example in which a transmission line and a tip end are coated at the time of one-side radiation in the second embodiment of the present technology.

Figure 230:
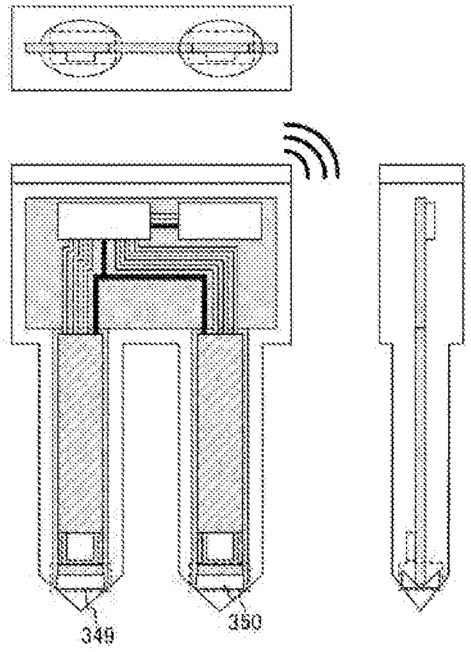

FIG. 230 is a diagram illustrating an example in which only a tip end is coated at the time of one-side radiation in the second embodiment of the present technology.

Figure 231:
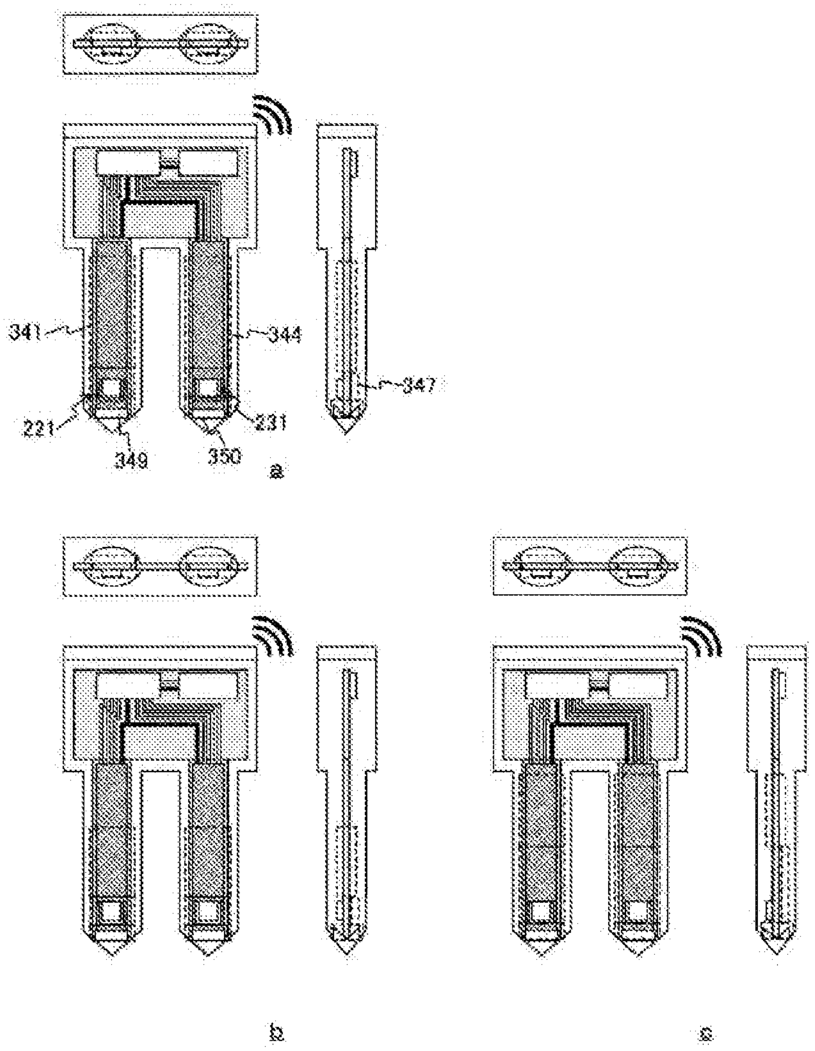

FIG. 231 is a diagram illustrating an example in which a transmission line, one face, and a tip end are coated at the time of one-side radiation in the second embodiment of the present technology.

FIG. 232 is a diagram illustrating an example of coating portions of an electric wave absorbing unit at the time of disposing a plurality of antenna pairs of two-sides radiation in the second embodiment of the present technology.

FIG. 233 is a diagram illustrating another example of coating portions of an electric wave absorbing unit at the time of disposing a plurality of antenna pairs of two-sides radiation in the second embodiment of the present technology.

FIG. 234 is a diagram illustrating an example in which an electric wave absorbing unit is formed in a sensor casing in the second embodiment of the present technology.

Figure 235:
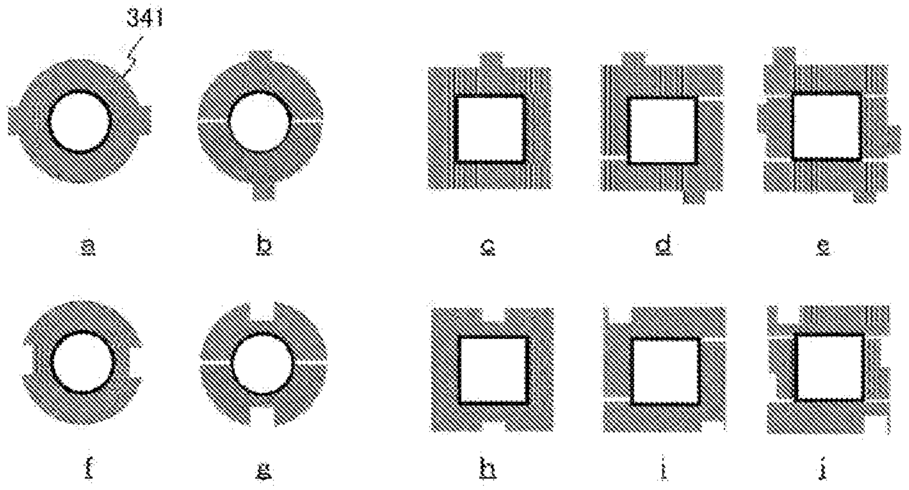

FIG. 235 is a diagram illustrating an example of a shape of an electric wave absorbing unit in the second embodiment of the present technology.

Figure 236:
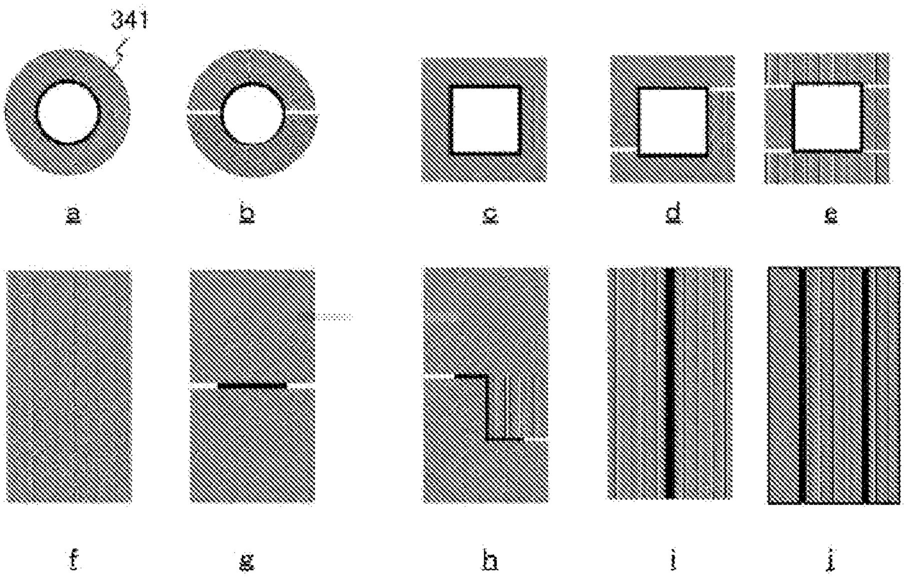

FIG. 236 is a diagram illustrating another example of a shape of an electric wave absorbing unit in the second embodiment of the present technology.

Figure 237:
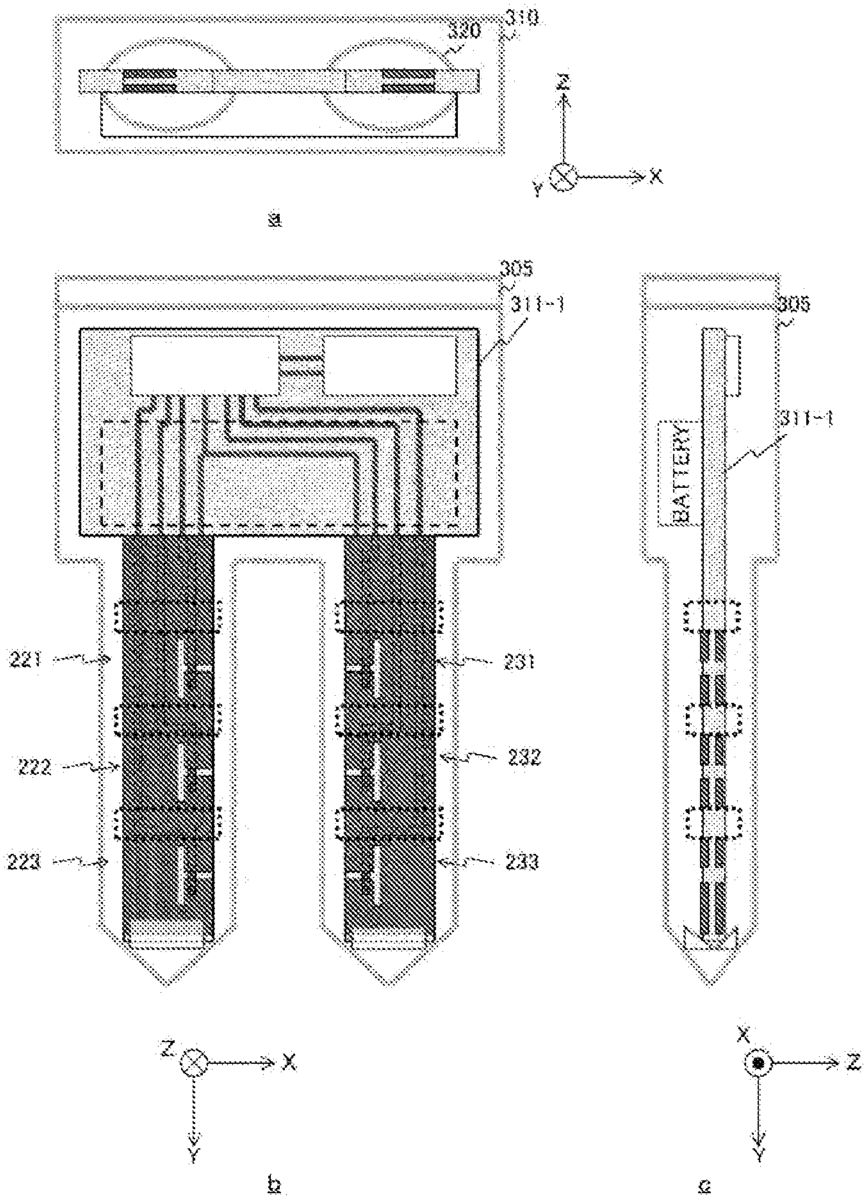

FIG. 237 is a diagram illustrating an example of a sensor device in which an antenna of a slot shape is disposed in a first modification example of the second embodiment of the present technology.

Figure 238:
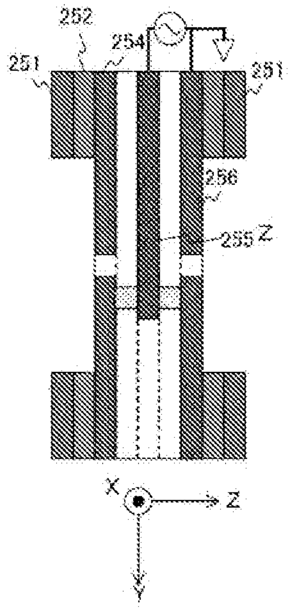

FIG. 238 is a diagram illustrating a structure of an antenna of a planar shape and a slot shape and a horizontal-direction radiation type in the first modification example of the second embodiment of the present technology.

Figure 239:
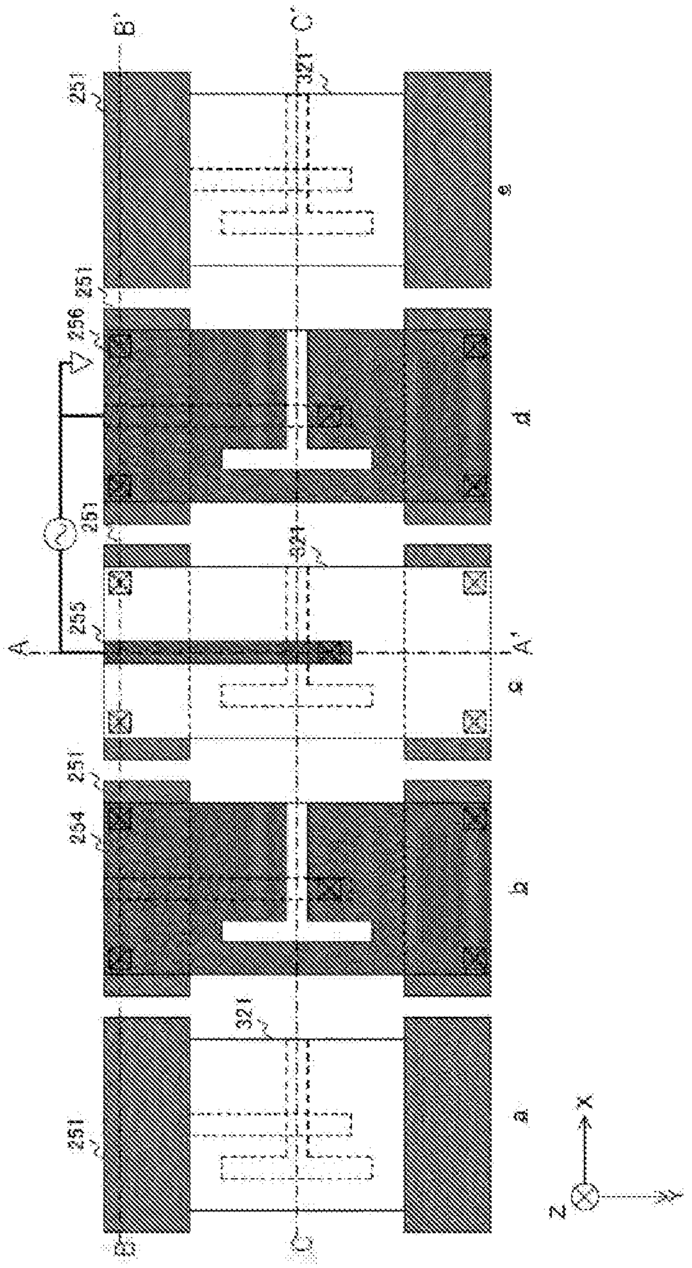

FIG. 239 is a diagram illustrating a structure of an antenna of a planar shape and a slot shape and a horizontal-direction radiation type in the first modification example of the second embodiment of the present technology.

Figure 240:
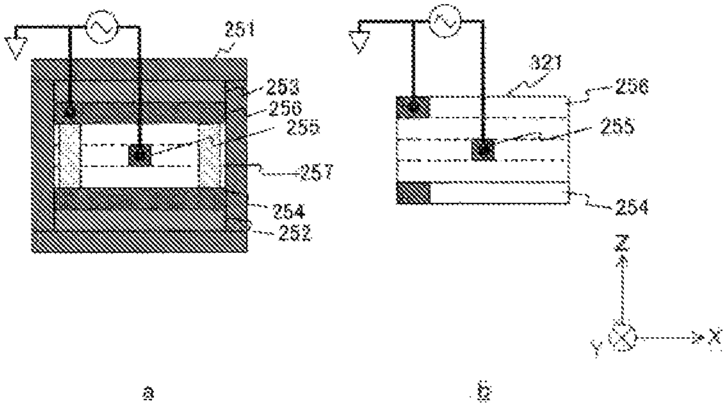

FIG. 240 is a diagram illustrating a structure of an antenna of a planar shape and a slot shape and a horizontal-direction radiation type in the first modification example of the second embodiment of the present technology.

Figure 241:
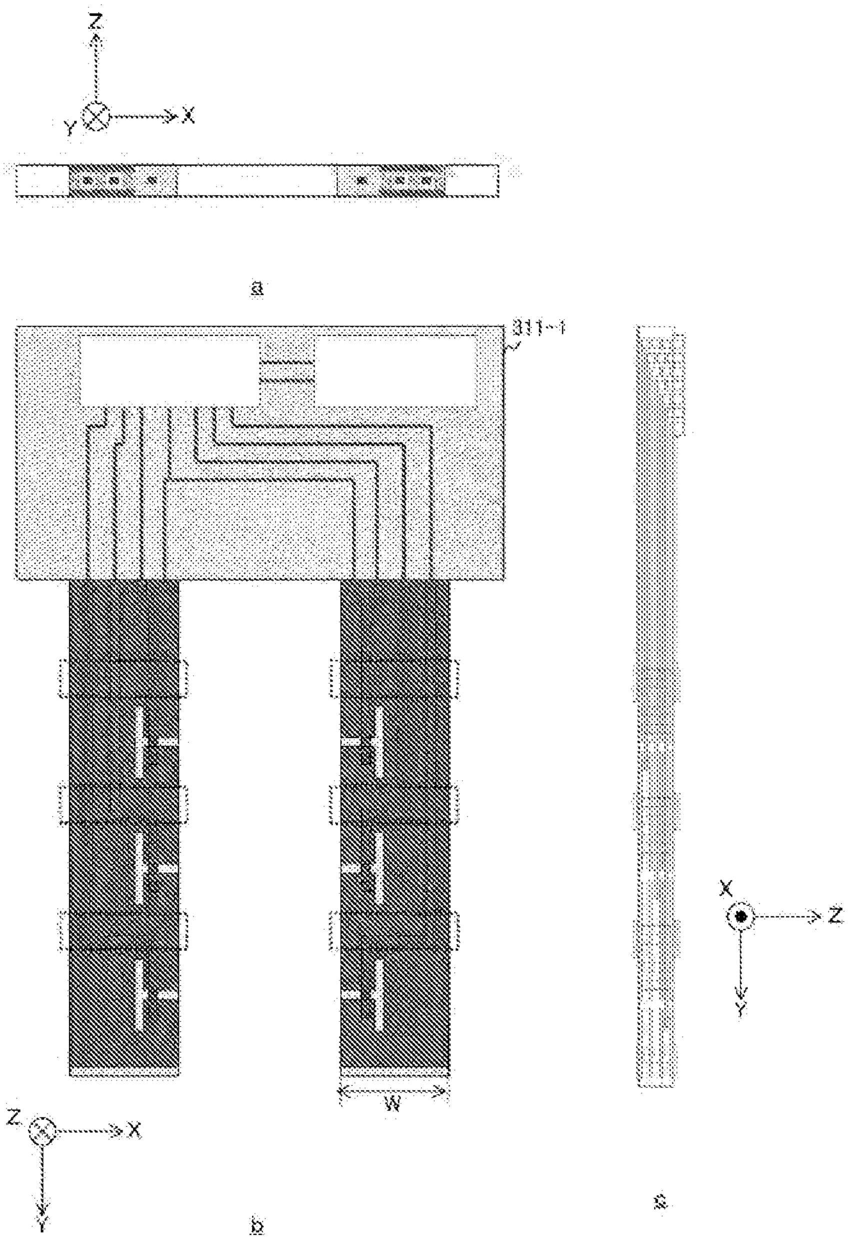

FIG. 241 is a diagram illustrating one configuration example of an electronic substrate in a second modification example of the second embodiment of the present technology.

Figure 242:
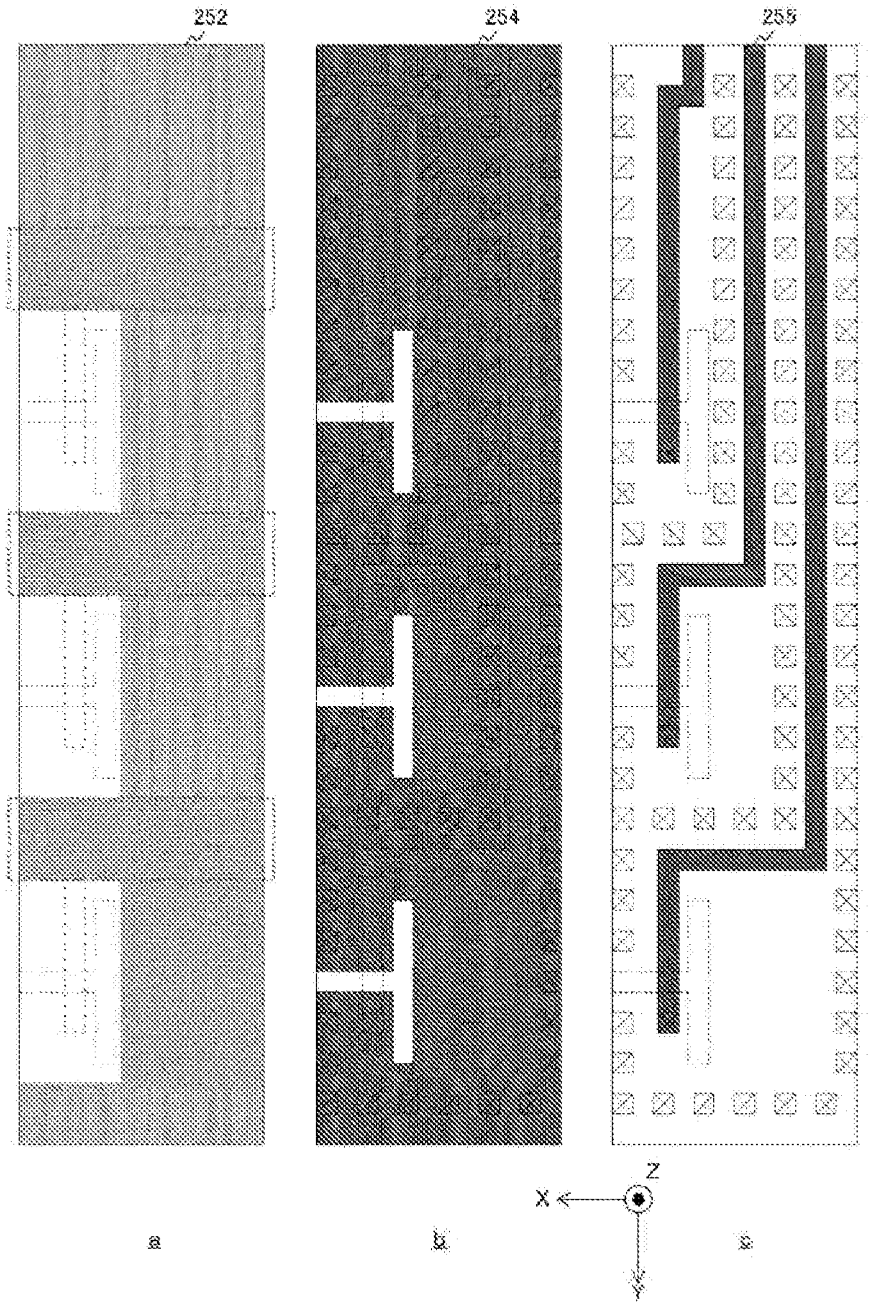

FIG. 242 is a diagram illustrating an example of a plan view of a first layer to a third layer among five layers of an electronic substrate in the first modification example of the second embodiment of the present technology.

Figure 243:
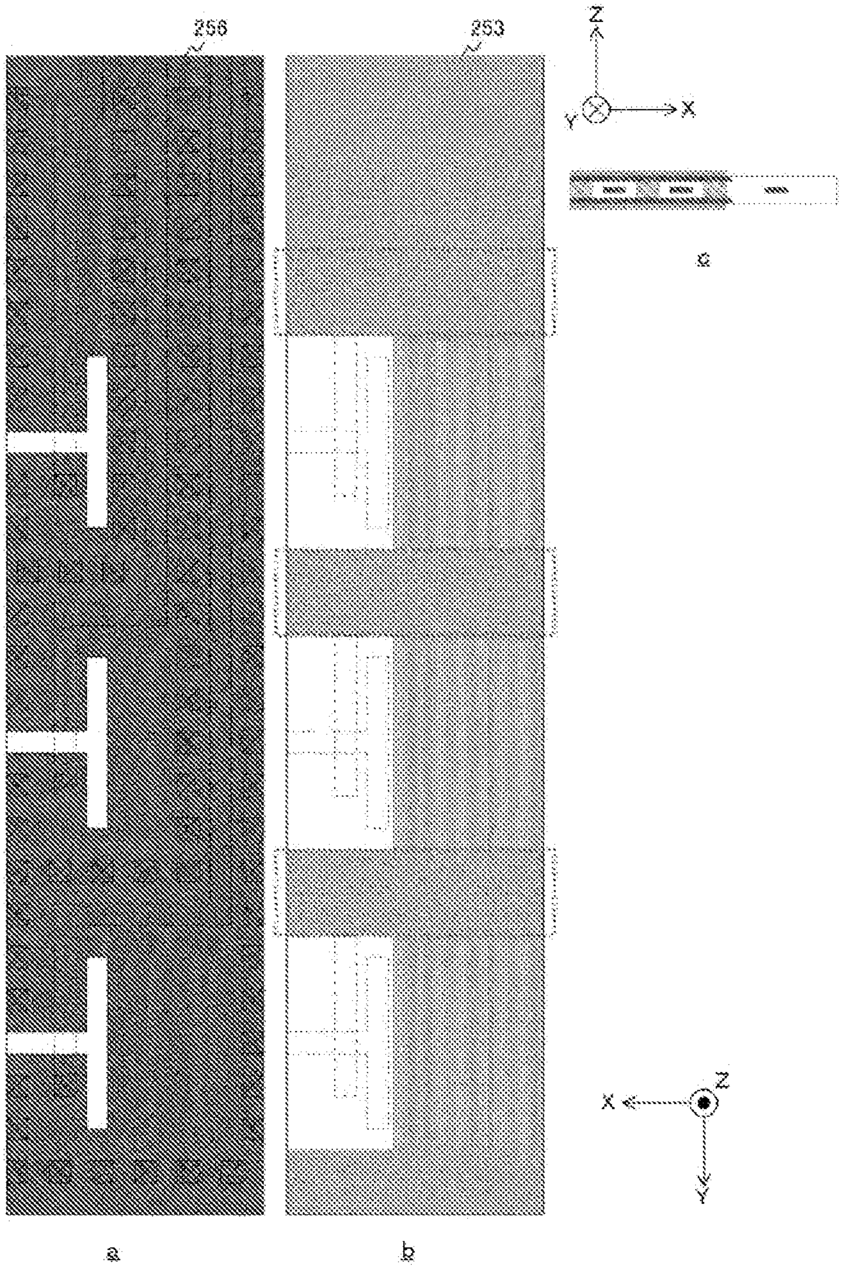

FIG. 243 is a diagram illustrating an example of a plan view and a top view of a fourth layer and a fifth layer among five layers of an electronic substrate in the first modification example of the second embodiment of the present technology.

Figure 244:
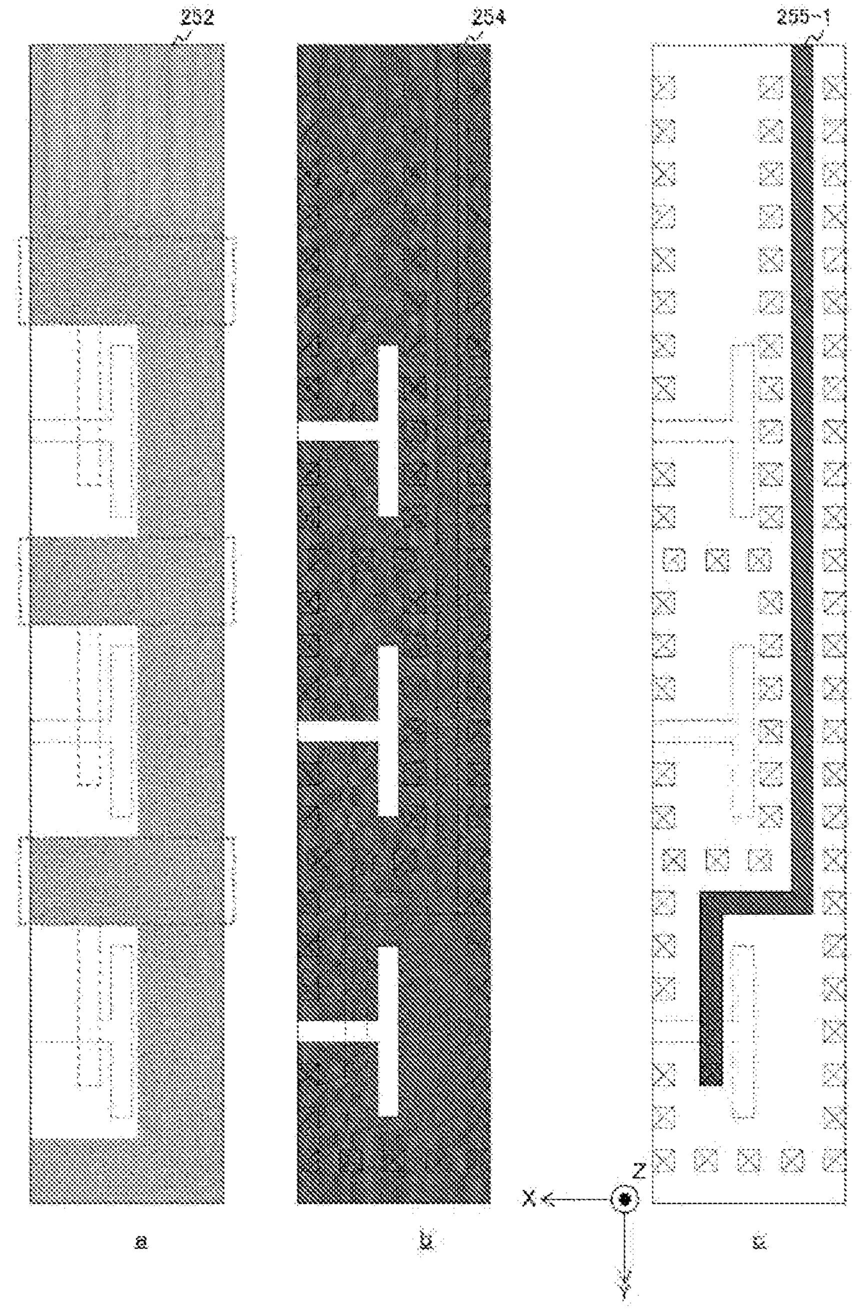

FIG. 244 is a diagram illustrating an example of a plan view of a first layer to a third layer among seven layers of an electronic substrate in the first modification example of the second embodiment of the present technology.

Figure 245:
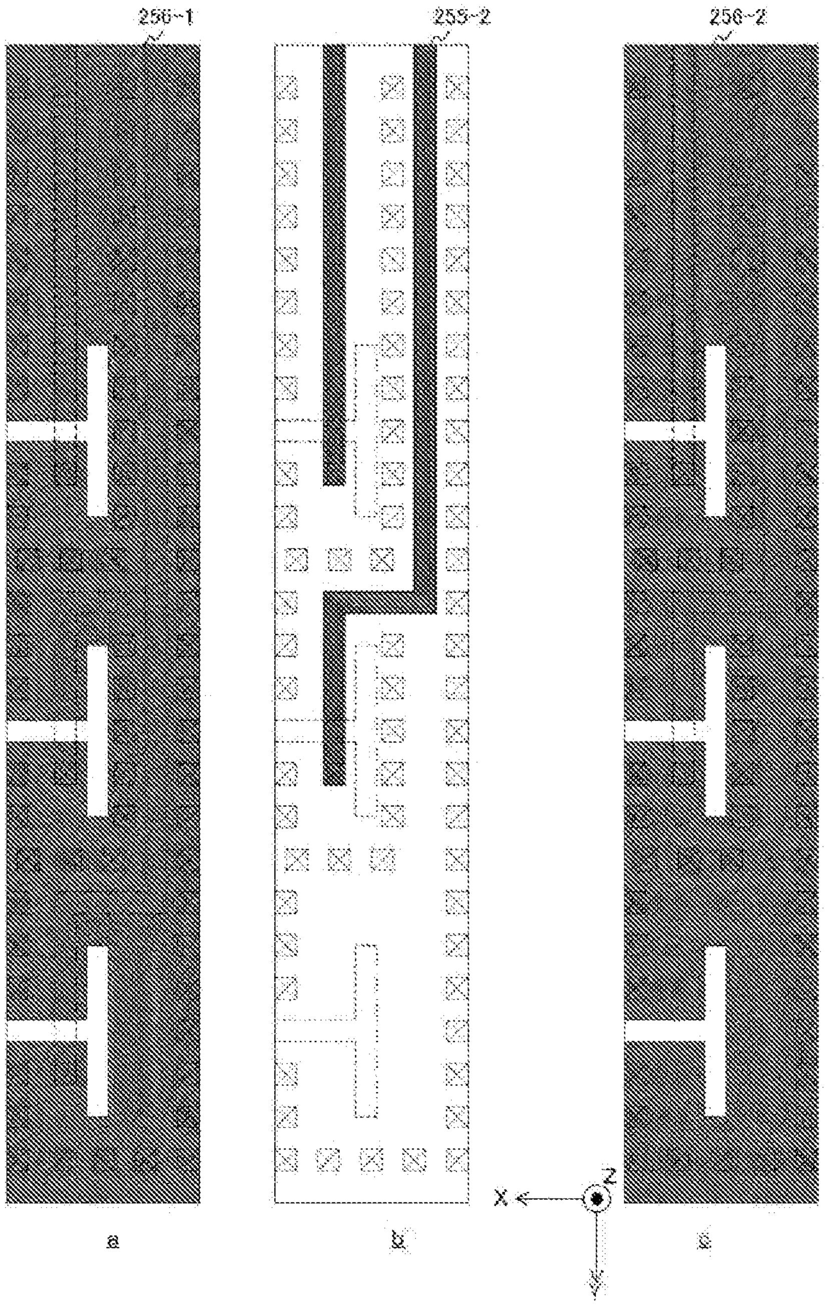

FIG. 245 is a diagram illustrating an example of a plan view of a fourth layer to a sixth layer among seven layers of an electronic substrate in the first modification example of the second embodiment of the present technology.

Figure 246:
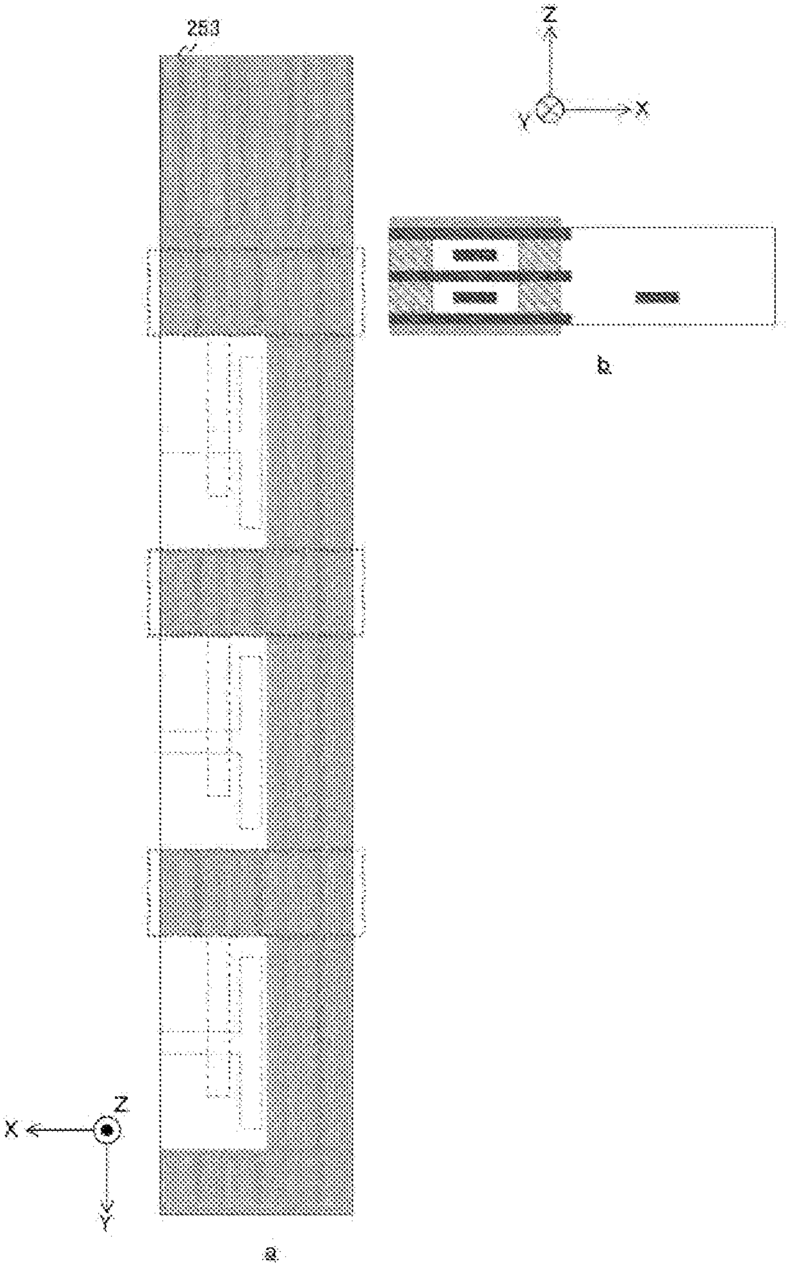

FIG. 246 is a diagram illustrating an example of a plan view and a top view of a seventh layer among seven layers of an electronic substrate in the first modification example of the second embodiment of the present technology.

Figure 247:
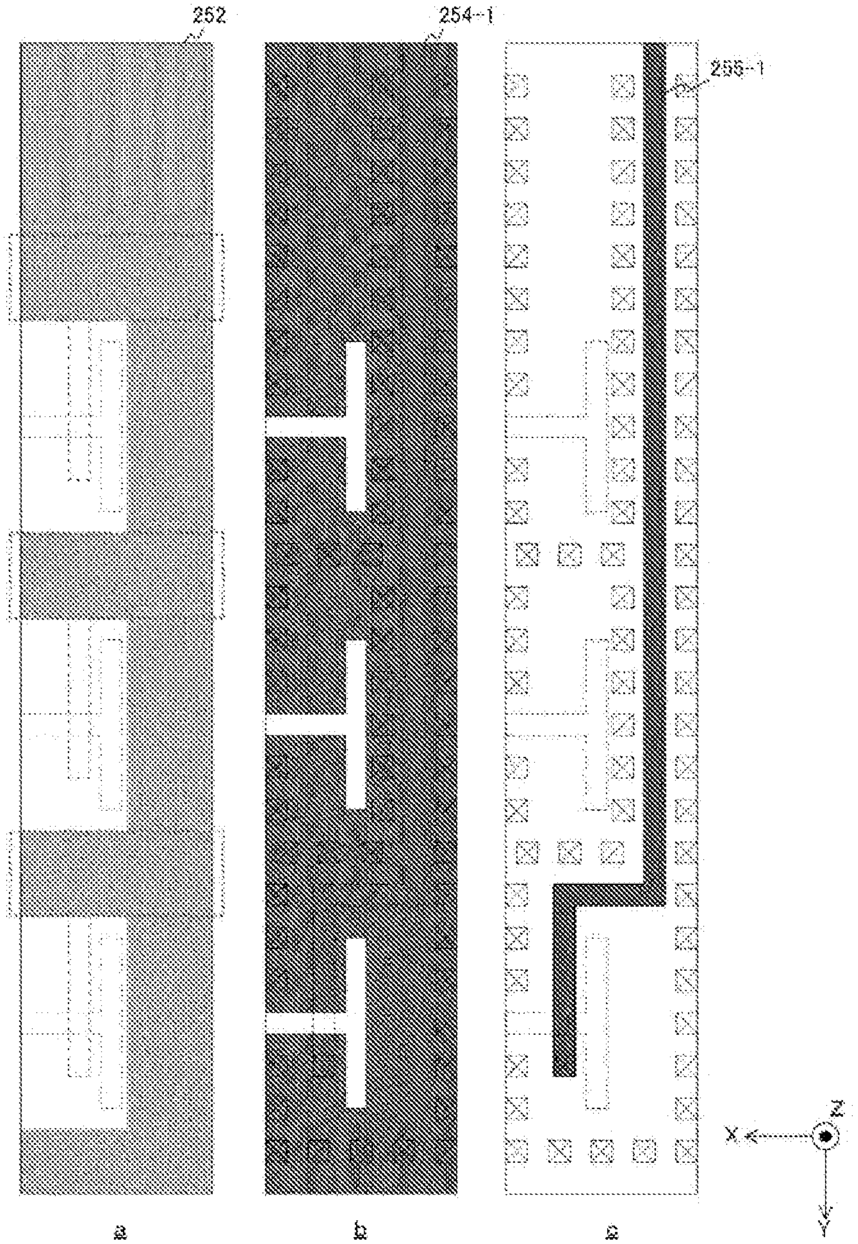

FIG. 247 is a diagram illustrating an example of a plan view of a first layer to a third layer among nine layers of an electronic substrate in the first modification example of the second embodiment of the present technology.

Figure 248:
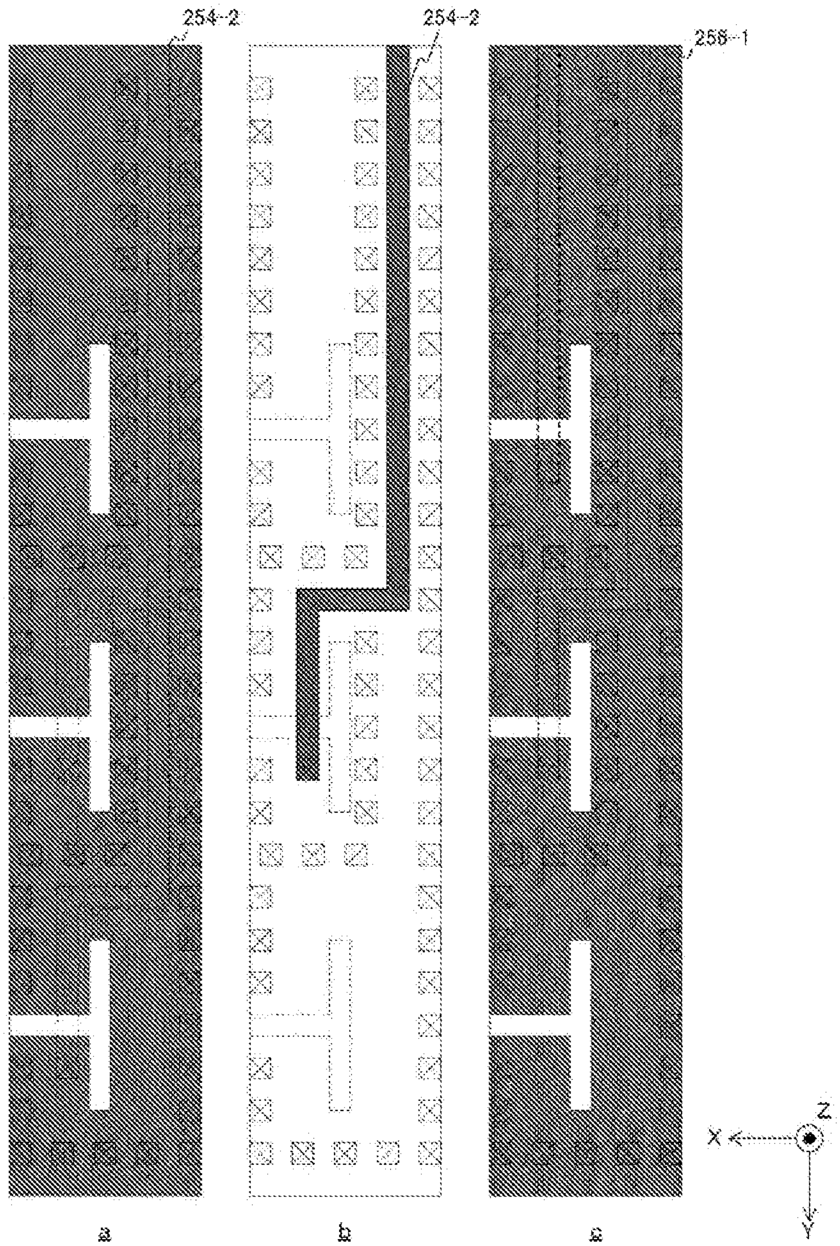

FIG. 248 is a diagram illustrating an example of a plan view of a fourth layer to a sixth layer among nine layers of an electronic substrate in the first modification example of the second embodiment of the present technology.

Figure 249:
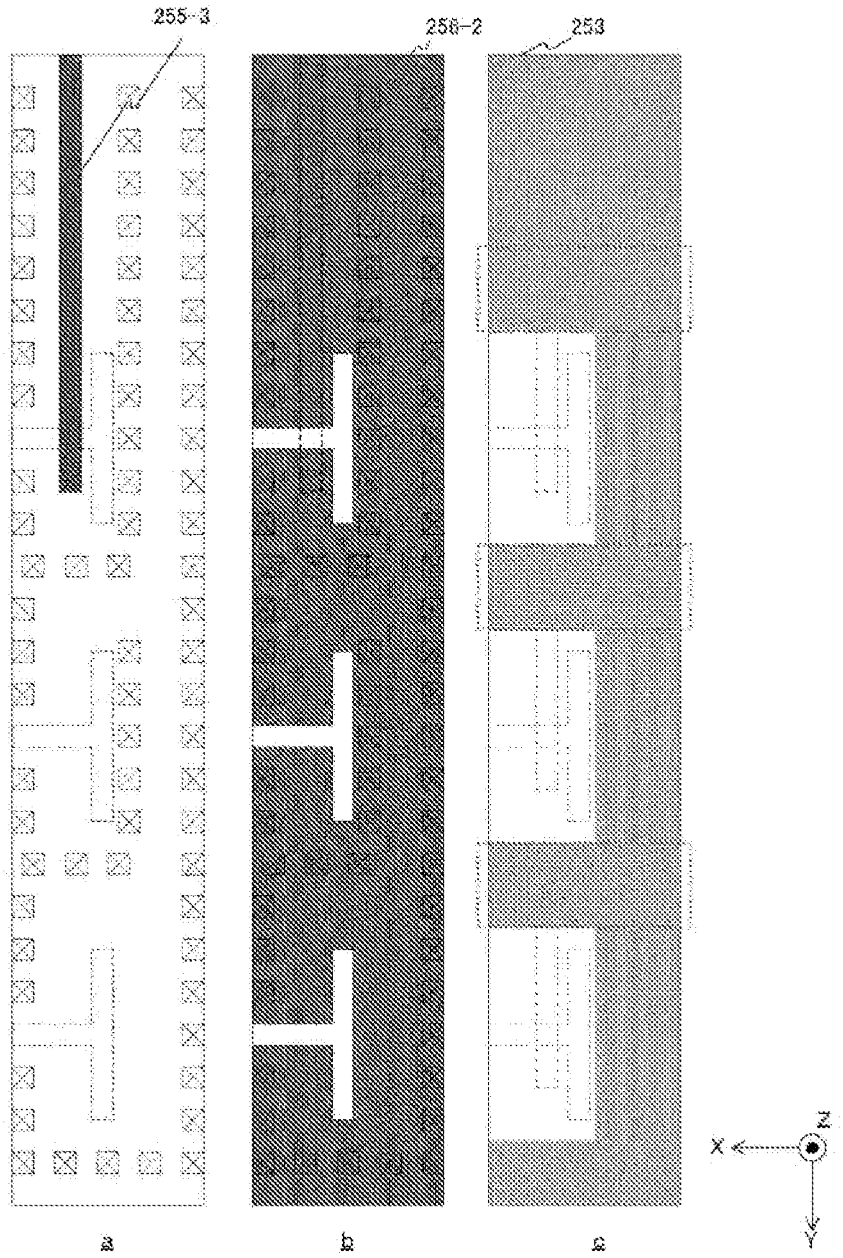

FIG. 249 is a diagram illustrating an example of a plan view of a seventh layer to a ninth layer among nine layers of an electronic substrate in the first modification example of the second embodiment of the present technology.

Figure 250:
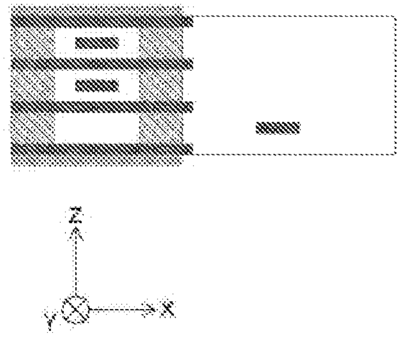

FIG. 250 is a diagram illustrating an example of a top view of an electronic substrate of nine-layer structure in the first modification example of the second embodiment of the present technology.

Figure 251:
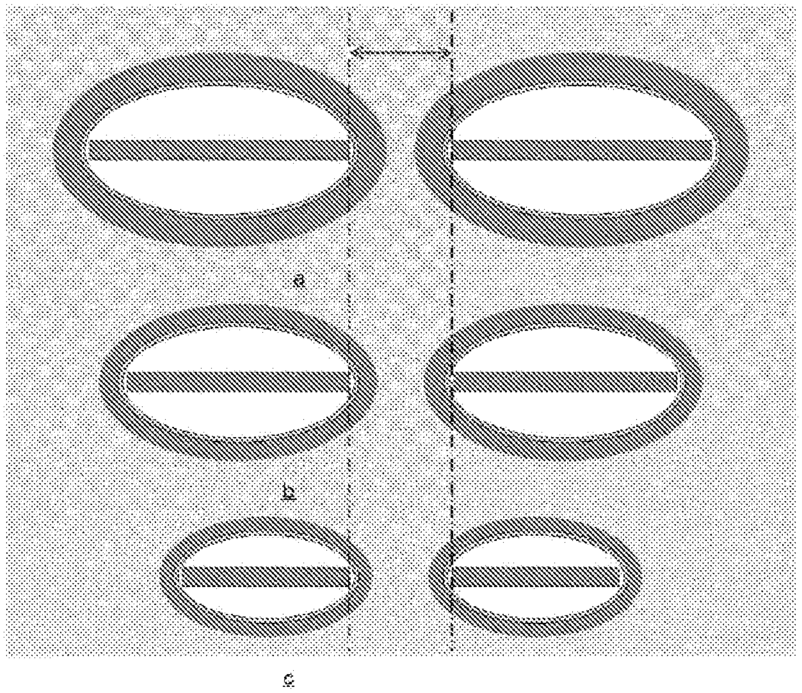

FIG. 251 is a diagram illustrating a width of a substrate in the first modification example of the second embodiment of the present technology.

Figure 252:
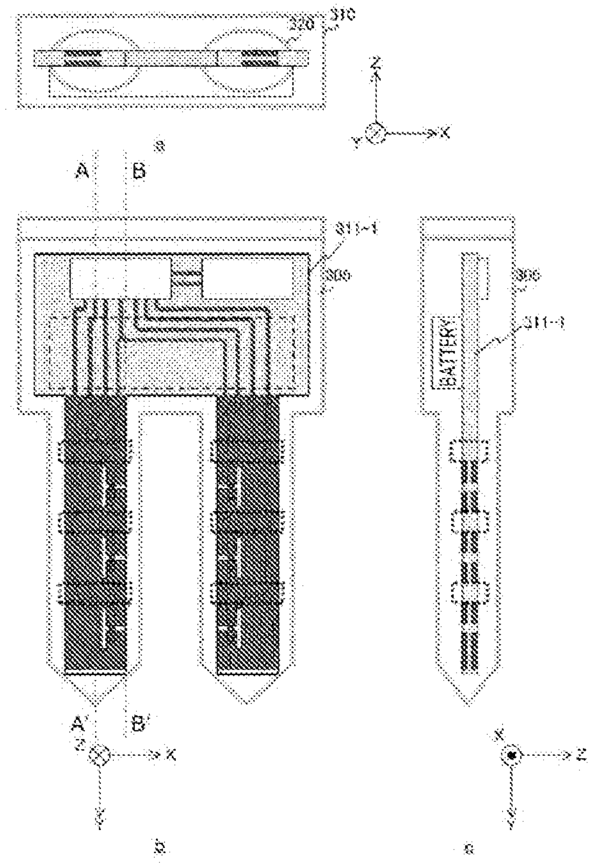

FIG. 252 is a diagram illustrating an example of a sensor device in which an in-probe substrate is butted against a sensor casing in the second modification example of the second embodiment of the present technology.

Figure 253:
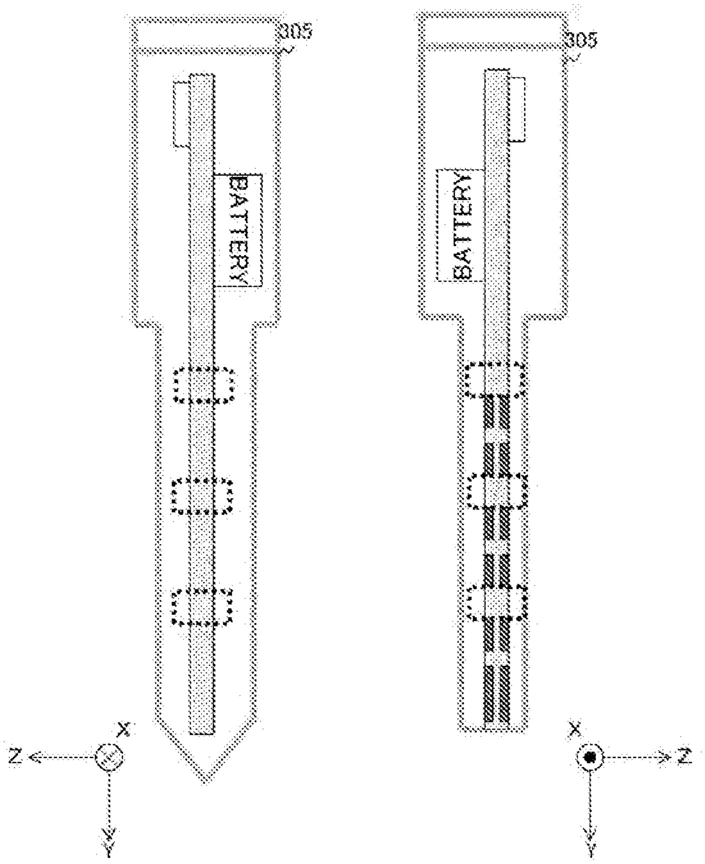

FIG. 253 is an example of a cross-sectional view of a sensor casing in the second modification example of the second embodiment of the present technology.

Figure 254:
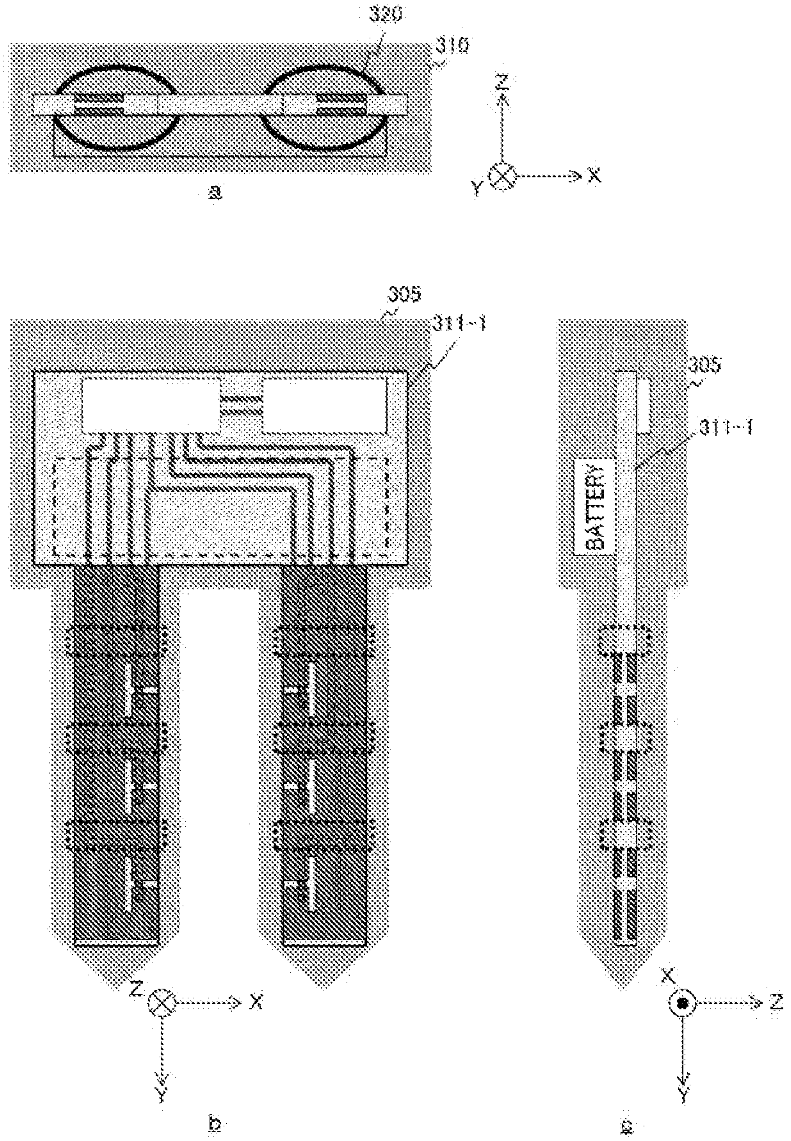

FIG. 254 is a diagram illustrating an example of a sensor device filled with a resin in a third modification example of the second embodiment of the present technology.

Figure 255:
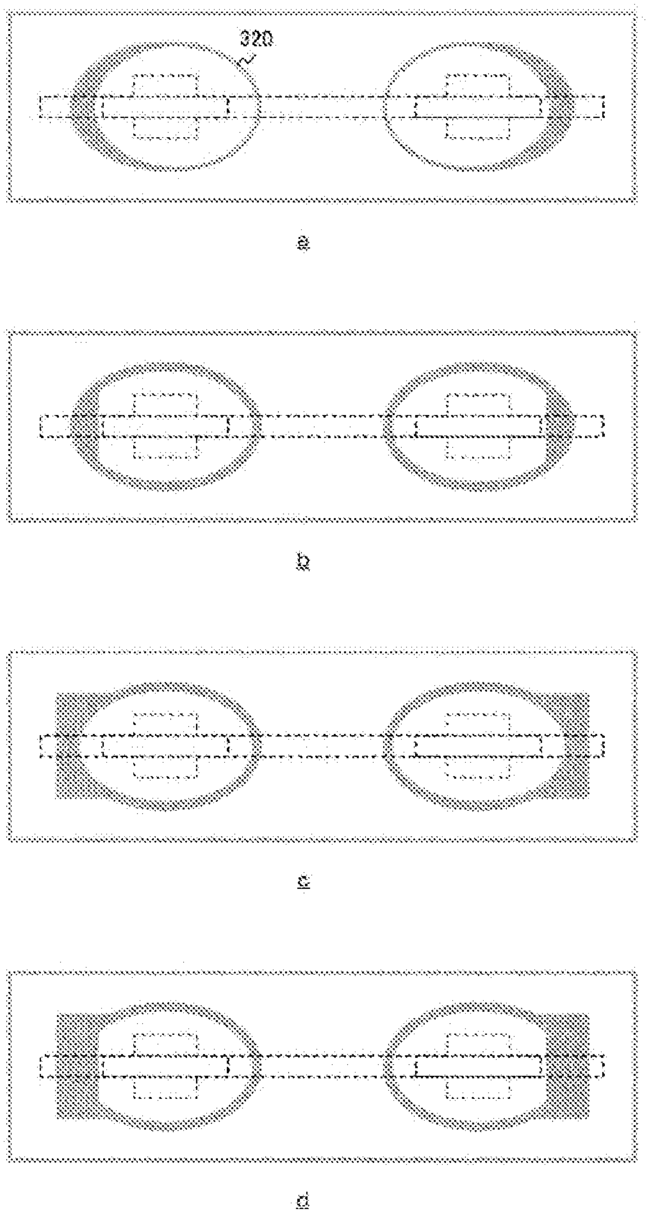

FIG. 255 is an example of a cross-sectional view of a probe casing of which a thickness in a direction parallel to an electronic substrate is thickened in two-sides radiation in a fourth modification example of the second embodiment of the present technology.

Figure 256:
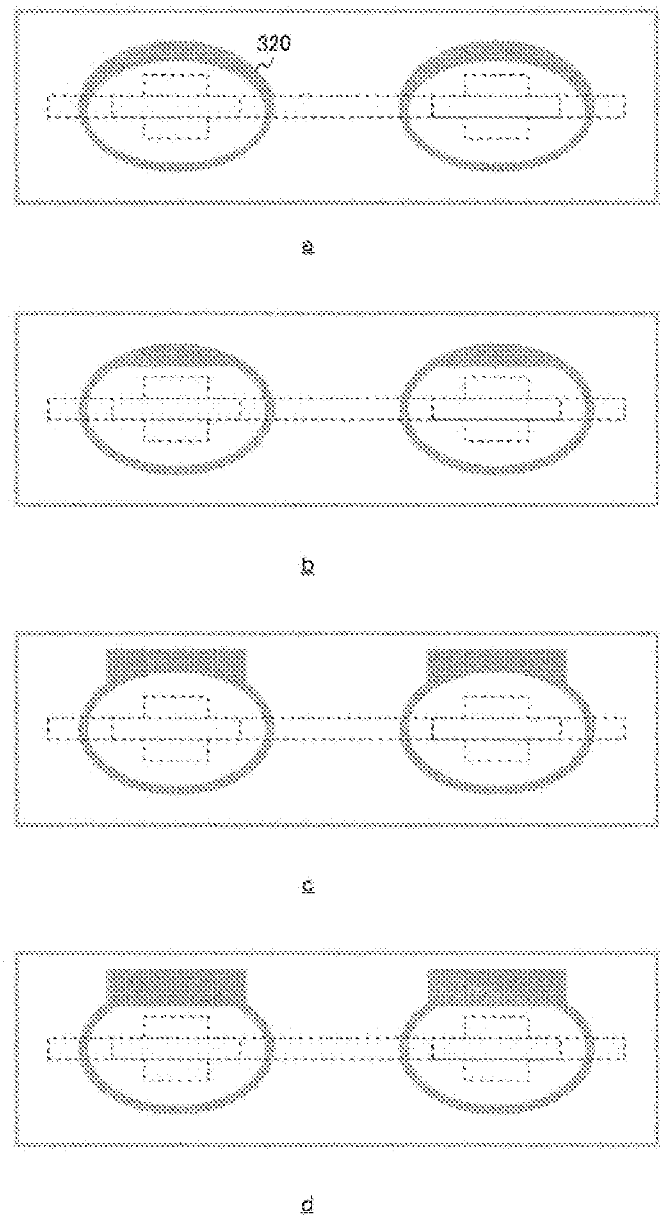

FIG. 256 is an example of a cross-sectional view of a probe casing of which a thickness in a direction perpendicular to an electronic substrate is thickened in two-sides radiation in the fourth modification example of the second embodiment of the present technology.

Figure 257:
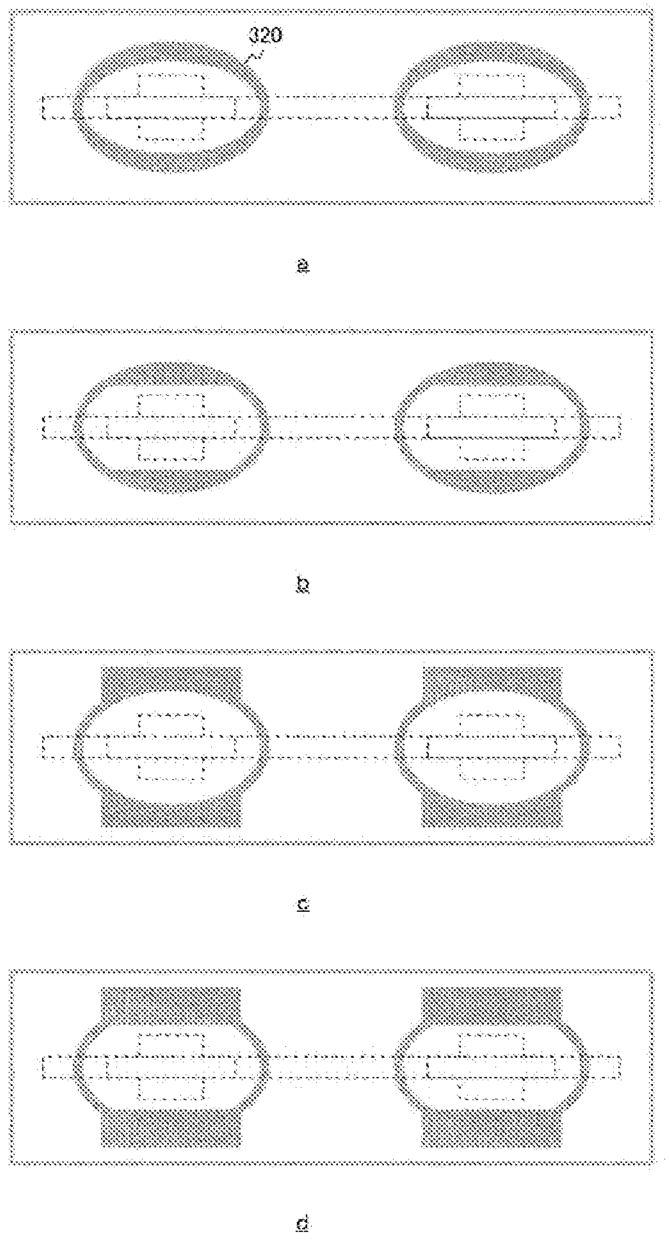

FIG. 257 is another example of a cross-sectional view of a probe casing of which a thickness in a direction perpendicular to an electronic substrate is thickened in two-sides radiation in the fourth modification example of the second embodiment of the present technology.

FIG. 258 is another example of a cross-sectional view of a probe casing of which a thickness in a direction parallel to an electronic substrate is thickened in two-sides radiation in the fourth modification example of the second embodiment of the present technology.

FIG. 259 is an example of a cross-sectional view of a probe casing of which a thickness in a direction perpendicular to an electronic substrate and an outer side is thickened in two-sides radiation in the fourth modification example of the second embodiment of the present technology.

FIG. 260 is an example of a cross-sectional view of a probe casing of which a thickness in a direction parallel to an electronic substrate is thickened in two-sides radiation in the fourth modification example of the second embodiment of the present technology.

FIG. 261 is an example of a cross-sectional view of a probe casing of which a thickness in a direction perpendicular to an electronic substrate is thickened in two-sides radiation in the fourth modification example of the second embodiment of the present technology.

Figure 262:
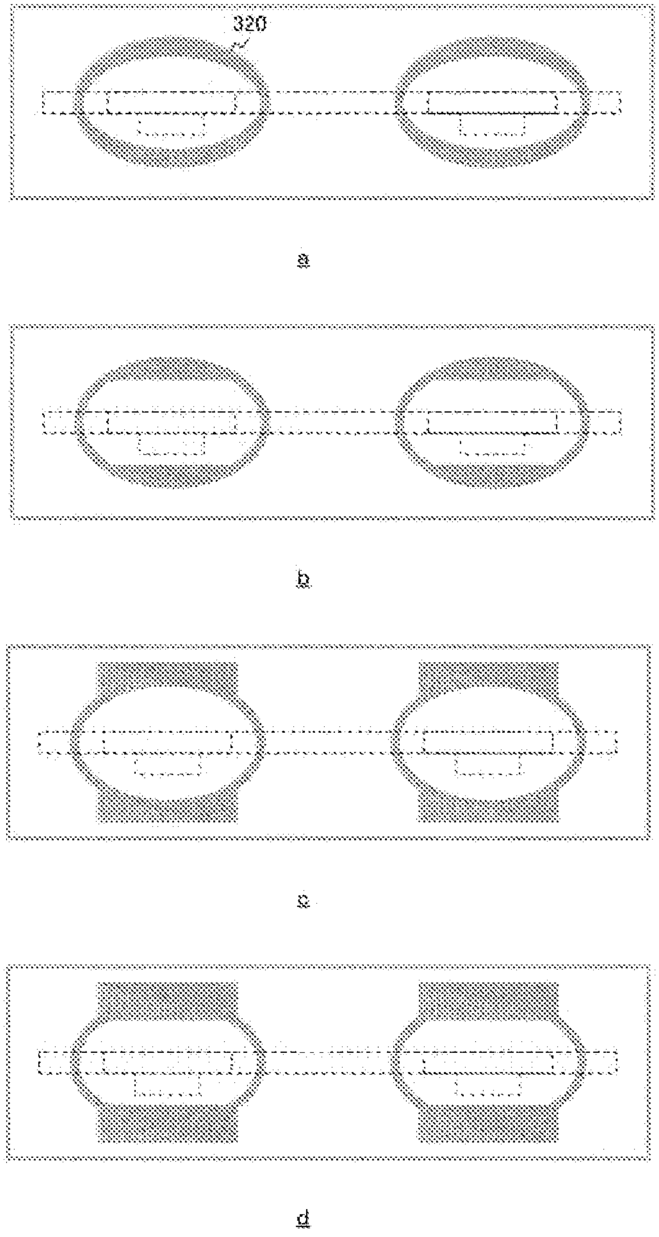

FIG. 262 is another example of a cross-sectional view of a probe casing of which a thickness in a direction perpendicular to an electronic substrate is thickened in two-sides radiation in the fourth modification example of the second embodiment of the present technology.

FIG. 263 is another example of a cross-sectional view of a probe casing of which a thickness in a direction parallel to an electronic substrate is thickened in two-sides radiation in the fourth modification example of the second embodiment of the present technology.

Figure 264:
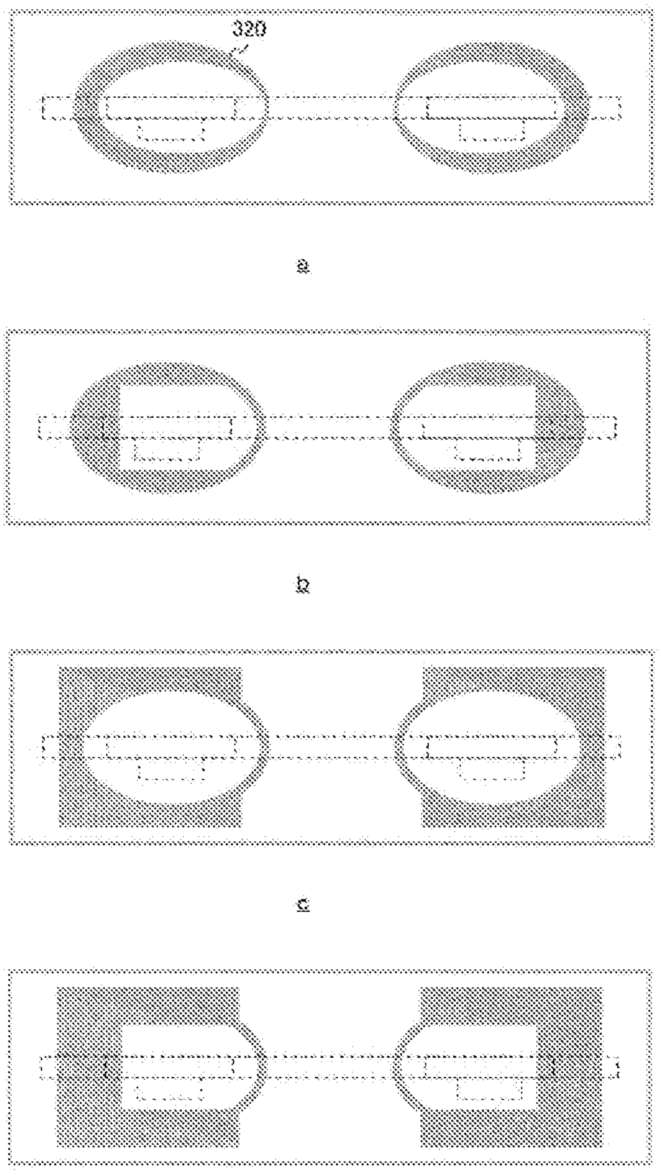

FIG. 264 is an example of a cross-sectional view of a probe casing of which a thickness in a direction perpendicular to an in-probe substrate and an outer side is thickened in two-sides radiation in the fourth modification example of the second embodiment of the present technology.

Figure 265:
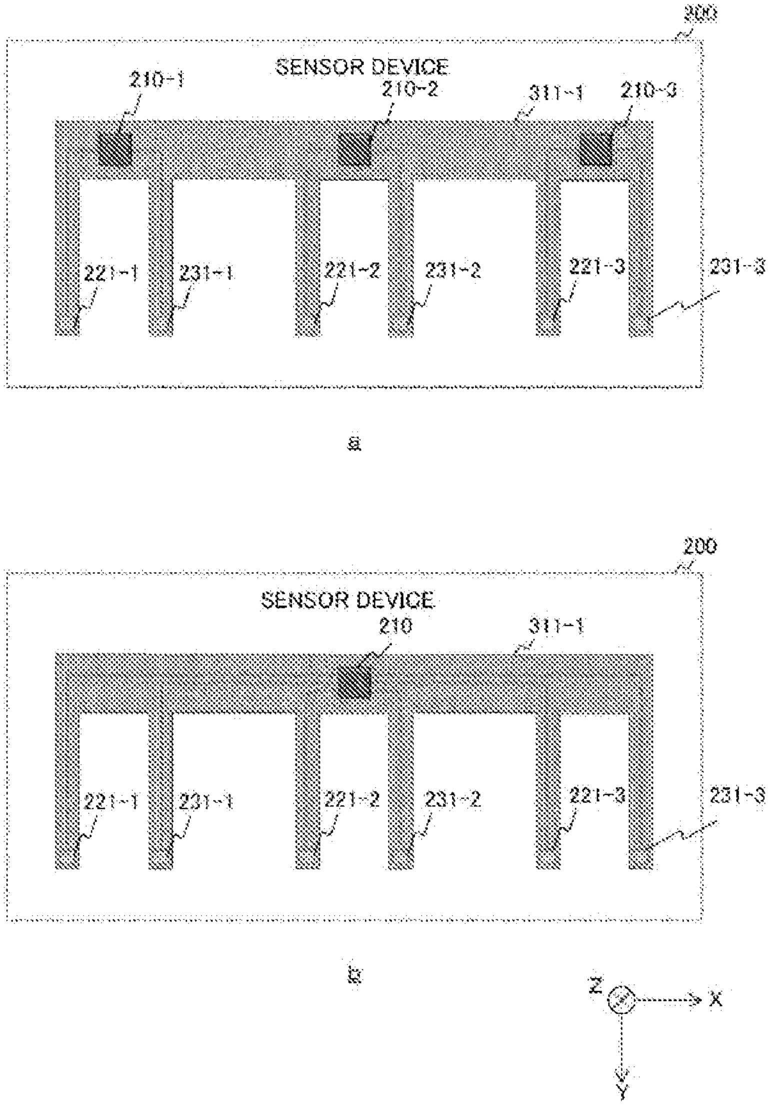

FIG. 265 is a diagram illustrating one configuration example of a sensor device in a fifth modification example of the second embodiment of the present technology.

Figure 266:
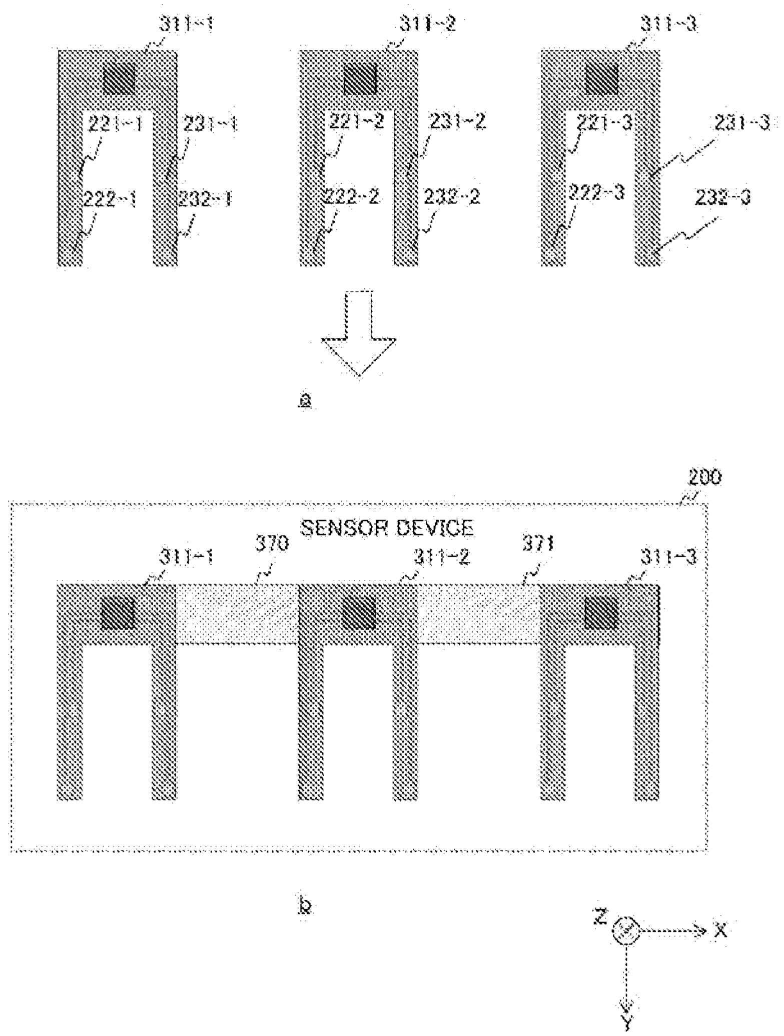

FIG. 266 is a diagram illustrating an example of a sensor device before/after connection of an electronic substrate in the fifth modification example of the second embodiment of the present technology.

FIG. 267 is a diagram illustrating one configuration example of a sensor device in which a plurality of pairs of antennas are disposed for each probe in the fifth modification example of the second embodiment of the present technology.

FIG. 268 is a diagram illustrating one configuration example of a sensor device in which lengths of antennas are different for each probe pair in the fifth modification example of the second embodiment of the present technology.

FIG. 269 is a diagram illustrating one configuration example of a sensor device in which a transmission antenna is shared by a plurality of reception antennas in the fifth modification example of the second embodiment of the present technology.

Figure 270:
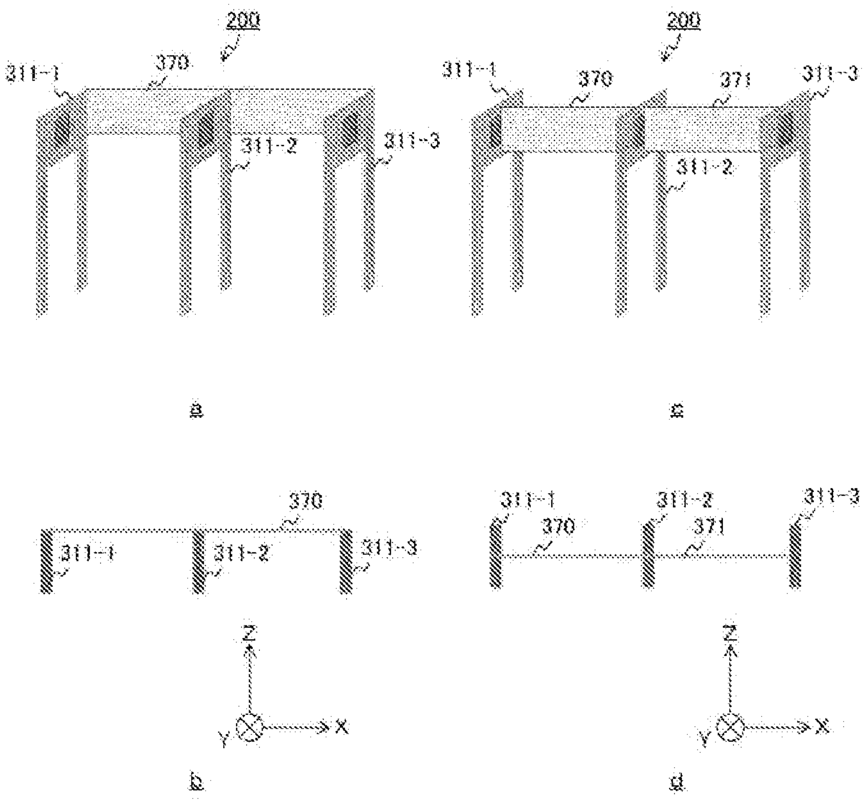

FIG. 270 is a diagram illustrating one configuration example of a sensor device in which substrate faces of an electronic substrate face each other in the fifth modification example of the second embodiment of the present technology.

Figure 271:
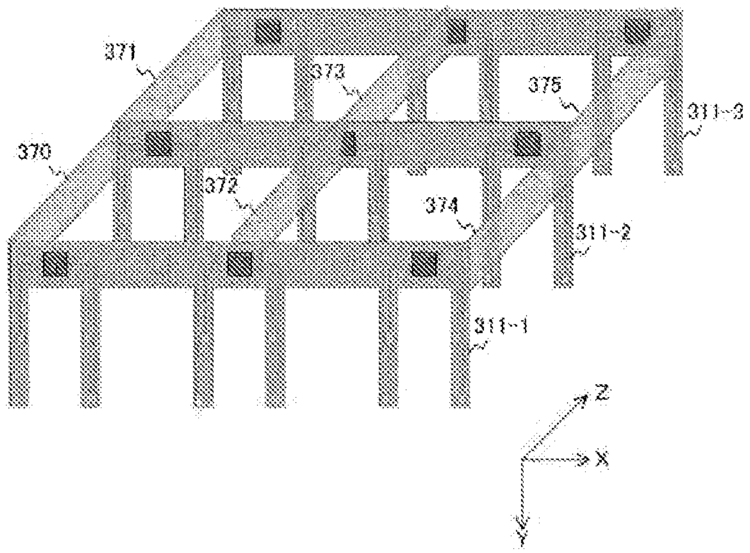

FIG. 271 is a diagram illustrating one configuration example of a sensor device measuring a plurality of positions arranged in a two-dimensional lattice shape in the fifth modification example of the second embodiment of the present technology.

Figure 272:
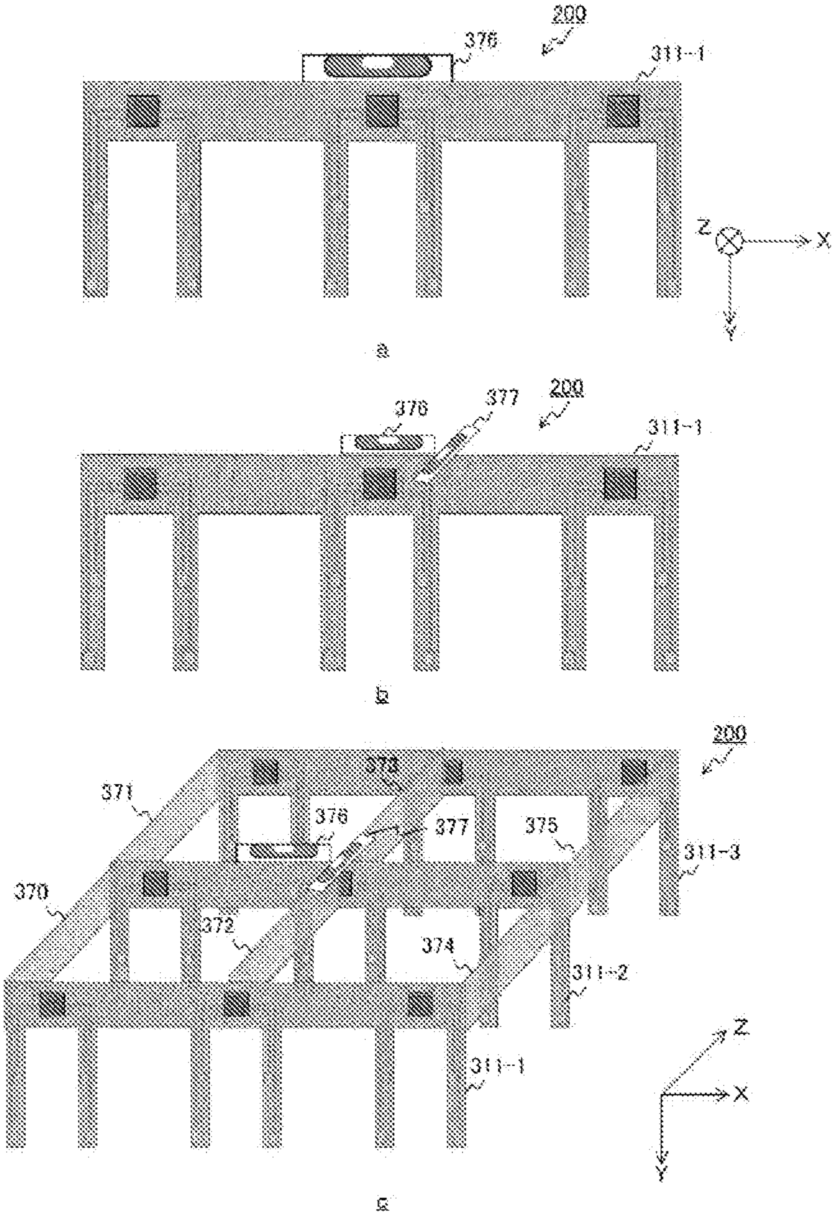

FIG. 272 is a diagram illustrating one configuration example of a sensor device in which a level is added in the fifth modification example of the second embodiment of the present technology.

FIG. 273 is a diagram illustrating one configuration example of a sensor device in which transmission/reception directions of electromagnetic waves intersect with each other in the fifth modification example of the second embodiment of the present technology.

Figure 274:
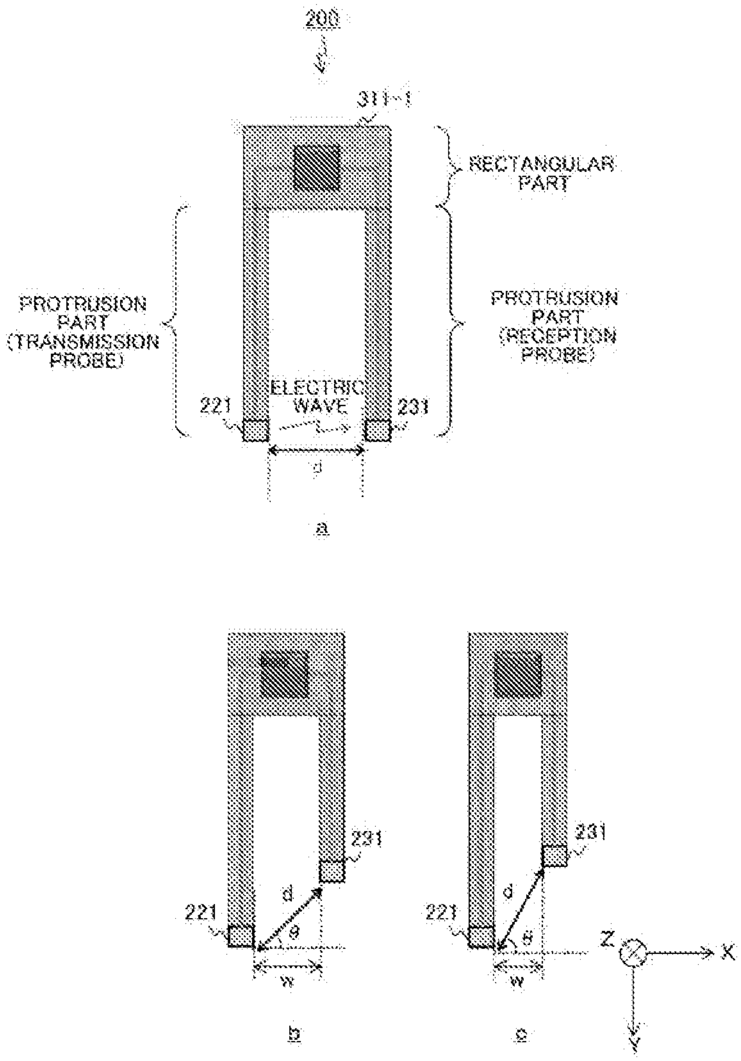

FIG. 274 is a diagram illustrating an effect acquired when positions of antennas are configured to be asymmetrical in a sixth modification example of the second embodiment of the present technology.

Figure 275:
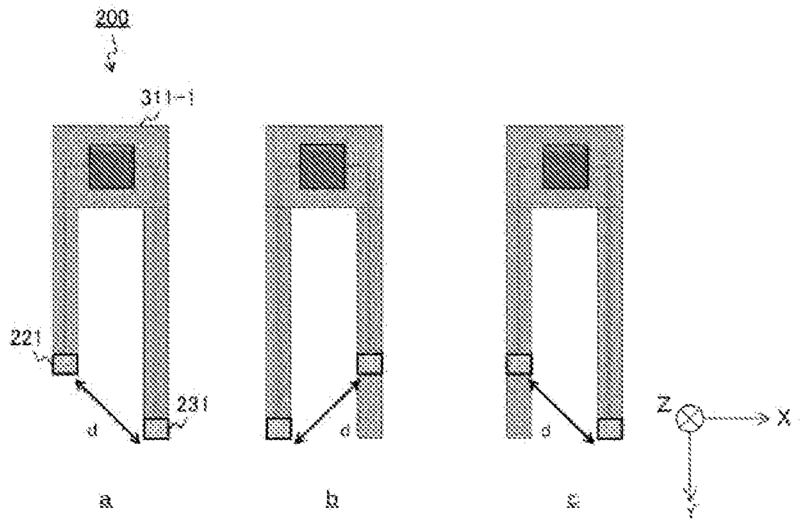

FIG. 275 is a diagram illustrating one configuration example of a sensor device in the sixth modification example of the second embodiment of the present technology.

Figure 276:
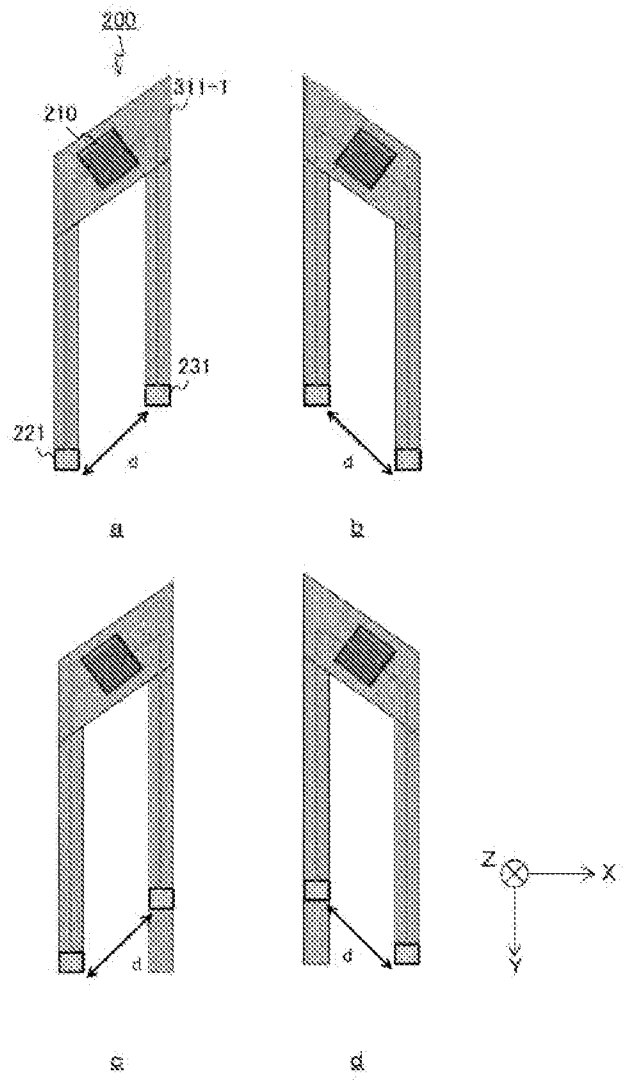

FIG. 276 is a diagram illustrating one configuration example of a sensor device in which a rectangular part is formed in a parallelogram shape in the sixth modification example of the second embodiment of the present technology.

Figure 277:
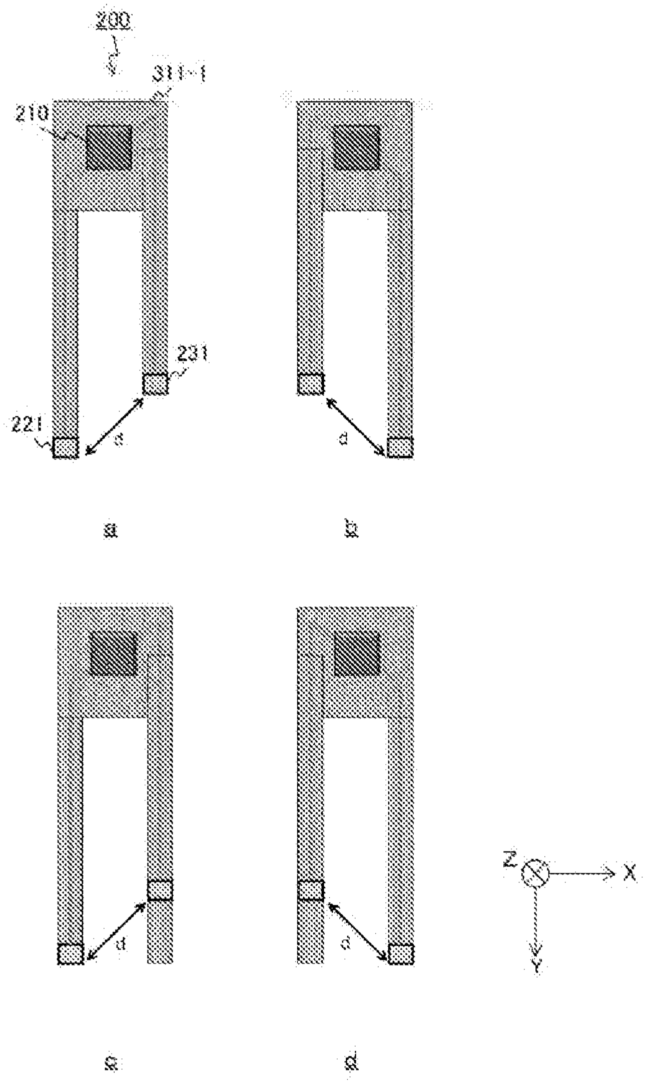

FIG. 277 is a diagram illustrating one configuration example of a sensor device in which a quadrangle part is formed in rectangular shape, and lengths of transmission lines on a transmission side and a reception side coincide with each other in the sixth modification example of the second embodiment of the present technology.

Figure 278:
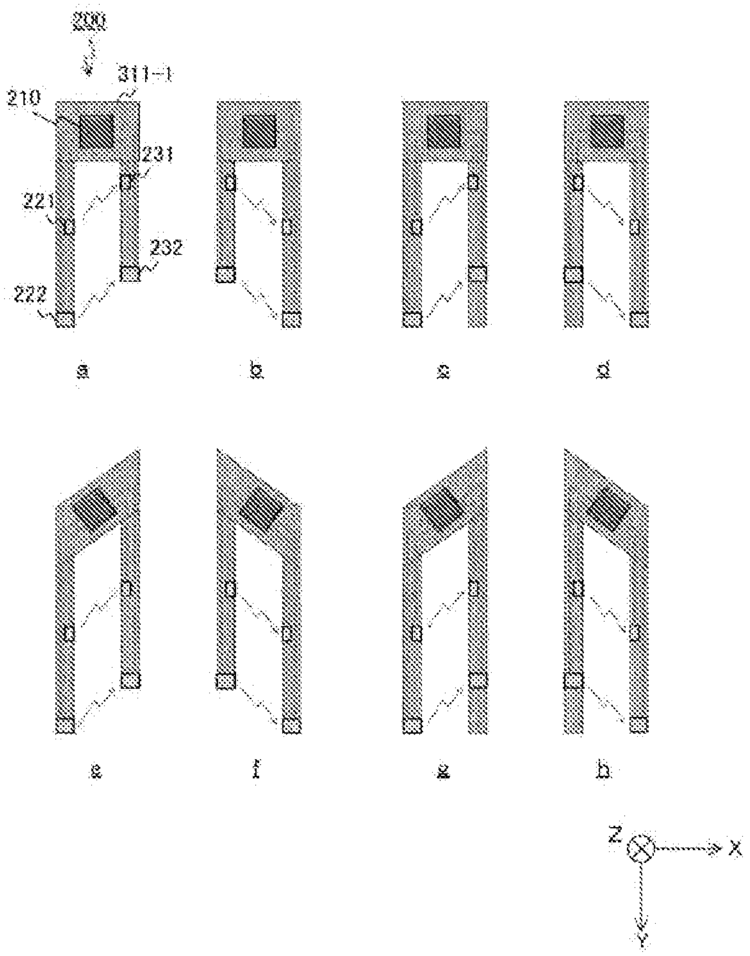

FIG. 278 is a diagram illustrating one configuration example of a sensor device measuring a plurality of points in the sixth modification example of the second embodiment of the present technology.

Figure 279:
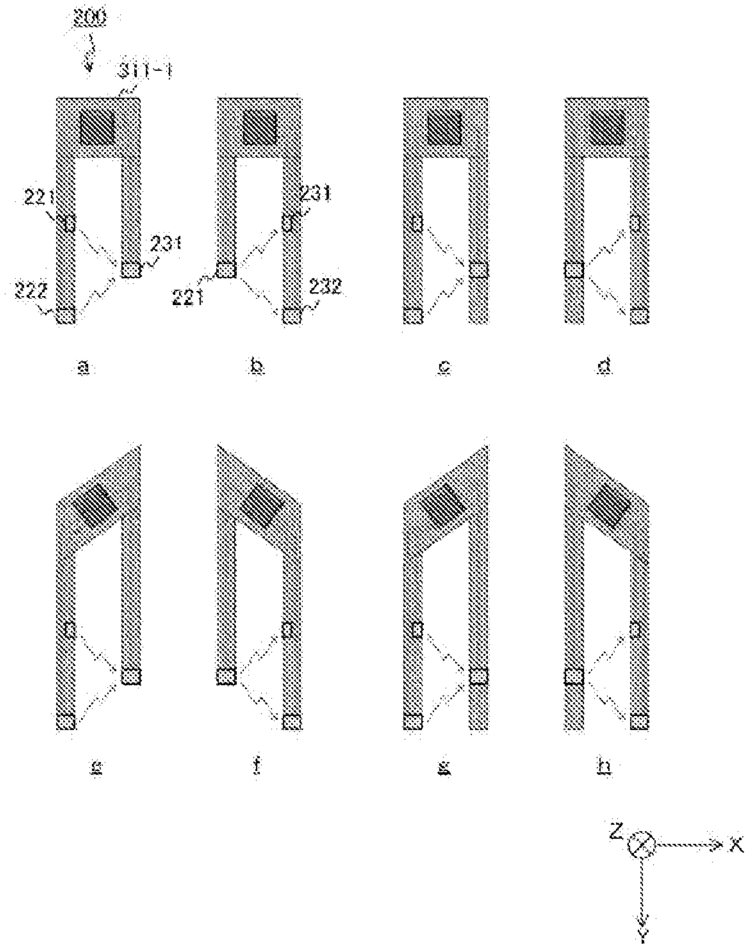

FIG. 279 is a diagram illustrating one configuration example of a sensor device measuring two points by sharing an antenna in the sixth modification example of the second embodiment of the present technology.

Figure 280:
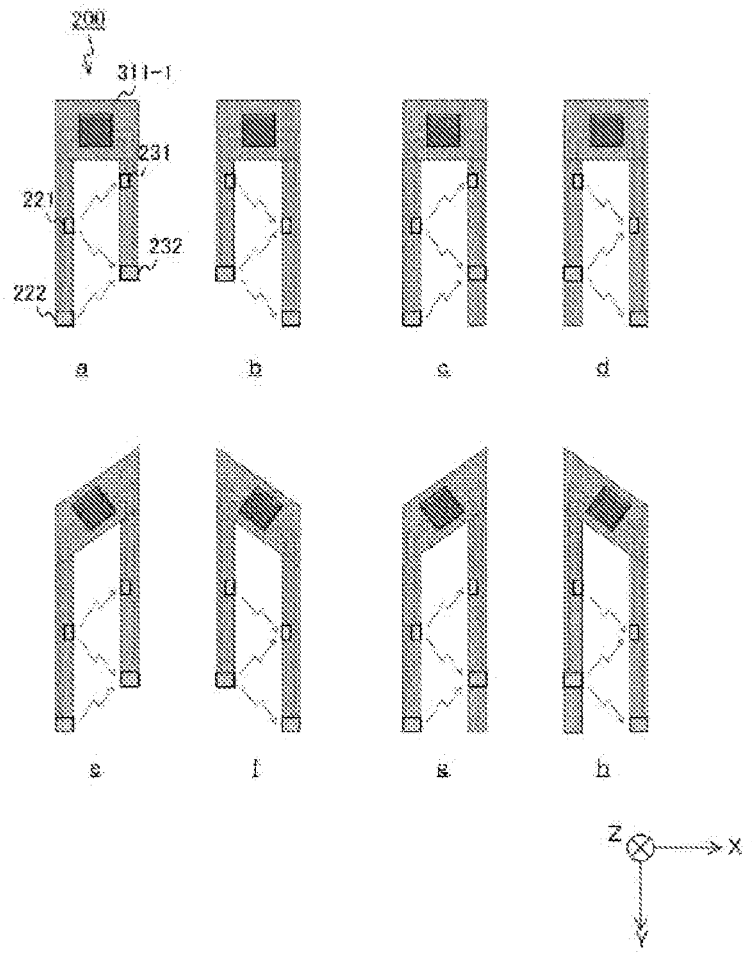

FIG. 280 is a diagram illustrating one configuration example of a sensor device measuring three or more points by sharing an antenna in the sixth modification example of the second embodiment of the present technology.

Figure 281:
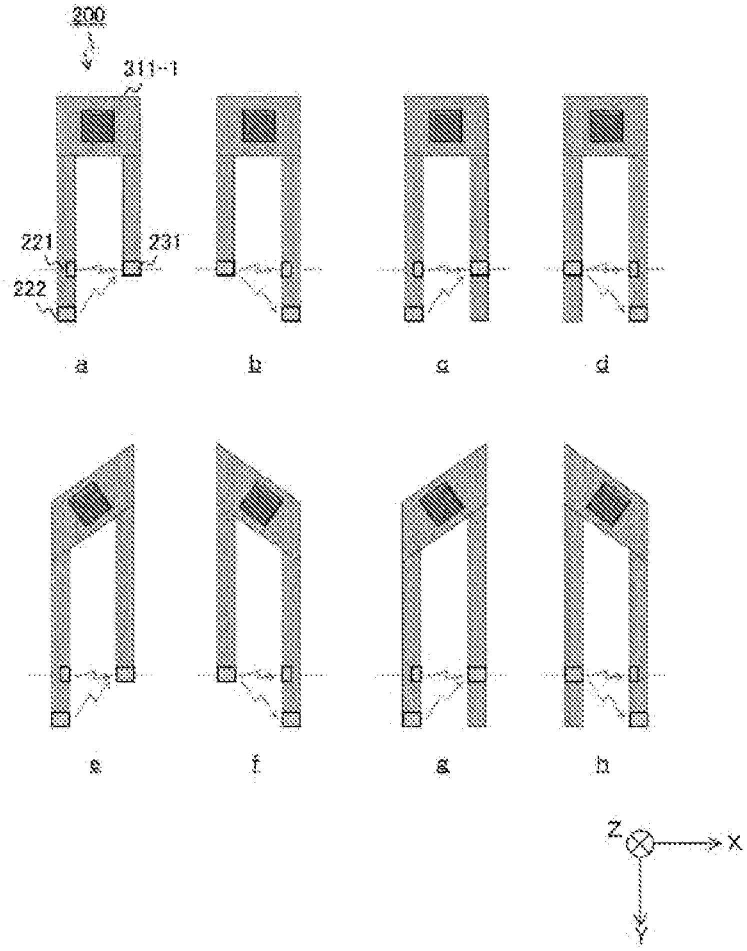

FIG. 281 is a diagram illustrating another example of a sensor device measuring two points by sharing an antenna in the sixth modification example of the second embodiment of the present technology.

Figure 282:
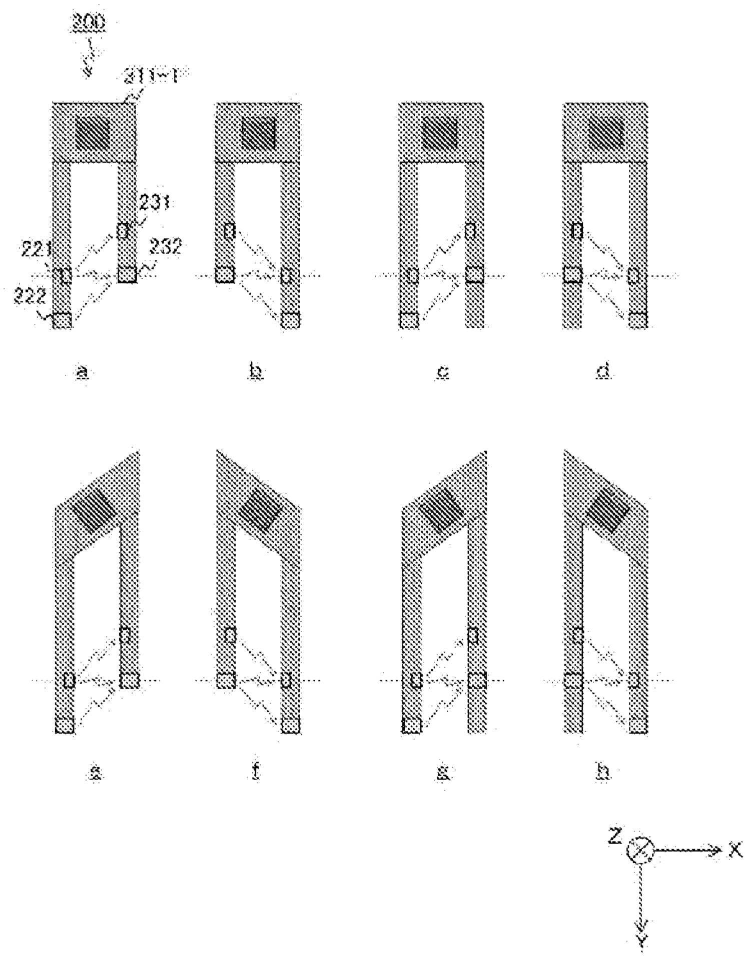

FIG. 282 is a diagram illustrating another example of a sensor device measuring three or more points by sharing an antenna in the sixth modification example of the second embodiment of the present technology.

Figure 283:
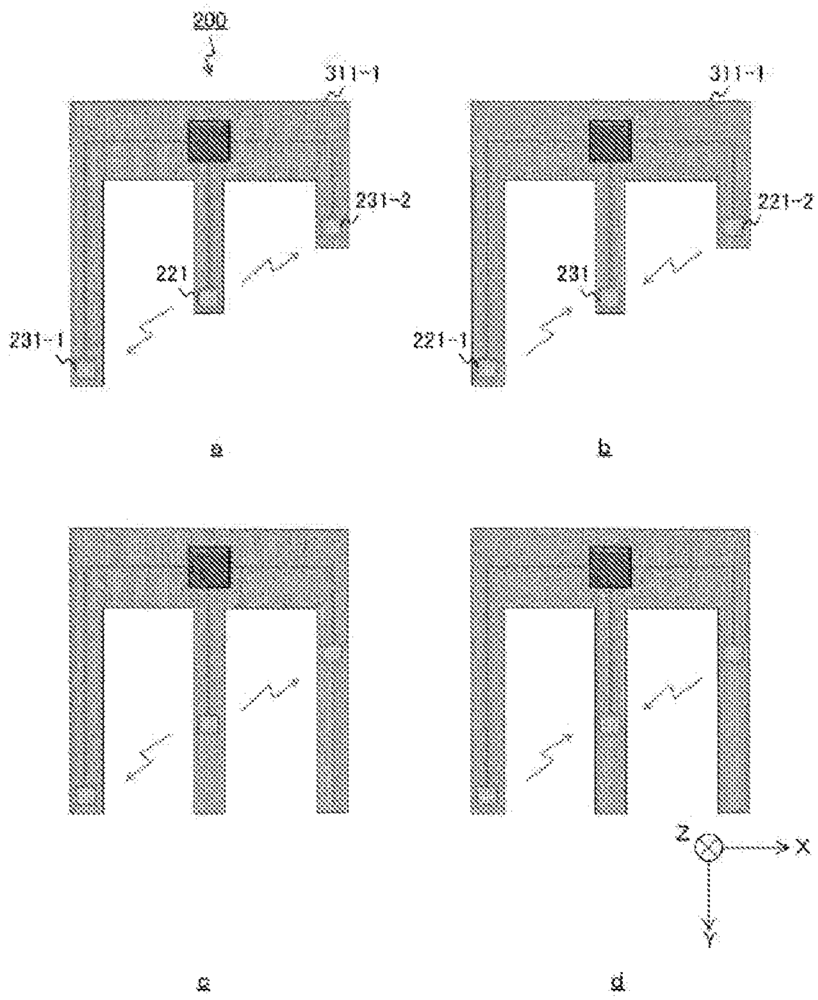

FIG. 283 is a diagram illustrating one configuration example of a sensor device in which the number of probes is increased in the sixth modification example of the second embodiment of the present technology.

Figure 284:
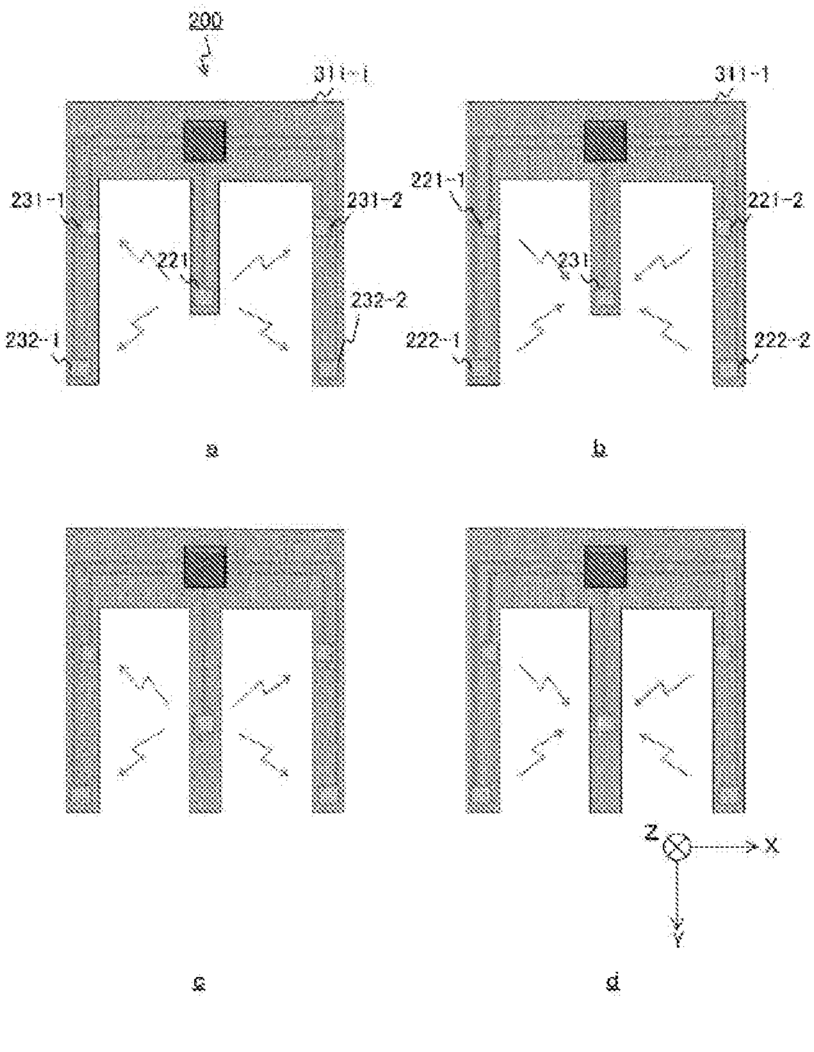

FIG. 284 is a diagram illustrating one configuration example of a sensor device in which the number of probes and the number of antennas are increased in the sixth modification example of the second embodiment of the present technology.

FIG. 285 is a diagram illustrating an example of a sensor device according to a third embodiment of the present technology.

Figure 286:
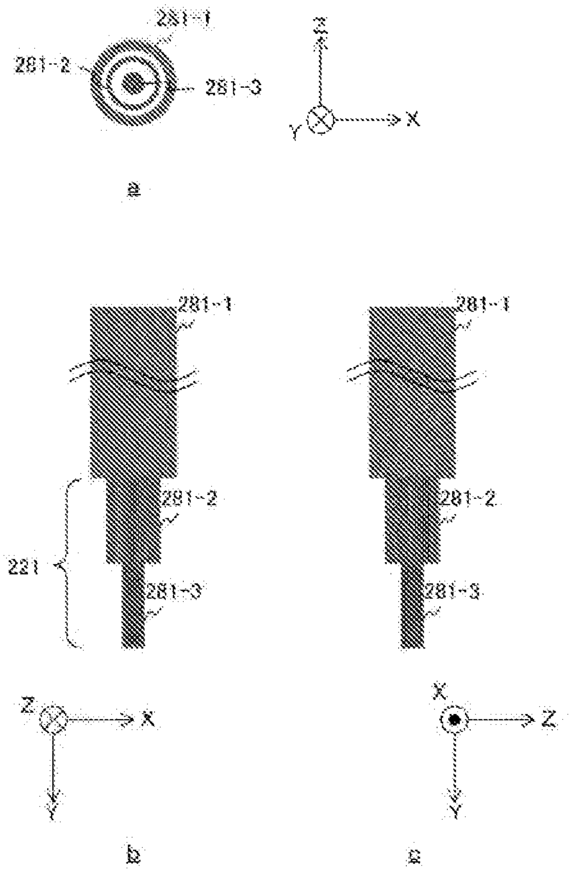

FIG. 286 is an example of a cross-sectional view and a side view of an antenna in the third embodiment of the present technology.

FIG. 287 is an example of a cross-sectional view of a coaxial cable in the third embodiment of the present technology.

FIG. 288 is a diagram illustrating an example of a sensor device in which the number of antennas is reduced in the third embodiment of the present technology.

Figure 289:
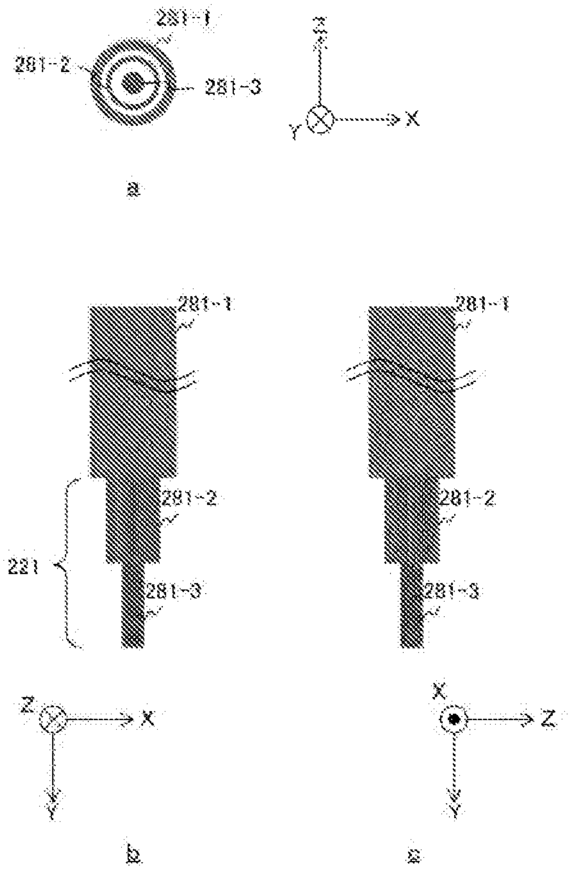

FIG. 289 is an example of a cross-sectional view and a side view of antennas acquired when the number of antennas is reduced in the third embodiment of the present technology.

Figure 290:
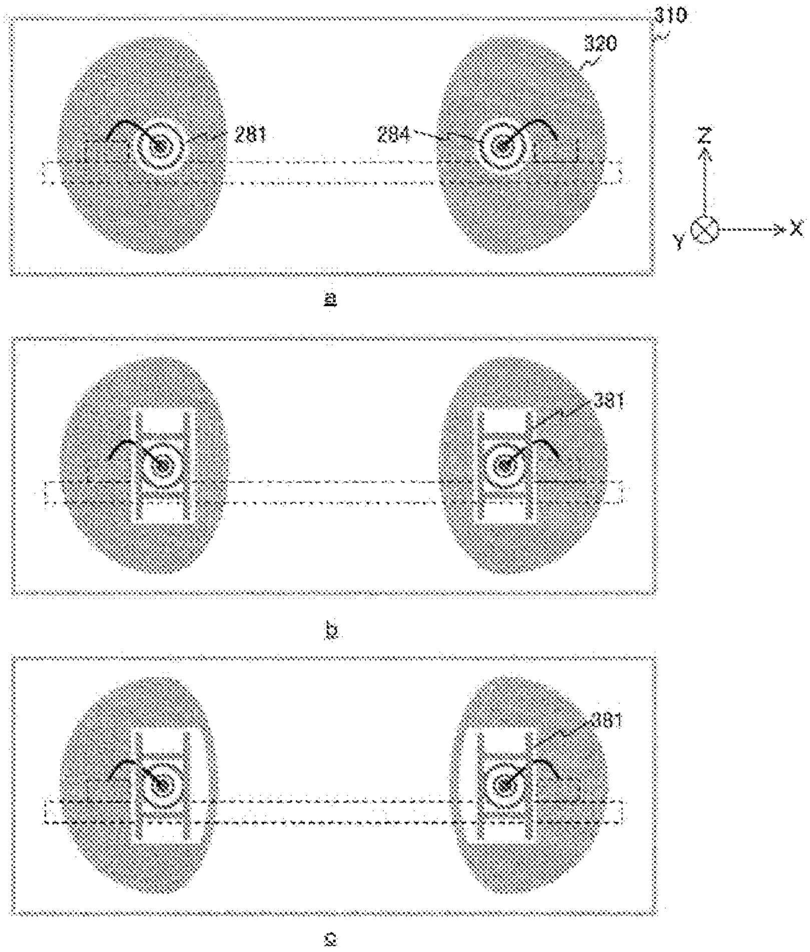

FIG. 290 is an example of a cross-sectional view of a coaxial cable acquired when the number of antennas is reduced in the third embodiment of the present technology.

Figure 291:
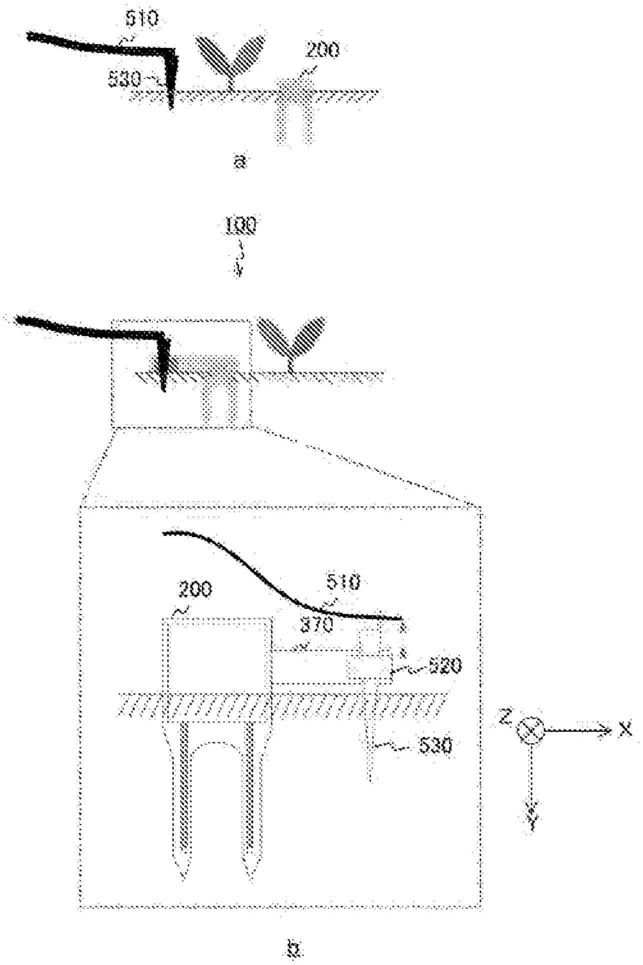

FIG. 291 is a diagram illustrating an example of moisture measuring systems according to a fourth embodiment of the present technology and a comparative example.

FIG. 292 is a diagram illustrating an example of a moisture measuring system in which a plurality of sensor devices are connected in the fourth embodiment of the present technology.

Figure 293:
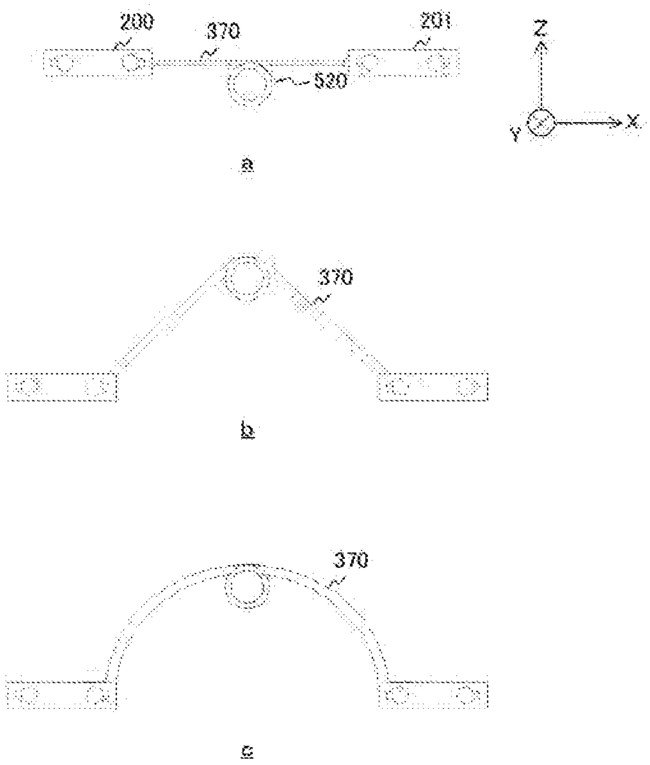

FIG. 293 is an example of a top view of a moisture measuring system in which a plurality of sensor devices are connected in the fourth embodiment of the present technology.

FIG. 294 is a diagram illustrating an example of a moisture measuring system in which a support member is disposed in the fourth embodiment of the present technology.

FIG. 295 is a diagram illustrating an example of a moisture measuring system in which a plurality of sensor devices and a plurality of watering nozzle holders are connected in the fourth embodiment of the present technology.

Figure 296:
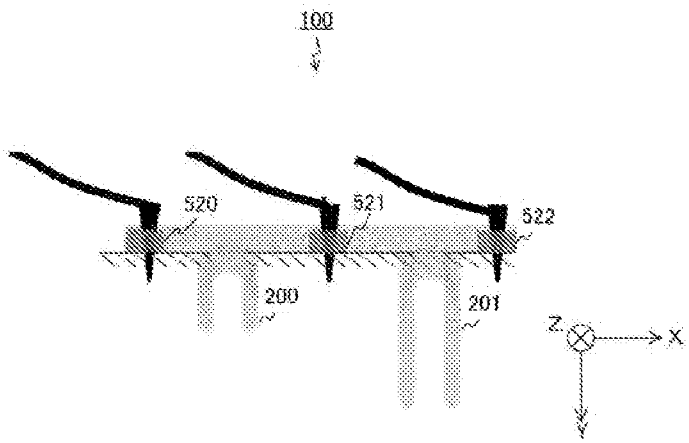
Figure 296:
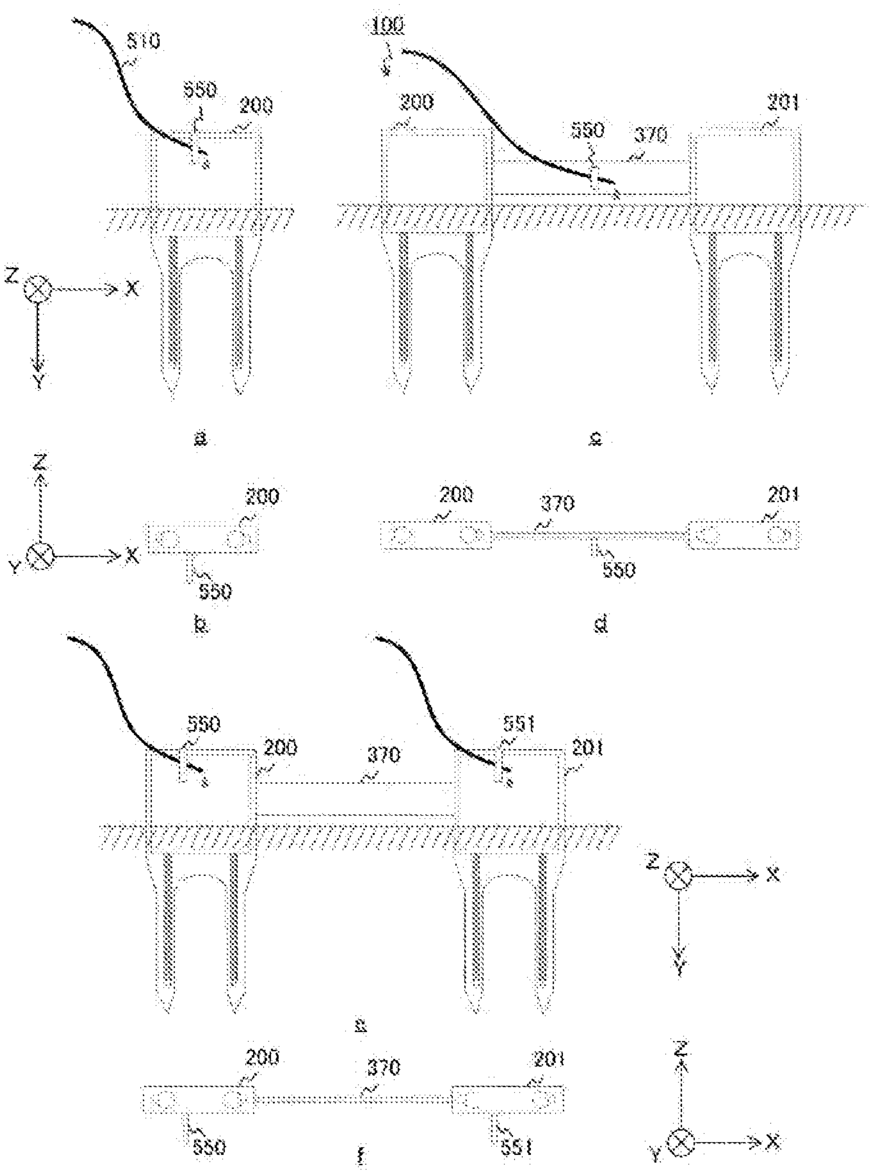

FIG. 296 is a diagram illustrating an example of a moisture measuring system in which a watering tube holder is connected in the fourth embodiment of the present technology.

FIG. 297 is a diagram illustrating an example of a moisture measuring system that waters through a watering nozzle in the fourth embodiment of the present technology.

FIG. 298 is a diagram illustrating an example of a moisture measuring system in which a direction of arrangement of probes and a segment parallel to a connection part are orthogonal to each other in the fourth embodiment of the present technology.

Figure 299:
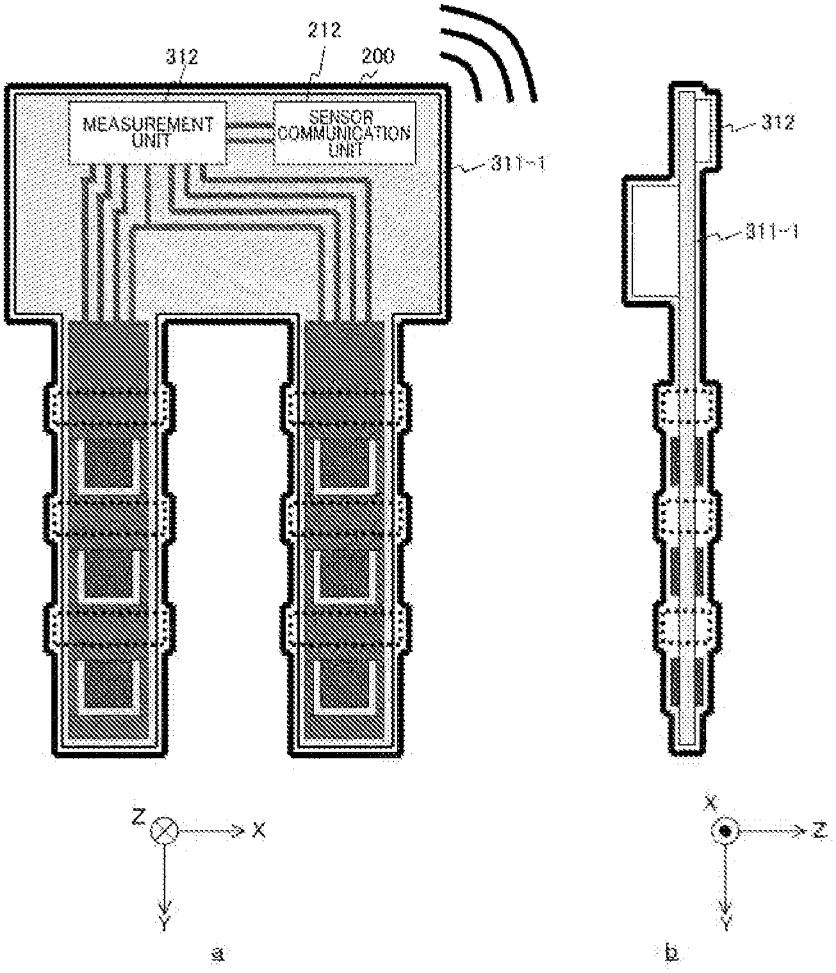

FIG. 299 is a diagram illustrating an example of a front view and a side view of a sensor device according to a fifth embodiment of the present technology.

Figure 300:
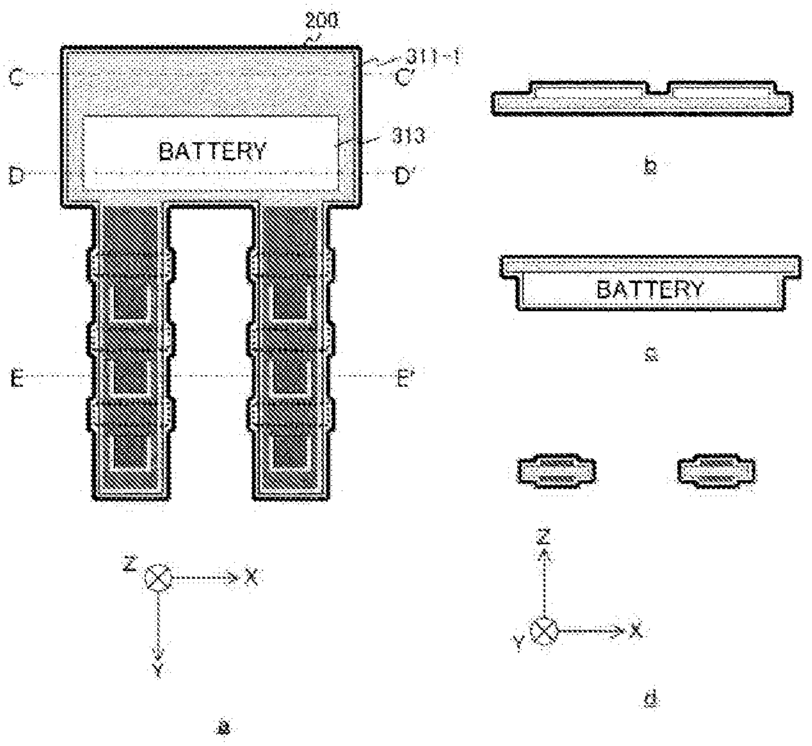

FIG. 300 is a diagram illustrating an example of a rear view and a cross-sectional view of a sensor device according to the fifth embodiment of the present technology.

Figure 301:
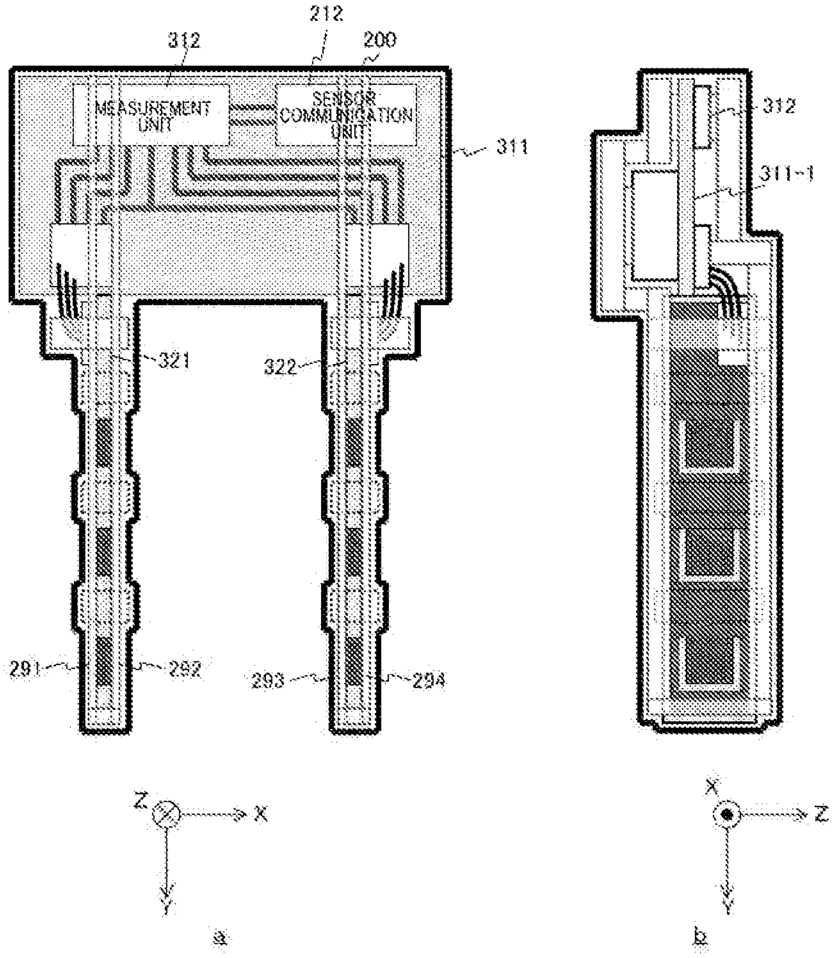

FIG. 301 is a diagram illustrating an example of a rear view and a cross-sectional view of a sensor device in which substrates are orthogonal to each other, and a frame is disposed in the fifth embodiment of the present technology.

Figure 302:
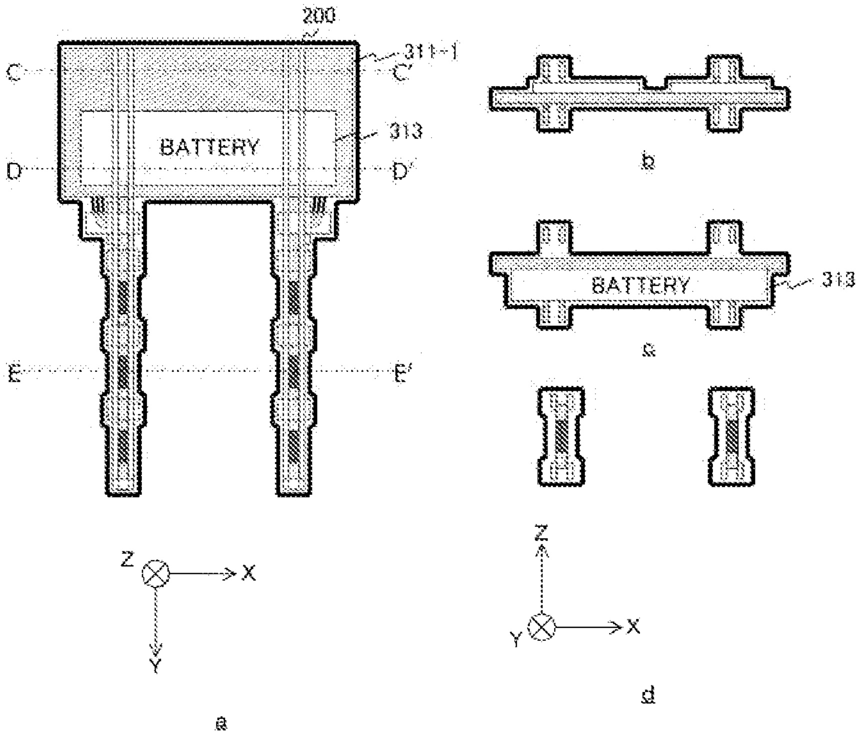

FIG. 302 is a diagram illustrating an example of a rear view and a cross-sectional view of a sensor device in which substrates are orthogonal to each other, and a frame is disposed in the fifth embodiment of the present technology.

Figure 303:
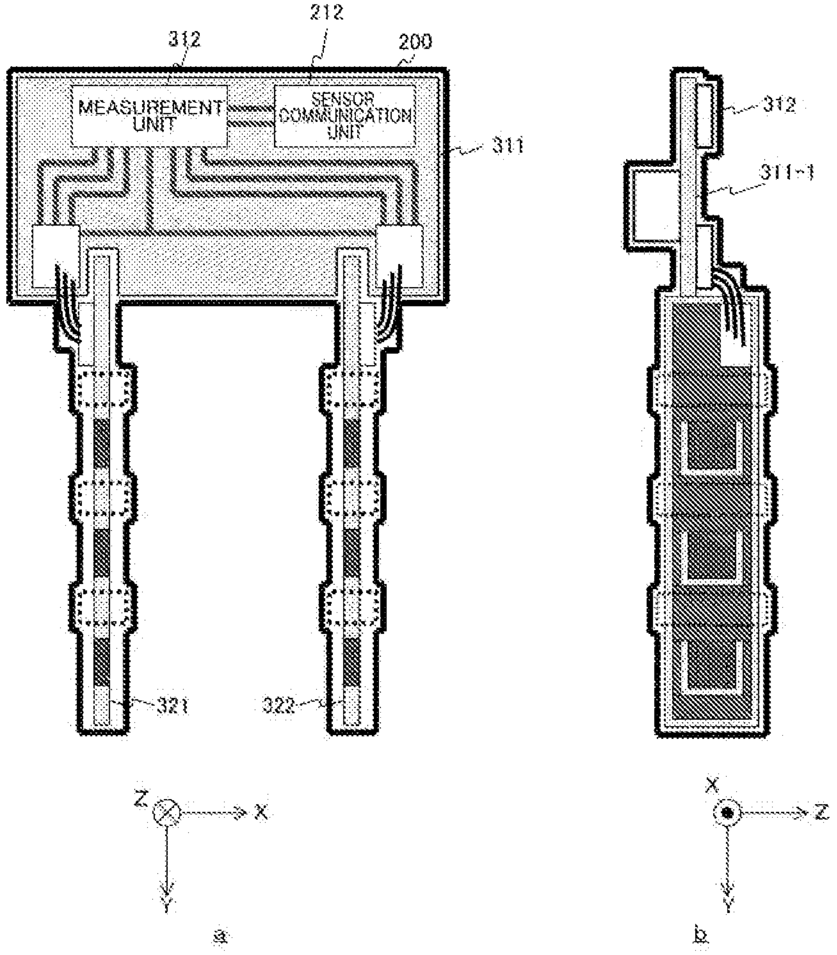

FIG. 303 is a diagram illustrating an example of a rear view and a cross-sectional view of a sensor device in which substrates are orthogonal to each other in the fifth embodiment of the present technology.

Figure 304:
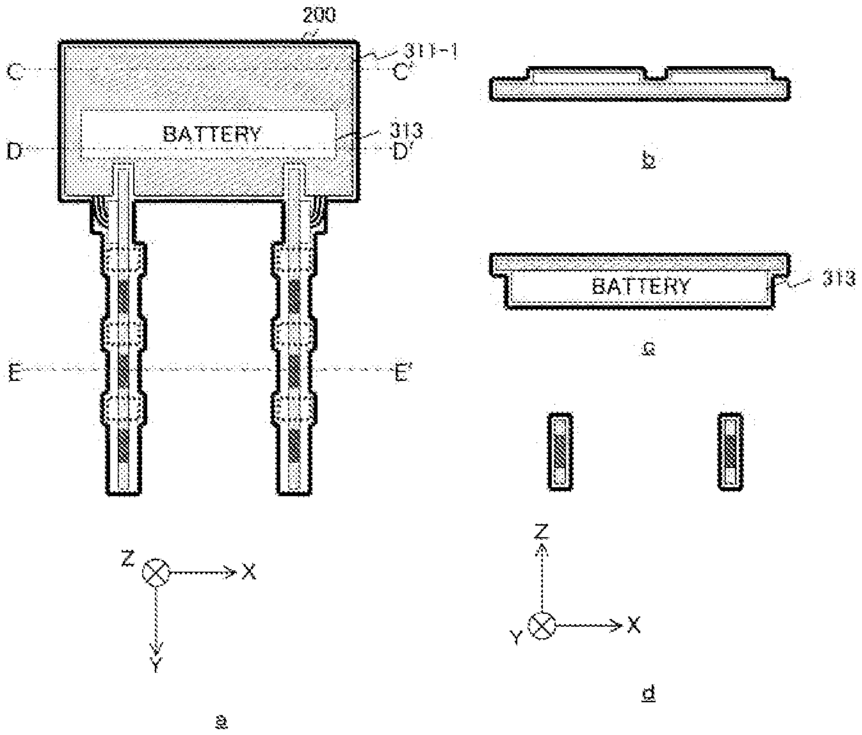

FIG. 304 is a diagram illustrating an example of a rear view and a cross-sectional view of a sensor device in which substrates are orthogonal to each other in the fifth embodiment of the present technology.

Figure 305:
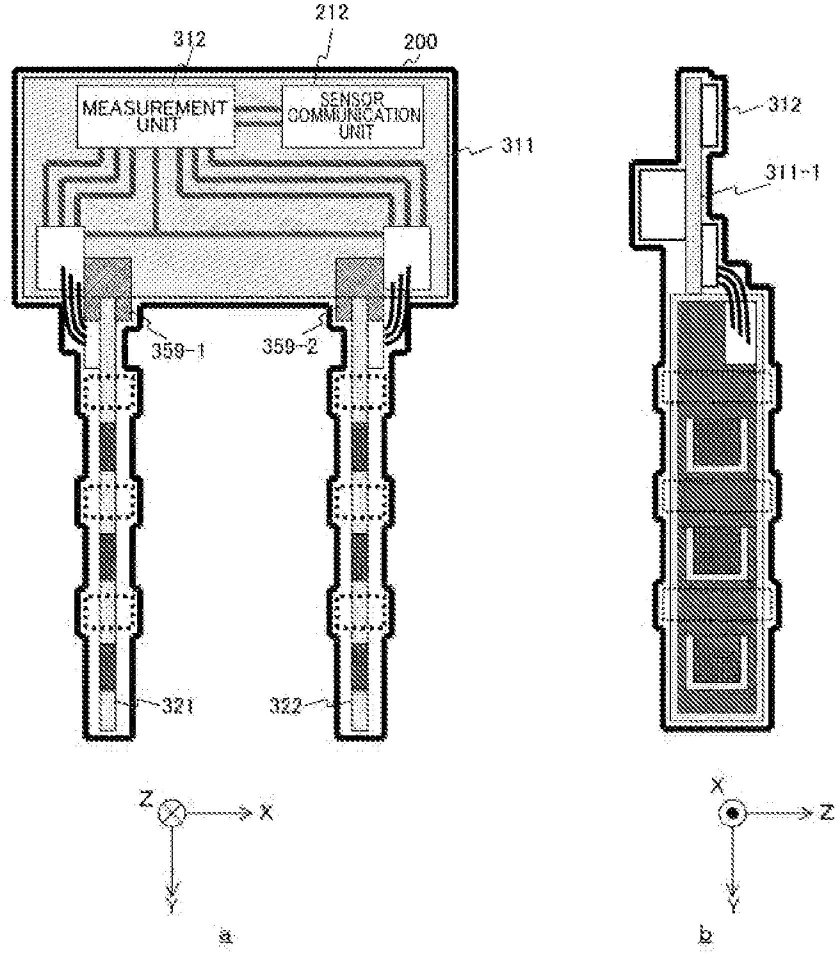

FIG. 305 is a diagram illustrating an example of a rear view and a cross-sectional view of a sensor device in which substrates are orthogonal to each other, and a jig is disposed in the fifth embodiment of the present technology.

Figure 306:
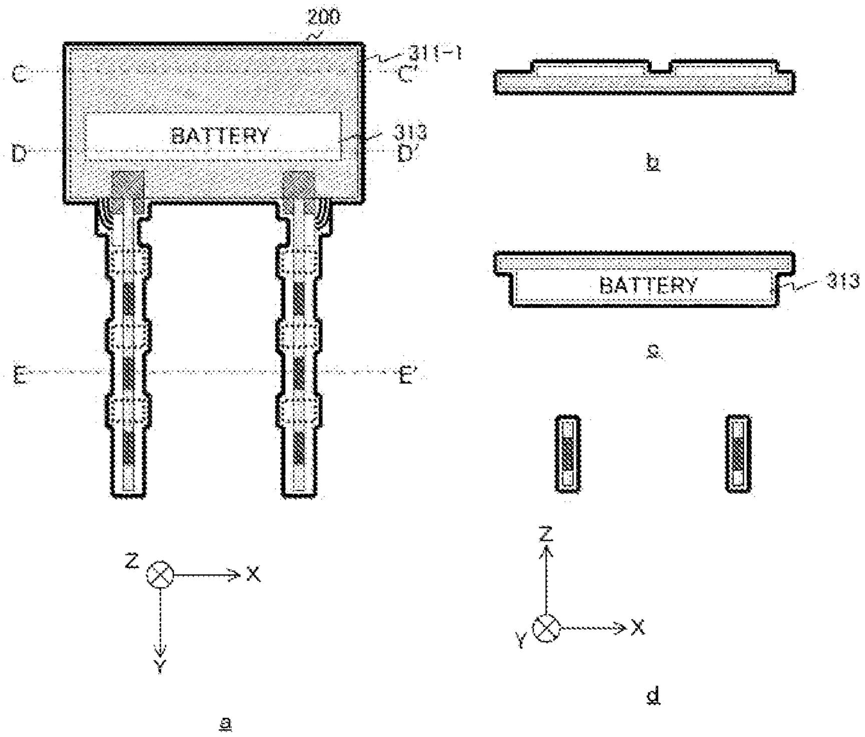

FIG. 306 is a diagram illustrating an example of a rear view and a cross-sectional view of a sensor device in which substrates are orthogonal to each other, and a jig is disposed in the fifth embodiment of the present technology.

Figure 307:
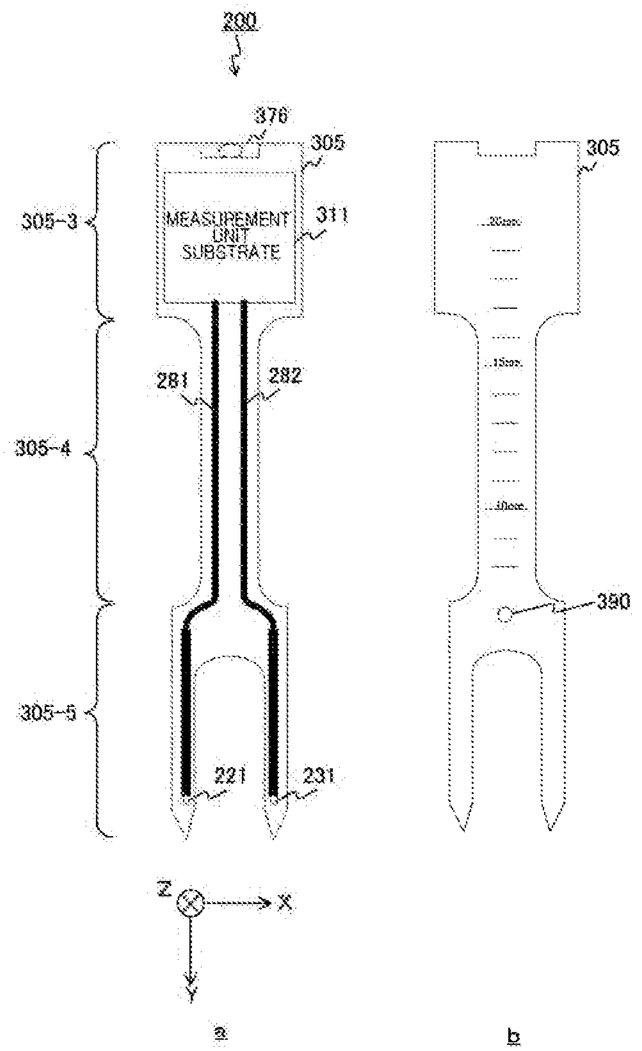

FIG. 307 is a diagram illustrating an example of a sensor device according to a sixth embodiment of the present technology.

Figure 308:
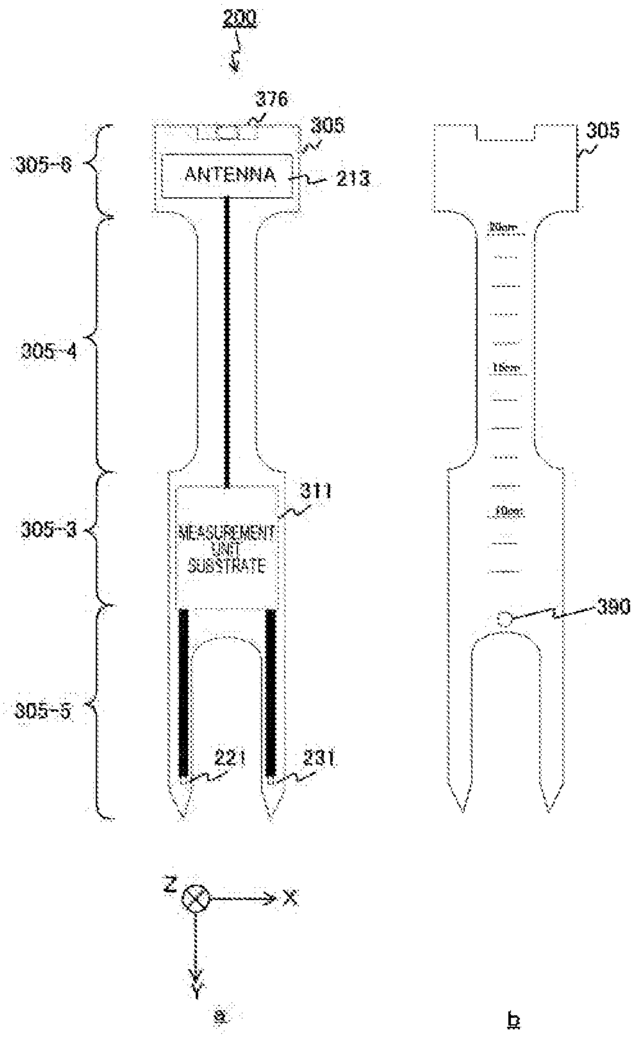

FIG. 308 is a diagram illustrating an example of a sensor device in which a position of a main body part is changed in the sixth embodiment of the present technology.

Figure 309:
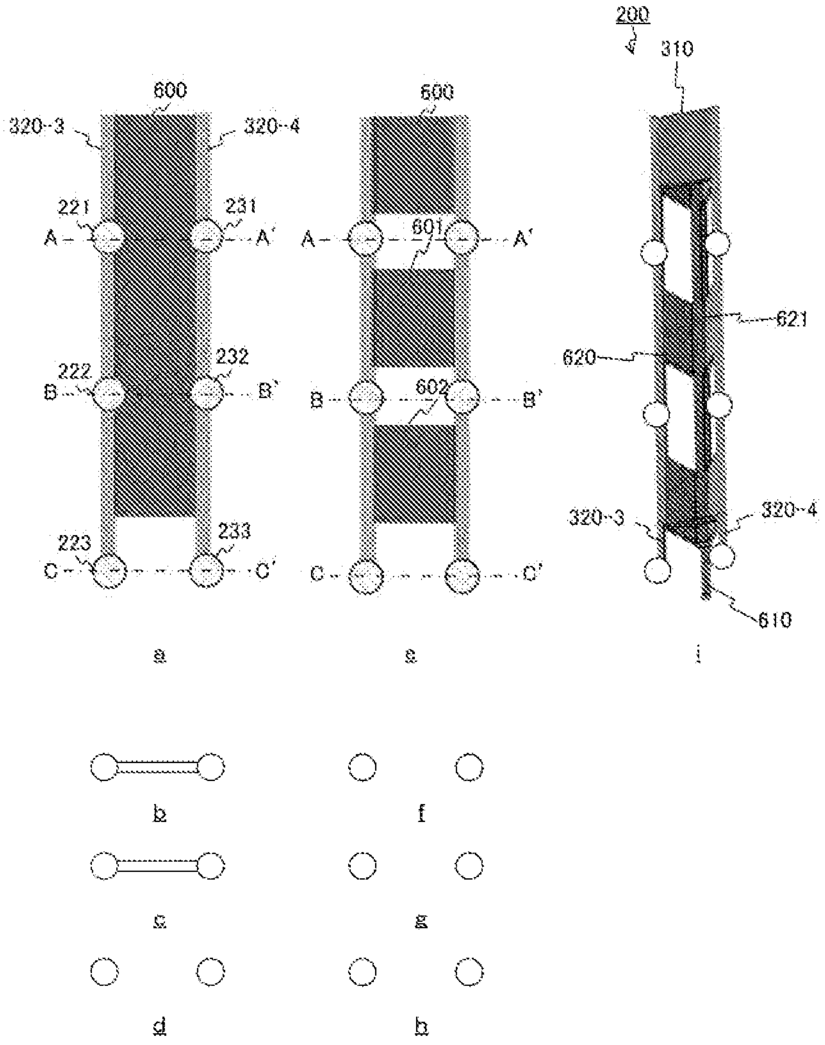

FIG. 309 is a diagram illustrating an example of sensor devices according to a seventh embodiment of the present technology and a comparative example.

Figure 310:
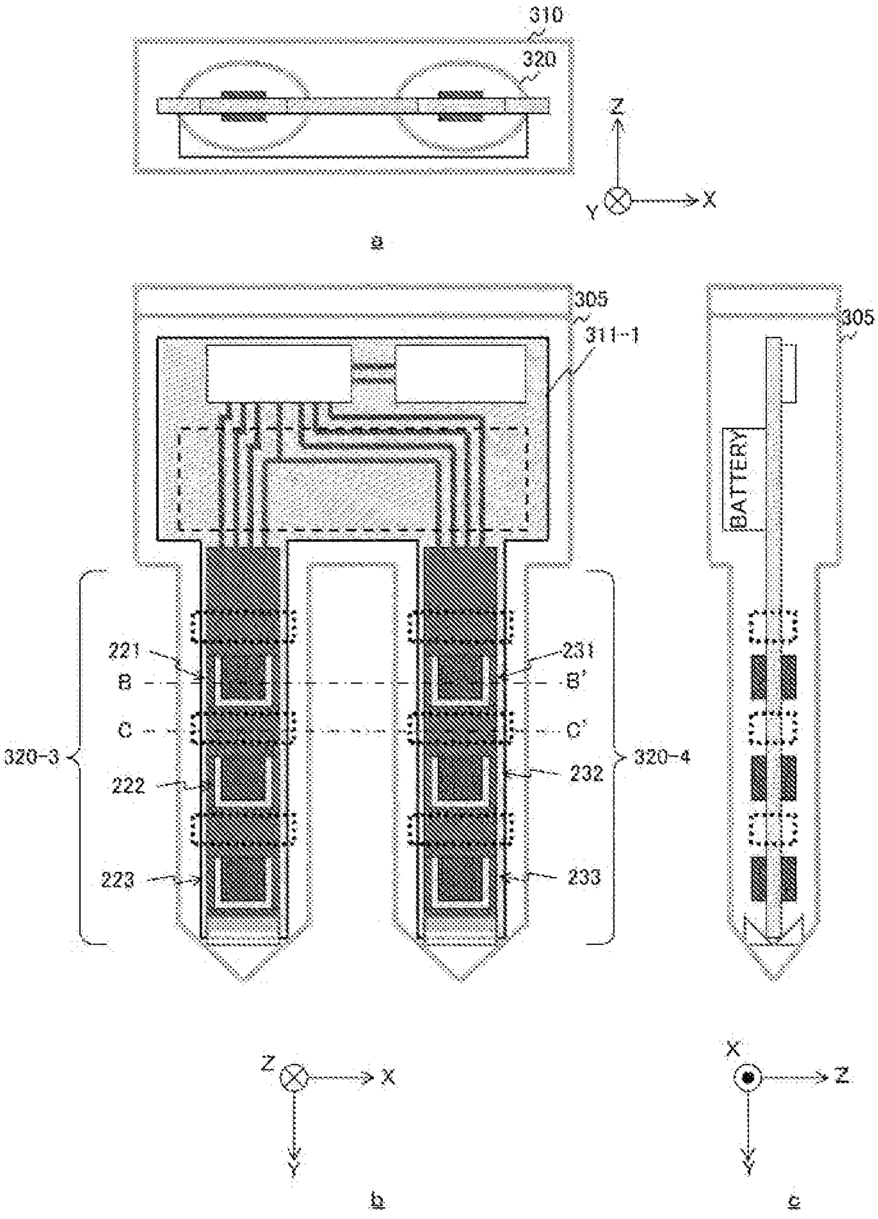

FIG. 310 is a diagram illustrating an example of a cutout face of the sensor device according to the seventh embodiment of the present technology.

Figure 311:
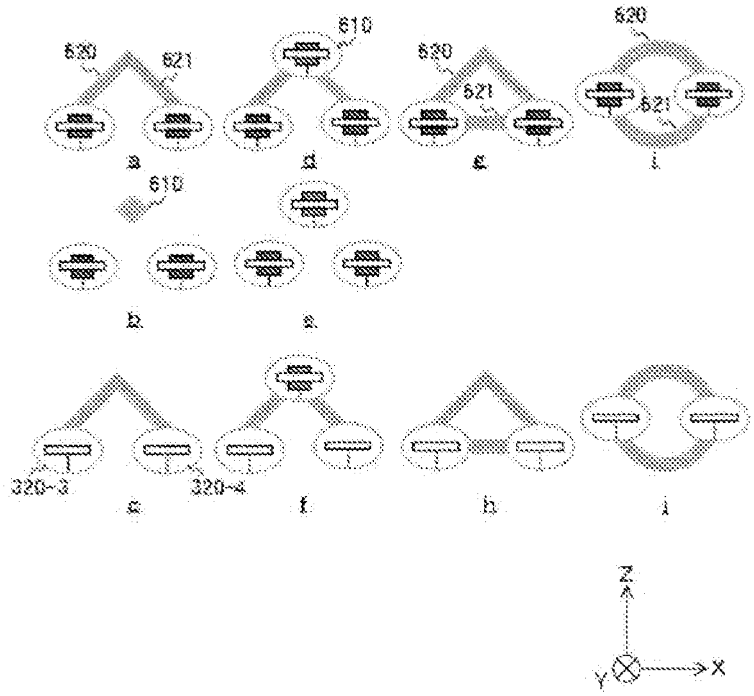

FIG. 311 is a diagram illustrating an example of a cross-sectional view of the sensor device according to the seventh embodiment of the present technology.

Figure 312:
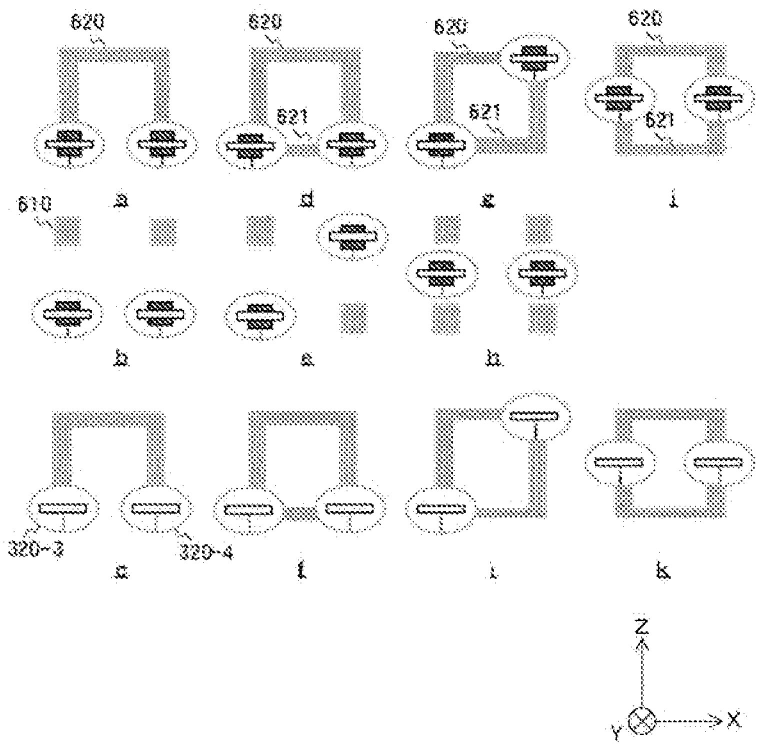

FIG. 312 is a diagram illustrating an example of a cross-sectional view of a rectangular part of the sensor device according to the seventh embodiment of the present technology.

Figure 313:
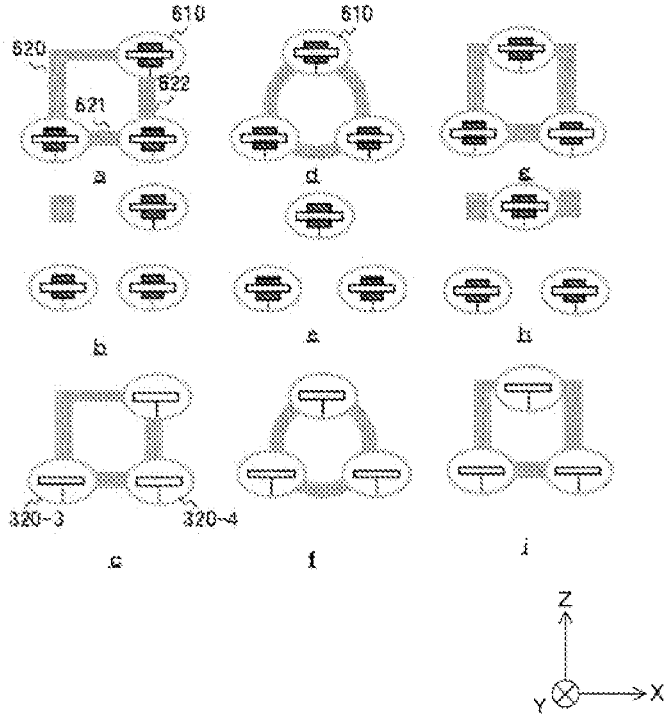

FIG. 313 is a diagram illustrating an example of a cross-sectional view of a sensor device in which the number of probes is three in the seventh embodiment of the present technology.

Figure 314:
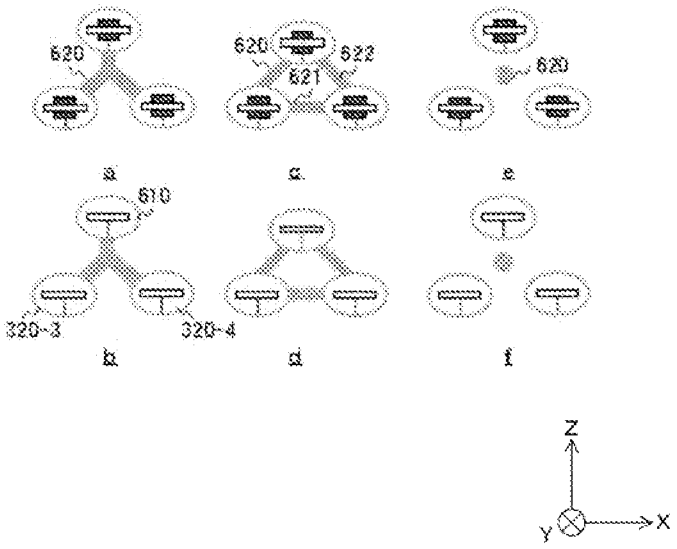

FIG. 314 is a diagram illustrating another example of a cross-sectional view of a sensor device in which the number of probes is three in the seventh embodiment of the present technology.

Figure 315:
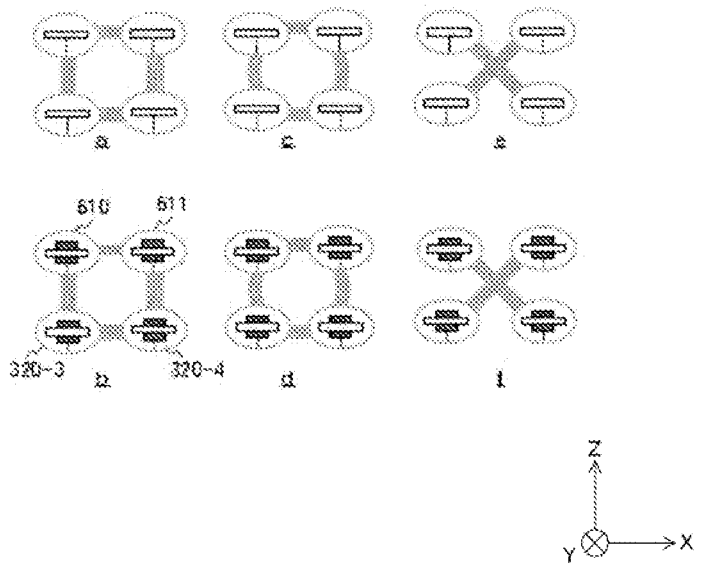

FIG. 315 is a diagram illustrating an example of a cross-sectional view of a sensor device in which the number of probes is four in the seventh embodiment of the present technology.

Figure 316:
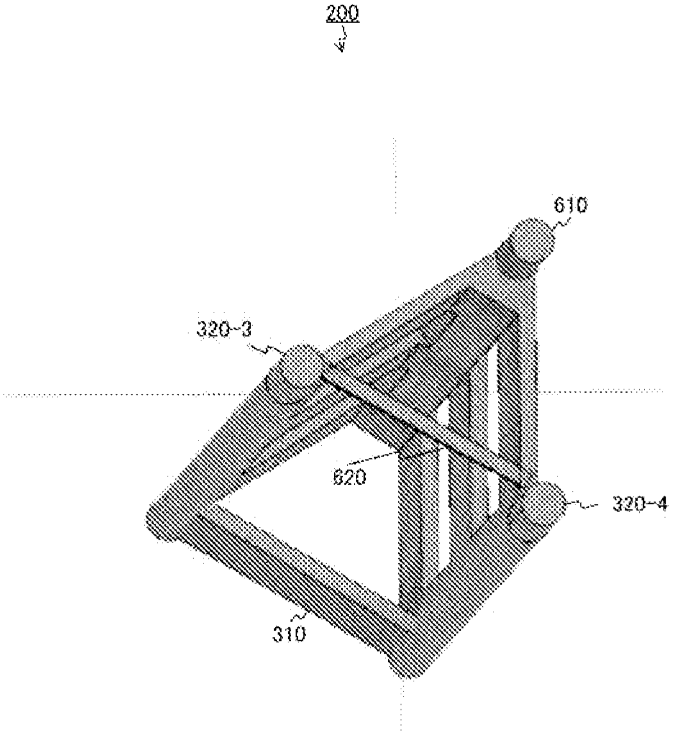

FIG. 316 is an example of a perspective views of the sensor device according to the seventh embodiment of the present technology.

Figure 317:
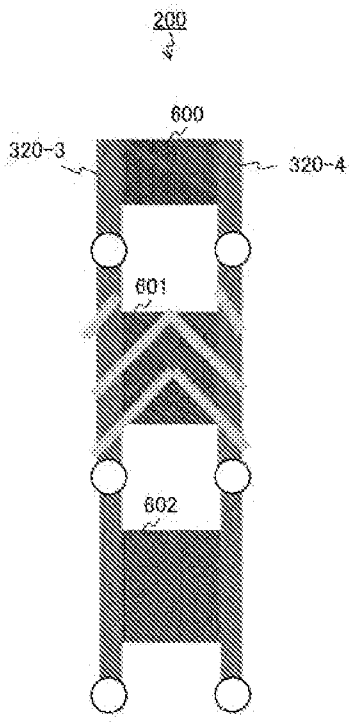

FIG. 317 is an example of a sensor device 200 in which a groove is formed in a spacer in the seventh embodiment of the present technology.

Figure 318:
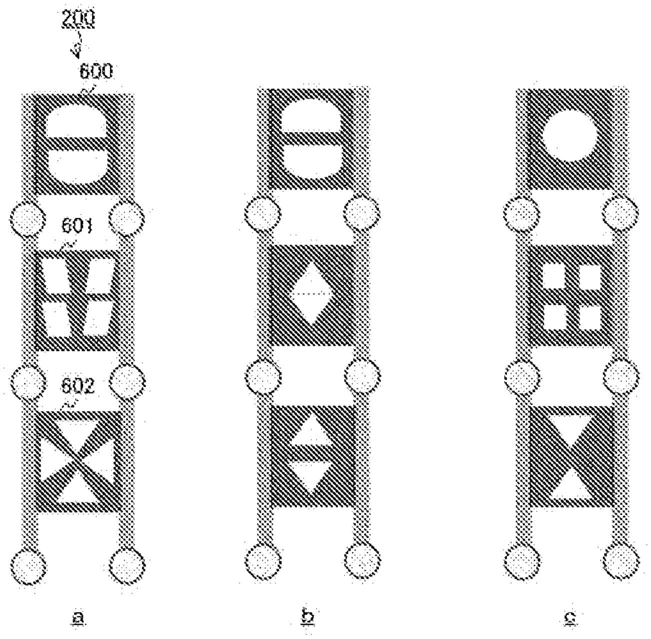

FIG. 318 is a diagram illustrating an example of a groove of a spacer in the seventh embodiment of the present technology.

Figure 319:
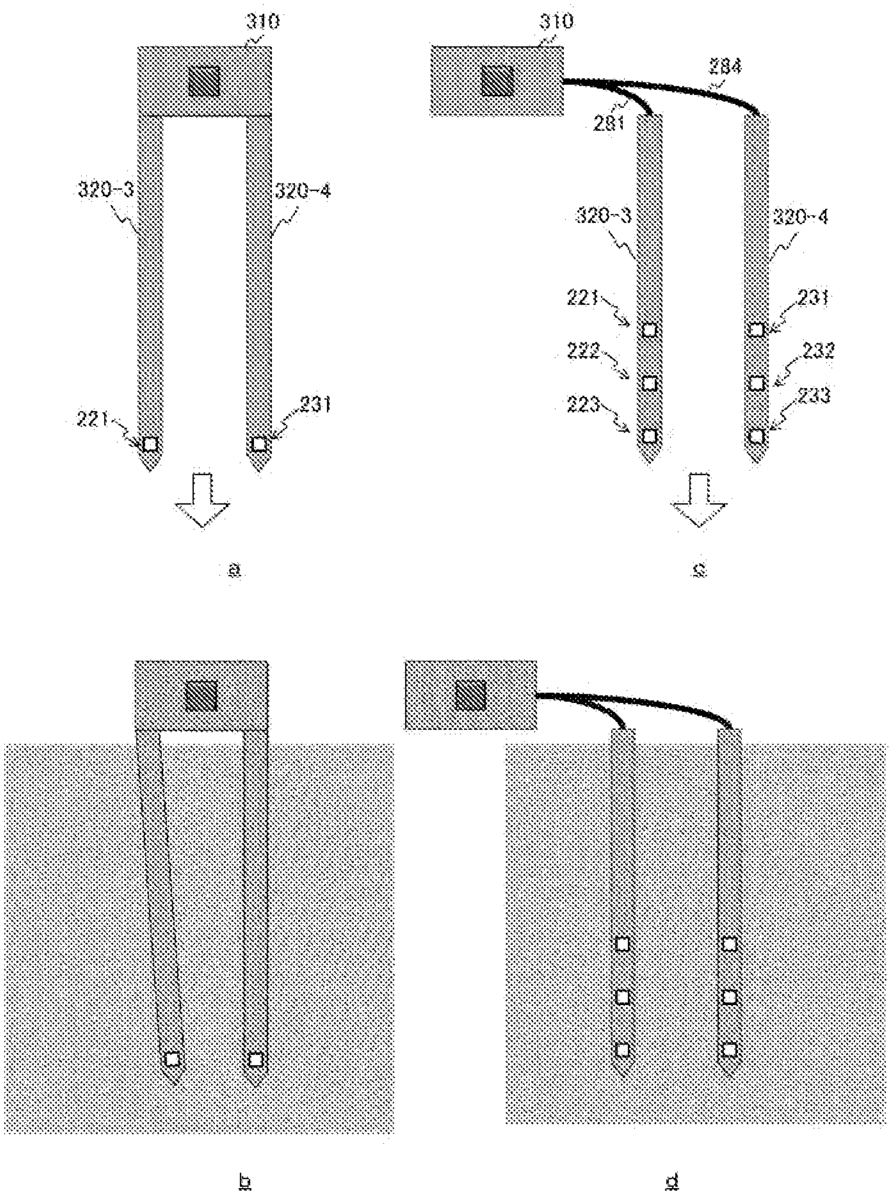

FIG. 319 is a diagram illustrating an example of sensor devices according to a comparative example and an eighth embodiment of the present technology.

Figure 320:
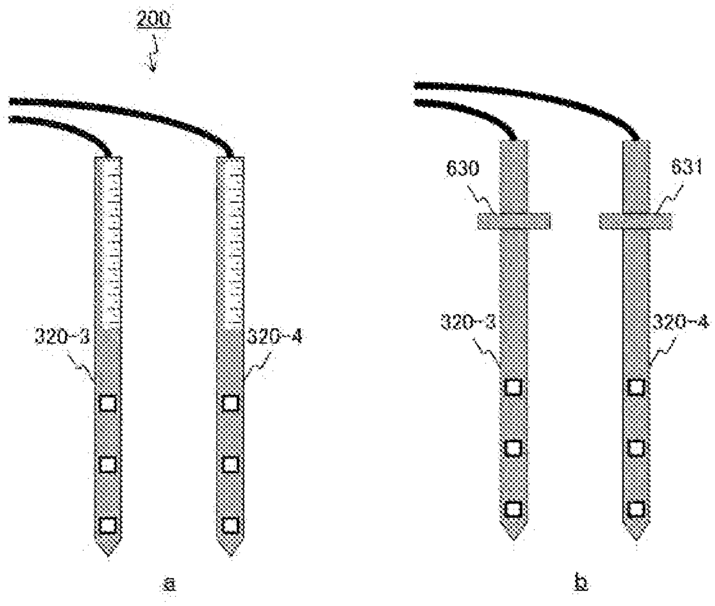

FIG. 320 is a diagram illustrating an example of a sensor device in which scales and a stopper are disposed in the eighth embodiment of the present technology.

Figure 321:
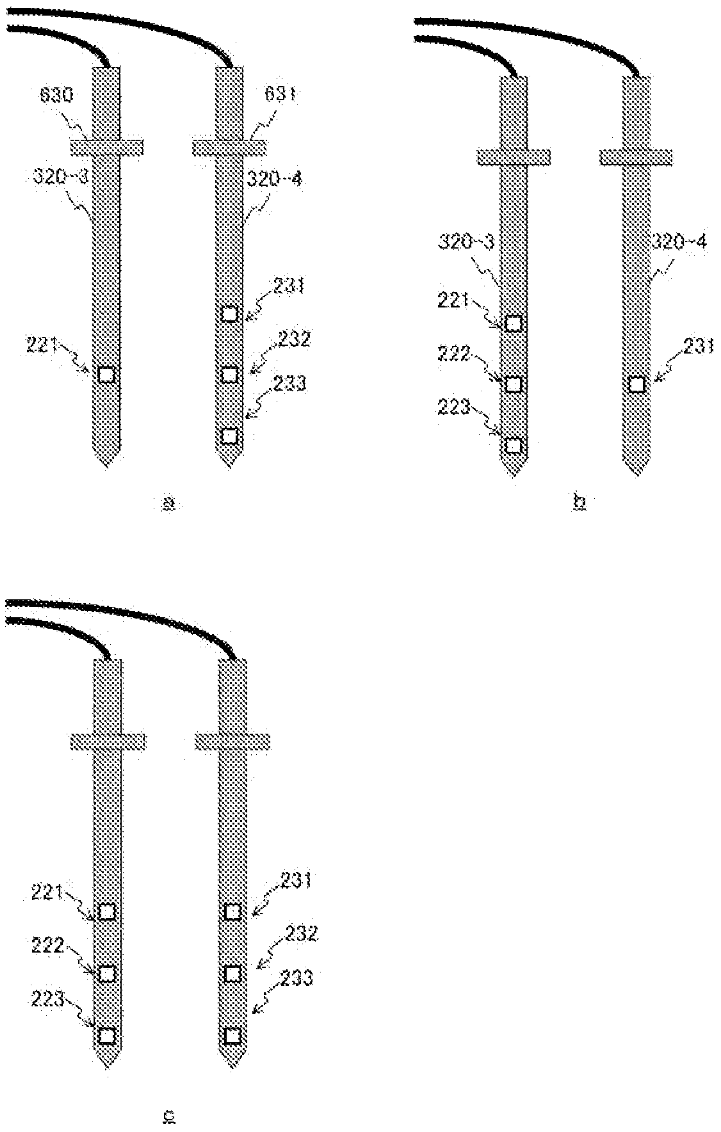

FIG. 321 is a diagram illustrating an example of the numbers of antennas on a transmission side and a reception side in the eighth embodiment of the present technology.

Figure 322:
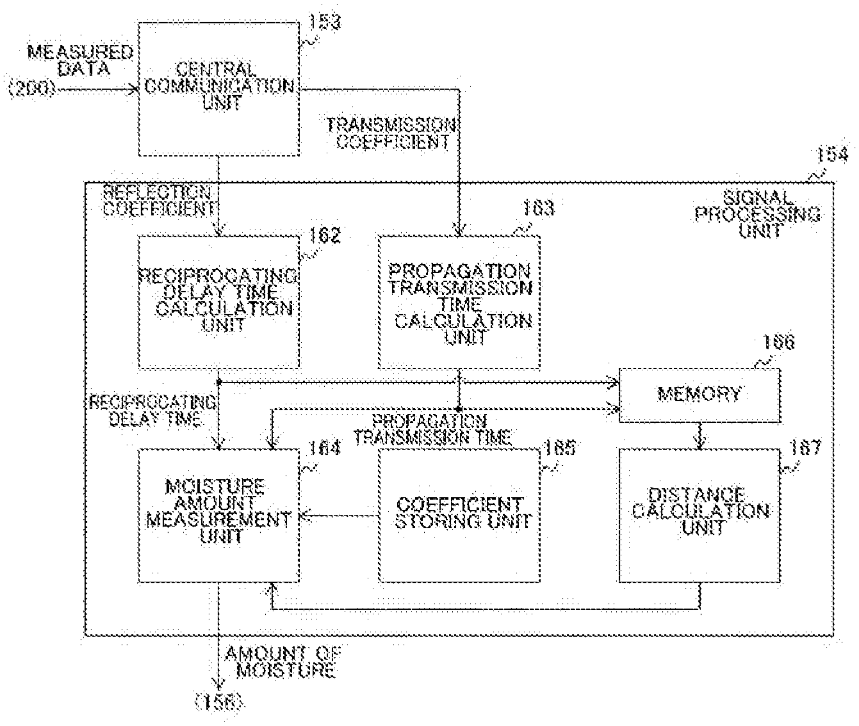

FIG. 322 is a block diagram illustrating one configuration example of a signal processing unit disposed inside a central processing device in the eighth embodiment of the present technology.

FIG. 323 is a diagram illustrating an example of a sensor device in which a plate shaped member-attached memory and a stopper are disposed in the eighth embodiment of the present technology.

Figure 324:
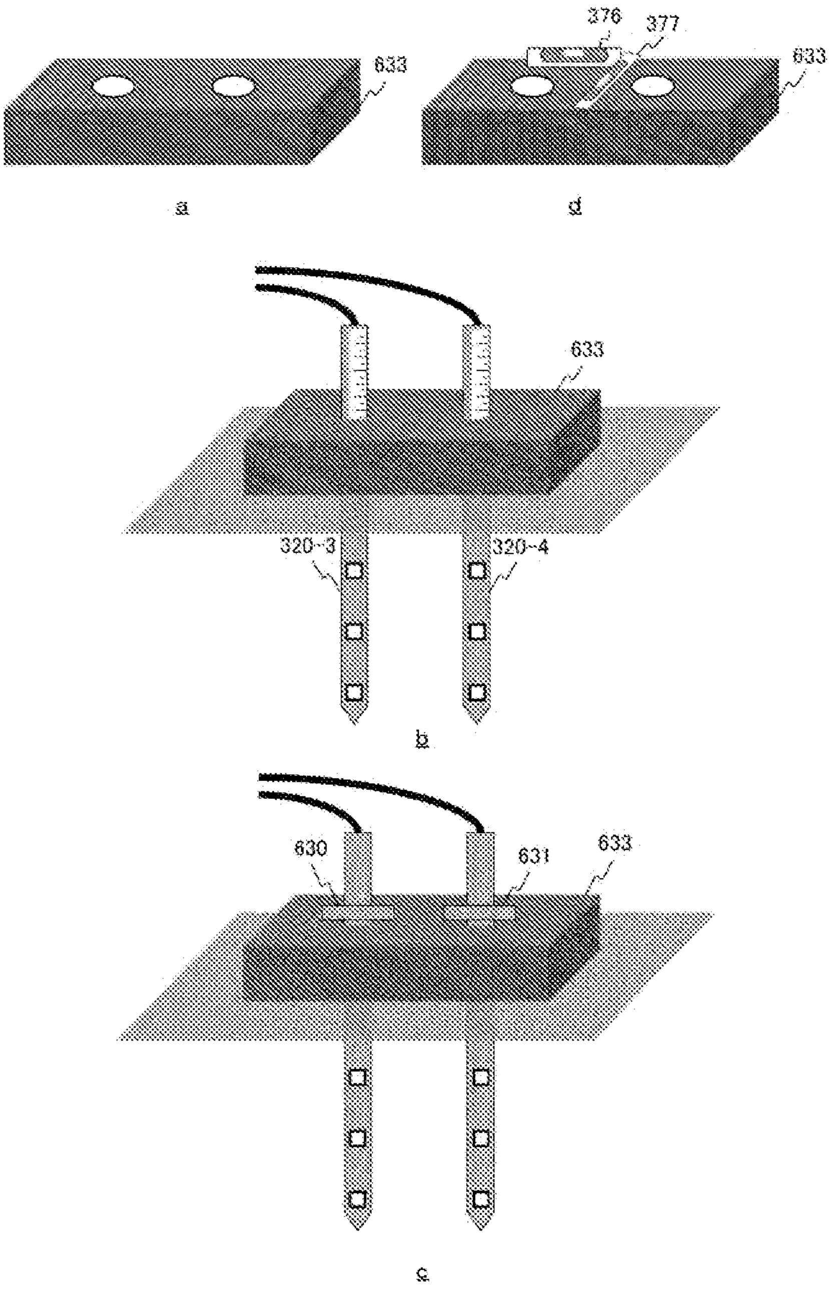

FIG. 324 is a diagram illustrating an example of a sensor device in which a parallelepiped member-attached memory and a stopper are disposed in the eighth embodiment of the present technology.

Figure 325:
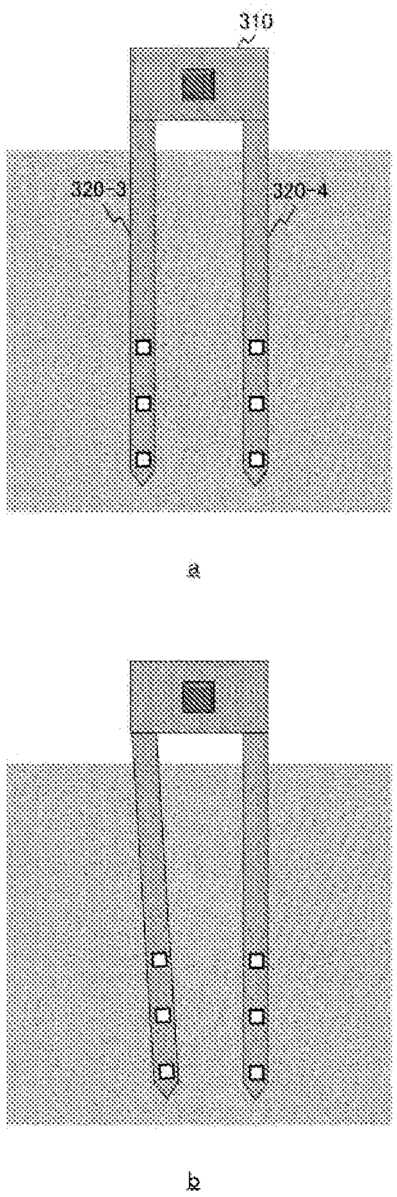

FIG. 325 is a diagram illustrating an example of a sensor device in which a probe casing is not divided in the eighth embodiment of the present technology.

FIG. 326 is a diagram illustrating a method of measuring a distance between antennas in the eighth embodiment of the present technology.

Figure 327:
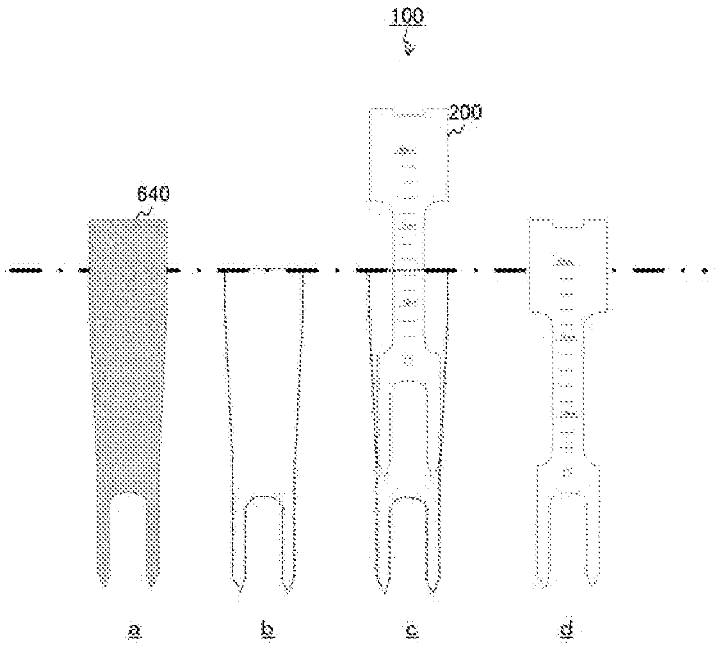

FIG. 327 is a diagram illustrating an example of a method of inserting a sensor device in the ninth embodiment of the present technology.

Figure 328:
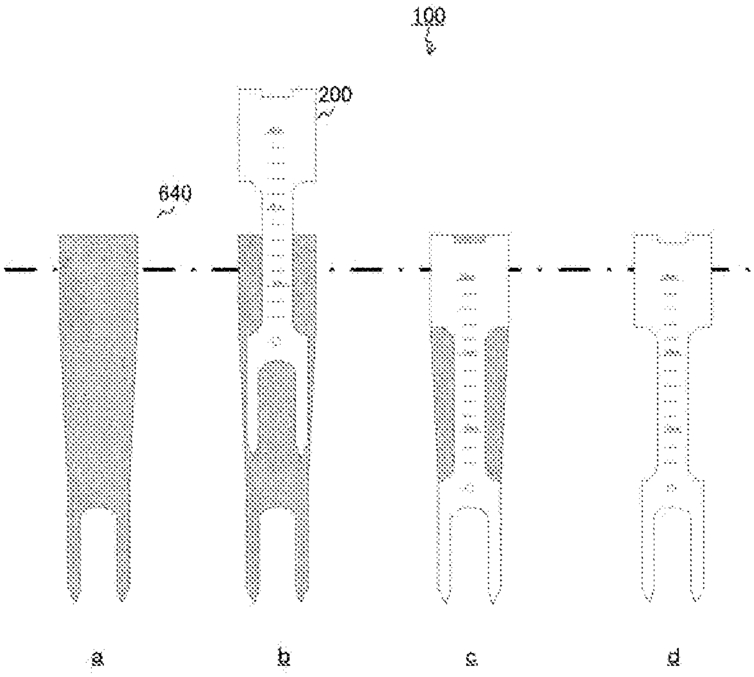

FIG. 328 is a diagram illustrating another example of a method of inserting a sensor device in the ninth embodiment of the present technology.

FIG. 329 is a diagram illustrating an example of a sensor device according to a tenth embodiment of the present technology.

FIG. 330 is a diagram illustrating an example of a spiral shaped member and a sensor casing in the tenth embodiment of the present technology.

Figure 331:
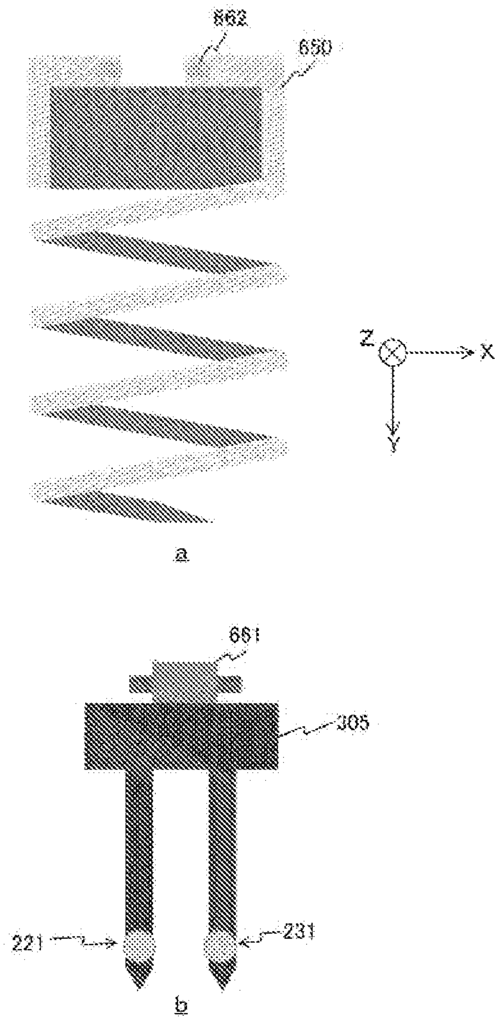

FIG. 331 is a diagram illustrating another example of a spiral shaped member and a sensor casing in the tenth embodiment of the present technology.

Figure 332:
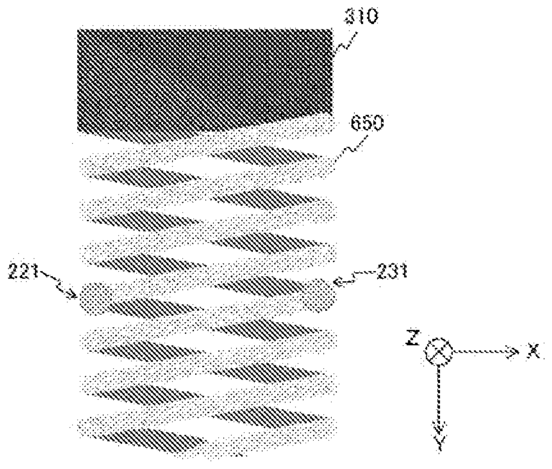

FIG. 332 is a diagram illustrating an example of a sensor device in which a double-spiral shaped probe is disposed in the tenth embodiment of the present technology.

Figure 333:
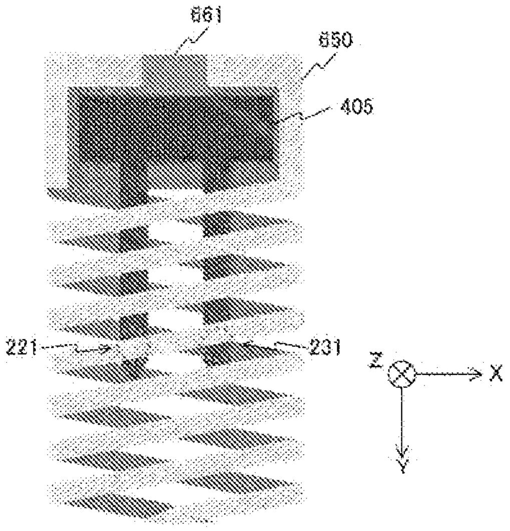

FIG. 333 is a diagram illustrating an example of a sensor device in which a double-spiral shaped member is disposed in the tenth embodiment of the present technology.

Figure 334:
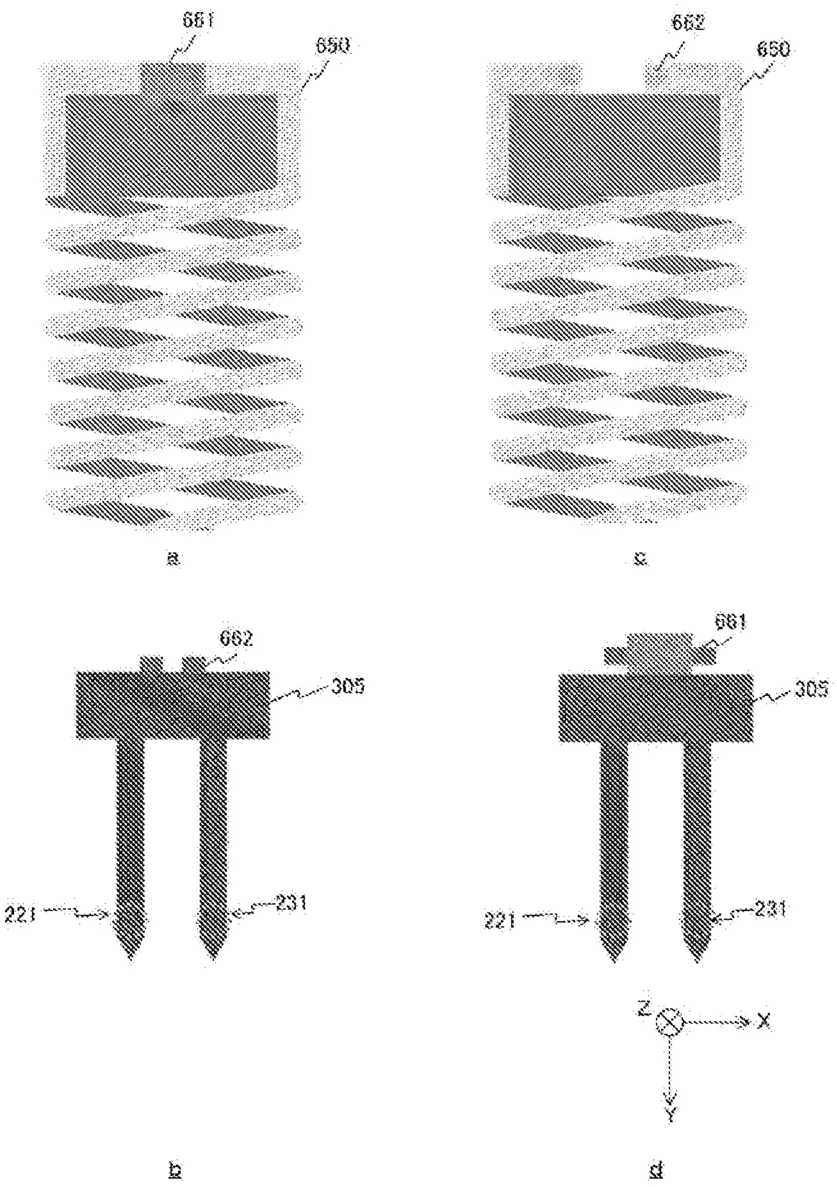

FIG. 334 is a diagram illustrating an example of a double-spiral shaped member and a sensor casing in the tenth embodiment of the present technology.

Figure 35:
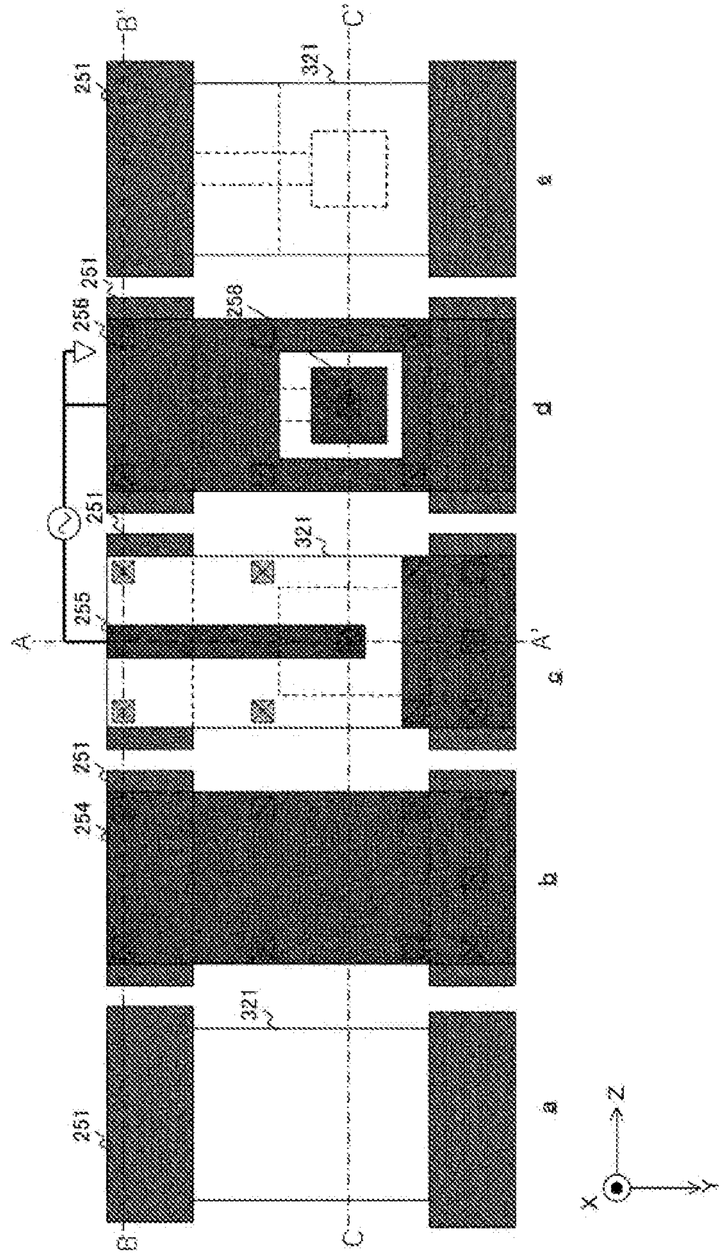
FIG. 35 is another example of a plan view of each layer of the inside of a probe casing having the third structure according to the first embodiment of the present technology.

FIG. 35 is a diagram illustrating an example of a positional relation between a spiral shaped member and an antenna in the tenth embodiment of the present technology.

Figure 336:
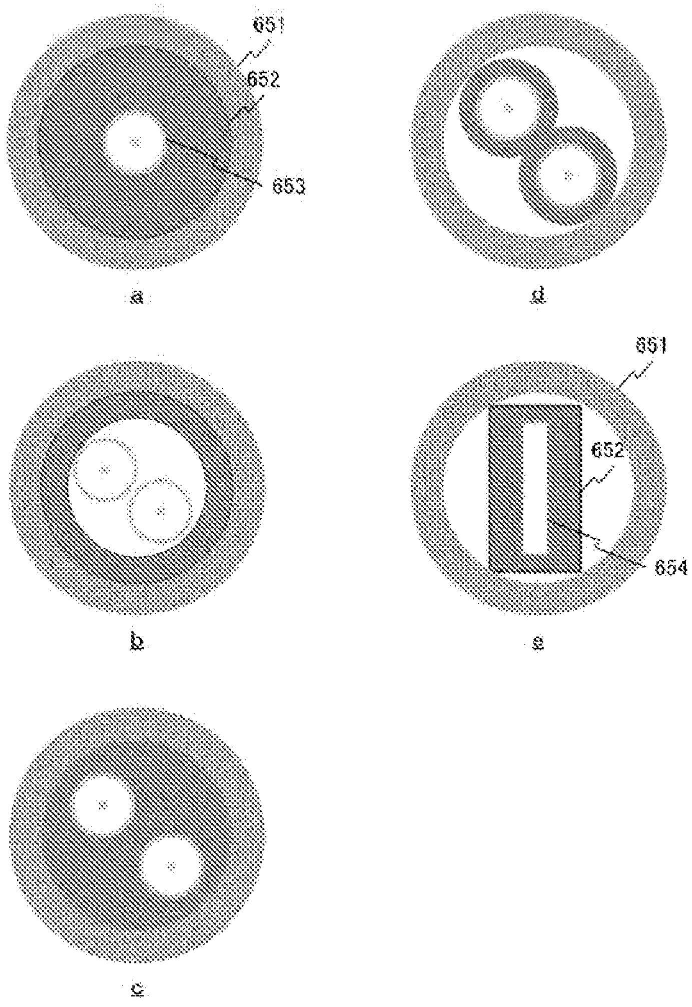

FIG. 336 is an example of a cross-sectional view of a spiral shaped member in the tenth embodiment of the present technology.

Figure 337:
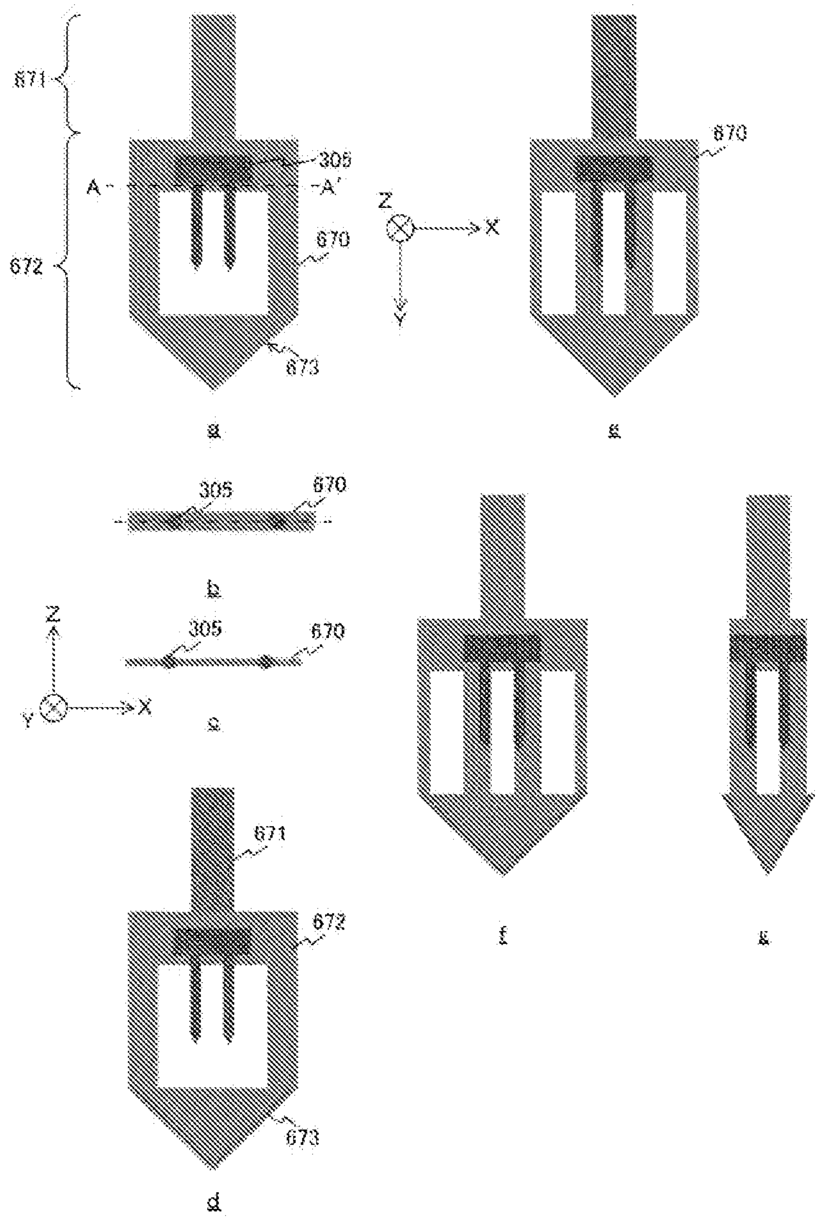

FIG. 337 is a diagram illustrating an example of a sensor device including a shovel-type casing in the tenth embodiment of the present technology.

Figure 338:
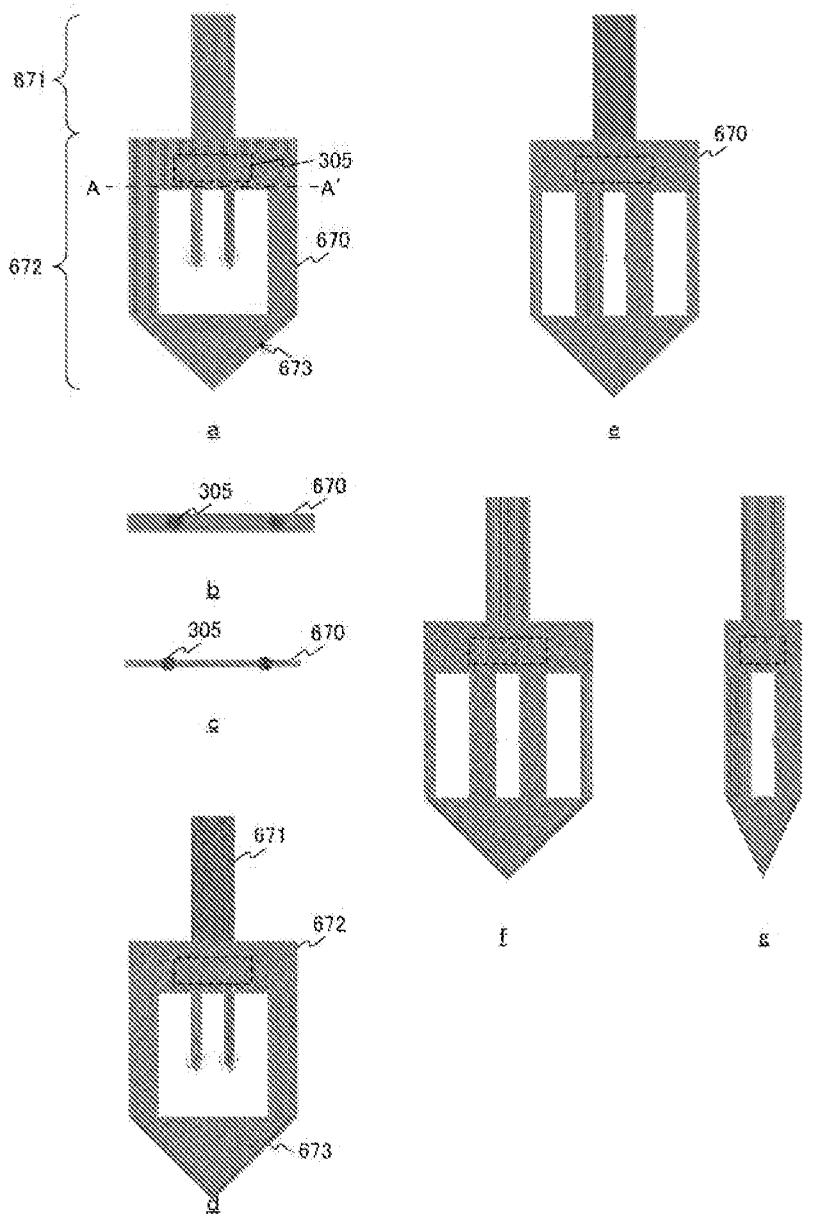

FIG. 338 is a diagram illustrating an example of a shovel-type casing in the tenth embodiment of the present technology.

Figure 339:
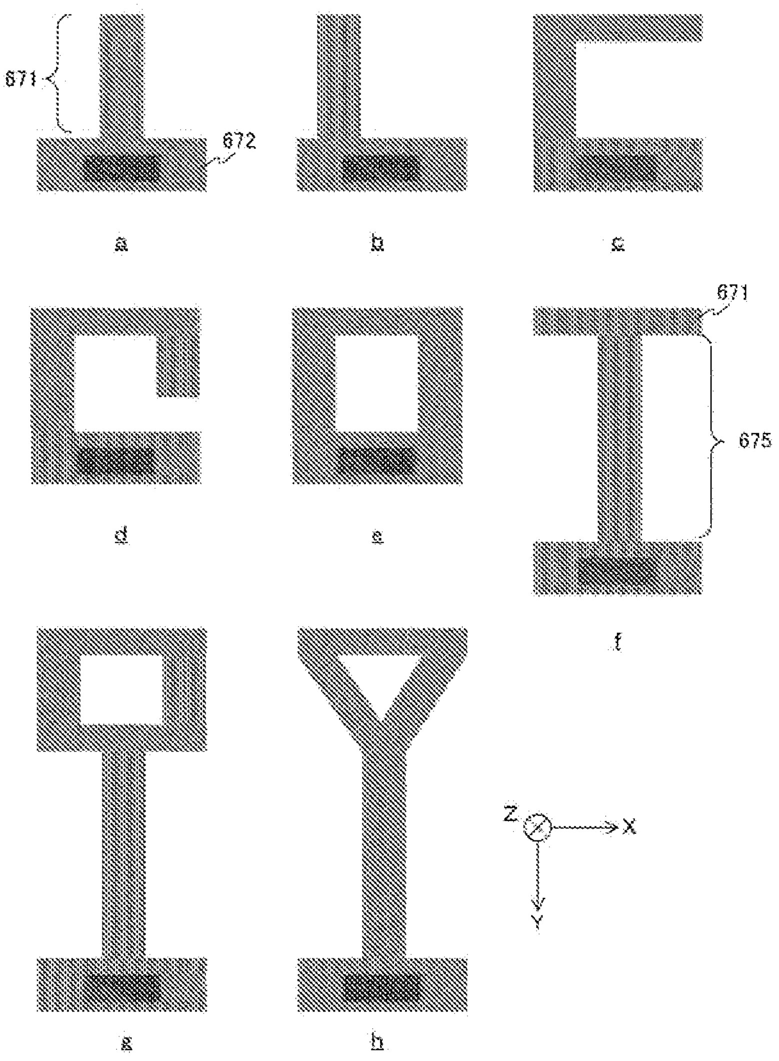

FIG. 339 is a diagram illustrating an example of a shape of a handle in the tenth embodiment of the present technology.

Figure 340:
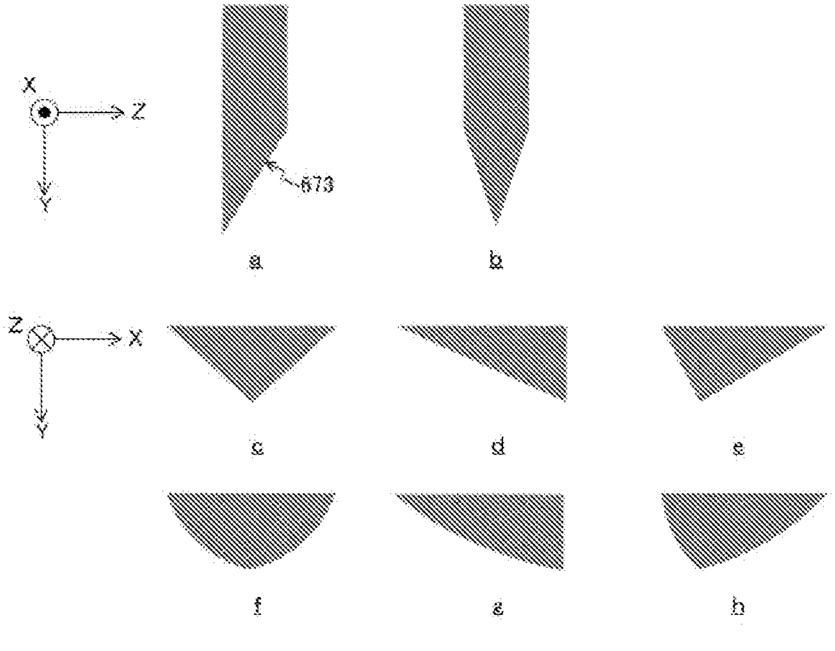

FIG. 340 is a diagram illustrating an example of a shape of a blade in the tenth embodiment of the present technology.

FIG. 341 is a diagram illustrating an example of a sensor device in which a scaffold member is added in the tenth embodiment of the present technology.

FIG. 342 is a block diagram illustrating an example of a sensor device according to an eleventh embodiment of the present technology.

Figure 343:
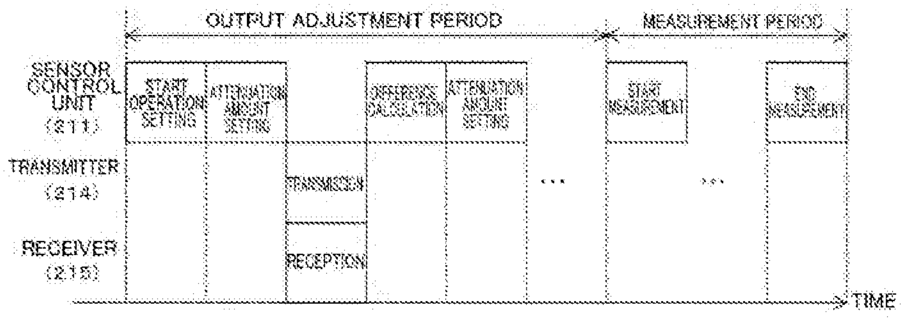

FIG. 343 is an example of a timing diagram illustrating operations of respective units disposed inside the sensor device according to the eleventh embodiment of the present technology.

Figure 344:
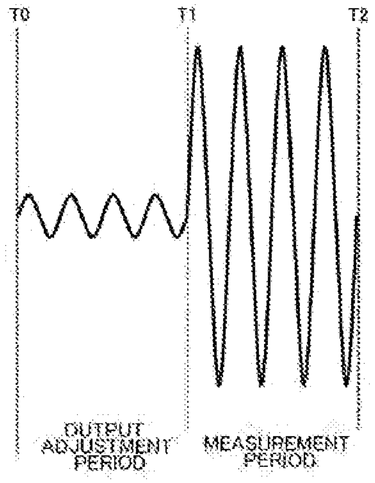

FIG. 344 is a diagram illustrating an example of a transmission waveform in the eleventh embodiment of the present technology.

Figure 345:
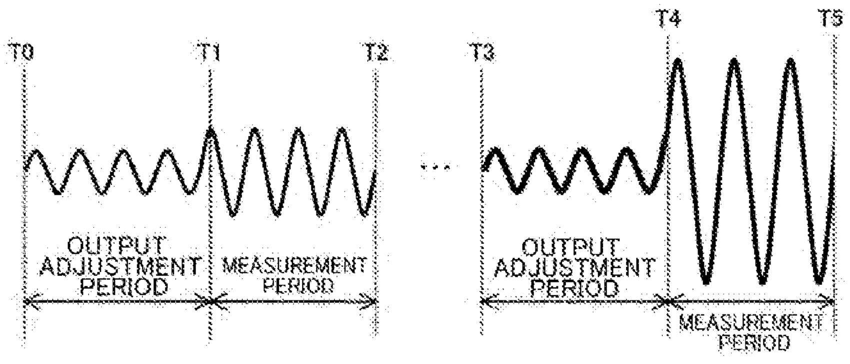

FIG. 345 is a diagram illustrating an example of a transmission waveform used at the time of adjusting transmission power according to the amount of moisture in the eleventh embodiment of the present technology.

Figure 346:
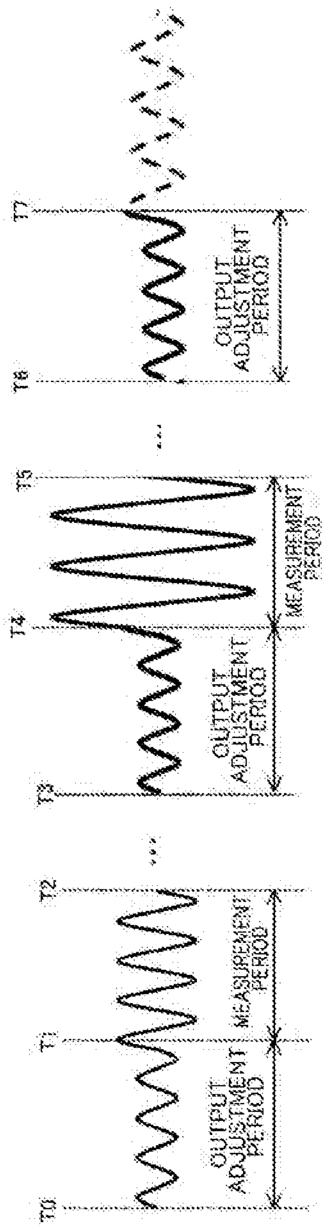

FIG. 346 is a diagram illustrating an example of a transmission waveform used when transmission power is adjusted in accordance with the amount of moisture, and error is output as necessary in the eleventh embodiment of the present technology.

FIG. 347 is a diagram illustrating an example of waveforms of transmission/reception signals in the eleventh embodiment of the present technology.

Figure 348:
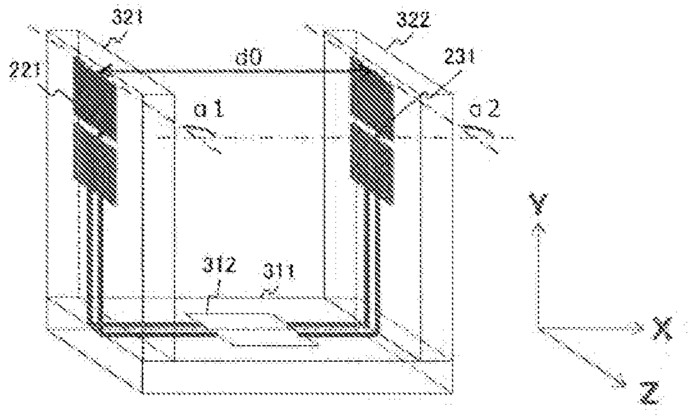

FIG. 348 is a diagram illustrating one configuration example of a sensor device according to a twelfth embodiment of the present technology.

Figure 349:
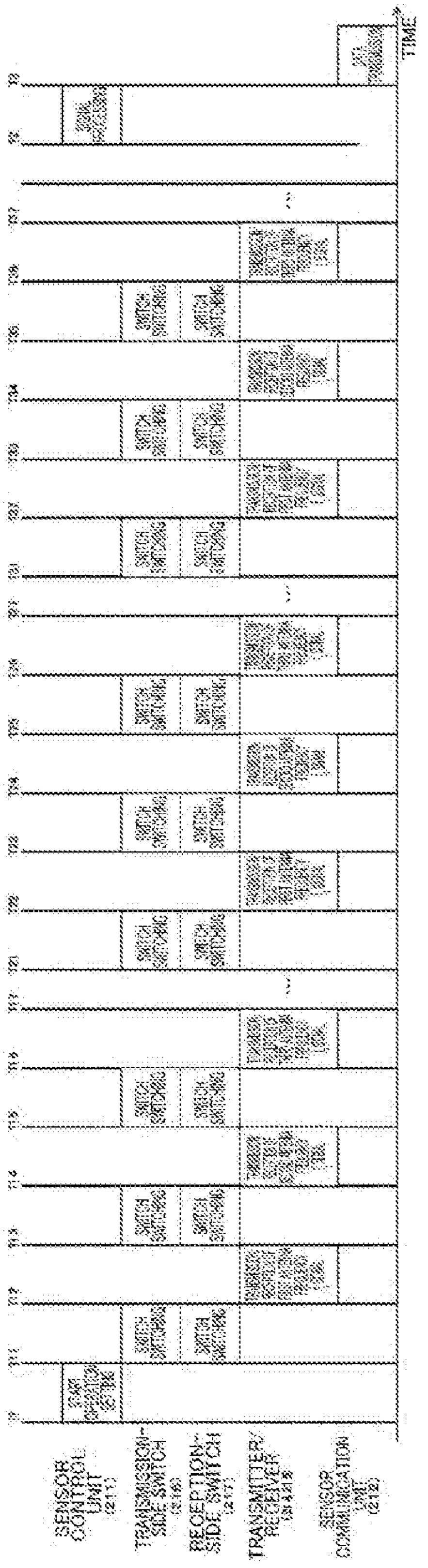

FIG. 349 is a timing diagram illustrating operations of respective units disposed inside a sensor device performed when the sequence of a transmission, reception, and wave detecting operation is changed in the first embodiment of the present technology.

Figure 350:
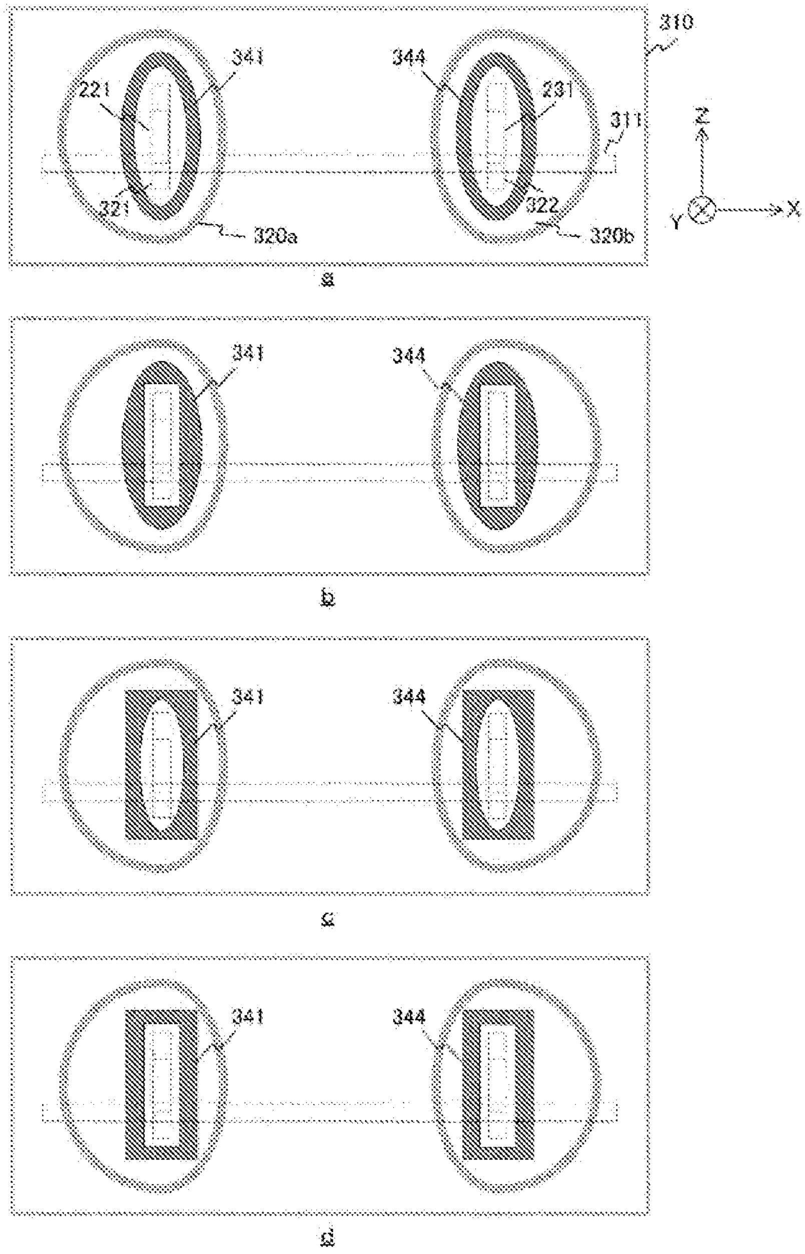

FIG. 350 is a top view of the sensor device 200 of a case in which electric wave absorbing units illustrated in FIGS. 153*a* to 153*d* are applied to the electric wave absorbing unit included in the sensor device illustrated in FIG. 147*a* as examples of an application to a sensor device.

Figure 351:
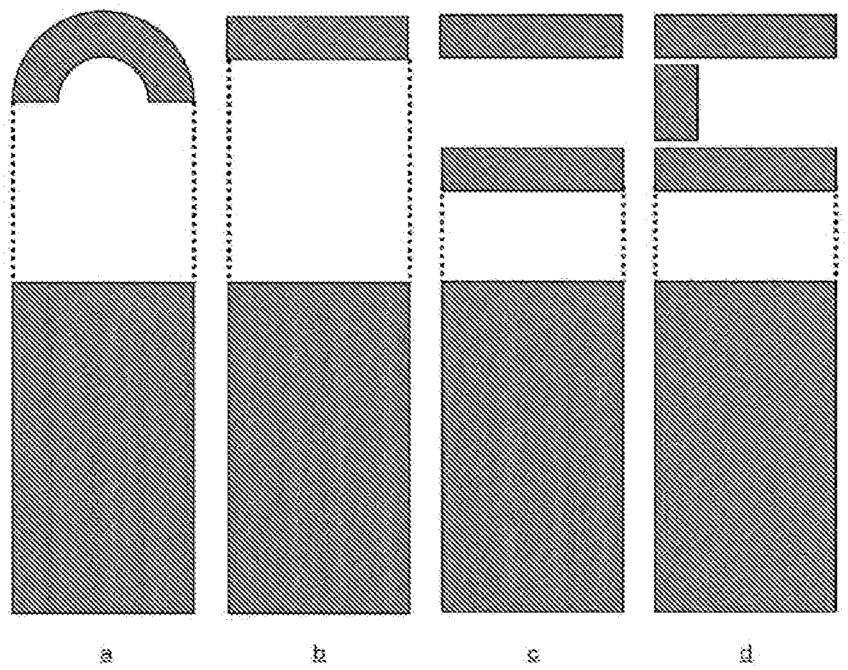

FIG. 351 is a diagram illustrating another example of a shape of an electric wave absorbing unit in the first embodiment of the present technology.

Figure 352:
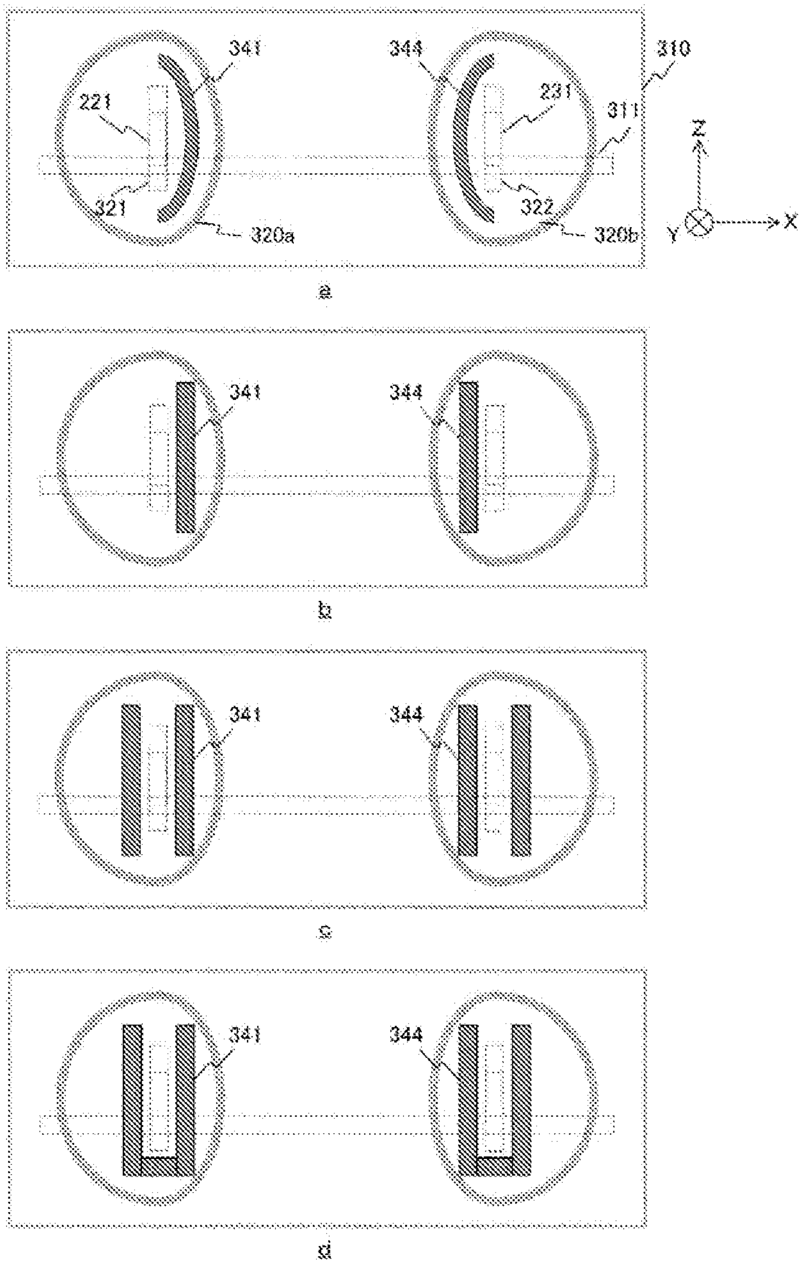

FIG. 352 is a diagram illustrating another example of a shape of an electric wave absorbing unit in the first embodiment of the present technology.

FIG. 353 is a top view (a projected view) of a sensor device of a case in which electric wave absorbing units illustrated in FIGS. 153*a* to 153*d* are applied to the electric wave absorbing unit included in the sensor device illustrated in FIG. 222*a* as examples of an application to a sensor device.

Figure 354:
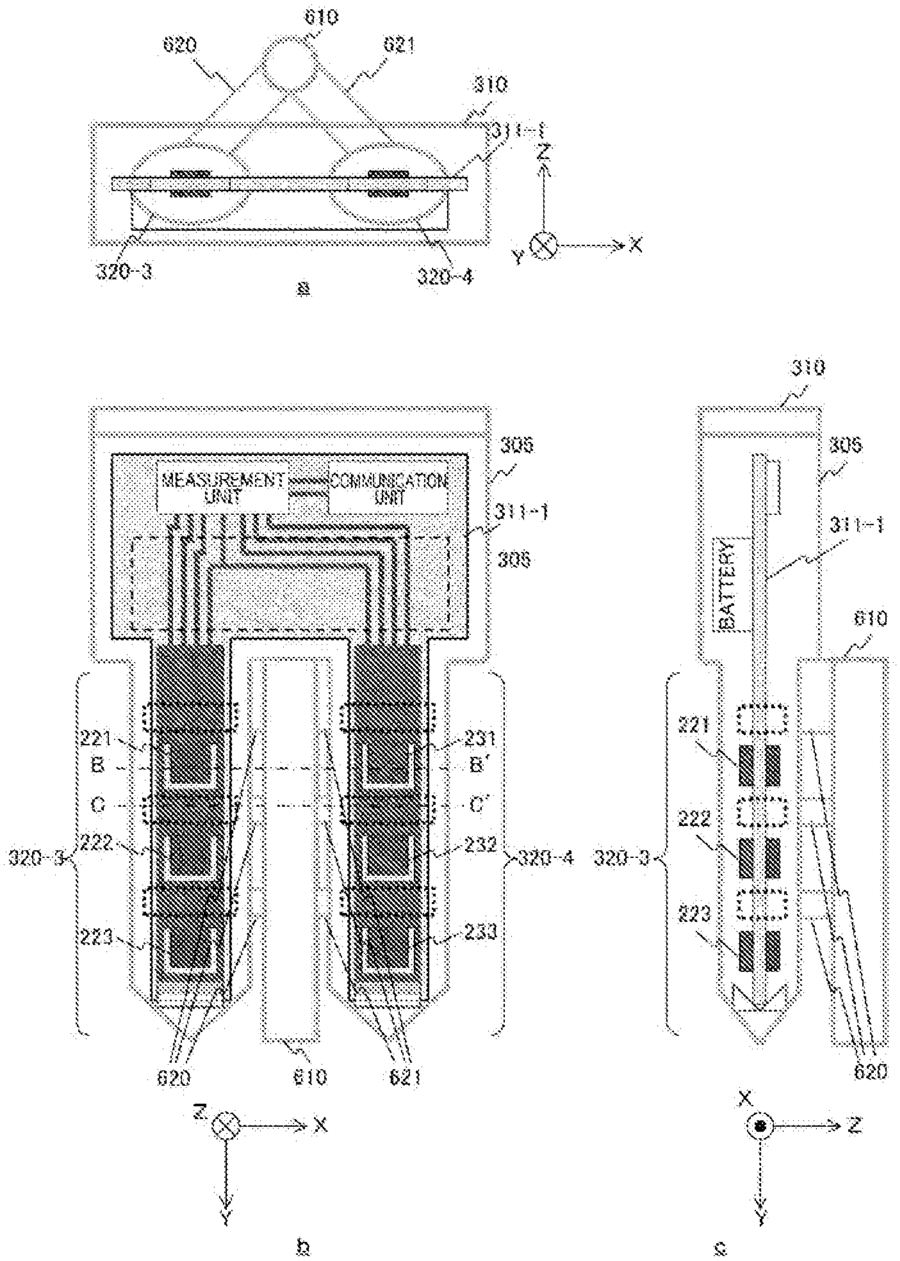

FIG. 354 is a diagram illustrating an example of a cutout face of the sensor device according to the seventh embodiment of the present technology.

FIG. 355 is a diagram illustrating an example of a cutout face of the sensor device according to the seventh embodiment of the present technology.

Figure 356:
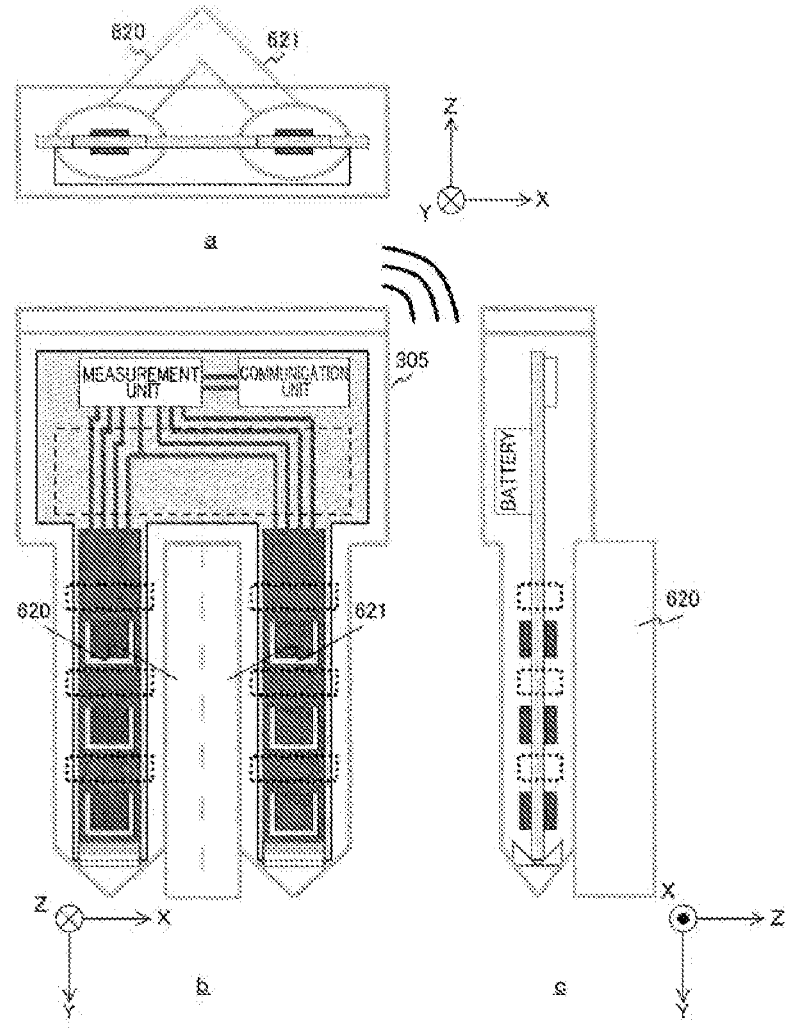

FIG. 356 is a diagram illustrating a structure of a sensor device of a case in which a and c in FIG. 311 are combined.

Figure 357:
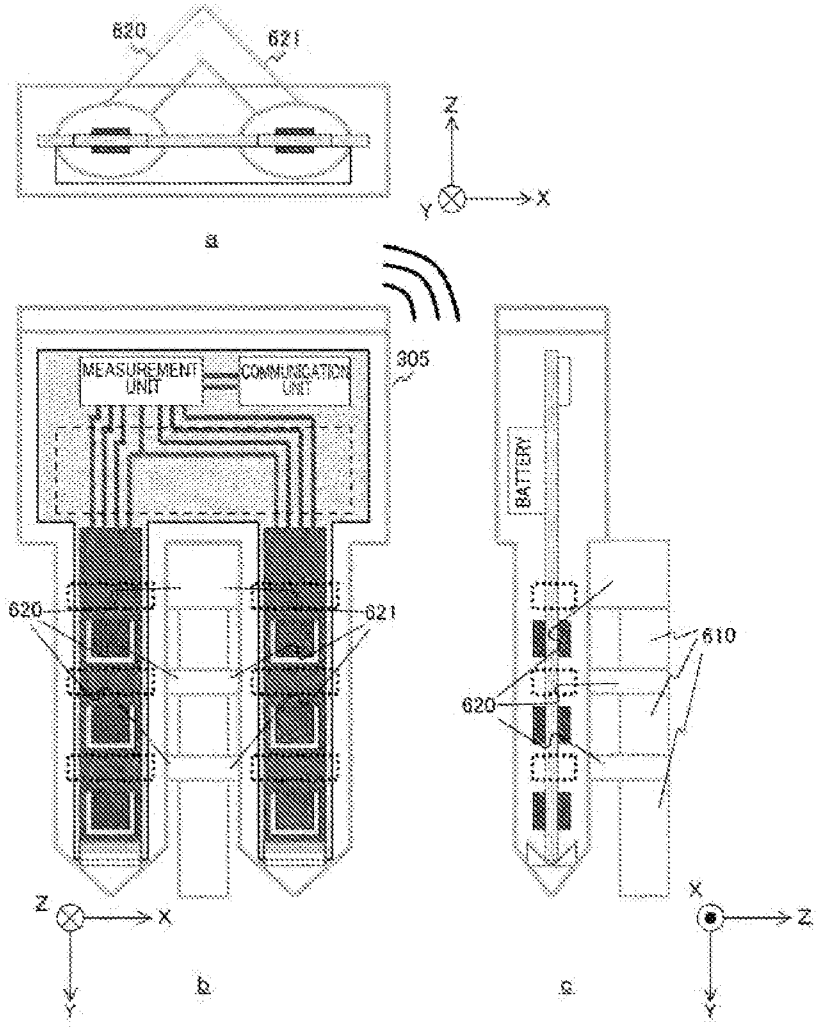

FIG. 357 is a diagram illustrating a structure of a sensor device of a case in which b and c in FIG. 311 are combined.

Figure 358:
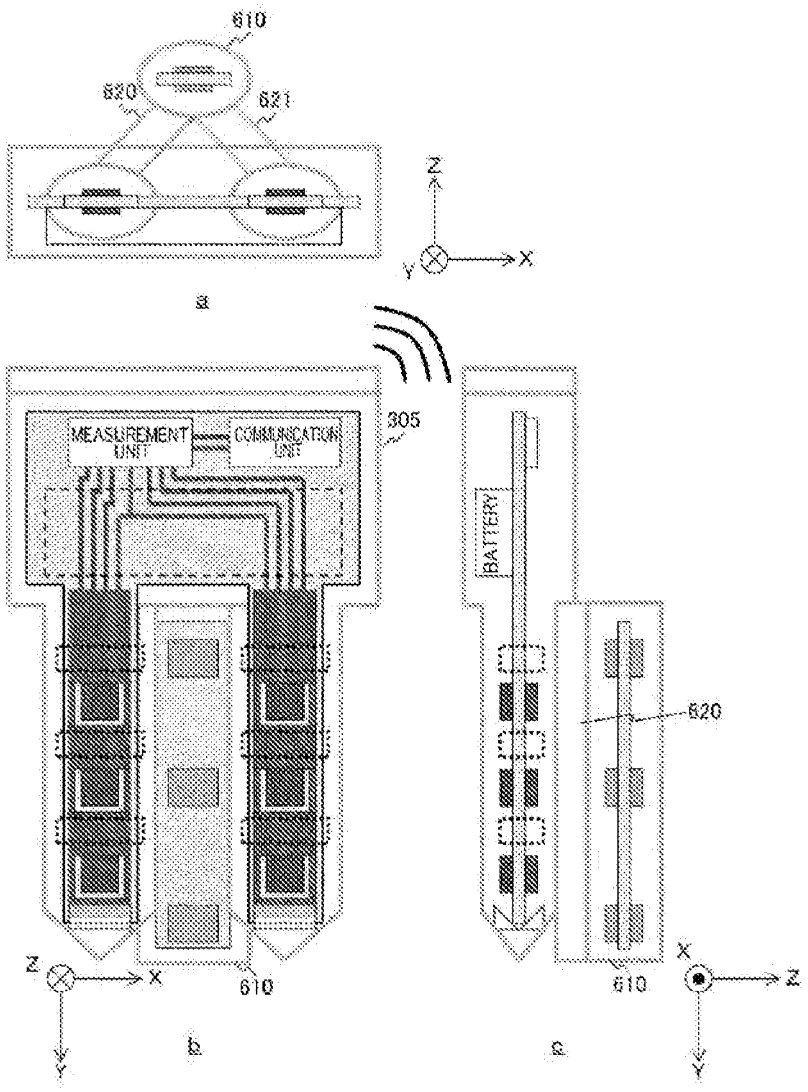

FIG. 358 is a diagram illustrating a structure of a sensor device of a case in which d and f in FIG. 311 are combined.

Figure 359:
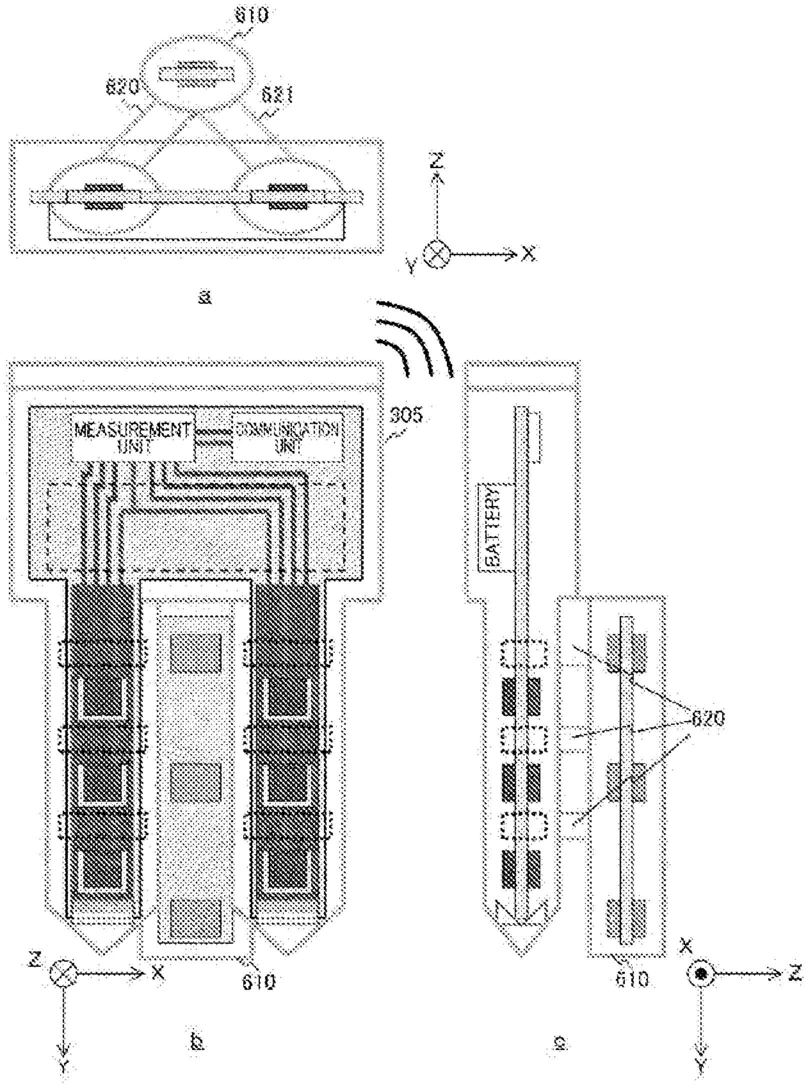

FIG. 359 is a diagram illustrating a structure of a sensor device of a case in which e and f in FIG. 311 are combined.

Figure 360:
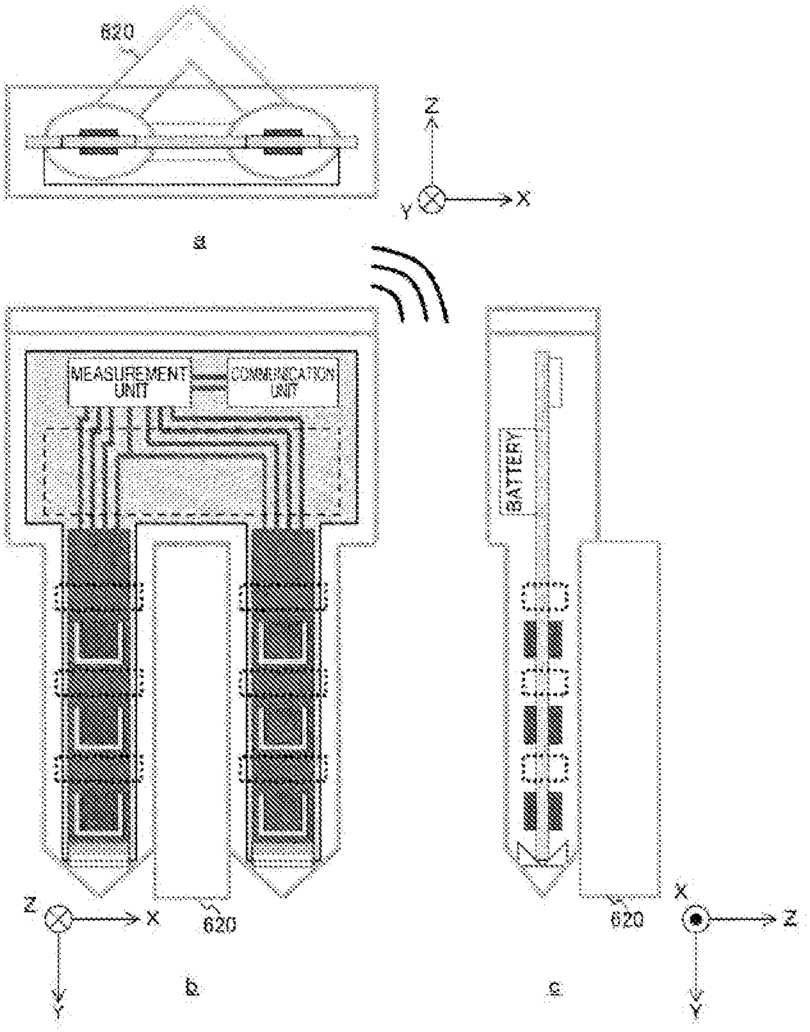

FIG. 360 is a diagram illustrating a structure of a sensor device of a case in which g and h in FIG. 311 are combined.

Figure 361:
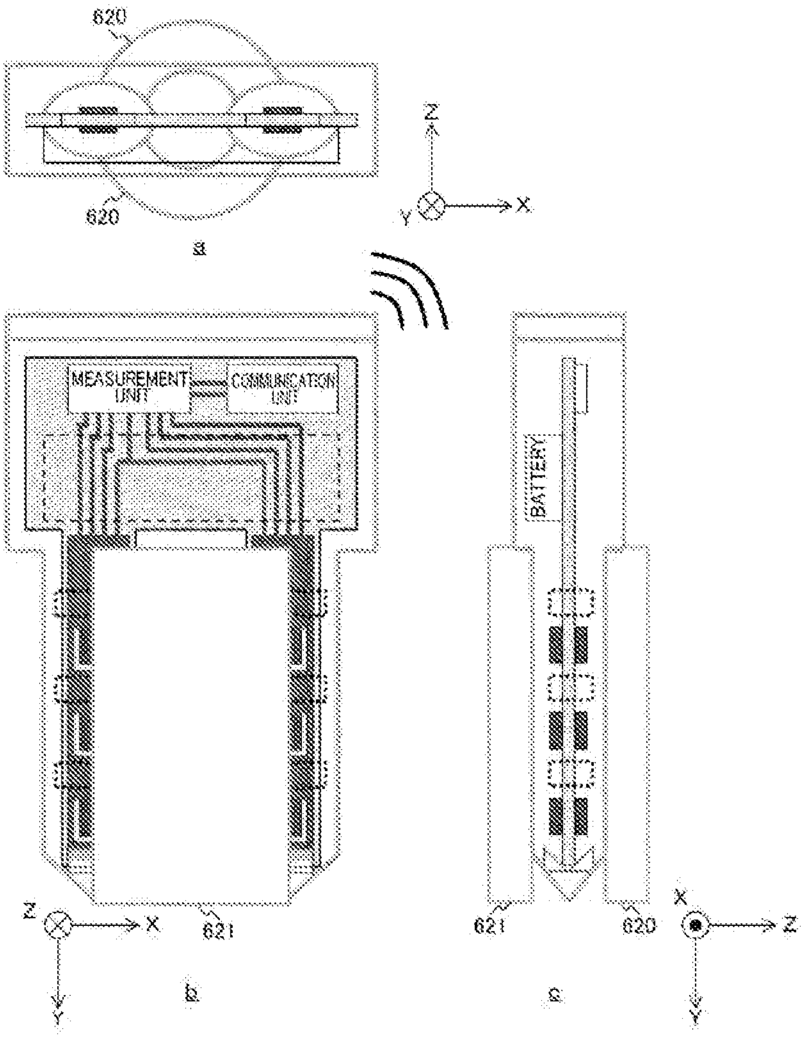

FIG. 361 is a diagram illustrating a structure of a sensor device of a case in which i and j in FIG. 311 are combined.

Figure 362:
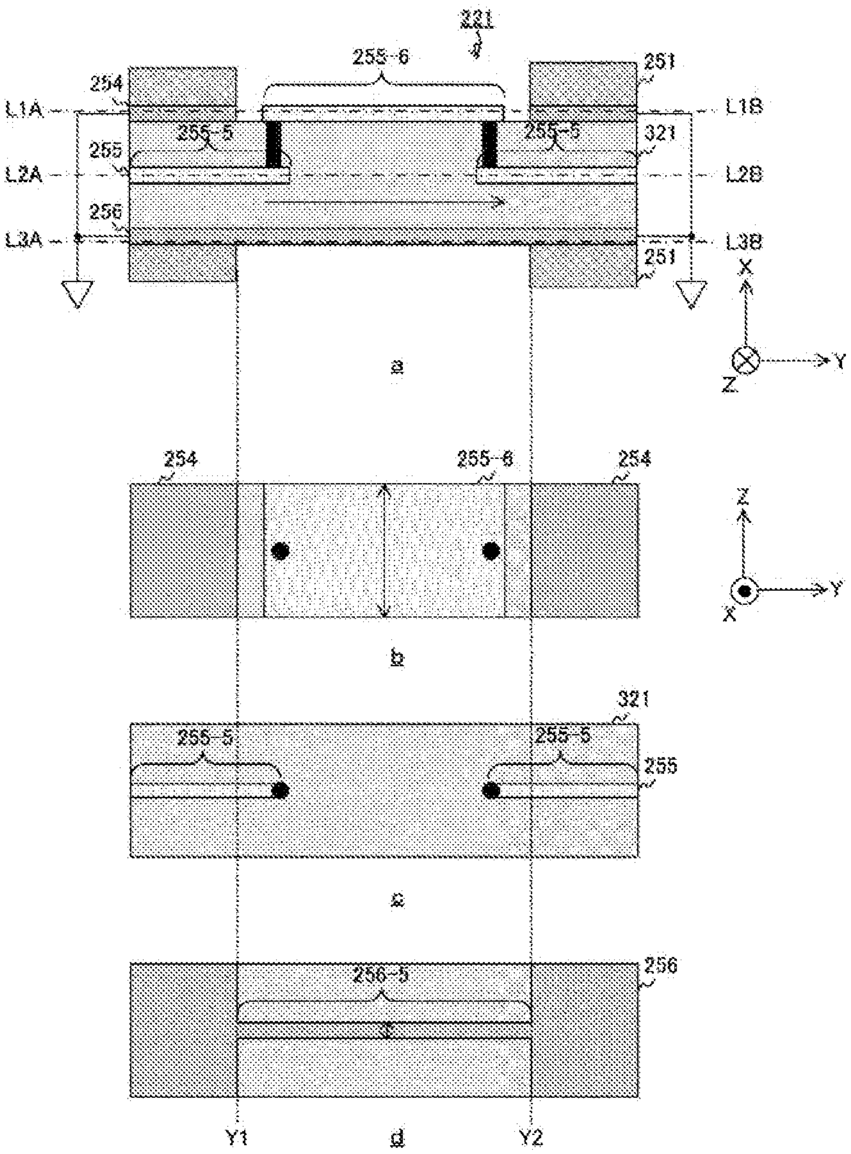

FIG. 362 is an example of a cross-sectional view and a plan view illustrating one configuration example of a transmission antenna in a thirteenth embodiment of the present technology.

Figure 363:
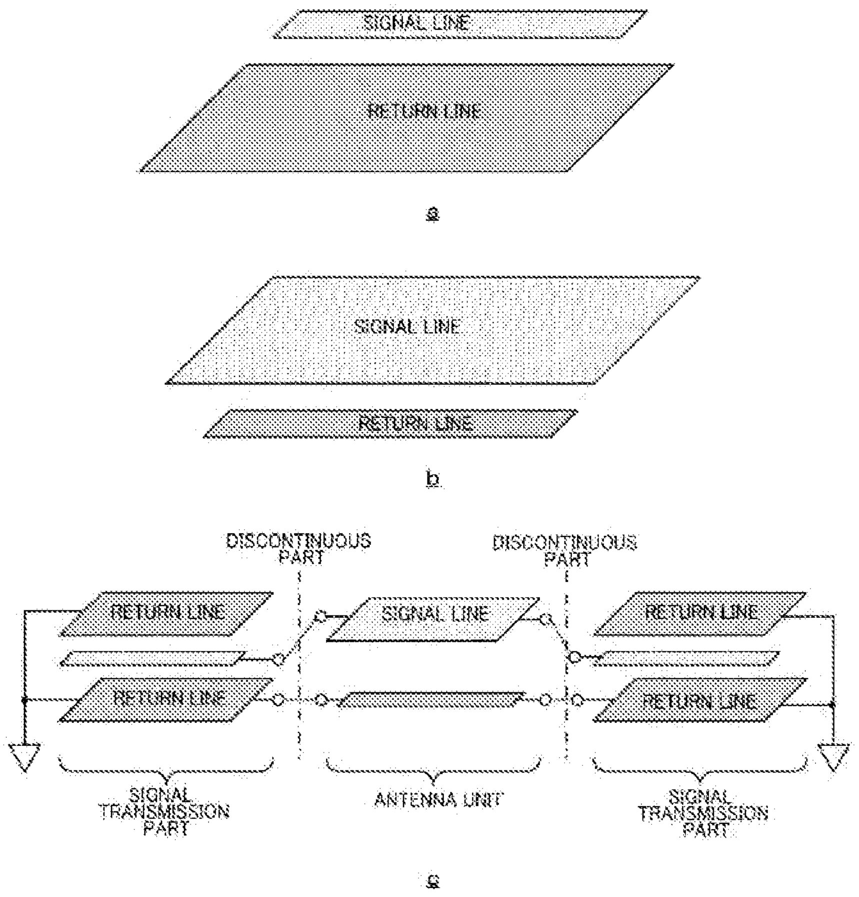

FIG. 363 is a diagram illustrating the principle of a transmission antenna in the thirteenth embodiment of the present technology.

Figure 364:
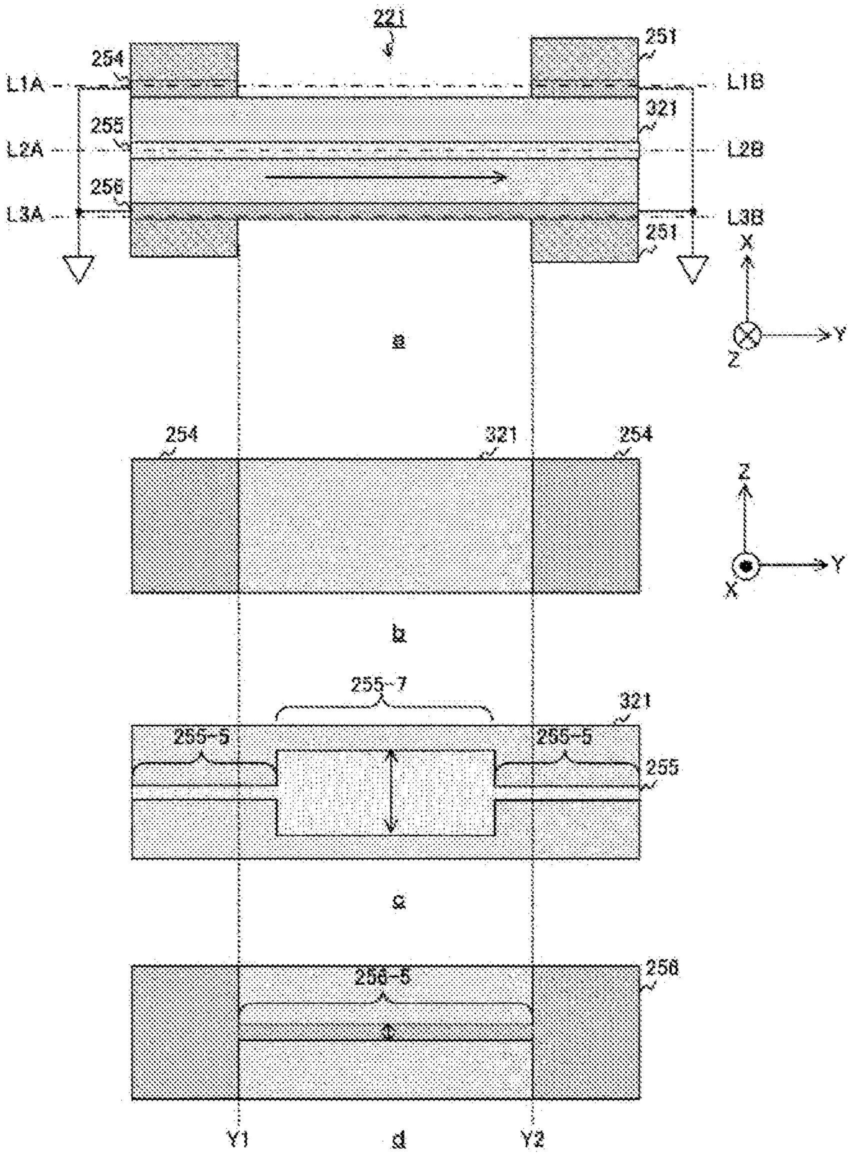

FIG. 364 is an example of a cross-sectional view and a plan view illustrating one configuration example of a transmission antenna of another type in the thirteenth embodiment of the present technology.

Figure 365:
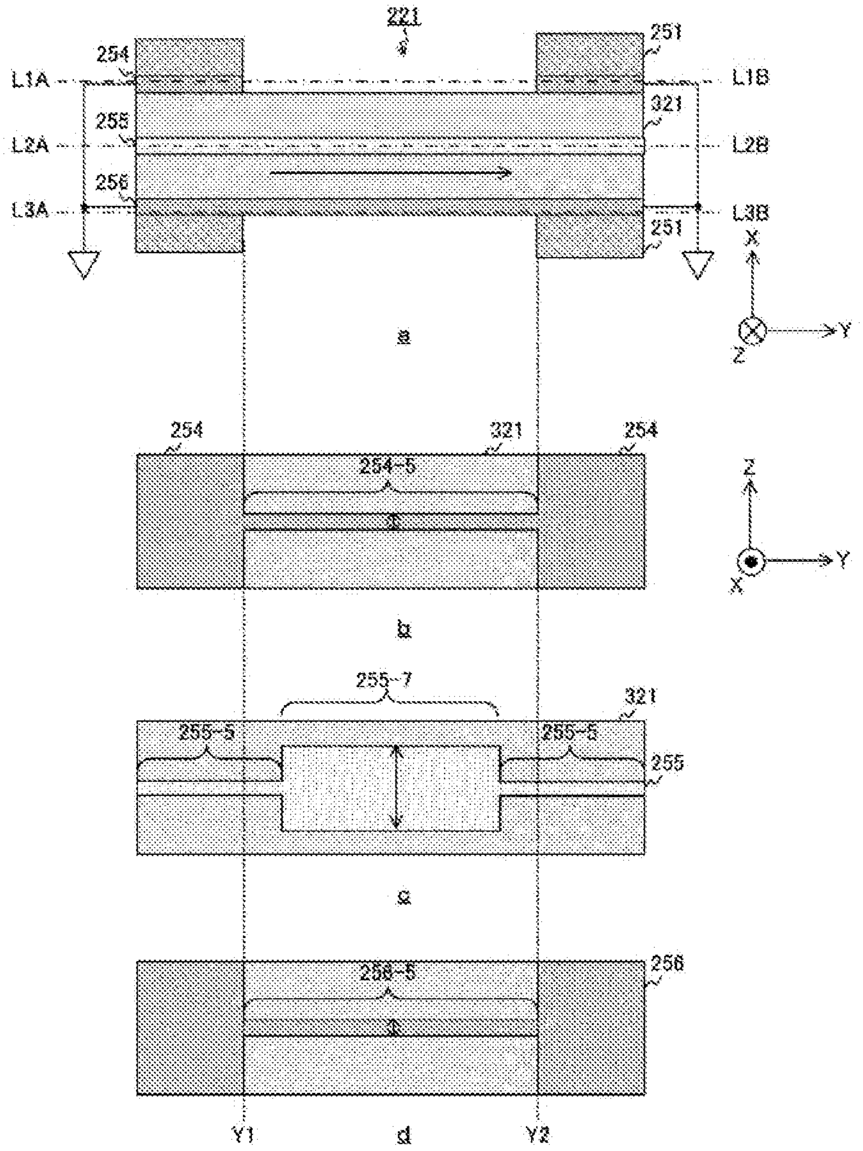

FIG. 365 is an example of a cross-sectional view and a plan view illustrating one configuration example of a transmission antenna of another type in the thirteenth embodiment of the present technology.

Figure 366:
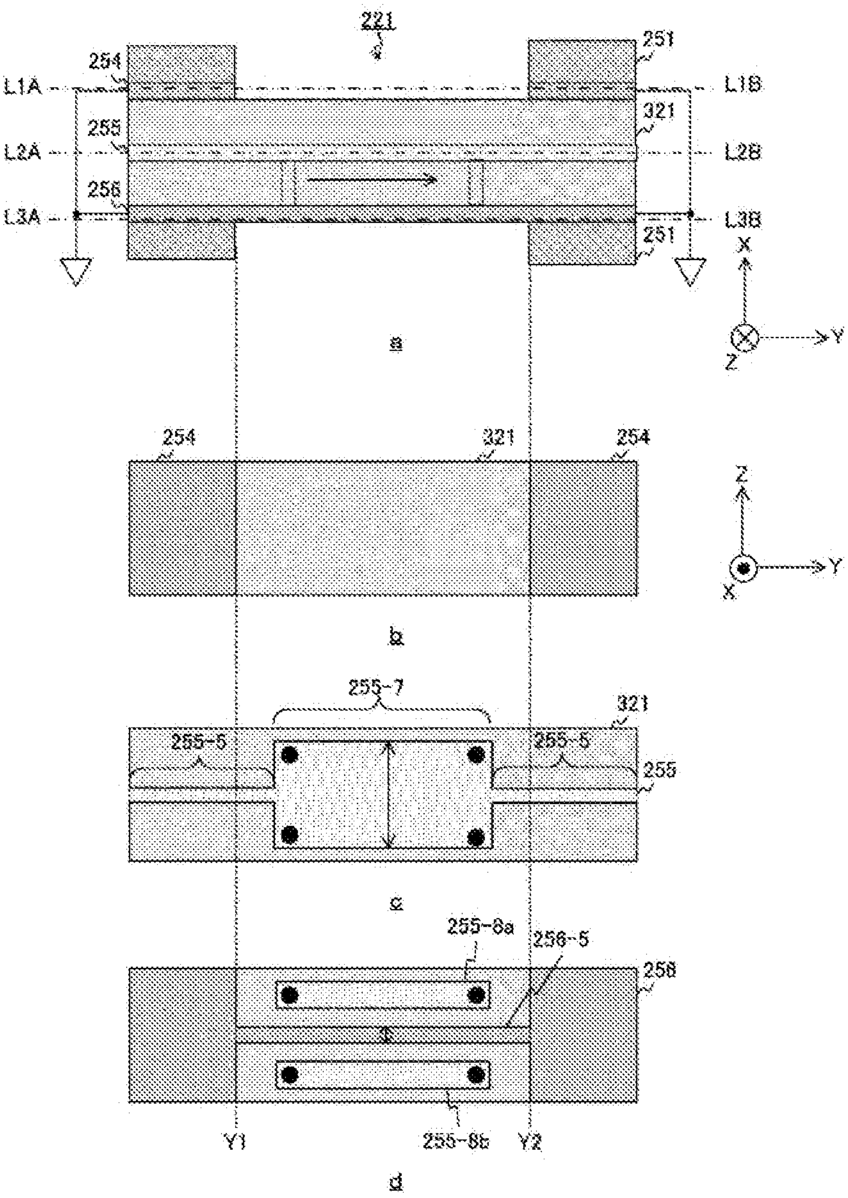

FIG. 366 is an example of a cross-sectional view and a plan view illustrating one configuration example of a transmission antenna of another type in the thirteenth embodiment of the present technology.

Figure 367:
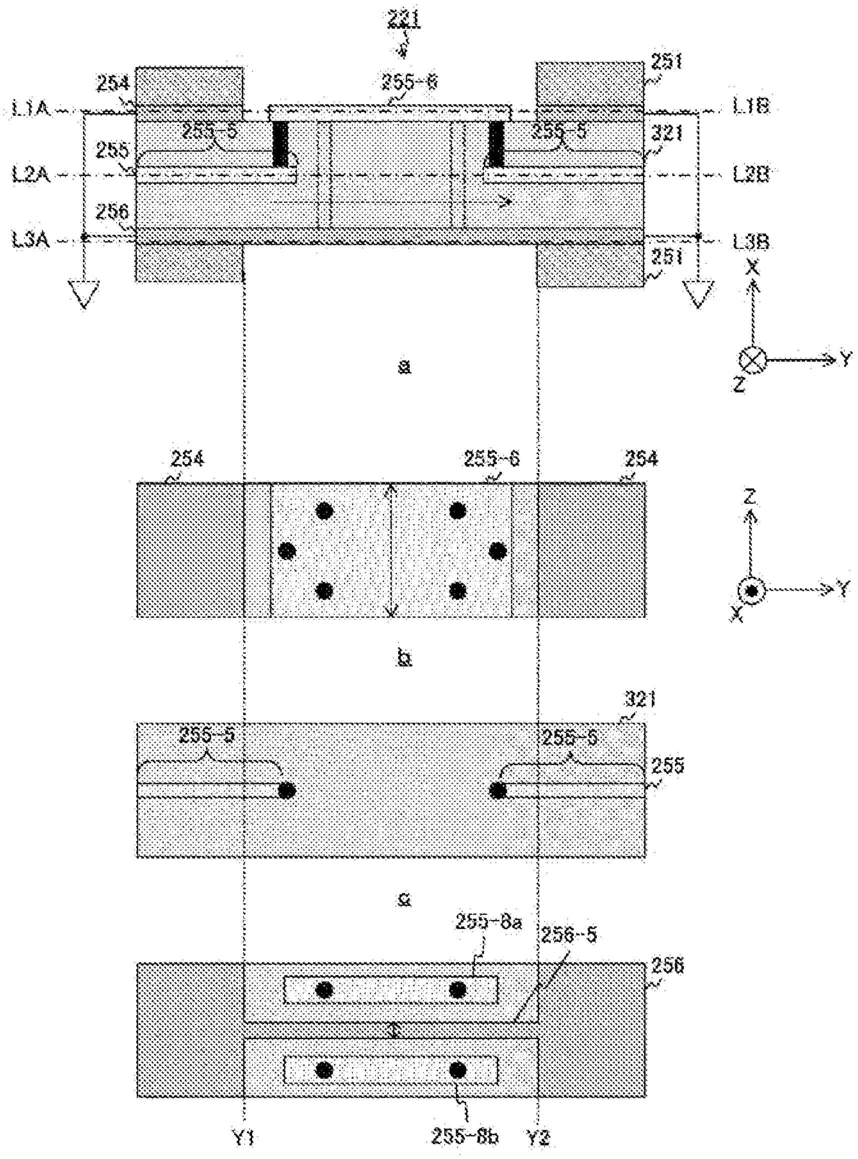

FIG. 367 is an example of a cross-sectional view and a plan view illustrating one configuration example of a transmission antenna of another type in the thirteenth embodiment of the present technology.

Figure 368:
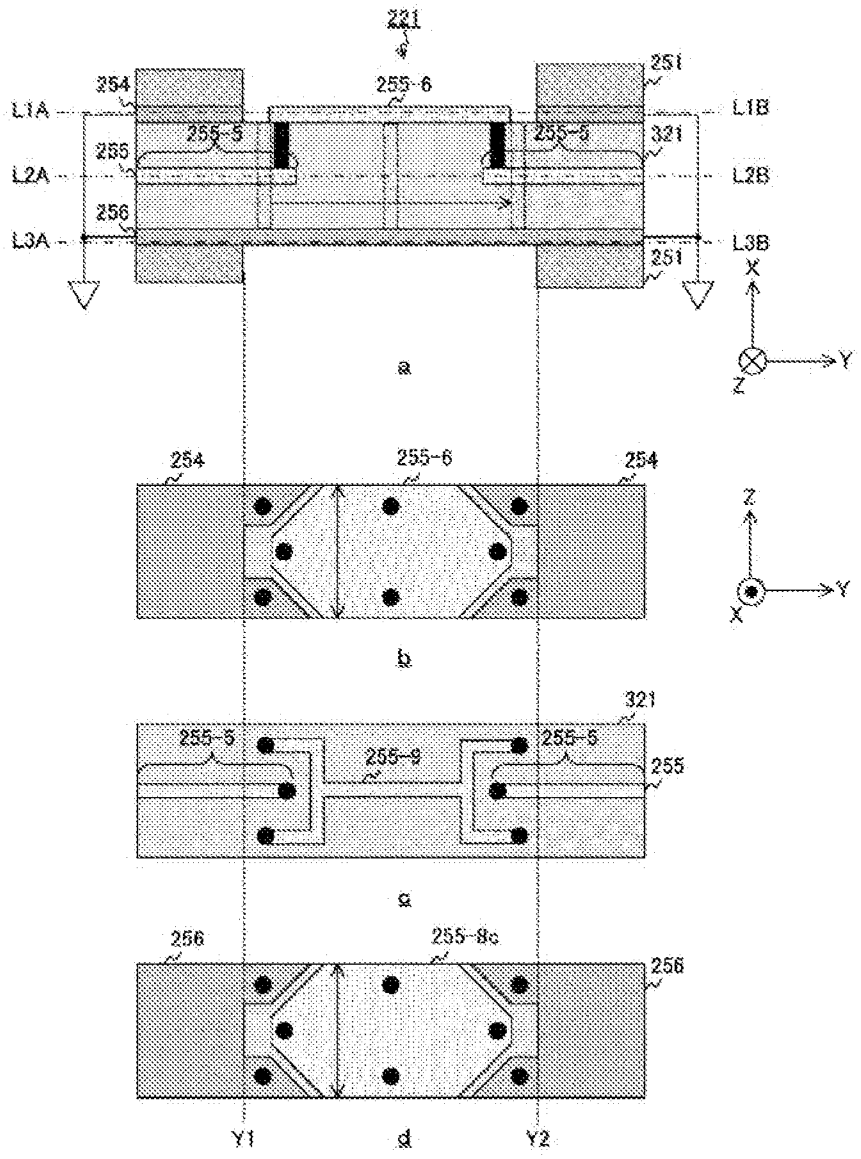

FIG. 368 is an example of a cross-sectional view and a plan view illustrating one configuration example of a transmission antenna of another type in the thirteenth embodiment of the present technology.

DESCRIPTION OF EMBODIMENTS

Modes for carrying out the present technology (hereinafter also referred to as "embodiments") will be described below. The description will be given in the following order.

1. First embodiment (an example in which a measurement unit substrate and in-probe substrate are orthogonally connected)
2. Second embodiment (an example in which an antenna is formed on one electronic substrate)
3. Third embodiment (an example in which an antenna having a column shape is included)
4. Fourth embodiment (an example in which a watering nozzle is fixed at an appropriate position)
5. Fifth embodiment (an example in which a sensor casing is not included)
6. Sixth embodiment (an example in which a stem is connected to a probe)
7. Seventh embodiment (an example in which a pillar or a reinforcing part are added)
8. Eighth embodiment (an example in which one pair of probe casings are divided)
9. Ninth embodiment (an example in which a guide is inserted before insertion of a sensor device)
10. Tenth embodiment (an example in which a spiral shaped member or a shovel-type casing is included)
11. Eleventh embodiment (an example, in which a transmission power is adjusted)
12. Twelfth embodiment (an example in which a measurement unit substrate is disposed at a position at which a direction in which a probe grows and a substrate plane are perpendicular to each other)
13. Thirteenth embodiment (an example in which a part of a signal line inside a split line is thickened)

1. First Embodiment

[Configuration Example of Moisture Measuring System]

Figure 1:
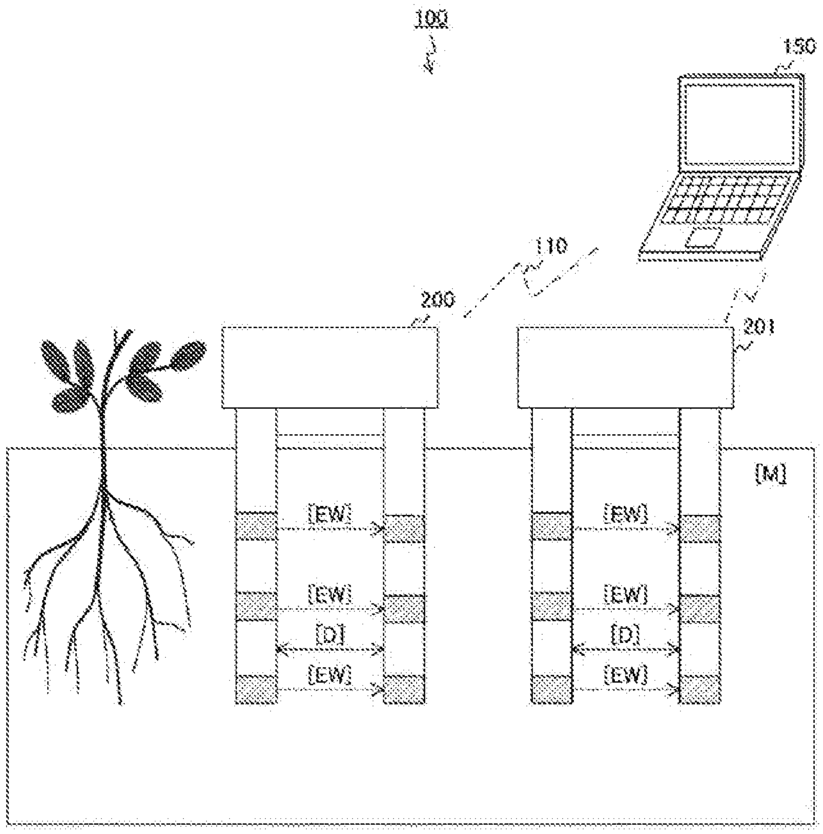
FIG. 1 is an example of a whole view of a moisture measuring system according to a first embodiment of the present technology.

FIG. 1 is an example of a whole view of a moisture measuring system 100 according to a first embodiment of the present technology. This moisture measuring system 100 measures an amount of moisture contained in a medium M and includes a central processing device 150 and at least one sensor device among sensor devices 200 and 201 and the like. As the medium M, for example, soil for growing crops may be conceived.

The sensor device 200 acquires data required for measuring an amount of moisture as measurement data. Details of the measurement data will be described below. This sensor device 200 transmits the measurement data to the central processing device 150 via a communication path 110 (a wireless communication path or the like). The configuration of the sensor device 201 is similar to that of the sensor device 200. The central processing device 150 measures an amount of moisture using measurement data. In addition, the communication path 110 may be a wired communication path.

In addition, a plurality of central processing devices 150 may be disposed inside the moisture measuring system 100.

A user uses the sensor devices 200 and 201 with being inserted into soil by applying a weight thereto from above the soil. The sensor device 200 and the like are used with at least an antenna part (an antenna 213 illustrated in FIG. 3 to be described below) included in the sensor device 200 and the like being exposed above the soil surface such that they are able to communicate with the central processing device 150. In the drawing, gray parts represent antennas (transmission antennas 221 to 223 and reception antennas 231 to 233 illustrated in FIG. 3 to be described below). The antenna part described above (the antenna 213 described above) may be used with being buried in the soil as long as the depth enables communication with the central processing device 150.

Each of the sensor devices 200 and 201 includes one pair of probes. A length of the probes is 5 to 200 centimeters (cm), and 1 to 40 antennas to be described below are disposed in the probes. In accordance with this, amounts of moisture can be measured for a plurality of depths in the range of the depth of the soil from 5 to 200 centimeters (cm).

[Configuration Example of Central Processing Device]

Figure 2:
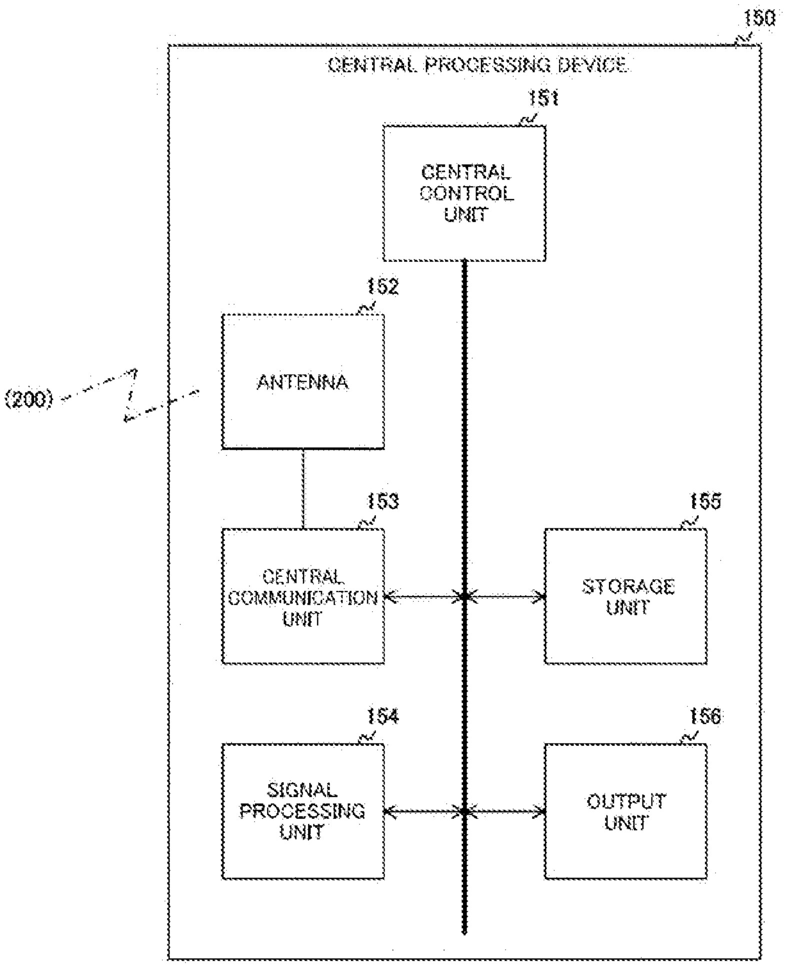
FIG. 2 is a block diagram illustrating one configuration example of a central processing device according to the first embodiment of the present technology.

FIG. 2 is a block diagram illustrating one configuration example of the central processing device 150 according to the first embodiment of the present technology. This central processing device 150 includes a central control unit 151, an antenna 152, a central communication unit 153, a signal processing unit 154, a storage unit 155, and an output unit 156.

The central control unit 151 performs overall control of the central processing device 150. The central communication unit 153 transmits information (for example, an instruction relation to measurement) to the sensor devices 200 and 201 through the antenna 152 and receives measurement data from the sensor devices 200 and 201.

The signal processing unit 154 acquires an amount of moisture on the basis of measurement data. The storage unit 155 stores measurement results of amounts of moisture and the like. The output unit 156 outputs measurement results of amounts of moisture to a display device (not illustrated in the drawing) and the like.

[Configuration Example of Sensor Device]

Figure 3:
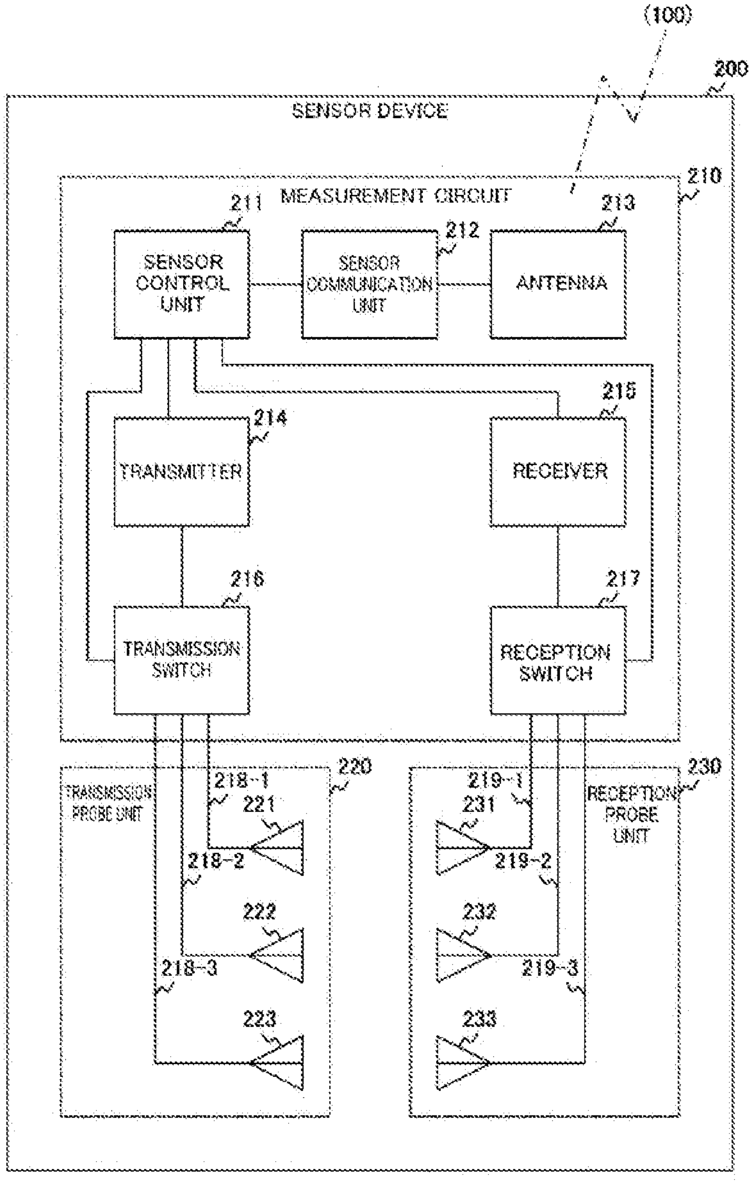
FIG. 3 is a block diagram illustrating one configuration example of a sensor device according to the first embodiment of the present technology.

FIG. 3 is a block diagram illustrating one configuration example of the sensor device 200 according to the first embodiment of the present technology. This sensor device 200 includes a measurement circuit 210, a transmission probe unit 220, and a reception probe unit 230. In the measurement circuit 210, a sensor control unit 211, a sensor communication unit 212, an antenna 213, a transmitter 214, a receiver 215, a transmission switch 216, and a reception switch 217 are disposed.

Inside the transmission probe unit 220, a predetermined number of transmission antennas such as transmission antennas 221 to 223 are disposed. Inside the reception probe unit 230, a predetermined number of reception antennas such as reception antennas 231 to 233 are disposed.

The sensor control unit 211 controls each circuit of the inside of the measurement circuit 210. The transmission switch 216 selects one of the transmission antennas 221 to 223 and connects the selected transmission antenna to the transmitter 214 in accordance with control of the sensor control unit 211. The reception switch 217 selects one of the reception antennas 231 to 233 and connects the selected reception antenna to the receiver 215 in accordance with control of the sensor control unit 211. The transmission antennas 221 to 223 are connected to the transmission switch 216 respectively via transmission lines 218-1 to 218-3. In addition, the reception antennas 231 to 233 are connected to the reception switch 217 respectively via transmission lines 219-1 to 219-3.

The transmitter 214 transmits an electrical signal of a predetermined frequency through a selected transmission antenna as a transmission signal. As an incident wave inside a transmission signal, for example, a CW (Continuous Wave) wave is used. This transmitter 214, for example, transmits a transmission signal, by sequentially switching the frequency in steps of 50 megahertz (MHz) within a frequency band of 1 to 9 gigahertz (GHz).

The receiver 215 receives a transmitted wave through a selected reception antenna. Here, the transmitted wave is acquired by the reception antenna converting an electromagnetic wave transmitted through a medium between probes into an electrical signal.

The sensor communication unit 212 receives information (an instruction relating to measurement) sent from the central processing device 150 and transmits data representing a reception result of the receiver 215 to the central processing device 150 through the antenna 213 as measurement data.

In addition, the configuration of the sensor device 201 is similar to that of the sensor device 200.

FIG. 4 is an example of a whole view of the sensor device 200 according to the first embodiment of the present technology. In the drawing, a is a projected view seen from above the sensor device 200 with a side inserted into the soil set as a lower side (in other words, a drawing in which features of units of the sensor device 200 seen from the top are superimposed). In the drawing, b is a front view of the sensor device 200. In the drawing, c is a projected view seen from a lateral side of the sensor device 200 (in other words, a diagram in which features of units of the sensor device 200 seen from the lateral side are superimposed). Hereinafter, similar to FIG. 4, trihedral figures in this specification are projected views (views in which features of units are superimposed) unless otherwise mentioned.

Figure 5:
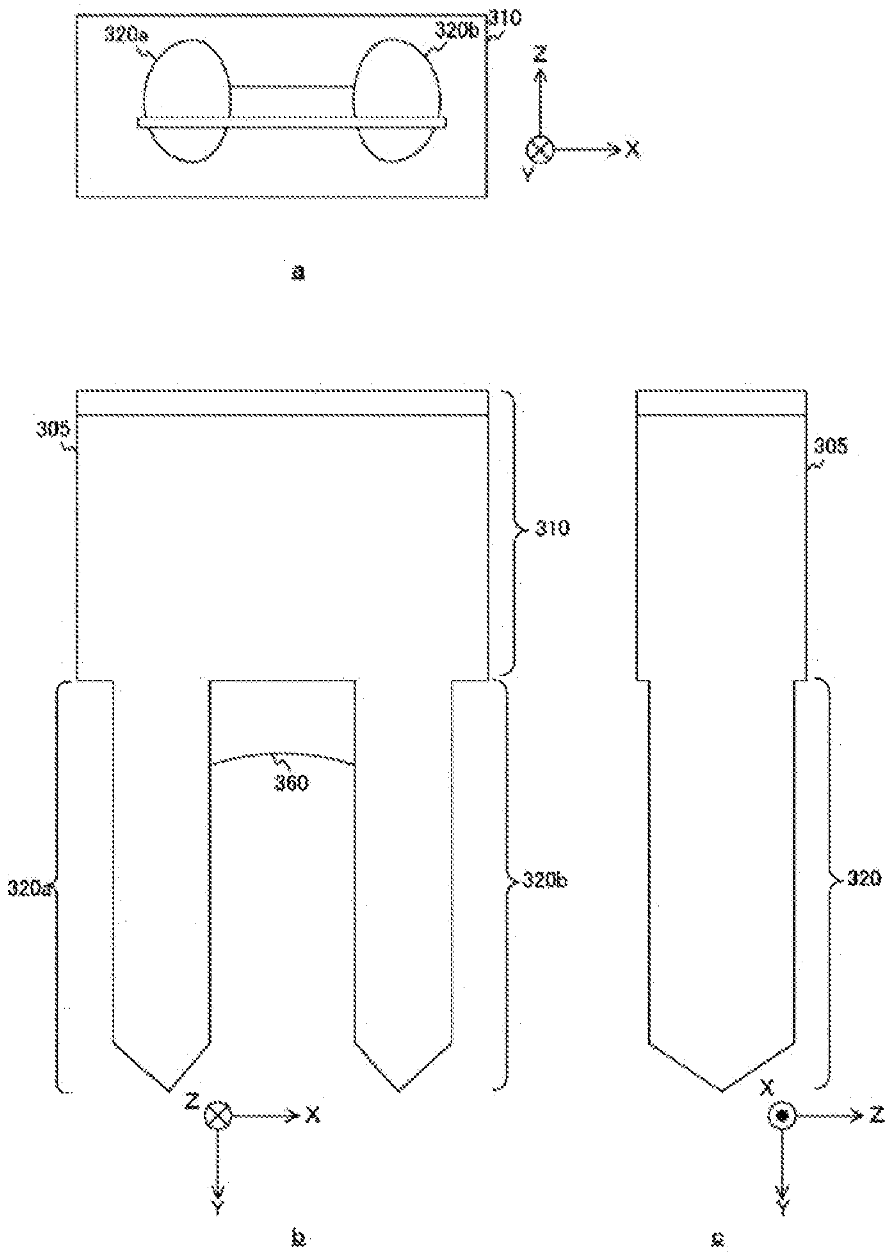
FIG. 5 is an example of a whole view of a sensor casing according to the first embodiment of the present technology.

The sensor device 200 includes a sensor casing 305 in which one pair of protrusion parts are disposed on a lower part thereof. As will be described below, FIG. 5 is an example of a whole view of the sensor casing 305. In the sensor casing 305, portions in which one pair of protrusion parts are disposed will be conveniently referred to as probe casings 320, and the other portion will be conveniently referred to as a measurement unit casing 310. A casing housing the transmission probe unit 220 will be referred to as a probe casing 320*a*, and a casing housing the reception probe unit 230 will be referred to as a probe casing 320*b*. In addition, a combination of the transmission probe unit 220 and the probe casing 320*a* housing this will be referred to as a transmission probe, and a combination of the reception probe unit 230 and the probe casing 320*b* housing this will be referred to as a reception probe.

Inside the measurement unit casing 310, a measurement unit substrate 311 is disposed. The measurement unit substrate 311 is an electronic substrate including a plurality of wirings that are stacked (in other words, a wiring substrate). In this measurement unit substrate 311, the measurement circuit 210 is formed. Here, a measurement unit 312 illustrated in FIG. 4 represents the measurement circuit 210 illustrated in FIG. 3. In FIG. 3, the antenna 213 is included in the measurement circuit 210. In FIG. 4, the antenna 213 is disposed outside the measurement circuit 210, which represents a modification example of the measurement circuit 210 illustrated in FIG. 3. In FIG. 4, a form in which the antenna 213 is included in the measurement circuit 210 may be employed. In addition, a battery 313, a connector 314, and a connector 315 are connected to the measurement substrate 311. The measurement unit 312 illustrated in FIG. 4 may be configured using one semiconductor device or may be configured using a plurality of semiconductor devices. The measurement unit 312 and the connector 314 and the connector 315 are connected using strip lines including signal lines and a shield layer. In the drawing, three white thick lines represent signal lines, and a black thick line represents a shield layer for the convenience. Actually, although a strip line in which each signal line is shielded is formed by disposing a shield wiring between signal lines and disposing shield layers above and below signal lines in a direction orthogonal to a substrate plane, this is displayed in a simplified manner in FIG. 4.

In addition, inside the probe casing 320, in-probe substrates 321 and 322, electric wave absorbing units 341 to 346, and positioning parts 351 and 352 are disposed.

The in-probe substrate 321 is an electronic substrate including a plurality of wiring layers that are stacked (in other words, a wiring substrate). In the in-probe substrate 321, a connector 323, radiation elements 330 to 332, shield layers 325, and a plurality of signal lines (not illustrated) are formed. In addition, in the in-probe substrate 321, a plurality of the shield layers are formed. In the radiation element 330 and the shield layer 325, parts formed from portions exposed from the electric wave absorbing unit 341 and the like function as one transmission antenna 221. Similarly, the radiation elements 331 and 332 respectively function as the transmission antennas 222 and 223. In the drawing, three transmission antennas are disposed. The connector 323 and the radiation elements 330 to 332 respectively included in the transmission antennas 221 to 223 are connected using transmission lines 218-1 to 218-3 that are independent for each transmission antenna. Such transmission lines are formed by strip lines in which each of the plurality of signal lines is shielded by a shield layer, a shield wiring, or a shield via formed in the in-probe substrate 321 in both a substrate parallel direction (on left and right sides of the signal line) and a substrate perpendicular direction (on upper and lower sides of the signal line). Also in the measurement unit substrate 311, the measurement unit 312 and the connector 314 are connected using transmission lines that are independent for each transmission antenna, and such transmission lines are formed by strip lines using signal lines and a shield layer included in the measurement unit substrate 311. In accordance with this, all the transmission antennas (in the example illustrated in FIGS. 3 and 4, the transmission antennas 221 to 223) included in the measurement unit 312 to the sensor device 200 are connected using transmission lines (particularly, strip lines) that are independent for each transmission antenna.

The in-probe substrate 322 is also an electronic substrate including a plurality of wiring layers that are stacked (in other words, a wiring substrate). In the in-probe substrate 322, a connector 324, elements (reception elements) 333 to 335, a shield layer 326, and a plurality of signal lines (not illustrated) are formed. In addition, also in the in-probe substrate 322, a plurality of the shield layers are formed. In the element (the reception element) 333 and the shield layer 326, parts formed from portions exposed from the electric wave absorbing unit 344 and the like function as one reception antenna 231. Similarly, the radiation elements 334 and 335 respectively function as the reception antennas 232 and 233. In the drawing, three reception antennas are disposed. The connector 324 and the elements (reception elements) 333 to 335 respectively included in the reception antennas 231 to 233 are connected using lines 219-1 to 219-3 that are independent for each reception antenna. Such transmission lines are formed by strip lines in which each of the plurality of signal lines is shielded by a shield layer, a shield wiring, or a shield via formed in the in-probe substrate 322 in both a substrate parallel direction (on left and right sides of the signal line) and a substrate perpendicular direction (on upper and lower sides of the signal line). Also in the measurement unit substrate 311, the measurement unit 312 and the connector 315 are connected using transmission lines that are independent for each reception antenna, and such transmission lines are formed by strip lines using signal lines and a shield layer included in the measurement unit substrate 311. In accordance with this, all the reception antennas (in the example illustrated in FIGS. 3 and 4, the reception antennas 231 to 233) included in the measurement unit 312 to the sensor device 200 are connected using transmission lines (particularly, strip lines) that are independent for each transmission antenna.

A part including the probe casing 320*a* and the in-probe substrate 321 included in FIG. 4 corresponds to the transmission probe unit 220 illustrated in FIG. 3. A part including the probe casing 320*b* and the in-probe substrate 322 in FIG. 4 corresponds to the reception probe unit 230 illustrated in FIG. 3, and a reinforcing part 360 is disposed between such probe units.

Hereinafter, an axis parallel to a direction in which the sensor device 200 is inserted into the soil will be set as a Y axis. The probe casings 320*a* and 320*b* extend in the Y-axis direction. The in-probe substrates 321 and 322 also extend in the Y-axis direction. An axis parallel to a direction orthogonal to the Y axis on a first plane including a center line of the in-probe substrate 321 in the Y-axis direction and a center line of the in-probe substrate 322 in the Y-axis direction is set as an X axis. In the sensor device 200 illustrated in FIG. 4, the measurement unit substrate 311 extends on a second plane including a line parallel to the X-axis direction and a line parallel to the Y-axis direction. An axis perpendicular to the X axis and the Y axis will be set as a Z axis. The first and second planes described above are planes that are orthogonal to the Z axis.

As described above, the sensor device 200 is a device that measures an amount of moisture of the inside of a medium on the basis of characteristics of an electromagnetic wave that has propagated through the medium between transmission/reception antennas.

In addition, the shape of each of transmission antennas and reception antennas is a planar shape, and these are formed in electronic substrates such as the in-probe substrates 321 and 322 and the like. Hereinafter, this configuration will be referred to as "Constituent element (1)". In accordance with this, compared to a form in which, after antennas are formed as separate components, the antennas are assembled in electronic substrates (the in-probe substrates 321 and 322), processing accuracy and mounting accuracy of antennas are high, and an amount of moisture can be accurately measured. In addition, the electronic substrates and the antennas described above can be compactly formed, and the casing cross-section can be configured to be small. As a result, occurrence of an unnecessary space inside the casing is reduced, and also in accordance with this, the amount of moisture can be accurately measured. Details of this effect will be described below.

In addition, a transmission antenna and a reception antenna are fixedly disposed inside the sensor casing 305 such that they face each other, and a distance between the antennas is a predetermined distance. Hereinafter, a configuration in which these two antennas are configured to face each other and are fixedly disposed with a predetermined distance therebetween will be referred to as "Constituent element (2)". In accordance with this, compared to a form in which planar antennas are configured not to face each other or a form in which two antennas are not fixedly disposed to form a distance therebetween being a predetermined distance, the gain of the antennas is improved, the sensitivity is increased, and an amount of moisture can be accurately measured.

The transmission lines 218-1 to 218-3 connecting the measurement unit 312 and the transmission antennas 221 to 223 and the transmission lines 219-1 to 219-3 connecting the measurement unit 312 and the reception antennas 231 to 233, which are included in the measurement unit substrate 311, are formed using electronic substrates (the measurement unit substrate 311 and the in-probe substrates 321 and 322). Hereinafter, this configuration will be referred to as "Constituent element (3)". In accordance with this, compared to a case in which transmission lines are formed using coaxial cables, expansion/contraction of transmission lines are reduced, and an amount of moisture can be accurately measured.

In addition, the sensor device 200 includes the measurement unit substrate 311 and the in-probe substrate 321 and 322 as electronic substrate, and the measurement unit substrate 311 is disposed to be orthogonal to the in-probe substrates 321 and 322. More specifically, (1) the measurement unit substrate 311 is disposed in parallel with the first plane, (2) the in-probe substrates 321 and 322 are disposed to face each other and are disposed to be orthogonal to the first plane described above, and (3), as a result, the measurement unit substrate 311 is disposed to be orthogonal to the in-probe substrates 321 and 322. Hereinafter, this configuration will be referred to as "Constituent element (4)".

In addition, the sensor casing 305 includes the probe casings 320*a* and 320*b*, and transmission antennas are disposed at a plurality of positions in a direction in which the probe casing 320*a* extends, and also reception antennas are disposed at a plurality of positions in a direction in which the probe casing 320*b* extends. Hereinafter, this configuration will be referred to as "Constituent element (5)".

In addition, transmission lines include a plurality of transmission lines respectively connecting the measurement unit 312 included in the measurement unit substrate 311 and all the transmission antennas included in the sensor device 200 and a plurality of transmission lines respectively connecting the measurement unit 312 included in the measurement unit substrate 311 and all the reception antennas included in the sensor device 200. The measurement unit 312 included in the measurement unit substrate 311 time-divisionally drives a plurality of transmission antennas and a plurality of reception antennas. Hereinafter, this configuration will be referred to as "Constituent element (6)".

In addition, transmission lines between two substrates disposed to be orthogonal to each other (in other words, between the measurement unit substrate 311 and the in-probe substrate 321 and between the measurement unit substrate 311 and the in-probe substrate 322) are connected through transmission lines, which are transmission lines including a plurality of shielded signal lines, having flexibility higher than that of the measurement unit substrates 311 and 312. Hereinafter, this configuration will be referred to as "Constituent element (7)". In accordance with this, a plurality of planar transmission antennas and a plurality of planar reception antennas can be disposed to face each other. As a result, moisture can be accurately measured over the entire soil positioned between a plurality of transmission/reception antennas using transmission/reception antennas having high gains.

In addition, the probe casings 320*a* and 320*b* are formed using electromagnetic wave transmissive materials, and the strength of the probe casings 320*a* and 320*b* is higher than the strength of electronic substrates stored in the inside thereof. Hereinafter, this configuration will be referred to as "Constituent element (8)".

In addition, transmission antennas are formed in the in-probe substrate 321, and reception antennas are formed in the in-probe substrate 322. In cross-sections thereof in a direction orthogonal to an extending direction (the Y-axis direction) of the probe casing 320*a* and the in-probe substrate 321, (1) a distance from the center of the in-probe substrate 321 to a casing end of the probe casing 320*a* in a direction perpendicular to the in-probe substrate 321 is shorter than (2) a distance from the center of the in-probe substrate 321 to a casing end of the probe casing 320*a* in a direction parallel to the in-probe substrate 321. Similarly, in cross-sections thereof in a direction orthogonal to an extending direction (the Y-axis direction) of the probe casing 320*b* and the in-probe substrate 322, (1) a distance from the center of the in-probe substrate 322 to a casing end of the probe casing 320*b* in a direction perpendicular to the in-probe substrate 322 is shorter than (2) a distance from the center of the in-probe substrate 322 to a casing end of the probe casing 320*b* in a direction parallel to the in-probe substrate 322. Hereinafter, this configuration will be referred to as "Constituent element (9)".

The sensor device 200 illustrated in the drawing includes a transmission line coating part for transmission that is formed using a material absorbing electromagnetic waves and covers at least a part of "a transmission line for transmission connecting a transmission element (a transmission antenna) and the measurement unit" and a transmission line coating part for reception that is formed using a material absorbing electromagnetic waves and covers at least a part of "a transmission line for reception connecting a reception element (a reception antenna) and the measurement unit".

The transmission probe unit includes the transmission line coating part for transmission described above, and the reception probe unit includes the transmission line coating part for reception described above.

In addition, the sensor casing 305 includes a measurement unit casing 310 and a probe casing 320. In the probe casing 320, a part housing transmission antennas is the transmission probe casing 320*a*, and a part housing reception antennas is the reception probe casing 320*b*. The transmission probe casing 320*a* and the reception probe casing 320*b* are fixed to the measurement unit casing 310 and are in the form of being formed as one body. In addition, these may be in a separate state to be described below.

Here, the sensor casing 305 may be in a form in which, after the sensor casing 305 is divided into a plurality of components in advance, such components are fixed and formed as one body. In addition, the sensor casing 305 may be in a form in which, at a time point at which the transmission probe casing, the reception probe casing, and the measurement unit casing 310 are formed, these are formed as one body.

Although the sensor casing 305 includes the reinforcing part 360 used for improving the strength of the casing, the sensor casing 305 may have a configuration in which the reinforcing part 360 is not provided.

The reinforcing part 360 has a structure of being connected to at least two of the transmission probe casing 320*a*, the reception probe casing 320*b*, and the measurement unit casing 310. The reinforcing part 360 may have a structure of being connected to these three.

The whole sensor casing 305 may be formed using a material transmitting electromagnetic waves. Alternatively, at least parts that are the closest to transmission elements (transmission antennas) and reception elements (reception antennas) may be formed using a material transmitting electromagnetic waves, and at least a part of the other part may be formed using a material different from the material described above.

FIG. 5 is an example of a whole view of the sensor casing 305 according to the first embodiment of the present technology. In the drawing, a is a projected view seen from above the sensor casing 305. In the drawing, b is a front view of the sensor casing 305. In the drawing, c is a cross-sectional view of the sensor casing 305. In the sensor casing 305, a casing housing the transmission probe unit 220 will be referred to as a probe casing 320*a*, a casing housing the reception probe unit 230 will be referred to as a probe casing 320*b*, and a reinforcing structure that is disposed between the probe casings 320*a* and 320*b* and is used for improving the strength of the probe casings 320*a* and 320*b* will be referred to as a reinforcing part 360.

The whole of not only an antenna part from/to which electromagnetic waves are transmitted/received but also at least a transmission antenna, a part of the casing housing a transmission line for transmission, a reception antenna, and a part of the casing housing a transmission line for reception is formed using an electromagnetic wave transmissive material.

The measurement unit casing 310 housing the measurement unit substrate is in the state of being disposed to be erected in soil when it is inserted into the soil (in other words, a state in which it is disposed to extend in the first plane direction described above). More specifically, a thickness (a size in the Z-axis direction) of this measurement unit casing 310 is smaller than each one of a width (a size in the X-axis direction) and a height (a size in the Y-axis direction) of the measurement unit casing 310.

The sensor casing 305 including the reinforcing part 360 is formed using an electromagnetic wave transmissive material. Examples of this electromagnetic wave transmissive material include polymer system materials and inorganic system materials such as glass and PTEF (PolyTEtraFluoroethylene). As the polymer system material, PC (PolyCarbonate), PES (PolyEtherSulfone), PEEK (PolyEtherEtherKetone), PSS (PolyStyrene Sulfonic acid), and the like are used. Other than those, as polymer materials, PMMA (PolyMethylMethAcrylate), PET (PolyEthylene Terephthalate), and the like are also used.

Figure 6:
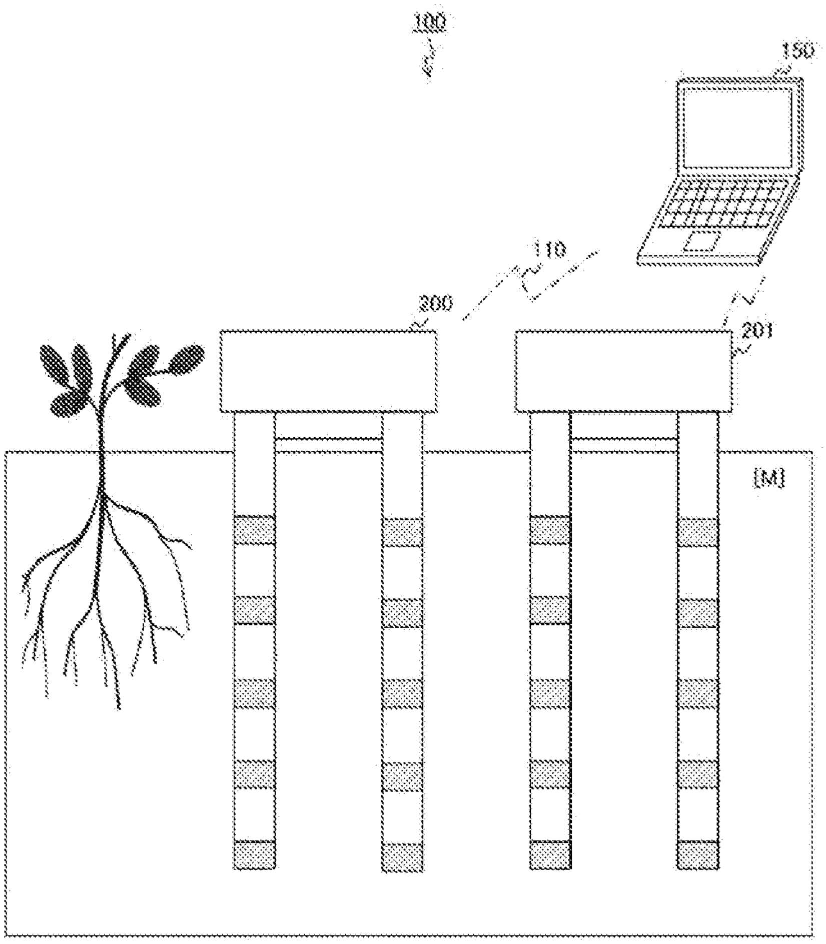
FIG. 6 is an example of a whole view of a moisture measuring system in which the number of antennas is increased in the first embodiment of the present technology.

FIG. 6 is another example of the first embodiment of the present technology and is an example of a whole view of a moisture measuring system 100 in which, compared to the moisture measuring system 100 illustrated in FIG. 1, lengths of a transmission probe and a reception probe included in sensor devices 200 and 201 are large, and the number of antennas disposed in the transmission probe and the reception probe is increased. Compared to the moisture measuring system 100 illustrated in FIG. 1, in the moisture measuring system 100 illustrated in FIG. 6, by configuring the lengths of the transmission probe and the reception probe to be large, increasing the number of antennas disposed in the transmission probe and the reception probe, and adding a reinforcing part 361 for improving strength of the transmission probe and the reception probe to be described below with reference to FIGS. 7 and 8, moisture of the soil can be measured more accurately in an area of the soil (particularly, a deep part of the soil) that is wider than that of the moisture measuring system 100 illustrated in FIG. 1.

Figure 7:
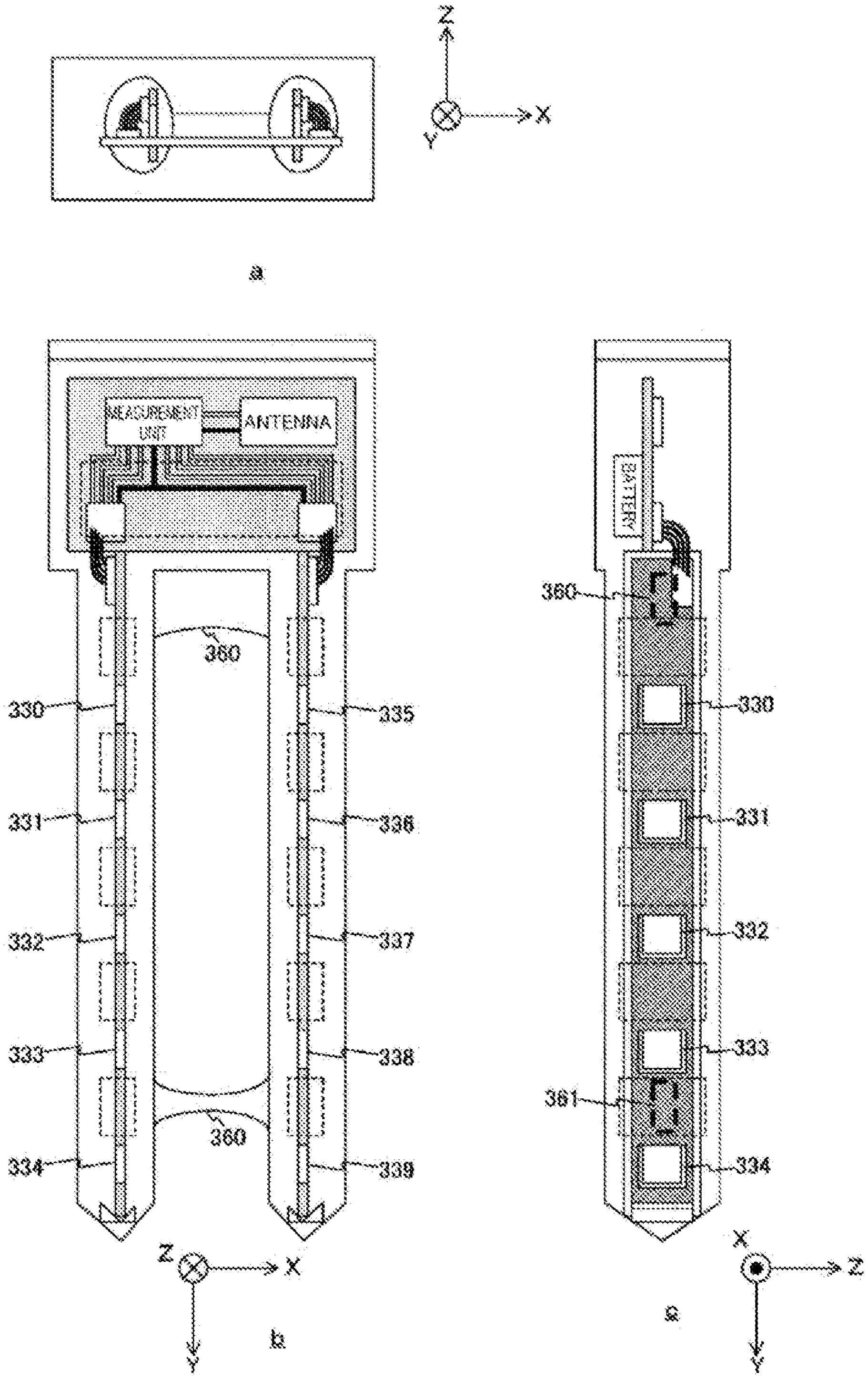
FIG. 7 is an example of a whole view of a sensor device in which the number of antennas is increased in the first embodiment of the present technology.

FIG. 7 is an example of a whole view of the sensor device 200 included in the moisture measuring system 100 illustrated in FIG. 6. Compared to the sensor device 200 illustrated in FIG. 4, the sensor device 200 illustrated in FIG. 7 has a structure in which the lengths of the transmission probe and the reception probe are large, the number of antennas disposed in the transmission probe and the reception probe is large, and the reinforcing part 361 for improving the strength of the transmission probe and the reception probe is added. In the example illustrated in FIG. 7, elements 330 to 339 are disposed, and five transmission antennas and five reception antennas are formed. Only in FIG. 7, the elements 330 to 334 represent radiation elements, and the elements 335 to 339 represent reception elements.

Figure 8:
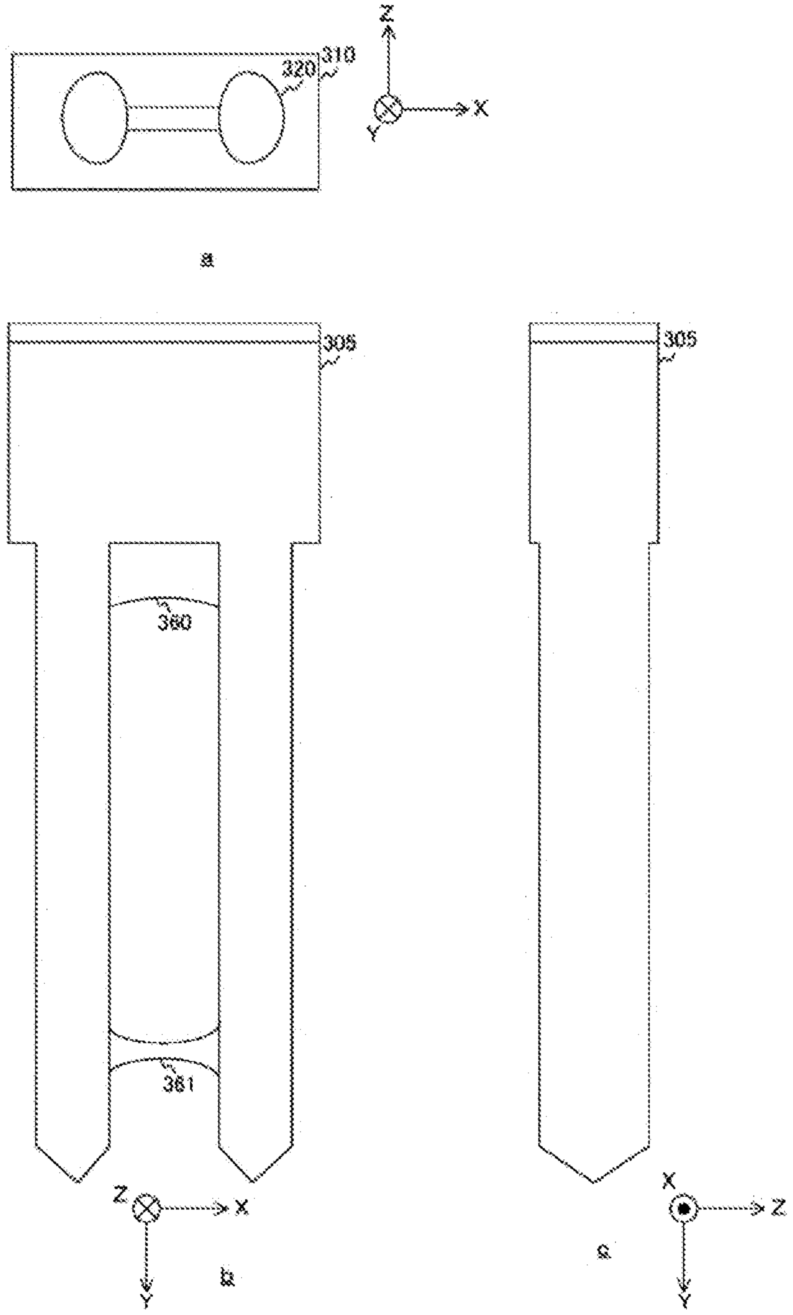
FIG. 8 is an example of a whole view of a sensor casing in which the number of antennas is increased in the first embodiment of the present technology.

FIG. 8 is an example of a whole view of a sensor casing 305 included in the sensor device 200 illustrated in FIG. 7. In order to improve the strength of the casing, the reinforcing part 361 is added below the probe casing 320.

In a case in which the length of the probe casing 320 is long, and the soil is hard, when the sensor device 200 is inserted into soil by applying a stress thereto, there is a likelihood of the probe casing 320 being deformed and a distance between the transmission antenna and the reception antenna being different from a distance of the time of design. By adding the reinforcing part 361, the likelihood of the deformation is decreased. In addition, in a case in which the soil is hard, when the sensor device 200 is inserted into the soil by applying a stress thereto, there is a likelihood of a portion between the measurement unit casing 310 and the probe casing 320 being broken. By adding the reinforcing part 361, the likelihood of the breaking is decreased.

Figure 9:
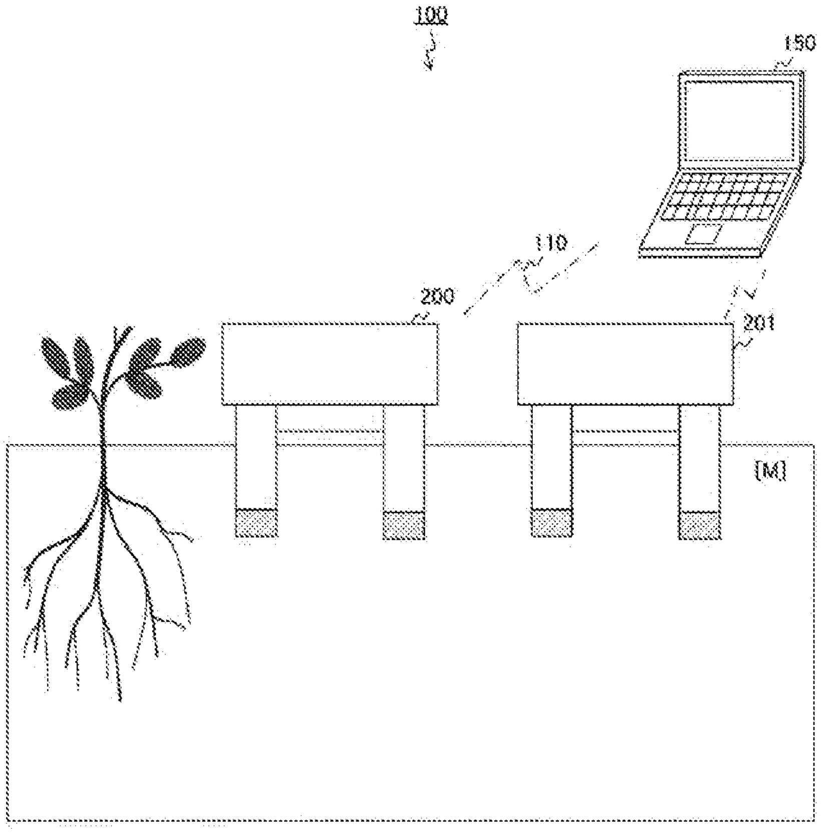
FIG. 9 is an example of a whole view of a moisture measuring system in which the number of antennas is decreased in the first embodiment of the present technology.

FIG. 9 is yet another example of the first embodiment of the present technology and is an example of a whole view of a moisture measuring system 100 in which, compared to the moisture measuring system 100 illustrated in FIG. 1, the number of antennas is reduced. As illustrated in the drawing, by reducing the number of antennas of the sensor device 200 and the like, one antenna may be configured in each of the transmission side and the reception side. By reducing the number of antennas, an amount of moisture of soil can be measured using simple constituent elements (a configuration in which the number of components is small). In addition, a means for driving a plurality of antennas is unnecessary. In this case, Constituent elements (5) and (6) are unnecessary. In addition, in a case in which the number of transmission antennas and the number of reception antennas are one, connection of a transmission line between two substrates (in other words, between the measurement unit substrate 311 and the in-probe substrate 321 and between the measurement unit substrate 311 and the in-probe substrate 322) that are disposed to be orthogonal to each other can be formed also using a metal connector, for example, such as an SMA connector or the like. In this case, Constituent element (7) is unnecessary as well.

Figure 10:
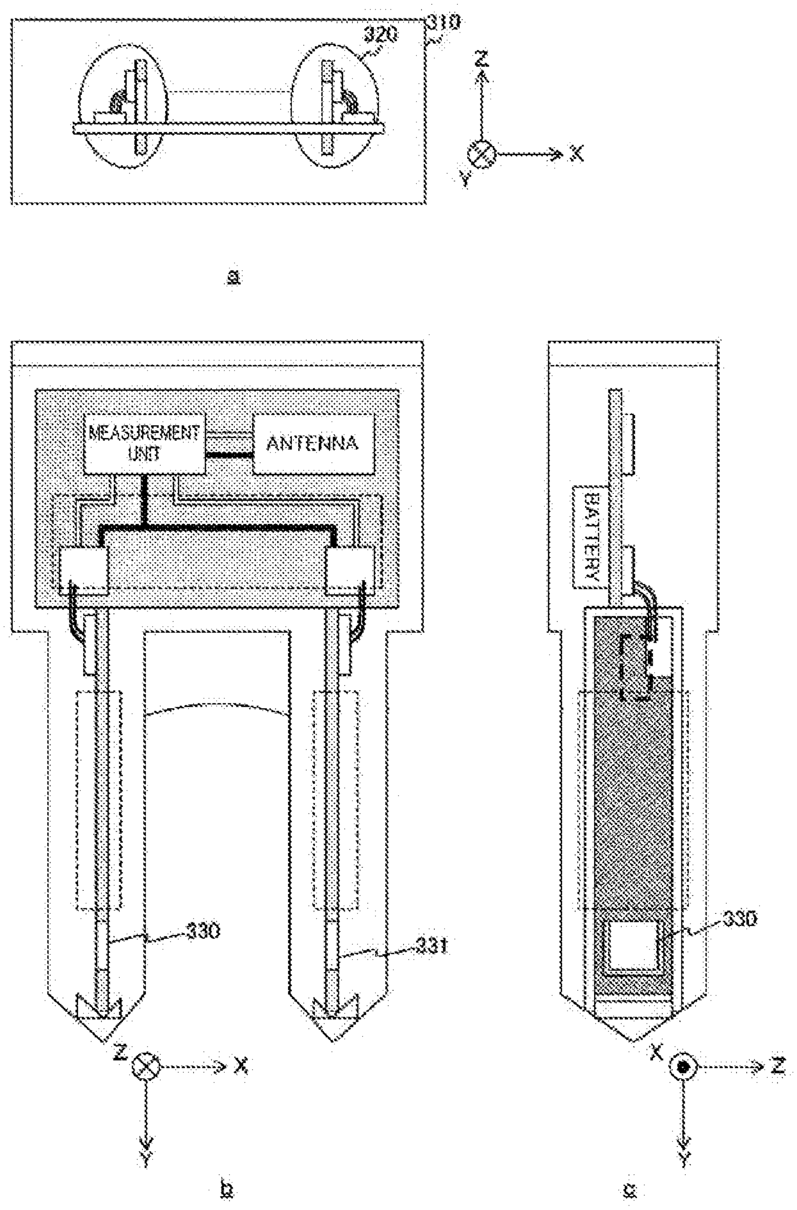
FIG. 10 is an example of a whole view of a sensor device in which the number of antennas is decreased in the first embodiment of the present technology.

FIG. 10 is an example of a whole view of a sensor device 200 included in the moisture measuring system 100 illustrated in FIG. 9.

FIG. 11 is an example of a whole view of a sensor casing 305 included in the sensor device 200 illustrated in FIG. 10.

Figure 12:
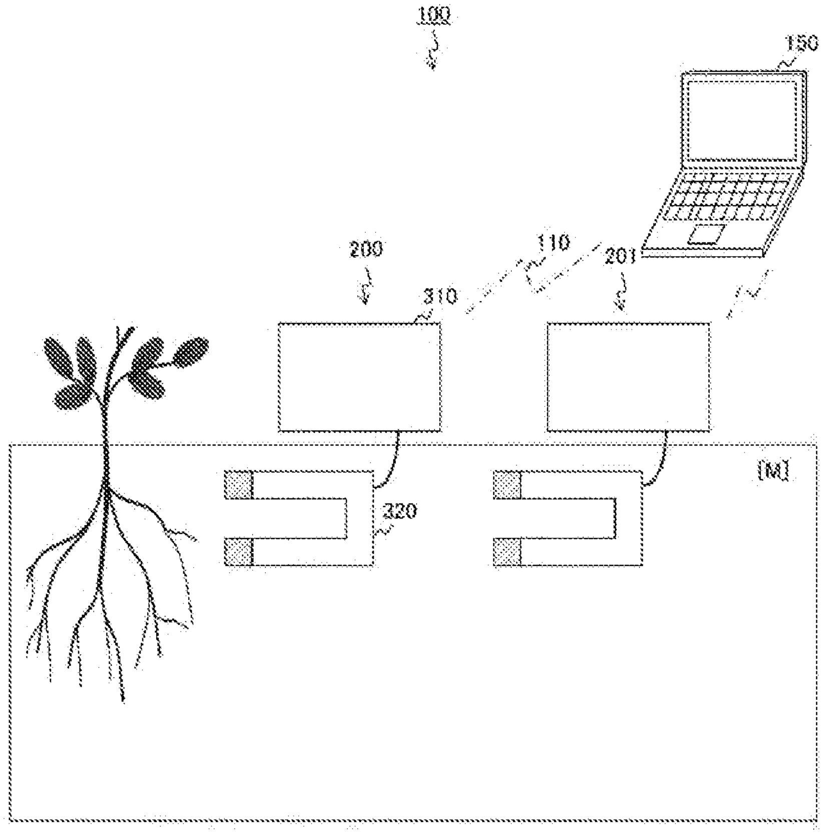
FIG. 12 is an example of a whole view of a moisture measuring system in which a casing in the first embodiment of the present technology is divided.

FIG. 12 is a yet another example of the first embodiment of the present technology and is an example of a whole view of a moisture measuring system 100 in which a casing included in sensor devices 200 and 201 are divided into two parts. As illustrated in the drawing, the measurement unit casing 310 and the probe casing 320 also can be divided. Connection between a transmission line formed in the measurement unit substrate 311 and a transmission line formed in each of the in-probe substrates 321 and 322 is made using a cable (for example, a coaxial cable). The number of antennas of the probe casing 320 is one on each of the transmission side and the reception side. In this case, Constituent elements (5) to (7) are unnecessary. In addition, the need for Constituent element (4) disappears as well in a case in which the measurement unit casing 310 and the probe casing 320 are disposed at a far position, and a direction in which the measurement unit casing 310 is disposed with respect to the soil surface has no influence on rainfall and water sprinkling for soil between the probe casings 320*a* and 320*b* that are measurement targets of soil moisture.

Figure 13:
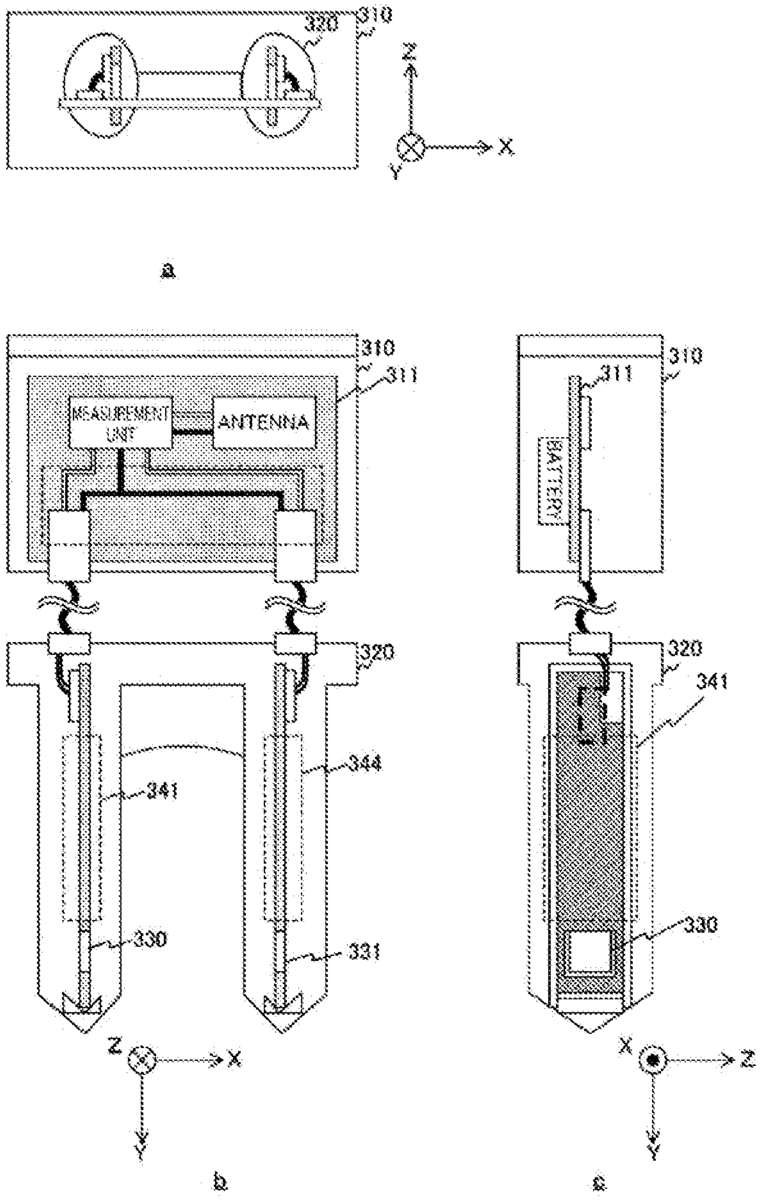
FIG. 13 is an example of a whole view of the sensor device in which a casing in the first embodiment of the present technology is divided.

FIG. 13 is an example of a whole view of a sensor device 200 included in the moisture measuring system 100 illustrated in FIG. 12. In the case of this drawing, the number of antennas is one on each of the transmission side and the reception side. A measurement unit casing 310 housing the measurement unit substrate 311 forms one independent casing. In addition, a probe casing 320*a* housing the in-probe substrate forming the transmission antenna 330 and a probe casing 320*b* housing the in-probe substrate 322 forming the reception antenna 331 are connected, thereby connecting one independent probe casing 320. The probe casing 320 further includes a reinforcing part 360.

FIG. 14 is an example of a whole view of a sensor casing 305 included in the sensor device 200 illustrated in FIG. 13.

Figure 15:
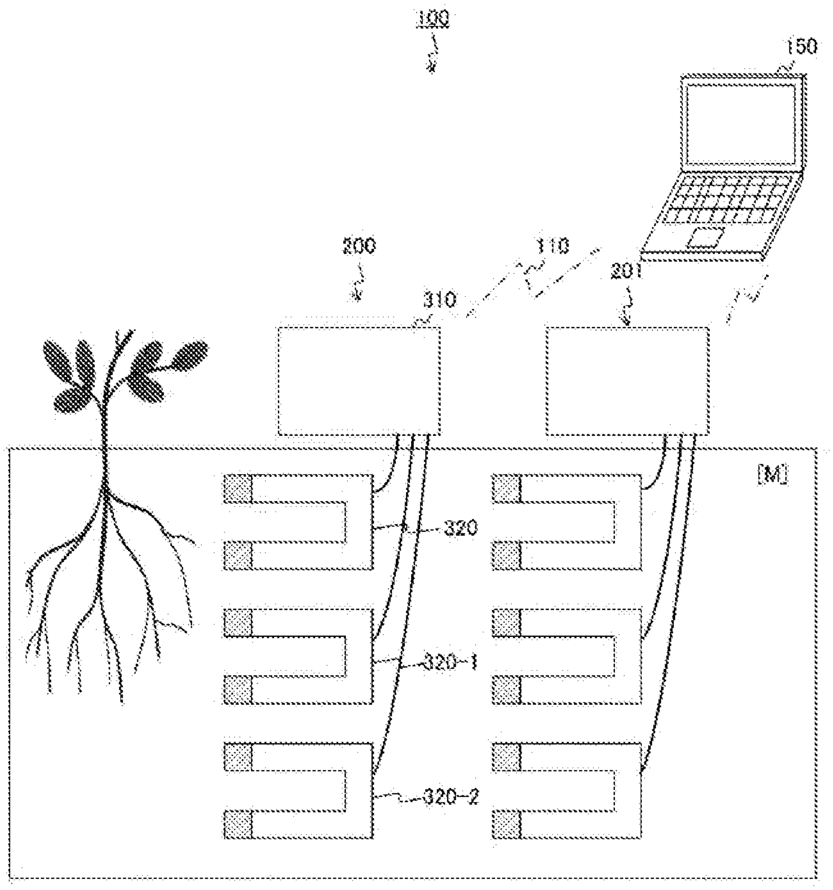
FIG. 15 is an example of a whole view of a moisture measuring system in which a casing in the first embodiment of the present technology is divided, and a plurality of probe casings are disposed for each sensor device.

FIG. 15 is yet another example of the first embodiment of the present technology and is an example of a whole view of a moisture measuring system 100 in which a casing included in the sensor devices 200 and 201 are divided, and a plurality of probe casings are disposed for each sensor device. As illustrated in the drawing, each of the sensor devices 200 and 201 includes a plurality of transmission antennas and a plurality of reception antennas. Each of the sensor devices 200 and 201 includes a probe casing for each pair of one transmission antenna and one reception antenna. In accordance with this, as illustrated in the drawing, a configuration in which a plurality of probe casings such as the measurement unit casing 310, the probe casings 320, 320-1, 320-2, and the like are disposed for each sensor device 200 is formed. The number of antennas of each probe casing is one on each of the transmission side and the reception side. In this case, Constituent elements (4) and (7) are unnecessary.

Figure 16:
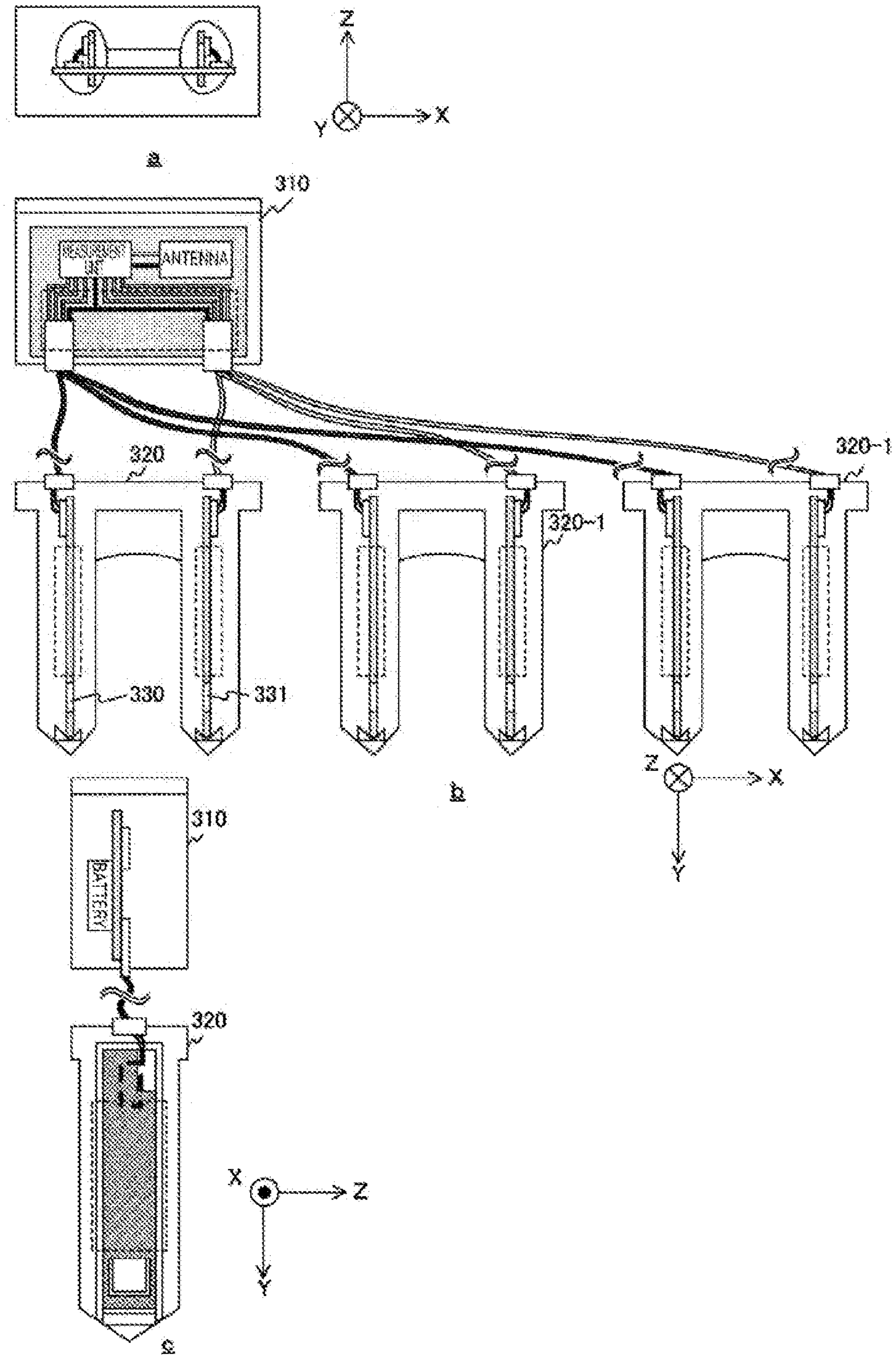
FIG. 16 is an example of a whole view of a sensor device in which a casing in the first embodiment of the present technology is divided, and a plurality of probe casings are disposed.

FIG. 16 is an example of a whole view of a sensor device 200 included in the moisture measuring system 100 illustrated in FIG. 15. In the case of this drawing, the number of antennas is one on each of the transmission side and the reception side.

Figure 17:
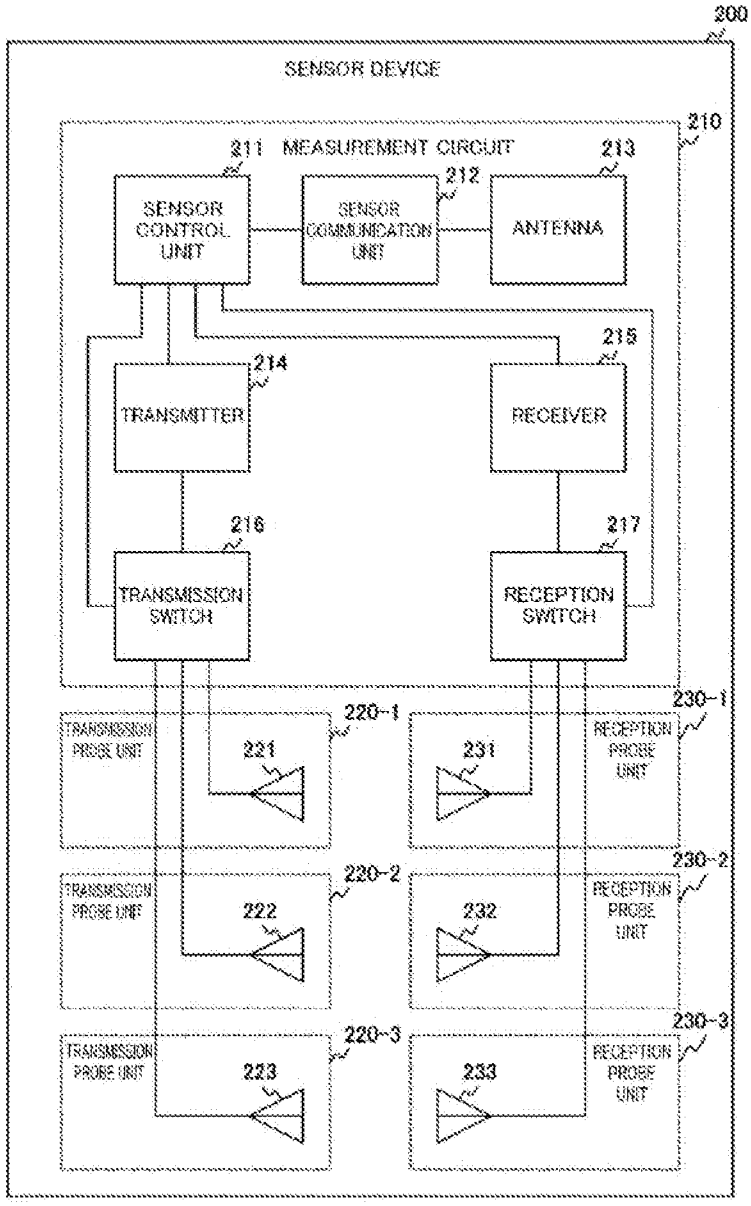
FIG. 17 is a block diagram illustrating one configuration example of the sensor device according to the first embodiment of the present technology illustrated in FIG. 15.

FIG. 17 is a block diagram illustrating one configuration example of the sensor device 200 illustrated in FIG. 15. As illustrated in this drawing, inside divided three probe casings, transmission probe units 220-1 to 220-3 and reception probe units 230-1 to 230-3 are disposed. In each of such three pairs of units, one antenna is disposed. For example, transmission antennas 221 to 223 are disposed in transmission probe units 220-1 to 220-3, and reception antennas 231 to 233 are disposed in reception probe units 230-1 to 230-3. Such antennas are connected to the measurement circuit 210 through transmission lines that are independent from each other.

Figure 18:
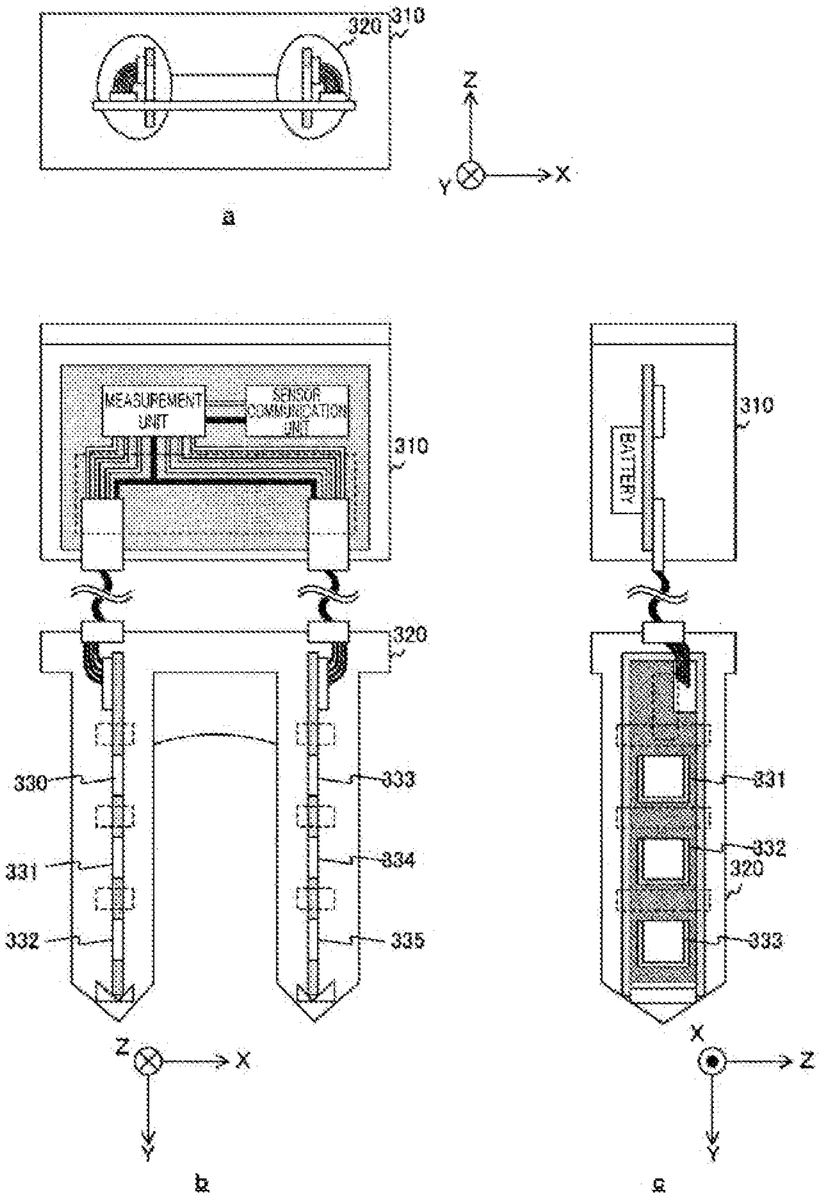
FIG. 18 is another example of a whole view of a sensor device in which a casing in the first embodiment of the present technology is divided.

FIG. 18 is yet another example of the first embodiment of the present technology and is another example of a whole view of a sensor device 200 in which a plurality of transmission antennas 330 to 332 and a plurality of reception antennas (333 to 335) are included, and the probe casing 320 housing these and the measurement unit casing 310 housing the measurement unit substrate 311 are divided. In a case in which the measurement unit casing 310 and the probe casing 320 are divided, the number of antennas may be three on the transmission side and the reception side.

In this case, Constituent elements (4) and (7) are unnecessary.

[Configuration Example of Antenna]

Figure 19:
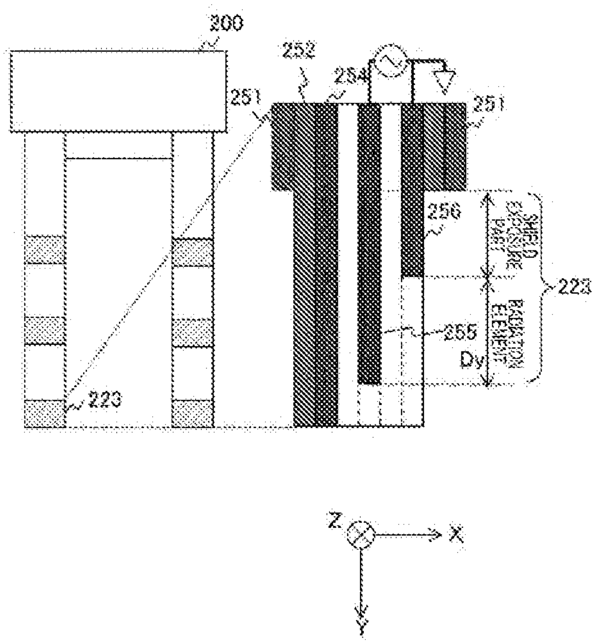
FIG. 19 is an example of a cross-sectional view of a probe having a first structure acquired when seen from a front face in the first embodiment of the present technology.

FIG. 19 is an example of a front view (a left diagram in FIG. 19) of the sensor device 200 according to the first embodiment of the present technology and a cross-sectional view of a transmission antenna 223 included in an in-probe substrate 321 and the vicinity thereof (a right diagram in FIG. 19) acquired when the sensor device 200 is seen on a front face. This diagram is an example of a cross-sectional view of the transmission antenna 223 and the vicinity thereof acquired when seen in the Z-axis direction. Parts to which colors of respective layers are applied and illustrated in the right diagram in FIG. 19 represent an electric wave absorbent material 251, a general solder resist 252, a conductor shield layer 254, a conductor signal line 255, a conductor shield layer 256, a solder resist 253, and an electric wave absorbent material 251 in order from the left side. A layer between the shield layer 254 the signal line 255 that is not colored and a layer between the shield layer 254 and the signal line 255 that is not colored represent insulators. The solder resist and the insulator allow electromagnetic waves to pass through them. Generally, the number of layers of an electronic substrate (a wiring substrate) is called as the number of layers of conductors included in the substrate. For this reason, the substrate illustrated in the right diagram in FIG. 19 is called as a three-layer substrate. However, in this specification, focusing on transmission and shielding of electromagnetic waves and absorption of electromagnetic waves, the electric wave absorbent material 251, the shield layer 254, the signal line 255, the shield layer 256, and the electric wave absorbent material 251 may be respectively referred to as a first layer, a second layer, a third layer, a fourth layer, and a fifth layer for the convenience of description. A cross-sectional view of each of the transmission antennas 221 and 222 is similar to that of the transmission antenna 223. In the X-axis direction, when a direction from the transmission side to the reception side is set as a rightward direction, cross-sectional views of the reception antennas 231 to 233 are horizontally symmetrical to the transmission antenna 223.

Figure 20:
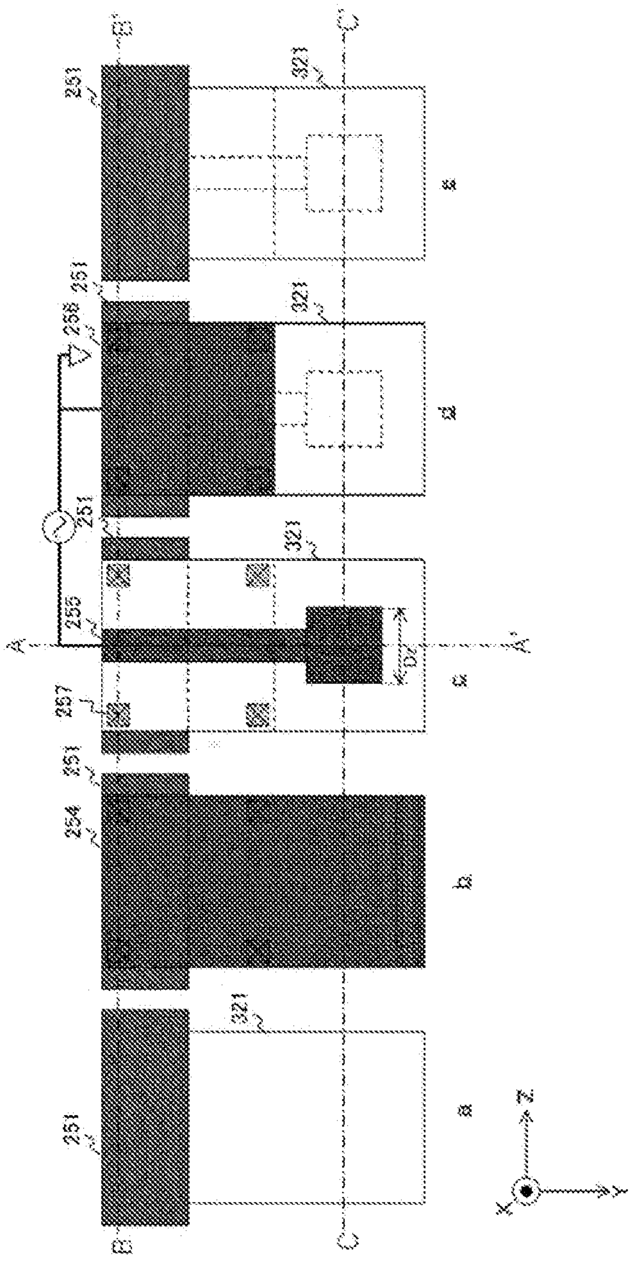
FIG. 20 is an example of a plan view of each layer of the inside of a probe casing having a first structure according to the first embodiment of the present technology.

FIG. 20 is an example of a plan view of each layer of the transmission antenna 223 of which the cross-section is illustrated in the right diagram in FIG. 19 and the vicinity thereof. This diagram illustrates a plan view of each layer when the transmission antenna 223 illustrated in the right diagram in FIG. 19 and the vicinity thereof are seen from the X-axis direction of the sensor device 200. In this diagram, a is a plan view of the first layer: the electric wave absorbent material 251 of the right drawing in FIG. 18. In this diagram, b is a plan view of the second layer: the shield layer 254. In this diagram, c is a plan view of the third layer: the signal line 255. In this diagram, d is a plan view of the fourth layer: the shield layer 256. In this diagram, e is a plan view of the fifth layer: the electric wave absorbent material 251. In addition, a cross-sectional view acquired when cutting along a line A-A' corresponds to the cross-sectional view illustrated in FIG. 18.

The second layer illustrated in FIG. 20*b* is a first wiring layer in which the shield layer 254 is wired. The third layer illustrated in FIG. 20*c* is a second wiring layer in which the signal line 255 having a linear shape is wired. The fourth layer illustrated in FIG. 20*d* is a third wiring layer in which the shield layer 256 is wired. A width of the signal line 255 in the Z-axis direction will be denoted as Dz. A symbol of a square with diagonal lines thereof being joined using segments illustrated in FIGS. 20*b*, 20*c*, and 20*d* represents a via (a reference sign 257 in FIG. 21*a*) connecting the shield layer 254 illustrated in FIG. 20*b* and the shield layer 256 illustrated in FIG. 20*d*. In FIGS. 20*b* and 20*d*, the symbol represents a position of a via 257 connecting the shield layer 254 and the shield layer 256. In FIG. 20*c*, the symbol represents a state in which the via 257 passes through a lateral side of the signal line 255. In accordance with this via 257, the shield layer 254 and the shield layer 256 have the same electric potential. Out of two dotted lines illustrated in FIG. 20*c*, a dotted line on a side close to "A" illustrated in FIG. 20*c* is acquired by conveniently projecting a contour line of the electric wave absorbent material 251 illustrated in FIG. 20*e* into FIG. 20*c*. A dotted line on a side close to "A'" illustrated in FIG. 20*c* is acquired by conveniently projecting a contour line of the shield layer 256 illustrated in FIG. 20*d* into FIG. 20*c*. Dotted lines illustrated in FIGS. 20*d* and 20*e* are acquired by conveniently projecting a contour line of the signal line 255 illustrated in FIG. 20*c* into FIGS. 20*d* and 20*e*.

Figure 21:
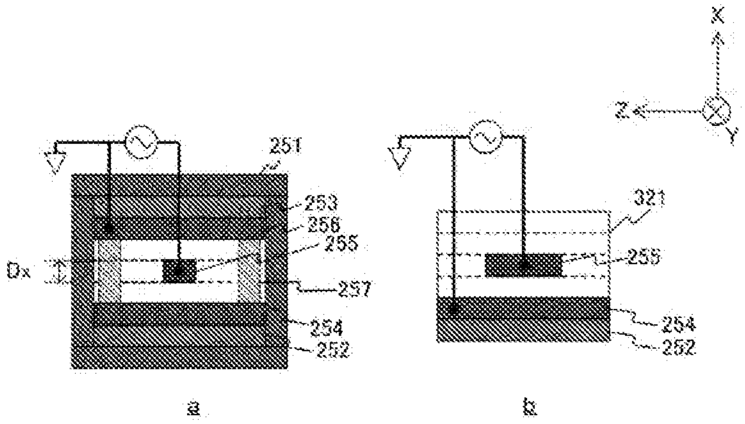
FIG. 21 is an example of a cross-sectional view of the probe having the first structure acquired when seen from the top in the first embodiment of the present technology.

FIG. 21 is an example of a cross-sectional view of the transmission antenna 223 and the vicinity thereof, of which the cross-sectional view is illustrated on the right side in FIG. 19, acquired when seen from the upper side. a in FIG. 21 is a cross-sectional view acquired when cutting along line B-B' illustrated in FIG. 20, and b in FIG. 21 is a cross-sectional view acquired when cutting along line C-C' illustrated in FIG. 20.

A cross-sectional view of the reception probe is similar to that of the transmission probe. The transmission probe is coated with the electric wave absorbent material 251. By using this electric wave absorbent material 251, the electric wave absorbing unit 341 and the like are formed.

In addition, between both faces of the in-probe substrate 321 and the electric wave absorbent material 251, the solder resists 252 and 253 are formed. In the in-probe substrate 321, a wiring layer in which the shield layer 254 is wired, a wiring layer in which the signal line 255 is wired, and a wiring layer in which the shield layer 256 is wired are formed. As will be described below, the signal line 255 functions as a radiation element in the transmission antenna. A thickness of the wiring layer in which the signal line 255 that is the radiation element is wired will be denoted by Dx. A ground electric potential is supplied to the shield layers 254 and 256, and the signal line 255 transmits and radiates an AC signal (a transmission signal) that is a transmission wave transmitted from the transmission antenna. Thereafter, the signal line 255 transmitting and radiating a transmission wave (a transmission signal) may be referred to as a signal line layer. In addition, a part of the signal line 255 particularly relating to radiation of a transmission wave may be referred to as a radiation element. When this is applied to the reception antenna, a signal line 255 receiving and transmitting a reception wave (a reception signal) may be referred to as a signal line or a signal line layer, and a part of the conductor 255 relating to reception of an electromagnetic wave received by the reception antenna (a reception wave or a reception signal) may be referred to as a reception element.

As illustrated in FIGS. 19 to 21, in an electronic substrate (the in-probe substrate) in which a signal line layer (the signal line 255) is disposed, on both a rear face side of the substrate (a side on which the shield layer 254 is disposed) and a front face side (a side on which the shield layer 256 is disposed) of the signal line layer, the shield layer 254 and the shield layer 256 are disposed through insulators disposed between the shield layer and the signal line layer. By using this structure, a transmission line (a strip line) in which both the rear face side and the front face side of the signal line layer are shielded using the shield layers 254 and 256 is formed. This transmission line (a transmission line for transmission) is independently wired for each antenna from all the transmission antennas included in the in-probe substrate to the connector 323 in the in-probe substrate 321. A similar transmission line (a transmission line for reception) is independently wired for each antenna from all the reception antennas included in the in-probe substrate to the connector 324 in the in-probe substrate 322.

With reference to FIGS. 19 to 21, First layer: a rear face-side electric wave absorbent material 251, Second layer: a shield layer 254, Third layer: a signal line layer (a signal line 255), Fourth layer: a shield layer 256, and Fifth layer: a front face-side electric wave absorbent material 251 relating to transmission, radiation (or reception), and shielding of electromagnetic waves and absorption of electromagnetic waves will be further described. In addition, in FIGS. 19 and 20, a direction approaching a transmission source (a transmitter included in the measurement unit) of a transmission wave will be referred to as a transmission source direction, and a direction being separated away from the transmission source will be conveniently referred to as a tip end direction or simply as a destination direction. In the case of a reception antenna, a direction approaching a reception destination (a receiver included in the measurement unit) of a signal (a reception wave) received by the reception antenna will be referred to as a reception destination direction and a direction being separated away from the reception destination will be conveniently referred to as a tip end direction or simply as a destination direction. As illustrated in the right diagram in FIGS. 19 and 20, on the rear face side of the in-probe substrate, a part of the shield layer 254 is exposed from the rear face side electromagnetic wave absorbent material 251 to a further front side of the tip end of the rear face side electromagnetic wave absorbent material 251. In other words, a part of the shield layer 254 is exposed to the space (in addition, in this specification, in a certain conductor, a state in which a member shielding or absorbing electromagnetic waves is not disposed on the outer side thereof may be conveniently referred to as "the conductor being exposed to the space"). In addition, on the front face side of the in-probe substrate, a part of the shield layer 256 is exposed from the front face side electromagnetic wave absorbent material 251 to a further front side of the tip end of the front face side electromagnetic wave absorbent material 251. In other words, a part of the shield layer 256 is exposed to the space. Furthermore, a part of the signal line layer (the signal line 255) is exposed from the shield layer 256 to further front of the tip end of the shield layer 256. In other words, a part of the signal line layer is exposed to the space. In the signal line layer, this part exposed from the shield layer 256 (the part exposed to the space) functions as a radiation element transmitting a transmission wave (in the case of the reception antenna, in the signal line layer, a part exposed from the shield layer 256 (a part exposed to the space) functions as a reception element receiving an electromagnetic wave (a transmission wave that has propagated from the transmission antenna through a medium, that is, a reception wave)). In the case of the transmission antenna 223, the radiation element 332 corresponds to this (in the case of the reception antenna 233, the reception element 335 corresponds to this). A transmission wave is radiated the largest in a direction perpendicular to a face that is a face on which the radiation element extends and is on a side exposed from the shield layer. This direction in which a transmission wave is radiated the largest will be referred to as "a direction of main radiation" or simply as "a direction in which an electromagnetic wave is radiated". In addition, a part that is a part of the shield layer, is exposed from the electromagnetic wave absorbent material 251 (in other words, exposed to the space), and is disposed in a direction in which an electromagnetic wave is radiated from the radiation element will be referred to as a "shield exposed part" or simply as a "shield part". Such shield exposed part and the radiation element function as the transmission antenna 223. Here, a length of the radiation element in the Y-axis direction will be denoted by Dy. In the shield exposed part exposed to the space, particularly, a part that has a length from the line end of the shield exposed part that is the same as the length Dy of the radiation element in a transmission source direction (a negative direction of the Y axis in FIGS. 19 and 20) or is disposed in an area within the length functions especially effectively as a part of the transmission antenna 223. Thus, in this specification, a structure formed from (1) a radiation element (the signal line layer that is exposed from the shield layer and is exposed to a space) and (2), in the shield exposed part that is exposed from the electromagnetic wave absorbent material and is exposed to a space, a part that has a length from the tip end of the shield exposed part in a transmission source direction (a negative direction of the Y axis in FIGS. 19 and 20) that is the same as that of the radiation element or is disposed in an area within the distance may be conveniently referred to as a "transmission antenna". This similarly applies also to the reception antenna. In this specification, a structure formed from (1) a reception element (the signal line layer that is exposed from the shield layer and is exposed to a space) and (2), in the shield exposed part that is exposed from the electromagnetic wave absorbent material and is exposed to a space, a part that has a length from the tip end of the shield exposed part in a reception destination direction (a negative direction of the Y axis in FIGS. 18 and 19) that is the same as that of the reception element or is disposed in an area within the distance may be conveniently referred to as a "reception antenna".

As illustrated in FIGS. 19 to 21, the planar transmission antenna 223 includes a shield part and a radiation element. The transmission antenna 223 is formed using an electronic substrate (the in-probe substrate 321 or the like) including a plurality of wiring layers. In the radiation element, a size Dz in a second direction (a width direction of the electronic substrate; the Z-axis direction in the drawing) that is orthogonal to a first direction is larger than a size Dx in the first direction (a thickness direction of the electronic substrate; the X-axis direction in the drawing). In addition, a size Dy in a third direction (a length direction in which the electronic substrate extends; the Y-axis direction in the drawing) that is orthogonal to both the first direction and the second direction is larger than the size Dx. In this specification, in a radiation element included in a transmission antenna, in a case in which both Dz and Dy are larger than Dx, this transmission antenna is defined as a "planar antenna" and a "planar transmission antenna". In addition, a part that is a part of the radiation element and extends on a plane defined by the second direction and the third direction is defined as "a plane of the radiation element". Furthermore, in the transmission antenna, preferably, Dy may be larger than both Dx and Dz. This similarly applies also to a reception antenna. When the structure of the reception antenna is described with reference to FIGS. 19 to 21, in a reception element included in the reception antenna, a size Dz in a second direction (a width direction of the electronic substrate; the Z-axis direction in the drawing) that is orthogonal to a first direction is larger than a size Dx in the first direction (a thickness direction of the electronic substrate; the X-axis direction in the drawing). In addition, a size Dy in a third direction (a length direction in which the electronic substrate extends; the Y-axis direction in the drawing) that is orthogonal to both the first direction and the second direction is larger than the size Dx. In this specification, in a reception element included in a reception antenna, in a case in which both Dz and Dy are larger than Dx, this reception antenna is defined as a "planar antenna" and a "planar reception antenna". In addition, a part that is a part of the reception element and extends on a plane defined by the second direction and the third direction is defined as "a plane of the reception element". Furthermore, in the reception antenna, preferably, Dy may be larger than both Dx and Dz.

As illustrated in FIGS. 20 and 21, the periphery of a transmission line including the signal line 255 to which a signal is given and the shield layer 256 to which the ground electric potential is given (the periphery of a cross-section orthogonal to an extending direction of the transmission line) is coated, surrounded, or enclosed with the electric wave absorbent material 251. This electric wave absorbent material 251 extends in the extending direction (the Y-axis direction) of the transmission line, and antennas (the transmission antenna and the reception antenna) are connected to the front side of an outer edge of the transmission line of coating using the electric wave absorbent material 251.

As illustrated in FIG. 19, an antenna is formed in an electronic substrate (the in-probe substrate 321 and the like) including at least three wiring layers (first, second, and third wiring layers in order from the rear face side to the front face) that are stacked. The antenna includes a signal line 255 to which a signal is given and shield layers 254 and 256 to which the ground electric potential is given. In the antenna, the signal line 255 to which a signal is given is formed in the second wiring layer. The shield layer 254 is formed in the first wiring layer, and the shield layer 256 is formed in the third wiring layer.

As illustrated in FIG. 20, when the shape of the signal line 255 formed in the second wiring layer is projected onto the third wiring layer, at least a part of projection of the conductor 255 extends to an area in which the shield layer 256 is not disposed. When the shape of the signal line 255 is projected onto the first wiring layer, the shield layer 254 of the first wiring layer is disposed at a position at which the projection of the signal line 255 is disposed.

In accordance with such a shape, in the transmission antenna 223 illustrated in FIG. 19, an electromagnetic wave is radiated from the planar transmission antenna 223 in the front face direction (in a rightward direction in the sheet surface; the positive direction of the X axis). In this way, an antenna in which an electromagnetic wave is radiated from one side of the plane of a planar radiation element will be referred to as "an antenna of one-side radiation" and, in this specification, this will be referred to as a "first structure" of the antenna. In the case of the reception antenna, an antenna in which an electromagnetic wave is received from one side of the plane of a planar reception element will be referred to as "an antenna of one-side reception" and such a reception antenna corresponds to the first structure.

Figure 22:
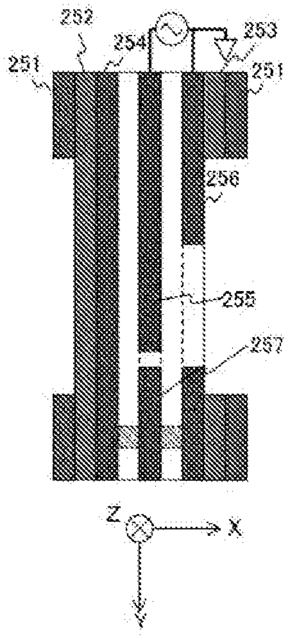
FIG. 22 is another example of a cross-sectional view of the probe having the first structure acquired when seen from a front face in the first embodiment of the present technology.

FIG. 22 is a cross-sectional view illustrating another example of the first structure acquired when the sensor device 200 according to the first embodiment of the present technology is seen from a front face like FIG. 4*b*. This diagram is an example of a cross-sectional view of the transmission antenna 223 and the vicinity thereof acquired when being seen in the Z-axis direction.

Figure 23:
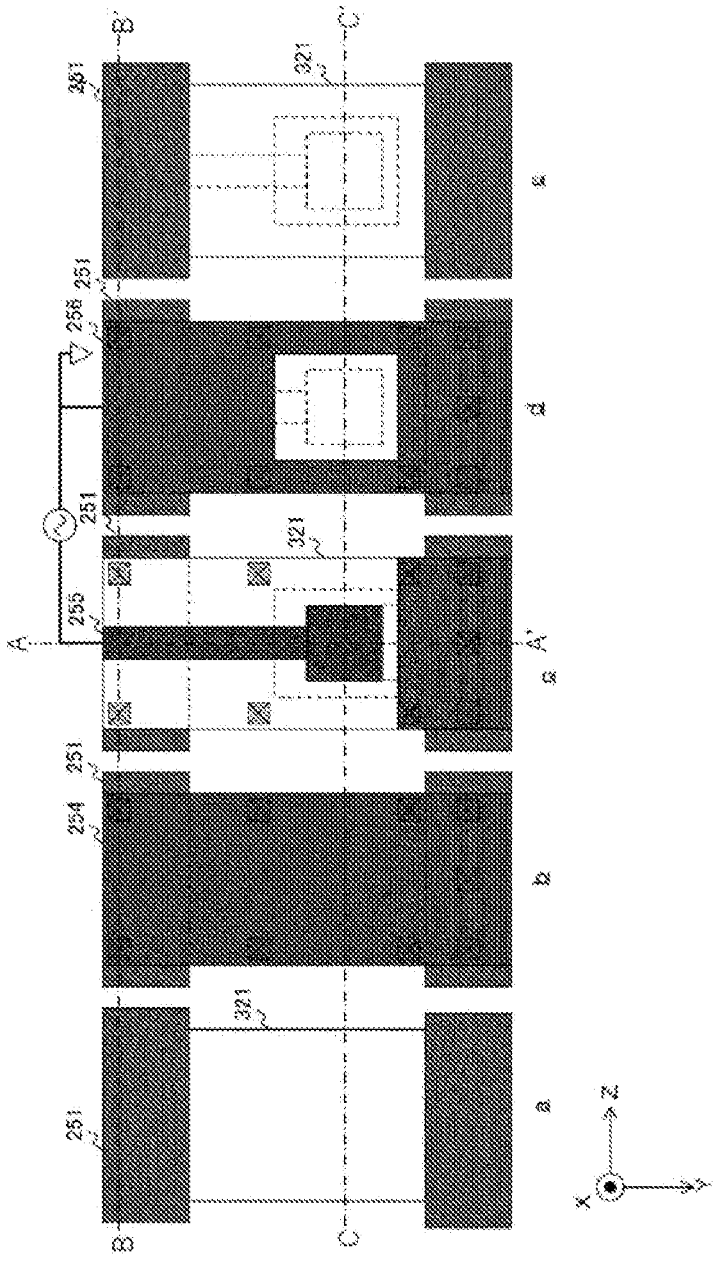
FIG. 23 is another example of a plan view of each layer of the inside of the probe casing having the first structure according to the first embodiment of the present technology.

FIG. 23 is a plan view of each layer for another example of the first structure of which the cross-section is illustrated in FIG. 22.

Figure 24:
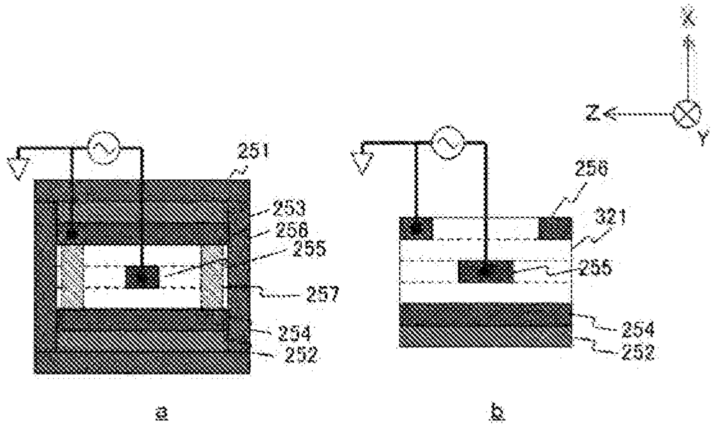
FIG. 24 is another example of a cross-sectional view of the probe having the first structure acquired when seen from the top in the first embodiment of the present technology.

FIG. 24 is a cross-sectional view of another example of the first structure, of which the cross-section is illustrated in FIG. 22, acquired when seen from the upper side.

In another example of the first structure illustrated in FIGS. 22 to 24, (1) the first wiring layer (the shield layer 254) to which the ground electric potential is given extends to a further front side of the radiation element (the signal line 255), which is the same as the first structure. On the other hand, (2) a conductor 257 to which the ground electric potential is given is formed in an area disposed on the front side of the radiation element using the second wiring layer that is different from the radiation element and the signal line that are a part of the second wiring layer, and (3) the third wiring layer (the shield layer 256) extends to the front side of the radiation element through a lateral side of projection by avoiding the projection (a dotted line in FIG. 23*d*) of the radiation element onto the third wiring layer so as not to overlap with the radiation element, which are different from the first structure. In a case in which, at the destination of the transmission antenna 223 illustrated in FIGS. 22 to 24, the transmission antenna different from this is disposed, this shape brings an effect of the wiring of the shield layer 256 applying the ground electric potential at least thereto being able to be easily performed. This similarly applies also to the reception antenna. (1) The first wiring layer (the shield layer 254) to which the ground electric potential is given extends to a further front side of the reception element (the signal line 255), which is the same as the first structure. On the other hand, (2) a conductor 257 to which the ground electric potential is given is formed in an area disposed on the front side of the reception element using the second wiring layer that is different from the reception element and the signal line that are a part of the second wiring layer, and (3) the third wiring layer (the shield layer 256) extends to the front side of the reception element through a lateral side of projection by avoiding the projection (a dotted line in FIG. 23*d*) of the reception element onto the third wiring layer so as not to overlap with the reception element, which are different from the first structure. In a case in which, at the destination of the reception antenna 233 illustrated in FIGS. 22 to 24, a reception antenna different from this is disposed, this shape brings an effect of the wiring of the shield layer 256 applying the ground electric potential at least thereto being able to be easily performed.

Figure 25:
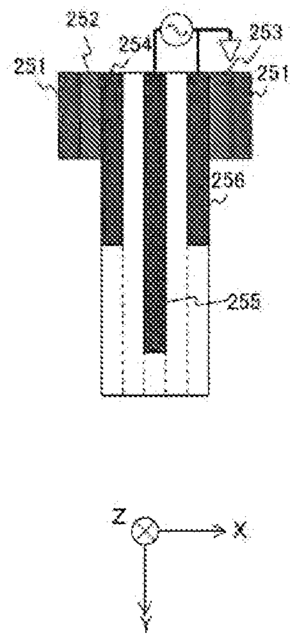
FIG. 25 is an example of a cross-sectional view of a probe having a second structure acquired when seen from a front face in the first embodiment of the present technology.

FIG. 25 is an example of a cross-sectional view of the second structure relating to a transmission antenna 223 included in the in-probe substrate 321 and the vicinity thereof acquired when the sensor device 200 according to the first embodiment of the present technology is seen from a front face like FIG. 4*b*.

FIG. 24 is an example of a plan view of each layer of the second structure of which the cross-section is illustrated in FIG. 25.

Figure 27:
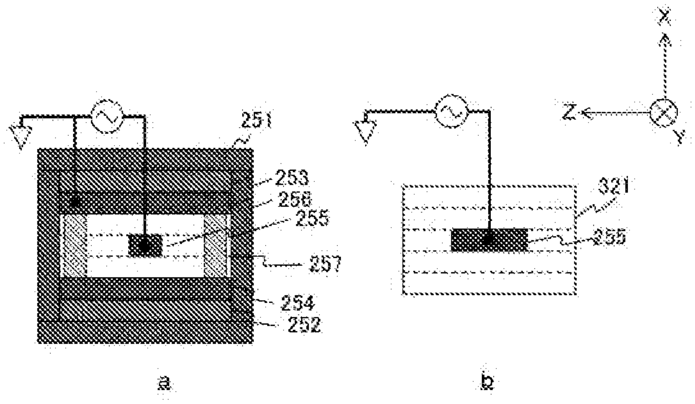
FIG. 27 is an example of a cross-sectional view of the probe having the second structure acquired when seen from the top in the first embodiment of the present technology.

FIG. 27 is an example of a cross-sectional view acquired when the second structure of which the cross-section is illustrated in FIG. 25 is seen from the upper side.

Figure 26:
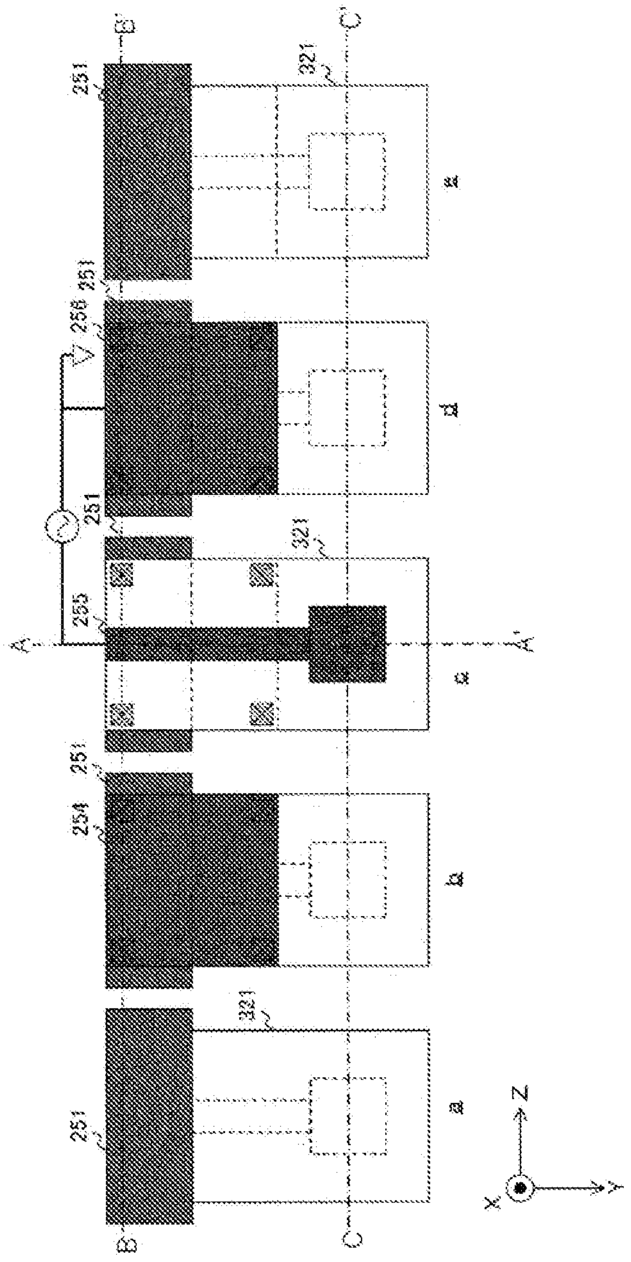
FIG. 26 is an example of a plan view of each layer of the inside of a probe casing having the second structure according to the first embodiment of the present technology.

As illustrated in FIGS. 25 and 26, in the second structure, when the shape of the signal line 255, to which a signal is given, formed in the second wiring layer is projected onto the first wiring layer disposed on a rear face side (a leftward direction in the sheet surface; a negative direction of the X axis), similar to the third wiring layer disposed on the front face side (a rightward direction on the sheet surface; a positive direction of the X axis), at least a part of projection of the signal line 255 extends to an area in which the conductor 254 is not disposed. In accordance with this shape, in the transmission antenna 223 illustrated in FIG. 25, an electromagnetic wave is radiated from the planar transmission antenna 223 in both directions including the front face direction (a rightward direction in the sheet surface; a positive direction of the X axis) and the rear face direction (a leftward direction in the sheet surface; a negative direction of the X axis). In this way, an antenna in which an electromagnetic is radiated from both sides of the plane of the planar radiation element will be referred to as a "an antenna of two-sides radiation", and this will be referred to as a "second structure" of the antenna in this specification. Compared to a transmission antenna of the first structure, a transmission antenna of this structure has an effect of being able to radiate an electromagnetic wave (transmission wave) more efficiently. In the case of a reception antenna, an antenna in which electromagnetic waves are received from both sides of the plane of a planar reception element will be referred to as "an antenna of two-sides reception", and such a reception antenna corresponds to the second structure. Compared to a reception antenna of the first structure, the reception antenna of this structure brings an effect of being able to receive an electromagnetic wave (a transmission wave that has propagated through a medium from a transmission antenna, in other words, a reception wave) more efficiently.

Figure 28:
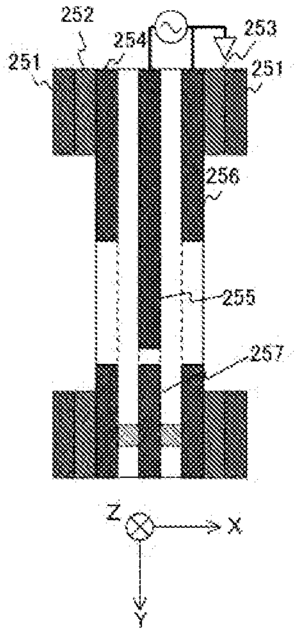
FIG. 28 is another example of a cross-sectional view of the probe having the second structure acquired when seen from a front face in the first embodiment of the present technology.

FIG. 28 is a cross-sectional view illustrating another example of the second structure acquired when the sensor device 200 according to the first embodiment of the present technology is seen from a front face like FIG. 4*b*. This diagram is an example of a cross-sectional view of the transmission antenna 223 and the vicinity thereof acquired when seen in the Z-axis direction.

Figure 29:
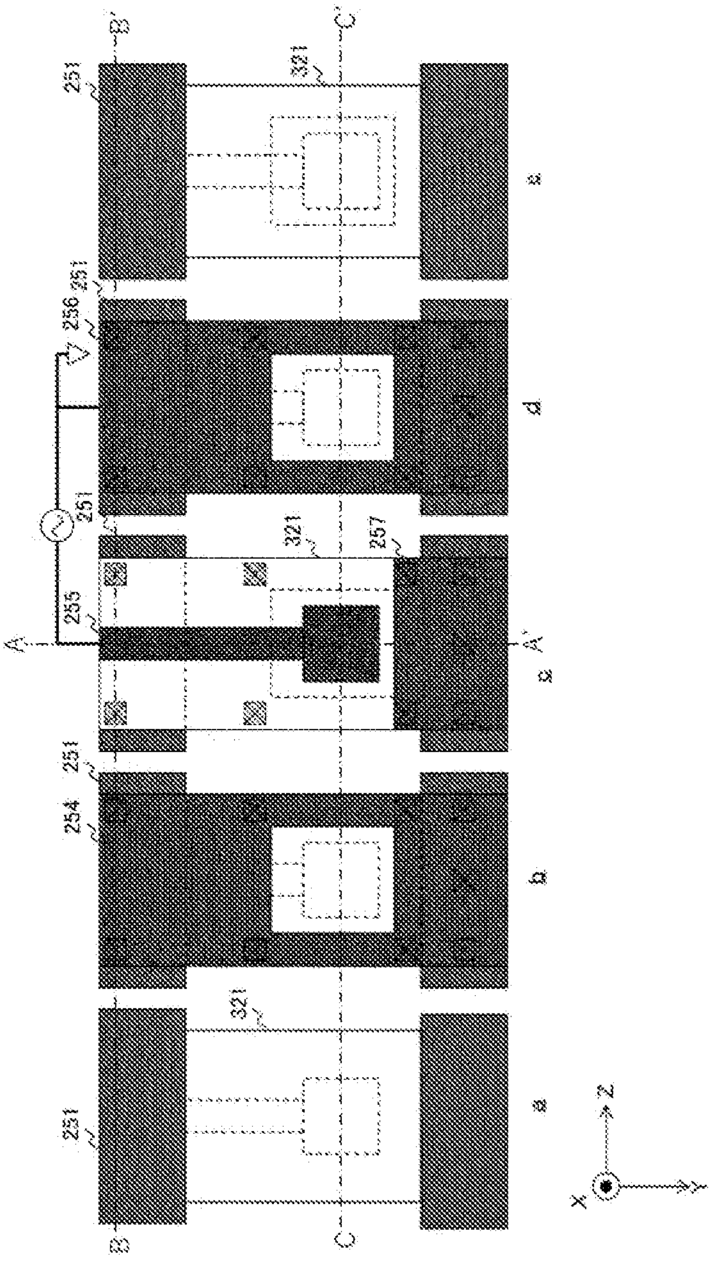
FIG. 29 is another example of a plan view of each layer of the inside of a probe casing having the second structure according to the first embodiment of the present technology.

FIG. 29 is a plan view of each layer in another example of the second structure of which the cross-section is illustrated in FIG. 28.

FIG. 230 is a cross-sectional view acquired when another example of the second structure of which the cross-section is illustrated in FIG. 28 is seen from the upper side.

Figure 30:
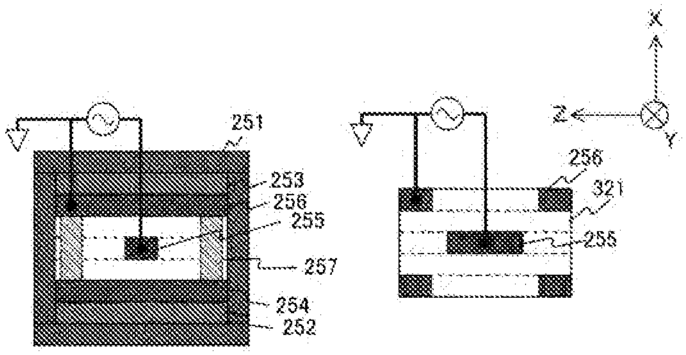
FIG. 30 is another example of a cross-sectional view of the probe having the second structure acquired when seen from the top in the first embodiment of the present technology.

In another example of the second structure illustrated in FIGS. 28 to 30, (1) the first wiring layer (the shield layer 254) extends to a front side of a radiation element through a lateral side of projection by avoiding the projection (a dotted line in FIG. 29*b*) of the radiation element onto the first wiring layer so as not to overlap with the radiation element, (2) a conductor 257 to which the ground electric potential is given is formed in an area disposed on the front side of the radiation element using the second wiring layer that is different from the radiation element and the signal line that are a part of the second wiring layer, and (3) the third wiring layer (the shield layer 256) extends to a front side of a radiation element through a lateral side of projection by avoiding the projection (a dotted line in FIG. 29*d*) of the radiation element onto the third wiring layer so as not to overlap with the radiation element, which are different from the second structure. In a case in which, at the destination of the transmission antenna 223 illustrated in FIGS. 28 to 30, a transmission antenna different from this is disposed, this shape brings an effect of the wiring of the shield layers 254 and 256 applying the ground electric potential at least thereto being able to be easily performed. This similarly applies also to a reception antenna. (1) The first wiring layer (the shield layer 254) extends to a front side of a reception element through a lateral side of projection by avoiding the projection (a dotted line in FIG. 29*b*) of the reception element onto the first wiring layer so as not to overlap with the reception element, (2) a conductor 257 to which the ground electric potential is given is formed in an area disposed on the front side of the reception element using the second wiring layer that is different from the reception element and the signal line that are a part of the second wiring layer, and (3) the third wiring layer (the shield layer 256) extends to a front side of a reception element through a lateral side of projection by avoiding the projection (a dotted line in FIG. 29*d*) of the reception element onto the third wiring layer so as not to overlap with the reception element, which are different from the second structure. In a case in which, at the destination of the reception antenna 223 illustrated in FIGS. 28 to 30, a reception antenna different from this is disposed, this shape brings an effect of the wiring of the shield layers 254 and 256 applying the ground electric potential at least thereto being able to be easily performed.

Figure 31:
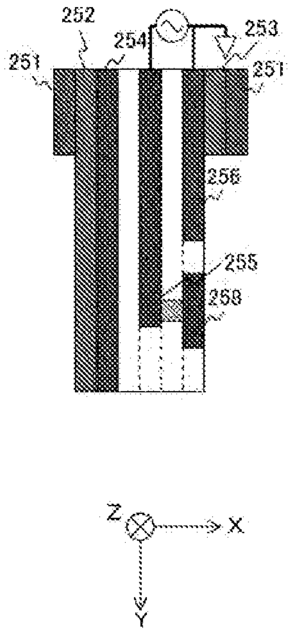
FIG. 31 is an example of a cross-sectional view of the probe having the third structure acquired when seen from a front face in the first embodiment of the present technology.

FIG. 31 is an example of a cross-sectional view of the third structure relating to a transmission antenna 223 included in the in-probe substrate 321 and the vicinity thereof acquired when the sensor device 200 according to the first embodiment of the present technology is seen from a front face like FIG. 4*b*.

Figure 32:
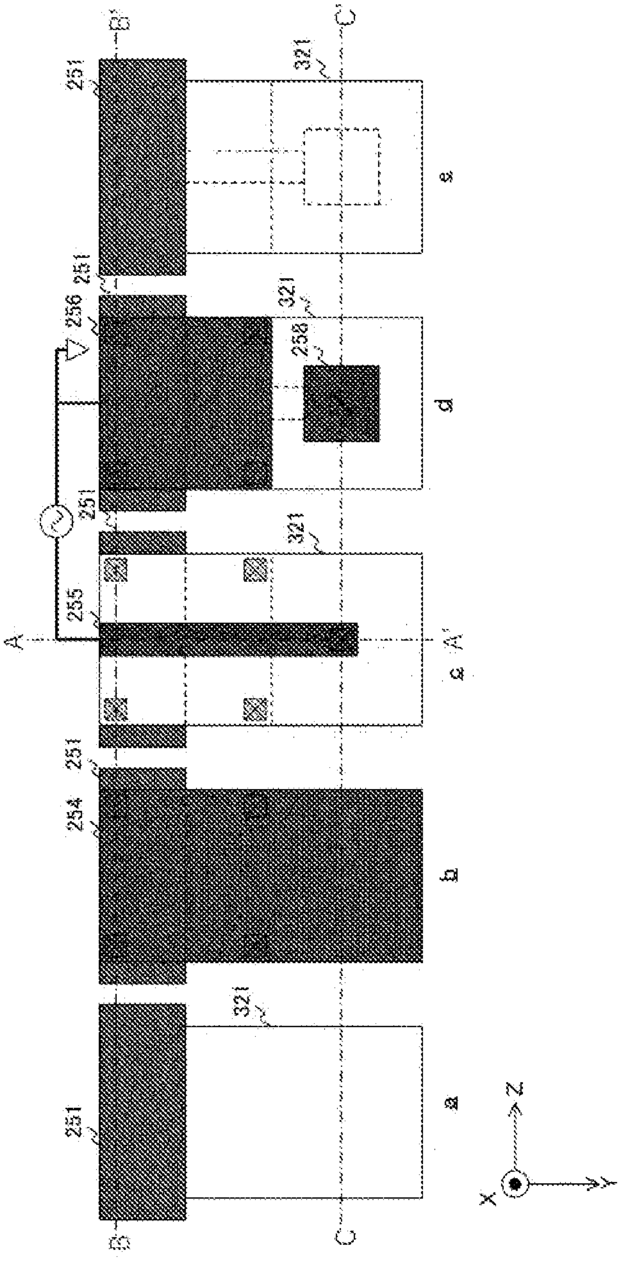
FIG. 32 is an example of a plan view of each layer of the inside of a probe casing having a third structure according to the first embodiment of the present technology.

FIG. 32 is an example of a plan view of each layer of the third structure of which the cross-section is illustrated in FIG. 31.

Figure 33:
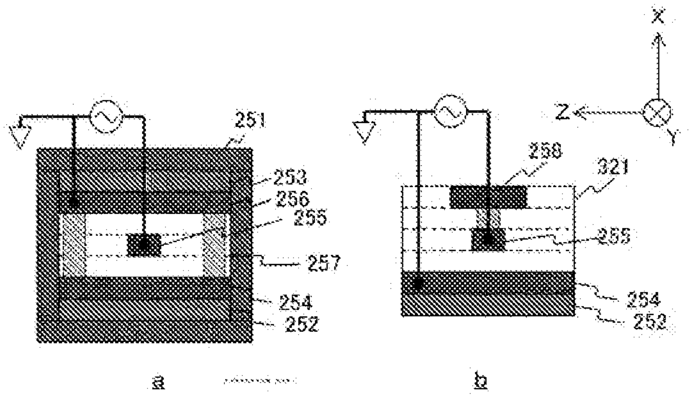
FIG. 33 is an example of a cross-sectional view of the probe having the third structure acquired when seen from the top in the first embodiment of the present technology.

FIG. 33 is an example of a cross-sectional view of the third structure, of which the cross-section is illustrated in FIG. 31, acquired when seen from the upper side.

As illustrated in FIGS. 31 and 32, in the third structure, (1) a shield layer 256 is formed in a third wiring layer that is a wiring layer of the front-most face side (a rightmost side in the ground surface in FIG. 30; a positive-most direction of the X axis) using a part of this third wiring layer. (2) In addition, a radiation element (the conductor 258) is formed in an area disposed on the front side of the shield layer 256, which is a part of the third wiring layer, using a third wiring layer different from the shield layer 256. Then, by disposing vias connecting the radiation element formed using the third wiring layer and the signal line 255 formed using the second wiring layer, the radiation element and the signal line 255 are electrically connected. In FIG. 31, parts to which a color is applied (a part denoted by diagonal lines) between the radiation element and the signal line 255 represent these vias. In FIG. 32, symbols of a square with diagonal lines thereof joining using segments disposed inside the radiation element illustrated in FIG. 32*d* and the same symbol described above disposed inside the signal line 255 illustrated in FIG. 32*c* represent positions of the vias. (3) A first wiring layer (the shield layer 254), which is a wiring layer of the rear-most face side (the rightmost side in the sheet surface in FIG. 31; the most negative direction of the X axis), to which the ground electric potential is given extends to a further front side of the radiation element, which is the same as the first structure. In accordance with this shape, in the third structure, a radiation element is formed using a wiring layer of a front-most face (a wiring layer of a front layer) of one side of the in-probe substrate 321 forming a transmission antenna, and an antenna of one-side radiation in which this radiation element is exposed to the space is formed. Compared to the transmission antenna of the first structure, the transmission antenna of this structure brings an effect of being able to radiate an electromagnetic wave (a transmission wave) more efficiently. In the case of a reception antenna, a reception element is formed using a wiring layer of a front-most face (a wiring layer of a front layer) of one side of the in-probe substrate 322 forming a reception antenna, and an antenna of one-side reception in which this reception element is exposed to the space corresponds to the third structure. Compared to the reception antenna of the first structure, the reception antenna of this structure brings an effect of being able to receive an electromagnetic wave (a transmission wave that has propagated through a medium from the transmission antenna, in other words, a reception wave) more efficiently.

Figure 34:
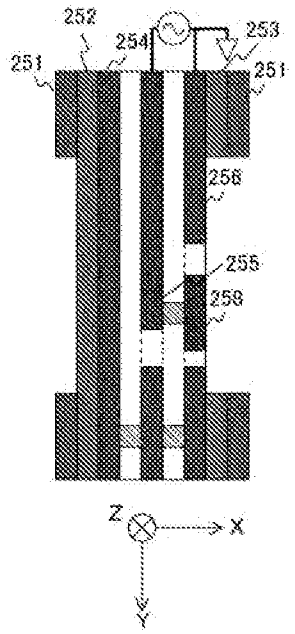
FIG. 34 is another example of a cross-sectional view of the probe having the third structure acquired when seen from a front face in the first embodiment of the present technology.

FIG. 34 is a cross-sectional view illustrating another example of the third structure acquired when the sensor device 200 according to the first embodiment of the present technology is seen from a front face like FIG. 4*b*. This diagram is an example of a cross-sectional view of the transmission antenna 223 and the vicinity thereof acquired when seen in the Z-axis direction.

FIG. 35 is an example of a plan view of each layer in another example of the third structure of which the cross-section is illustrated in FIG. 34.

Figure 36:
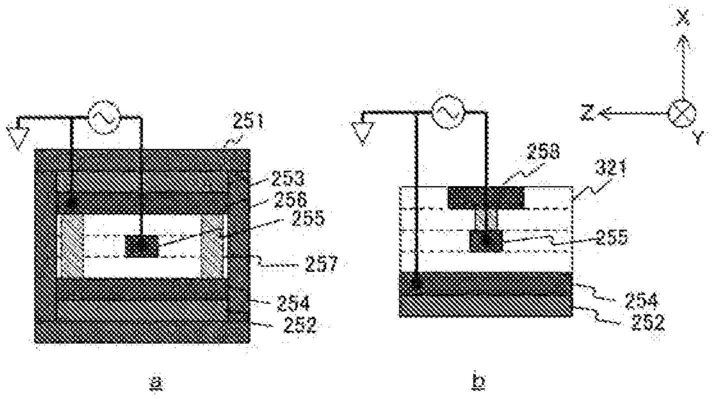
FIG. 36 is another example of a cross-sectional view of the probe having the third structure acquired when seen from the top in the first embodiment of the present technology.

FIG. 36 is an example of a cross-sectional view acquired when the other example of the third structure of which the cross-section is illustrated in FIG. 34 is seen from the upper side.

In the other example of the third structure illustrated in FIGS. 34 to 36, (1) the first wiring layer (the shield layer 254) to which the ground electric potential is given extends to a further front side of the radiation element, which is the same as the third structure. On the other hand, (2) the conductor 257 to which the ground electric potential is given is formed in an area disposed in a front side of the signal line using the second wiring layer different from the signal line that is a part of the second wiring layer, and (3) the shield layer 256 out of the shield layer 256 and the radiation element formed using the third wiring layer extends to a front side of the radiation element through a lateral side of the radiation element, which are different from the third structure. In a case in which, at the destination of the transmission antenna 223 illustrated in FIGS. 34 to 36, a transmission antenna different from this is disposed, this shape brings an effect of the wiring of the conductor 256 applying the ground electric potential at least thereto being able to be easily performed. This similarly applies also to the reception antenna. (1) the first wiring layer (the shield layer 254) to which the ground electric potential is given extends to a further front side of the radiation element, which is the same as the third structure. On the other hand, (2) the conductor 257 to which the ground electric potential is given is formed in an area disposed on a front side of the signal line using the second wiring layer different from the signal line that is a part of the second wiring layer, and (3) the shield layer 256 out of the shield layer 256 and the reception element (the conductor 258) formed using the third wiring layer extends to a front side of the radiation element through a lateral side of the reception element, which are different from the third structure. In a case in which, at the destination of the reception antenna 223 illustrated in FIGS. 34 to 36, a reception antenna different from this is disposed, this shape brings an effect of the wiring of the shield layer 256 applying the ground electric potential at least thereto being able to be easily performed.

Figure 37:
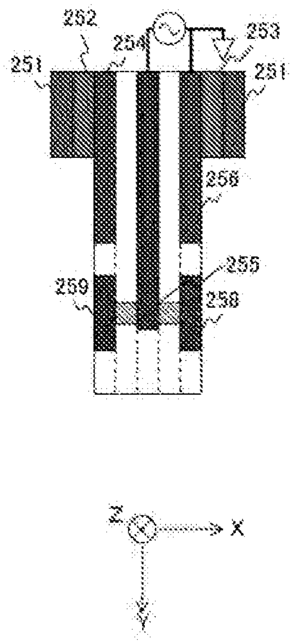
FIG. 37 is an example of a cross-sectional view of a probe having a fourth structure acquired when seen from a front face in the first embodiment of the present technology.

FIG. 37 is an example of a cross-sectional view of a fourth structure of a transmission antenna 223 included in an in-probe substrate 321 and the vicinity thereof acquired when the sensor device 200 according to the first embodiment of the present technology is seen from a front face like FIG. 4*b*.

Figure 38:
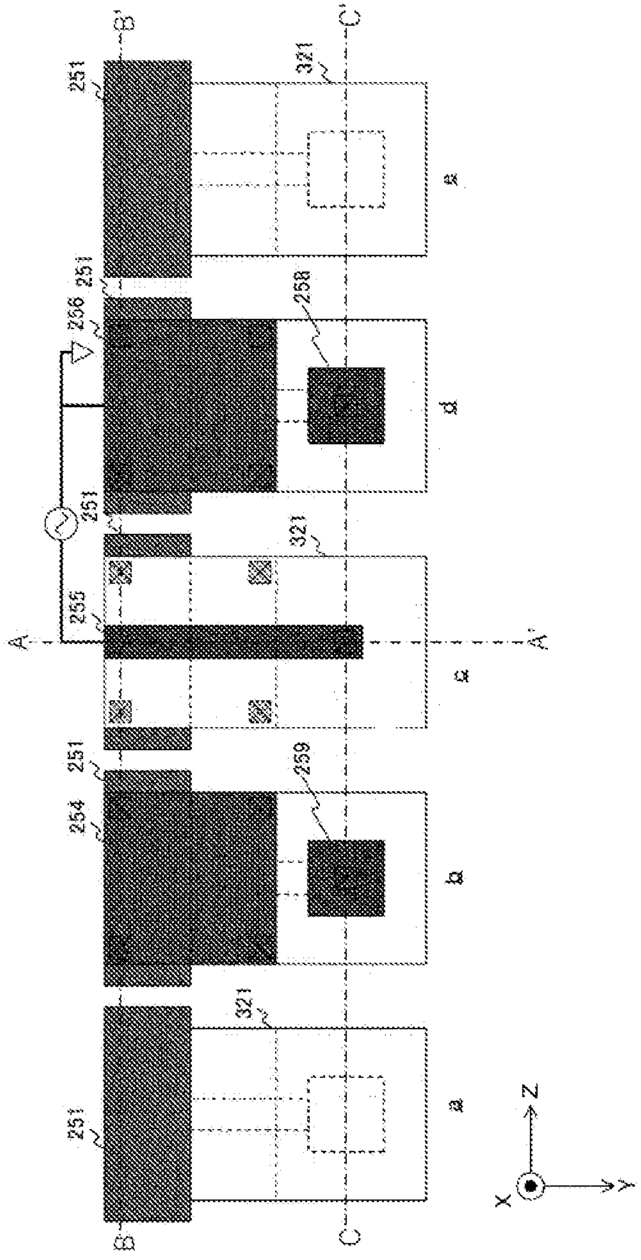
FIG. 38 is an example of a plan view of each layer of the inside of a probe casing having a fourth structure according to the first embodiment of the present technology.

FIG. 38 is an example of a plan view of each layer in the fourth structure of which the cross-section is illustrated in FIG. 37.

Figure 39:
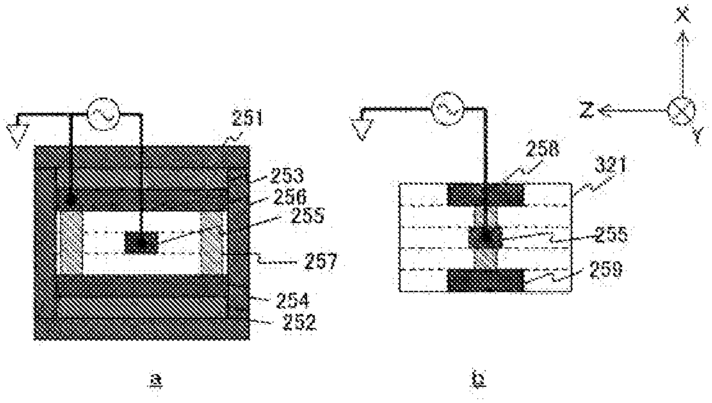
FIG. 39 is an example of a cross-sectional view of the probe having the fourth structure acquired when seen from the top in the first embodiment of the present technology.

FIG. 39 is an example of a cross-sectional view acquired when the fourth structure of which the cross-section is illustrated in FIG. 37 is seen from the upper side.

In the fourth structure, as illustrated in FIGS. 37 and 38, in the fourth structure, (1) similar to the third structure, in the third wiring layer that is a wiring layer of the frontmost face side (a rightmost side in the sheet surface in FIG. 37; the most positive direction of the X axis), a shield layer 256 is formed using a part of this third wiring layer. (2) In addition, similar to the third structure, a radiation element is formed in an area disposed on a front side of the shield layer 256 using a third wiring layer different from the shield layer 256 that is a part of the third wiring layer. By disposing a via connecting the radiation element formed using the third wiring layer and the signal line 255 formed using the second wiring layer, the radiation element and the signal line 255 are electrically connected. (3) As described in (1) described above, in the first wiring layer that is a wiring layer of the rearmost face side (the leftmost side in the sheet surface in FIG. 37; the most negative direction of the X axis), by using a part of this first wiring layer, a shield layer 254 is formed. (4) In addition, as described in (2) described above, by using a first wiring layer different from the shield layer 254 that is a part of the first wiring layer, a radiation element (a conductor 259) is formed in an area disposed on a front side of the shield layer 254. By disposing a via connecting the radiation element formed using the first wiring layer and the signal line 255 formed using the second wiring layer, the radiation element and the signal line 255 are electrically connected. In accordance with this shape, in the fourth structure, a radiation element is formed using a wiring layer of the frontmost face (a wiring layer of the front layer) of both sides of the in-probe substrate 321 forming a transmission antenna, and an antenna of two-sides radiation in which this radiation element is exposed to the space is formed. Even when compared to a transmission antenna of any one of first to third structures, the transmission antenna of this structure brings an effect of being able to radiate an electromagnetic wave (a transmission wave) more efficiently. In the case of a reception antenna, a reception element is formed using a wiring layer of the frontmost face (a wiring layer of the front layer) of both sides of the in-probe substrate 322 forming the reception antenna, and an antenna of two-sides reception in which this reception element is exposed to the space corresponds to the fourth structure. When compared with the reception antenna of the first structure, the reception antenna of this structure brings an effect of being able to receive an electromagnetic wave (a transmission wave that has propagated through a medium from a transmission antenna, in other words, a reception wave) more efficiently.

Figure 40:
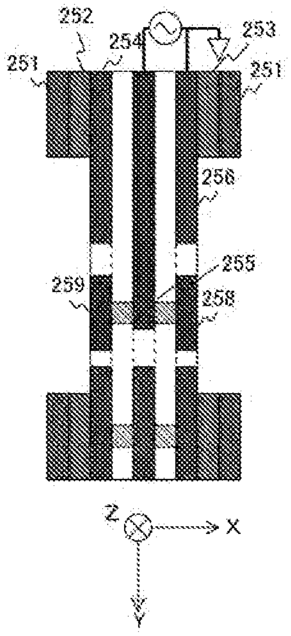
FIG. 40 is another example of a cross-sectional view of the probe having the fourth structure acquired when seen from a front face in the first embodiment of the present technology.

FIG. 40 is a cross-sectional view illustrating another example of the fourth structure acquired when the sensor device 200 according to the first embodiment of the present technology is seen from a front face like FIG. 4*b*. This diagram is an example of a cross-sectional view of the transmission antenna 223 and the vicinity thereof acquired when seen in the Z-axis direction.

Figure 41:
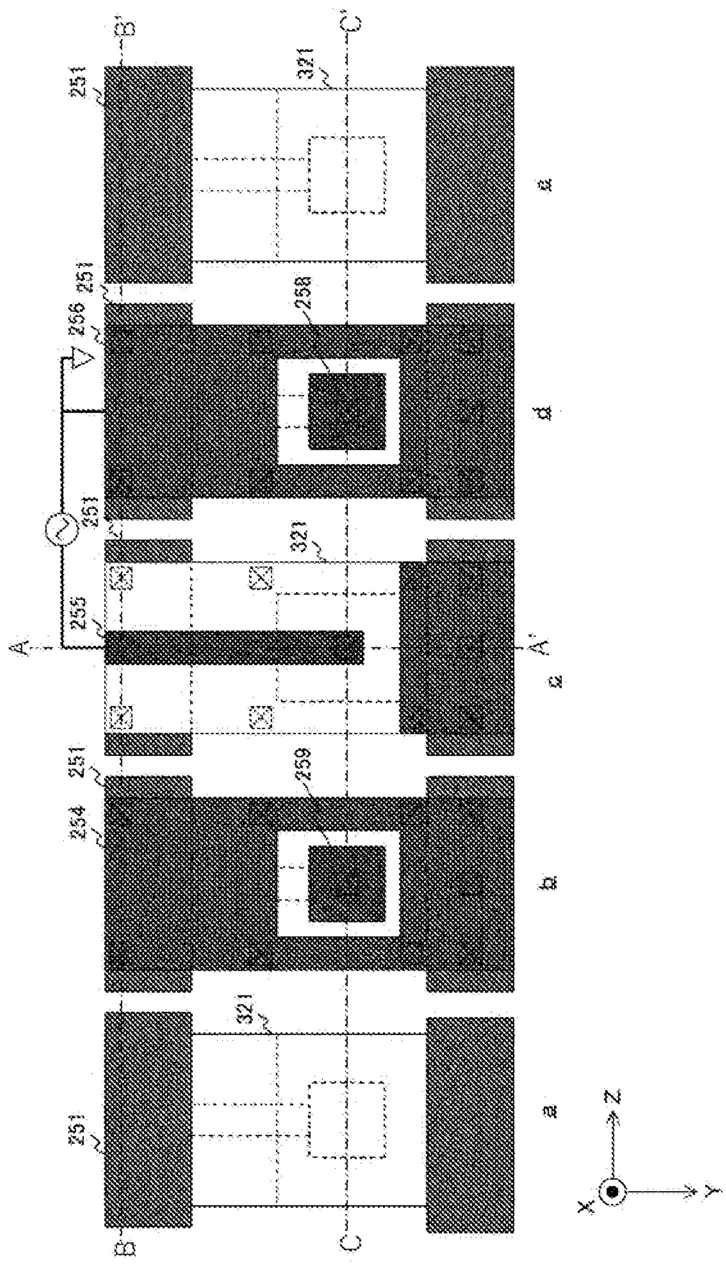
FIG. 41 is another example of a plan view of each layer of the inside of a probe casing having the fourth structure according to the first embodiment of the present technology.

FIG. 41 is an example of a plan view of each layer in the other example of the fourth structure of which the cross-section is illustrated in FIG. 40.

Figure 42:
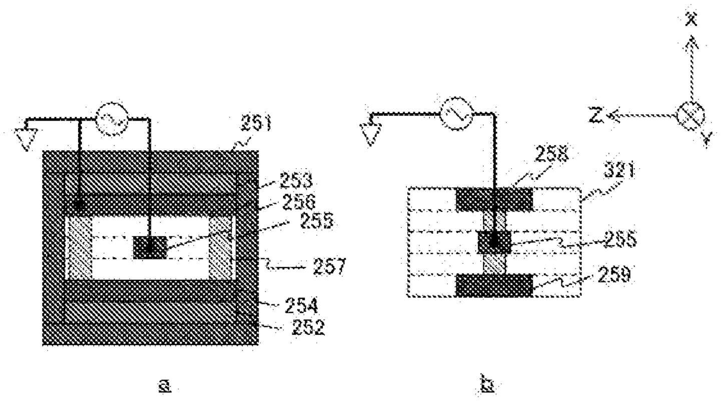
FIG. 42 is another example of a cross-sectional view of the probe having the fourth structure acquired when seen from the top in the first embodiment of the present technology.

FIG. 42 is an example of a cross-sectional view acquired when the other example of the fourth structure of which the cross-section is illustrated in FIG. 40 is seen from the upper side.

In the other example of the fourth structure illustrated in FIGS. 40 to 42, (1) the shield layer 254 out of the shield layer 254 and the radiation element formed using the first wiring layer extends to a front side of the radiation element through a lateral side of the radiation element (2) a conductor 257 to which the ground electric potential is given is formed in an area disposed on a front side of the signal line using a second wiring layer different from the signal line that is a part of the second wiring layer, and (3) the shield layer 256 out of the shield layer 256 and the radiation element formed using the third wiring layer extends to a front side of the radiation element through the lateral side of the radiation element, which is different from the fourth structure. In a case in which, at a destination of the transmission antenna 223 illustrated in FIGS. 40 to 42, a transmission antenna different from this is disposed, this shape brings an effect of being able to easily perform wiring of the shield layers 254 and 256 applying the ground electric potential at least thereto. This similarly applies also to a reception antenna. (1) The shield layer 254 out of the shield layer 254 and the reception element formed using the first wiring layer extends to a front side of the reception element through a lateral side of the reception element (2) a conductor 257 to which the ground electric potential is given is formed in an area disposed on a front side of the signal line using a second wiring layer different from the signal line that is a part of the second wiring layer, and (3) the shield layer 256 out of the shield layer 256 and the reception element formed using the third wiring layer extends to a front side of the radiation element through a lateral side of the reception element, which are different from the fourth structure. In a case in which, at a destination of the reception antenna 223 illustrated in FIGS. 40 to 42, a reception antenna different from this is disposed, this shape brings an effect of being able to easily perform wiring of the shield layers 254 and 256 applying the ground electric potential at least thereto.

Figure 43:
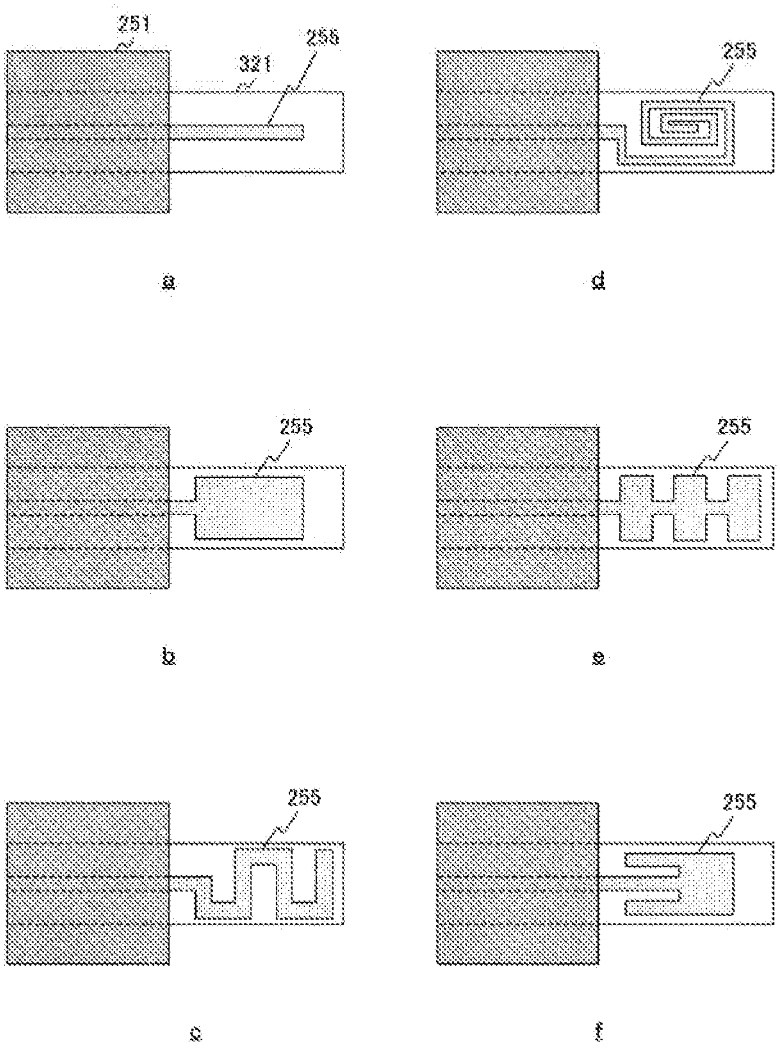
FIG. 43 is a diagram illustrating an example of the shape of a transmission antenna applied to the first structure according to the first embodiment of the present technology.

FIG. 43 is a diagram illustrating an example of the shape of the transmission antenna 223 applied to the first structure in the first embodiment of the present technology. In this diagram, a tip end of the electromagnetic wave absorbent material 251 and a tip end of the shield layer are at the same position, and a signal line 255 (a radiation element denoted by a solid line) giving a transmission wave (a transmission signal) is exposed to a further front side from such tip ends.

In this way, a configuration in which the shield layer 256 (a shield part) is not exposed from the tip end of the electromagnetic wave absorbent material 251 in the transmission antenna 223 may be employed as well. At that time, as illustrated in a in this drawing, a width of the signal line 255 exposed from the tip end of the electromagnetic wave absorbent material 251 (in other words, the radiation element denoted by the solid line) may be configured to be the same as the width of a strip line (a signal line 255) denoted by a dotted line below the sheet surface of the electromagnetic wave absorbent material 251. A direction perpendicular to the sheet surface is a main radiation direction (the X-axis direction) of an electric wave. In addition, the shape of the reception antenna 233 may be configured to be a shape illustrated in FIG. 43*a*. In such a case, the radiation element in the transmission antenna 223 serves as a reception element in the reception antenna 233. By using this antenna with facing the transmission antenna and the reception antenna, the gain of the antenna is improved.

As illustrated in b in FIG. 43, a width of a radiation element denoted by solid lines may be configured to be thicker than the width of a line (a signal line 255) of a strip line denoted by dotted lines. As illustrated in c in this drawing, a radiation element of a meandering structure also can be formed. As illustrated in d in this drawing, a radiation element of a spiral shape also can be formed. As illustrated in e in this drawing, a plurality of radiation elements thicker than the width of the strip line (the signal line 255) also can be formed. As illustrated in f in this drawing, a radiation element thicker than the line width of a strip line may be formed, and a slit may be formed in a connection part for the strip line.

In accordance with the shapes of b to e in this drawing, the gain of the main radiation direction can be improved more than a in this drawing. In accordance with the shape of f in this drawing, impedance matching can be taken more than b in this drawing, and an electric wave can be efficiently radiated. In addition, the shape of the reception antenna 233 can be configured to be any one of the shapes illustrated in FIGS. 43*a* to 43*f*. In such a case, a radiation element in the transmission antenna 223 serves as a reception element in the reception antenna 233.

Figure 44:
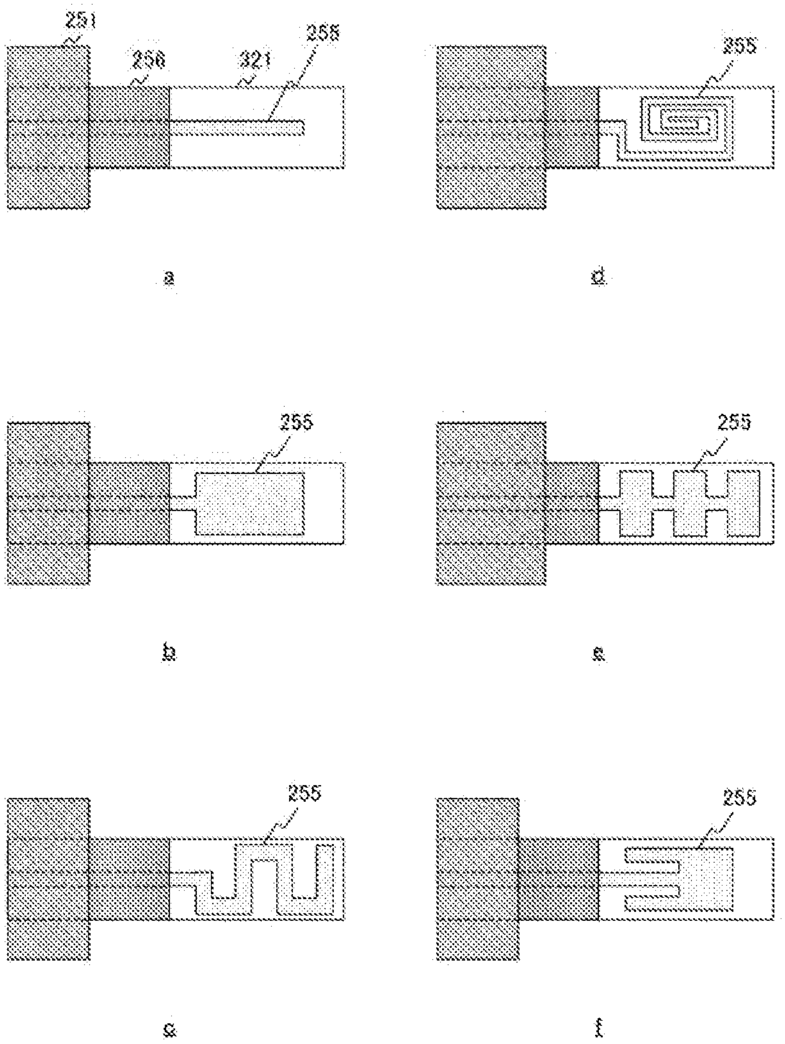
FIG. 44 is a diagram illustrating another example of the shape of a transmission antenna applied to the first structure according to the first embodiment of the present technology.

FIG. 44 is a diagram illustrating another example of the shape of the transmission antenna 223 applied to the first structure according to the first embodiment of the present technology. a to f in FIG. 44 respectively correspond to a to f in FIG. 43 in which the shield layer 256 (the shield part) is exposed from the tip end of the electromagnetic wave absorbent material 251.

In a in FIG. 44, a high-frequency current flows also through the shield layer of the main radiation direction, and the shield layer becomes a part of the antenna, and accordingly, the gain is improved more than a in FIG. 43. In accordance with the shapes of b to e in FIG. 44, the gain of the main radiation direction can be improved more than that of a in this drawing. In accordance with the shape of f of this drawing, impedance matching can be taken more than b of this drawing, and thus an electric wave can be efficiently radiated. In addition, the shape of the reception antenna 233 also can be configured to be any one of the shapes illustrated in FIGS. 44*a* to 44*f*. In such a case, a radiation element in the transmission antenna 223 becomes a reception element in the reception antenna 233.

In addition, each of the shapes illustrated in FIGS. 43 and 44 can be applied also to the second structure.

Figure 45:
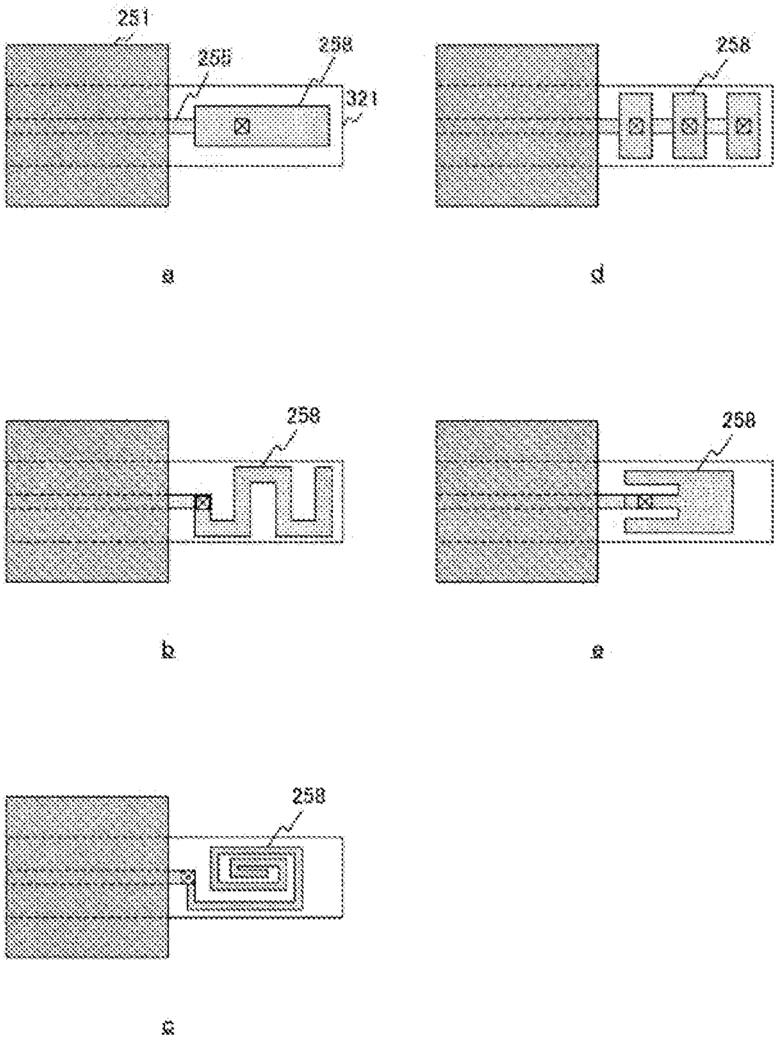
FIG. 45 is a diagram illustrating another example of the shape of a transmission antenna applied to the third structure according to the first embodiment of the present technology.

FIG. 45 is a diagram illustrating an example of the shape of the transmission antenna 223 applied to the third structure according to the first embodiment of the present technology. In this drawing, the tip end of the electromagnetic wave absorbent material 251 and the tip end of the shield layer are at the same position, and a signal line 255 (a radiation element) giving a transmission wave (a transmission signal) is exposed from such tip ends. In this way, a configuration in which the shield layer 256 (the shield part) is not exposed from the tip end of the electromagnetic wave absorbent material 251 in the transmission antenna 223 may be employed as well. At that time, as illustrated in a in this drawing, the width of the radiation element can be configured to be thicker than the width of the strip line denoted by dotted lines. As illustrated in b in this drawing, a radiation element of a meandering structure also can be formed. As illustrated in c in this drawing, a radiation element of a spiral shape also can be formed. As illustrated in d in this drawing, a plurality of radiation elements thicker than the width of the strip line can be also formed. As illustrated in e in this drawing, a radiation element thicker than the width of the strip line (the signal line 255) may be formed, and a slit can be formed in a connection part for a strip line.

In accordance with the shape of a in FIG. 45, impedance matching can be taken more than a in FIG. 43, and an electric wave can be efficiently radiated. In accordance with the shapes of b to d in FIG. 45, the gain of the main radiation direction can be improved more than a in this drawing. In accordance with the shape of e in this drawing, impedance matching can be taken more than a in this drawing, and an electric wave can be efficiently radiated. In addition, the shape of the reception antenna 233 may be configured to be any one the shapes illustrated in FIGS. 45*a* to 45*e*. In such a case, a radiation element in the transmission antenna 223 becomes a reception element in the reception antenna 233.

Figure 46:
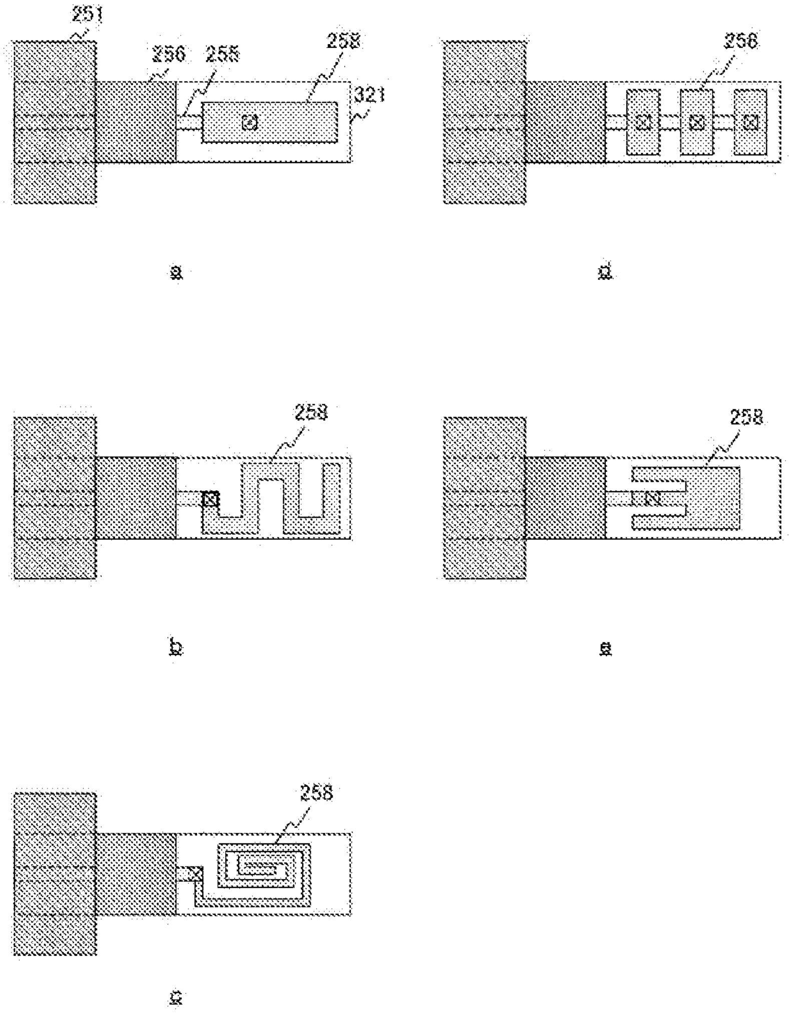
FIG. 46 is a diagram illustrating another example of the shape of a transmission antenna applied to the third structure according to the first embodiment of the present technology.

FIG. 46 is a diagram illustrating another example of the shape of the transmission antenna 223 applied to the third structure according to the first embodiment of the present technology. a to e in FIG. 46 corresponds to a to e in FIG. 45 in which the shield layer 256 (the shield part) is exposed from the tip end of the electromagnetic wave absorbent material 251.

In a in FIG. 46, a high-frequency current flows also through the shield layer of the main radiation direction, and the shield layer becomes a part of the antenna, and accordingly, the gain is improved more than a in FIG. 45. In accordance with the shapes of b to d in FIG. 46, the gain of the main radiation direction can be improved more than that of a in this drawing. In accordance with the shape of e of this drawing, impedance matching can be taken more than a of this drawing, and thus an electric wave can be efficiently radiated. In addition, the shape of the reception antenna 233 also can be configured to be any one of the shapes illustrated in FIGS. 46*a* to 46*e*. In such a case, a radiation element in the transmission antenna 223 becomes a reception element in the reception antenna 233.

In addition, each of the shapes illustrated in FIGS. 45 and 46 can be applied also to the fourth structure.

Figure 47:
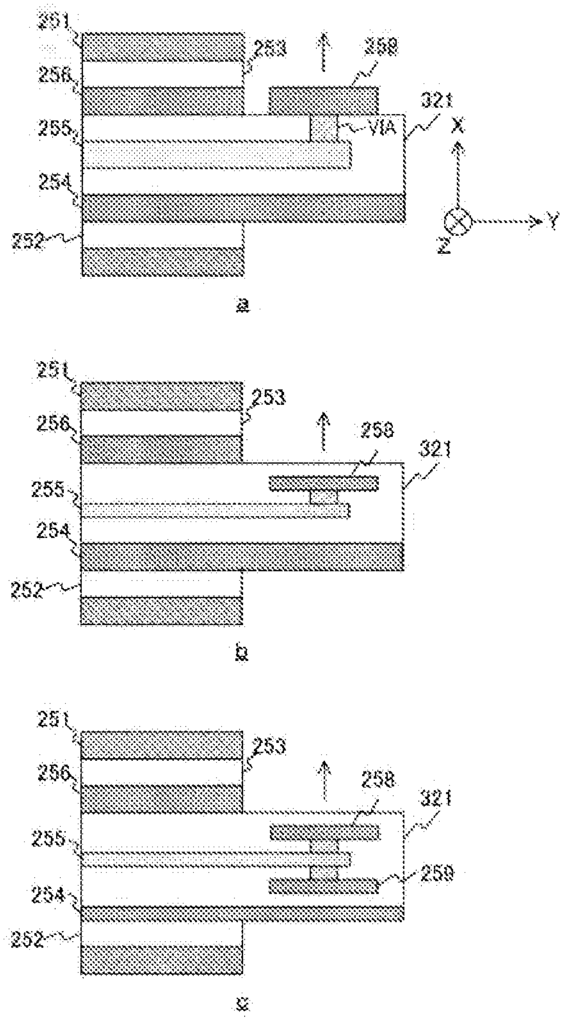
FIG. 47 is a cross-sectional view seen from a front face of the transmission antenna applied to the third structure according to the first embodiment of the present technology.

FIG. 47 is a cross-sectional view acquired by seeing the transmission antenna 233 applied to the third structure according to the first embodiment of the present technology from a front face like FIG. 4*b*. a in FIG. 47 corresponds to a cross-sectional view acquired when a is seen from a front face (the Z-axis direction) in FIG. 46.

As illustrated in a in FIG. 47, a radiation element (a conductor 258) is formed using a front layer of an in-probe substrate 321. In addition, as illustrated in b in this drawing, a radiation element 258 can be formed using an inner layer of an in-probe substrate 321 instead of being formed using the front layer of the in-probe substrate 321. When applied to the fourth structure, as illustrated in c in this diagram, both conductors 258 and 259 also can be formed using an inner layer.

Figure 48:
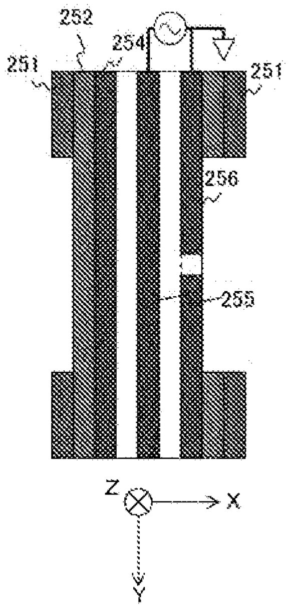
FIG. 48 is an example of a cross-sectional view of a probe in which a slot of a fifth structure, in which the slot is formed, is formed when seen from a front face in the first embodiment of the present technology.

FIG. 48 is an example of a cross-sectional view of a fifth structure relating to a transmission antenna 223 included in an in-probe substrate 321 and the vicinity thereof acquired when the sensor device 200 according to the first embodiment of the present technology is seen from a front face (seen in the Z-axis direction) like FIG. 4*b*.

Figure 49:
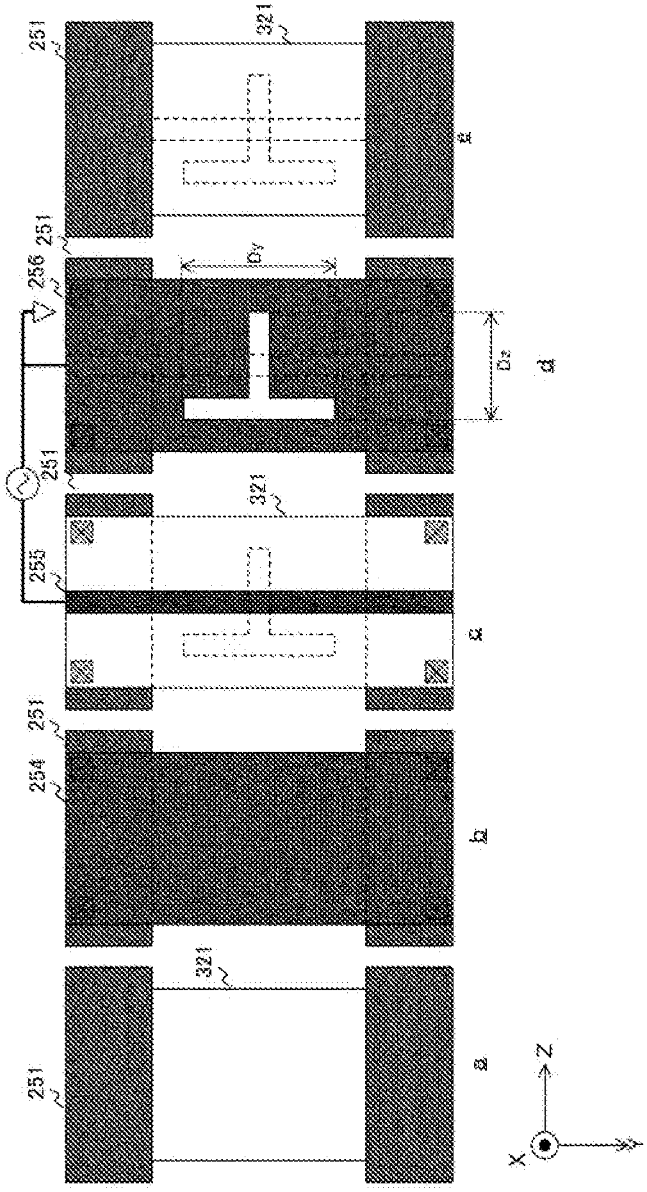
FIG. 49 is an example of a plan view of each layer of the inside of a probe casing of the fifth structure in which a slot is formed in the first embodiment of the present technology.

FIG. 49 is an example of a plan view of each layer in the fifth structure of which the cross-section is illustrated in FIG. 48.

Figure 50:
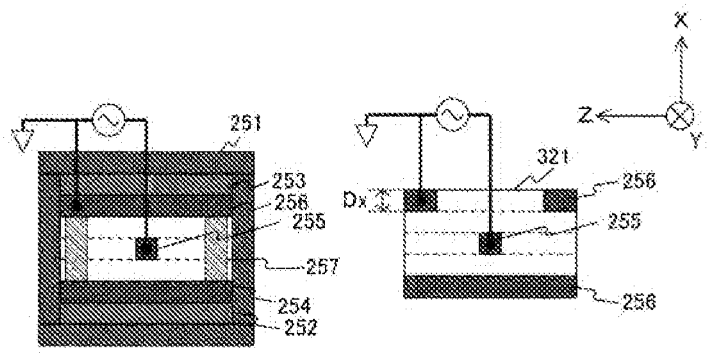
FIG. 50 is an example of a cross-sectional view of a probe of the fifth structure in which a slot is formed when seen from the top in the first embodiment of the present technology.

FIG. 50 is an example of a cross-sectional view acquired when the fifth structure of which the cross-section is illustrated in FIG. 48 is seen from the upper side.

The transmission antenna 223 of the fifth structure illustrated in FIGS. 48 to 50 is acquired by changing the transmission antenna 232 of the first structure illustrated in FIGS. 19 to 21 to an antenna of a planar shape and a slot shape.

In the case of a transmission antenna, "the antenna of the planar shape and the slot shape" is a shield layer that is exposed from the electromagnetic wave absorbent material 251 and is exposed to a space, and, in the example of the shield layer including a slot (examples of FIGS. 48 to 50), the shield layer 256 becomes a radiation element. "The antenna of the planar shape and the slot shape" includes this radiation element 256, a dielectric (or an insulator), and a power feed unit (a signal line 255 to which a signal is given) that is superimposed in the slot with the dielectric (or the insulator) interposed therein and traverses the slot. Similarly, in the case of a reception antenna, a shield layer (the shield layer 256 in the example of FIGS. 48 to 50) that is a shield layer being exposed from an electromagnetic wave absorbent material 251 and exposed to the space and includes a slot becomes a reception element 256. "The antenna of the planar shape and the slot shape" includes this reception element, a dielectric (or an insulator), and a power feed unit (a signal line 255 to which a signal is given) that is superimposed in the slot with the dielectric (or the insulator) interposed therein and traverses the slot.

In FIG. 48, a layer, to which no color is applied, disposed between the signal line 255 and the shield layer 256 (a radiation element 256) corresponds to the dielectric (or the insulator) described above.

As illustrated in FIGS. 48 to 50, the antenna of the planar shape and the slot shape is formed in an electronic substrate (the in-probe substrate 321 or the like) including a plurality of wiring layers. Both a size Dz of the slot in a second direction (a widthwise direction of the electronic substrate; the Z-axis direction illustrated in FIG. 49) that is orthogonal to a first direction and a size Dy of the slot in a third direction (a lengthwise direction in which the electronic substrate extends; the y-axis direction in FIG. 50) that are orthogonal to the first direction and the second direction are larger than a size Dx of the radiation element (the shield layer 256 including a slot) in the first direction (a thickness direction of the electronic substrate; the X-axis direction in FIG. 50) (in other words, a size of the slot included in the radiation element in the direction described above). In this specification, in a radiation element (in the example illustrated in FIGS. 48 to 50, the shield layer 256) included in a transmission antenna having a slot, in a case in which both Dz and Dy are larger than Dx, this transmission antenna is defined as "an antenna of a planar shape and a slot shape" and "a transmission antenna of a planar shape and a slot shape". Then, a part that is a part of the radiation element and extends on a plane set by the second direction and the third direction is defined as "a plane of the radiation element". In addition, an area of a quadrangle set by the width Dz of the slot and the length Dy of the slot illustrated in FIG. 49*d* is conveniently defined as an area of the transmission antenna. This similarly applies also to a reception antenna. In this specification, in a reception element (in the example illustrated in FIGS. 48 to 50, the shield layer 256) included in a reception antenna having a slot, in a case in which both Dz and Dy are larger than Dx, this reception antenna is defined as "an antenna of a planar shape and a slot shape" and "a reception antenna of a planar shape and a slot shape". A part that is a part of the reception element and extends on a plane set by the second direction and the third direction is defined as "a plane of the reception element". In addition, an area of a quadrangle set by the width Dz of the slot and the length Dy of the slot illustrated in FIG. 49*d* is conveniently defined as an area of the reception antenna. Furthermore, relating to the transmission antenna and the reception antenna, it is preferable that Dy be larger than both Dx and Dz.

In the fifth structure illustrated in FIGS. 48 to 50, in an in-probe substrate in which "an antenna of a planar shape and a slot shape" is formed, no slot is formed in a first wiring layer (the shield layer 254) of the rearmost face side (the negative direction of the X axis), and a slot is formed in a third wiring layer of the frontmost face side (the positive direction of the X axis). In accordance with such a shape, the antenna of a planar shape and a slot shape of the fifth structure becomes an antenna of one-side radiation.

Figure 51:
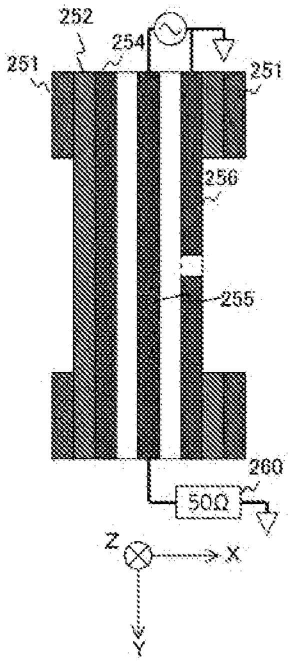
FIG. 51 is another example of a cross-sectional view of a probe of the fifth structure in which a slot is formed when seen from a front face in the first embodiment of the present technology.

FIG. 51 is a cross-sectional view illustrating another example of the fifth structure when the sensor device 200 according to the first embodiment of the present technology is seen from a front face (seen in the Z-axis direction) like FIG. 4*b*.

Figure 52:
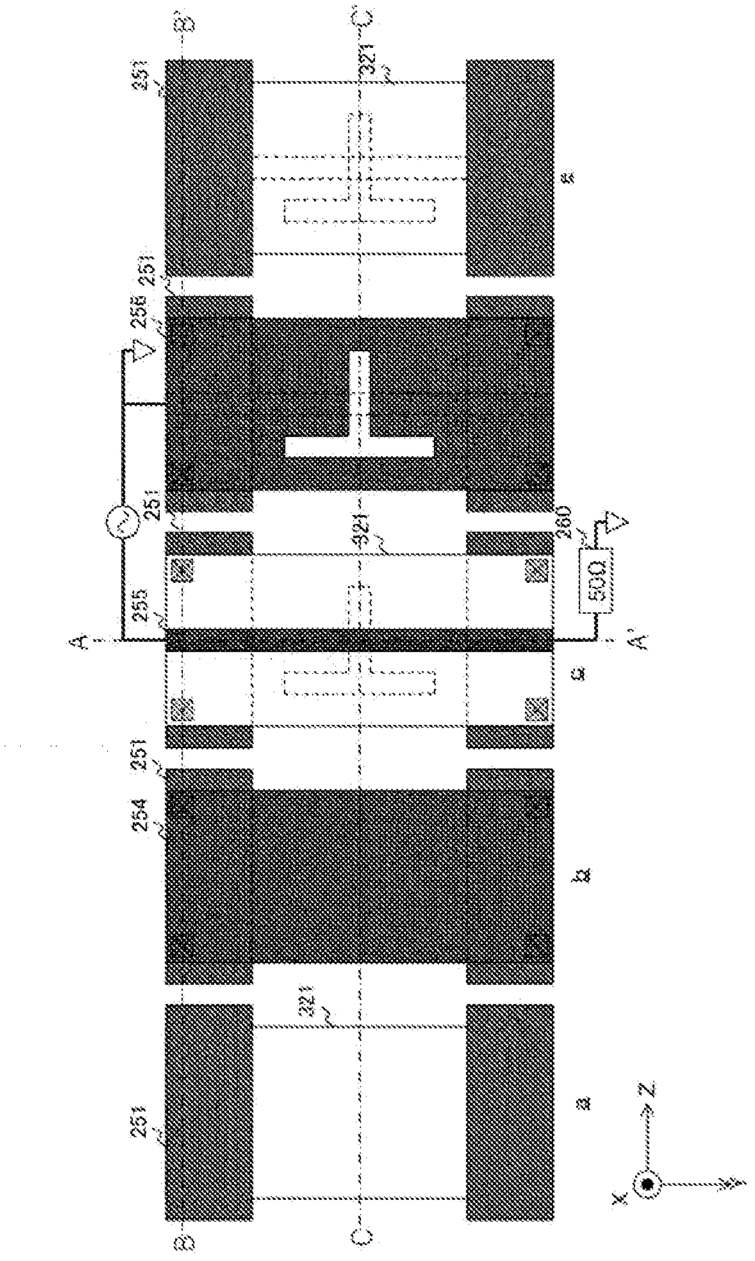
FIG. 52 is another example of a plan view of each layer of the inside of a probe casing of the fifth structure in which a slot is formed in the first embodiment of the present technology.

FIG. 52 is an example of a plan view of each layer in the other example of the fifth structure of which the cross-section is illustrated in FIG. 51.

Figure 53:
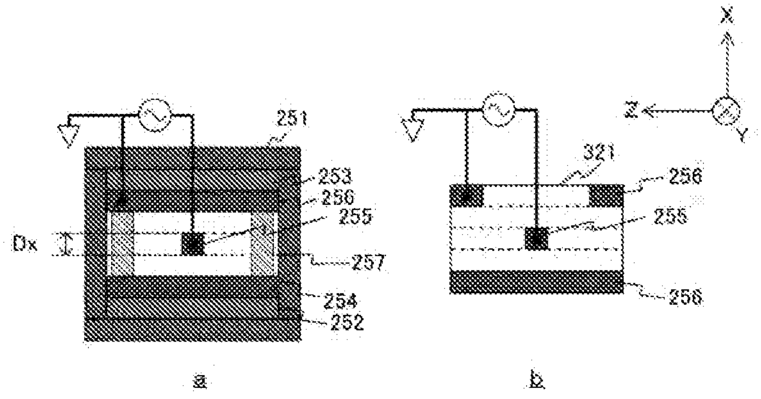
FIG. 53 is another example of a cross-sectional view of a probe of the fifth structure in which a slot is formed when seen from the top in the first embodiment of the present technology.

FIG. 53 is an example of a cross-sectional view acquired when the other example of the fifth structure of which the cross-section is illustrated in FIG. 51 is seen from the upper side.

Figure 54:
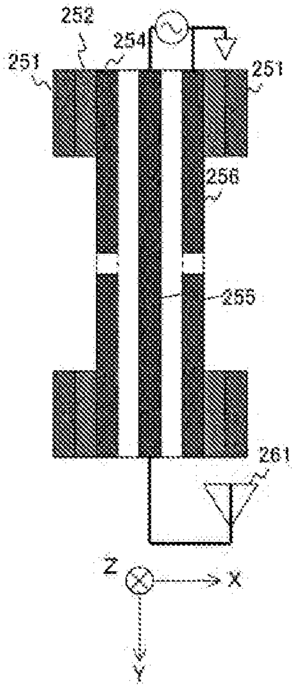
FIG. 54 is another example of a cross-sectional view of a probe of the fifth structure in which a slot is formed when seen from a front face in the first embodiment of the present technology.

FIG. 54 is a cross-sectional view illustrating yet another example of the fifth structure acquired when the sensor device 200 according to the first embodiment of the present technology is seen from a front face (seen in the Z-axis direction) similar to FIG. 4*b*.

Figure 55:
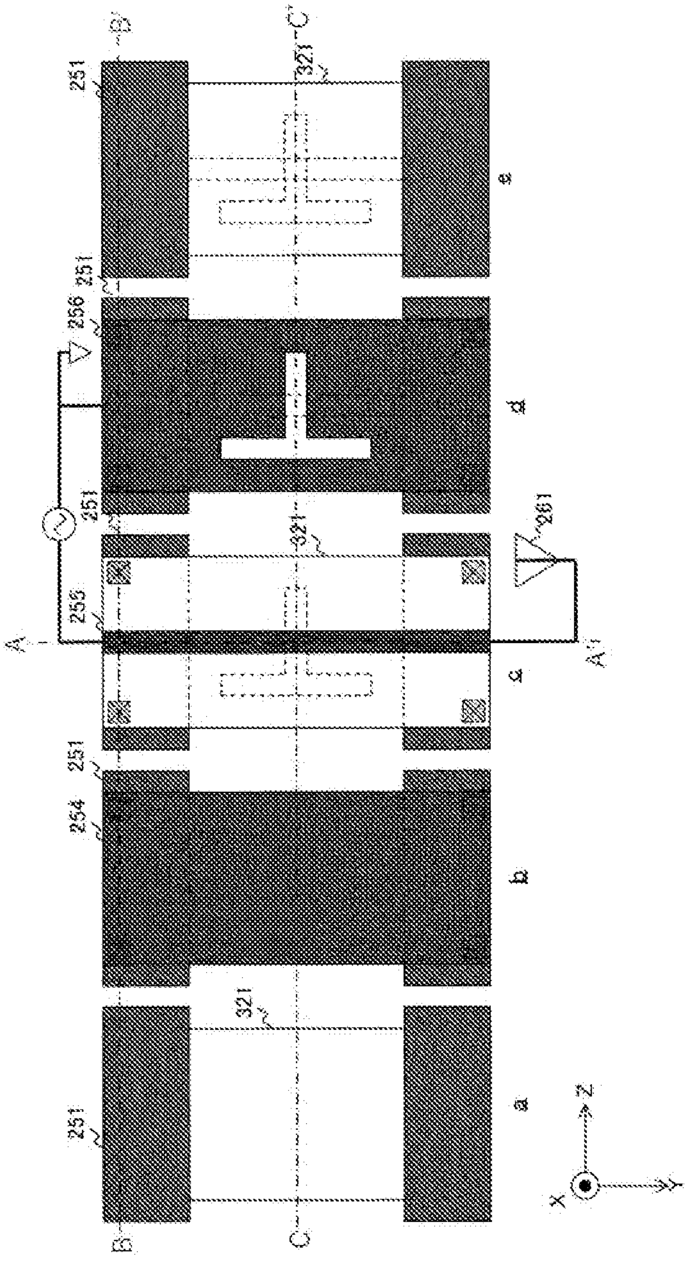
FIG. 55 is another example of a plan view of each layer of the inside of a probe casing of the fifth structure in which a slot is formed in the first embodiment of the present technology.

FIG. 55 is an example of a plan view of each layer in the yet another example of the fifth structure of which the cross-section is illustrated in FIG. 54.

Figure 56:
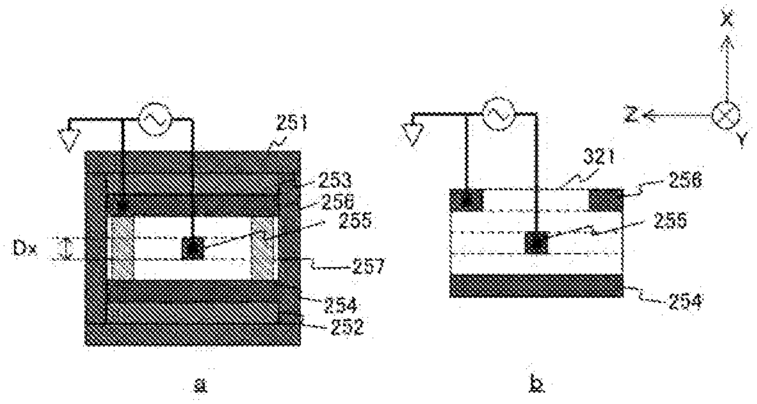
FIG. 56 is another example of a cross-sectional view of a probe of the fifth structure in which a slot is formed when seen from the top in the first embodiment of the present technology.

FIG. 56 is an example of a cross-sectional view acquired when the yet another example of the fifth structure of which the cross-section is illustrated in FIG. 54 is seen from the upper side.

As illustrated in FIGS. 51 to 53, as another example of the fifth structure, a signal line 255 included in "an antenna of a planar shape and a slot shape" can be also terminated by connecting it to the ground through a resistor 260 of 50 ohm (Ω) or the like in an area disposed on a further front side of the slot included in this antenna. In addition, as illustrated in FIGS. 54 to 56, as yet another example of the fifth structure, a signal line 255 included in "an antenna of a planar shape and a slot shape" can be also terminated by connecting it to another antenna 261 in an area disposed on a further front side of the slot included in this antenna.

Figure 57:
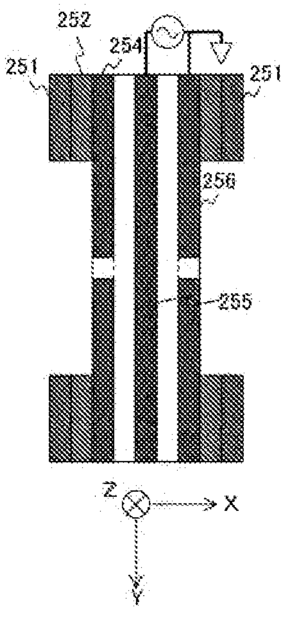
FIG. 57 is an example of a cross-sectional view of a probe of a sixth structure in which a slot is formed when seen from a front face in the first embodiment of the present technology.

FIG. 57 is an example of a cross-sectional view of a sixth structure relating to a transmission antenna 223 included in an in-probe substrate 321 and the vicinity thereof acquired when the sensor device 200 according to the first embodiment of the present technology is seen from a front face (seen in the Z-axis direction) similar to FIG. 4*b*.

Figure 58:
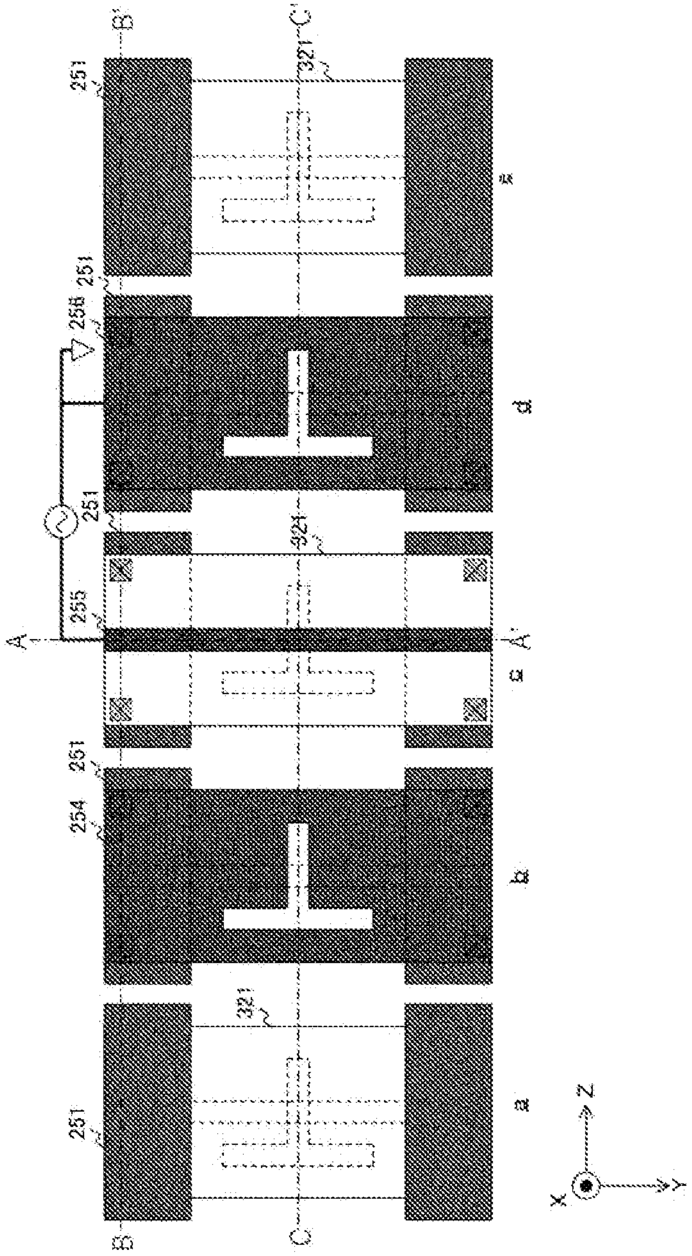
FIG. 58 is an example of a plan view of each layer of the inside of a probe casing of the sixth structure in which a slot is formed in the first embodiment of the present technology.

FIG. 58 is an example of a plan view of each layer in the sixth structure of which the cross-section is illustrated in FIG. 57.

Figure 59:
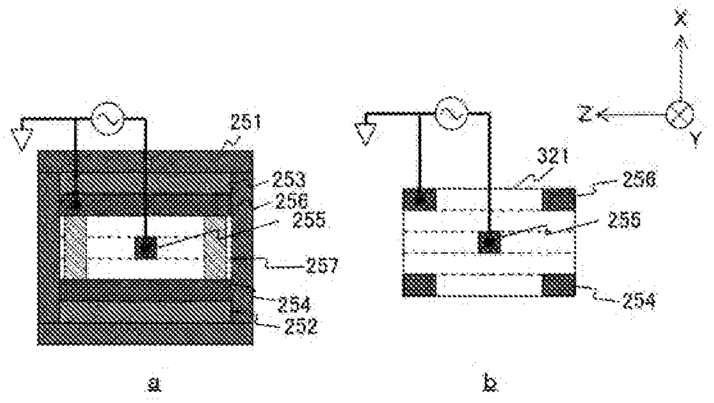
FIG. 59 is an example of a cross-sectional view of a probe of the sixth structure in which a slot is formed when seen from the top in the first embodiment of the present technology.

FIG. 59 is an example of a cross-sectional view acquired when the sixth structure of which the cross-section is illustrated in FIG. 57 is seen from the upper side.

The transmission antenna 223 of the sixth structure illustrated in FIGS. 57 to 59 is acquired by changing the antenna of a planar shape and a slot shape of the fifth structure illustrated in FIGS. 48 to 50 to an antenna of two-sides radiation. In a case in which "the antenna of a planar shape and a slot shape" of the sixth structure is a transmission antenna, a shield layer (shield layers 256 and 254) that is a shield layer being exposed from an electromagnetic wave absorbent material 251 and exposed to the space and includes a slot becomes a radiation element. In accordance with such a shape, the antenna of the planar shape and the slot shape of the sixth structure becomes an antenna of two-sides radiation. This similarly applies also to a reception antenna. In a case in which "the antenna of a planar shape and a slot shape" of the sixth structure illustrated in FIGS. 57 to 59 is a reception antenna, a shield layer (shield layers 256 and 254) that is a shield layer being exposed from an electromagnetic wave absorbent material 251 and exposed to the space and includes a slot becomes a reception element.

Figure 60:
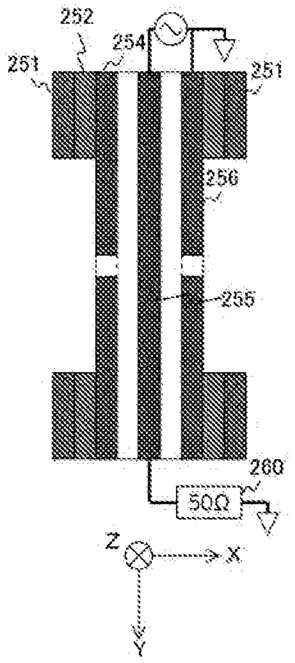
FIG. 60 is another example of a cross-sectional view of a probe of the sixth structure in which a slot is formed when seen from a front face in the first embodiment of the present technology.

FIG. 60 is a cross-sectional view illustrating another example of the sixth structure acquired when the sensor device 200 according to the first embodiment of the present technology is seen from a front face (seen in the Z-axis direction) like FIG. 4*b*.

Figure 61:
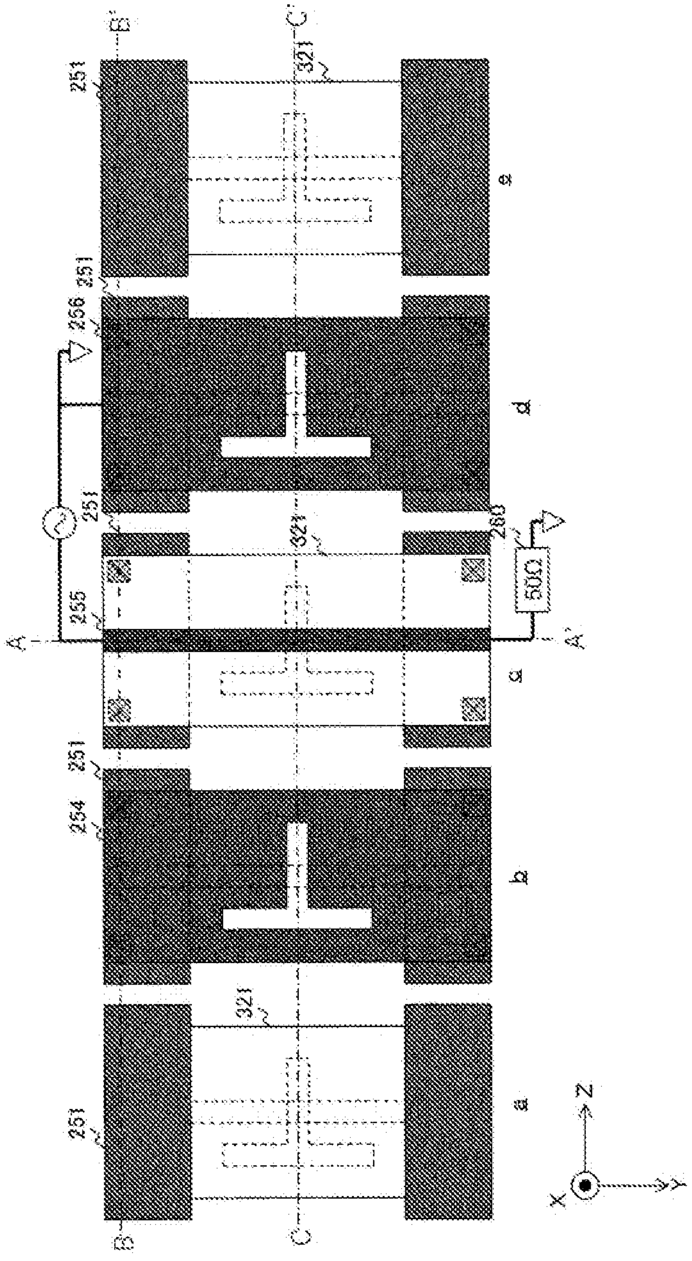
FIG. 61 is another example of a plan view of each layer of the inside of a probe casing of the sixth structure in which a slot is formed in the first embodiment of the present technology.

FIG. 61 is an example of a plan view of each layer in the other example of the sixth structure of which the cross-section is illustrated in FIG. 60.

Figure 62:
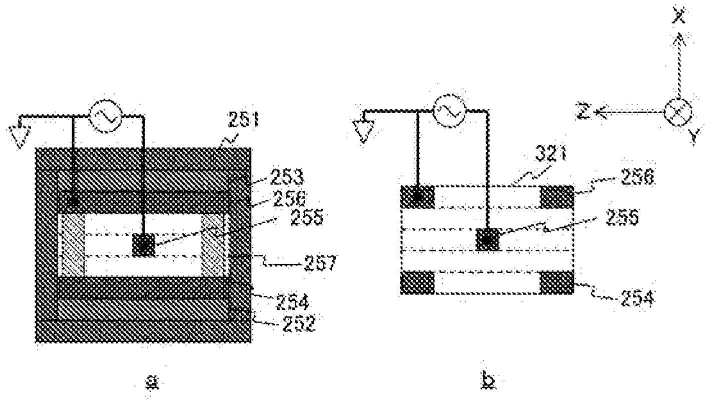
FIG. 62 is another example of a cross-sectional view of a probe of the sixth structure in which a slot is formed when seen from the top in the first embodiment of the present technology.

FIG. 62 is an example of a cross-sectional view acquired when the other example of the sixth structure of which the cross-section is illustrated in FIG. 60 is seen from the upper side.

Figure 63:
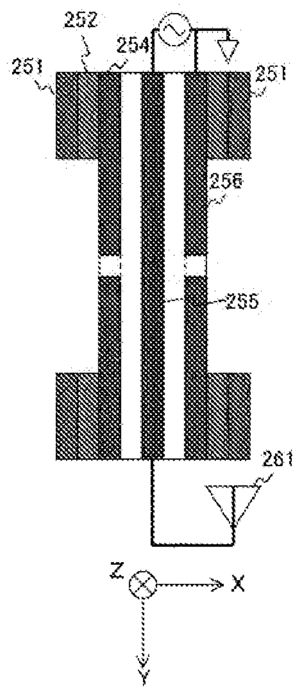
FIG. 63 is another example of a cross-sectional view of a probe of the sixth structure in which a slot is formed when seen from a front face in the first embodiment of the present technology.

FIG. 63 is a cross-sectional view illustrating yet another example of the sixth structure acquired when the sensor device 200 according to the first embodiment of the present technology is seen from a front face (seen in the Z-axis direction) like FIG. 4*b*.

Figure 64:
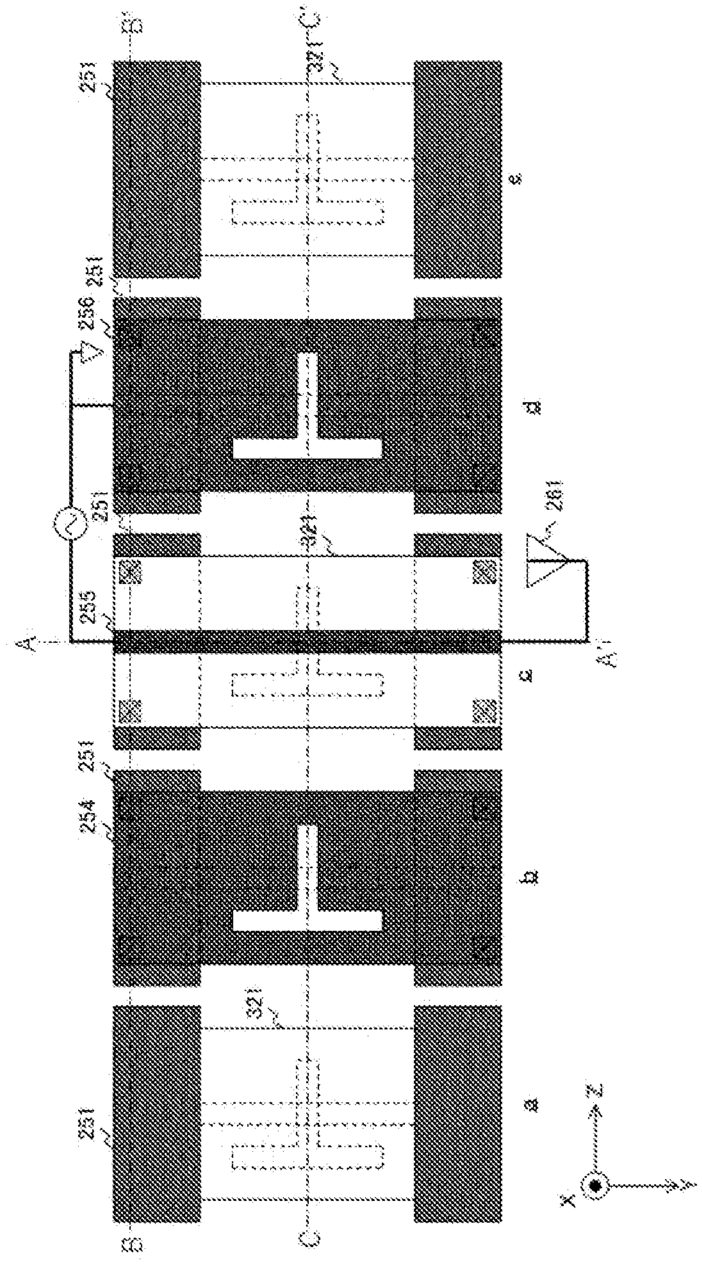
FIG. 64 is another example of a plan view of each layer of the inside of a probe casing of the sixth structure in which a slot is formed in the first embodiment of the present technology.

FIG. 64 is an example of a plan view of each layer in the yet another example of the sixth structure of which the cross-section is illustrated in FIG. 63.

Figure 65:
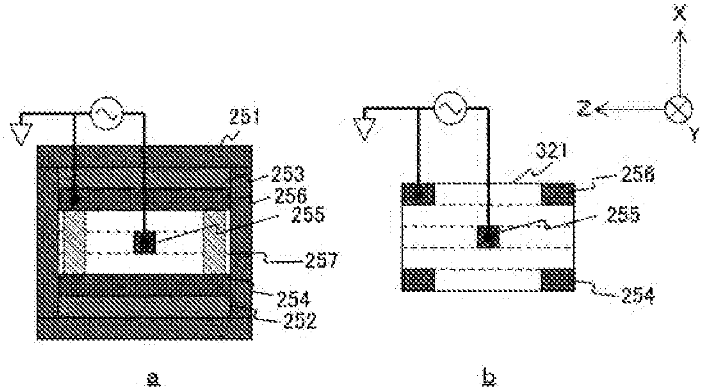
FIG. 65 is another example of cross-sectional view of a probe of the sixth structure in which a slot is formed when seen from the top in the first embodiment of the present technology.

FIG. 65 is an example of a cross-sectional view acquired when the yet another example of the sixth structure of which the cross-section is illustrated in FIG. 63 is seen from the upper side.

As illustrated in FIGS. 60 to 62, as another example of the sixth structure, a signal line 255 included in "an antenna of a planar shape and a slot shape" can be also terminated by connecting it to the ground through a resistor 260 of 50 ohm (Ω) or the like in an area disposed on a further front side of the slot included in this antenna. In addition, as illustrated in FIGS. 63 to 65, as yet another example of the sixth structure, a signal line 255 included in "an antenna of a planar shape and a slot shape" can be also terminated by connecting it to another antenna 261 in an area disposed on a further front side of the slot included in this antenna.

Figure 66:
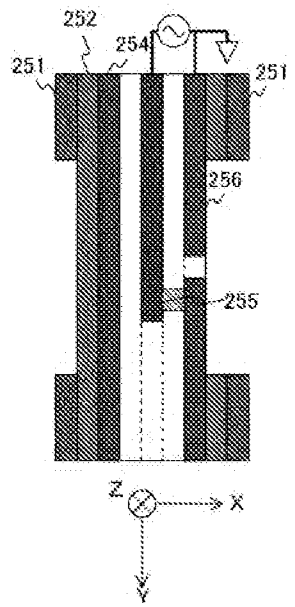
FIG. 66 is an example of a cross-sectional view of a probe of a seventh structure in which a slot is formed when seen from the top in the first embodiment of the present technology.

FIG. 66 is an example of a cross-sectional view of a seventh structure relating to a transmission antenna 223 of a planar shape and a slot shape included in an in-probe substrate 321 and the vicinity thereof acquired when the sensor device 200 according to the first embodiment of the present technology is seen from a front face (seen in the Z-axis direction) similar to FIG. 4*b*.

Figure 67:
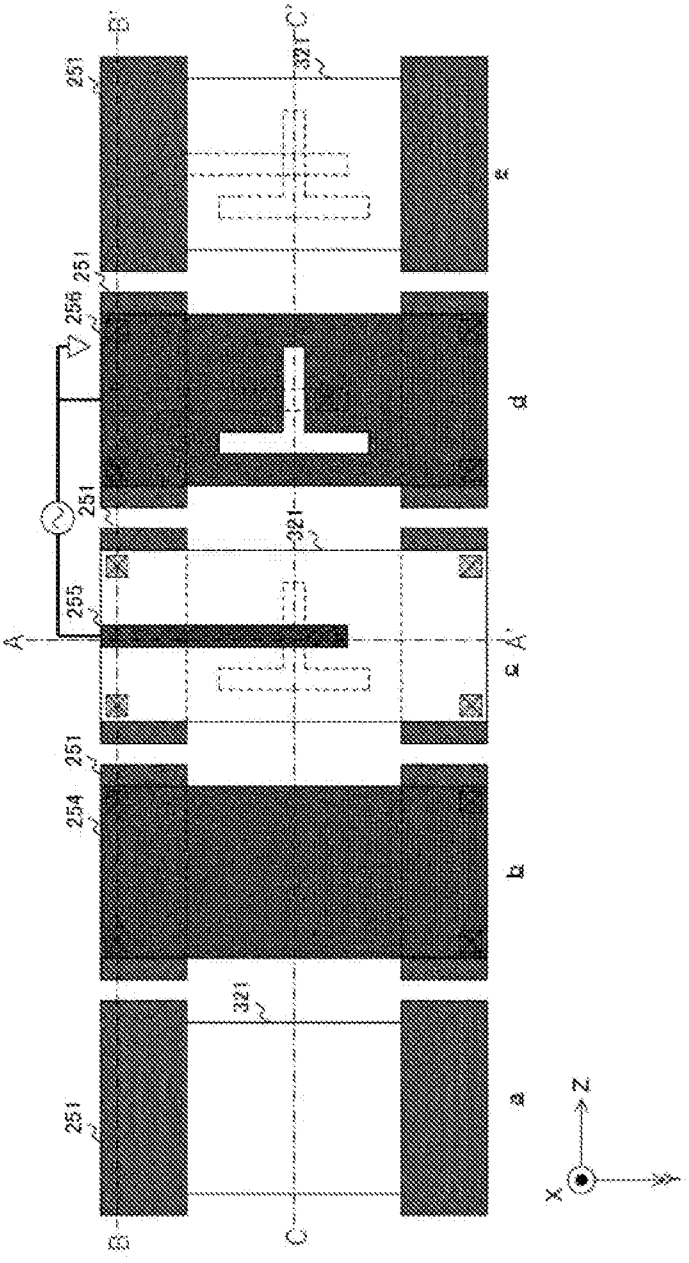
FIG. 67 is an example of a plan view of each layer of the inside of a probe casing of the seventh structure in which a slot is formed in the first embodiment of the present technology.

FIG. 67 is an example of a plan view of each layer in the seventh structure of which the cross-section is illustrated in FIG. 66.

Figure 68:
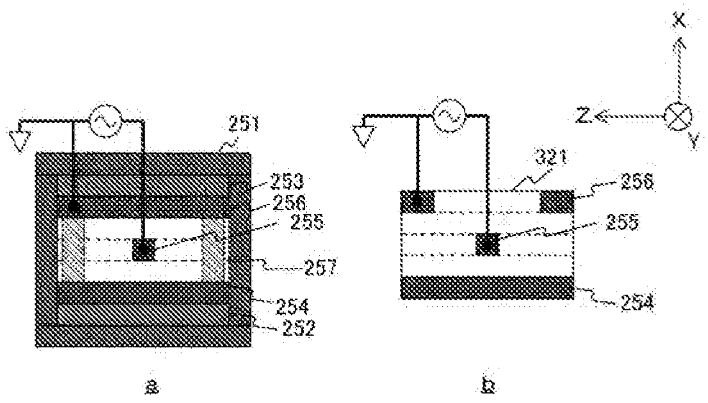
FIG. 68 is another example of a cross-sectional view of a probe of the seventh structure in which a slot is formed when seen from a front face in the first embodiment of the present technology.

FIG. 68 is an example of a cross-sectional view when the seventh structure of which the cross-section is illustrated in FIG. 66 is seen from the upper side.

The transmission antenna 223 of a planar shape and a slot shape that is the seventh structure illustrated in FIGS. 66 to 68 is different from the transmission antenna 223 of the fifth structure in the following points. In other words, in the transmission antenna 223 of a planar shape and a slot shape that is the seventh structure, inside an area (more preferably, inside an area of the transmission antenna that is conveniently defined using an area of a quadrangle set by a width Dz of the slot and a length Dy of the slot) that is an area disposed on a front side of a position at which a signal line 255 extending from a transmission source direction traverses a part of the slot (in other words, an area disposed on a front side of a position at which the signal line 255 extending from a transmission source direction overlaps a part of the slot) and is near the slot, the signal line 255 is connected to a radiation element (the shield layer 256) including the slot through a via denoted by diagonal lines in FIG. 66 and is terminated. By having such a structure, compared to the antenna of the fifth structure, the antenna of a planar shape and a slot shape that is the seventh structure can increase a current flowing through the radiation element 256 from the signal line 255 over the slot and efficiently radiate an electromagnetic wave. This similarly applies also to a reception antenna. In a case in which "the antenna of a planar shape and a slot shape" of the seventh structure illustrated in FIGS. 66 to 68 is a reception antenna, the shield layer 256 that is a shield layer being exposed from the electromagnetic wave absorbent material 251 and exposed to the space and includes the slot becomes a reception element.

Figure 69:
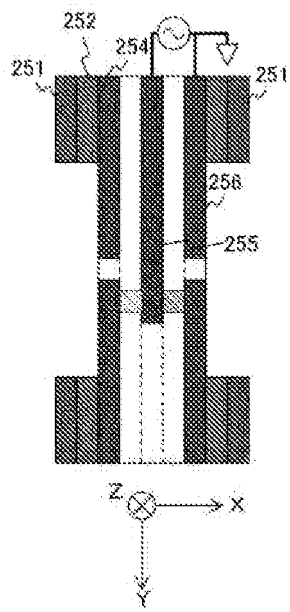
FIG. 69 is an example of a cross-sectional view of a probe of an eighth structure in which a slot is formed when seen from the top in the first embodiment of the present technology.

FIG. 69 is an example of a cross-sectional view of an eighth structure relating to a transmission antenna 223 included in an in-probe substrate 321 and the vicinity thereof acquired when the sensor device 200 according to the first embodiment of the present technology is seen from a front face (seen in the Z-axis direction) similar to FIG. 4*b*.

Figure 70:
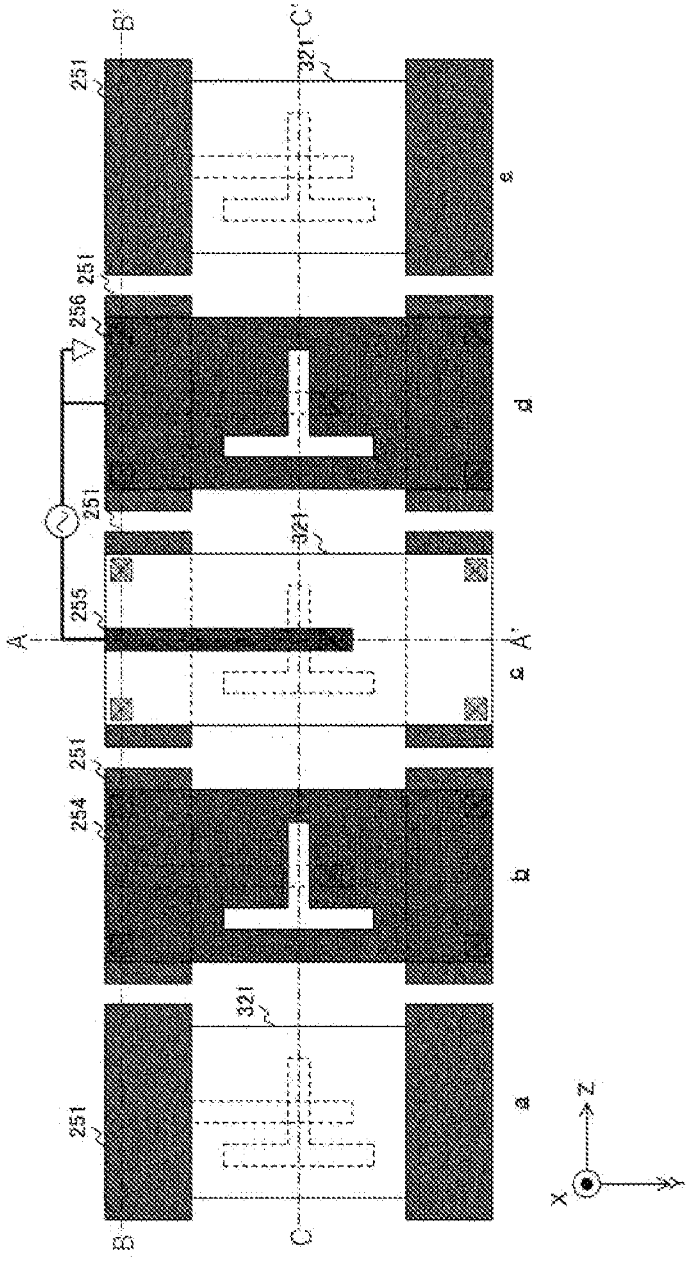
FIG. 70 is an example of a plan view of each layer of the inside of a probe casing of the eighth structure in which a slot is formed in the first embodiment of the present technology.

FIG. 70 is an example of a plan view of each layer in the eighth structure of which the cross-section is illustrated in FIG. 69.

Figure 71:
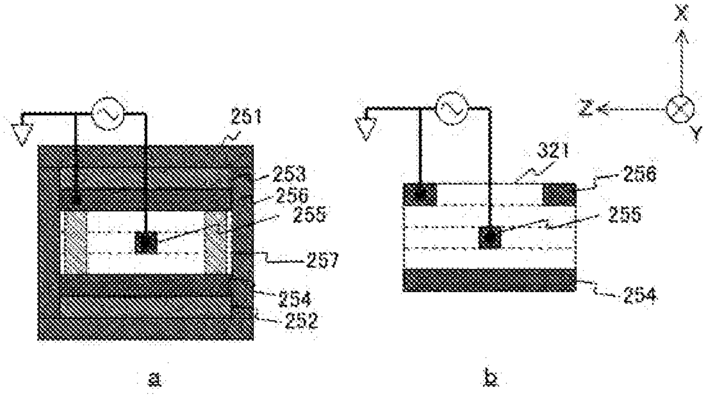
FIG. 71 is another example of a cross-sectional view of a probe of the eighth structure in which a slot is formed when seen from a front face in the first embodiment of the present technology.

FIG. 71 is an example of a cross-sectional view acquired when the eighth structure of which the cross-section is illustrated in FIG. 69 is seen from the upper side.

The transmission antenna 223 of the eighth structure illustrated in FIGS. 69 to 71 is acquired by changing the antenna of a planar shape and a slot shape of the seventh structure illustrated in FIGS. 66 to 68 to an antenna of two-sides radiation. In a case in which "the antenna of a planar shape and a slot shape" of the eighth structure is a transmission antenna, a shield layer (shield layers 256 and 254) that is a shield layer being exposed from an electromagnetic wave absorbent material 251 and exposed to the space and includes a slot becomes a radiation element. In addition, inside an area (more preferably, inside an area of the transmission antenna that is conveniently defined using an area of a quadrangle set by a width Dz of the slot and a length Dy of the slot) that is an area disposed on a front side of a position at which a signal line 255 extending from a transmission source direction traverses a part of the slot (in other words, an area disposed on a front side of a position at which the signal line 255 extending from a transmission source direction overlaps a part of the slot) and is near the slot, the signal line 255 is connected to both radiation elements (shield layers 256 and 254) including the slot through a via denoted by diagonal lines in FIG. 69 and is terminated. In accordance with such a shape, the antenna of the planar shape and the slot shape of the eighth structure becomes an antenna of two-sides radiation. This similarly applies also to a reception antenna. In a case in which "the antenna of a planar shape and a slot shape" of the eighth structure illustrated in FIGS. 69 to 71 is a reception antenna, shield layers (shield layers 256 and 254) that are shield layers being exposed from an electromagnetic wave absorbent material 251 and exposed to the space and includes a slot become reception elements.

Figure 72:
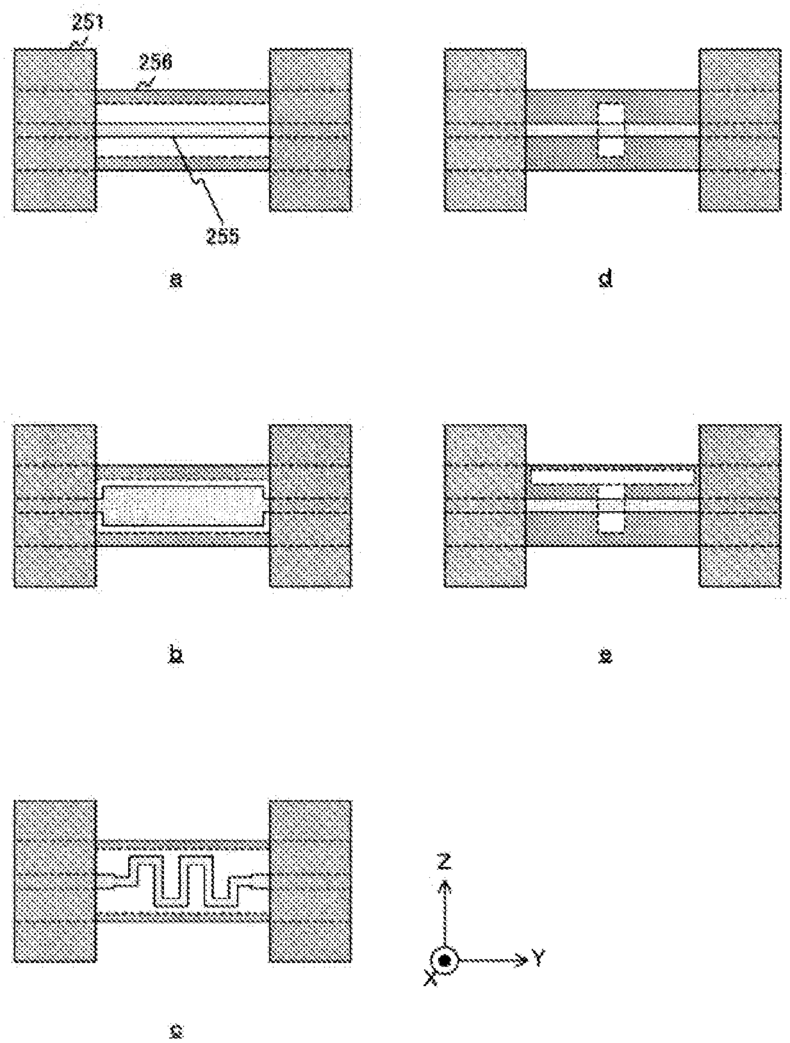
FIG. 72 is a diagram illustrating an example of the shape of a transmission antenna applied to the fifth structure in which a slot is formed in the first embodiment of the present technology.

FIG. 72 is a diagram illustrating an example of the shape of a transmission antenna applied to the fifth structure of the antenna of a planar shape and a slot shape according to the first embodiment of the present technology. As illustrated in a in this drawing, in a shield layer 256 exposed from an electromagnetic wave absorbent material 251, the whole area overlapping a signal line 255 may be formed as a slot. As illustrated in b in this drawing, a line width of a signal line 255 exposed from an electromagnetic wave absorbent material 251 may be configured to be larger than a width of the signal line 255 extending in an area in which the electromagnetic wave absorbent material 251 is disposed, and, in the shield layer 256, the whole area overlapping the signal line 255 of which the width is configured to be large may be formed as a slot. As illustrated in c in this drawing, a signal line 255 exposed from an electromagnetic wave absorbent material 251 may be configured to have a meandering structure, and, in a shield layer 256, the whole area overlapping the signal line 255 configured to have the meandering structure may be formed as a slot. As illustrated in d in this drawing, a slot formed in a shield layer 256 exposed from an electromagnetic wave absorbent material 251 may be configured to traverse a signal line 255 exposed from the electromagnetic wave absorbent material 251. As illustrated in e in this drawing, a slot disposed in a shield layer 256 exposed from an electromagnetic wave absorbent material 251 may be configured to traverse a signal line 255 exposed from the electromagnetic wave absorbent material 251, and, in a front area in which the slot traverses the signal line 255, the slot may be configured to branch (for example, branching into a letter T).

In accordance with the shapes of a and d in this drawing, a sheet surface vertical direction (the X-axis direction) becomes a main radiation direction of an electric wave, and the gain of the antenna is improved. In accordance with the shapes of b and c in this drawing, radiation resistance is higher than that of a in this drawing, and thus electric waves can be efficiently radiated. In accordance with the shape of e in this drawing, radiation resistance is higher than that of d in this drawing, and thus electric waves can be efficiently radiated.

In addition, the shape of a in this drawing also can be applied to the sixth structure of the antenna of a planar shape and a slot shape. In this case, compared to when a in this drawing is applied to the fifth structure, impedance matching can be easily taken, and electric waves can be efficiently radiated.

Figure 73:
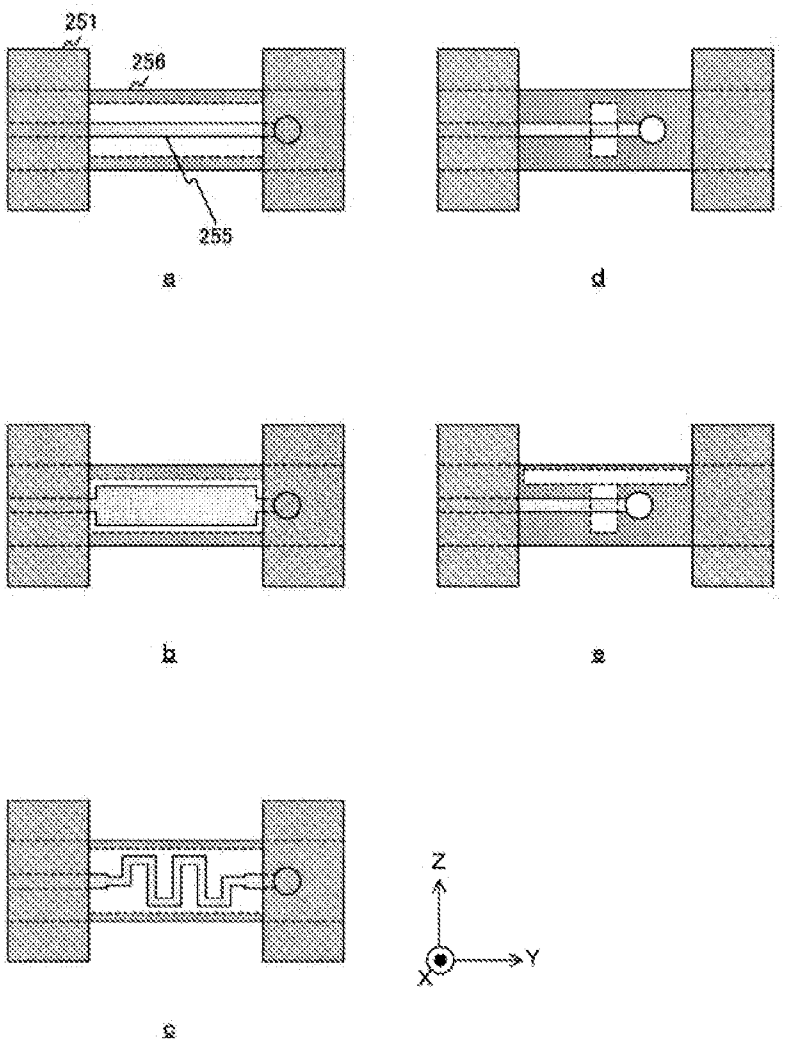
FIG. 73 is a diagram illustrating an example of the shape of a transmission antenna applied to the seventh structure in which a slot is formed in the first embodiment of the present technology.

FIG. 73 is a diagram illustrating an example of the shape of a transmission antenna applied to a seventh structure of an antenna of a planar shape and a slot shape according to the first embodiment of the present technology. In a to e illustrated in FIG. 73, tip ends of the signal lines 255 of a to e in FIG. 72 are connected to radiation elements through vias (in other words, slots are connected to the shield layers 256) and thus are terminated. A white circle represents a via. By including this structure, compared to the antenna illustrated in FIG. 72, a current flowing through a radiation element from the signal line 255 over a slot increases, and electromagnetic waves can be efficiently radiated.

Figure 74:
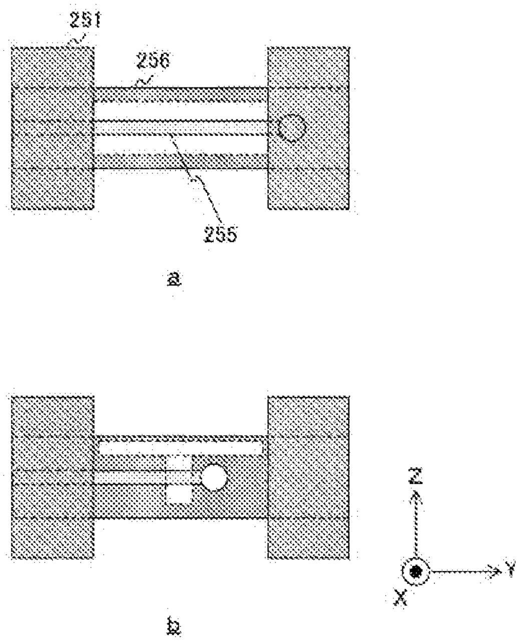
FIG. 74 is a diagram illustrating an example of the shape of a transmission antenna applied to the eighth structure in which a slot is formed in the first embodiment of the present technology.

FIG. 74 is a diagram illustrating an example of the shape of a transmission antenna applied to an eighth structure of the antenna of a planar shape and a slot shape according to the first embodiment of the present technology.

FIG. 75 is a diagram for describing an operation principle of the sensor device 200 according to the first embodiment of the present technology and an effect brought by the structure of the sensor device 200. As illustrated in a in this drawing, the sensor device 200 according to the present technology fixes a distance between the transmission antenna 221 and the reception antenna 231 to a predetermined distance d0. In consideration of an increase of a propagation time of an electromagnetic wave required for propagation of this predetermined distance d0 being proportional to an amount of moisture in a medium between the transmission antenna 221 and the reception antenna 231, a propagation delay time Δt of the electromagnetic wave is measured, and an amount of moisture thereof is acquired.

In order to measure an amount of moisture accurately, as illustrated in b in this drawing, the sensor device 200 includes a transmission antenna 221 and a reception antenna 231 of a planar shape or a planar shape and a slit shape having a high gain. In order to improve processing accuracy and positioning accuracy of such antennas and in order to maintain an environment of the periphery of the antennas and transmission lines (for example, a size of a space of the periphery of the antennas and the transmission lines, distances from the antennas and the transmission lines to a casing, and distances from the antennas and the transmission lines to soil) to be constant, the transmission antenna and a transmission line connected to the transmission antenna are formed using the same first electronic substrate (an in-probe substrate 321), and the reception antenna and a transmission line connected to the reception antenna are formed using the same second electronic substrate (an in-probe substrate 322).

Then, the sensor device 200 has such a new structure that, under a condition of the amount of moisture of the medium between antennas being a constant value, even when measurement of an amount of moisture is repeated, measurement results thereof are constantly fixed (in other words, even when measurement is repeatedly performed, a time required for an electromagnetic wave to propagate from the transmission antenna to the reception antenna and a size of a propagating signal are constantly fixed). In other words, as illustrated in b in this diagram, the sensor device 200 includes a transmission antenna and a reception antenna of a planar shape or of a planar shape and a slot shape and has a structure in which positions of such antennas are fixed such that directions thereof are fixed by configurating planes of such antennas to face each other, and a distance between the transmission antenna and the reception antenna is constantly a predetermined distance.

In addition, a transmission line for transmission connected to the transmission antenna and a transmission line for reception connected to the reception antenna are connected to a measurement unit 312. The measurement unit 312 transmits a transmission wave to the transmission antenna and receives a reception wave from the reception antenna. A measurement unit substrate 311 including this measurement unit 312 is orthogonal to a first electronic substrate and a second electronic substrate. A transmission line electrically extends between such orthogonal substrates through a transmission line cable that is a transmission line including a plurality of shielded signal lines and has flexibility higher than that of the measurement unit substrate 311 and the in-probe substrates 321 and 322.

In PTL 1, a form in which planes of a transmission antenna and a reception antenna are configured to face each other, and directions of the antennas are fixed is not described.

Meanwhile, in the field of a radio communication terminal device, there are cases in which an antenna of a planar shape or of a planar shape and a slot shape is used. However, generally, in a radio communication device, a transmitter and a receiver are housed in different casings, and thus a distance between the transmission antenna and the reception antenna is not fixed, and directions of the transmission antenna and the reception antenna are not fixed.

In PTL 1, there is no recognition of an object of accurately measuring an amount of moisture by configuring a transmission antenna and a reception antenna of a planar shape to face each other and fixing directions thereof, and there is no motivation for combining a structure for configuring a transmission antenna and a reception antenna of a planar shape to face each other and fixing directions thereof.

A function of the present invention of being able to accurately measure a propagation delay time of an electromagnetic wave propagating a distance set in advance and an amount of moisture in a propagation medium can be acquired for the first time by using a configuration in which a transmission antenna and a reception antenna of a planar shape or a planar and slit shape are fixed to a predetermined direction, in other words, a direction for facing each other, and such antennas are fixed at positions for a distance set in advance.

In addition, the effect of accurately measuring an amount of moisture using a configuration in which a transmission antenna and a reception antenna of a planar shape or a planar and slit shape are fixed to a predetermined direction, in other words, a direction for facing each other, and such antennas are fixed at positions for a distance set in advance can be acquired not only in the forms illustrated in FIGS. 4 and 74 in which the measurement unit substrate extends in parallel with one plane set by the X axis and the Y axis but also in a form illustrated in FIG. 348 in which the measurement unit substrate extends in parallel with one plane set by the X axis and the Z axis. As another example of the first embodiment of the present technology, a form in which the direction in which the measurement unit substrate according to the first embodiment of the present technology illustrated in FIG. 4 is changed such that the measurement unit substrate extends in parallel with one plane set by the X axis and the Z axis as illustrated in FIG. 348, and this measurement unit substrate, the transmission probe substrate, and the reception probe substrate are housed in one sensor casing similar to FIG. 4 may be employed as well.

Here, a comparative example in which an antenna is not formed inside an electronic substrate (an in-probe substrate 321 and the like), for example, an example in which an antenna is assembled using a plurality of components will be considered. Compared to this comparative example, in the sensor device 200, antennas are formed inside an electronic substrate, and thus processing accuracy of antennas is improved, and moisture can be accurately measured. In addition, the volume of antennas and the probe casing 320 included in the sensor device 200 can be configured to be small. In accordance with this, when the probe casing 320 is inserted into the ground, an amount of soil pushed by the probe casing 320 in the direction of soil that is a measurement target can be decreased. By decreasing the amount of soil to be pushed and increased, the state of the soil that is a measurement target can be inhibited from being changed at the time of inserting the probe casing, and, in accordance with this, moisture of the soil that is a measurement target can be accurately measured.

In addition, as an angle of the transmission antenna plane formed with respect to the measurement unit substrate and an angle of the reception antenna plane formed with respect to the measurement unit substrate, an arbitrary angle between 0° to 90° may be taken.

FIG. 76 is a diagram illustrating an example of an angle formed between an antenna plane and a measurement unit substrate according to the first embodiment of the present technology. As illustrated in a in this drawing, on both the transmission side and the reception side, an angle formed between the antenna plane and the measurement unit substrate can be configured to be 90 degrees. As illustrated in b in this drawing, on both the transmission side and the reception side, an angle formed between the antenna plane and the measurement unit substrate can be configured to be 0 degrees.

As illustrated in c in this drawing, on both the transmission side and the reception side, an angle formed between the antenna plane and the measurement unit substrate can be configured to be an angle other than 0 degrees and 90 degrees. As illustrated in d in this drawing, on both the transmission side and the reception side, an angle formed between the antenna plane and the measurement unit substrate can be configured to be an angle other than 0 degrees and 90 degrees, the angle of one side can be configured to be $+\alpha$, and the angle of the other side can be configured to be $-\alpha$. In addition, as illustrated in e and f in this drawing, the angle of one of the transmission side and the reception side can be configured to be 90 degrees, and the other thereof can be configured to be 0 degrees.

Figure 77:
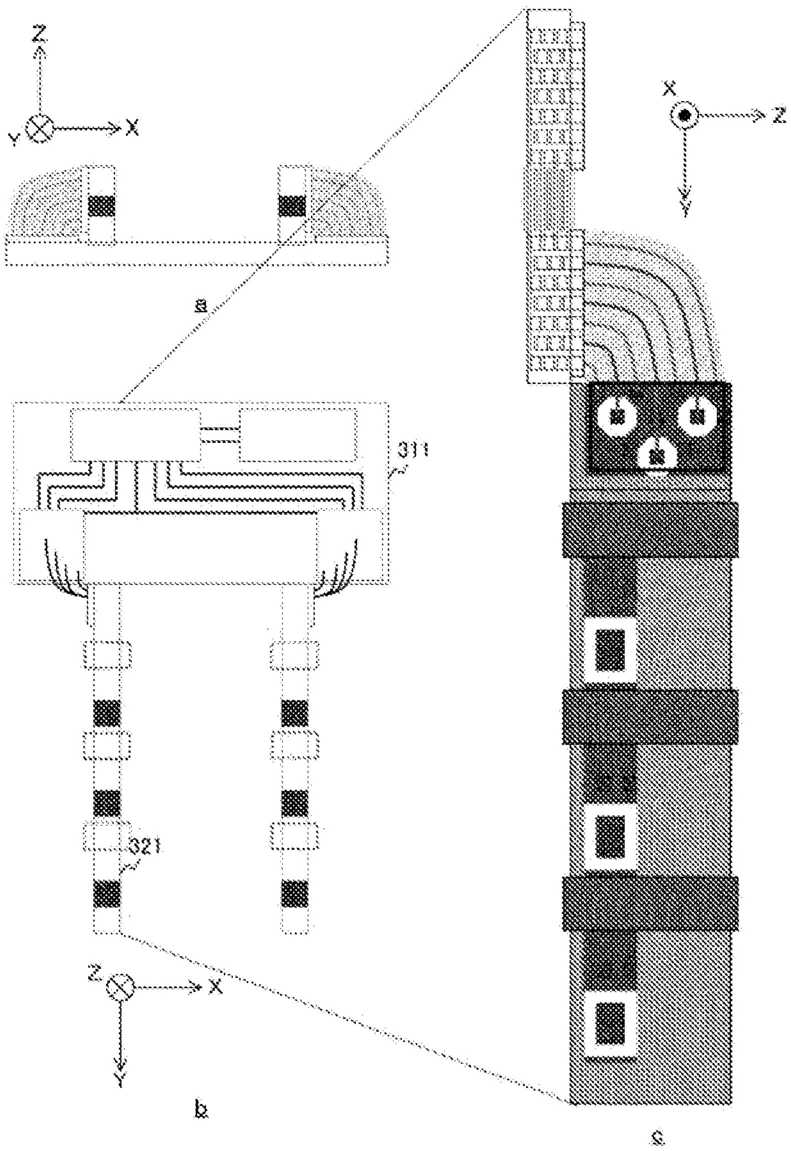
FIG. 77 is a diagram illustrating a method of connecting substrates according to the first embodiment of the present technology.

FIG. 77 is a diagram for describing a method of connecting a measurement unit substrate 311 and in-probe substrates 321 and 322 included in the sensor device 200 according to the first embodiment of the present technology. a in this diagram is a diagram of a connection place between such substrates seen from the upper side of the sensor device 200. b in this diagram is a diagram of such substrates seen from a front face of the sensor device 200. c in this diagram is a detailed diagram acquired when such substrates are seen from a lateral face (the X-axis direction) of the sensor device 200. The configuration of this diagram corresponds to Constituent element (7).

A transmission line connecting unit illustrated in FIG. 77*c* electrically connects a transmission line inside the measurement unit substrate 311 and a transmission line inside the in-probe substrate 321 or 322. This transmission line connecting unit includes signal lines corresponding to the number of antennas, and each of these signal lines is shielded. In this diagram, as the transmission line connecting unit, a parallel cable is used. Inside this parallel cable, shield lines are further wired on both sides of each signal line, and these are arranged to be aligned. For example, when the number of signal lines is three, four shield lines are wired, and these are arranged to be aligned. On each of an upper side and a lower side of the signal lines and shield lines that are arranged to be aligned, a shield layer is disposed. The circumference of the signal lines is shielded using shield wirings between signal lines and the shield layers of the upper and lower sides of the signal lines. An outer circumference of a structure in which the signal lines, the shield lines, and the shield layers are included and integrated is coated with an insulating protection member. In addition, as the transmission line connecting unit, coaxial cables corresponding to the number of antennas may be used.

Figure 78:
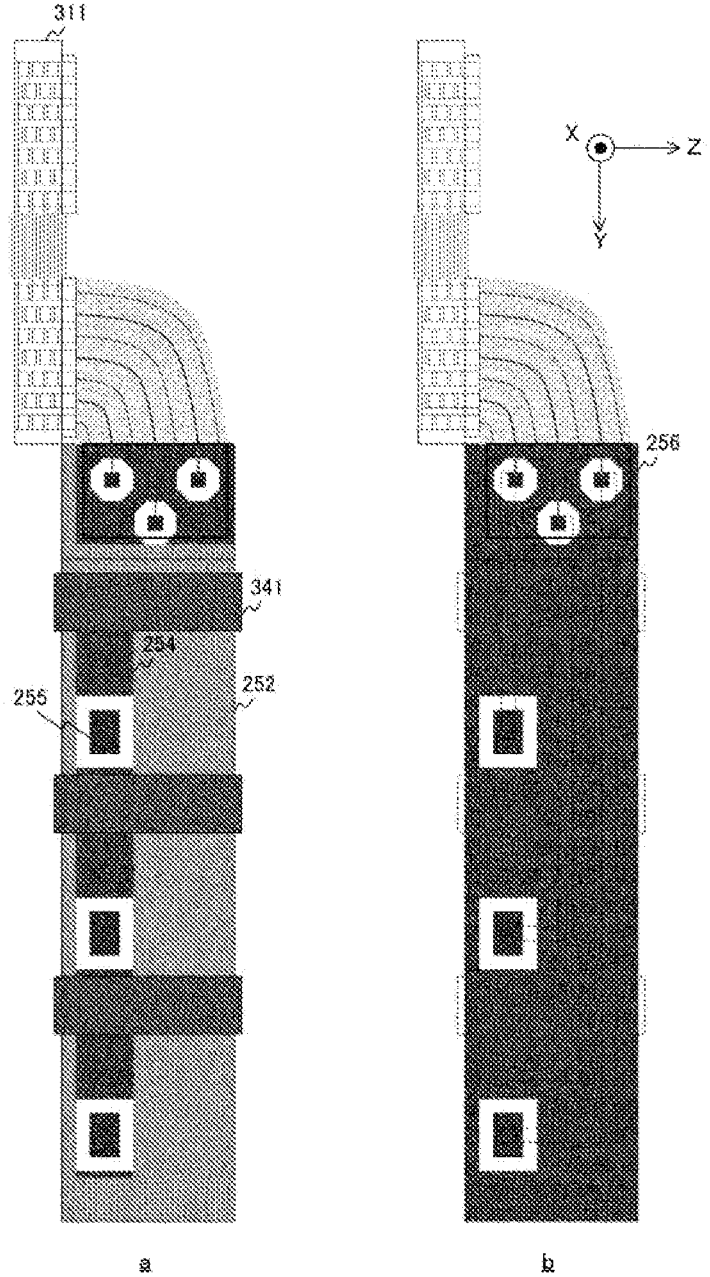
FIG. 78 is an example of a detailed diagram of substrates according to the first embodiment of the present technology.

FIG. 78 is an example of a detailed diagram of the measurement unit substrate 311, the in-probe substrate 321 or 322, and the transmission line connecting unit included in the sensor device 200 according to the first embodiment of the present technology. An in-probe substrate illustrated in a in this diagram represents a state in which this is seen from the outside. In an in-probe substrate illustrated in b in this drawing, the shape of a wiring layer of a front layer thereof is represented as a pattern to which colors are applied, and vias connected to the wiring layer of the front layer and the shape of a wiring layer of an inner layer are denoted using dotted lines.

Figure 79:
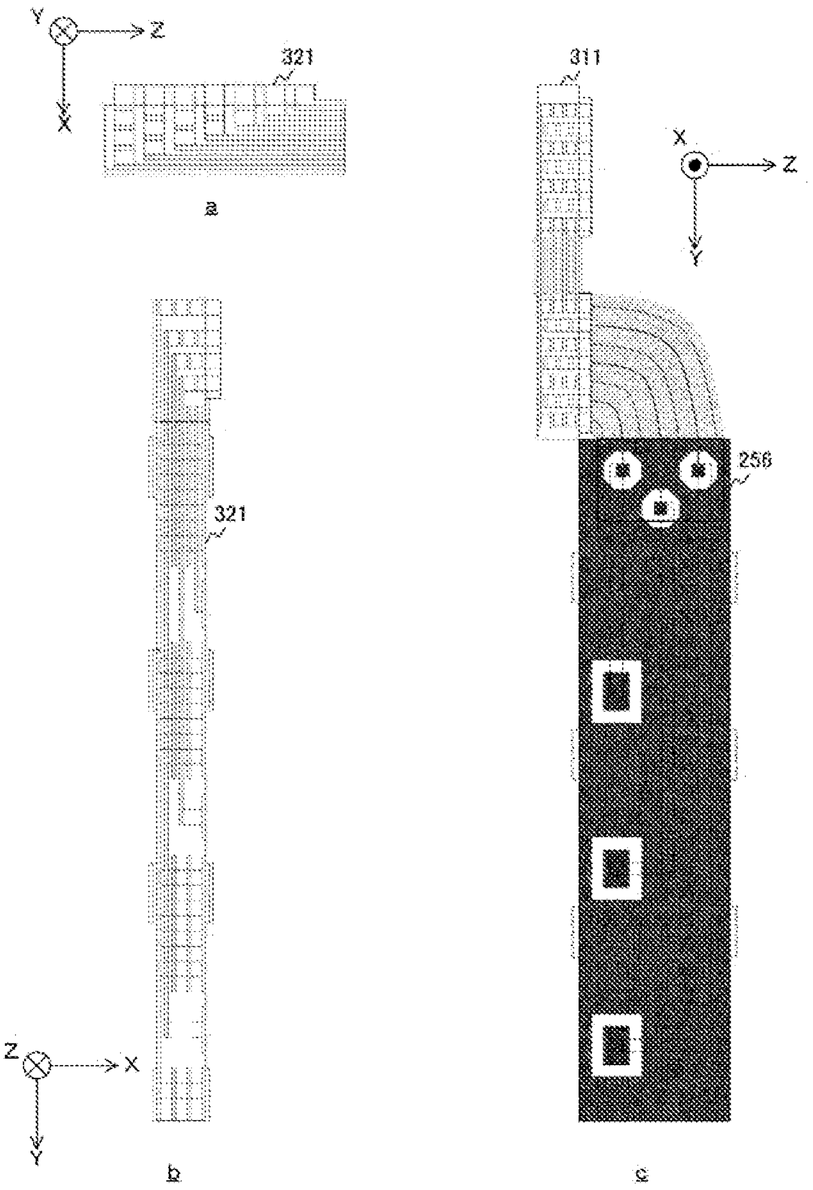
FIG. 79 is an example of a detailed diagram and a cross-sectional view of substrates according to the first embodiment of the present technology.

FIG. 79 is an example of a detailed drawing and a cross-sectional view of the measurement unit substrate 311, the in-probe substrate 321, and the transmission line connecting unit included in the sensor device 200 according to the first embodiment of the present technology. a in this diagram illustrates a cross-sectional view of the in-probe substrate 321 acquired when it is seen from the upper side (the Y-axis direction) of the sensor device 200. b in this diagram illustrates a cross-sectional view of the in-probe substrate 321 acquired when it is seen from a front face (the Z-axis direction) of the sensor device 200. c in this diagram illustrates the shape of wirings of the in-probe substrate 321 acquired when it is seen from a lateral side (the X-axis direction) of the sensor device 200. In an in-probe substrate illustrated in c in this drawing, the shape of a wiring layer of a front layer thereof is represented as a pattern to which colors are applied, and vias connected to the wiring layer of the front layer and the shape of a wiring layer of an inner layer are denoted using dotted lines. The number of antennas is three.

Figure 80:
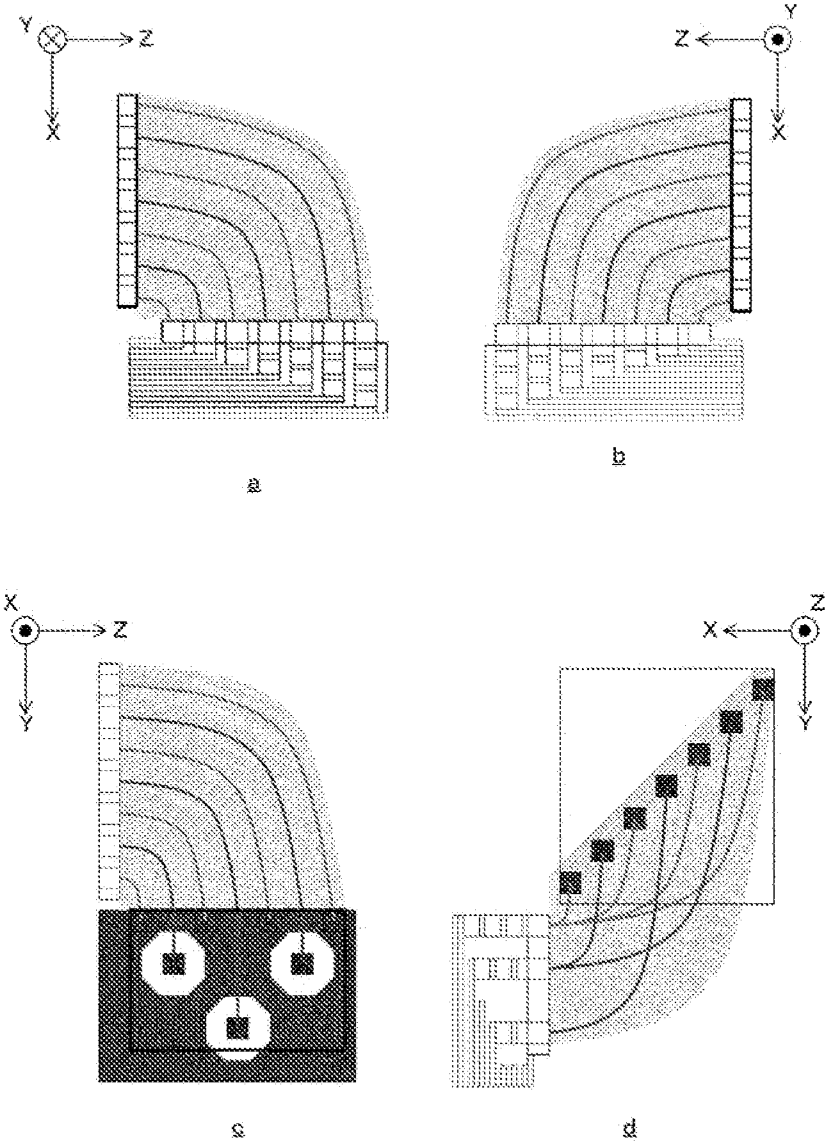
FIG. 80 is an example of a detailed diagram of a connection portion according to the first embodiment of the present technology.

FIG. 80 is an example of a detailed diagram of the transmission line connecting unit included in the sensor device 200 according to the first embodiment of the present technology. a in this diagram is a diagram of the transmission line connecting unit acquired when the sensor device 200 is seen from the upper side in the positive direction of the Y axis. Below this diagram, a cross-sectional view acquired when a connector 323 connecting the transmission line connecting unit and the in-probe substrate 321 is seen from the upper side and a cross-sectional view acquired when the in-probe substrate 321 is seen from the upper side are illustrated. On a left side of this diagram, a cross-sectional view acquired when a connector 314 connecting the transmission line connecting unit and the measurement unit substrate 311 is seen from the upper side is illustrated. b in this diagram is a diagram of the transmission line connecting unit acquired when the sensor device 200 is seen from the lower side in the negative direction of the Y axis. On a lower side of this diagram, a cross-sectional view acquired when a connector 323 connecting the transmission line connecting unit and the in-probe substrate 321 is seen from the lower side and a cross-sectional view acquired when the in-probe substrate 321 is seen from the lower side are illustrated. On a right side of this diagram, a cross-sectional view acquired when the connector 314 connecting the transmission line connecting unit and the measurement unit substrate 311 is seen from the lower side is illustrated. c in this diagram is a diagram of the transmission line connecting unit acquired when the sensor device 200 is seen from a lateral side in the positive direction of the X axis. On a lower side of this diagram, a plan view acquired when the connector 323 connecting the transmission line connecting unit and the in-probe substrate 321 is seen from a lateral side in the positive direction of the X axis is illustrated. On the left side of this diagram, a cross-sectional view acquired when the connector 314 connecting the transmission line connecting unit and the measurement unit substrate 311 is seen from a lateral side is illustrated.

d in this diagram is a diagram of the transmission line connecting unit and the connector 314 connecting the transmission line connecting unit and the measurement unit substrate 311 acquired when the sensor device 200 is seen from a front face rear side in the negative direction of the Z axis. On a lower side of this diagram, a cross-sectional view acquired when the connector 323 connecting the transmission line connecting unit and the in-probe substrate 321 is seen from a front face rear side in the negative direction of the Z axis and a cross-sectional view of a part connected to the connector 323 acquired when the in-probe substrate 321 is seen from the front face rear side in the negative direction of the Z axis are illustrated.

As illustrated in a to d in this diagram, transmission lines included in two substrates (the measurement unit substrate 311 and the in-probe substrate 321) that are orthogonally disposed are connected using a transmission line connecting unit that has flexibility higher than the measurement unit substrate 311 and the in-probe substrate 321 and includes a plurality of transmission lines.

Figure 81:
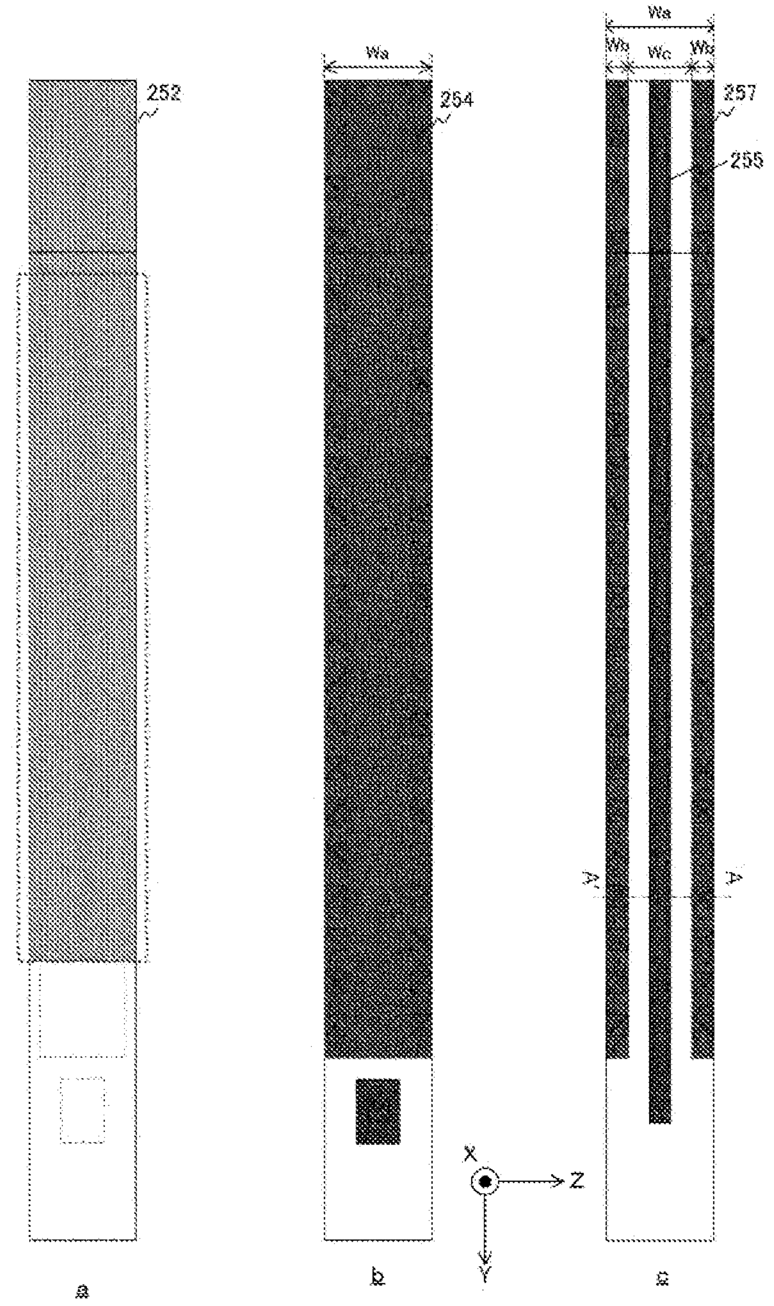
FIG. 81 is an example of a plan view of a first layer to a third layer of the inside of an in-probe substrate according to the first embodiment of the present technology.
Figure 82:
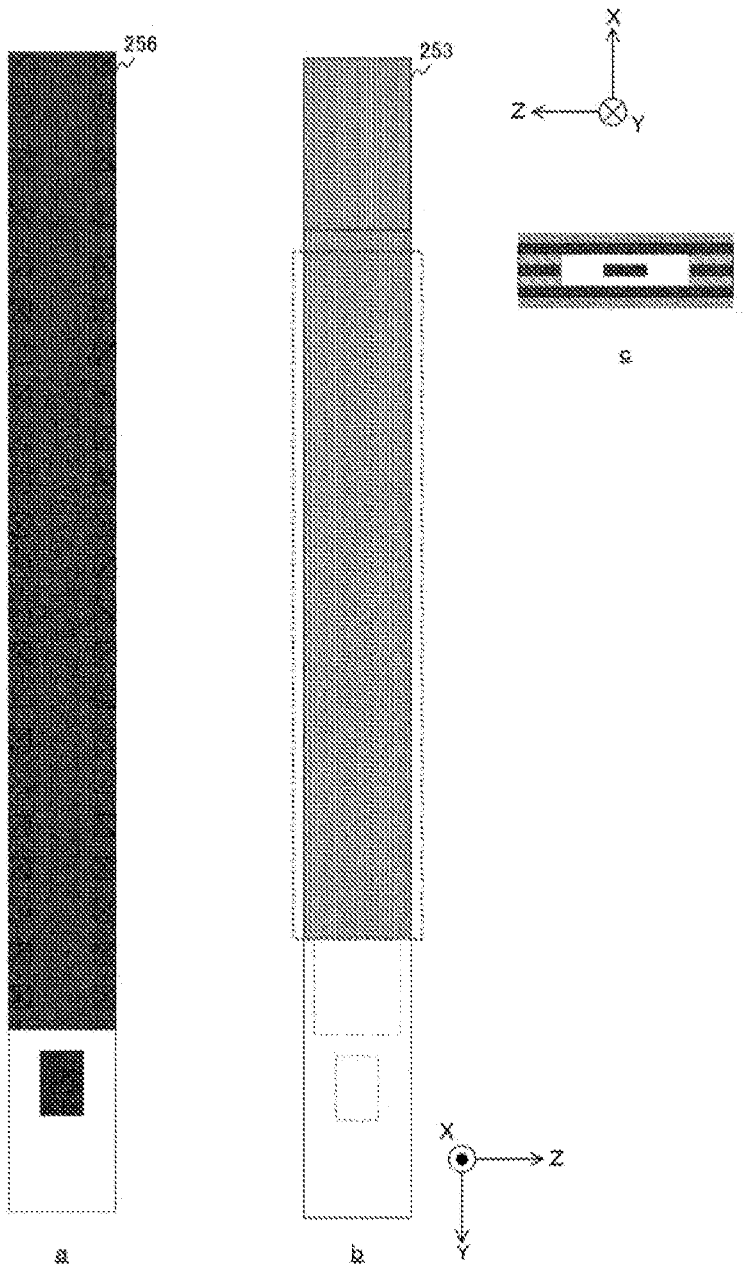
FIG. 82 is an example of a plan view of a fourth layer and a fifth layer of the in-probe substrate and a cross-sectional view of the in-probe substrate in the first embodiment of the present technology.

FIGS. 81 and 82 illustrate an example of a planar shape of the in-probe substrate 321 according to the first embodiment of the present technology. The example illustrated in FIGS. 81 and 82 illustrates a planar shape of the in-probe substrate 321 including one antenna in which a transmission line for the antenna includes a total of three wiring layers formed from one signal line layer and two shield layers having this signal line layer interposed therebetween. In addition, the example illustrated in FIGS. 81 and 82 illustrates an example in which a shield wiring is disposed on a lateral side of a signal line 255 using a part of the same wiring layer as that of the signal line 255. a in FIG. 81 illustrates a planar shape of a solder resist 252 and an electromagnetic wave absorbent material 251 disposed on an outer side of the first wiring layer. The solder resist 252 is a pattern to which a color is applied, and an outer shape of the electromagnetic wave absorbent material 251 is denoted by dotted lines. b in FIG. 81 illustrates a planar shape of the first wiring layer (a shield layer 254 and a radiation element). c in FIG. 81 illustrates a second wiring layer (a signal line) and shield wirings (conductors 257) disposed on both sides of the signal line 255 using a part of the second wiring layer. A symbol of a square with diagonal lines thereof joining using segments disposed in the shield wiring 257 represents a via. Particularly in c in FIG. 81, a via connecting a shield layer 254 and the shield wiring (a conductor 257) and a via connecting the shield wiring and a shield layer 256 to be described below are illustrated on the pattern of the shield wiring 257. In this drawing, Wa represents a width of the in-probe substrate 321. In addition, Wb represents a width of the shield wiring, and We represents a gap between shield wiring ends.

a in FIG. 82 illustrates a planar shape of a third wiring layer (a shield layer 256 and a radiation element). b in FIG. 82 illustrates a planar shape of a solder resist 253 and an electromagnetic wave absorbent material 251 that are disposed on an outer side of a third wiring layer. The solder resist 253 is a pattern to which a color is applied, and an outer shape of the electromagnetic wave absorbent material 251 is denoted by dotted lines. c in FIG. 82 is a cross-sectional view of an in-probe substrate 321 taken along line A-A' illustrated in c in FIG. 81.

In the cross-sectional view of c in FIG. 82, a solder resist 252 and a first wiring layer (a shield layer 254) are disposed in order from the lower side of the sheet surface, and a signal line 255 and shield wirings 257 of both sides thereof are disposed thereon using a second wiring layer. Thereon, a shield layer 256 and a solder resist 253 are disposed. In an area in which a transmission line of the in-probe substrate 321 is formed, an electromagnetic wave absorbent material 251 (not illustrated) is disposed in the periphery of this cross-section.

Figure 83:
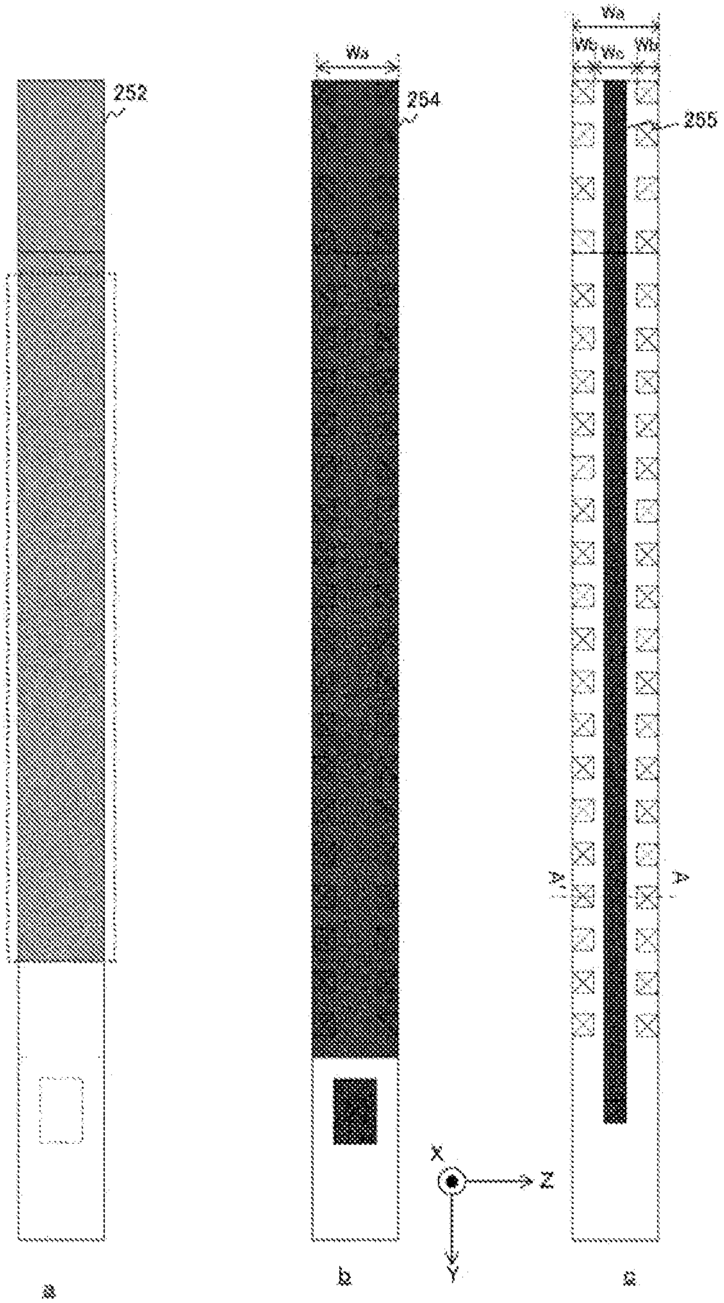
FIG. 83 is an example of a plan view of a first layer to a third layer of the inside of an in-probe substrate in which no shield wiring is present in the first embodiment of the present technology.
Figure 84:
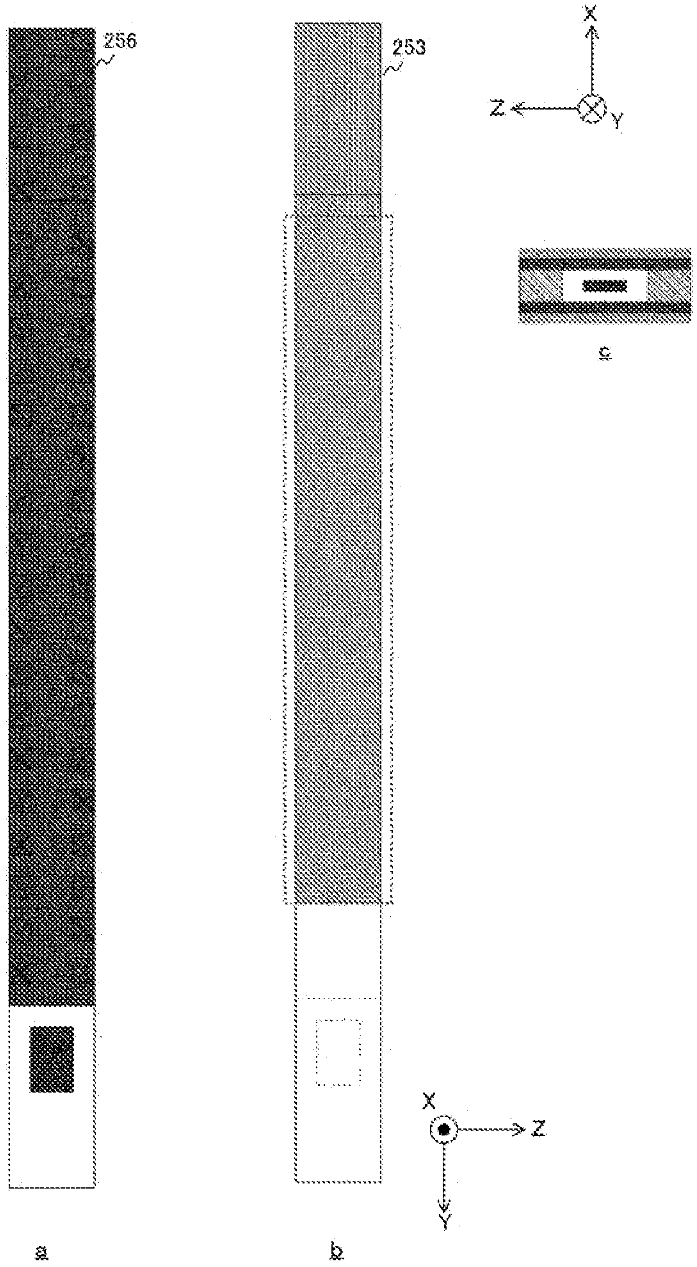
FIG. 84 is an example of a plan view of a fourth layer and a fifth layer of the inside of an in-probe substrate in which no shield wiring is present and a cross-sectional view of the substrate in the first embodiment of the present technology.

FIGS. 83 and 84 illustrate another example of a planar shape of the in-probe substrate 321 according to the first embodiment of the present technology. The example illustrated in FIGS. 83 and 84 illustrates an in-probe substrate 321 including one antenna in which a transmission line for the antenna is formed from a total of three wiring layers formed from one signal line layer and two shield layers having this signal line layer interposed therebetween. In addition, the example illustrated in FIGS. 83 and 84 illustrates an example in which vias that pass a lateral side of a signal line 255 from a shield layer 256 disposed on the upper side of the signal line 255 and reach a shield layer 254 disposed on the lower side of the signal line 255 are used, and, by disposing these vias along the signal line 255 in a column shape, the lateral side of the signal line 255 is shielded. c in FIG. 83 represents a column of vias for this shield. In this drawing, symbols of squares with diagonal lines thereof joining using segments that are disposed on both sides of the signal line 255 represent vias. Such vias to which no color is applied in this drawing are not formed in a second wiring layer that is the same layer as that of the signal line 255 and are represented to be vias that pass a lateral side of the signal line 255 from an upper layer of the signal line 255 and extends to a lower layer of the signal line 255. The planar shapes illustrated in FIGS. 83 and 84 other than c in FIG. 83 are similar to those illustrated in FIGS. 81 and 82, and thus description thereof will be omitted. In addition, c in FIG. 84 is a cross-sectional view of the in-probe substrate 321 taken along line A-A' illustrated in c in FIG. 83. Wa represented in FIG. 83 represents a width of the in-probe substrate 321. In addition, Wb represents a width of a shield via column, and We represents a gap between via column ends.

Next, effects brought by the structure illustrated in c in FIG. 83 will be described. In the case of a structure in which the lateral side of the signal line 255 is shielded using the shield wiring illustrated in c in FIG. 81, the signal line 255 and the shield wiring are formed using the same wiring layer (a second wiring layer). For this reason, when a pattern of the signal line 255 and a pattern of the shield wiring 257 are formed by processing the second wiring layer, a gap between the signal line 255 and the shield wiring cannot be processed to be equal to or smaller than a minimum processing dimension of a pattern forming device. At least a distance corresponding to a minimum processing dimension of the pattern forming device needs to be provided between them. In contrast to this, in the case of a structure in which the lateral side of the signal line 255 is shielded using a column of vias for shielding illustrated in c in FIG. 83, the signal line 255 and vias for shielding that pass through the lateral side of the signal line 255 from an upper layer of the signal line 255 and extend to a lower layer of the signal line 255 are formed using different wiring layers. In other words, the pattern of the signal line 255 is independently formed using a pattern forming device. The vias for shielding are independently formed using a pattern forming device in an upper layer of the signal line 255. For this reason, a distance between the signal line 255 and the via passing through the lateral side of the signal line 255 can be set to an arbitrary value when the layout of such a pattern is designed. In accordance with this, in the case of the structure illustrated in c in FIG. 83, a distance between the signal line 255 and the column of the vias for shielding (in the case illustrated in FIG. 81, the shield wiring) can be configured to be smaller than that of the structure illustrated in c in FIG. 81. As a result, there is an effect of the width of the in-probe substrate 321 illustrated in FIGS. 83 and 84 being able to be configured smaller than the width of the in-probe substrate 321 illustrated in FIGS. 81 and 82. In addition, in a case in which the width of the in-probe substrate can be configured to be small, the cross-section of a probe casing housing this can be configured to be small, and, in accordance with this, there is also an effect of being able to accurately measure moisture. This will be described below in detail.

Figure 85:
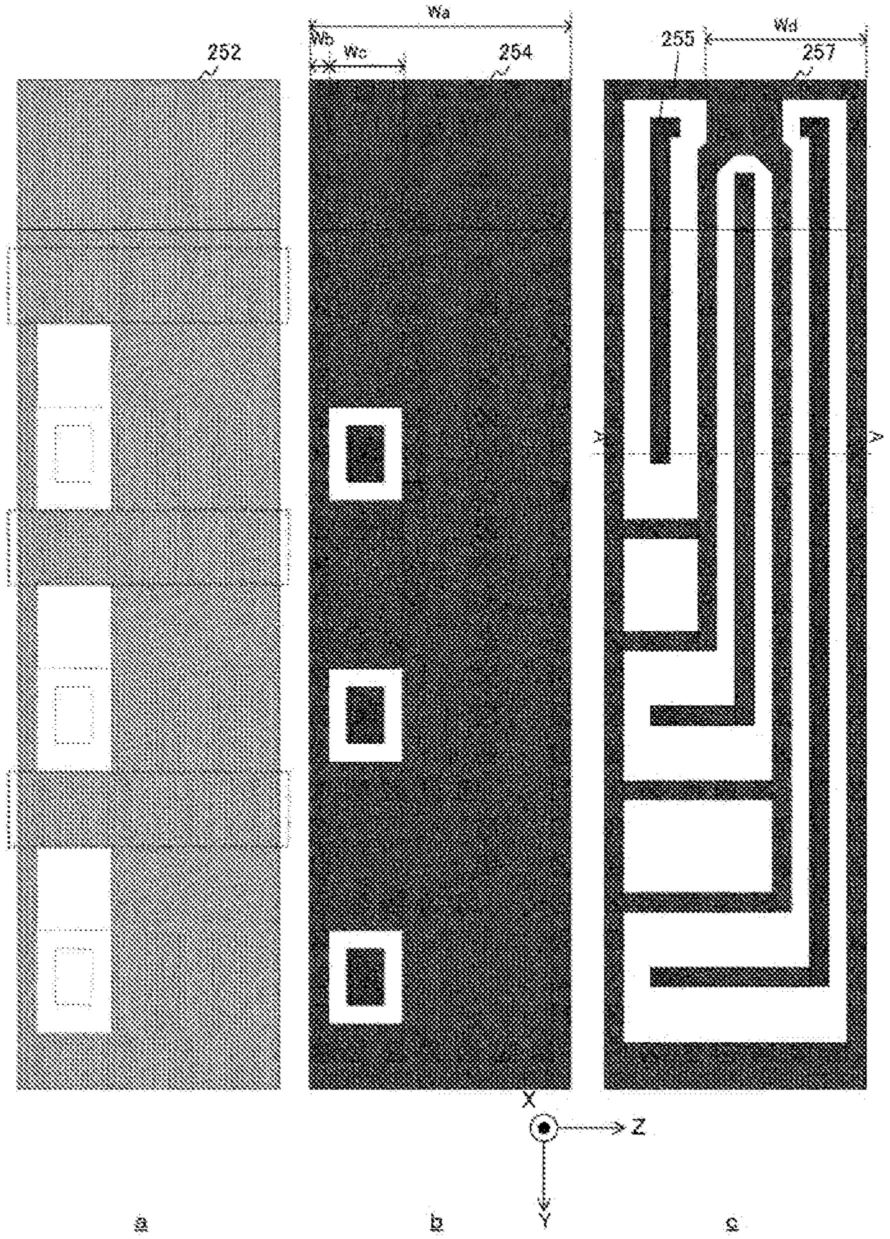
FIG. 85 is an example of a plan view of a first layer to a third layer of the inside of an in-probe substrate in which the number of antennas is three in the first embodiment of the present technology.
Figure 86:
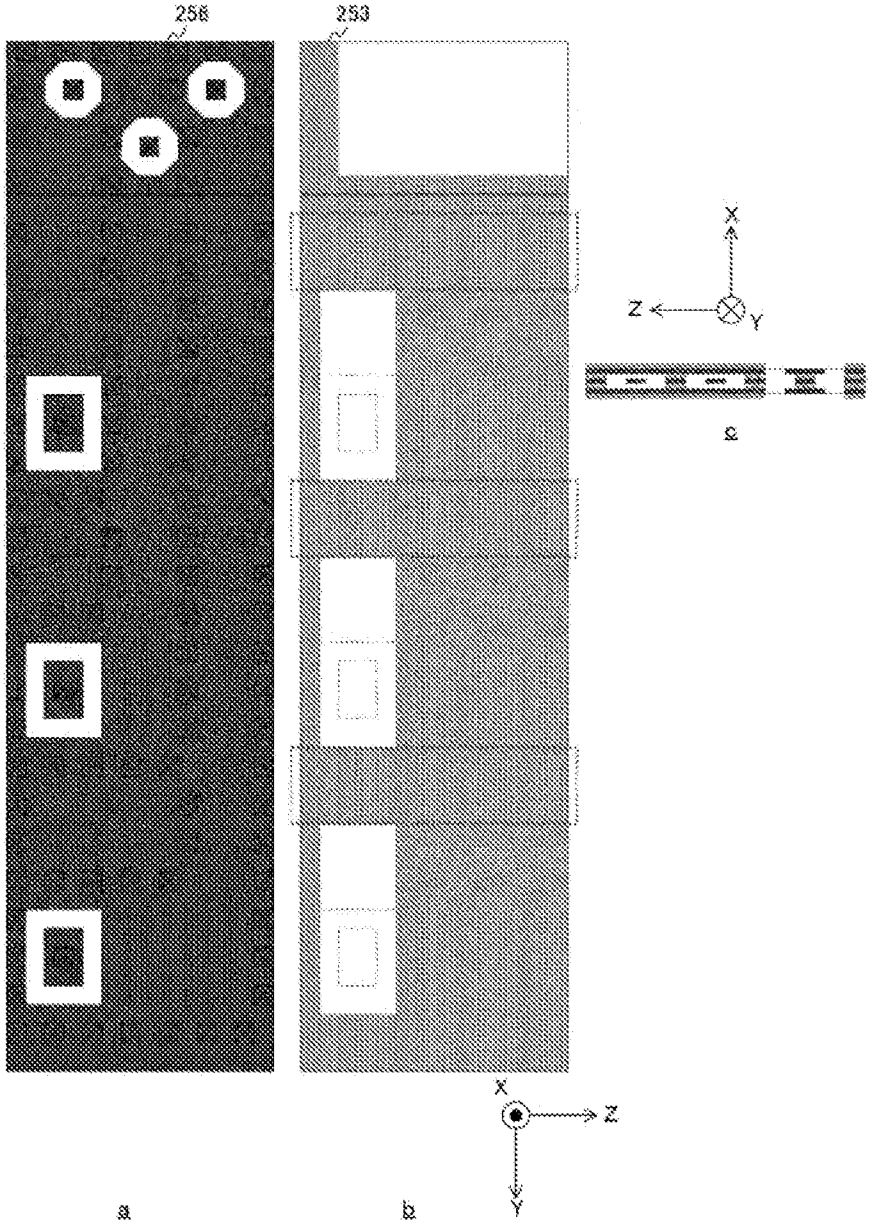
FIG. 86 is an example of a plan view of a fourth layer and a fifth layer of the inside of an in-probe substrate in which the number of antennas is three and a cross-sectional view of the substrate in the first embodiment of the present technology.

FIGS. 85 and 86 illustrate yet another example of the planar shape of the in-probe substrate 321 according to the first embodiment of the present technology. The example illustrated in FIGS. 85 and 86 illustrates an in-probe substrate 321 including n (for example, n=3) antennas in which a transmission line for the antenna includes a total of three wiring layers formed from one signal line layer and two shield layers having this signal line layer interposed therebetween. In addition, the example illustrated in FIGS. 85 and 86 illustrates an example in which the lateral side of the signal line 255 is shielded using a part of the same wiring layer as that of the signal line 255. The roles of layers illustrated in FIGS. 85 and 86 are similar to those illustrated in FIGS. 81 and 82, and thus description thereof will be omitted.

In b in FIG. 85, a shield layer 254 is formed using a part of a first wiring layer, and three radiation elements included in three antennas are formed using the other part of the first wiring layer. Similar to c in FIG. 81, c in FIG. 85 illustrates an example in which a shield wiring is disposed on a lateral side of a signal line 255 using a part of the same wiring layer as that of the signal line 255. In c in FIG. 85, three signal lines 255 used for connection to three radiation elements illustrated in b in FIG. 85 are formed using a part of a second wiring layer. In addition, in order to shield lateral sides of these three signal lines 255, between these three signal lines and on the outer sides thereof, a total of four shield wirings 257 are formed using a second wiring layer that is the same as that of the three signal lines 255. In addition, c in FIG. 86 is a cross-sectional view of the in-probe substrate 321 taken along line A-A' illustrated in c in FIG. 85. Wa illustrated in FIG. 85 represents a width of the in-probe substrate 321. In addition, Wb represents a width of the shield layer, and We represents a gap between shield layer ends. Wd represents a width of two transmission lines and three shield wirings.

Figure 87:
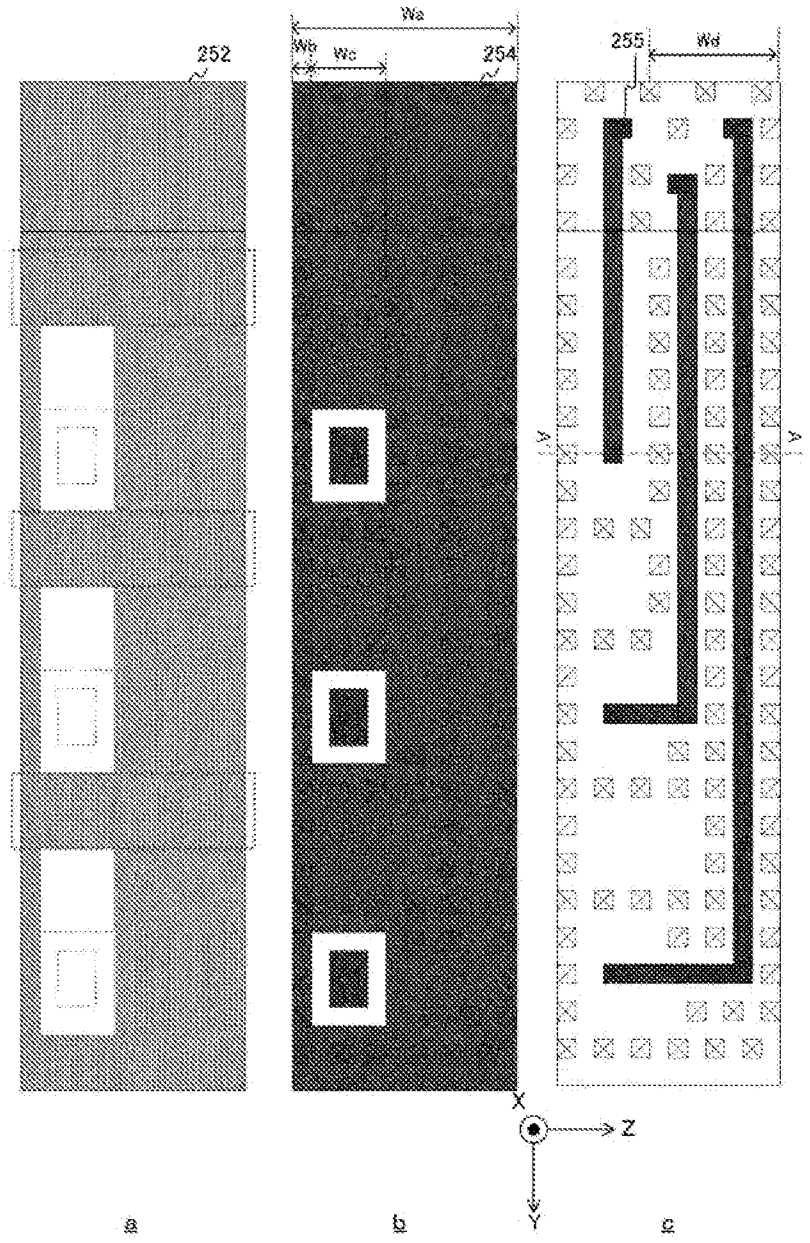
FIG. 87 is an example of a plan view of a first layer to a third layer of the inside of an in-probe substrate in which no shield wiring is present, and the number of antennas is three in the first embodiment of the present technology.
Figure 88:
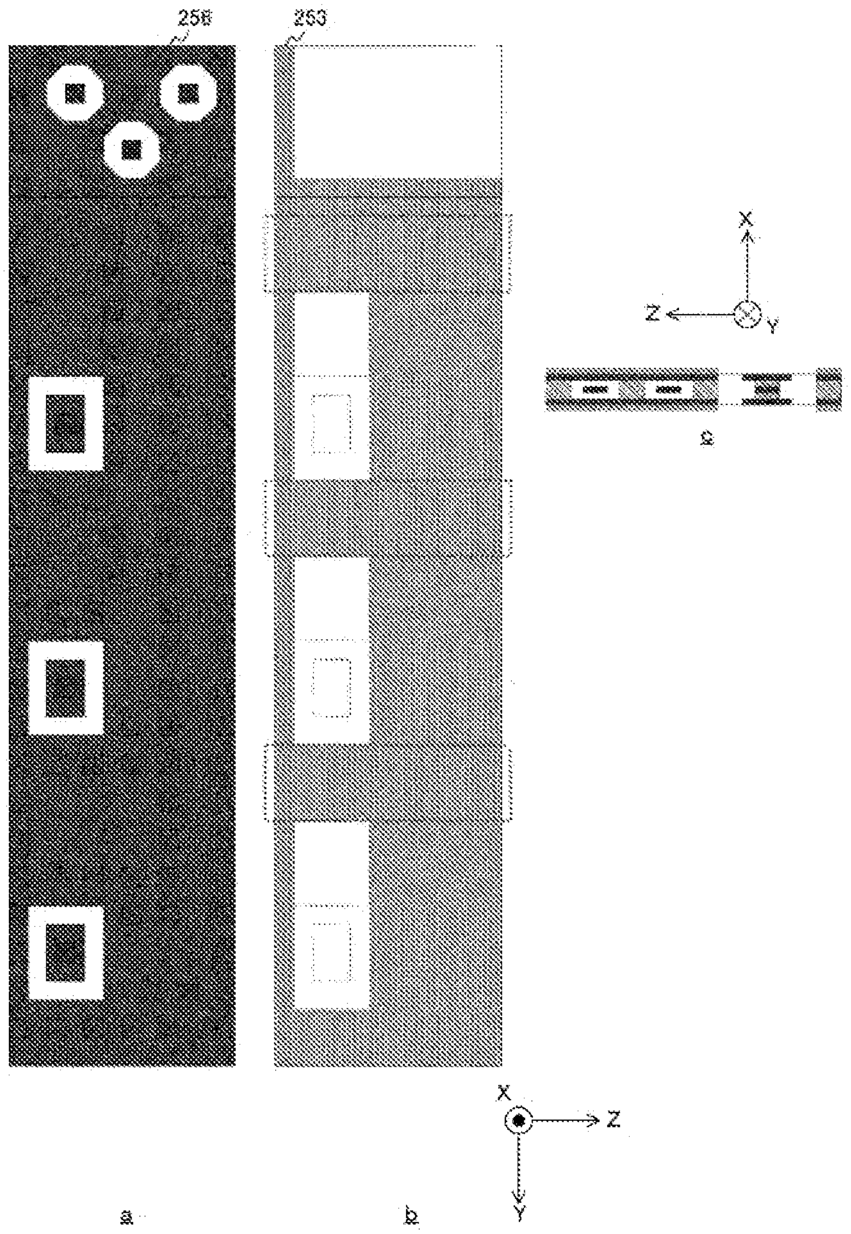
FIG. 88 is an example of a plan view of a fourth layer and a fifth layer of an in-probe substrate in which no shield wiring is present, and the number of antennas is three ana a cross-sectional view of the substrate in the first embodiment of the present technology.

FIGS. 87 and 88 illustrate yet another example of a planar shape of the in-probe substrate 321 according to the first embodiment of the present technology. The example illustrated in FIGS. 87 and 88 illustrates an in-probe substrate 321 including n (for example, n=3) antennas in which a transmission line for the antenna includes a total of three wiring layers formed from one signal line layer and two shield layers having this signal line layer interposed therebetween. In addition, the example illustrated in FIGS. 87 and 88 illustrates an example in which vias that pass a lateral side of a signal line 255 from a shield layer 256 disposed on the upper side of the signal line 255 and reach a shield layer 254 disposed on the lower side of the signal line 255 are used, and, by disposing these vias along the signal line 255 in a column form, the lateral side of the signal line 255 is shielded. In b in FIG. 87, a shield layer 254 is formed using a part of a first wiring layer, and three radiation elements included in three antennas are formed using the other part of the first wiring layer. Similar to c in FIG. 83, c in FIG. 87 illustrates an example in which a lateral side of a signal line 255 is shielded using a column of vias for shielding. In c in FIG. 87, three signal lines 255 used for connection to three radiation elements illustrated in b in FIG. 87 are formed using a part of a second wiring layer. In addition, in order to shield lateral sides of these three signal lines 255, between these three signal lines and on the outer sides thereof, a column of vias for shielding that is a total of four columns is disposed.

In addition, c in FIG. 88 is a cross-sectional view of the in-probe substrate 321 taken along line A-A' illustrated in c in FIG. 87. Wa illustrated in FIG. 87 represents a width of the in-probe substrate 321. In addition, Wb represents a width of the shield layer, and We represents a gap between shield layer ends. Wd represents a width of two transmission lines and three shield via columns.

Next, effects brought by the structure illustrated in c in FIG. 87 will be described.

Similar to c in FIG. 83, patterns of the three signal lines 255 and a column of vias of four columns illustrated in c in FIG. 87 are separately (in other words, independently) formed. As a result, a distance between the three signal lines 255 and a column of vias of four columns illustrated in c in FIG. 87 can be configured to be smaller than a distance between the three signal lines 255 and the four shield wirings illustrated in c in FIG. 85. As a result, the width of the in-probe substrate 321 illustrated in FIGS. 87 and 88 is able to be configured smaller than the width of the in-probe substrate 321 illustrated in FIGS. 85 and 86. In addition, in a case in which the width of the in-probe substrate can be configured to be small, the cross-section of a probe casing housing this can be configured to be small, and, in accordance with this, there is also an effect of being able to accurately measure moisture. This will be described below in detail.

Figure 89:
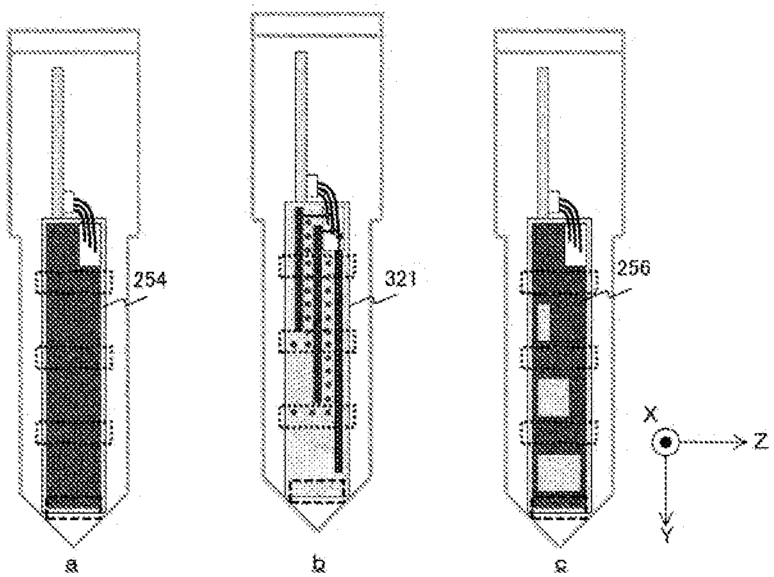
FIG. 89 is a diagram illustrating shielding according to a via column according to the first embodiment of the present technology.

FIG. 89 is a diagram illustrating shielding using a via column according to the first embodiment of the present technology. a in this diagram illustrates a first wiring layer, and b in this diagram illustrates a second wiring layer. c in this diagram illustrates a third wiring layer. In the second wiring layer, shielding may be performed by disposing a via column on the periphery of the signal line 255 without disposing a shield wiring. A white circle represents a via. In accordance with such vias, electric coupling between transmission lines decreases, and thus unintended radiation from an antenna opening part (a radiation element) can be inhibited, and moisture can be measured with high accuracy.

In addition, a gap between vias that are adjacent to each other is preferably 1/10 of the wavelength of the center frequency of an electromagnetic wave or less and is more preferably 1/10 of the wavelength of a maximum frequency or less. For example, when a measurement frequency band is 1 to 9 GHz, the center frequency is 5 GHz, thus a gap between vias is preferably 6 mm or less, and the maximum frequency is 9 GHz, and thus the gap is more preferably 3.3. mm or less.

Figure 90:
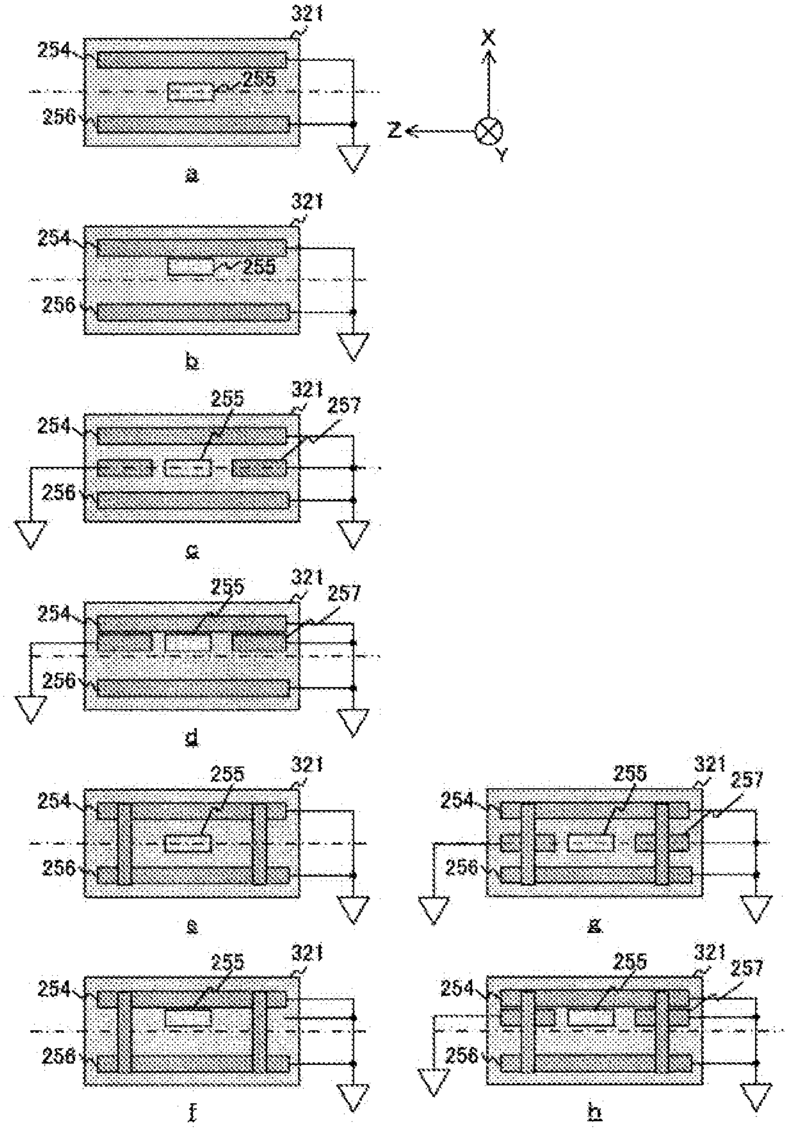
FIG. 90 is a diagram illustrating an example of a strip line according to the first embodiment of the present technology.

FIG. 90 is a diagram illustrating an example of a strip line according to the first embodiment of the present technology. For example, this diagram illustrates a cross-sectional view of a strip line formed in an in-probe wiring substrate. As illustrated in a in this diagram, the strip line may be a strip line that is vertically symmetrical in which shield layers 254 and 256 are configured as upper and lower faces. In addition, as illustrated in b in this diagram, the strip line may be a vertically asymmetrical strip line, in other words, a strip line in which an electronic substrate including three or more wiring layers is used, and wiring layers in which a distance from a layer forming a signal line 255 to a layer forming a shield layer 254 is different from a distance from the layer forming the signal line 255 to a layer forming a shield layer 254 are used. As illustrated in c in this diagram, the strip line may be a strip line that is vertically symmetrical in which shield wirings are disposed on lateral sides and both sides of a signal line 255. As illustrated in d in this drawing, the strip line may be a strip line that is vertically asymmetrical in which a shield wiring is disposed on a lateral side of a signal line 255.

As illustrated in e in this diagram, the strip line may be a post wall-attached strip line that is vertically symmetrical. Here, the post wall represents a plurality of via columns disposed approximately in parallel with a transmission line. In accordance with arrangement of the post wall, radiation from a substrate end to the outside of the substrate and electric coupling between lines that are adjacent to each other decrease. As illustrated in f in this diagram, the strip line may be a post wall-attached strip line that is vertically asymmetrical. As illustrated in g in this drawing, the strip line may be a vertically-symmetrical strip line including both a post wall and a shield wiring. As illustrated in h in this diagram, the strip line may be a vertically-symmetrical strip line including both a post wall and a shield wiring.

In addition, although the in-probe substrate 321 is typically a glass epoxy substrate using FR-4 as a base material, it may be a substrate using modified-PolyPhenyleneEther (m-PPE), PolyteTraFluoroEthylene (PTFE), or the like having superior high-frequency characteristics. In addition, the in-probe substrate 321 may be a substrate using ceramics having a high dielectric constant or may be a build-up substrate acquired by combining a plurality of kinds of the substrates described above. Furthermore, the in-probe substrate may be a flexible substrate using polyimide, polyester, polyethylene terephthalate, or the like having flexibility or may be a rigid flexible substrate acquired by combining a rigid substrate and a flexible substrate.

Figure 91:
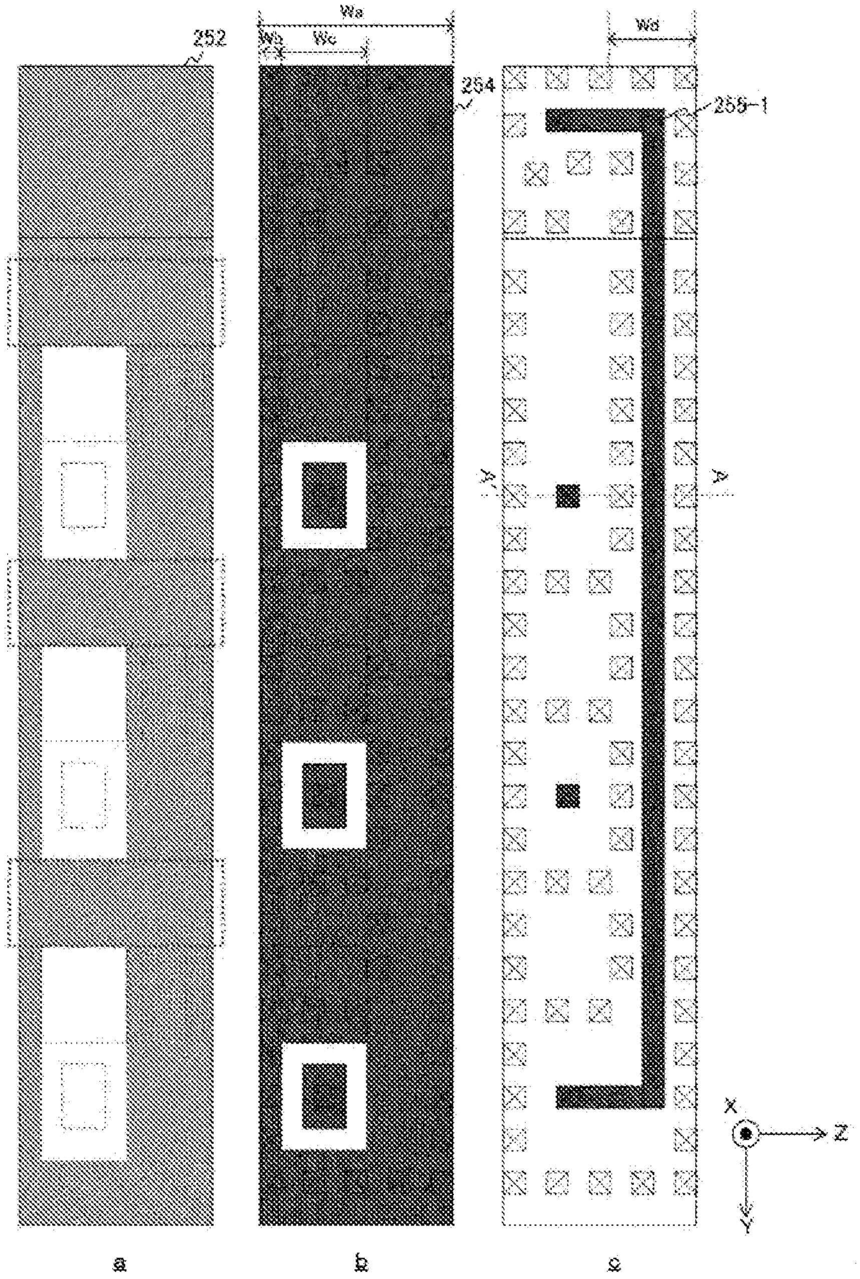
FIG. 91 is an example of a plan view of a first layer to a third layer among seven layers of the inside of an in-probe substrate according to the first embodiment of the present technology.
Figure 92:
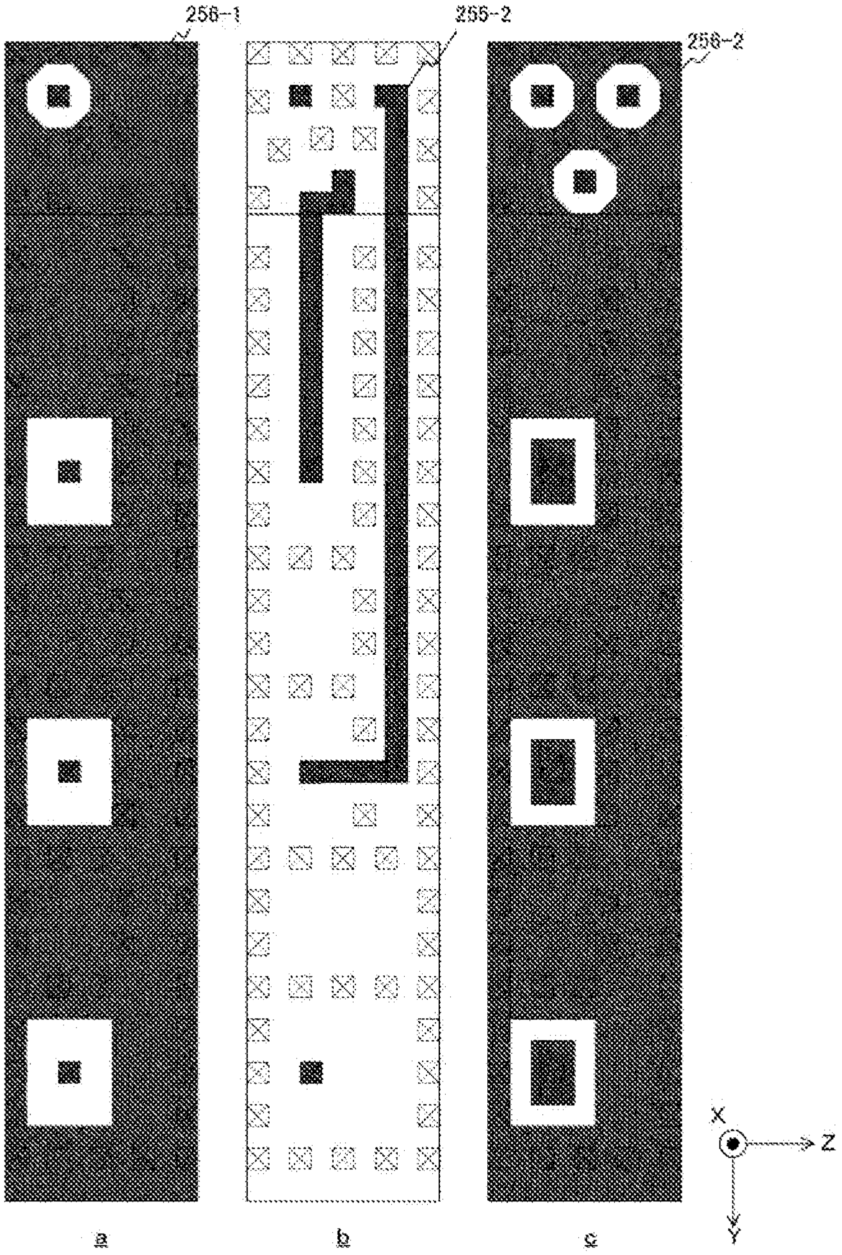
FIG. 92 is an example of a plan view of a fourth layer to a sixth layer among seven layers of the inside of an in-probe substrate according to the first embodiment of the present technology.
Figure 93:
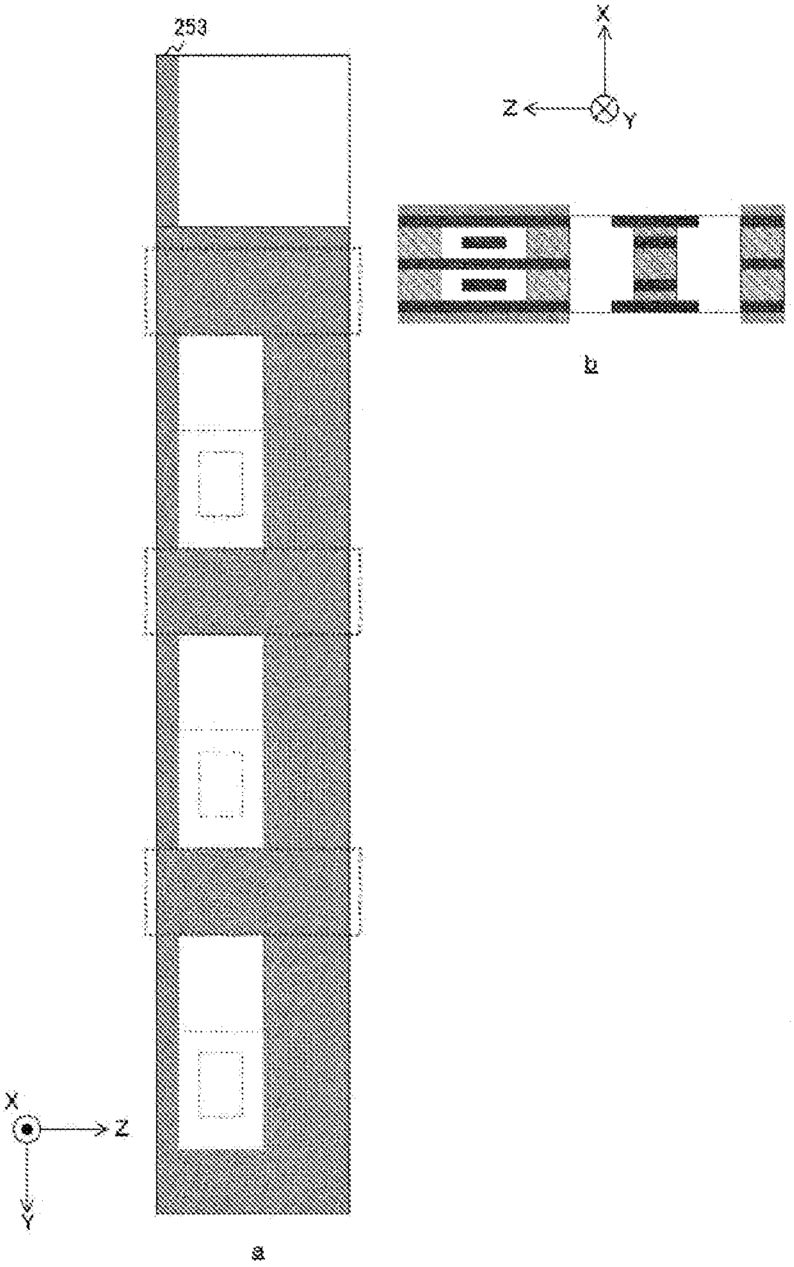
FIG. 93 is an example of a plan view of the seventh layer of the inside an in-probe substrate and a cross-sectional view of the substrate in the first embodiment of the present technology.

FIGS. 91 to 93 illustrate yet another example of the planar shape of an in-probe substrate 321 according to the first embodiment of the present technology. The example illustrated in FIGS. 91 to 93 illustrates an example in which n (for example, n=3) antennas are included, and n transmission lines connected to the n antennas are formed in the in-probe substrate 321 including a total of (2n−1) wiring layers formed from (n−1) signal line layers and n shield layers having the signal line layers interposed therebetween. In addition, the example illustrated in FIGS. 91 to 93 is an example in which vias passing through a lateral side of a signal line 255 from a shield layer disposed on the upper side of the signal line 255 and reaching a shield layer disposed on the lower side of the signal line 255 are used, and the lateral side of the signal line 255 is shielded by disposing these vias along the signal line 255 in a column shape.

In b in FIG. 91, a shield layer 254 is formed using a part of a first wiring layer, and three radiation elements 259 included in three antennas are formed using the other part of the first wiring layer. In FIG. 91, Wa represents a width of the in-probe substrate 321. In addition, Wb represents a width of the shield layer, and We represents a gap between shield layer ends. Wd represents a width of one transmission line and two shield via columns.

In the example illustrated in FIGS. 91 to 93, three signal lines respectively connected to three antennas are formed using two signal line layers (second and fourth wiring layers) included in a substrate having five wiring layers.

In the second wiring layer illustrated in c in FIG. 91, (1) among three radiation elements illustrated in b in FIG. 91, one signal line 255 used for connection to a first radiation element is formed.

(2) For connection with three radiation elements disposed on one front layer (a fifth wiring layer) with signal lines 255 for respective connection of three radiation elements 259 disposed on the other front layer (a first wiring layer) of the in-probe substrate 321 interposed therebetween, in a second wiring layer, for second and third radiation elements to which the signal line 255 is not connected, at positions located right below, vias used for connection to such radiation elements are formed.

(3) In order to shield the lateral side of the signal line 255 of (1) described above, columns of vias for shielding are disposed on both sides of this signal line.

(4) In order to densely connect the shield layer 254 formed using the wiring layer of the first layer to the shield layer 256 formed using wiring layers of third and fifth layers, a column of vias is also disposed near the outer edge of these shield layers.

On the other hand, in the fourth wiring layer illustrated in b in FIG. 92, (1) among the three radiation elements illustrated in b in FIG. 91, for the second and third radiation elements to which the signal line 255 is not connected, two signal lines 255 used for connection thereto are formed in the second wiring layer.

(2) For connection with three radiation elements disposed in a front layer of one side (a fifth wiring layer) with signal lines 255 used for respective connection to three radiation elements 259 disposed on a front layer (a first wiring layer) of the other side of the in-probe substrate 321 interposed therebetween, in the fourth wiring layer, for the first radiation element to which no signal line 255 is connected, a via used for connection with this radiation element is formed at a position right below the first radiation element.

(3) In order to shield the lateral side of the signal line 255 of (1) described above, columns of vias for shielding are disposed on both sides of such a signal line.

(4) In order to densely connecting the shield layer 254 formed using the first wiring layer to the shield layer 256 formed using the wiring layers of the third layer and the fifth layer, columns of vias are also disposed near outer edges of these shield layers.

In addition, b in FIG. 93 is a cross-sectional view of the in-probe substrate 321 taken along line A-A' illustrated in c in FIG. 91.

Next, effects brought by the structures illustrated in c in FIG. 91 and b in FIG. 92 will be described.

In the structures described in such diagrams, the lateral side of the signal line 255 is shielded using the via columns for shielding illustrated in c in FIG. 87, and thus an effect of decreasing the width of the in-probe substrate 321 is acquired. In the structure illustrated in c in FIG. 91 and b in FIG. 92, compared to the structure illustrated in c in FIG. 87, by using more signal line layers, the number of signal lines disposed in one signal line layer is decreased. In accordance with this structure, an effect of decreasing the width of the in-probe substrate 321 more than that of the structure illustrated in c in FIG. 87 is acquired.

Figure 94:
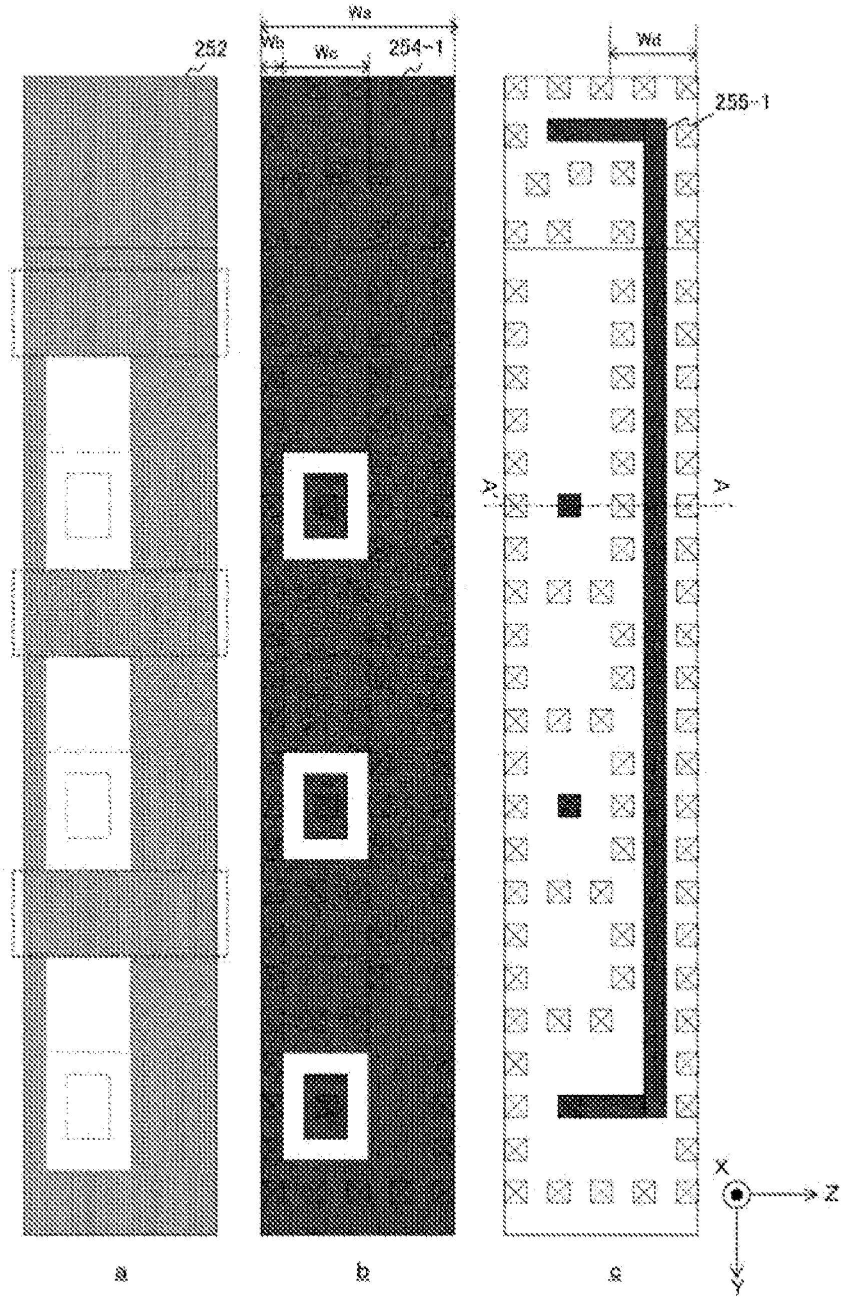
FIG. 94 is an example of a plan view of a first layer to a third layer among nine layers of the inside of an in-probe substrate according to the first embodiment of the present technology.
Figure 95:
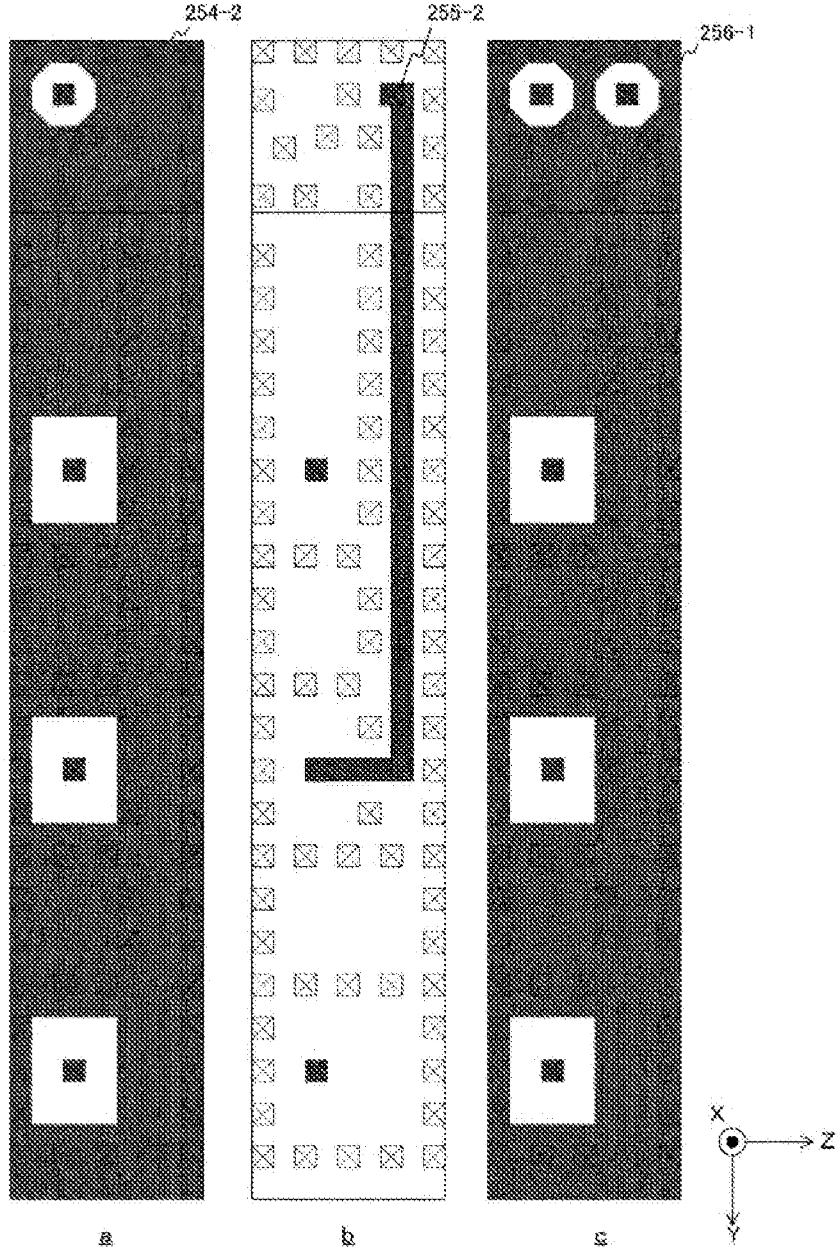
FIG. 95 is an example of a plan view of a fourth layer to a sixth layer among nine layers of the inside of an in-probe substrate according to the first embodiment of the present technology.
Figure 96:
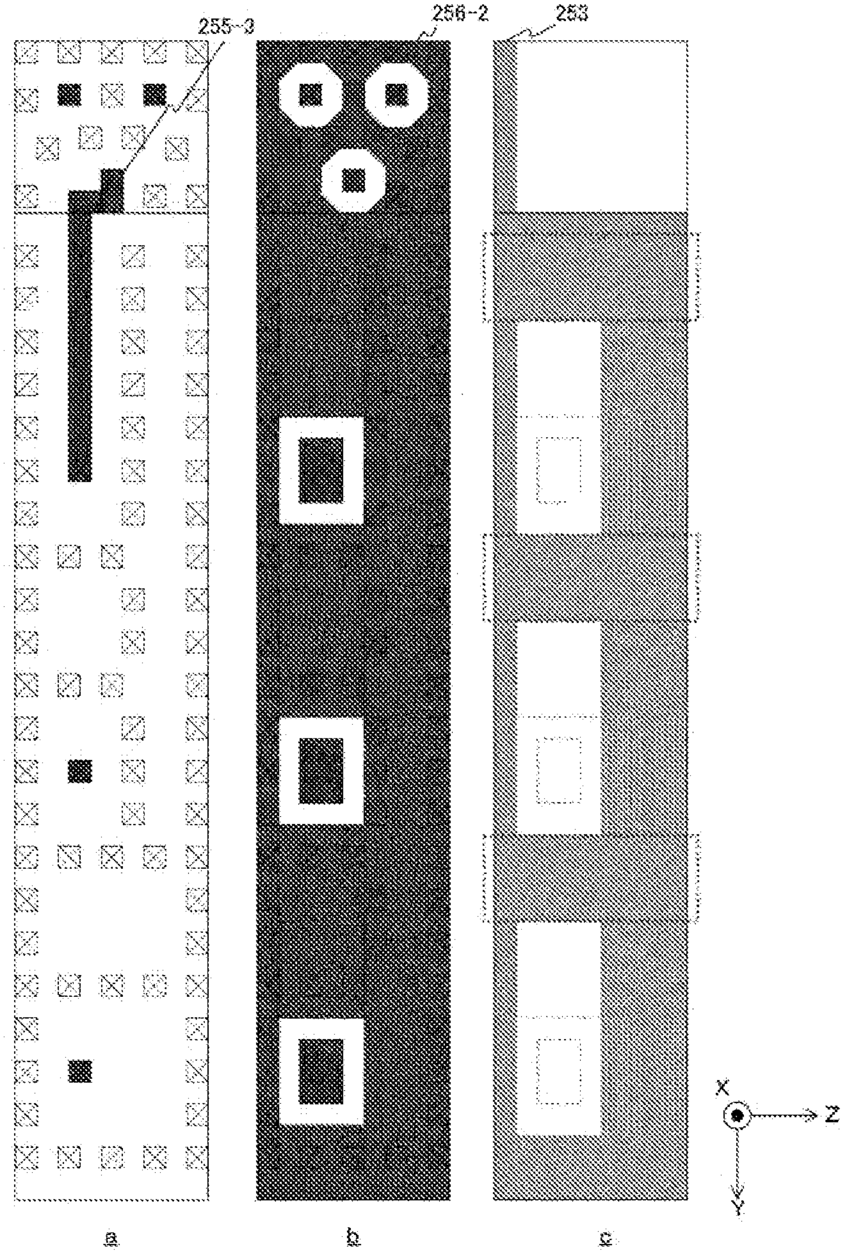
FIG. 96 is an example of a plan view of a seventh layer to a ninth layer among nine layers of the inside of an in-probe substrate according to the first embodiment of the present technology.

FIGS. 94 to 96 illustrate yet another example of the planar shape of an in-probe substrate 321 according to the first embodiment of the present technology. The example illustrated in FIGS. 94 to 96 illustrates an example in which n (for example, n=3) antennas are included, and n transmission lines connected to the n antennas are formed in the in-probe substrate 321 including a total of (2n+1) wiring layers formed from n signal line layers and (n+1) shield layers having the signal line layers interposed therebetween. In addition, the example illustrated in FIGS. 94 to 96 is an example in which vias passing through a lateral side of a signal line 255 from a shield layer disposed on the upper side of the signal line 255 and reaching a shield layer disposed on the lower side of the signal line 255 are used, and the lateral side of the signal line 255 is shielded by disposing these vias along the signal line 255 in a column shape.

In b in FIG. 94, a shield layer 254 is formed using a part of a first wiring layer, and three radiation elements 259 included in three antennas are formed using the other part of the first wiring layer.

In the example illustrated in FIGS. 94 to 96, three signal lines respectively connected to three antennas are formed using three signal line layers (second, fourth, and sixth wiring layers) included in a substrate having seven wiring layers. In FIG. 91, Wa represents a width of the in-probe substrate 321. In addition, Wb represents a width of the shield layer, and We represents a gap between shield layer ends. Wd represents a width of one transmission line and two shield via columns.

In the second wiring layer illustrated in c in FIG. 94, (1) among three radiation elements illustrated in b in FIG. 94, one signal line 255 used for connection to the first radiation element is formed.

(2) For connection with three radiation elements disposed on one front layer (a fifth wiring layer) with signal lines 255 for connection of three radiation elements disposed on the other front layer (a first wiring layer) of the in-probe substrate 321 interposed therebetween, in the second wiring layer, for second and third radiation elements to which the signal line 255 is not connected, at positions located right below, vias used for connection to such radiation elements are formed.

(3) In order to shield the lateral side of the signal line 255 of (1) described above, columns of vias for shielding are disposed on both sides of this signal line.

(4) In order to densely connect the shield layer formed using the wiring layer of the first layer to the shield layer formed using wiring layers of the third, fifth, and seventh layers, a column of vias is also disposed near the outer edge of these shield layers.

In the fourth wiring layer illustrated in b in FIG. 95, (1) among the three radiation elements illustrated in b in FIG. 94, one signal line 255 used for connection to the second radiation element is formed.

(2) For connection with three radiation elements disposed in a surface layer of one side (a fifth wiring layer) with signal lines 255 used for respective connection to three radiation elements disposed on a surface layer (a first wiring layer) of the other side of the in-probe substrate 321 interposed therebetween, in the fourth wiring layer, for the first and third radiation elements to which no signal line 255 is connected, vias used for connection with these radiation elements are formed at positions right below the first and third radiation elements.

(3) In order to shield the lateral side of the signal line 255 of (1) described above, columns of vias for shielding are disposed on both sides of such a signal line.

(4) In order to densely connecting the shield layer formed using the first wiring layer to the shield layer formed using the wiring layers of the third layer, the fifth layer, and the seventh layer, columns of vias are disposed also near outer edges of these shield layers.

In the sixth wiring layer illustrated in a in FIG. 96, (1) among three radiation elements illustrated in b in FIG. 94, one signal line 255 used for connection to a third radiation element is formed.

(2) For connection with three radiation elements disposed on one front layer (a fifth wiring layer) with signal lines 255 for connection of three radiation elements disposed on the other front layer (a first wiring layer) of the in-probe substrate 321 interposed therebetween, in the sixth wiring layer, for first and second radiation elements to which the signal line 255 is not connected, at positions located right below, vias used for connection to such radiation elements are formed.

(3) In order to shield the lateral side of the signal line 255 of (1) described above, columns of vias for shielding are disposed on both sides of this signal line.

(4) In order to densely connect the shield layer formed using the wiring layer of the first layer to the shield layer formed using wiring layers of third, fifth, and seventh layers, a column of vias is also disposed near the outer edge of these shield layers.

Figure 97:
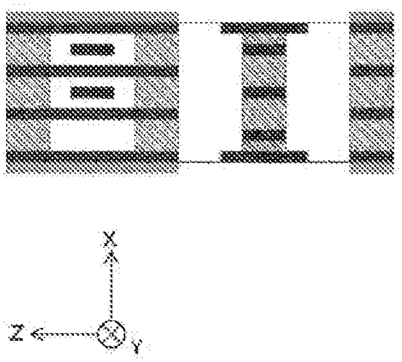
FIG. 97 is an example of a cross-sectional view of an in-probe substrate of a nine-layer structure according to the first embodiment of the present technology.

In addition, FIG. 97 is a cross-sectional view of the in-probe substrate 321 taken along line A-A' illustrated in c in FIG. 94.

Next, effects brought by the structure illustrated in c in FIG. 94, b in FIG. 95, and a in FIG. 96 will be described. In the structure described in such diagrams, the lateral side of the signal line 255 is shielded using the via columns for shielding illustrated in c in FIG. 87, and thus an effect of decreasing the width of the in-probe substrate 321 is acquired. In the structure illustrated in c in FIG. 94, b in FIG. 95, and a in FIG. 96, compared to the structure illustrated in c in FIG. 87, by using more signal line layers, the number of signal lines disposed in one signal line layer is decreased. In accordance with this structure, an effect of decreasing the width of the in-probe substrate 321 more than that of the structure illustrated in c in FIG. 87 is acquired.

In addition, the width of the in-probe substrate 321 illustrated in FIGS. 94 to 96 is the same as the width of the in-probe substrate 321 illustrated in FIGS. 91 to 93.

Figure 98:
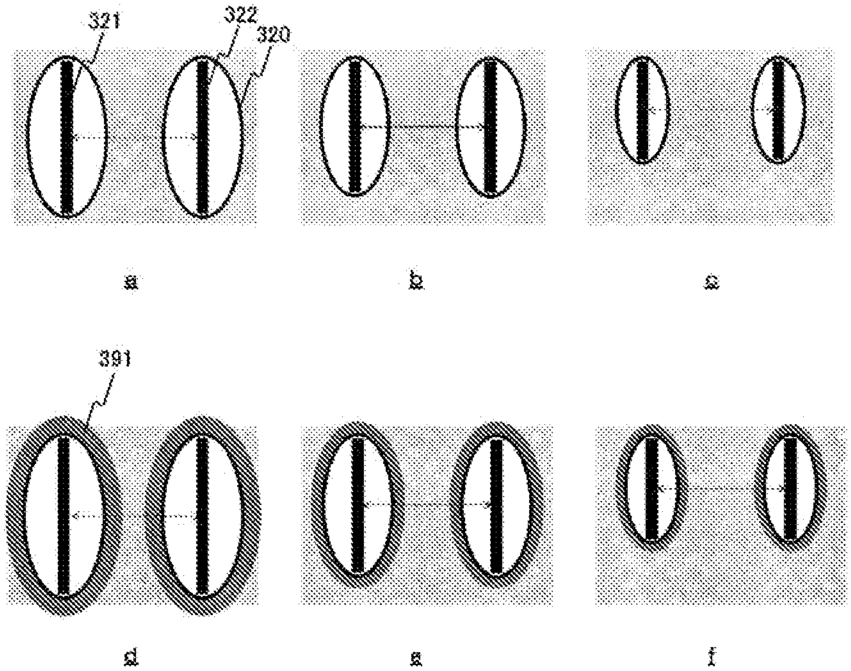
FIG. 98 is a diagram for describing influences of a width of an in-probe substrate and a cross-sectional area of the probe casing on measurement of an amount of moisture from two points of views in the first embodiment of the present technology.

FIG. 98 is a diagram for describing effects of the width of the in-probe substrate and the cross-sectional area of the probe casing on measurement of an amount of moisture in the first embodiment of the present technology from two points of views.

[First Point of View]

a, b, and c in this diagram are cross-sectional views of a transmission probe casing 320*a* and a reception probe casing 320*b* acquired when the sensor device 200 according to the first embodiment of the present technology is seen in the positive direction of the Y axis from the upper side thereof. In each of a, b, and c in this diagram, a rectangle on the left side represents a transmission probe substrate 321, and an oval disposed on the outer circumference thereof represents the transmission probe casing 320*a*. A rectangle on the right side represents a reception probe substrate 322, and an oval disposed on the outer circumference thereof represents the reception probe casing 320*b*. A white part inside the probe casing represents a space inside the probe casing. A part disposed outside the probe casing to which a color is applied represents soil. a, b, and c in this diagram are diagrams for describing, in a case in which (1) three types of transmission probe substrate 321 and reception probe substrate 322 having different widths are housed in a transmission probe casing 320*a* and a reception probe casing 320*b* of ovals of which a ratio between lengths of a major axis and a minor axis is 2:1, and (2), in these three types, the transmission probe substrate 321 and the reception probe substrate 322 are disposed such that distances therebetween are the same, (3) changes in the ratio of the area of soil in an area between the transmission probe substrate 321 and the reception probe substrate 322 according to the widths of the probe substrates of the three types. When a, b, and c in this diagram are compared with each other, the larger the width of the in-probe substrate, the lower the ratio of the area of soil in the area between the transmission probe substrate 321 and the reception probe substrate 322. In consideration of a time required for an electromagnetic wave to propagate from a transmission antenna to a reception antenna having a linear relation with an amount of moisture of soil, the moisture measuring system 100 according to the present invention acquires an amount of moisture of soil by measuring a propagation delay time of this electromagnetic wave. For this reason, in accordance with a decrease in the ratio of a soil area in an area between the transmission probe substrate 321 and the reception probe substrate 322, the relation between a propagation delay time of an electromagnetic wave and an amount of soil moisture described above deviates from the linear relation. In accordance with this, error included in a measurement result becomes large. In contrast to this, the smaller the width of the in-probe substrate, the higher the ratio of a soil area in an area between the transmission probe substrate 321 and the reception probe substrate 322. As a result, the relation between a propagation delay time of an electromagnetic wave and the amount of soil moisture described above becomes close to a linear relation, error included in a measurement result decreases, and the amount of moisture of soil can be accurately measured.

[Second Point of View]

d, e, and f in this diagram are diagrams acquired by adding destinations of movement of soil pushed in accordance with insertion of the transmission probe casing 320*a* and the reception probe casing 320*b* illustrated in a, b, and c in this diagram when these probe casings are inserted into the soil. In d, e, and f of this drawing, an area (reference numeral 391), to which a thick color is applied, added to the outer circumference of the probe casing represents an area to which soil pushed as a result of insertion of the probe casing moves and, in accordance with this, having the density of soil to be higher than that of the original soil that is a measurement target.

For an area to which soil has been pushed in accordance with insertion of a probe casing moves and in which the density of soil has increased, compared to d, e, and f in this drawing, the larger the width of the in-probe substrate, the larger the width of the area. As a result, the larger the width of the in-probe substrate, the higher the ratio of an area in which the density of soil has increased in the area between the transmission probe substrate 321 and the reception probe substrate 322. When the density of soil increases, a degree of easiness in penetration of moisture and the surface area of a grain boundary of the soil change, and the amount of moisture held by the soil changes. For this reason, the higher the ratio of the area in which the density of soil has increased, a result of measurement of an amount of moisture of soil deviates more greatly from the amount of moisture of the original soil that is a measurement target. In contrast to this, the smaller the width of the in-probe substrate, the smaller the width of an area in which the density of soil has increased. As a result, the smaller the width of the in-probe substrate, the lower the ratio of an area in which the density of soil has increased in the area between the transmission probe substrate 321 and the reception probe substrate 322. In accordance with this, a result of measurement of the amount of moisture of soil is closer to the amount of moisture of the original soil that is a measurement target. In other words, the amount of moisture of soil can be accurately measured.

From both the first and second points of view described above, the smaller the width of the in-probe substrate, a sensor device including this inside a probe casing can accurately measure the amount of moisture of soil.

The sensor device 200 according to the first embodiment of the present technology (1) uses a column of vias used for shielding as a structure for shielding a lateral side of a signal line in an in-probe substrate, thereby being able to decrease the width of the in-probe substrate.

In accordance with this, an effect of accurately measuring the amount of moisture of soil can be acquired.

(2) In an in-probe substrate, in a case in which a plurality of antennas are included, and a plurality of signal lines are included for connection to the plurality of antennas, by forming at least one or more of the plurality of signal lines in a different wiring layer by using a plurality of wiring layers, the width of the in-probe substrate can be configured to be small. In accordance with this, an effect of being able to accurately measure the amount of moisture of soil can be acquired.

Figure 99:
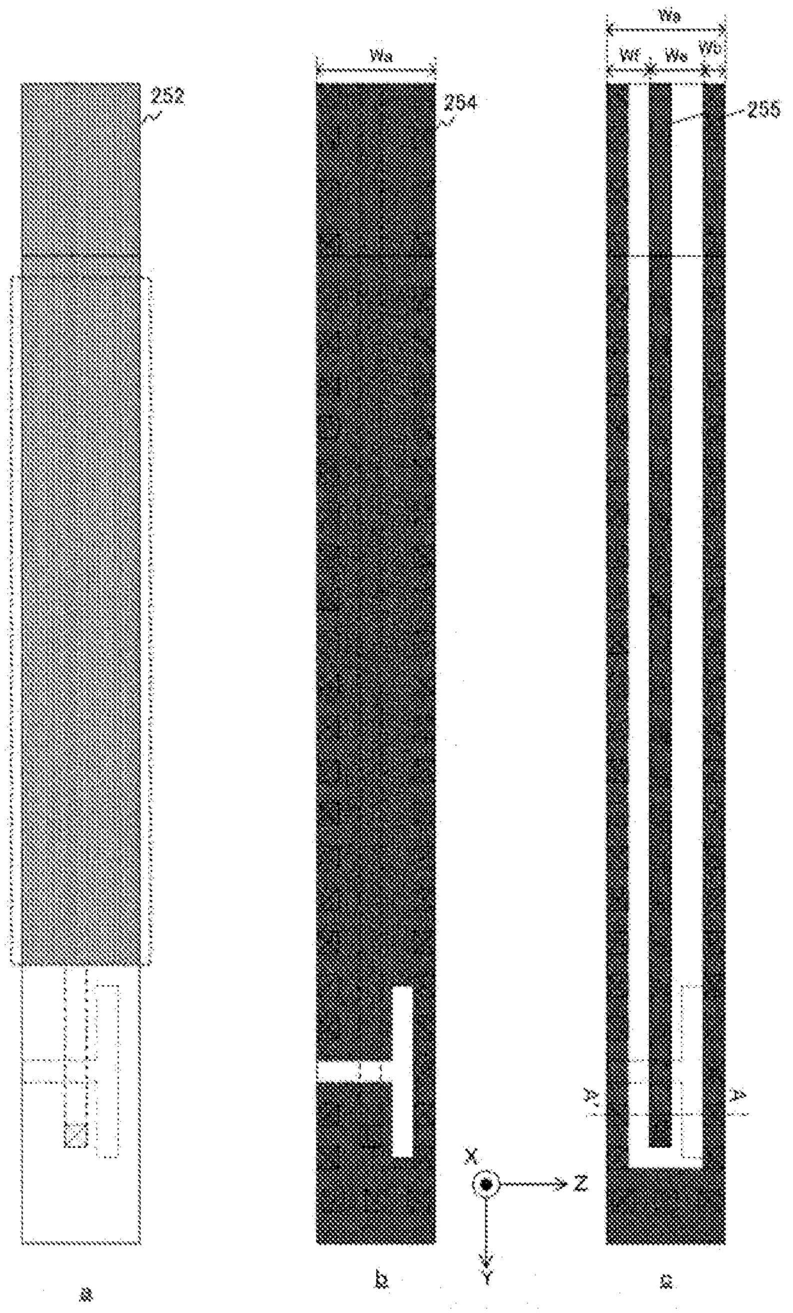
FIG. 99 is an example of a plan view of a first layer to a third layer of the inside of an in-probe substrate in which a slot is formed in the first embodiment of the present technology.
Figure 100:
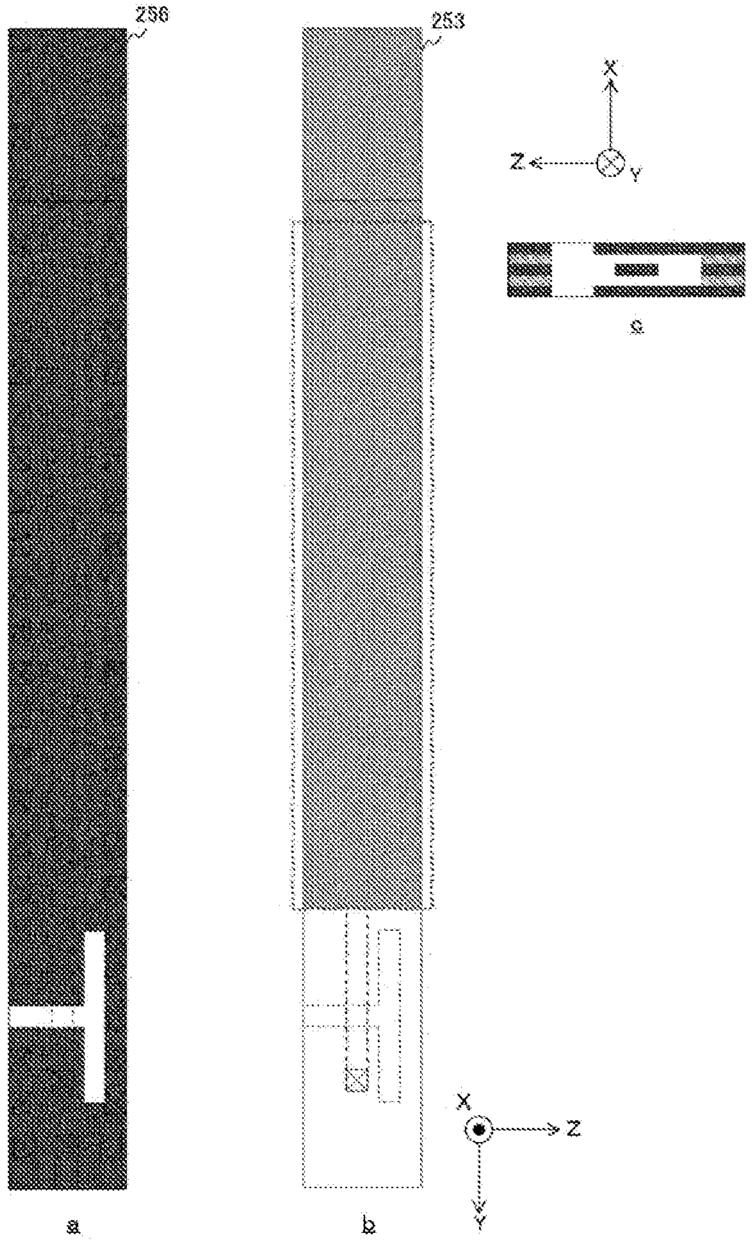
FIG. 100 is an example of a plan view of a fourth layer and a fifth layer of the inside of an in-probe substrate in which a slot is formed and a cross-sectional view of the substrate in the first embodiment of the present technology.

FIGS. 99 and 100 illustrate another example of a planar shape of the in-probe substrate 321 according to the first embodiment of the present technology. The example illustrated in FIGS. 99 and 92 illustrates a planar shape of an in-probe substrate 321 including one antenna of a planar shape and a slot shape in which a transmission line for the antenna is formed from a total of three wiring layers formed from one signal line layer and two shield layers having this signal line layer interposed therebetween. In addition, the example illustrated in FIGS. 99 and 100 illustrates an example in which a shield wiring is disposed on a lateral side of a signal line 255 using a part of the same wiring layer as that of the signal line 255.

a in FIG. 99 illustrates a planar shape of a solder resist 252 and an electromagnetic wave absorbent material 251 disposed on an outer side of the first wiring layer. The solder resist 252 is a pattern to which a color is applied, and an outer shape of the electromagnetic wave absorbent material 251 is denoted by dotted lines. b in FIG. 99 illustrates a planar shape of the first wiring layer (a shield layer 254 including a slot, in other words, a radiation element 254). c in FIG. 99 illustrates a second wiring layer (a signal line 255 and shield wirings 257 disposed on both sides of the signal line 255 using a part of the second wiring layer).

A symbol of a square with diagonal lines thereof joining using segments disposed in the shield wiring 257 represents a via. Particularly in c in FIG. 99, a via connecting the shield layer 254 and the shield wiring and a via connecting the shield wiring and a shield layer 256 to be described below are illustrated on the pattern of the shield wiring. In FIG. 99, Wa represents a width of the in-probe substrate 321. In addition, Wb represents a width of the shield wiring. We represents a length from the slot to the shield wiring, and Wf represents a length from a signal line end to the shield wiring.

a in FIG. 100 illustrates a planar shape of a third wiring layer (a shield layer 256 including a slot, in other words, a radiation element 256). b in FIG. 100 illustrates a planar shape of a solder resist 253 and an electromagnetic wave absorbent material 251 disposed on an outer side of the third wiring layer. The solder resist 253 is a pattern to which a color is applied, and an outer shape of the electromagnetic wave absorbent material 251 is denoted by dotted lines. c in FIG. 100 is a cross-sectional view of an in-probe substrate 321 taken along line A-A' illustrated in c in FIG. 99.

In the cross-sectional view of c in FIG. 100, the first wiring layer (the shield layer 254) is disposed on the lowest side of the sheet surface, and the signal line and the shield wirings of both sides thereof are disposed thereon using the second wiring layer. The shield layer 256 is disposed thereon. In an area in which a transmission line of the in-probe substrate 321 is formed, solder resists are disposed on upper and lower sides of the cross-section thereof, and the electromagnetic wave absorbent material 251 is disposed in the periphery of the cross-section.

Figure 101:
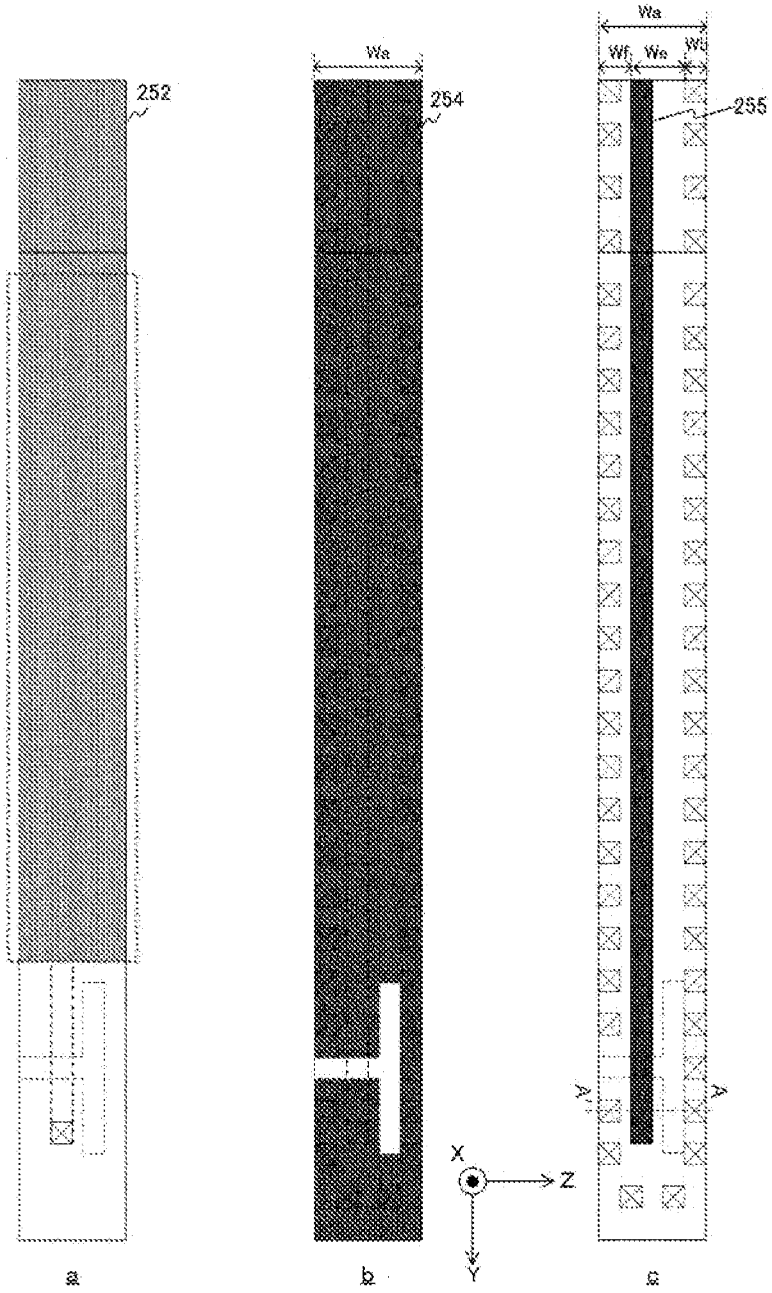
FIG. 101 is an example of a plan view of a first layer to a third layer of the inside of an in-probe substrate in which a slot is formed, and no shield wiring is present in the first embodiment of the present technology
Figure 102:
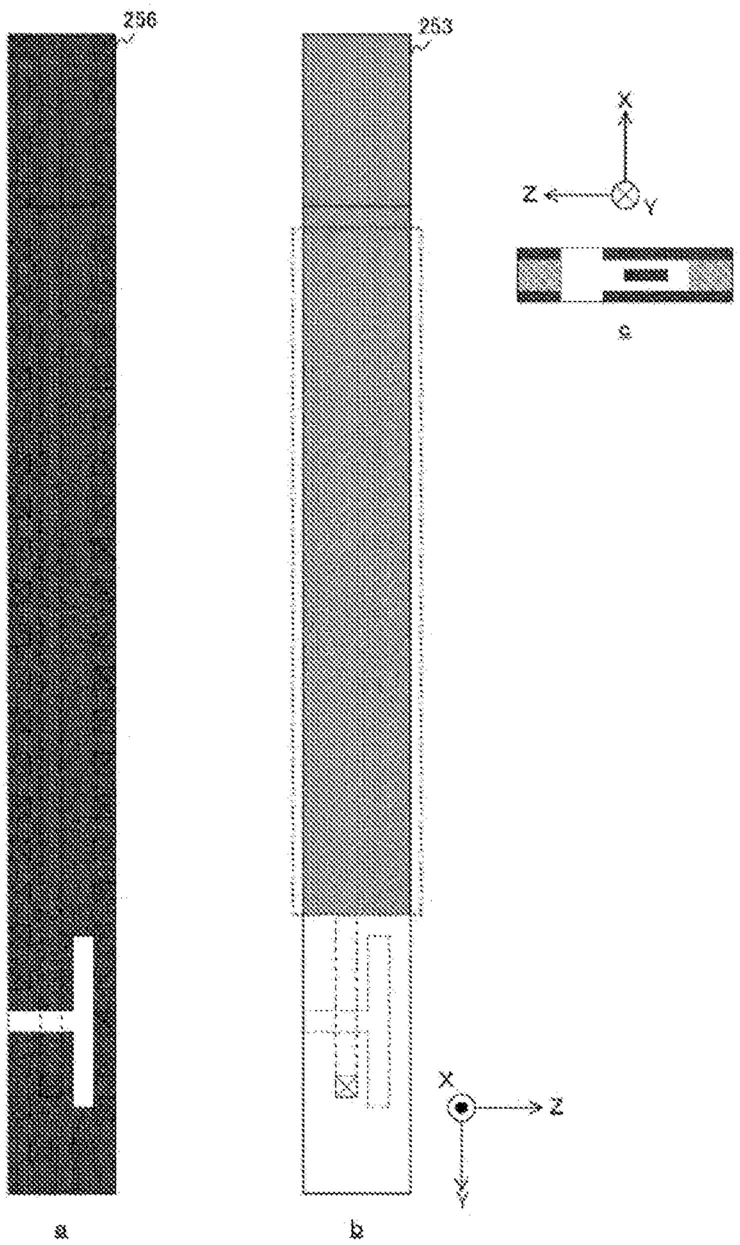
FIG. 102 is an example of a plan view of a fourth layer and a fifth layer of the inside of an in-probe substrate in which a slot is formed, and no shield wiring is present and a cross-sectional view of the substrate in the first embodiment of the present technology.

FIGS. 101 and 102 illustrate another example of a planar shape of the in-probe substrate 321 according to the first embodiment of the present technology. The example illustrated in FIGS. 101 and 102 illustrates an in-probe substrate 321 including one antenna of a planar shape and a slot shape in which a transmission line for the antenna is formed from a total of three wiring layers formed from one signal line layer and two shield layers having this signal line layer interposed therebetween. In addition, the example illustrated in FIGS. 101 and 102 illustrates an example in which vias that pass a lateral side of a signal line 255 from a shield layer 256 disposed on the upper side of the signal line 255 and reach a shield layer 254 disposed on the lower side of the signal line 255 are used, and, by disposing these vias along the signal line 255 in a column form, the lateral side of the signal line 255 is shielded. c in FIG. 101 illustrates the column of vias used for shielding. In this diagram, symbols of squares with diagonal lines thereof joining using segments that are disposed on both sides of the signal line 255 represent vias. Such vias to which no color is applied in this drawing are not formed in a second wiring layer that is the same layer as that of the signal line 255 and are represented to be vias that pass a lateral side of the signal line 255 from an upper layer of the signal line 255 and extends to a lower layer of the signal line 255. The planar shapes illustrated in FIGS. 101 and 102 other than c in FIG. 101 are similar to those illustrated in FIGS. 99 and 100, and thus description thereof will be omitted. In addition, c in FIG. 102 is a cross-sectional view of the in-probe substrate 321 when the part of the slot antenna is cut out in the structure illustrated in FIGS. 102 and 103.

Next, effects brought by the structure illustrated in c in FIG. 101 will be described. Similar to c in FIG. 83, the planar shape illustrated in c in FIG. 101 has a structure in which a lateral side of the signal line 255 is shielded using a column of vias used for shielding. In accordance with this, a distance between the signal line 255 and the column of vias used for shielding (in the case of FIG. 99, the shield wiring) can be configured to be smaller than that of the structure illustrated in c in FIG. 99. As a result, there is an effect of the width of the in-probe substrate 321 illustrated in FIGS. 101 and 102 being smaller than the width of the in-probe substrate 321 illustrated in FIGS. 99 and 100. In addition, in a case in which the width of the in-probe substrate can be configured to be small, the cross-section of a probe casing housing this can be configured to be small, and, in accordance with this, there is also an effect of being able to accurately measure moisture. Details thereof are as described with reference to FIG. 98. In FIG. 101, Wa represents a width of the in-probe substrate 321. In addition, Wb represents a width of the shield via column. We represents a length from the slot to the via column, and Wf represents a length from a signal line end to the shield via column.

Figure 103:
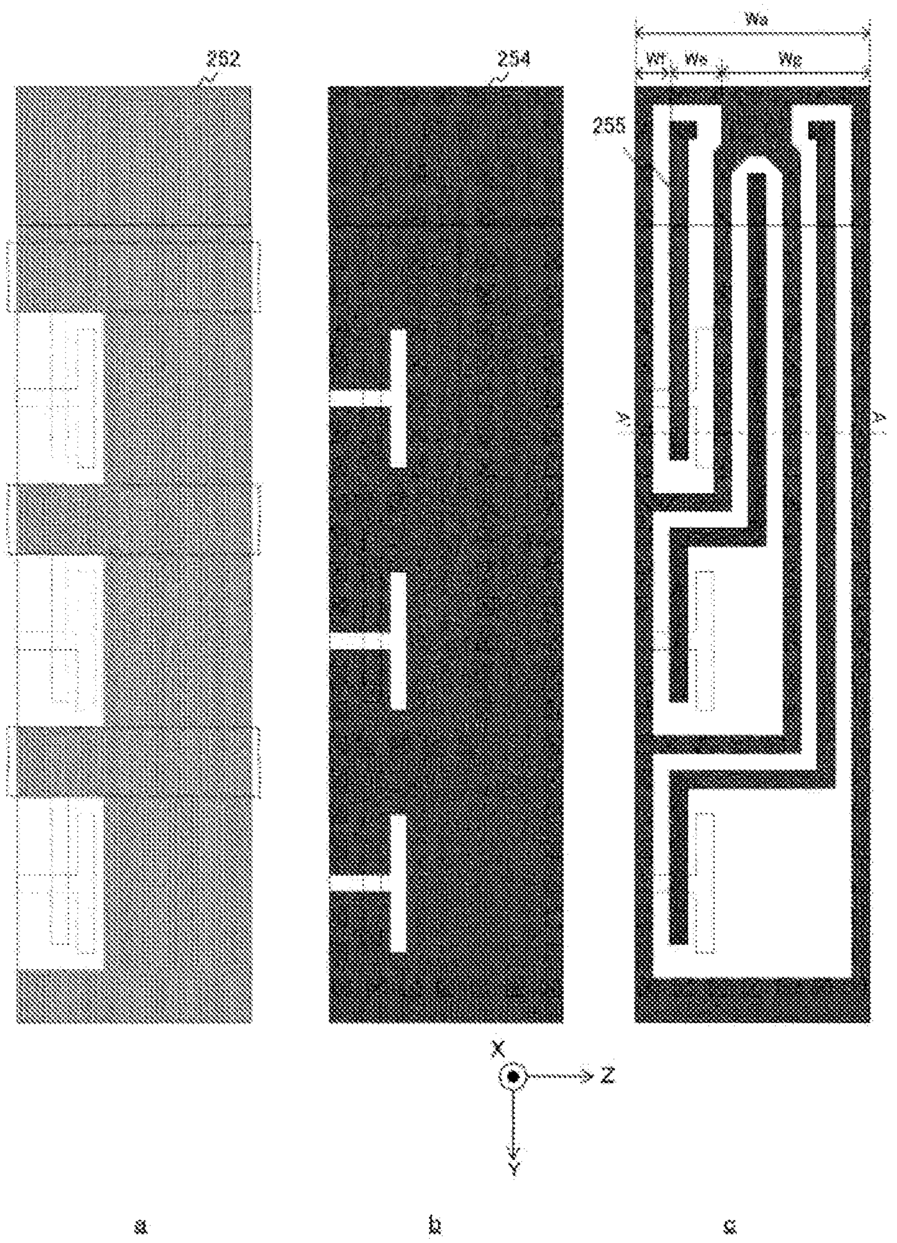
FIG. 103 is an example of a plan view of a first layer to a third layer of the inside of an in-probe substrate in which a slot is formed, and three antennas are disposed in the first embodiment of the present technology.
Figure 104:
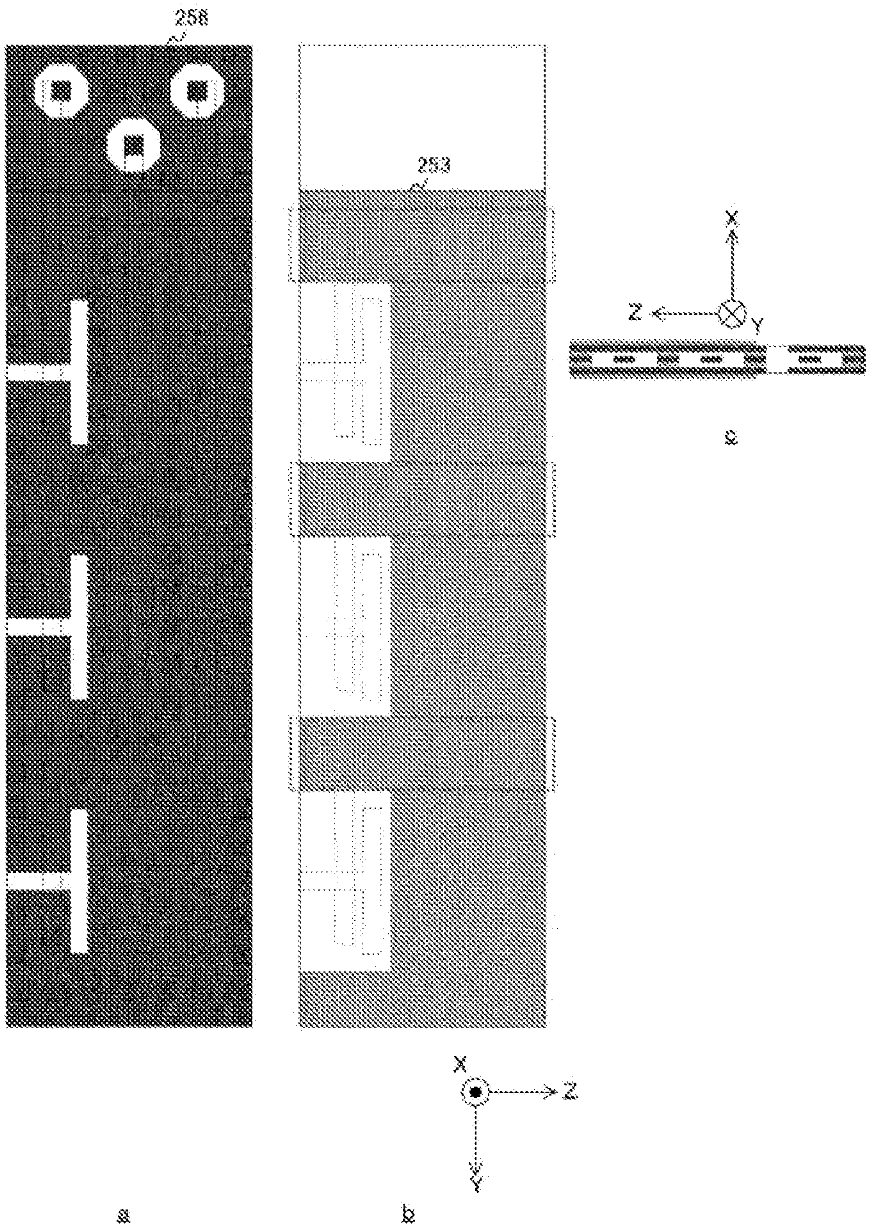
FIG. 104 is an example of a plan view of a fourth layer and a fifth layer of the inside of an in-probe substrate in which a slot is formed, and three antennas are disposed and a cross-sectional view of the substrate in the first embodiment of the present technology.

FIGS. 103 and 104 illustrate yet another example of the planar shape of an in-probe substrate 321 according to the first embodiment of the present technology. The example illustrated in FIGS. 103 and 104 illustrates the in-probe substrate 321 including n (for example, n=3) antennas of a planar shape and a slot shape in which a transmission line for the antenna includes a total of three wiring layers formed from one signal line layer and two shield layers having this signal line layer interposed therebetween. In addition, the example illustrated in FIGS. 103 and 104 illustrates an example in which the lateral side of the signal line 255 is shielded using a part of the same wiring layer as that of the signal line 255. The roles of layers illustrated in FIGS. 103 and 104 are similar to those illustrated in FIGS. 99 and 100, and thus description thereof will be omitted.

b in FIG. 103 illustrates a planar shape in which slots of three antennas of a planar shape and a slot shape are formed using a first wiring layer (a shield layer 254 including slots, in other words, a radiation element 254).

Similar to c in FIG. 99, c in FIG. 103 illustrates an example in which a shield wiring is disposed on a lateral side of a signal line 255 using a part of the same wiring layer as that of the signal line 255. In c in FIG. 103, three signal lines 255 for intersecting with the three slots illustrated in b in FIG. 101 are formed using a part of the second wiring layer.

In addition, in order to shield a lateral side of each of these three signal lines 255, between these three signal lines and on an outer side, a total of four shield wirings are formed using the second wiring layer that is the same as that of the three signal lines 255. In addition, c in FIG. 104 is a cross-sectional view of the in-probe substrate 321 taken along line A-A' illustrated in c in FIG. 103. In FIG. 103, Wa represents a width of the in-probe substrate 321. In addition, We represents a length from the slot to the signal line, and Wf represents a length from a signal line end to the shield wiring. Wg represents a width of two signal lines and three shield wirings.

Figure 105:
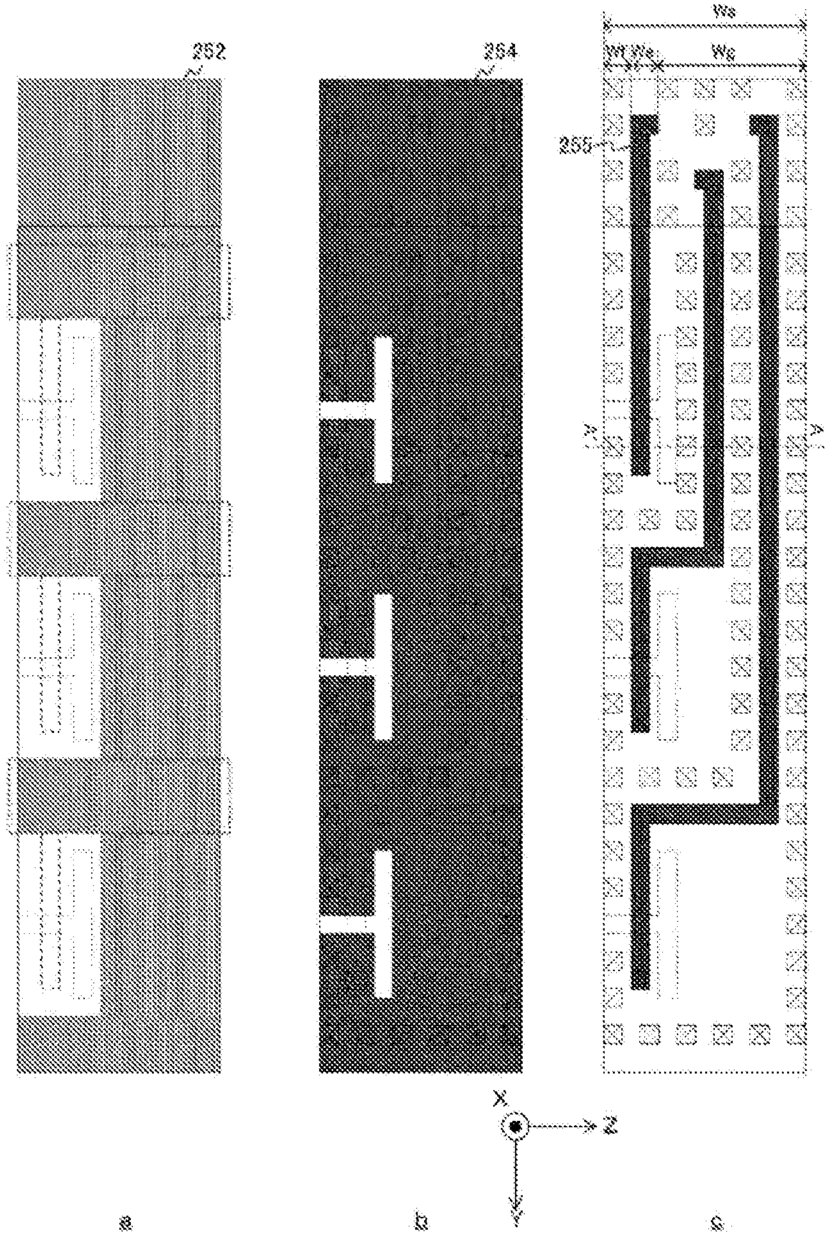
FIG. 105 is an example of a plan view of a first layer to a third layer of the inside of an in-probe substrate in which a slot is formed, no shield wiring is present, and three antennas are disposed in the first embodiment of the present technology.
Figure 106:
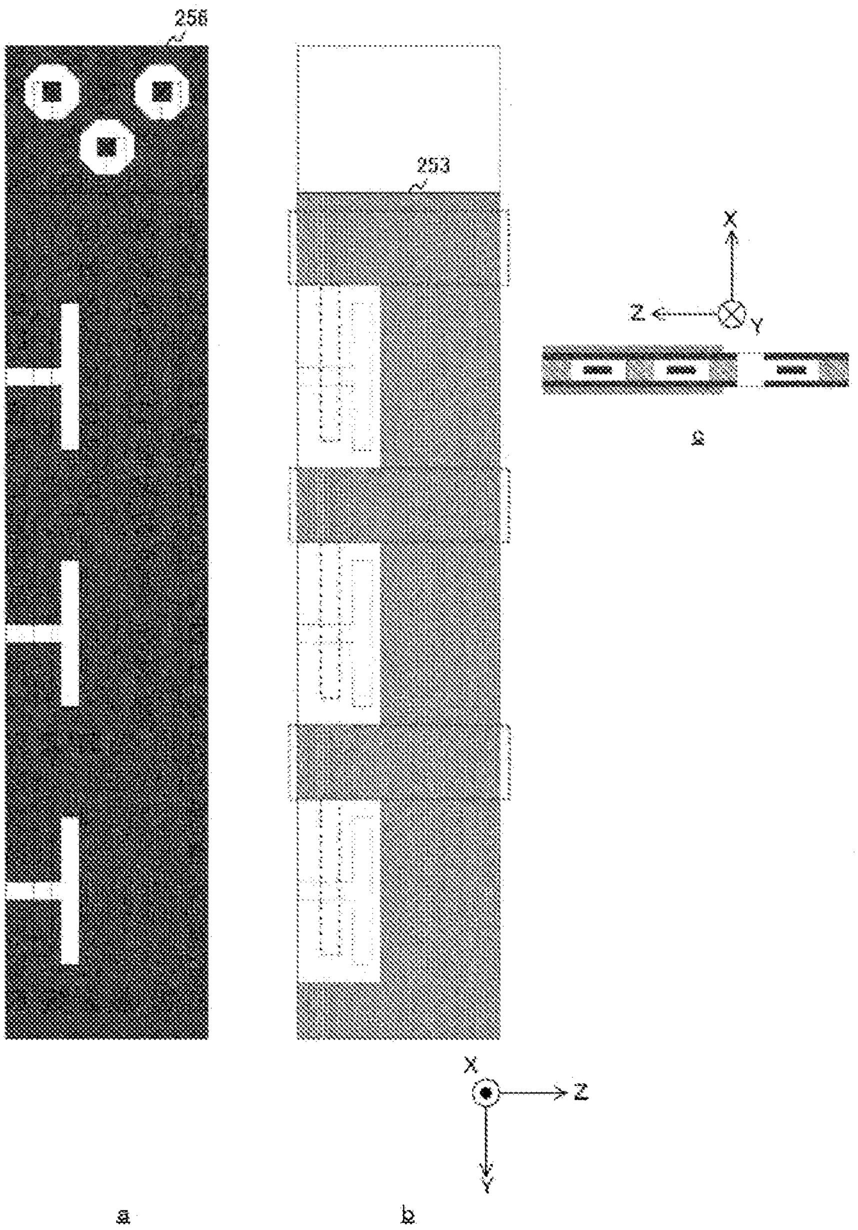
FIG. 106 is an example of a plan view of a fourth layer and a fifth layer of the inside of an in-probe substrate in which a slot is formed, no shield wiring is present, and three antennas are disposed and a cross-sectional view of the substrate in the first embodiment of the present technology.

FIGS. 105 and 106 illustrate yet another example of the planar shape of an in-probe substrate 321 according to the first embodiment of the present technology. The example illustrated in FIGS. 105 and 106 illustrates the in-probe substrate 321 including n (for example, n=3) antennas of a planar shape and a slot shape in which a transmission line for the antenna includes a total of three wiring layers formed from one signal line layer and two shield layers having this signal line layer interposed therebetween. In addition, the example illustrated in FIGS. 105 and 106 illustrates an example in which vias that pass a lateral side of a signal line 255 from a shield layer 256 disposed on the upper side of the signal line 255 and reach a shield layer 254 disposed on the lower side of the signal line 255 are used, and, by disposing these vias along the signal line 255 in a column form, the lateral side of the signal line 255 is shielded.

b in FIG. 105 illustrates a planar shape in which slots of three antennas of a planar shape and a slot shape are formed using a first wiring layer (a shield layer 254 including slots, in other words, a radiation element). In FIG. 105, Wa represents a width of the in-probe substrate 321. In addition, We represents a length from the slot to a shield via column, and Wf represents a length from a signal line end to a shield wiring. Wg represents a width of two signal lines and three shield via columns.

Similar to c in FIG. 101, c in FIG. 105 illustrates an example in which a lateral side of a signal line 255 is shielded using a column of vias for shielding. In c in FIG. 105, three signal lines 255 used for intersecting with three radiation elements illustrated in b in FIG. 105 are formed using a part of a second wiring layer. In addition, in order to shield lateral sides of these three signal lines 255, between these three signal lines and on the outer sides thereof, a column of vias for shielding that is a total of four columns is disposed. In addition, c in FIG. 106 is a cross-sectional view of the in-probe substrate 321 taken along line A-A' illustrated in c in FIG. 105.

Next, effects brought by the structure illustrated in c in FIG. 105 will be described. Similar to c in FIG. 101, patterns of the three signal lines 255 and a column of vias of four columns illustrated in c in FIG. 105 are separately (in other words, independently) formed. As a result, a distance between the three signal lines 255 and a column of vias of four columns illustrated in c in FIG. 105 can be configured to be smaller than a distance between the three signal lines 255 and the four shield wirings illustrated in c in FIG. 103. As a result, the width of the in-probe substrate 321 illustrated in FIGS. 105 and 106 is able to be configured smaller than the width of the in-probe substrate 321 illustrated in FIGS. 103 and 104. In addition, in a case in which the width of the in-probe substrate can be configured to be small, the cross-section of a probe casing housing this can be configured to be small, and, in accordance with this, there is also an effect of being able to accurately measure moisture. Details thereof are as described with reference to FIG. 98.

Figure 107:
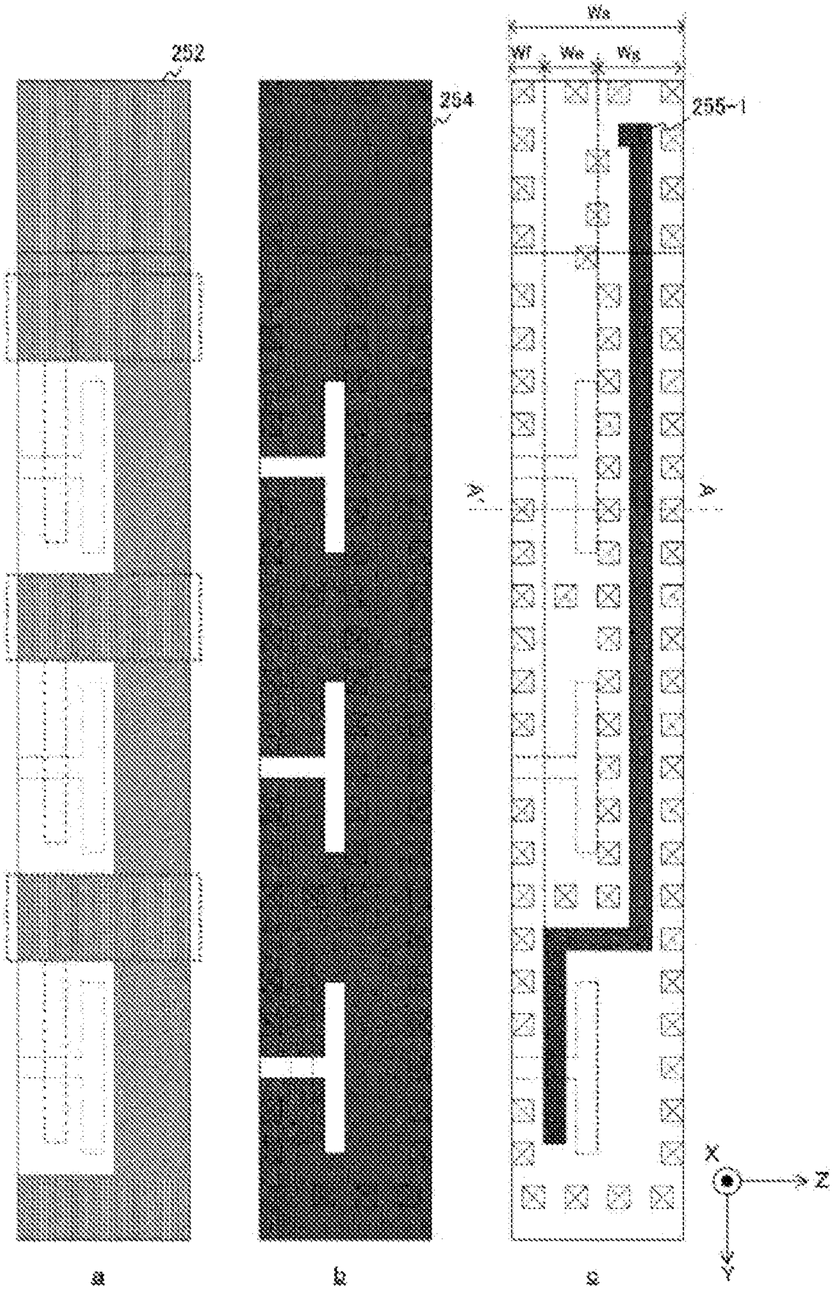
FIG. 107 is an example of a plan view of a first layer to a third layer among seven layers of the inside of an in-probe substrate in which a slot is formed in the first embodiment of the present technology.
Figure 108:
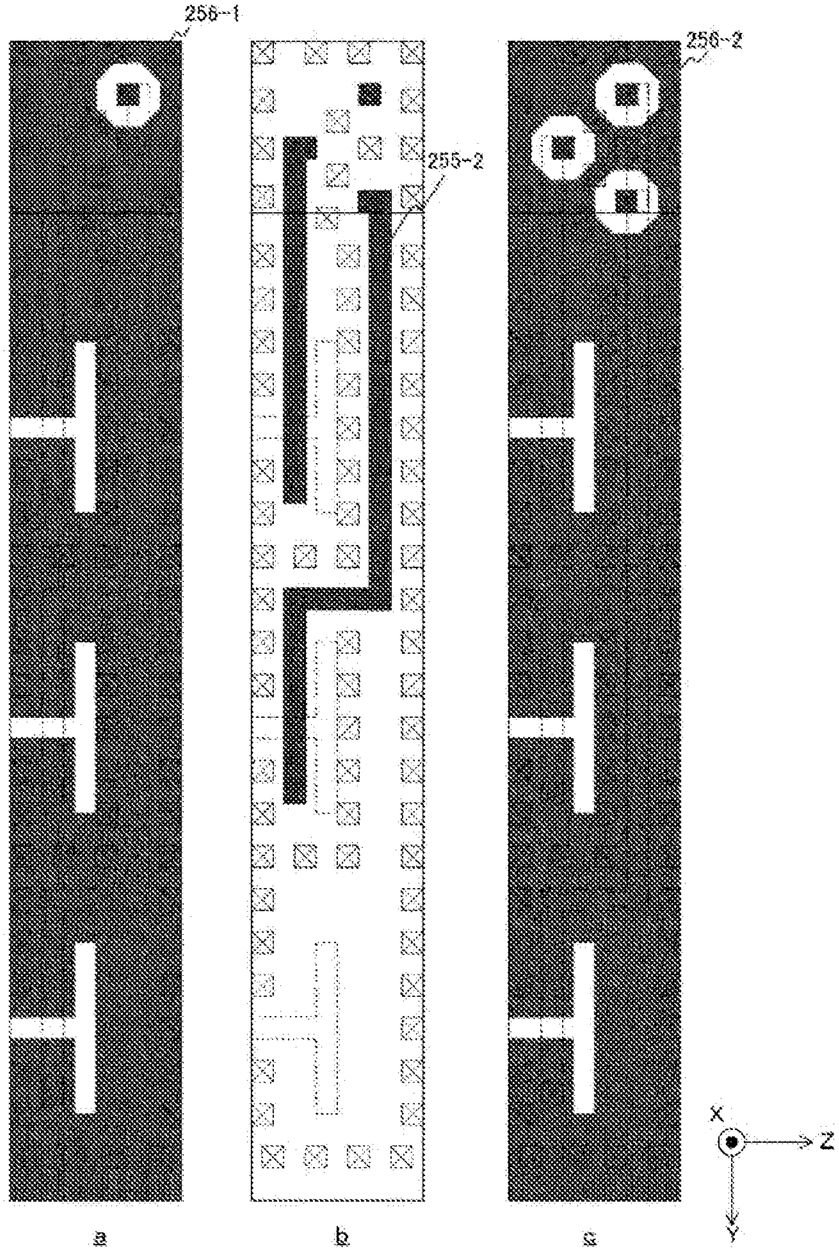
FIG. 108 is an example of a plan view of a fourth layer to a sixth layer among seven layers of the inside of an in-probe substrate in which a slot is formed in the first embodiment of the present technology.

FIGS. 107 to 109 illustrate yet another example of the planar shape of an in-probe substrate 321 according to the first embodiment of the present technology. The example illustrated in FIGS. 107 to 109 illustrates an example in which n (for example, n=3) antennas of a planar shape and a slot shape are included, and n transmission lines intersecting with slots of n antennas are formed in an in-probe substrate 321 including a total of (2n−1) wiring layers formed from (n−1) signal line layers and n shield layers having these signal lines interposed therebetween. In addition, the example illustrated in FIGS. 107 to 109 is an example in which vias passing through a lateral side of a signal line 255 from a shield layer disposed on the upper side of the signal line 255 and reaching a shield layer disposed on the lower side of the signal line 255 are used, and the lateral side of the signal line 255 is shielded by disposing these vias along the signal line 255 in a column shape.

b in FIG. 107 illustrates a planar shape in which slots of three antennas of a planar shape and a slot shape are formed using a first wiring layer (a shield layer 254 including slots, in other words, a radiation element). a in FIG. 108 illustrates a planar shape in which slots of three antennas of a planar shape and a slot shape are formed using a third wiring layer (a shield layer 256-1 including slots, in other words, a radiation element 256-1). c in FIG. 108 illustrates a planar shape in which slots of three antennas of a planar shape and a slot shape are formed using a fifth wiring layer (a shield layer 256-2 including slots, in other words, a radiation element 256-2). In FIG. 107, Wa represents a width of the in-probe substrate 321. In addition, We represents a length from the slot to a shield via column, and Wf represents a length from a signal line end to a shield wiring. Wg represents a width of one signal line and two shield via columns.

In the example illustrated in FIGS. 107 to 109, three signal lines intersecting with three antennas are formed using two signal line layers (second and fourth wiring layers) included in a substrate including five wiring layers.

In the second wiring layer illustrated in c in FIG. 107, (1) one signal line 255 for intersecting with a first slot among three slots illustrated in b in FIG. 107 is formed.

(2) In order to shield the lateral side of the signal line 255 of (1) described above, columns of vias for shielding are disposed on both sides of such a signal line.

(3) In order to densely connect the shield layer formed using the wiring layer of the first layer to the shield layer formed using wiring layers of third and fifth layers, a column of vias is also disposed near the outer edge of these shield layers.

On the other hand, in the fourth wiring layer illustrated in b in FIG. 108, (1) for second and third slots for which a signal line 255 for intersecting with a slot is not disposed among three slots illustrated in b in FIG. 107 in the second wiring layer, two signal lines 255 for intersecting with these are formed.

(2) In order to shield the lateral side of the signal line 255 of (1) described above, columns of vias for shielding are disposed on both sides of such a signal line.

(3) In order to densely connecting the shield layer formed using the first wiring layer to the shield layer formed using the wiring layers of the third layer and the fifth layer, columns of vias are also disposed near outer edges of these shield layers.

In addition, b in FIG. 109 is a cross-sectional view of the in-probe substrate 321 taken along line A-A' illustrated in c in FIG. 107.

Next, effects brought by the structures illustrated in c in FIG. 107 and b in FIG. 108 will be described. In the structures described in such diagrams, the lateral side of the signal line 255 is shielded using the via columns for shielding illustrated in c in FIG. 101, and thus an effect of decreasing the width of the in-probe substrate 321 is acquired. In the structure illustrated in c in FIG. 107 and b in FIG. 108, compared to the structure illustrated in c in FIG. 105, by using more signal line layers, the number of signal lines disposed in one signal line layer is decreased. In accordance with this structure, an effect of decreasing the width of the in-probe substrate 321 more than that of the structure illustrated in c in FIG. 105 is acquired.

Figure 110:
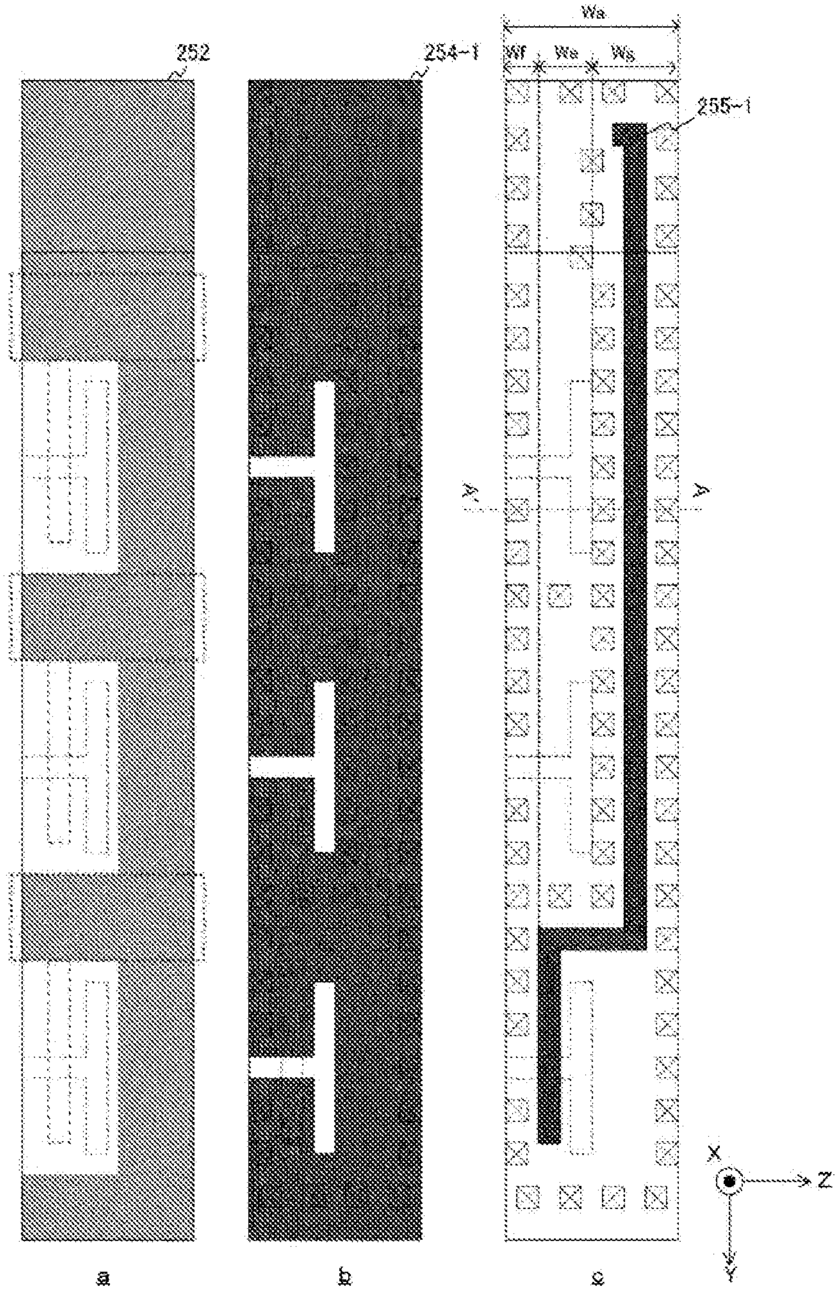
FIG. 110 is an example of a plan view of a first layer to a third layer among nine layers of the inside of an in-probe substrate in which a slot is formed in the first embodiment of the present technology.
Figure 111:
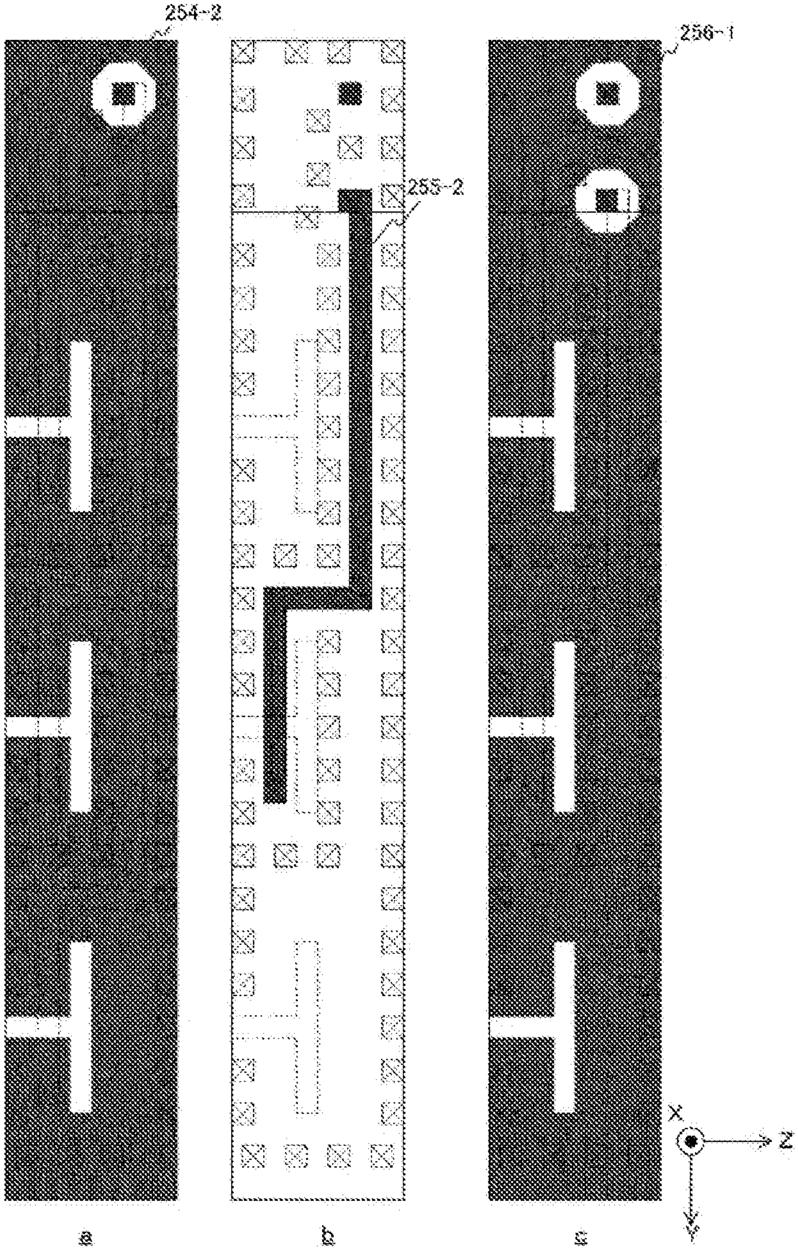
FIG. 111 is an example of a plan view of a fourth layer to a sixth layer among nine layers of the inside of an in-probe substrate in which a slot is formed in the first embodiment of the present technology.
Figure 112:
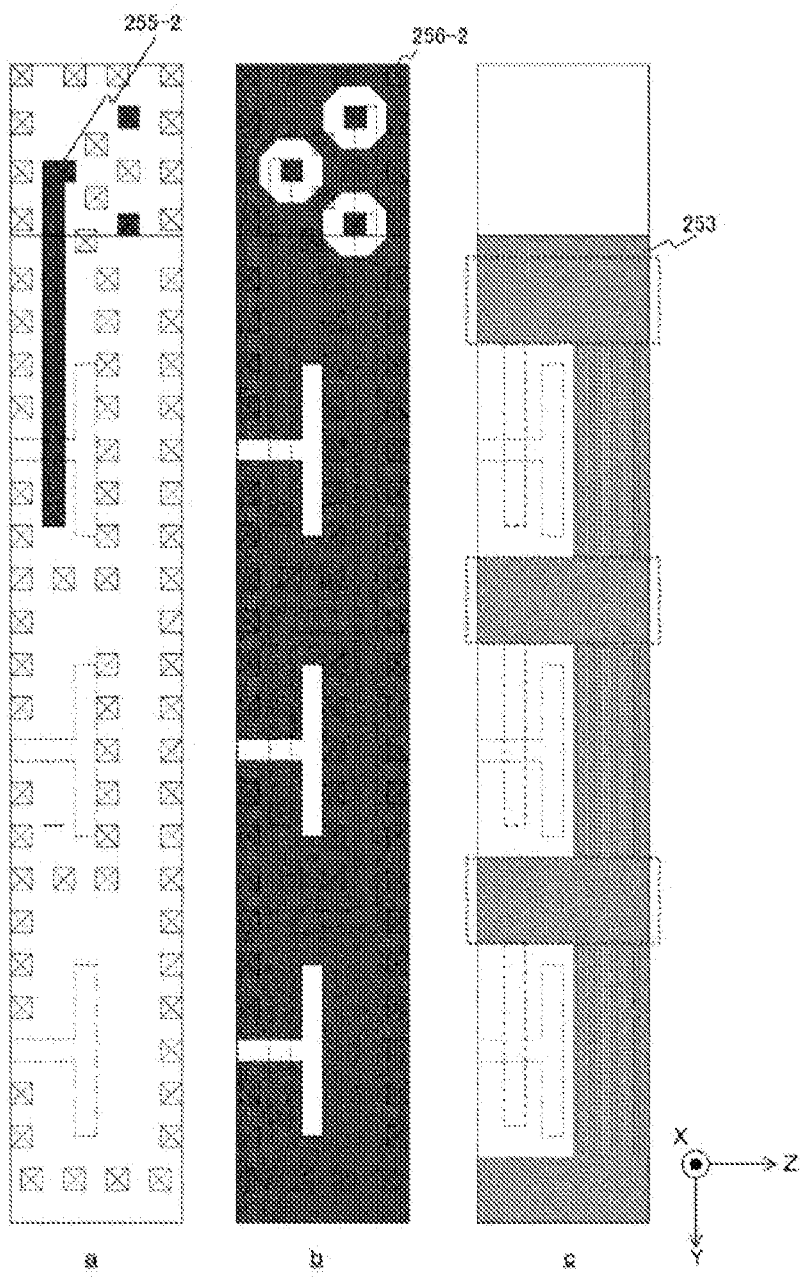
FIG. 112 is an example of a plan view of a seventh layer to a ninth layer among nine layers of the inside of an in-probe substrate in which a slot is formed in the first embodiment of the present technology.

FIGS. 110 to 113 illustrate yet another example of the planar shape of an in-probe substrate 321 according to the first embodiment of the present technology. The example illustrated in FIGS. 110 to 112 illustrates an example in which n (for example, n=3) antennas of a planar shape and a slot shape are included, and n transmission lines intersecting with the n antennas are formed in the in-probe substrate 321 including a total of (2n+1) wiring layers formed from n signal line layers and (n+1) shield layers having the signal line layers interposed therebetween. In addition, the example illustrated in FIGS. 110 to 112 is an example in which vias passing through a lateral side of a signal line 255 from a shield layer disposed on the upper side of the signal line 255 and reaching a shield layer disposed on the lower side of the signal line 255 are used, and the lateral side of the signal line 255 is shielded by disposing these vias along the signal line 255 in a column shape.

b in FIG. 110 illustrates a planar shape in which slots of three antennas of a planar shape and a slot shape are formed using a first wiring layer (a shield layer 254-1 including slots, in other words, a radiation element). a in FIG. 111 illustrates a planar shape in which slots of three antennas of a planar shape and a slot shape are formed using a third wiring layer (a shield layer 254-2 including slots, in other words, a radiation element). c in FIG. 111 illustrates a planar shape in which slots of three antennas of a planar shape and a slot shape are formed using a fifth wiring layer (a shield layer 256-1 including slots, in other words, a radiation element). b in FIG. 112 illustrates a planar shape in which slots of three antennas of a planar shape and a slot shape are formed using a seventh wiring layer (a shield layer 256-2 including slots, in other words, a radiation element). In FIG. 110, Wa represents a width of the in-probe substrate 321. In addition, We represents a length from the slot to a shield via column, and Wf represents a length from a signal line end to a shield wiring. Wg represents a width of one signal line and two shield via columns.

In the example illustrated in FIGS. 110 to 112, three signal lines intersecting with three antennas are formed using three signal line layers (second, fourth, and sixth wiring layers) included in a substrate including seven wiring layers.

In the second wiring layer illustrated in c in FIG. 110, (1) one signal line 255 for intersecting with the first slot among three slots illustrated in b in FIG. 110 is formed.

(2) In order to shield the lateral side of the signal line 255 of (1) described above, columns of vias for shielding are disposed on both sides of such a signal line.

(3) In order to densely connect the shield layer formed using the wiring layer of the first layer to the shield layer formed using wiring layers of third, fifth, and seventh layers, a column of vias is also disposed near the outer edge of these shield layers.

On the other hand, in the fourth wiring layer illustrated in b in FIG. 111, (1) for a second slot out of second and third slots for which a signal line 255 for intersecting with a slot is not disposed among three slots illustrated in b in FIG. 111 in the second wiring layer, two signal lines 255 for intersecting with this are formed.

(2) In order to shield the lateral side of the signal line 255 of (1) described above, columns of vias for shielding are disposed on both sides of such a signal line.

(3) In order to densely connecting the shield layer formed using the first wiring layer to the shield layer formed using the wiring layers of the third layer, the fifth layer, and the seventh layer, columns of vias are disposed also near outer edges of these shield layers.

On the other hand, in the sixth wiring layer illustrated in a in FIG. 112, (1) in the second wiring layer and the fourth wiring layer among three slots illustrated in b in FIG. 111, for the third slot for which a signal line 255 for intersecting with a slot is not disposed, two signal lines 255 for intersecting with this are formed.

(2) In order to shield the lateral side of the signal line 255 of (1) described above, columns of vias for shielding are disposed on both sides of such a signal line.

(3) In order to densely connecting the shield layer formed using the first wiring layer to the shield layer formed using the wiring layers of the third layer, the fifth layer, and the seventh layer, columns of vias are disposed also near outer edges of these shield layers.

Figure 113:
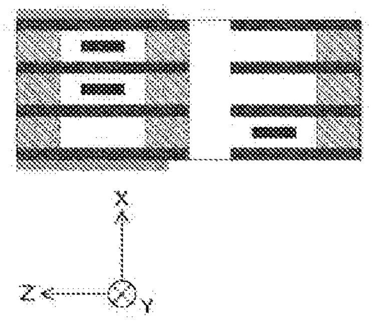
FIG. 113 is an example of a cross-sectional view of an in-probe substrate of a nine-layer structure in which a slot is formed in the first embodiment of the present technology.

In addition, FIG. 113 is a cross-sectional view of the in-probe substrate 321 taken along line A-A' illustrated in c in FIG. 110.

Next, effects brought by the structures illustrated in c in FIG. 110, b in FIG. 111, and a in FIG. 112 will be described. In the structures described in such diagrams, the lateral side of the signal line 255 is shielded using the via columns for shielding illustrated in c in FIG. 101, and thus an effect of decreasing the width of the in-probe substrate 321 is acquired. In the structures illustrated in c in FIG. 110, b in FIG. 111, and a in FIG. 112, compared to the structure illustrated in c in FIG. 105, by using more signal line layers, the number of signal lines disposed in one signal line layer is decreased. In accordance with this structure, an effect of decreasing the width of the in-probe substrate 321 more than that of the structure illustrated in c in FIG. 105 is acquired.

In addition, the width of the in-probe substrate 321 illustrated in FIGS. 110 to 113 is the same as the width of the in-probe substrate 321 illustrated in FIGS. 107 to 109.

Figure 114:
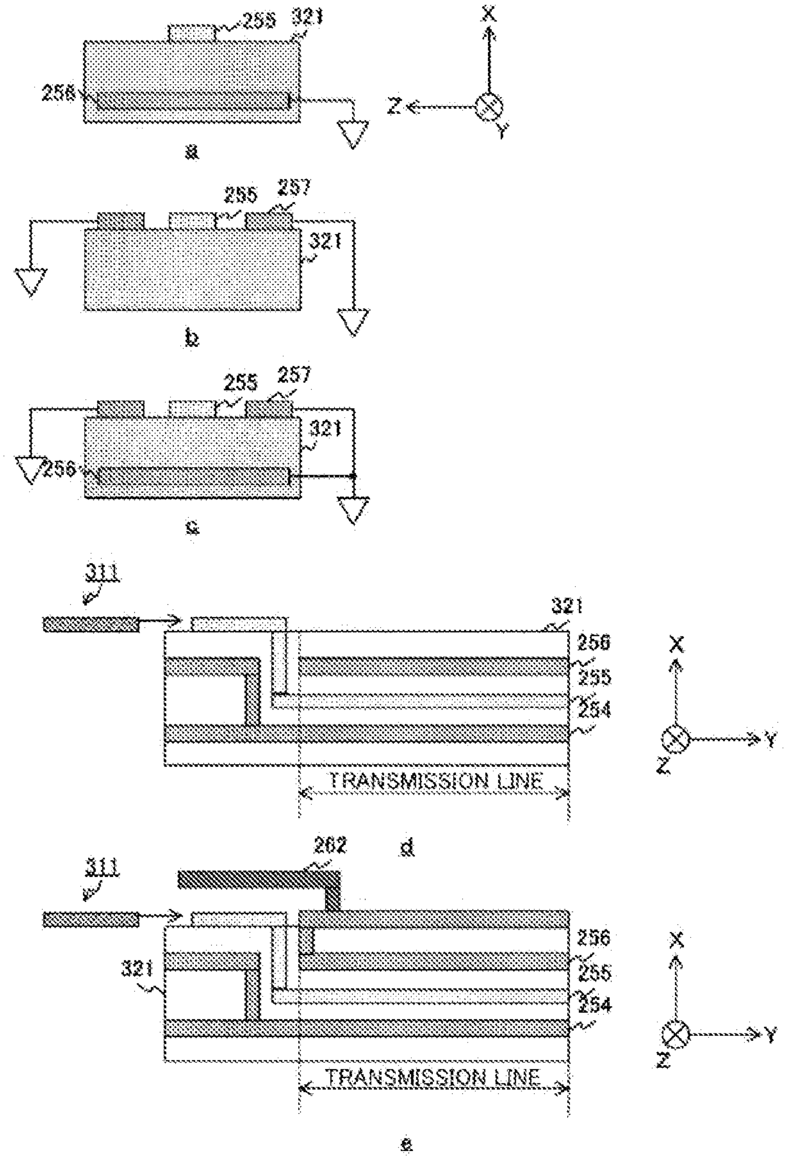
FIG. 114 is a diagram for supplementarily describing a structure of a strip line according to the first embodiment of the present technology.

FIG. 114 is a diagram illustrating a cross-sectional structure of a substrate of an area in which a connector 323 (and 324) used for connecting an in-probe substrate 321 and a transmission line connecting unit in the in-probe substrate 321 (and 322) included in the first embodiment of the present technology and a structure of the transmission line used in the area. In the in-probe substrate 321, as described above, a transmission line connecting a transmission antenna 223 and the like included in this substrate and a connector 323 is formed using a strip line. On the other hand, in an area in which the connector 323 is disposed, in order to electrically connect a signal line 255 disposed in an inner layer of the in-probe substrate 321 and the transmission line connecting unit through the connector 323 using a strip line, the signal line 255 disposed in the inner layer of the in-probe substrate 321 needs to be drawn out to a surface layer of the substrate. The signal line 255 drawn out to the surface layer of the in-probe substrate 321 can use a transmission line of a structure illustrated in a, b, or c in this diagram as a structure of the transmission line. More specifically, as illustrated in a in this diagram, the transmission line may be configured as a micro strip line in which a signal line 255 transmitting a signal is disposed in a surface layer, and s shield layer 256 is disposed in an inner layer. As illustrated in b in this diagram, the transmission line may be configured as a coplanar line in which a signal line 255 and a shield wiring are disposed in a surface layer. As illustrated in c in this diagram, the transmission line may be configured as a coplanar line in which a signal line 255 is disposed in a surface layer, and a shield wiring 257 and a shield layer 256 are disposed in the surface layer and an inner layer.

In addition, d and e in this diagram are diagrams illustrating a cross-sectional structure of the substrate described above in an area in which a connector 323 (and 324) used for connecting the in-probe substrate 321 and the transmission line connecting unit is disposed. In d in this diagram, an area denoted by a transmission line represents a strip line extending to a transmission antenna. A structure illustrated on the left side of the strip line described above illustrates a structure for drawing out a signal line 255 formed in the substrate inner layer described above to the surface layer of the substrate described above through a via extending in a vertical direction of the sheet surface. On the periphery of the via connected to the signal line 255 described above, a shielding via connecting the shield layers 254 and 256 is disposed. In accordance with this, the periphery of the via connected to the signal line 255 described above is shielded. A reference numeral 311 in this diagram represents a transmission line connecting unit brought into electric contact with the signal line 255 disposed in the surface layer described above. e in this diagram illustrates a structure in which a shield layer 254 or a shield wiring is further disposed in the surface layer of the substrate described above, and a can-shield (or a shield casing) is further disposed to cover the periphery of the transmission line extracted to the surface layer. The can-shield may have a structure to which the ground electric potential is applied by being connected to the shield layer. By disposing the can-shield described above, radiation of an electromagnetic wave from the transmission line of the surface layer to the outside or reception of an electromagnetic wave (noise) from the outside in the transmission line of the surface layer can be reduced. In a case in which the substrate described above includes a plurality of transmission lines, a plurality of signal lines 255 extracted to the surface layer may be parallel-shielded using a plurality of shield wirings 257 disposed in the surface layer. It is preferable that the length of the micro strip line of the surface layer be short as possibly as can.

[Example of Time-Divisional Driving of Antenna]

Figure 115:
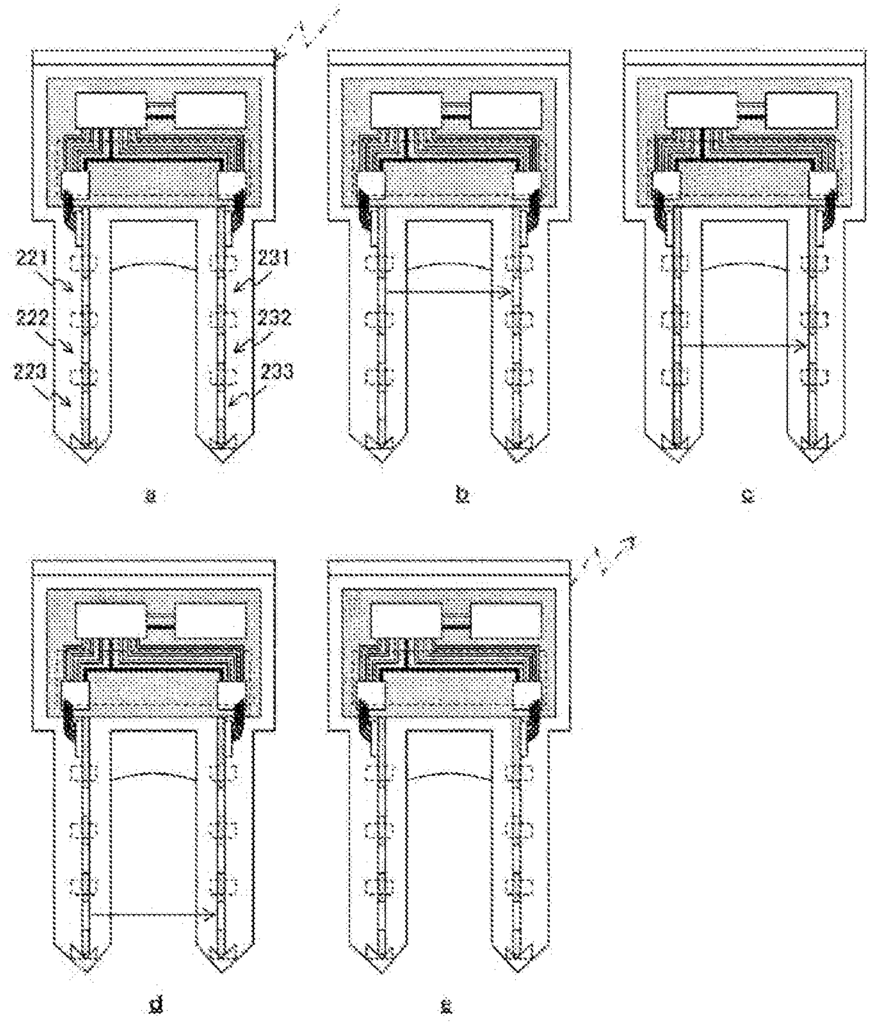
FIG. 115 is a diagram for describing time-divisional driving of antennas in the first embodiment of the present technology.

FIG. 115 is a diagram for describing measurement of the amount of moisture of soil by causing a plurality of antennas included in the sensor device 200 according to the first embodiment of the present technology to perform a scanning operation in a time divisional manner.

The sensor device 200 illustrated in FIG. 115, similar to FIG. 4*b*, is a diagram seen from a front face (seen in the Z-axis direction). As an example, the sensor device 200 illustrated in FIG. 115 includes three transmission antennas and three reception antennas. Among these three transmission antennas and three reception antennas, one transmission antenna and one reception antenna that is disposed nearest when seen from this transmission antenna form a combination of a transmission antenna and a reception antenna that is appropriate for measurement of the amount of moisture. In this specification, this combination of a transmission antenna and a reception antenna that is appropriate for measurement of the amount of moisture may be referred to as a "transmission/reception antenna pair".

The sensor device 200 illustrated in FIGS. 115*a* to 115*e* includes three sets of transmission/reception antenna pairs. More specifically, the sensor device 200 includes (1) a first transmission/reception antenna pair formed from a transmission antenna 221 and a reception antenna 231, (2) a second transmission/reception antenna pair formed from a transmission antenna 222 and a reception antenna 232, and (3) a third transmission/reception antenna pair formed from a transmission antenna 223 and a reception antenna 233.

Here, relating to a plurality of transmission/reception antenna pair included in the sensor device 200, a gap between one transmission/reception antenna pair included therein and a transmission/reception antenna pair adjacent thereto (in other words, a gap between two transmission/reception antenna pairs that are adjacent to each other) will be described. In this description, when measurement of an amount of moisture of soil is performed, in all the transmission/reception antenna pairs included in the sensor device 200, all the transmission antennas included therein are assumed to perform operations of simultaneously radiating electromagnetic waves, and all the reception antennas included therein are assumed to simultaneously perform operations of receiving electromagnetic waves.

Here, generally, in a case in which an electromagnetic wave is radiated from an antenna of a planar shape, it is difficult to radiate an electromagnetic wave with high directivity only for a vertical direction with respect to a plane of the antenna, and, actually, the electromagnetic wave is radiated with a certain spread.

[First Problem]

In a case in which a gap between two transmission/reception antenna pairs that are adjacent to each other is small, for example, there is a likelihood of a part of an electromagnetic wave radiated from the transmission antenna of the second transmission/reception antenna pair being received by the reception antenna of the first transmission/reception antenna pair. In this case, the reception antenna included in the first transmission/reception antenna pair receives an electromagnetic wave radiated by the transmission antenna (a desired transmission antenna) included in the first transmission/reception antenna pair and a part of an electromagnetic wave radiated by the transmission antenna (an undesired transmission antenna) included in the second transmission/reception antenna pair with being mixed. In other words, a state in which signals are mixed is formed. In a state in which such signal mixing has occurred, there is a problem in that error occurs in a result of measurement of the amount of moisture of soil.

[Second Problem]

The larger a gap between two transmission/reception antenna pair that are adjacent to each other, the less the signal mixing described above. In accordance with this, error included in a result of measurement of the amount of moisture of soil decreases. However, in a case in which a gap between two transmission/reception antenna pairs that are adjacent to each other is large, there is a problem in that only amounts of moisture of positions of a small part of soil in which the sensor device 200 is disposed can be measured.

[Condition Under which First Problem Occur]

Here, cases in which the first problem described above occurs will be considered. As systems for measuring an amount of moisture of soil, several systems have been proposed. However, when a plurality of transmission antennas and a plurality of reception antennas are included, and an amount of moisture disposed between such transmission antennas and reception antennas is measured, in a case in which a plurality of these antennas are simultaneously operated, an electromagnetic wave is received not only from a desired antenna but also from an undesired antenna, and error occurs in a reception result, which is the first problem described above is, originally, a problem due to radiation ranges (or directivity) of electromagnetic waves radiated from transmission antennas.

For this reason, the first problem described above is a problem that is unique to a sensor device that includes transmission antennas and reception antennas and measures an amount of moisture in a medium disposed between such antennas by transmitting and receiving electromagnetic waves between such antennas.

[Means for Solving First and Second Problem]

In order to simultaneously solve these two problems, in other words, (1) relating to soil in which the sensor device 200 is disposed, a density of positions at which measurement of an amount of moisture is performed is raised (in other words, amounts of moisture are measured at as many positions as possible in soil in which the sensor device 200 is disposed), and (2) in order to reduce error included in measurement results, the sensor device 200 according to the present invention measures amounts of moistures of soil by causing a plurality of antennas included therein to perform scanning operations in a time divisional manner. Thus, the sensor device 200 includes a configuration for causing a plurality of antennas included therein to perform scanning operations in a time divisional manner, and a measurement unit 312 included in the sensor device 200 performs control for measuring amounts of moisture between antennas by causing the plurality of antennas to perform scanning operations in a time divisional manner. When an overview of an operation of measurement by causing the sensor device 200 to perform scanning operations in a time divisional manner (time-divisional scanning measurement operations) is described in brief, (1) among a plurality of transmission/reception antenna pairs included in the sensor device 200, one transmission/reception antenna pair is selected at each time in accordance with an order set in advance, and an operation for measuring moisture of soil (a measurement operation, for example, an operation of transmitting an electromagnetic wave from the transmission antenna for measurement, an operation of receiving a transmitted electromagnetic wave using the reception antenna and detecting an electromagnetic wave using a receiver of the measurement unit, or an operation of performing a transmission operation and an electromagnetic wave detection operation and acquiring an amount of moisture of soil from a detection result) is performed. Then, (2) until the measurement operations described above are performed, and results thereof are acquired for all the transmission/reception antenna pairs set in advance, the measurement operation described above is performed in order for each transmission/reception antenna pair. The overview of the time-divisional scanning measurement is as described above. Details thereof will be described as below.

[Operation of Time-Divisional Scanning Measurement]

An operation of measuring an amount of moisture of soil by causing a plurality of antennas included in the sensor device 200 to perform scanning operations in a time divisional manner will be described with reference to a to e in FIG. 115.

As illustrated in a in this diagram, when an instruction for measurement of moisture is received at certain timing 1, the sensor device 200 wakes up. As illustrated in b in this diagram, at timing 2, the sensor device 200 performs measurement of moisture using a first transmission/reception antenna pair.

Subsequently, as illustrated in c in this diagram, at timing 3, the sensor device 200 performs measurement of moisture using a second transmission/reception antenna pair. As illustrated in d in this diagram, at timing 4, the sensor device 200 performs measurement of moisture using a third transmission/reception antenna pair.

As illustrated in e in this diagram, at timing 5, the sensor device 200 transmits measurement results acquired by all the antennas. Thereafter, the sensor device 200 transitions to a sleep mode. As illustrated in this diagram, the sensor device 200 performs measurement of moisture in order for each of a plurality of sets of antennas while using each set of a transmission antenna and a reception antenna and dividing a time frame in which measurement is performed. Finally, over the whole area of soil in which the plurality of antennas are disposed, results of measurements of moisture can be acquired. This control corresponds to time-divisional scanning measurement driving of Constituent element (6).

[Hardware Configuration for Performing Time-Divisional Scanning Measurement]

Here, as a hardware configuration for performing time-divisional scanning measurement, a configuration (FIG. 3) including a plurality of transmission lines connecting the measurement unit substrate 311 in Constituent element (6) and a plurality of transmission antennas and a first comparative example (FIG. 116) not including a plurality of transmission lines connecting the measurement unit substrate 311 and a plurality of reception antennas will be considered.

Figure 116:
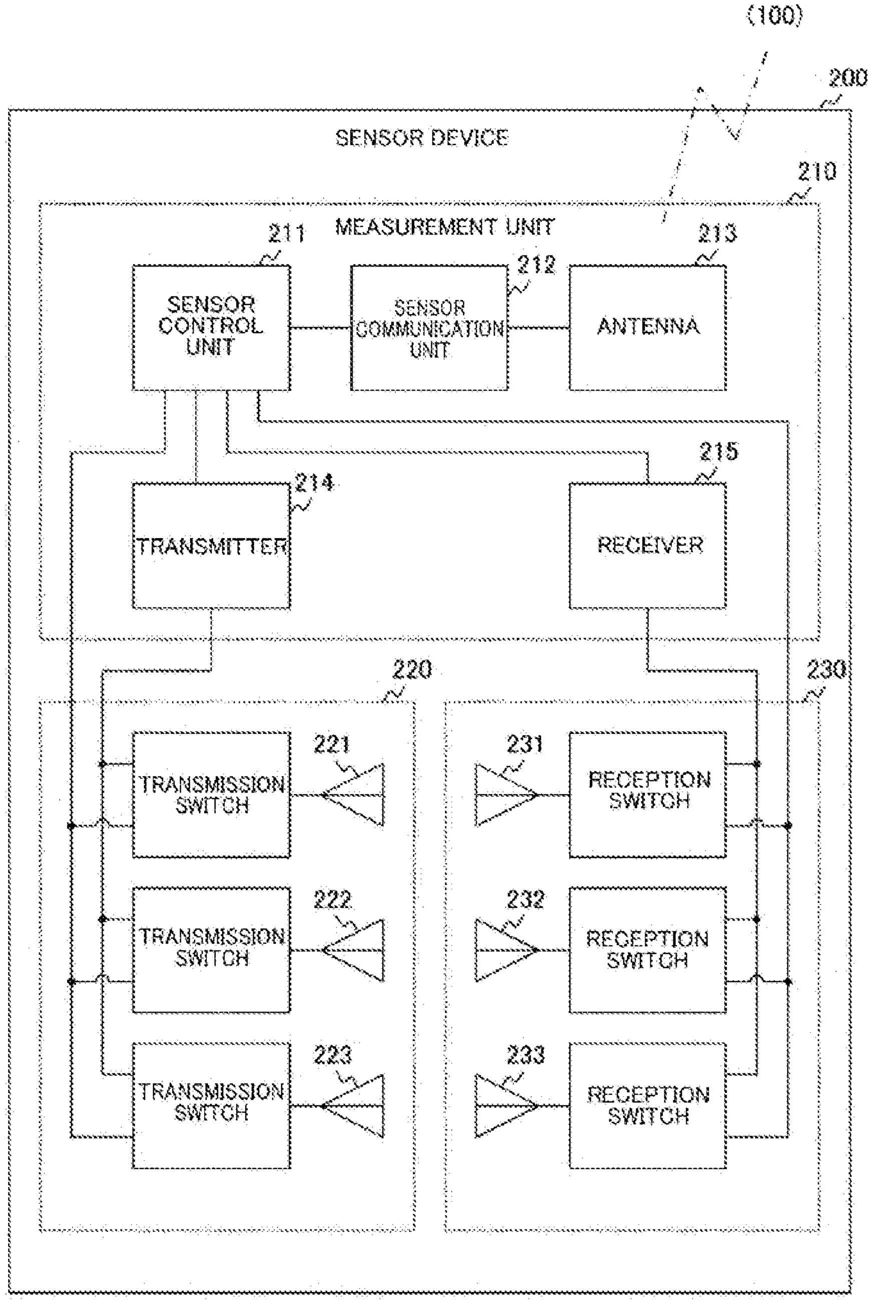
FIG. 116 is a block diagram illustrating one configuration example of a sensor device according to a first comparative example.

FIG. 116 is a block diagram illustrating one configuration example of a sensor device according to a first comparative example. In the first comparative example, one transmission line branches into a plurality of transmission lines in each of a transmission side and a reception side and is connected to a plurality of antennas.

In this first comparative example, since a plurality of branches are present on a transmission line, reflection of signals occurs at tip ends of the plurality of branches and becomes noises, whereby measurement accuracy of the amount of moisture of soil is degraded. In addition, by also disposing switches of a plurality of antennas disposed in a casing, a volume of a probe casing housing these is larger than a volume of the probe casing 320 according to the present invention. In accordance with this, when a probe casing of a moisture sensor device is inserted into soil, the probe casing pushes more soil, the pushed soil participates to soil that is a measurement target part, and the density of the soil that is the measurement target part becomes higher than the density of the original soil. Also in accordance with this, the measurement accuracy of the amount of moisture of soil is degraded.

Next, a second comparative example in which the transmission switch 216 and the reception switch 217 are not disposed will be considered.

Figure 117:
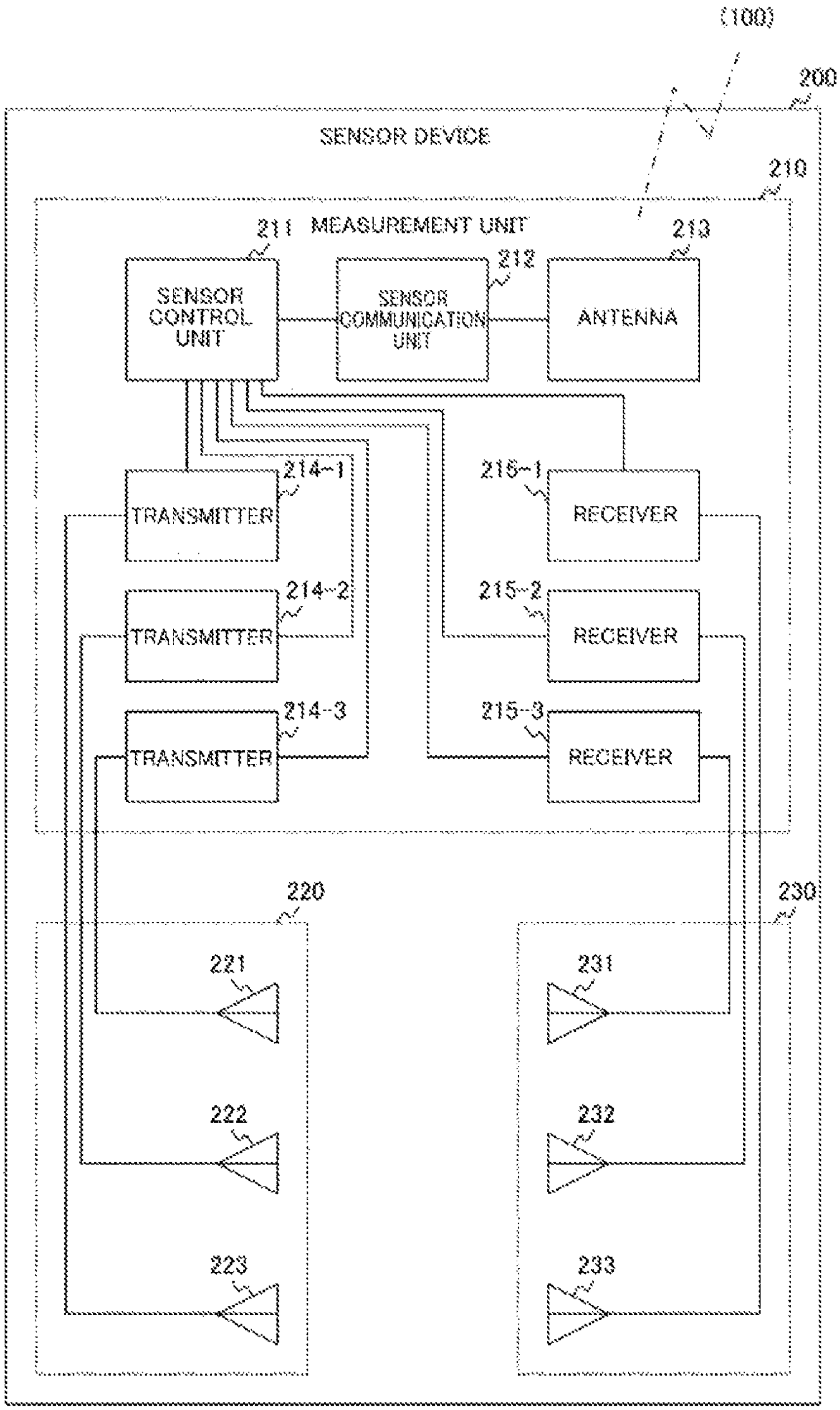
FIG. 117 is a block diagram illustrating one configuration example of a sensor device according to a second comparative example.

FIG. 117 is a block diagram illustrating one configuration example of a sensor device according to the second comparative example. In the second comparative example, on a transmission side and a reception side, a transmitter or a receiver is disposed in a measurement unit substrate 311 for each antenna.

In this second comparative example, a plurality of transmitters and a plurality of receivers corresponding to the number of antennas included in the sensor device need to be disposed. For this reason, the area of the measurement unit substrate 311 is larger than that of a case in which only one set of a transmitter and a receiver is disposed, and a length of transmission lines on the measurement unit substrate 311 that connect them and antennas is essentially increased. As a result, in a case in which one set of a transmitter and a receiver on the substrate is operated, the power consumption of the second comparative example in which the length of the transmission lines is long essentially increases.

Furthermore, in the second comparative example, in accordance with an increase in the area of the measurement unit substrate 311, the measurement unit casing 310 housing the measurement unit substrate 311 is essentially large. In this case, for example, a horizontal wind blows against the sensor device, there is a high likelihood of the sensor casing 305 being broken in a boundary between the measurement unit casing 310 against which the horizontal wind has blown and the probe casing 320 buried in soil.

In addition, in the second comparative example, in accordance with an increase in the area of the measurement unit substrate 311, for example, there are problems such as water sprinkling in a horizontal direction using a sprinkler being blocked by the measurement unit casing 310, and, for example, in a case in which a plant is short in an initial stage of growth, emission of sun light to the plant or a plant adjacent thereto being blocked, and the like.

The sensor device 200 according to the present invention, as hardware for performing time-divisional scanning measurement and as hardware not causing the problems described above occurring in the first and second comparative examples, includes the following configurations illustrated in FIG. 3. In other words, (1) transmission lines for transmission 218-1 to 218-3 connecting transmission antenna and a measurement circuit 210 are independently included for respective transmission antennas such that only one transmission antenna to be operated can be selected from among all the transmission antennas 221 to 223 included in the sensor device 200. In accordance with this, a plurality of the transmission lines for transmission are included. (2) As a device selecting one transmission antenna and one transmission line for transmission among all the transmission antennas 221 to 223 included in the sensor device 200 and the transmission lines for transmission 218-1 to 218-3 connected thereto, a transmission switch 216 is included between a transmitter 214 and the plurality of the transmission lines for transmission 218-1 to 218-3. (3) Transmission lines for reception 219-1 to 219-3 connecting respective reception antennas and the measurement circuit 210 are independently included for respective reception antennas such that only one reception antenna to be operated can be selected among all the reception antennas 231 to 233 included in the sensor device 200. In accordance with this, a plurality of the transmission lines for reception are included. (4) As a device selecting one reception antenna and one transmission line for reception among all the reception antennas 221 to 223 included in the sensor device 200 and transmission lines for reception 219-1 to 219-3 connected thereto, a reception switch 217 is included between the receiver 215 and a plurality of the transmission lines for reception 219-1 to 219-3.

Figure 118:
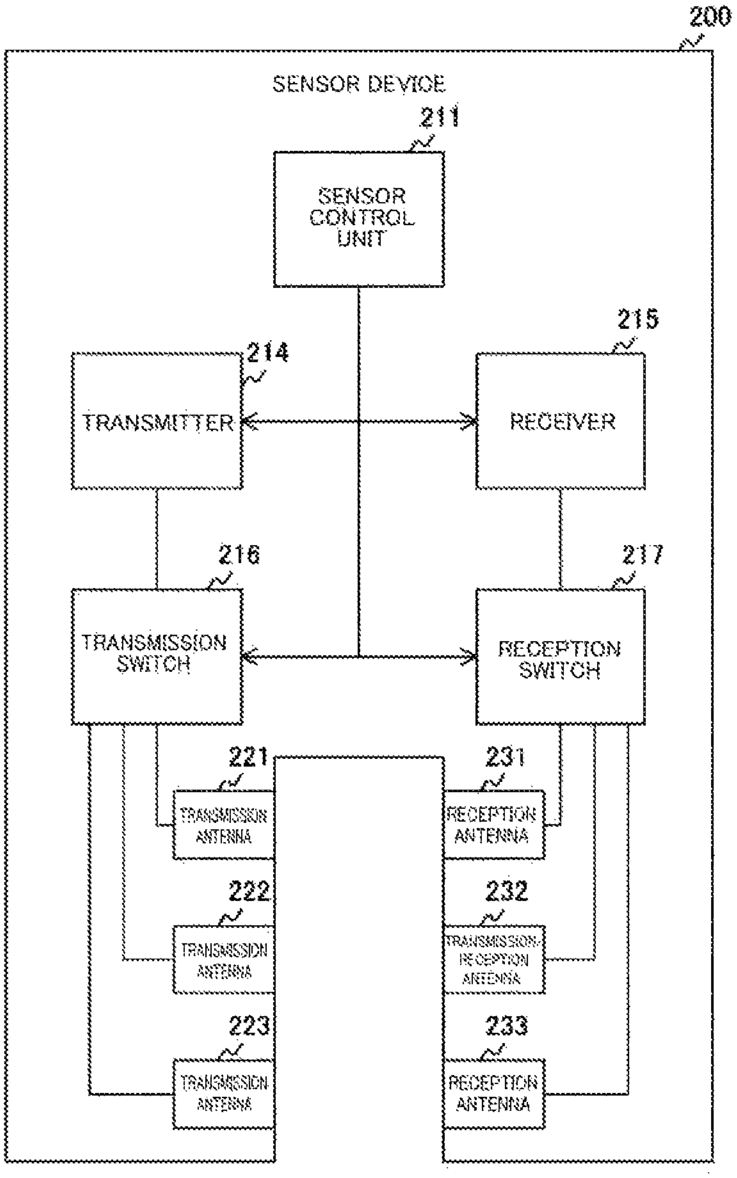
FIG. 118 is a block diagram illustrating one configuration example of a sensor device focusing on time-divisional driving of antennas in the first embodiment of the present technology.

FIG. 118 is a block diagram illustrating one configuration example in which the sensor device 200 according to the first embodiment of the present technology illustrated in FIG. 3 is simplified with focusing on time-divisional driving of antennas.

The sensor device 200 includes a transmission switch 216 and a reception switch 217, and a sensor control unit 211 controls these in a time divisional manner, thereby selecting one transmission line for transmission and one transmission line for reception. In accordance with this, an antenna of a desired depth direction can be selected.

In addition, as described above with reference to the measurement circuit 210 illustrated in FIG. 3 and the measurement unit 312 illustrated in FIG. 4, the measurement unit 312 illustrated in FIG. 4 and the measurement circuit 210 including the sensor control unit 211, the transmitter 214, the transmission switch 216, the receiver 215, and the reception switch 217 may be configured using one semiconductor device or may be configured using a plurality of semiconductor devices. In other words, the sensor control unit 211, the transmitter 214, the transmission switch 216, the receiver 215, and the reception switch 217 illustrated in FIG. 118 in which FIG. 3 is simplified may be configured using one semiconductor device or may be configured using a plurality of semiconductor devices.

FIG. 119 is a block diagram illustrating one configuration example in which a transmission switch 216 and a reception switch 217 are respectively built into a transmitter 214 and a receiver 215 as another configuration example of the sensor device 200 according to the first embodiment of the present technology. As illustrated in a in this diagram, the transmission switch 216 may be disposed inside the transmitter 214, and the reception switch 217 may be disposed inside the receiver 215. Here, the transmitter 214 and the receiver 215, for example, refer to a transmitter IC (Integrated Circuit), a receiver IC, a transmitter module, and a receiver module. In other words, a in this diagram is one example in which the measurement circuit 210 and the measurement unit 312 are configured using a plurality of semiconductor devices. In addition, it is an example in which the sensor control unit 211, the transmitter 214, and the receiver 215 are configured using different semiconductor devices. a in this diagram is an example in which the sensor control unit 211, the transmission switch 216, and the reception switch 217 are configured respectively using different semiconductor devices. As illustrated in b in this diagram, in place of the transmitter 214 and the receiver 215, a transceiver 214-4 having functions thereof may be disposed as well. In addition, in place of the transmission switch 216 and the reception switch 217, a switch 216-1 having functions thereof may be disposed, and the switch 216-1 may be built into the transceiver 214-4. In other words, b in this diagram is another example in which the measurement circuit 210 and the measurement unit 312 are configured using a plurality of semiconductor devices. In addition, it is an example in which the sensor control unit 211 and the transceiver 214-4 are configured respectively using different semiconductor devices. b in this diagram is an example in which the sensor control unit 211 and the switch 216-1 are configured using different semiconductor devices.

FIG. 120 is a block diagram illustrating one configuration example of a sensor device 200 in which a switch is disposed only in a reception side as yet another configuration example of the sensor device 200 according to the first embodiment of the present technology. As illustrated in a in this diagram, a configuration in which the transmission switch 216 is not disposed may be employed. In a in this diagram, a sensor control unit 211, a transmitter 214, a receiver 215, and a reception switch 217 may be configured using one semiconductor device or may be configured using different semiconductor devices. As illustrated in b in this diagram, the reception switch 217 may be disposed inside the receiver 215 without disposing the transmission switch 216. In b in this diagram, the sensor control unit 211, the transmitter 214, and the receiver 215 may be configured using one semiconductor device or may be configured using different semiconductor devices.

As illustrated in FIGS. 119 and 120, by having the switch built therein, compared to the case illustrated in FIG. 118, space saving can be achieved. In FIG. 120, since the switch is disposed only on the reception side, the configuration is simpler than that illustrated in FIG. 119, and space saving can be further achieved. In addition, although the sensor device 200 illustrated in FIG. 120 cannot avoid signal mixing at the time of measurement described above, an effect of being able to decrease the size of the device can be acquired.

Figure 121:
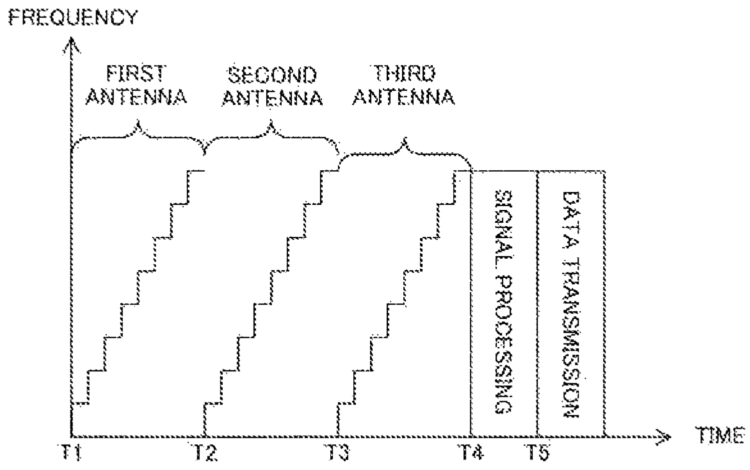

FIG. 121 is an example of a timing diagram of time divisional driving according to the first embodiment of the present technology.

Figure 122:
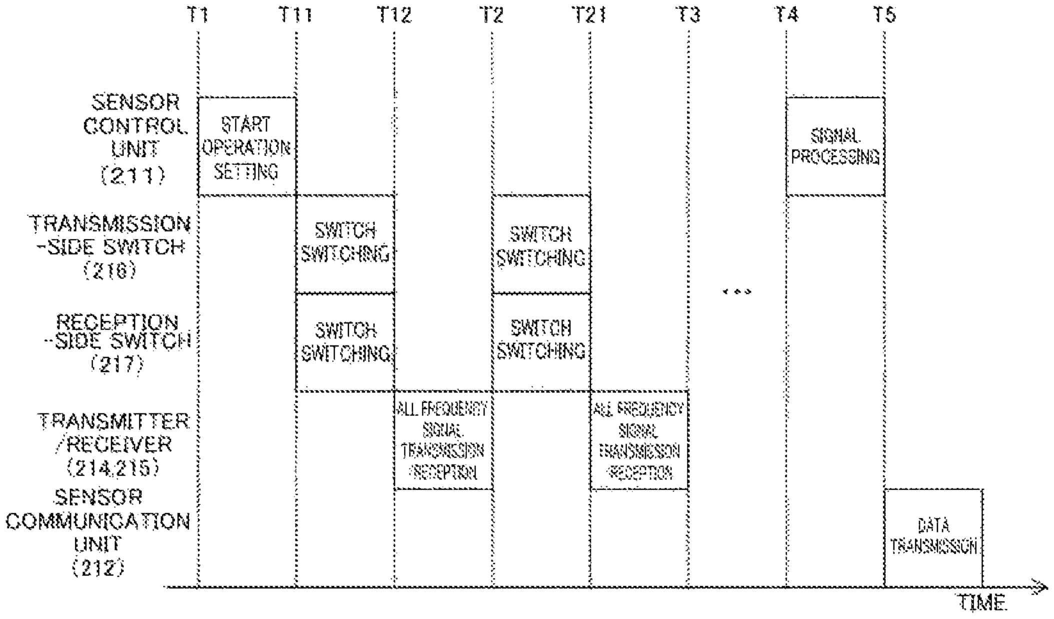

FIG. 122 is an example of a timing diagram illustrating an operation of each unit disposed inside the sensor device 200.

As illustrated in FIGS. 121 and 122, after sleeping for a period scheduled in advance, the sensor device 200 starts to operate. Each of the transmission switch 216 and the reception switch 217 selects one antenna among a plurality of antennas in a time divisional manner. While changing a frequency used for measurement in a stepped pattern with respect to time for one antenna that has been selected, each of the transmitter 214 and the receiver 215 performs a transmission, reception, and wave detecting operation for measurement for each of all the frequencies used for measurement. In the transmission, reception, and wave detecting operation, transmission, reception, and wave detection of signals, AD conversion of a complex amplitude that is a detection result, and storage of a result of the conversion into a memory are performed. For example, the memory is disposed inside the measurement unit substrate 311. In addition, in order to perform a wave detecting operation of one time, it is preferable that an electromagnetic wave to be detected be transmitted from a transmission antenna to a reception antenna over a plurality of periods. In other words, in a transmission, reception, and wave detecting operation of one time, it is preferable that an electromagnetic wave corresponding to a plurality of periods be transmitted from a transmission antenna, and this be detected using the measurement circuit 210.

In addition, although details will be described below, intention of performing measurement by changing the frequency will be briefly described here. After performing the transmission, reception, and wave detecting operation described above (in other words, transmission, reception, and wave detection of signals, AD conversion of a complex amplitude that is a wave detection result, and storage of a result of the conversion into a memory), the moisture measuring system 100 according to the first embodiment of the present technology calculates a reflection coefficient and a transmission coefficient to be described below from the wave detection result (the complex amplitude), acquires an impulse response by performing an inverse Fourier transform of these, acquires a delay time on the basis of this, and further acquires an amount of moisture on the basis of this. In order to acquire one impulse response, the moisture measuring system 100 performs a transmission, reception, and wave detecting operation for a plurality of frequencies. This is the intention of performing measurement by changing the frequency described with reference to FIG. 121.

When execution of the operation described above completely ends for all the frequencies for which measurement is performed using one transmission/reception antenna pair, the sensor device 200 performs the operation described above in a time divisional manner for each of the remaining transmission/reception antenna pairs. Selection of a transmission/reception antenna pair is performed in an order set in advance. This order may be selected in accordance with order of positions of disposed antennas, and arbitrary order different from this may be set in advance.

When the execution of the operation described above ends for all the transmission/reception antenna pairs, the sensor control unit 211 performs signal processing for each transmission/reception antenna pair. For example, this signal processing is a process of calculating a reflection coefficient and a transmission coefficient from a wave detection result (a complex amplitude) for each frequency, acquiring an impulse response by performing an inverse Fourier transform thereof, and acquiring a delay time on the basis of this.

When the signal process ends for each of all the transmission/reception antenna pairs, the sensor communication unit 212 wirelessly transmits signal processing result data of all the transmission/reception antenna pairs to the central processing device altogether.

The central processing device 150 calculates an amount of moisture of soil for each transmission/reception antenna pair on the basis of the received results. When wireless communication ends, the sensor device 200 sleeps again for a period scheduled in advance.

In addition, in place of the central processing device 150, the sensor device 200 may calculate an amount of moisture of soil for each transmission/reception antenna pair and transmit calculation results to the central processing device 150. In addition, switch switching of the transmission side and switch switching of the reception side may be simultaneously performed, the switch switching of the transmission side may be performed first, or the switch switching of the reception side may be performed first. In addition, a method for changing the frequency in a stepped pattern may be in a direction for going up the steps or a direction for going down the steps. Alternatively, by replacing the order of the frequency, the order may be changed to be discontinuous or in arbitrary order set in advance.

In addition, in order to improve accuracy of measurement (in order to improve reproducibility of a measurement result), the transmission, reception, and wave detecting operation for measurement described above that is performed for one measurement frequency of one transmission/reception antenna pair may be repeated a plurality of number of times (for example, 100 times).

For example, in a case in which the operation is repeated 100 times for each measurement frequency of each antenna, the sensor device 200 performs the transmission, reception, and wave detecting operation 100 times for a first frequency of the first transmission/reception antenna pair and thereafter, performs the transmission, reception, and wave detecting operation 100 times for a second frequency of the first transmission/reception antenna pair. When the repetitive operation for each of remaining frequencies ends for the first transmission/reception antenna pair, the repetitive operation described above may be performed for each of remaining transmission/reception antenna pair. In addition, the order in which the operation is performed is not limited to that described above as long as operation results of a predetermined number of times are acquired for each measurement frequency of each transmission/reception antenna pair.

The control example illustrated in FIGS. 121 and 122 will be referred to as Control example a.

Figure 123:
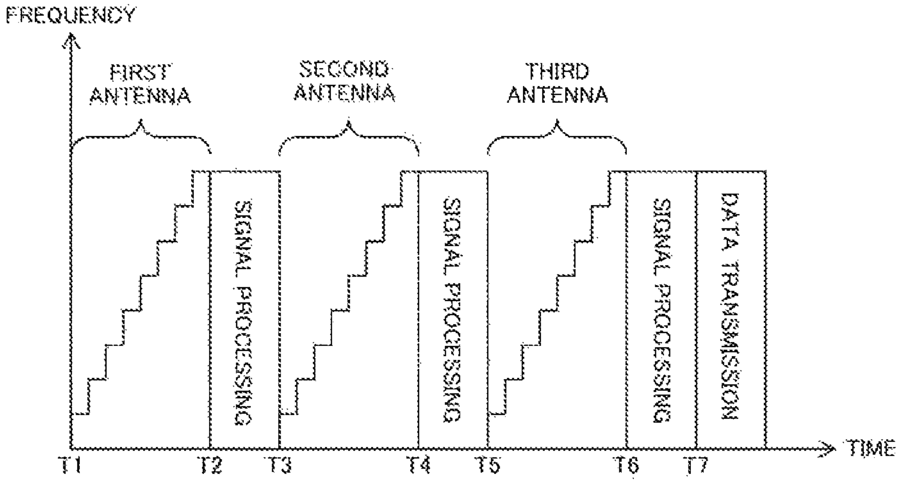

FIG. 123 is an example of a timing diagram of time divisional driving acquired when timings of signal processing according to the first embodiment of the present technology are changed.

Figure 124:
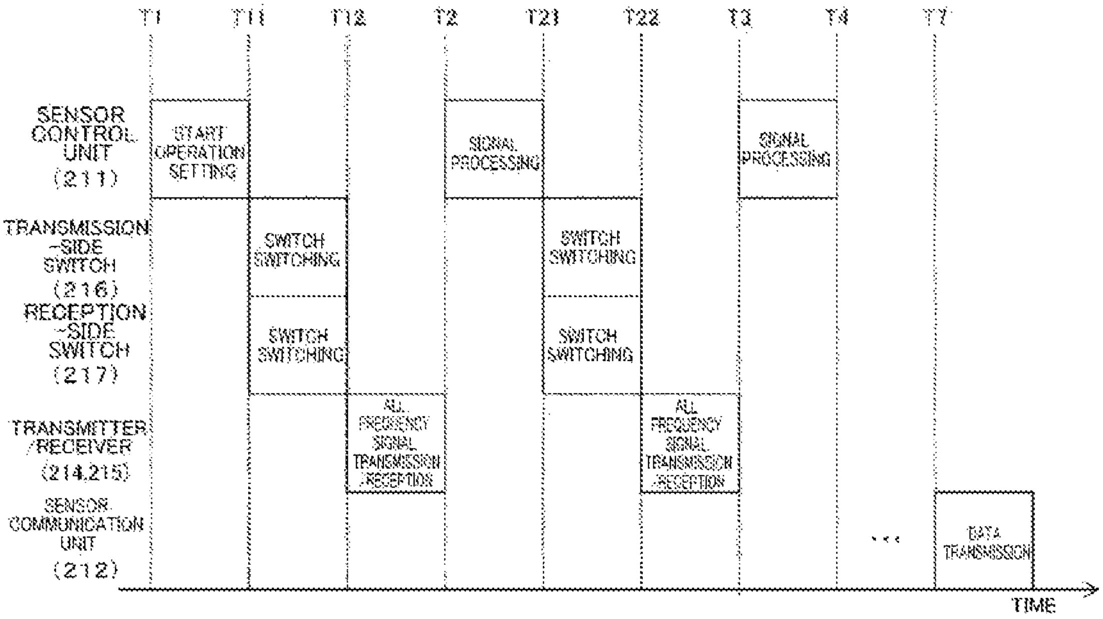

FIG. 124 is an example of a timing diagram illustrating operations of respective units disposed inside of the sensor device acquired when timings of signal processing according to the first embodiment of the present technology are changed.

As illustrated in FIGS. 123 and 124, timings of the signal processing can be changed. In this Control example b, the sensor control unit 211 performs signal processing when a series of transmission, reception, and wave detecting operations for a plurality of frequencies ends. In accordance with this, a data amount of detection results to be maintained for performing the signal processing described above can be configured to be smaller than that of Control example a.

More specifically, in a case in which the sensor device includes n transmission/reception antenna pairs, the scale of the memory can be reduced to 1/n of the original scale. In addition, the number of times wireless transmission of data to be described below is performed may be 1/n of that of Control example c. In accordance with this, in each wireless transmission operation, the number of times processing performed before and after transmission of payload data is performed is reduced to 1/n, and power consumption required for this processing becomes 1/n of that of Control example c to be described below.

Figure 125:
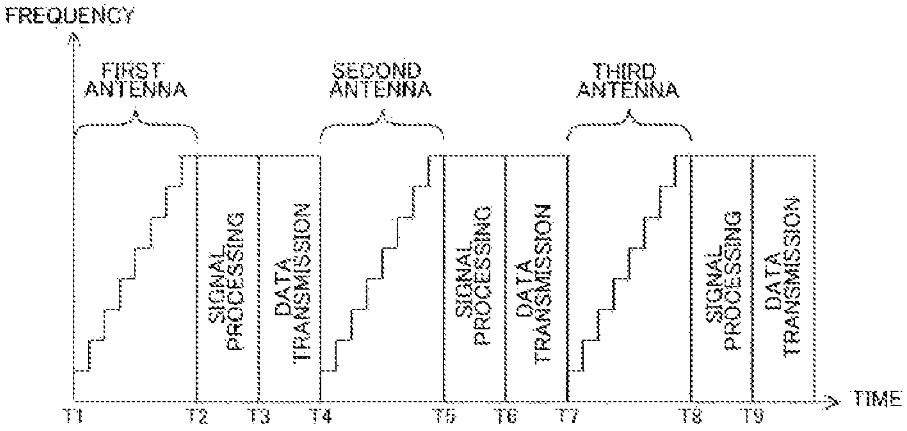

FIG. 125 is an example of a timing diagram of time divisional driving acquired when timings of signal processing and data transmission according to the first embodiment of the present technology are changed.

Figure 126:
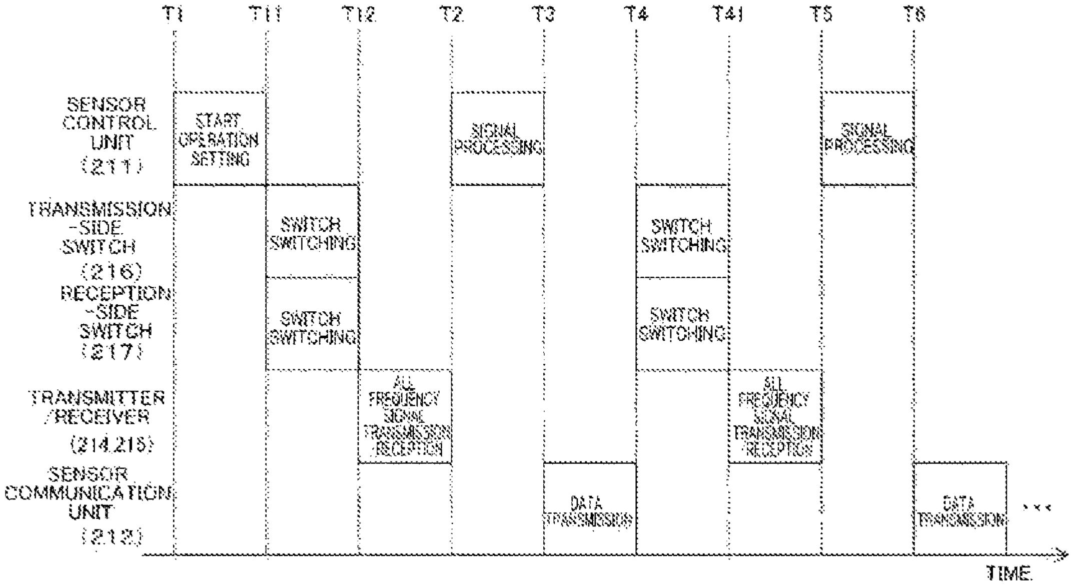

FIG. 126 is an example of a timing diagram illustrating operations of respective units disposed inside of the sensor device acquired when timings of signal processing and data transmission according to the first embodiment of the present technology are changed.

As illustrated in FIGS. 125 and 126, timings of signal processing and data transmission may be changed as well. In this Control example c, for each transmission/reception antenna pair, when all the transmission, reception, and wave detecting operations for a series of frequencies and signal processing following this end, the sensor communication unit 212 wirelessly transmits acquired data. In accordance with this, the amount of data of signal processing results to be stored for performing wireless communication is smaller than that of Control example b. More specifically, in a case in which the sensor device includes n transmission/reception antenna pairs, the scale of the memory used for storing data of the signal processing results may be 1/n of that of Control example b.

Figure 127:
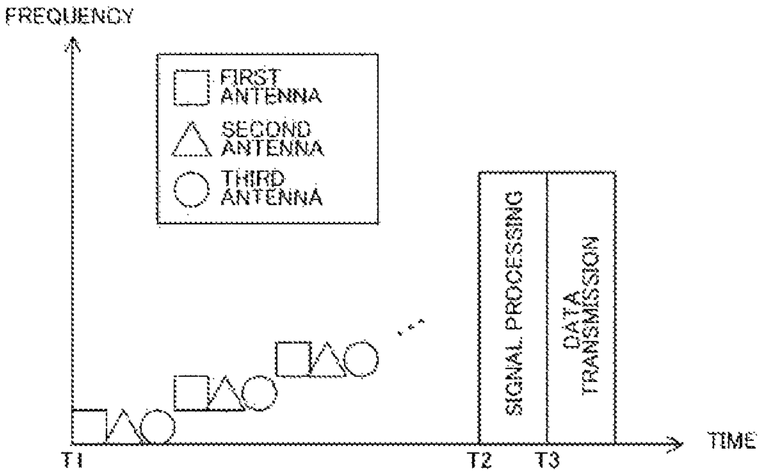

FIG. 127 is an example of a timing diagram of time divisional driving acquired when the order of the transmission, reception, and wave detecting operation according to the first embodiment of the present technology is changed.

Figure 128:
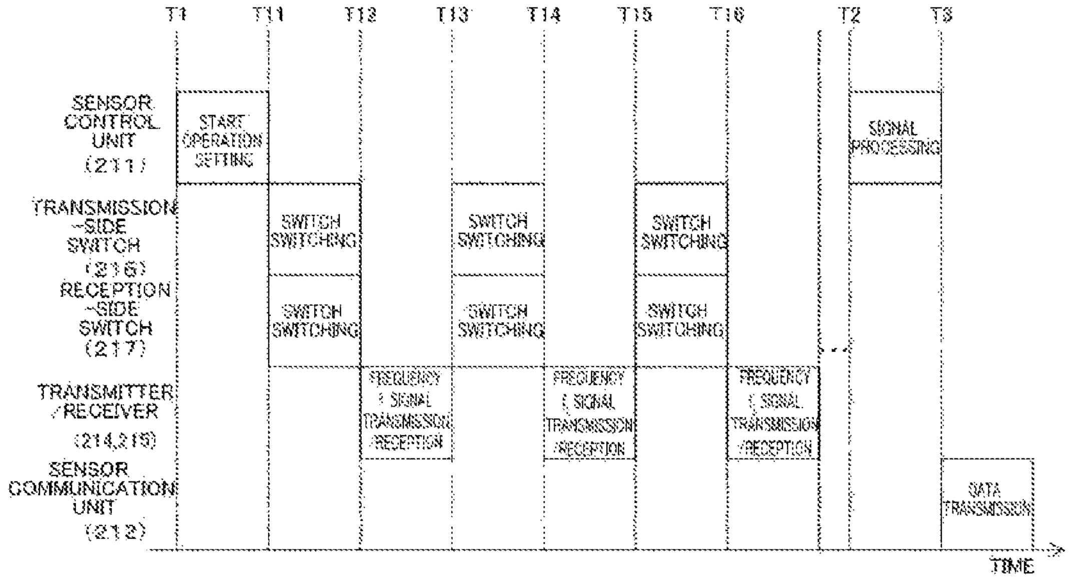

FIG. 128 is an example of a timing diagram illustrating operations of respective units disposed inside the sensor device acquired when the order of the transmission, reception, and wave detecting operation according to the first embodiment of the present technology is changed.

As illustrated in FIGS. 127 and 128, the order of the transmission, reception, and wave detecting operation can be changed as well. In this Control example d, the transmitter 214 and the receiver 215 change the frequency in a stepped manner, and, for each frequency, the transmission switch 216 and the reception switch 217 selects all the transmission/reception antenna pairs in order. In accordance with this, a data amount of signal processing results to be stored for performing wireless transmission is configured to be smaller than that of Control example b. More specifically, in a case in which the sensor device includes n transmission/reception antenna pairs, the scale of the memory used for storing the data of the signal processing results may be 1/n of that of Control example b.

A difference between the operation of Control example d described with reference to FIGS. 127 and 128, in other words, "the operation of the transmitter 214 and the receiver 215 changing the frequency in a stepped manner and, for each frequency, the transmission switch 216 and the reception switch 217 selecting all the transmission/reception antenna pairs in order and performing a transmission, reception, and wave detecting operation" and the operation of Control example a described above will be described by contrasting them with each other.

In the operation of Control example a described with reference to FIGS. 121 and 122, as described above, (1) by using one transmission/reception antenna pair, "while changing the frequency of an electromagnetic wave, in each of all the frequencies for which measurement is performed, an operation of transmitting, receiving, and detecting an electromagnetic wave in order (a transmission, reception, and wave detecting operation) is performed, (2) after execution of the operation described above for one transmission/reception antenna pair ends, among a plurality of transmission/reception antenna pairs included in the sensor device 200, in each of remaining transmission/reception antenna pairs used for measurement, "an operation of transmitting, receiving, and detecting an electromagnetic wave in order for each of all the frequencies for which measurement is performed while changing the frequency of an electromagnetic wave" is performed.

On the other hand, in the operation of Control example d illustrated in FIGS. 127 and 128, as described above, (1) for one frequency, "while performing switching of a transmission/reception antenna pair to transmit and receive an electromagnetic wave, among a plurality of transmission/reception antenna pairs included in the sensor device 200, in each of all the transmission/reception antenna pairs used for measurement, an operation of transmitting, receiving, and detecting an electromagnetic wave in order (a transmission, reception, and wave detecting operation)" is performed, and (2) after execution of the operation described above for one frequency ends, for each of remaining frequencies, "while performing switching of a transmission/reception antenna pair, among a plurality of transmission/reception antenna pairs included in the sensor device 200, in each of all the transmission/reception antenna pairs performing measurement, an operation of transmitting, receiving, and detecting an electromagnetic wave in order" is performed.

The example illustrated in FIG. 127 as an example of Control example d illustrates an example in which (i) while performing switching of a transmission/reception antenna pair transmitting and receiving an electromagnetic wave among a plurality of transmission/reception antenna pairs included in the sensor device 200, in each of all the transmission/reception antenna pair performing measurement, an operation of transmitting, receiving, and detecting an electromagnetic wave is performed in order by using a first frequency, (ii) after execution of the operation ends using the first frequency, by using a second frequency, while performing switching of a transmission/reception antenna pair transmitting and receiving an electromagnetic wave, in each of all the transmission/reception antenna pair performing the measurement described above, an operation of transmitting, receiving, and detecting an electromagnetic wave is performed in order, (iii) after execution of the operation described above ends using the second frequency, by using a third frequency, while performing switching of a transmission/reception antenna pair transmitting and receiving an electromagnetic wave, in each of all the transmission/reception antenna pairs performing the measurement described above, an operation of transmitting, receiving, and detecting an electromagnetic wave is performed in order, (iv) after execution of the operation described above ends using the third frequency, in remaining frequencies used for measurement, an operation similar to that described above, in other words, while performing switching of a transmission/reception antenna pair transmitting and receiving an electromagnetic wave, among a plurality of transmission/reception antenna pairs included in the sensor device 200, in each of all the transmission/reception antenna pairs performing measurement, an operation of transmitting, receiving, and detecting an electromagnetic wave is repeated in order, and (v) for all the frequencies used for measurement, when execution of the operation of transmitting, receiving, and detecting an electromagnetic wave ends in each of all the transmission/reception antenna pairs used for measurement, signal processing is performed on results acquired by the transmission, reception, and wave detecting operation, and data of a result of the signal processing is transmitted.

This operation can be also represented as in FIG. 349 as a timing diagram illustrating operations of respective units disposed inside of the sensor device. FIG. 349 is a timing diagram illustrating operations of respective units disposed inside a sensor device acquired when the order of the transmission, reception, and wave detecting operation according to the first embodiment of the present technology is changed and illustrates operations (i) to (v) described above.

In addition, when the numbers of times a transmitter performs switching of a frequency of a transmission signal between start-up to sleep of the sensor device 200 are compared with each other, among Control examples a to d, the number of times of switching of the frequency is the smallest in Control example d. Compared to Control examples a, b, and c, Control example d can shorten a total time in which frequency switching of a PLL (Phase Locked Loop) inside the transmitter 214 is performed between start-up to sleep of the sensor device 200 the most, and thus a measurement time can be shortened, and low power consumption can be implemented. Generally, a frequency switching time of a PLL is about 100 microseconds (s), and a switching time of the transmission switch 216 is about 100 nanoseconds (ns). When the number of channels is 161, and the number of antennas is 3, times relating to switching in Control examples a, b, and c are acquired using the following expression.

$$161\times3\times100\ \mu s+50\ ns\times3=0.048\ s \quad \text{Expression 1}$$

On the other hand, a time relating to switching in Control example d is acquired using the following expression.

$$161\times1\times100\ \mu s+50\ ns\times161\times3=0.016\ s \quad \text{Expression 2}$$

From Expression 1 and Expression 2, a time relating to switching becomes about ⅓.

Figure 129:
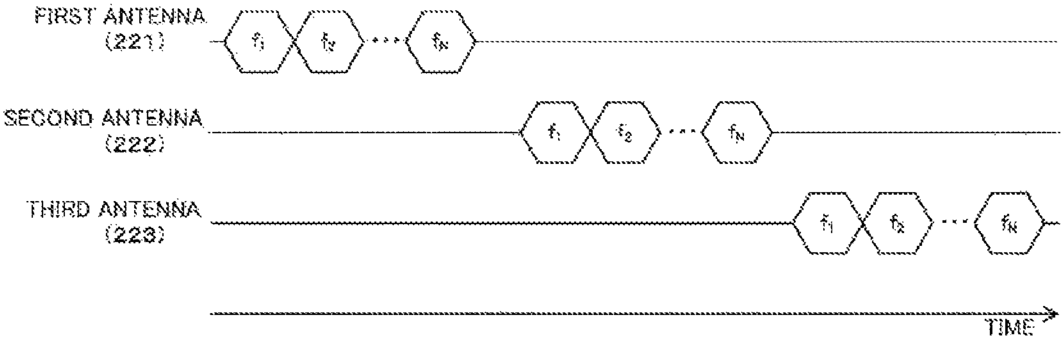

FIG. 129 is a diagram illustrating an example of a transmission signal for each antenna (for each transmission/reception antenna pair) in Control examples a, b, and c according to the first embodiment of the present technology. As illustrated in this diagram, a first antenna (a transmission antenna 221) sequentially outputs transmission signals of frequencies $f_1$ to $f_N$, and next, a second antenna (a transmission antenna 222) sequentially outputs transmission signals of frequencies $f_1$ to $f_N$. Then, next, a third antenna (a transmission antenna 223) sequentially outputs transmission signals of frequencies $f_1$ to $f_N$.

Figure 130:
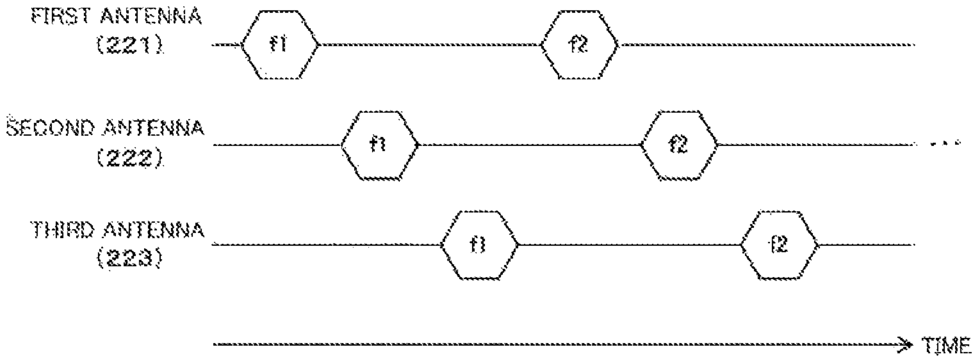

FIG. 130 is a diagram illustrating an example of a transmission signal of each antenna (each transmission/reception antenna pair) of Control example d according to the first embodiment of the present technology. As illustrated in this diagram, the first to third antennas sequentially output transmission signals of the frequency f1, and next, the first to third antennas sequentially output transmission signals of a frequency f2. Hereinafter, similar control is performed up to the frequency $f_N$.

[Configuration Example of Casing]

Figure 131:
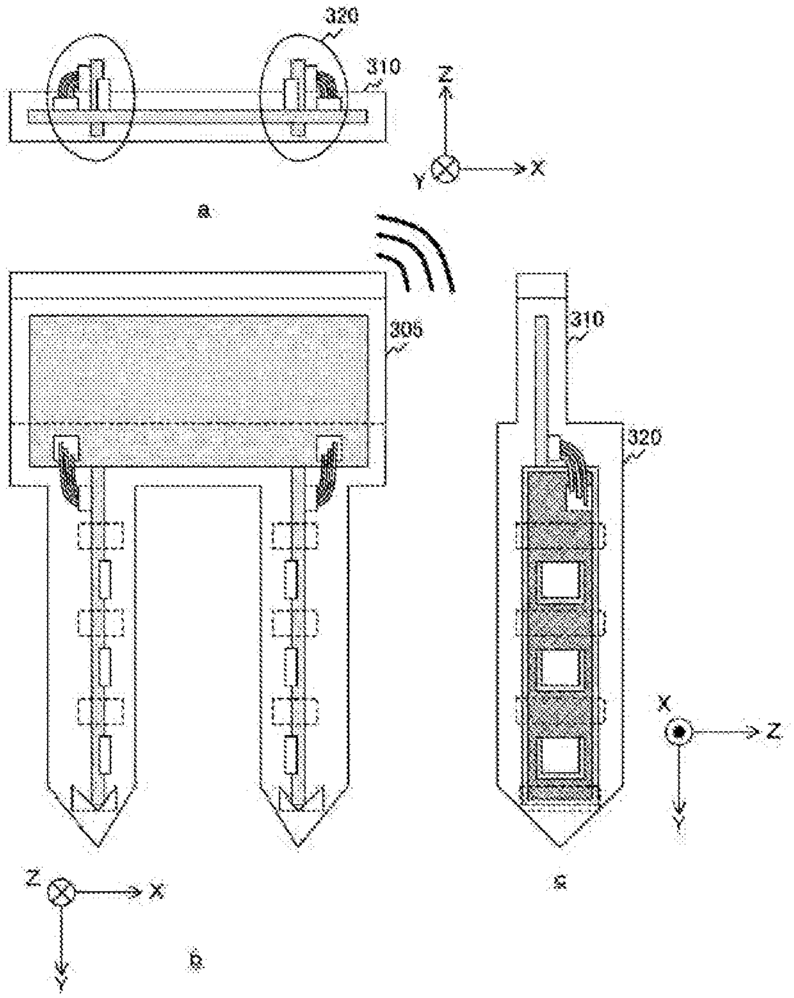

FIG. 131 is a diagram illustrating another example of the sensor device 200 according to the first embodiment of the present technology. When the sensor device 200 illustrated in FIG. 4 and the sensor device 200 illustrated in FIG. 131 are compared with each other, while the former (FIG. 4) includes a battery inside the measurement unit casing 310, the latter (FIG. 131) does not include a battery inside the measurement unit casing 310 and is a form in which power is assumed to be supplied from outside of the sensor device 200 or the sensor device 200 is assumed to generate power using a solar cell or the like.

In the sensor device 200 illustrated in FIG. 131, the measurement unit substrate 311 is disposed such that sizes in the X-axis direction and the Y-axis direction are larger than a size in the Z-axis direction. In other words, the measurement unit substrate 311 is disposed in a state in which a maximum face included in the measurement unit substrate 311 extends in a direction perpendicular to the ground surface. When described using a relation between two probe casings 320 included in the sensor device 200, the measurement unit substrate 311 is disposed such that one plane including two segments including a center line of a transmission probe casing 320*a* representing an extending direction of the transmission probe casing 320*a* and a center line of a reception probe casing 320*b* representing an extending direction of the reception probe casing 320*b* and a maximum face included in the measurement unit substrate 311 are in parallel with each other.

In addition, in the sensor device 200 illustrated in FIG. 131, also a measurement unit casing 310 housing the measurement unit substrate 311 is similarly disposed such that sizes in the X-axis direction and the Y-axis direction are larger than a size in the Z-axis direction. In other words, the measurement unit casing 310 is disposed in a state in which a maximum face included in the measurement unit casing 310 extends in a direction perpendicular to the ground surface. When described using a relation between two probe casings 320 included in the sensor device 200, the measurement unit casing 310 is disposed such that one plane including two segments including the center line of the transmission probe casing 320*a* representing an extending direction of the transmission probe casing 320*a* and the center line of the reception probe casing 320*b* representing an extending direction of the reception probe casing 320*b* and a maximum face included in the measurement unit casing 310 are in parallel with each other.

The sensor device 200 illustrated in FIG. 131 includes this disposition structure and thus, compared to a form not including this disposition structure, obtains an effect of rainfalls or sprinkle water supplied from the upper side of the sensor device 200 being easily inserted into soil that is a measurement target for an amount of moisture positioned between two probe casings 320 (in other words, it can be easily the same as soil in which the sensor device is not disposed).

Figure 132:
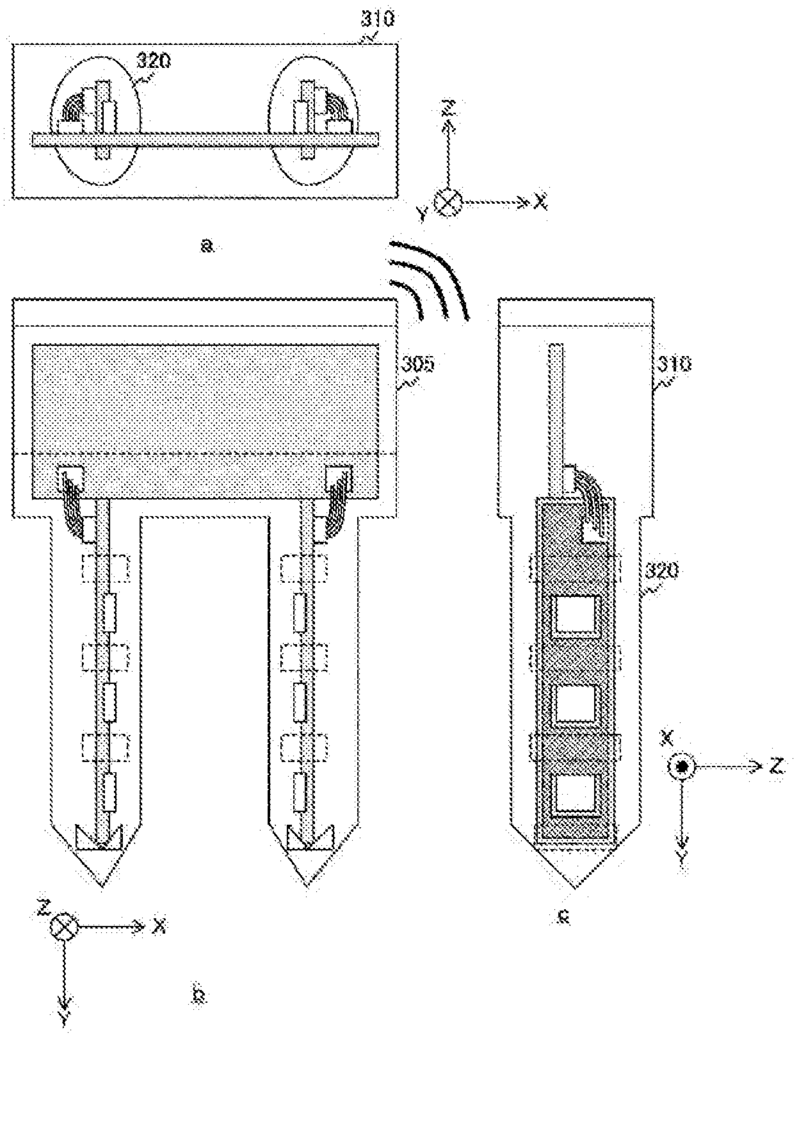

FIG. 132 is a diagram illustrating an example of a sensor device 200 according to the first embodiment of the present technology illustrated in FIG. 4 in a simplified manner.

The sensor device 200 illustrated in FIG. 132, similar to the sensor device 200 illustrated in FIG. 4, represents a form in which a battery is included inside a measurement unit casing 310. For this reason, in the sensor device 200 illustrated in FIG. 132, a size of the measurement unit casing 310 in the Z-axis direction is larger than that of the sensor device 200 illustrated in FIG. 131.

Also in the sensor device 200 illustrated in FIG. 132, the measurement unit substrate 311 is disposed such that sizes in the X-axis direction and the Y-axis direction are larger than a size in the Z-axis direction. In other words, the measurement unit substrate 311 is disposed in a state in which a maximum face included in the measurement unit substrate 311 extends in a direction perpendicular to the ground surface. When described using a relation between two probe casings 320 included in the sensor device 200, the measurement unit substrate 311 is disposed such that one plane including two segments including a center line of a transmission probe casing 320*a* representing an extending direction of the transmission probe casing 320*a* and a center line of a reception probe casing 320*b* representing an extending direction of the reception probe casing 320*b* and a maximum face included in the measurement unit substrate 311 are in parallel with each other.

In addition, in the sensor device 200 illustrated in FIG. 132, a measurement unit casing 310 is disposed such that sizes in the X-axis direction and the Y-axis direction are larger than a size in the Z-axis direction. In other words, the measurement unit casing 310 is disposed in a state in which a maximum face included in the measurement unit casing 310 extends in a direction perpendicular to the ground surface. When described using a relation between two probe casings 320 included in the sensor device 200, the measurement unit casing 310 is disposed such that one plane including two segments including the center line of the transmission probe casing 320*a* representing an extending direction of the transmission probe casing 320*a* and the center line of the reception probe casing 320*b* representing an extending direction of the reception probe casing 320*b* and a maximum face included in the measurement unit casing 310 are in parallel with each other.

The sensor device 200 illustrated in FIG. 132 includes this disposition structure and thus, compared to a form not including this disposition structure, obtains an effect of rainfalls or sprinkle water supplied from the upper side of the sensor device 200 being easily inserted into soil that is a measurement target for an amount of moisture positioned between two probe casings 320 (in other words, it can be easily the same as soil in which the sensor device is not disposed).

FIGS. 133 and 134 are diagrams illustrating examples of the sensor devices 200 in which rain gutters are added to the sensor devices 200 illustrated in FIGS. 131 and 132 as bases. As illustrated in FIGS. 133 and 134, rain gutters 362 to 364 that drain rainfalls and sprinkle water to the outside may be added. The rain gutter 362 is disposed in a lower part of the measurement unit casing 310, and the rain gutters 363 and 364 are disposed in an upper part of the probe casing 320. In accordance with this, the measurement unit casing 310 is inhibited from collecting rainfalls and sprinkle water scatter in a horizontal direction and causing them to flow into a boundary face between a probe and soil.

FIG. 135 is a diagram illustrating a strength of the probe casing 320 included in the sensor device 200 according to the first embodiment of the present technology.

a in this diagram illustrates a state before deformation acquired when one end of the probe casing 320 is fixed, and a predetermined weight is applied to the other end. b in this diagram illustrates a state of the probe casing 320 after deformation. c in this diagram illustrates a state before deformation acquired when one end of the in-probe substrate 321 is fixed, and a predetermined weight is applied to the other end. d in this diagram illustrates a state of the in-probe substrate 321 after deformation. A strength of the in-probe substrate 322 is similar to that of the in-probe substrate 321.

It is assumed that the strength of the probe casing 320 is higher than those of the in-probe substrates 321 and 322. Here, as illustrated in this diagram, "a strength being higher" represents that an amount of deformation of the probe casing 320 acquired when one end of the casing is fixed, and a predetermined weight is applied to the other end is smaller than an amount of deformation of the in-probe substrate 321 acquired when one end of the substrate is fixed, and a predetermined weight is applied to the other end.

In this way, the sensor device 200 according to the present invention is (1) a sensor device that includes a transmission probe casing 320*a* housing a transmission antenna (for example, 223) transmitting an electromagnetic wave and a reception probe casing 320*b* housing a reception antenna (for example, 233) receiving an electromagnetic wave and measures propagation characteristics of an electromagnetic wave transmitted from the transmission antenna and received by the reception antenna, thereby measuring an amount of moisture in a medium, (2) has both the transmission probe casing 320*a* and the reception probe casing 320*b* formed using materials allowing transmission of an electromagnetic wave transmitted from the transmission antenna described above and an electromagnetic wave received by the reception antenna described above (electromagnetic wave transmissive materials), and (3) has a structure in which the strengths of the transmission probe casing 320*a* and the reception probe casing 320*b* formed using the electromagnetic wave transmissive materials described above are configured to be higher than the strength of an electronic substrate (a wiring substrate) inserted into the inside of such casings.

By including such a structure, the sensor device 200 according to the present invention inhibits "the probe casing is deformed when the probe casing is inserted into soil, as a result, the electronic substrate inserted into the inside of the casing is deformed, furthermore, as a result, a distance between the transmission antenna and the reception antenna formed in this electronic substrate changes from a predetermined value, and error occurs in a result of measurement of the amount of moisture in accordance therewith" and obtains an effect of being able to accurately measure moisture in accordance with this.

[Method for measuring amount of moisture]

FIG. 136 is a block diagram illustrating one configuration example of the measurement circuit 210 according to the first embodiment of the present technology. This measurement circuit 210 includes a directional coupler 410, a transmitter 420, an incident wave receiver 430, a reflected wave receiver 440, a transmitted wave receiver 450, a sensor control unit 470, a sensor communication unit 212, and an antenna 213. As the measurement circuit 210, for example, a vector network analyzer is used.

The transmitter 420 illustrated in FIG. 136 corresponds to the transmitter 214 illustrated in FIG. 3. In addition, the incident wave receiver 430, the reflected wave receiver 440, and the transmitted wave receiver 450 correspond to the receiver 215 illustrated in FIG. 3. The sensor control unit 470 corresponds to the sensor control unit 211 illustrated in FIG. 3. In FIG. 3, the directional coupler 410 is omitted.

The directional coupler 410 separates an electrical signal transmitted through the transmission lines for transmission 229-1 to 229-3 into an incident wave and a reflected wave. The incident wave is a wave of an electrical signal transmitted from the transmitter 420, and the reflected wave is obtained from reflection of the incident wave at an end of the transmission probe. The directional coupler 410 provides the incident wave to the incident wave receiver 430 and provides the reflected wave to the reflected wave receiver 440.

The transmitter 420 transmits an electrical signal of a predetermined frequency to the transmission probe through the directional coupler 410 and the transmission lines for transmission 229-1 to 229-3 as a transmission signal. For example, as an incident wave inside a transmission signal, a CW (Continuous Wave) is used. For example, in a frequency band of 1 to 9 gigahertz (GHz), this transmitter 420 transmits a transmission signal with the frequency sequentially being switched in steps of 50 megahertz (MHz).

The incident wave receiver 430 receives the incident wave from the directional coupler 410. The reflected wave receiver 440 receives the reflected wave from the directional coupler 410. The transmitted wave receiver 450 receives a transmitted wave from the reception probe. Here, the transmitted wave is obtained by converting an electromagnetic wave transmitted through a medium between the transmission probe and the reception probe into an electrical signal using the reception probe.

The incident wave receiver 430, the reflected wave receiver 440, and the transmitted wave receiver 450 perform quadrature detection and analog-to-digital (AD) conversion on the received incident wave, reflected wave, and transmitted wave and supply the resultant waves to the sensor control unit 470 as reception data.

The sensor control unit 470 performs control of the transmitter 420 to cause the transmission signal including the incident wave to be transmitted and a process of acquiring a reflection coefficient and a transmission coefficient. Here, the reflection coefficient is a ratio between complex amplitudes of the incident wave and the reflected wave, as described above. The transmission coefficient is a ratio between complex amplitudes of the incident wave and the transmitted wave. The sensor control unit 470 supplies the reflection coefficient and the transmission coefficient that have been acquired to the sensor communication unit 212.

The sensor communication unit 212 transmits data representing the reflection coefficient and the transmission coefficient to the central processing device 150 through a communication path 110 as measurement data.

Meanwhile, to measure an accurate reflection coefficient and transmission coefficient, calibration of frequency characteristics of the directional coupler 410, the transmitter 420, and the receiver (incident wave receiver 430 and the like) is executed before measurement.

FIG. 137 is a diagram showing a configuration example of the directional coupler 410 in the first embodiment of the present technology. The directional coupler 410 includes transmission lines 411, 412, and 413 and terminating resistors 414 and 415. The directional coupler 410 can be implemented as, for example, a bridge coupler suitable for miniaturization.

One end of the transmission line 411 is connected to the transmitter 420, and the other end thereof is connected to the transmission probe through the transmission switch 216. The transmission line 412 is shorter than the transmission line 411 and is a line coupled to the transmission line 411 through electromagnetic field coupling. One end of the transmission line 412 is connected to the terminating resistor 414 and the other end is connected to the reflected wave receiver 440. The transmission line 413 is shorter than the transmission line 411 and is a line coupled to the transmission line 411 through electromagnetic field coupling. One end of the transmission line 413 is connected to the terminating resistor 415 and the other end is connected to the incident wave receiver 430.

According to the above-described configuration, the directional coupler 410 separates an electrical signal into an incident wave and a reflected wave and provides the incident wave and the reflected wave to the incident wave receiver 430 and the reflected wave receiver 440.

FIG. 138 is a circuit diagram illustrating one configuration example of the transmitter 420 and the receivers in the first embodiment of the present technology. In the diagram, a is a circuit diagram illustrating one configuration example of the transmitter 420 and b is a circuit diagram illustrating one configuration example of the incident wave receiver 430. In the diagram, c is a circuit diagram illustrating one configuration example of the reflected wave receiver 440 and d is a circuit diagram illustrating one configuration example of the transmitted wave receiver 450.

As illustrated in a in the diagram, the transmitter 420 includes a transmission signal oscillator 422 and a driver 421.

The transmission signal oscillator 422 generates an electrical signal as a transmission signal in accordance with control of the sensor control unit 470. The driver 421 outputs the transmission signal to the directional coupler 410. For example, this transmission signal S(t) is represented using the following expression.

$$S(t)=|A|\cos(2\pi ft+\theta)$$

In the expression represented above, t represents a time, and the unit, for example, is nanoseconds (ns). |A| represents an amplitude of the transmission signal. cos( ) represents a cosine function. f represents the frequency, and the unit, for example, is hertz (Hz). 0 represents a phase, and the unit, for example, is radian (rad).

As illustrated in b in this diagram, the incident wave receiver 430 includes a mixer 431, a band pass filter 432, an ADC 433.

The mixer 431 performs quadrature detection by mixing two local signals having a phase difference of 90 degrees therebetween and the transmission signal. A complex amplitude composed of an in-phase component $I_1$ and a quadrature component $Q_I$ is obtained according to the quadrature detection. These in-phase component $I_1$ and quadrature component $Q_I$ are represented by the following formula, for example. The mixer 431 supplies the complex amplitude to the ADC 433 through the band pass filter 432.

$$I_I=|A|\cos(\theta)$$

$$Q_I=|A|\sin(\theta)$$

In the above formula, sin( ) represents a sine function.

The band pass filter 432 passes a component of a predetermined frequency band. The ADC 433 performs AD conversion. The ADC 433 generates data representing the complex amplitude by performing AD conversion and supplies the data to the sensor control unit 470 as reception data.

As illustrated in c in this diagram, the reflected wave receiver 440 includes a mixer 441, a band pass filter 442, and an ADC 443. The configurations of the mixer 441, the band pass filter 442, and the ADC 443 are similar to those of the mixer 431, the band pass filter 432, and the ADC 433. The reflected wave receiver 440 performs quadrature detection on a reflected wave to acquire a complex amplitude composed of an in-phase component $I_R$ and a quadrature component $Q_R$ and supplies reception data representing the complex amplitude to the sensor control unit 470.

As illustrated in d in this diagram, the transmitted wave receiver 450 includes a receiver 451, a local signal oscillator 452, a mixer 453, a band pass filter 454, and an ADC 455. The configurations of the mixer 453, the band pass filter 454, and the ADC 455 are similar to those of the mixer 431, the band pass filter 432, and the ADC 433.

The receiver 451 receives an electrical signal including a transmitted wave through the reception switch 217 and outputs the received electrical signal to the mixer 453. The local signal oscillator 452 generates two local signals having a phase difference of 90 degrees therebetween.

The transmitted wave receiver 450 performs quadrature detection on the transmitted wave to acquire a complex amplitude composed of an in-phase component $I_T$ and a quadrature component $Q_T$ and supplies data representing the complex amplitude to the sensor control unit 470 as reception data.

Meanwhile, the circuits of the transmitter 420 and the receivers (incident wave receiver 430 and the like) are not limited to the circuits illustrated in the diagram as long as they can transmit and receive an incident wave and the like.

FIG. 139 is a block diagram illustrating one configuration example of the sensor control unit 470 according to the first embodiment of the present technology. This sensor control unit 470 includes a transmission control unit 471, a reflection coefficient calculation unit 472, and a transmission coefficient calculation unit 473.

The transmission control unit 471 controls the transmitter 420 such that the transmitter 420 transmits a transmission signal.

The reflection coefficient calculation unit 472 calculates a reflection coefficient F for each frequency. The reflection coefficient calculation unit 472 receives complex amplitudes of an incident wave and a reflected wave from the incident wave receiver 430 and the reflected wave receiver 440 and calculates a ratio between the complex amplitudes as a reflection coefficient F according to the following formula.

$$\Gamma=(I_R+jQ_R)/(I_I+jQ_I) \quad \text{Expression 3}$$

In the above formula, j is an imaginary unit. $I_R$ and $Q_R$ are the in-phase component and the quadrature component generated by the reflected wave receiver 440.

The reflection coefficient calculation unit 472 calculates reflection coefficients for N (N is an integer) frequencies $f_1$ to $f_N$ using Expression 3. These N reflection coefficients are denoted by $\Gamma_1$ to $\Gamma_N$. The reflection coefficient calculation unit 472 supplies the reflection coefficients to the sensor communication unit 212.

The transmission coefficient calculation unit 473 calculates a transmission coefficient T for each frequency. The transmission coefficient calculation unit 473 receives complex amplitudes of an incident wave and a transmitted wave from the incident wave receiver 430 and the transmitted wave receiver 450 and calculates a ratio between the complex amplitudes as a transmission coefficient T according to the following formula.

$$T=(I_T+jQ_T)/(I_I+jQ_I) \quad \text{Expression 4}$$

$I_T$ and $Q_T$ are the in-phase component and the quadrature component generated by the transmitted wave receiver 450.

The transmission coefficient calculation unit 473 calculates transmission coefficients with respect to the N frequencies $f_1$ to $f_N$ according to Formula 4. These N reflection coefficients are denoted by $T_1$ to $T_N$. The transmission coefficient calculation unit 473 supplies the transmission coefficients to the central processing device 150 through the sensor communication unit 212.

FIG. 140 is a block diagram illustrating one configuration example of the signal processing unit 154 disposed inside of the central processing device 150 according to the first embodiment of the present technology. This central processing device 150 includes a reciprocating delay time calculation unit 162, a propagation transmission time calculation unit 163, a moisture amount measurement unit 164, and a coefficient storing unit 165 inside the signal processing unit 154. In this diagram, the antenna 152, the central control unit 151, the storage unit 155, and the output unit 156 illustrated in FIG. 2 are omitted.

The central communication unit 153 supplies reflection coefficients $\Gamma_1$ to $\Gamma_N$ included in the measurement data to the reciprocating delay time calculation unit 162 and supplies transmission coefficients $T_1$ to $T_N$ included in the measurement data to the propagation transmission time calculation unit 163.

The reciprocating delay time calculation unit 162 calculates a time over which an electrical signal reciprocates in the transmission lines for transmission 229-1 to 229-3 as a reciprocating delay time on the basis of the reflection coefficients. Then, the reciprocating delay time calculation unit 162 acquires an impulse response hΓ(t) by performing inverse Fourier transform on the reflection coefficients $\Gamma_1$ to $\Gamma_N$. Then, the reciprocating delay time calculation unit 162 acquires a time difference between the timing of a peak value of the impulse response hΓ(t) and a CW wave transmission timing as a reciprocating delay time $\tau_{11}$ and supplies it to the moisture amount measurement unit 164.

The propagation transmission time calculation unit 163 calculates a time over which an electromagnetic wave and an electrical signal propagate and are transmitted through the medium, the transmission lines for transmission 229-1 to 229-3, and the transmission lines for reception 239-1 to 239-3 as a propagation transmission time on the basis of the transmission coefficients. This propagation transmission time calculation unit 163 acquires an impulse response hT(t) by performing inverse Fourier transform on the transmission coefficients $T_1$ to $T_N$. Then, the propagation transmission time calculation unit 163 acquires a time difference between the timing of a peak value of the impulse response hT(t) and a CW wave transmission timing as a propagation transmission time $\tau_{21}$ and supplies it to the moisture amount measurement unit 164.

The moisture amount measurement unit 164 measures an amount of moisture on the basis of the reciprocating delay time $\tau_{11}$ and the propagation transmission time $\tau_{21}$. First, the moisture amount measurement unit 164 calculates a propagation delay time $\tau_d$ from the reciprocating delay time $\tau_{11}$ and the propagation transmission time $\tau_{21}$. Here, the propagation delay time is a time over which an electromagnetic wave propagates through a medium between the transmission probe and the reception probe. The propagation delay time $\tau_d$ is calculated using the following expression.

$$\tau_d = \tau_{21} - \tau_1 1 \qquad \text{Expression 5}$$

In the expression represented above, the unit of the reciprocating delay time $\tau_{11}$, the propagation transmission time 121, and the propagation delay time $T_d$, for example, is nanoseconds (ns).

Then, the moisture amount measurement unit 164 reads coefficients a and b representing a relation between the amount of moisture and the propagation delay time τd from the coefficient storing unit 165 and measures an amount of moisture x by substituting the propagation delay time τd calculated using Expression 5 into the following expression. In addition, the moisture amount measurement unit 164 outputs the measured amount of moisture to an external device or apparatus as necessary.

$$\tau_d = a \cdot x + b \qquad \text{Expression 6}$$

In the above formula, the unit of the amount of moisture x is, for example, percent by volume (%).

The coefficient storing unit 165 stores the coefficients a and b. A nonvolatile memory is, for example, used as the coefficient storing unit 165.

FIG. 141 is a diagram for describing a propagation path and a transmission path of electromagnetic waves and an electrical signal in the first embodiment of the present technology. As described above, the transmitter 420 transmits an electrical signal including an incident wave to the transmission probe as a transmission signal through the transmission lines for transmission 229-1 to 229-3 of which tip ends are embedded in the transmission probe. In this diagram, only one of the transmission lines for reception 239-1 to 239-3 is illustrated. In addition, only one of the transmission lines for transmission 229-1 to 229-3 is illustrated.

The incident wave is reflected at the end of the transmission probe, and the reflected wave is received by the reflected wave receiver 440. In accordance with this, the electrical signal including the incident wave and the reflected wave reciprocates in the transmission lines for transmission 229-1 to 229-3. In this diagram, an arrow in a thick solid line indicates a path through which an electrical signal reciprocates in the transmission lines for transmission 229-1 to 229-3. A time over which the electrical signal reciprocates through this path corresponds to the reciprocating delay time iii.

In addition, the electrical signal including the incident wave is converted into an electromagnetic wave EW by the transmission probe and is transmitted (in other words, propagates) through the medium between the transmission probe and the reception probe. The reception probe converts the electromagnetic wave EW into an electrical signal. The transmitted wave receiver 450 receives a transmitted wave included in the electrical signal through the transmission lines for reception 239-1 to 239-3. In other words, the electrical signal including an incident wave is transmitted through the transmission lines for transmission 229-1 to 229-3, is converted into an electromagnetic wave EW to propagate through the medium, is converted into an electrical signal including a transmitted wave, and is transmitted through the transmission lines for reception 239-1 to 239-3. In this diagram, an arrow in a thick dotted line represents a path in which the electromagnetic wave and the electrical signal (the incident wave and the transmitted wave) propagate and are transmitted through the medium, the transmission lines for transmission 229-1 to 229-3, and the transmission lines for reception 239-1 to 239-3. A time over which the electromagnetic wave and the electrical signal propagate and are transmitted through this path corresponds to the propagation transmission time τ21.

The sensor control unit 470 acquires the reflection coefficient F and the transmission coefficient T using Expression 3 and Expression 4. Then, the central processing device 150 acquires the reciprocating delay time $\tau_{11}$ and the propagation transmission time $\tau_{21}$ from the reflection coefficient F and the transmission coefficient T.

Here, a path from transmission of the incident wave to reception of the transmitted wave includes the medium, the transmission lines for transmission 229-1 to 229-3, and the transmission lines for reception 239-1 to 239-3. For this reason, the propagation delay time $\tau_d$ over which an electromagnetic wave propagates through the medium is acquired using a difference between the propagation transmission time $\tau_{21}$ and a delay time over which the electrical signal is transmitted through the transmission lines for transmission 229-1 to 229-3 and the transmission lines for reception 239-1 to 239-3. When a length of the transmission lines for transmission 229-1 to 229-3 and a length of the transmission lines for reception 239-1 to 239-3 are assumed to be the same, a delay time for transmission through the transmission lines for transmission 229-1 to 229-3 and a delay time for transmission through the transmission lines for reception 239-1 to 239-3 are the same. In this case, a total delay time over which an electrical signal is transmitted through the transmission lines for transmission 229-1 to 229-3 and the transmission lines for reception 239-1 to 239-3 is equal to the reciprocating delay time $\tau_{11}$ for reciprocation through the transmission lines for transmission 229-1 to 229-3. Accordingly, Expression 5 is established, and the central processing device 150 can calculate the propagation delay time $\tau_d$ using Expression 5.

Then, the central processing device 150 calculates a propagation delay time from the reciprocating delay time $\tau_{11}$ and the propagation transmission time $\tau_{21}$ that have been acquired and performs a process of measuring the amount of moisture contained in the medium from the propagation delay time and the coefficients a and b.

FIG. 142 is a graph showing an example of a relationship between a reciprocating delay time and a propagation transmission time and an amount of moisture in the first embodiment of the present technology. In the diagram, a vertical axis represents a reciprocating delay time or a propagation transmission time and a horizontal axis represents an amount of moisture.

In this diagram, a dotted line indicates a relation between the reciprocating delay time and the amount of moisture. A solid line indicates a relation between the propagation transmission time and the amount of moisture. As illustrated in this diagram, the reciprocating delay time is constant regardless of the amount of moisture. On the other hand, the propagation transmission delay time increases as the amount of moisture increases.

FIG. 143 is a graph showing an example of a relationship between a propagation delay time and an amount of moisture in the first embodiment of the present technology. In the diagram, a vertical axis represents a propagation delay time and a horizontal axis represents an amount of moisture. In the diagram, a straight line is acquired by obtaining a difference between the propagation transmission time and the reciprocating delay time for each amount of moisture in FIG. 142.

As illustrated in FIG. 143, the propagation delay time increases as the amount of moisture increases, and thus both are in a proportional relationship. Accordingly, Expression 6 is established. The coefficient a in Expression 6 is a slope of the straight line in the diagram and the coefficient b is the intercept.

FIG. 144 is a block diagram illustrating another configuration example of a measurement circuit 210 according to the first embodiment of the present technology. The measurement circuit 210 illustrated in FIG. 136 includes two receivers including the reflected wave receiver 440 and a transmitted wave receiver 450 as receivers used for receiving a reflected wave and a transmitted wave. On the other hand, the measurement circuit 210 illustrated in FIG. 144 has a configuration in which one second receiver 455 is commonly used as a receiver used for receiving a reflected wave and a transmitted wave. More specifically, in the measurement circuit 210, a reflected wave and a transmitted wave are switched by a switch 445 controlled by the sensor control unit 470 and are received by one second receiver 455 in a time divisional manner. Results of reception in the second receiver 455 are output to the sensor control unit 470. In accordance with this configuration, the size of the measurement circuit 210 is configured to be smaller than that of the case illustrated in FIG. 136, and, as a result, the size of the moisture measuring system 100 is reduced, and a manufacturing cost thereof is reduced.

FIG. 145 is a block diagram illustrating another configuration example of a sensor device 200 according to the first embodiment of the present technology. A measurement circuit 210 illustrated in this diagram includes a sensor signal processing unit 460 in place of the sensor communication unit 212, which is different from the circuit illustrated in FIG. 136. The configuration of the sensor signal processing unit 460 is similar to that of the signal processing unit 154 disposed inside the central processing device 150 according to the first embodiment. In addition, the function of a sensor control unit 470, for example, is realized by a DSP (Digital Signal Processing) circuit.

In addition, a measurement circuit 210 may be mounted in a single semiconductor chip. In accordance with this, the functions of the measurement circuit 210 and the signal processing unit 154 can be realized by the single semiconductor chip.

When FIG. 145 is compared with FIG. 136, the functions required for the central processing device 150 are reduced. As a result, functions and performance required for an electronic device used for implementing the central processing device 150 are reduced, and, as an electronic device used for implementing the central processing device 150, for example, a terminal device that is available in the market such as a smartphone, a tablet terminal, or the like can be used more easily than in the case illustrated in FIG. 136.

FIG. 146 is a flowchart illustrating an example of an operation of the moisture measuring system 100 according to the first embodiment of the present technology. The operation in the diagram starts, for example, when a predetermined application for measuring an amount of moisture has been executed.

One pair of a transmission probe and a reception probe transmit and receive electromagnetic waves (step S901). The measurement circuit 210 calculates a reflection coefficient from an incident wave and a reflected wave (step S902) and calculates a transmission coefficient from the incident wave and a transmitted wave (step S903).

Next, the central processing device 150 calculates a reciprocating delay time from the reflection coefficient (step S904) and calculates a propagation transmission time from the transmission coefficient (step S905). The central processing device 150 calculates a propagation delay time from the reciprocating delay time and the propagation transmission time (step S906) and calculates an amount of moisture from the propagation delay time and coefficients a and b (step S907). After step S907, the moisture measuring system 100 ends the operation for measurement.

[Configuration Example of Electric Wave Absorbing Unit]

Subsequently, an electric wave absorbing unit will be described. Different from a TDR (Time Domain Reflectometry) system or a TDT (Time Domain Transmissometry) system, a moisture sensor of a transmission type according to the invention of this application needs to transmit an electric wave of a broadband, and the transmitted electric wave needs to be received by a receiver. However, when the electric wave is reflected, and a peak of an impulse response that is a noise is calculated, there are cases in which a deviation in the peak position and a deviation in the delay time occur. For this reason, a countermeasure for not generating a noise source in a broad band and noise elimination of a case in which noise is generated are demanded.

Particularly, in a case in which a plurality of antennas are included in one probe, unnecessary radiation significantly increases, and it is difficult to suppress an electric wave.

Thus, in the sensor device 200, in the periphery of the probe except for the antenna, an electric wave absorbing unit 341 and the like are disposed.

As methods for installing an electric wave absorber unit, three methods may be considered. A first method is a method in which an electric wave absorber is installed on a substrate or a coaxial cable. For example, a method of inserting it into a substrate, a method of causing it to ride on a substrate, a method of attaching it to a substrate, a method of winding it around a substrate are used. In a case in which only upper and lower sides or left and right sides are installed on the substrate, the electric wave absorbent material unit may be formed to be larger than the substrate width.

A second method is a method in which the electric wave absorbent material unit is installed in an exterior casing in advance, or it is installed simultaneously with installation of a substrate layer. For example, a method of causing it to be buried in a resin at the time of casing molding or a method in which the electric wave absorber is mixed into a resin and is molded is used. In a case in which the electric wave absorber has hygroscopicity, additionally, the outer side may be covered with another resin or may be coated with paint or the like. Other than those, a method in which the electric wave absorber is inserted after casing molding, a pasting method, or a method in which a solution in which the electric wave absorber is mixed and a substrate are inserted and hardened at the time of casing molding is used. At that time, it is preferable that electric wave transmitting/receiving parts be covered with another resin, an O ring, or the like such that the electric wave absorber is not attached. A method in which the inner side of the casing is coated with an electric wave absorbent material may be also considered.

A third method is a method in which an electric wave absorbing unit is combined with a ferrite, a sheet, an electric wave absorber film, or a coating material. In this case, a gap of ferrite or the like may be coated with the electric wave absorbing unit.

Relating to an installation position and an installation method of an electric wave absorber for a substrate, although it is installed on upper and lower faces of which a width is equal to or larger than a substrate width, the effect of installation of an electric wave absorbing unit is high if it is wider than the substrate width, and it is preferable that it cover all the faces.

In addition, it is preferable that a lower end of the electric wave absorbing unit be an upper end of an antenna. In addition, it is preferable that a distance between a lower end of the antenna to a lower end of the electric wave absorbing unit including the length of the antenna be equal to or smaller than a half wavelength of the wavelength of a center frequency or be within a wavelength bandwidth. For example, when 1 to 9 gigahertz (GHz) is used, a center frequency is 5 gigahertz (GHz), and a wavelength thereof is 60 millimeters (mm). In this case, it is preferable that a distance from the lower end of the antenna to the lower end of the electric wave absorbing unit be within 30 millimeters. Since the bandwidth is 8 gigahertz, the resolution is 37.5 millimeters (mm), and a distance up to the lower end of the electric wave absorbing unit can be configured to be less than the resolution.

In addition, the electric wave absorber may be installed in a probe or may be installed in an external case. In a case in which the electric wave absorbent material is externally installed, the exterior casing may be coated with the electric wave absorbent material, or the electric wave absorbent material may be installed when the exterior casing is molded, cut, or kneaded or after the exterior casing is completed.

As components of materials of the electric wave absorbing unit, the followings can be used.

(1) magnetic material (2) conductive polymer (3) dielectric polymer (4) metamaterial In addition, as states of the material, there are the following examples.

(a) The electric wave absorbing unit is be formed only using an electric wave absorbent material and is a rigid body (a plate of a ferrite sintered body, a molding material of a conductive polymer, or the like).

(b) The electric wave absorbing unit is formed only using an electric wave absorbent material and is a sheet having flexibility (a sheet of a conductive polymer or the like).

(c) The electric wave absorbing unit is obtained by dispersing an electric wave absorbent material in a dispersion medium and is a rigid body (an organic resin rigid body in which ferrite is dispersed or the like).

(d) The electric wave absorbing unit is obtained by dispersing an electric wave absorbent material in a dispersion medium and is a sheet having flexibility (a sheet in which ferrite is dispersed or the like).

(e) fluid (a material that is solidified after coating or the like)

Relating to a combination of a state of a material and a component, in the state (a), any one of components (1), (2), (3), and (4) may be used. This similarly applies also to states (b), (c), and (d). In the state (e), the components (1), (2), and (3) are used.

Relating to a method of forming an electric wave absorbing unit, a bonding method, a mounting method using a fixing member such as an O ring or the like, an embedding method, a plugging method, a winding method, or a coating method can be used.

FIG. 147 is a diagram illustrating an example of coating positions of electric wave absorbing units 341 and 344 according to the first embodiment of the present technology. The number of antennas is one on each of the transmission side and the reception side. A transmission antenna 221 including a radiation element 330 is disposed on the transmission side, and a reception antenna 231 including a radiation element 333 is disposed on the reception side. In places other than those of such antennas, electric wave absorbing units 341 and 344 are formed.

As illustrated in a in this diagram, it is the most preferable that the whole probe other than the antenna is coated with the electric wave absorbing unit. In a case in which a part of the probe other than the antenna is coated, as illustrated in b in this diagram, it is preferable that a lower end of the electric wave absorbing unit be an upper end of the antenna. As illustrated in c in this diagram, the lower end of the electric wave absorbing unit may be separate from the upper end of the antenna. However, it is preferable that a distance from the lower end of the antenna to the lower end of the electric wave absorbing unit including a length of the antenna be equal to or smaller than a half wavelength of the wavelength of a center frequency or be within a wavelength bandwidth.

FIG. 148 is a diagram illustrating a comparative example in which coating using the electric wave absorbing unit is not performed. By disposing the electric wave absorbing units in parts other than the antennas, compared to the comparative example, electric waves of unnecessary radiation that causes noise can be absorbed.

FIG. 149 is a diagram illustrating an example in which one face of each of in-probe substrates 321 and 322 according to the first embodiment of the present technology is coated. As illustrated in a in this diagram, a face out of both faces of the in-probe substrate 321 in which the transmission antenna 221 is not formed may be further coated with the electric wave absorbing unit 347. Also a face out of both faces of the in-probe substrate 322 in which the reception antenna 231 is not formed is coated with the electric wave absorbing unit 348.

When one face of each of the in-probe substrates 321 and 322 is coated, a part of the probe other than the antenna may be coated. In this case, as illustrated in b in this diagram, it is preferable that the lower end of the electric wave absorbing unit be the upper end of the antenna. As illustrated in c in this diagram, the lower end of the electric wave absorbing unit may be configured to be separate from the upper end of the antenna.

FIG. 150 is a diagram illustrating an example in which a tip end of a probe according to the first embodiment of the present technology is further coated. As illustrated in a in this diagram, tip ends of probes in which the positioning parts 351 and 352 are disposed can be further coated with electric wave absorbing units 349 and 350.

When the tip end of the probe is coated, a part of the probe other than the antenna may be coated as well. In such a case, as illustrated in b in this diagram, it is preferable that the lower end of the electric wave absorbing unit be the upper end of the antenna. As illustrated in c in this diagram, the lower end of the electric wave absorbing unit may be configured to be separate from the upper end of the antenna as well.

FIG. 151 is a diagram illustrating an example in which only tip ends are coated in the first embodiment of the present technology. As illustrated in this diagram, only the tip ends may be coated with the electric wave absorbing units 349 and 350 as well.

FIG. 152 is a diagram illustrating an example in which one face and a tip end of each of the in-probe substrates 321 and 322 are coated in the first embodiment of the present technology. As illustrated in a in this diagram, both one face of each of the in-probe substrates 321 and 322 and the tip ends of the probes may be further coated.

When one face and the tip end are further coated, a part of the probe other than the antenna may be coated. In such a case, as illustrated in b in this diagram, it is preferable that the lower end of the electric wave absorbing unit be the upper end of the antenna. As illustrated in c in this diagram, the lower end of the electric wave absorbing unit may be configured to be separate from the upper end of the antenna as well.

FIG. 153 is a diagram illustrating an example of the shape of the electric wave absorbing unit 341 according to the first embodiment of the present technology. The electric wave absorbing unit 341 is composed of one or more parts. The shape of the outer side and the inner side of the electric wave absorbing unit 341 may be a circle or a polygon.

a in this drawing illustrates an upper view (an upper stage of FIG. 153*a*) and a side view (a lower stage of FIG. 153*a*) of an electric wave absorbing unit 341 of which the outer side and the inner side have a circular shape or an oval shape. b in this diagram illustrates an upper view and a side view of an electric wave absorbing unit 341 of which the outer side has a circular shape or an oval shape and the inner side has a rectangular shape. c in this diagram illustrates an upper view and a side view of an electric wave absorbing unit 341 of which the outer side have a rectangular shape and the inner side has a circular shape or an oval shape. d in this diagram illustrates an upper view and a side view of an electric wave absorbing unit 341 of which the outer side and the inner side has a rectangular shape. e in this drawing illustrates a side view of an electric wave absorbing unit 341 in which a spiral groove is formed. A structure that can be easily disposed in advance in a casing into which a substrate and a semi rigid cable are inserted may be formed when the spiral groove is formed. In a case in which a ferrite material is used, the electric wave absorbing unit 341 is formed to have a thickness of 5 mm or more. In the case of a film and a coating film, the thickness is 100 um or more. The structures of the electric wave absorbing units other than the electric wave absorbing unit 341 (in other words, the structures of the electric wave absorbing units other than the electric wave absorbing unit 341 described in this specification) are similar to that of the electric wave absorbing unit 341.

On the inner side of the electric wave absorbing unit 341 illustrated in FIG. 153 and the other electric wave absorbing units described in this specification (in other words, the electric wave absorbing units 341 to 346), the in-probe substrates 321 and 322 are disposed. More precisely described, on the inner side of the electric wave absorbing unit 341 illustrated in FIG. 153 and the other electric wave absorbing units described in this specification (in other words, the electric wave absorbing units 341 to 346), a part of each of the in-probe substrates 321 and 322 is disposed.

FIGS. 350*a* to 350*d* are top views of sensor devices 200 in a case in which the electric wave absorbing units 341 illustrated in FIG. 153*a* to 153*d* are respectively applied to the electric wave absorbing units 341 and 344 included in the sensor device 200 illustrated in FIG. 147*a* as examples of applications to the sensor devices 200. Here, similar to various kinds of three-plane drawings in this specification, FIG. 350 is a projected view (a diagram in which features of respective units are superimposed together). For this reason, a measurement unit substrate 311, a transmission antenna 221, a reception antenna 231, and electric wave absorbing units 341 and 344 are superimposed on one diagram. Positional relations of the measurement unit substrate 311, the transmission antenna 221, the reception antenna 231, and the electric wave absorbing units 341 and 344 in the Y direction are illustrated in a front view and a side view of FIG. 147*a*. In addition, a front view and a side view of the sensor device 200 in a case in which the electric wave absorbing units 341 illustrated in FIGS. 153*a* to 153*d* are respectively applied to the electric wave absorbing units 341 and 344 included in the sensor device 200 illustrated in FIG. 147*a* are the same as the front view and the side view of the sensor device 200 illustrated in FIG. 147*a*.

a in FIG. 350 illustrates a top view of the sensor device 200 including the electric wave absorbing unit 341 of which the inner side and the outer side have an oval shape. b in this diagram illustrates a top view of the sensor device 200 including the electric wave absorbing unit 341 of which the outer side has an oval shape and the inner side has a rectangular shape. c in this diagram illustrates a top view of the sensor device 200 including the electric wave absorbing unit 341 of which the outer side has a rectangular shape and the inner side has an oval shape. d in this diagram illustrates a top view of the sensor device 200 including the electric wave absorbing unit 341 of which the outer side and the inner side have a rectangular shape.

As a positional relation of the transmission in-probe substrate 321, the transmission antenna 221, the reception in-probe substrate 322, the reception antenna 231, and the electric wave absorbing units 341 and 344 on the top view (the top view that is a projected view), it is illustrated in FIGS. 350*a* to 350*d* that positions at which the transmission in-probe substrate 321, the transmission antenna 221, the reception in-probe substrate 322, and the reception antenna 231 are disposed are on the inner side of positions at which the electric wave absorbing units 341 and 344 are disposed.

In addition, as a positional relation of the transmission in-probe substrate 321, the transmission antenna 221, the reception in-probe substrate 322, the reception antenna 231, and the electric wave absorbing units 341 and 344 on the top view (the top view that is a projected view), it is illustrated in FIGS. 350*a* to 350*d* that positions at which the electric wave absorbing units 341 and 344 are disposed are on the outer side and on a whole circumference of the positions at which the transmission in-probe substrate 321, the transmission antenna 221, the reception in-probe substrate 322, and the reception antenna 231 are disposed.

From the top view (a projected view) illustrated in FIG. 350, it can be understood that the electric wave absorbing unit 341 is disposed on the whole circumference of the outer side of the transmission in-probe substrate 321, and the electric wave absorbing unit 344 is disposed on the whole circumference of the outer side of the reception in-probe substrate 322, and it can be understood from the front view and the side view illustrated in FIG. 147 that an area in which the electric wave absorbing units 341 and 344 are disposed on the whole circumference of the outer side of the transmission in-probe substrate 321 and the reception in-probe substrate 322 in this way is an area in which a transmission antenna (221 in the example of FIG. 147) and a reception antenna (231 in the example of FIG. 147) are not disposed in the Y-axis direction of the sensor device 200.

In addition, the forms of the electric wave absorbing units illustrated in FIGS. 153 and 350 are not limited to be applied to the sensor device 200 illustrated in FIG. 147*a* and can be applied to various sensor devices 200 illustrated in this specification.

The electric wave absorbing units 341 and the like illustrated in FIGS. 153 and 350 may be configured using one structure (component) formed using the electric wave absorbing materials described above or may be configured using a plurality of structures (components) formed using electric wave absorbing materials.

FIG. 236 is a diagram illustrating an example in which the electromagnetic wave absorbing unit 341 illustrated in FIG. 153 is configured using one structure (component) and an example in which the electromagnetic wave absorbing unit 341 is configured using a plurality of structures (components). Here, a to e in FIG. 236 illustrate top views of the electric wave absorbing units 341, and f to j in this diagram illustrate side views of the electric wave absorbing units 341. As illustrated in a and c in FIG. 236, the electric wave absorbing unit 341 may be configured using one structure when seen from the top face. In addition, as illustrated in b and d in FIG. 236, the electric wave absorbing unit 341 may be configured using two structures in when seen from the top face. Furthermore, as illustrated in e in FIG. 236, the electric wave absorbing unit 341 may be configured using a plurality of structures more than two when seen from the top face.

In addition, as illustrated in f in FIG. 236, the electric wave absorbing unit 341 may be configured using one structure when seen from a side face. Furthermore, as illustrated in g and h in FIG. 236, the electric wave absorbing unit 341 may be configured using a plurality of structures in an extending direction of the electric wave absorbing unit 341 (in other words, the Y direction in the side view of the sensor device 200 illustrated in FIG. 147*a*) when seen from a side face. In addition, as illustrated in i in FIG. 236, the electric wave absorbing unit 341 may be configured using two structures in a direction orthogonal to the extending direction of the electric wave absorbing unit 341 (in other words, a direction orthogonal to the Y direction in the side view of the sensor device 200 illustrated in FIG. 147*a*, that is, the X direction or the Z direction) when seen from a side face. In addition, as illustrated in j in FIG. 236, the electric wave absorbing unit 341 may be configured using a plurality of structures more than two in a direction orthogonal to the extending direction of the electric wave absorbing unit 341 (in other words, a direction orthogonal to the Y direction in the side view of the sensor device 200 illustrated in FIG. 147*a*, that is, the X direction or the Z direction) when seen from a side face.

FIG. 235 is a top view illustrating another example of the shape of the electric wave absorbing unit 341 according to the first embodiment of the present technology. As illustrated in a, b, c, d, and e in this diagram, the electric wave absorbing unit 341 and the sensor casing 305 side may be configured to fitted to each other by forming a protrusion in the electric wave absorbing unit 341 and forming a groove on the sensor casing 305 side. As illustrated in f, g, h, i, and j in this diagram, the electric wave absorbing unit 341 and the sensor casing 305 side may be configured to fit to each other by forming a groove in the electric wave absorbing unit 341 and forming a protrusion on the sensor casing 305 side. In addition, the electric wave absorbing units illustrated in FIGS. 236 and 235 are not limited to be applied to the sensor device 200 illustrated in FIG. 147*a* and can be applied to various sensor devices 200 illustrated in this specification.

FIGS. 351 and 352 are diagrams illustrating yet another example of the shape of the electric wave absorbing unit 341 according to the first embodiment of the present technology. An upper stage of FIG. 351 is a top view of the electric wave absorbing unit 341, and a lower stage thereof is a side view of the electric wave absorbing unit 341. FIGS. 352*a* to 352*d* are top views (projected views) of the sensor device 200 in a case in which the electric wave absorbing units 341 illustrated in FIGS. 351*a* to 351*d* are respectively applied to the electric wave absorbing units 341 and 344 included in the sensor device 200 illustrated in FIG. 147*a* as an example of applications to the sensor device 200. Here, similar to FIG. 350, FIG. 352 is a projected view (a diagram in which features of respective units are superimposed). For this reason, the measurement unit substrate 311, the transmission antenna 221, the reception antenna 231, and the electric wave absorbing units 341 and 344 are superimposed on one diagram. Positional relations of the measurement unit substrate 311, the transmission antenna 221, the reception antenna 231, and the electric wave absorbing units 341 and 344 in the Y direction are illustrated in a front view and a side view of FIG. 147*a*. The electric wave absorbing units illustrated in FIGS. 153 and 350 are disposed at positions on an outer side and on the whole circumference of the transmission in-probe substrate 321 and the reception in-probe substrate 322 in the top view illustrated therein. In contrast to this, the electric wave absorbing units illustrated in FIGS. 351 and 352 are disposed at positions that are on an outer side and parts of the periphery of the transmission in-probe substrate 321 and the reception in-probe substrate 322 in the top views thereof. In more detail, the electric wave absorbing units illustrated in FIGS. 351 and 352 are disposed at positions that are on an outer side and a part of the periphery of the transmission in-probe substrate 321 and the reception in-probe substrate 322 and overlap with a part of a segment joining a part of the transmission in-probe substrate 321 and the reception in-probe substrate 322 or in an area including positions intersecting with the segment in the top view thereof. In addition, it can be understood from the front view and the top view of FIG. 147 that an area in which the electric wave absorbing units 341 and 344 are disposed in a part of the outer side of the transmission in-probe substrate 321 and the reception in-probe substrate 322 in this way is an area in which a transmission antenna (221 in the example of FIG. 147) and a reception antenna (231 in the example of FIG. 147) of the sensor device 200 in the Y-axis direction are not disposed. In the forms illustrated in FIGS. 351 and 352, although electric wave absorption power is lowered than that of the forms illustrated in FIGS. 153 and 350, the manufacturing process is simplified, and the manufacturing cost can decrease.

In addition, the electric wave absorbing units illustrated in FIGS. 351 and 352 are not limited to be applied to the sensor device 200 illustrated in FIG. 147*a* and can be applied to various sensor devices 200 illustrated in this specification.

In this way, according to the first embodiment of the present technology, since the planar transmission antenna 221 is disposed to face the reception antenna 231 and is fixedly disposed such that a distance between the antennas is a predetermined distance, the transmission loss decreases, and moisture in soil can be accurately measured.

First Modification Example

In the first embodiment described above, although the in-probe substrates 321 and 322 are connected in a direction orthogonal to the measurement unit substrate 311 such that the antennas are configured to face each other, in this configuration, connectors and cables for connection are necessary in addition to the three substrates, whereby the structure becomes complex. In a sensor device 200 according to this first modification example of the first embodiment, a part of a flexible substrate is twisted, whereby antennas are configured to face each other, which is different from the first embodiment.

FIG. 154 is a diagram illustrating an example of a sensor device 200 using a flexible substrate 271 according to the first modification example of the first embodiment of the present technology. Inside the sensor device 200 according to the first modification example of the first embodiment of the present technology, one flexible substrate 271 is disposed in place of three substrates including the measurement unit substrate 311 the in-probe substrate 321, and the in-probe substrate 322.

a in this diagram illustrates the flexible substrate 271 before a tip end thereof is twisted, and b in this diagram illustrates the flexible substrate 271 after the tip end thereof is twisted. A sensor casing 305 is omitted. The flexible substrate 271 includes one pair of protrusion parts, and a transmission antenna 221 and a reception antenna 231 are disposed at tip ends thereof. In addition, a measurement circuit 210 is disposed in the flexible substrate 271.

As illustrated in b in this diagram, by twisting the tip end of the flexible substrate 271, a state in which the transmission antenna 221 and the reception antenna 231 face each other can be formed. According to this configuration, compared to the first embodiment in which three substrates are connected, the number of components is reduced, and the structure can be simplified.

FIG. 155 is a diagram illustrating an example of a sensor device 200 in which a flexible substrate according to the first modification example of the first embodiment of the present technology and a rigid substrate are used. a in this diagram is an example in which one rigid substrate is used, and b in this diagram is an example in which three rigid substrates are used.

As illustrated in a in this drawing, the rigid substrate 275 and long and thin flexible substrates 271 and 272 may be disposed inside the sensor device 200 with being connected to each other. A measurement circuit 210 is disposed in the rigid substrate 275. A transmission antenna 221 is disposed in the flexible substrate 271, and a reception antenna 231 is disposed in the flexible substrate 272.

For example, there are cases in which a multi-layered structure is necessary in the vicinity of the measurement circuit 210 due to wirings, and a substrate having good thermal conductivity is necessary due to heat exhaust, and thus a rigid substrate is required. By also using the rigid substrate, not only such requests are satisfied, but also an arrangement in which antennas face each other can be realized.

As illustrated in b in this diagram, rigid substrates 275, 276, and 277 and long and thin flexible substrates 271 and 272 may be disposed inside the sensor device 200 with being connected to each other. The rigid substrate 276 is connected to a tip end of the flexible substrate 271, and a transmission antenna 221 is disposed in the rigid substrate 276. The rigid substrate 277 is connected to a tip end of the flexible substrate 272, and a reception antenna 231 is disposed in the rigid substrate 277.

FIG. 156 is a diagram illustrating an example of the sensor device 200 acquired when the number of antennas according to the first modification example of the first embodiment of the present technology is increased. a in this diagram illustrates a flexible substrate 271 before the tip end is twisted, and b in this diagram illustrates the flexible substrate 271 after the tip end is twisted.

As illustrated in this drawing, a plurality of pairs of antennas may be disposed. By disposing a plurality of antennas, moisture of a plurality of points can be measured in a depth direction.

FIG. 157 is a diagram illustrating an example of a sensor device 200 using a flexible substrate and a rigid substrate at a time when the number of antennas according to the first modification example of the first embodiment of the present technology is increased. a in this drawing is an example in which a plurality of antennas are disposed, and one rigid substrate is used, and b in this drawing is an example in which a plurality of antennas are disposed, and five rigid substrates are used.

In b in the diagram, a rigid substrate 276 is connected to a tip end of a flexible substrate 271, and a transmission antenna 221 is disposed in the rigid substrate 276. A rigid substrate 277 is connected to a tip end of a flexible substrate 272, and a reception antenna 231 is disposed in the rigid substrate 277. In addition, a flexible substrate 273 is disposed between the rigid substrate 276 and a rigid substrate 278, and a transmission antenna 222 is disposed in the rigid substrate 278. A flexible substrate 274 is disposed between the rigid substrate 277 and a rigid substrate 279, and a reception antenna 232 is disposed in the rigid substrate 278.

FIG. 158 is a diagram illustrating an example of a sensor device 200 in which a transmission line is wired for each antenna in the first modification example of the first embodiment of the present technology. a in this diagram represents a flexible substrate 271 before a tip end thereof is twisted, and b in this diagram illustrates the flexible substrate 271 after the tip end is twisted.

In a case in which a plurality of antennas are disposed, as illustrated in this diagram, a transmission line may be wired for each antenna.

FIG. 159 is a diagram illustrating an example of a sensor device 200 in which a transmission line is wired for each antenna, and a flexible substrate and a rigid substrate are used in the first modification example of the first embodiment of the present technology. a in this diagram is an example in which a plurality of antennas are disposed, and one rigid substrate is used, and b in this diagram is an example in which a plurality of antennas are disposed, and five rigid substrates are used.

FIG. 160 is a diagram illustrating an example of a sensor device 200 in which substrates are disposed inside a sensor casing 305 of a hard shell in the first modification example of the first embodiment of the present technology. a in this diagram is an example in which one rigid substrate 275 and flexible substrates 271 and 272 are disposed with being connected to each other, and b in this diagram illustrates an example in which flexible substrates 271 and 272 are coated using electric wave absorbing units 341 and 344.

Since it is easy for the flexible substrate 271 and the like to be flexibly transformed, for the purpose of maintaining a shape, as illustrated in a in this diagram, the flexible substrate 271 and the like may be disposed inside a sensor casing 305 of a hard shell. As illustrated in b in this diagram, coating may be performed using electric wave absorbing units 341 and 344 By using the hardshell, the shape can be maintained. Particularly, since a distance between antennas has an influence on characteristics, it is a substantially advantageous to maintain the distance between antennas. In addition, by also using the electric wave absorbing unit 341 and the like, unrequired reflected waves can be absorbed, which leads to improvement of the characteristics.

FIG. 161 is a diagram illustrating an example of a sensor device in which the number of antennas is increased, and substrates are disposed inside a sensor casing 305 of a hard shell in the first modification example of the first embodiment of the present technology. a in this diagram is an example in which a plurality of antennas are disposed, and one rigid substrate is used, and b in this diagram illustrates an example in which a plurality of antennas are disposed, and five rigid substrates are used.

In this way, according to the first modification example of the first embodiment of the present technology, by twisting a part of a flexible substrate, the antennas are configured to face each other, and thus the configuration of the sensor device 200 can be simplified more than that of the first embodiment.

Second Modification Example

In the first embodiment described above, although the in-probe substrates 321 and 322 are connected in a direction orthogonal to the measurement unit substrate 311 such that the antennas are configured to face each other, in this configuration, connectors and cables for connection are necessary in addition to the three substrates, whereby the structure becomes complex. In a sensor device 200 according to this second modification example of the first embodiment, a part of a flexible/rigid substrate is bent, whereby antennas are configured to face each other, which is different from the first embodiment.

FIG. 162 is a diagram illustrating examples of a sensor device 200 according to the second modification example of the first embodiment of the present technology and a comparative example. a in this diagram illustrates an example of the sensor device 200 according to the second modification example of the first embodiment, and b in this diagram illustrates an example of the sensor device 200 of the comparative example in which three substrates are connected.

Inside the sensor device 200 according to the second modification example of the first embodiment, a flexible/rigid substrate acquired by bonding flexible substrates 271 and 272 and rigid substrates 275 to 276 is disposed.

In the rigid substrate 275, a measurement circuit 210 is disposed. A transmission antenna 221 (not illustrated) is disposed in the rigid substrate 276, and a reception antenna 231 (not illustrated) is disposed in the rigid substrate 277.

The rigid substrate 275 and the rigid substrate 276 are connected using the flexible substrate 271, and the rigid substrate 275 and the rigid substrate 277 are connected using the flexible substrate 272. The flexible substrates 271 and 272 are bent such that a state in which the antenna disposed on the rigid substrate 276 and the antenna disposed on the rigid substrate 277 face each other is formed.

As illustrated in b in this diagram, a comparative example in which a rigid substrate 275 and rigid substrates 276 and 277 are respectively connected using connectors 314 and 315 may be considered. Compared to this comparative example, in a configuration in which a part of a flexible/rigid substrate is bent as in a in this diagram, no connector is used, and thus a cost for connectors and an assembling cost can be reduced. In addition, since three rigid substrates can be integrated, a cost for the substrates can be reduced. Furthermore, the directivity of conventional antennas can be used as it is, and a transmission loss can be reduced.

In this way, according to the second modification example of the first embodiment of the present technology, antennas are configured to face each other by bending a part of the flexible/rigid substrate, and thus a cost for connectors and an assembling cost can be reduced.

Third Modification Example

In the first embodiment described above although antennas of a planar shape or antennas of a planar shape and a slit shape and the measurement unit substrate 311 are connected to each other using transmission lines (strip lines and the like) of the inside of the in-probe substrate, they can be connected using coaxial cables. In a sensor device 200 according to this third modification example of the first embodiment, antennas of a planar shape or antennas of a planar shape and a slit shape and the measurement unit substrate 311 are connected using coaxial cables, which is different from the first embodiment.

FIG. 163 is a diagram illustrating an example of the sensor device 200 according to the third modification example of the first embodiment of the present technology. In the sensor device 200 according to this third modification example of the first embodiment, three antennas and the measurement unit substrate 311 are connected using coaxial cables 281 to 286, which is different from the first embodiment.

The transmission antennas 221 to 223 and the measurement unit substrate 311 are connected using the coaxial cables 281 to 283, and the reception antennas 231 to 233 and the measurement unit substrate 311 are connected using the coaxial cables 284 to 286.

In order to dispose antennas at desired positions using coaxial cables of a flexible material (a material having flexibility), for example, frames 291 to 294 formed to have a constant coefficient of thermal expansion may be used. The measurement unit substrate may be inserted into a sensor casing 305 with a transmission antenna and a corresponding coaxial cable interposed between frames 291 and 292 and with a reception antenna and a corresponding coaxial cable interposed between frames 293 and 294. Here, for example, when the frames 291 and 292 having transmission antennas and corresponding coaxial cables interposed therebetween are formed using materials of different coefficients of thermal expansion, there is a likelihood of these two frames being bent according to a change in the temperature of an environment in which the sensor device 200 is disposed. For this reason, in the third modification example, it is preferable that all the components configuring the frames be formed using materials having the same coefficients of thermal expansion. In addition, it is preferable that such components be formed using electromagnetic wave transmissive material not to disturb radiation and reception of electromagnetic waves.

FIG. 164 is a diagram illustrating an example of a top view and a cross-sectional view of the sensor device 200 according to the third modification example of the first embodiment of the present technology. a in this diagram illustrates an example of a top view of a measurement unit casing 310. b in this diagram illustrates a cross-sectional view of a part of a probe casing 320 in which no antenna is present, and c in this diagram illustrates a cross-sectional view of a part of the probe casing 320 in which an antenna is present.

As illustrated in a in this diagram, in the measurement unit casing 310, positioning parts 353 and 354 used for regulating a position of a measurement unit substrate 311 are disposed. As illustrated in b and c in this diagram, a coaxial cable 281 and the like are connected to a transmission antenna 221 and the like.

FIG. 165 is a diagram illustrating a method for housing substrates in the third modification example of the first embodiment of the present technology. First, as illustrated in a in this diagram, antennas of a transmission side connected to coaxial cables are interposed between the frames 291 and 292, and antennas of a reception side are interposed between the frames 293 and 294. As illustrated in b in this diagram, the positioning parts 353 and 354 are attached to lower parts of the measurement unit substrate 311, and the positioning parts 351 and 352 are attached to tip ends of the in-probe substrates 321 and 322. Next, as illustrated in c in this diagram, a structure to which such positioning parts are attached is inserted into the sensor casing 305.

FIG. 166 is a diagram illustrating another example of a method for housing substrates in the third modification example of the first embodiment of the present technology. As illustrated in a in this diagram, inside the sensor casing 305, the positioning parts 351 to 354 and the frames 291 to 294 can be mounted first. In this case, as illustrated in b and c in this diagram, the measurement unit substrate 311 and the like are inserted into the sensor casing 305, and, as illustrated in d in this diagram, the sensor casing 305 is sealed.

FIG. 167 is a diagram illustrating another example of a method for housing substrates in the third modification example of the first embodiment of the present technology. As illustrated in this diagram, a sensor casing 305 that can be divided into a front casing 305-1 and a rear casing 305-2 can be used. For example, it may be configured such that, as illustrated in a in this diagram, the rear casing 305-2 is placed, as illustrated in b and c in this diagram, the measurement unit substrate 311 and the like are inserted, and as illustrated in d and e in this diagram, the front casing 305-1 is mounted.

In this way, according to the third modification example of the first embodiment of the present technology, since antennas and the measurement unit substrates 311 are connected using coaxial cables, also in a case in which a transmission line is long, by disposing a transmission antenna and a reception antenna at predetermined positions, a predetermined distance between the antennas can be realized. In accordance with this, moisture can be accurately measured.

Fourth Modification Example

In the first embodiment described above, as a structure for fixing directions and positions of the transmission antenna and the reception antenna housed inside the probe casing, the positioning parts 351 and 352 are disposed inside the probe casing 320.

The structure for fixing the directions and the position of the transmission antenna and the reception antenna housed inside the probe casing is not limited to the structure according to the first embodiment illustrated in FIG. 4, and various modification examples may be considered.

Modification examples of the structure for fixing the directions and the positions of the transmission antenna and the reception antenna will be described as fourth modification examples.

In addition, in such various fourth modification examples, the structure for fixing directions and positions of the transmission antenna and the reception antenna (for example, positioning parts or grooves for positioning), unless otherwise mentioned, may have a form in which, after a casing is formed, a structure formed separately from the casing is mounted in the casing or may have a form in which a casing has a structure for fixing positions of the antennas from a time at which it is formed.

FIG. 168 is a diagram illustrating an example of a sensor device 200 as fourth modification example 1 of the first embodiment of the present technology. In this sensor device 200 according to fourth modification example 1 of the first embodiment, positioning parts 353 and 354 are further disposed inside a measurement unit casing 310, which is different from the first embodiment.

The positioning parts 351 and 352 are disposed at tip ends of a probe casing 320. Such positioning parts 351 and 352 are components used for fixing directions of in-probe substrates 321 and 322 to a predetermined direction and fixing such positions to predetermined positions (positions having a predetermined distance between the two substrates). Such positioning parts may be integrated with the sensor casing 305.

The positioning parts 353 and 354 are components used for fixing a position of the measurement unit substrate 311 to a predetermined position. Such positioning parts 353 and 354 may also have a shape for causing the transmission antenna and the reception antenna to be easily disposed at predetermined positions in a predetermined direction (a Y-axis direction or the like) set in advance while moving them inside the probe casing 320. For example, the positioning parts may have inclining faces toward a predetermined direction set in advance. In order to guide antennas to predetermined positions set in advance, the positioning parts may have inclining faces toward the positions. As a material of each of the positioning parts, for example, an electromagnetic transmissive material is used.

FIG. 169 is a diagram illustrating an example of a top view and a cross-sectional view of the sensor device 200 according to fourth modification example 1 of the first embodiment of the present technology. a in this diagram illustrates an example of a top view of a measurement unit casing 310. b in this diagram illustrates a cross-sectional view of a probe casing at positions at which the positioning parts 351 and 352 are disposed. In each of the measurement unit casing 310 and the probe casing 320, a groove used for mounting the positioning part 351 and the like are formed.

FIG. 170 is a diagram illustrating a method for housing substrates according to fourth modification example 1 of the first embodiment of the present technology. As illustrated in a in this diagram, the positioning parts 351 to 354 are mounted inside the sensor casing 305. Then, as illustrated in b and c in this diagram, the measurement unit substrate 311 and the like are inserted into the sensor casing 305, and, as illustrated in d in this diagram, the sensor casing 305 is sealed.

FIG. 171 is a diagram illustrating another example of a method for housing substrates according to fourth modification example 1 of the first embodiment of the present technology. As illustrated in this diagram, a sensor casing 305 that can be divided into a front casing 305-1 and a rear casing 305-2 also can be used.

FIG. 172 is a diagram illustrating an example of a sensor device 200 in which positions of positioning parts are changed as fourth modification example 2 of the first embodiment of the present technology. As illustrated in this diagram, the positioning parts 351 and 352 may be disposed near an upper end of the probe casing 320. In addition, the positioning parts 351 and 352 may be disposed at a center portion of the probe casing 320.

FIG. 173 is a diagram illustrating an example of a top view and a cross-sectional view of a sensor device 200 in which positions of positioning parts are changed as fourth modification example 2 of the first embodiment of the present technology.

FIG. 174 is a diagram illustrating an example of a sensor device 200 in which positioning parts are added as fourth modification example 3 of the first embodiment of the present technology. As illustrated in this diagram, positioning parts 355 and 356 may be added near an upper end of the probe casing 320. In addition, the positioning parts 355 and 356 may be disposed at a center portion of the probe casing 320. The positioning parts are not limited to the example illustrated in FIG. 174, and the positioning parts may be disposed at a plurality of positions inside the probe casing 320.

FIG. 175 is a diagram illustrating an example of a top view and a cross-sectional view of a sensor device 200 in which positioning parts are added as fourth modification example 3 of the first embodiment of the present technology.

FIG. 176 is a diagram illustrating an example of a sensor device 200 in which shapes of the positioning parts are different as fourth modification example 4 of the first embodiment of the present technology.

FIG. 177 is a diagram illustrating an example of a top view and a cross-sectional view of the sensor device in which shapes of positioning parts are different as fourth modification example 4 of the first embodiment of the present technology. As illustrated in FIGS. 176 and 177, positioning parts 351, 352, 355, and 356 may be in a form pressing sectional end portions of in-probe substrates 321 and 322 on probe cross-sections. In addition, the in-probe substrate 321 is interposed between frames 291 and 292, and the in-probe substrate 322 is interposed between frames 293 and 294.

In addition, for example, the positioning parts 355 and 356 may extend in a length direction (the Y-axis direction) of substrates of the inside of the probe casings such that positions of substrates inserted into the inside of the probe casing 320 are fixed. The length may be equal to or larger than a length (that is, a width) of the in-probe substrate 321 and the like in the Z-axis direction or equal to or larger than ½ of the length of the in-probe substrate 321 and the like in the Y-axis direction.

FIG. 178 is a diagram illustrating a method for housing substrates used in a case in which shapes of positioning parts are different as the fourth modification example 4 of the first embodiment of the present technology. As illustrated in a in this diagram, the positioning parts 351 to 354 and the frames 291 to 294 are mounted inside the sensor casing 305. As illustrated in b and c in this diagram, the measurement unit substrate 311 and the like are inserted into the sensor casing 305, and, as illustrated in d in this diagram, the sensor casing 305 is sealed. In addition, as the shape of the frames 291 to 294, various shapes may be selected as long as a structure allowing easy insertion of substrates and being able to fix the positions of the substrates is formed. As an example, the shape may be a groove shape or may be a rail shape.

FIG. 179 is another example of a diagram illustrating a method for housing substrates used in a case in which shapes of positioning parts are different as fourth modification example 4 of the first embodiment of the present technology. As illustrated in a in this diagram, before insertion of the sensor casing 305, the in-probe substrate 321 may be interposed between the frames 291 and 292, and the in-probe substrate 322 may be disposed between the frames 293 and 294. In this case, as illustrated in b in this diagram, the positioning parts 351 to 354 are mounted. Next, as illustrated in c in this diagram, a structure in which such positioning parts are mounted is inserted into the sensor casing 305.

FIG. 180 is a diagram illustrating an example of a sensor device 200 in which frames are extended as fourth modification example 5 of the first embodiment of the present technology. As illustrated in this diagram, the frames 291 to 294 can be also extended to an upper end of the sensor casing 305.

FIG. 181 is a diagram illustrating an example of a top view and a cross-sectional view of a sensor device in which frames are extended as fourth modification example 5 of the first embodiment of the present technology. a in this diagram illustrates an example of a top view of the measurement unit casing 310. b in this diagram illustrates a cross-sectional view of the probe casing 320 of a part in which no antenna is present, and c in this diagram illustrates a cross-sectional view of the probe casing 320 of a part in which an antenna is present.

FIG. 182 is a diagram illustrating an example of a sensor device 200 further including another structure fixing a position of a measurement unit substrate as fourth modification example 6 of the first embodiment of the present technology. As illustrated in this diagram, a structure allowing the measurement unit substrate and the in-probe substrate to fit each other may be included. More specifically, a structure in which a notch is formed in any one of the measurement unit substrate and the in-probe substrate, and two substrates are fitted to each other using these may be included.

FIG. 183 is a diagram illustrating an example of a cross-sectional view of a sensor device 200 further including another structure fixing a position of a measurement unit substrate as fourth modification example 6 of the first embodiment of the present technology. a in this diagram illustrates a cross-sectional view of a probe casing at positions at which positioning parts 351-1 and 352-1 are disposed.

FIG. 184 is a diagram illustrating an example a sensor device 200 in which jigs are added as fourth modification example 7 of the first embodiment of the present technology. As illustrated in this diagram, jigs 359-1 and 359-2 fixing a measurement unit substrate 311 and in-probe substrates 321 and 322 may be added. Such a jig includes both a part fitting or fixing the measurement unit substrate 311 and a part fitting or fixing the in-probe substrate 321 and the like. Also in the case of this form, by fixing a part of any one of the measurement unit substrate 311 and the in-probe substrate 321 and the like that have been integrated according to the fitting or fixing described above to the sensor casing 305, the positions of such substrates can be fixed.

FIG. 185 is a diagram illustrating an example of a top view and a cross-sectional view of a sensor device 200 in which jigs are added as fourth modification example 7 of the first embodiment of the present technology. a in this diagram illustrates an example of a top view of a measurement unit casing 310. b in this diagram illustrates a cross-sectional view of a probe casing at positions at which positioning parts 351-1 and 352-1 are disposed.

FIG. 186 is a diagram illustrating an example of a sensor device 200 in which a structure causing in-probe substrates 321 and 322 to butt against the sensor casing 305 is included as fourth modification example 8 of the first embodiment of the present technology. In accordance with causing tip ends (parts enclosed by dotted lines) of the in-probe substrates 321 and 322 to butt against the sensor casing 305 without disposing positioning parts, positions of such substrates can be fixed.

FIG. 187 is an example of a cross-sectional view of the sensor casing and the in-probe substrates of the sensor device 200 having a structure causing the in-probe substrates 321 and 322 to butt against the sensor casing 305 as fourth modification example 8 of the first embodiment of the present technology. a in this diagram illustrates a cross-sectional view of the sensor casing 305 taken along line A-A' illustrated in FIG. 186. b in FIG. 187 illustrates a cross-sectional view of the sensor casing 305 taken along line B-B' illustrated in FIG. 181. c in FIG. 187 illustrates a cross-sectional view of the sensor casing 305 taken along line C-C' illustrated in FIG. 186. In the structure causing the in-probe substrates 321 and 322 to abut against the probe casing 300 illustrated in FIGS. 186 and 187, the in-probe substrates are brought into contact with the probe casing 300 at least at two points among a total of four points of two points in a width direction (the Z-axis direction) of the substrate x two points in a thickness direction (the Z-axis direction) of the substrate in the width direction (the Z-axis direction) of the substrate, whereby the positions of the in-probe substrates 321 and 322 inside the casing are fixed.

FIG. 188 is a diagram illustrating fourth modification example 9 (a modification example of a structure fixing directions and positions of a transmission antenna and a reception antenna) according to the first embodiment of the present technology. As fourth modification example 9, the sensor device 200 illustrated in FIG. 188 does not include the sensor casing 305 included in the first embodiment (FIG. 4) of the present technology. The sensor device 200 illustrated in FIG. 188 does not include the sensor casing 305 but includes at least:

(1) A transmission probe formed using a structure in which the periphery of a transmission substrate (the same transmission probe substrate 321 as that included in the sensor device 200 illustrated in FIG. 4) including a transmission antenna and a transmission line for transmission connected thereto is hardened using a resin; and (2) a reception probe formed using a structure in which the periphery of a reception substrate (the same reception probe substrate 322 as that included in the sensor device 200 illustrated in FIG. 4) including a reception antenna and a transmission line for reception connected thereto is hardened using a resin.

In addition, a structure in which the transmission probe of (1) described above and the reception probe of (2) are fixed with respect to each other is included therein.

By including the transmission probe of (1) described above and the reception probe of (2) described above and further including (3) a third structure part different from (1) and (2) described above, the sensor device 200 included in fourth modification example 9 may have a structure in which the transmission probe of (1) described above and the reception probe of (2) are fixed with respect to each other. Here, an example of the third structure part of (3) described above is a reinforcing member like the reinforcing part 260 illustrated in FIG. 4.

The sensor device 200 illustrated in FIG. 188 includes the transmission probe of (1) described above, the reception probe of (2) described above, and the structure part of (3) described above in which the periphery of the measurement unit substrate 311 is hardened using a resin as the third structure part and has a structure in which the structures of (1) to (3) described above are integrated and fixed.

Here, regarding the transmission probe of (1) described above and the reception probe of (2) described above, in order to prevent "such probes being deformed when such probes are inserted into soil, electronic substrates disposed inside the probes being deformed, as a result, a distance between a transmission antenna and a reception antenna formed in the electronic substrate being changed from a predetermined value, and error occurring in a result of measurement of an amount of moisture", in the transmission probe formed using the structure in which the periphery of the transmission substrate of (1) described above is hardened using a resin described above, it is preferable that a strength of a resin part included in this probe is higher than the strength of the single transmission substrate included in this probe.

In other words, it is preferable that the strength of the transmission probe in which the periphery of the transmission substrate is hardened using a resin be twice the strength of the single transmission substrate included in this probe or more. Furthermore, in other words, in a case in which an amount of deformation of the transmission probe in which the periphery of the transmission substrate is hardened using a resin using the method illustrated in FIG. 135 and the amount of deformation of the single transmission substrate included in this probe are compared with each other, it is preferable that the amount of deformation of the transmission probe in which the periphery of the transmission substrate is hardened using a resin be ½ of the amount of deformation of the single transmission substrate included in this probe or less.

Similarly, regarding the reception probe of (2) described above that is formed using the structure in which the periphery of the reception substrate is hardened using a resin, it is preferable that a strength of a resin part included in this probe be higher than the strength of the single reception substrate included in this probe. In other words, it is preferable that the strength of the reception probe in which the periphery of the reception substrate is hardened using a resin be twice the strength of the single reception substrate included in this probe or more. Furthermore, in other words, in a case in which an amount of deformation of the reception probe in which the periphery of the reception substrate is hardened using a resin using the method illustrated in FIG. 135 and the amount of deformation of the single reception substrate included in this probe are compared with each other, it is preferable that the amount of deformation of the reception probe in which the periphery of the reception substrate is hardened using a resin be ½ of the amount of deformation of the single reception substrate included in this probe or less.

In this way, according to the fourth modification example of the first embodiment of the present technology, by including various structures used for fixing the directions and the positions of the transmission antenna and the reception antenna housed inside the probe casing, in accordance with this, the transmission antenna and the reception antenna can be fixed in a predetermined direction at a predetermined position.

Fifth Modification Example

In the first embodiment described above, as described with reference to FIG. 135, in order to prevent the probe casing 320 from being deformed at the time of inserting the probe casing 320 included in the sensor device 200 into soil, a structure in which the strength of the probe casing 320 is configured to be higher than that of the in-probe substrates 321 and 322 inserted into the inside of the probe casing 320 is included. The thickness of the probe casing 320 is a predetermined thickness such that the strength of the casing is above the strength of the substrate described above. However, in a case in which the hardness of soil in which the sensor device 200 according to the first embodiment is used is markedly high, in order to prevent deformation occurring when the probe casing 320 is inserted into the soil, there is a likelihood of the probe casing 320 being requested to have a higher strength. In order to increase the strength of the probe casing 320, a thickness of the casing needs to be enlarged. However, in a case in which the thickness of the probe casing 320 is carelessly enlarged (for example, a thickness of the casing near an antenna is markedly enlarged), the accuracy of measurement of the amount of moisture may be considered to be degraded in some cases. Thus, as a fifth modification example of the first embodiment, a structure for improving the strength of the probe casing 320 included in the sensor device 200 more than the first embodiment without a concern for degrading the accuracy of measurement of the amount of moisture will be described with reference to FIGS. 191 to 199.

Before a cross-sectional shape of a probe casing 320 included in a sensor device 200 according to a fifth modification example of the first embodiment of the present technology is described, the cross-sectional shape of the probe casing 320 included in the sensor device 200 according to the first embodiment of the present technology will be described with reference to FIGS. 189 and 190.

Referring to FIG. 4, in the first embodiment of the present technology, as a constituent element (9) thereof, in a cross-section in a direction orthogonal to the extending direction (the Y-axis direction) of the probe casings 320*a* and 320*b*, (1) a distance from the center of the in-probe substrate 321 to a casing end of the probe casing 320*a* in a direction vertical to the in-probe substrate 321 and in a direction toward the reception antenna has been described to be shorter than (2) a distance from the center of the in-probe substrate 321 to the casing end of the probe casing 320*a* in a direction parallel to the in-probe substrate 321.

Similarly, (1') a distance from the center of the in-probe substrate 322 to a casing end of the probe casing 320*b* in a direction vertical to the in-probe substrate 322 and in a direction toward the transmission antenna has been described to be shorter than (2') a distance from the center of the in-probe substrate 322 to the casing end of the probe casing 320*b* in a direction parallel to the in-probe substrate 322.

FIG. 189 is a diagram illustrating the structure of the constituent element (9) described above and the structure of a comparative example more specifically.

FIG. 189*a* is a diagram in which characteristic structures included in the sensor device 200 are superimposed acquired when the sensor device 200 according to the first embodiment of the present technology is seen from above in the positive direction of the Y axis. In this diagram, the measurement unit casing 310, the measurement unit substrate 311, the probe casing 320, and the in-probe substrates 321 and 322 are illustrated. In this diagram, (1) the distance from the center of the in-probe substrate 321 to a casing end of the probe casing 320*a* in a direction vertical to the in-probe substrate 321 and in a direction toward the reception antenna is denoted by reference sign dx, and (2) the distance from the center of the in-probe substrate 321 to the casing end of the probe casing 320*a* in a direction parallel to the in-probe substrate 321 is denoted by reference sign dz. In this diagram, the sensor device 200 according to the first embodiment of the present technology has a structure in which dx described above is smaller than dz described above in a cross-section in which the probe casing 320 included in the sensor device 200 as the constituent element (9) thereof is orthogonal to the extending direction thereof.

In contrast to this, b of FIG. 189 is a comparative example not having the structure of the constituent element (9) described above, in other words, a structure in which a distance from the center of the in-probe substrate 321 to a casing end of the probe casing 320*a* in a direction vertical to the in-probe substrate 321 and in a direction toward the reception antenna and a distance from the center of the in-probe substrate 321 to the casing end of the probe casing 320*a* in a direction parallel to the in-probe substrate 321 are the same is formed.

Here, referring to FIG. 190, various examples of the constituent element (9) of the sensor device 200 according to the first embodiment of the present technology will be described. This diagram illustrates a cross-sectional shape of the probe casing 320 in a direction orthogonal to the extending direction of the probe casing 320. In this diagram, the cross-sectional shape of the probe casing 320 is a shape in which (1) a distance dx from the center of the in-probe substrate 321 to a casing end of the probe casing 320*a* in a direction vertical to the in-probe substrate 321 and in a direction toward the reception antenna is shorter than (2) a distance dy from the center of the in-probe substrate 321 to the casing end of the probe casing 320*a* in a direction parallel to the in-probe substrate 321.

In addition, the cross-sectional shape of the probe casing 320, as illustrated in a in this diagram, may be an oval having a direction orthogonal to the in-probe substrate as a minor axis or a shape that is approximately the same as this, as illustrated in b in this diagram, may be a shape in which a width of the probe casing in a direction orthogonal to the in-probe substrate is smaller than a width of the probe casing in a direction parallel to the in-probe substrate and which is asymmetric with in a horizontal direction on the sheet surface and protruding to the rear face side (a side opposite to a direction in which an opposing antenna is present) of the in-probe substrate, as illustrated in c in this diagram, may be a shape in which a width of the probe casing in a direction orthogonal to the in-probe substrate is smaller than a width of the probe casing in a direction parallel to the in-probe substrate and which is asymmetric in a horizontal direction of the sheet surface and protrudes to the front face side (a side on which an opposing antenna is present) of the in-probe substrate, and, as illustrated in d in this diagram, may be a rectangle having a direction orthogonal to the in-probe substrate as a short side or a shape that is approximately the same as this.

A shape of the probe casing including a reception antenna is a shape that has line symmetry with respect to the shape of the probe casing including a transmission antenna, and thus description thereof will be omitted.

In addition, in b, c, and d in this diagram, rectangular diagrams are illustrated in a direction from the in-probe substrate to the center of the sensor device 200. These represent positions of radiation elements and reception elements of antennas being emphasized. Actually, such elements are formed on a front layer or an inner layer of the in-probe substrate.

Referring to FIG. 189, effects brought by the constituent element (9) of the sensor device 200 according to the first embodiment of the present technology will be described.

When a (the constituent element (9) of the present technology) and b (a comparative example) in this diagram are compared with each other, in these two diagrams, distances between the transmission in-probe substrates 321 and the reception in-probe substrates 322 are the same, and thus, distances between transmission antennas included in the transmission in-probe substrates 321 and reception antennas included in the reception in-probe substrate 322 are the same as well. When a and b in this diagram are compared with each other, only cross-sectional shapes of the probe casings 320 are different from each other.

Next, in a and b in this diagram, when ratios of areas of the outside of the casings (that is, areas that are soil) to areas between the transmission probe substrates 321 and the reception probe substrates 322 are compared with each other, the ratio of the area of the outside of the casing (in other words, an area that is soil) is smaller in b in this diagram than in a in this diagram.

As described above with reference to FIG. 98, in consideration of a time required for an electromagnetic wave to propagate from a transmission antenna to a reception antenna having a linear relation with an amount of moisture of soil, the moisture measuring system 100 according to the present invention acquires the amount of moisture of the soil. For this reason, in accordance with the ratio of a soil area to an area between the transmission probe substrate 321 and the reception probe substrate 322 decreasing, the above-described relation between a propagation delay time and the amount of moisture in soil deviates from a linear relation, and error included in a measurement result increases. In contrast to this, in accordance with the ratio of a soil area to an area between the two substrates described above increasing, the above-described relation between a propagation delay time and the amount of moisture in soil is close to a linear relation, and the amount of moisture in soil can be accurately measured.

By including the structure of the constituent element (9), the sensor device 200 according to the first embodiment of the present technology illustrated in a in FIG. 189, the ratio of a soil area to an area between the transmission probe substrate 321 and the reception probe substrate 322 is configured to be higher than that of the comparative example illustrated in b in this diagram, and, in accordance with this, an effect of accurately measuring the amount of moisture in soil is acquired.

Next, a fifth modification example of the first embodiment of the present technology will be described with reference to FIGS. 191 to 199.

FIGS. 191 to 199 are diagrams illustrating the fifth modification example of the first embodiment of the present technology, in other words, a structure for improving the strength of the probe casing 320 without causing a concern of degradation of the accuracy of measurement of the amount of moisture. In a probe casing 320 illustrated in such diagrams, in order to improve the strength thereof, the thickness of a part of the casing is configured to be larger than that of the probe casing 320 illustrated in a in FIG. 190. Here, when a thickness of the casing is enlarged, in order not to degrade the accuracy of measurement of the amount of moisture, a thickness of the casing is not enlarged in an area in which electromagnetic waves that are transmitted and received are transmitted. In addition, when a cross-sectional shape of the casing illustrated in FIGS. 191 to 199 is described, the shape of the casing illustrated in a in FIG. 190 will be referred to as a comparative example in which a thick casing is not included.

FIG. 191 is a diagram illustrating fifth modification example 1 of the first embodiment of the present technology.

FIG. 191 has a cross-sectional shape of the probe casing 320 illustrated in a in FIG. 190 and a shape in which antennas of a planar shape and two-sides radiation are disposed to face each other. In the in-probe casing 320 illustrated in FIG. 191, the antennas of two-sides radiation are disposed to face each other, and thus thicknesses of two places of an upward direction and a downward direction of the sheet surface are enlarged by avoiding a sheet surface inner direction in which electromagnetic waves are mainly transmitted through the casing.

In FIG. 191, as a shape for enlarging a thickness of the casing, as illustrated in a in FIG. 191, the thickness of the casing may be enlarged in a form in which a discontinuous point and an inflexion point are not present on both the outer circumference and the inner circumference of the casing. As illustrated of b of FIG. 191, the thickness may be enlarged in the inner direction of the casing. In this case, compared with the comparative example, the number of discontinuous points and inflexion points increases on the inner circumference of the casing. As illustrated of c of FIG. 191, the thickness may be enlarged in the outer direction of the casing. In this case, when compared with the comparative example, the number of discontinuous points or inflexion points increases on the outer circumference of the casing. As illustrated in d of FIG. 191, the thickness may be enlarged in both the inner direction and the outer direction of the casing. In this case, when compared with the comparative example, the number of discontinuous points or inflexion points increases on both the inner circumference and the outer circumference of the casing.

FIG. 192 is a diagram illustrating fifth modification example 2 of the first embodiment of the present technology and has a cross-sectional shape of the probe casing 320 illustrated in a in FIG. 190 and a shape in which antennas of a planar shape and two-sides radiation are disposed to face each other. In the probe casing 320 illustrated in FIG. 192, antennas of two-sides radiation are disposed to face each other, and thus the thickness is enlarged at one portion in the sheet surface outer direction by avoiding the sheet surface inner direction in which electromagnetic waves are mainly transmitted through the casing.

In FIG. 192, as a shape for enlarging a thickness of the casing, as illustrated in a of FIG. 192, in a shape in which a discontinuous point and an inflexion point are not present on both the outer circumference and the inner circumference of the casing, the thickness of the casing may be enlarged. As illustrated in b in FIG. 192, the thickness may be enlarged in the inner direction of the casing. In such a case, when compared with the comparative example, the number of discontinuous points or inflexion points increases on the inner circumference of the casing. As illustrated in c of FIG. 192, the thickness may be enlarged in the outer direction of the casing. In such case, when compared with the comparative example, the number of discontinuous points or inflexion points increases on the outer circumference of the casing. As illustrated in d of FIG. 192, the thickness may be enlarged in both the inner direction and the outer direction of the casing. In such a case, when compared with the comparative example, the number of discontinuous points or inflexion points increase on both the inner circumference and the outer circumference of the casing.

FIG. 193 is a diagram illustrating exceptional cases of the fifth modification example of the first embodiment of the present technology and has a cross-sectional shape of the probe casing 320 illustrated in a of FIG. 190 and a shape in which antennas of a planar shape and two-sides radiation are disposed to face each other. In the probe casing 320 illustrated in FIG. 193, although the antennas of two-sides radiation are disposed to face each other, exceptionally, a sheet surface inner direction in which electromagnetic waves are mainly transmitted through the casing is also included, and the thickness is enlarged at two portions in the sheet surface horizontal direction. In this case, although there is a concern for degradation of the accuracy of measurement of the amount of moisture, an effect of improving the strength of the probe casing 320 can be acquired.

In FIG. 193, as a shape for enlarging a thickness of the casing, as illustrated in a of FIG. 193, in a shape in which a discontinuous point and an inflexion point are not present on both the outer circumference and the inner circumference of the casing, the thickness of the casing may be enlarged. As illustrated in b of FIG. 193, the thickness may be enlarged in the inner direction of the casing. In this case, when compared with the comparative example, the number of discontinuous points or inflexion points increases on the inner circumference of the casing. As illustrated in c of FIG. 193, the thickness may be enlarged in the outer direction of the casing. In this case, when compared with the comparative example, the number of discontinuous points or inflexion points increases on the outer circumference of the casing. As illustrated in d of FIG. 193, the thickness may be enlarged in both the inner direction and the outer direction of the casing. In such a case, when compared with the comparative example, the number of discontinuous points or inflexion points increases on both the inner circumference and the outer circumference of the casing.

FIG. 194 is a diagram illustrating fifth modification example 3 of the first embodiment of the present technology and has a cross-sectional shape of the probe casing 320 illustrated in a in FIG. 190 and a shape in which antennas of a planar shape and two-sides radiation are disposed to face each other. In the probe casing 320 illustrated in FIG. 194, antennas of one-side radiation are disposed to face other, and thus the thickness is enlarged at three portions excluding the sheet surface inner direction by avoiding the sheet surface inner direction in which electromagnetic waves are mainly transmitted through the casing.

In FIG. 194, as a shape for enlarging a thickness of the casing, as illustrated in a of FIG. 194, in a shape in which a discontinuous point and an inflexion point are not present on both the outer circumference and the inner circumference of the casing, the thickness of the casing may be enlarged. As illustrated in b of FIG. 194, the thickness may be enlarged in the inner direction of the casing. In such a case, when compared with the comparative example, the number of discontinuous points or inflexion points increases on the inner circumference of the casing. As illustrated in c of FIG. 194, the thickness may be enlarged in the outer direction of the casing. In such case, when compared with the comparative example, the number of discontinuous points or inflexion points increases on the outer circumference of the casing. As illustrated in d of FIG. 194, the thickness may be enlarged in both the inner direction and the outer direction of the casing. In such a case, when compared with the comparative example, the number of discontinuous points or inflexion points increase on both the inner circumference and the outer circumference of the casing.

FIG. 195 is a diagram illustrating fifth modification example 4 of the first embodiment of the present technology.

In a structure illustrated in FIG. 195, only antennas of the structure illustrated in FIG. 191 are changed into one-side radiation, and the shape of the casing is the same.

FIG. 196 is a diagram illustrating fifth modification example 5 of the first embodiment of the present technology.

In a structure illustrated in FIG. 196, only antennas of the structure illustrated in FIG. 192 are changed into one-side radiation, and the shape of the casing is the same.

FIG. 197 is a diagram illustrating exceptional cases of the fifth modification example of the first embodiment of the present technology. In a structure illustrated in FIG. 197, only antennas of the structure illustrated in FIG. 193 are changed into one-side radiation, and the shape of the casing is the same.

FIG. 198 is a diagram illustrating fifth modification example 6 of the first embodiment of the present technology.

In a structure illustrated in FIG. 198, only antennas of the structure illustrated in FIG. 194 are changed into one-side radiation, and the shape of the casing is the same.

Each of the configurations illustrated in FIGS. 191 to 198 can be applied to each configuration illustrated in FIG. 190.

FIG. 199 is a diagram illustrating an example of setting of the thickness of the sensor casing 305 in the fifth modification example of the first embodiment of the present technology. As illustrated in a of this diagram, a thickness of the inner side of the probe casing 320 will be denoted by d1, and a thickness of the outer side will be denoted by d2. The thickness of the probe casing 320 in a direction (the Z-axis direction) parallel to the in-probe substrate 321 and the like will be denoted by d3. A thickness of the reinforcing part 360 in the Z-axis direction will be denoted by d6.

As illustrated in b of this diagram, a thickness of the measurement unit casing 310 in a face connected to the probe casing 320 (that is, a bottom face) among faces of the measurement unit casing 310 will be denoted by d4. A thickness of the measurement unit casing 310 on faces other than the bottom face will be denoted by d5. As illustrated in b of this diagram, the thickness of the measurement unit casing 310 in the Z-axis direction will be denoted by d8.

It is preferable that the sensor casing 305 according to the fifth modification example of the first embodiment of the present technology satisfy Condition 1 of d2>d1 or d3>d1. In accordance with this, when compared with a form not having this structure (in other words, a form in which a thick casing is not included), the mechanical strength of the casing can be improved, and, as a result, deformation of the casing and a change of the distance between transmission/reception antennas are reduced, and moisture can be accurately measured.

In addition, when compared with a form in which the thickness is enlarged on the whole circumference of the casing or a form in which the thickness of the casing is enlarged at a portion corresponding to d1 for improving the mechanical strength of the casing, the form satisfying Condition 1 described above can improve the strength of the casing without decreasing the ratio of the area of soil to the area between the transmission antenna and the reception antenna. In accordance with this, while the relation between the propagation delay time of an electromagnetic wave and an amount of moisture in the soil is maintained to be a linear relation, deformation of the casing and a change of the distance between the transmission/reception antennas are reduced, and moisture can be accurately measured.

In addition, it is preferable that Condition 2 of d6>d1 or d4>d1 be satisfied. In accordance with this, the strength of the casing can be improved without decreasing the ratio of the area of soil to the area between the transmission antenna and the reception antenna. In accordance with this, while the relation between the propagation delay time of an electromagnetic wave and an amount of moisture in the soil is maintained to be a linear relation, deformation of the casing and a change of the distance between the transmission/reception antennas are reduced, and moisture can be accurately measured. In addition, when the transmission probe and the reception probe are inserted into soil, even in a case in which stress is applied to such probes, the enlargement of d6 brings an effect of inhibiting a space between such probes from being broadened or narrowed from a predetermined distance, in other words, an effect of maintaining a distance between the transmission/reception antennas to be a predetermined distance, and also in accordance with this effect, moisture can be accurately measured.

Furthermore, the thickening of d4 brings an effect of inhibiting application of stress to a bottom face of the measurement unit casing 310 at the time of inserting the transmission probe and the reception probe into soil, deformation of the bottom face in accordance with this stress, and thus a change of a mounting angle of the probes in the bottom face. In accordance with this, an effect of inhibiting a space between the probes from being broadened or narrowed from a predetermined distance, in other words, an effect of maintaining a distance between the transmission/reception antennas to be a predetermined distance, and also in accordance with this effect, moisture can be accurately measured.

In a case in which Condition 2 is satisfied, at the same time, it may be configured such that d6>d5 or d4>d5. In this case, in a part of the casing of which contribution to accurate measurement of moisture is small, the thickness can be prevented from being unnecessarily enlarged more than in a form in which d1<d6<d5 or d1<d4<d5. As a result, an effect of easily manufacturing the casing, decreasing weights of the casing and the sensor device, and reducing a manufacturing cost of the casing is acquired.

In a case in which Condition 2 is satisfied, at the same time, it may be configured such that d6>d4. The thickening of d4 brings an effect of preventing deformation of the bottom face of the measurement unit casing 310 and maintaining a distance between the antennas to be a predetermined distance. On the other hand, the thickening of d6 can bring an effect of more effectively maintaining a distance between the antennas to be a predetermined distance at a position closer to the antenna than the bottom face. As a result, moisture can be accurately measured.

In addition, it is preferable that Condition 3 of d6<d8 be satisfied. When the reinforcing part 360 is formed using an electromagnetic wave transmissive material, reflectance of electromagnetic wave transmissive materials that are currently available in the market for electromagnetic waves is not zero. For this reason, reflection of electromagnetic waves may occur in the reinforcing part 360. By satisfying Condition 3 described above, compared to a case in which this Condition 3 is not satisfied, noise according to an electromagnetic wave radiated from an antenna being reflected by the reinforcing part 360 and being received by the reception antenna can be reduced. As a result, moisture can be accurately measured.

In addition, it is preferable that Condition 4 of d7>d6 be satisfied. In accordance with disposition of the reinforcing part 360, even in a case in which stress is applied to probes at the time of inserting the transmission probe and the reception probe into soil, a space between such probes can be inhibited from being broadened or narrowed from a predetermined distance. By configuring d7>d6, compared to a case in which this condition is not satisfied, an effect of effectively maintaining a distance between antennas to be a predetermined distance at a position close to the antennas can be acquired. As a result, moisture can be accurately measured.

In this way, according to the fifth modification example of the first embodiment of the present technology, the thickness of the probe casing 320 is adjusted, and thus moisture of the sensor device 200 can be measured more accurately. In addition, in the description presented above with reference to FIG. 199, as the structure of the casing illustrated in the diagram, although the structure illustrated in FIG. 194*a* is used, the description presented above can be also applied to any one of the structures illustrated in FIGS. 191 to 198.

Sixth Modification Example

In the first embodiment described above, although each pair of a plurality of antennas sequentially transmit/receive electromagnetic waves at each time, in this configuration, it is difficult to shorten the measurement time. This sensor device 200 according to the sixth modification example of the first embodiment enables a plurality of antennas to simultaneously transmit and receive electromagnetic waves through frequency division, which is different from the first embodiment.

FIG. 200 is a diagram illustrating one configuration example of a sensor device 200 in which a transceiver is disposed for each antenna in the sixth modification example of the first embodiment of the present technology. This sensor device 200 according to this sixth modification example of the first embodiment includes a transceiver for each set of antennas, which is different from the first embodiment. In a case in which there are three sets of antennas, transmitters 214-1, 214-2, and 214-3 and receivers 215-1, 215-2, and 215-3 are disposed. In addition, the number of sets of antennas is not limited to three as long as the number is two or more.

The transmitters 214-1 to 214-3 are respectively connected to transmission antennas 221 to 223, and the receivers 215-1 to 215-3 are respectively connected to reception antennas 231 to 232. The transmission switch 216 and the reception switch 217 become unnecessary. In accordance with this, the cost can be lowered.

The transmitters 214-1, 214-2, and 214-3 transmit transmission signals of mutually-different frequencies. In addition, the receivers 215-1, 215-2, and 215-3 receive reception signals of frequencies of corresponding transmitters. In accordance with control of such frequency division, signals from the transmission antennas 221 to 223 can be separated on a reception side.

FIG. 201 is a diagram illustrating one configuration example of the sensor device 200 in which one transmitter and one receiver are included in the sixth modification example of the first embodiment of the present technology. As illustrated in this diagram, the transmitter 214 may be connected to the transmission antennas 221 to 223, and the receiver 215 may be connected to the reception antennas 231 to 232. The transmitter 214 has a function equivalent to that of the transmitters 214-1 to 214-3, and the receiver 215 has a function equivalent to that of the receivers 215-1 to 215-3.

FIG. 202 is a diagram illustrating one configuration example of a sensor device 200 in which one receiver is included in the sixth modification example of the first embodiment of the present technology. As illustrated in this diagram, transmitters 214-1 to 214-3 may be respectively connected to transmission antennas 221 to 223, and a receiver 215 may be connected to reception antennas 231 to 232. The receiver 215 has a function equivalent to that of the receivers 215-1 to 215-3.

FIG. 203 is a diagram illustrating one configuration example of a sensor device 200 in which one transmitter is included in the sixth modification example of the first embodiment of the present technology. As illustrated in this diagram, the transmitter 214 may be connected to transmission antennas 221 to 223, and receivers 215-1 to 215-3 may be connected to reception antennas 231 to 232. The transmitter 214 has a function equivalent to the transmitters 214-1 to 214-3.

FIG. 204 is a diagram illustrating another example of a sensor device 200 in which a plurality of receivers are included in the sixth modification example of the first embodiment of the present technology. As illustrated in this diagram, a transmitter 214-1 may be connected to transmission antennas 221 and 223, a transmitter 214-2 may be connected to a transmission antenna 222, and a receiver 215 may be connected to reception antennas 231 to 232. The receiver 215 has a function equivalent to the receivers 215-1 to 215-3. In addition, the transmitter 214-1 supplies transmission signals of the same frequency to the transmission antennas 221 and 223. For this reason, it is preferable that the transmission antenna 221 and the transmission antenna 223 are separate away from each other to such a degree for which signal mixing does not occur.

FIG. 205 is a block diagram illustrating one configuration example of the receivers 215-1 to 215-3 in the sixth modification example of the first embodiment of the present technology. a in this diagram is a block diagram of the receiver 215-1. b in this diagram is a block diagram of the receiver 215-2. c in this diagram is a block diagram of the receiver 215-3.

The receiver 215-1 includes a mixer 241-1, a local oscillator 242-1, a low pass filter 243-1, and an ADC (Analog to Digital Converter) 244-1. The local oscillator 242-1 generates a local signal of a frequency $f_{LO1}$. The mixer 241-1 receives a reception signal of a frequency $f_1$ from the reception antenna 231, mixes the reception signal with a local signal, and supplies a signal of an intermediate frequency $f_{IF}$ to the ADC 244-1 through the low pass filter 243-1. The ADC 244-1 converts the signal of the intermediate frequency $f_{IF}$ into a digital signal and supplies the digital signal to the sensor control unit 211.

The receiver 215-2 includes a mixer 241-2, a local oscillator 242-2, a low pass filter 243-2, and an ADC 244-2. The receiver 215-3 includes a mixer 241-3, a local oscillator 242-3, a low pass filter 243-3, and an ADC 244-3. The configurations of such circuits are similar to circuits of the same names disposed inside the receiver 215-1.

FIG. 206 is a diagram illustrating an example of a frequency characteristic of a reception signal in the sixth modification example of the first embodiment of the present technology. Although there are three reception systems in FIG. 205, for the simplification of description, two systems will be assumed in FIG. 206.

The intermediate frequency is one wave $f_{IF}$ that is common to all the receivers. Cutoff frequencies $f_{cutoff}$ of low pass filters of two systems are the same. A reception frequency of the first antenna will be denoted by f1, and a reception frequency of the second antenna will be denoted by f2 (f1<f2). At this time, a relation between local frequencies $f_{1o1}$ and $f_{1o2}$ corresponding to respective systems is $f_{1o1}<f_{1o2}$. In addition, the intermediate frequency $f_{IF}$ is represented using the following expression.

$$f_{IF}=f1-f_{1o1}=f2-f_{1o2} \quad \text{Expression 7}$$

In a case in which a signal of the reception frequency f2 leaks into the reception system of the first antenna, a disturbance wave $f_{IF12}$ is represented using the following expression.

$$f_{IF12}=f2-f_{1o1} \quad \text{Expression 8}$$

In a case in which a signal of the reception frequency $f_1$ leaks into the reception system of the second antenna, a disturbance wave $f_{IF21}$ is represented using the following expression.

$$f_{IF21}=f1-f_{1o2} \quad \text{Expression 9}$$

At this time, a condition in which a disturbance wave does not enter a reception band is represented using the following expression.

$$f_{IF21}<-f_{cutoff} \quad \text{Expression 10}$$

$$f_{cutoff}<f_{IF12} \quad \text{Expression 11}$$

When Expression 8 and Expression 9 are substituted into Expression 10 and Expression 11, the following expressions are acquired.

$$f1-f_{1o2}<-f_{cutoff} \quad \text{Expression 12}$$

$$f_{cutoff}<f2-f_{1o1} \quad \text{Expression 13}$$

When Expression 12 and Expression 13 are transformed the following expressions are acquired.

$$f_{cutoff}<f_{1o2}-f1 \quad \text{Expression 14}$$

$$f_{cutoff}<f2-f_{1o1} \quad \text{Expression 15}$$

By substituting Expression 7 into Expression 14 and Expression 15, the following expressions are acquired.

$$f_{cutoff}<f2-f_{IF}-f1=f2-f1-f_{IF} \quad \text{Expression 16}$$

$$f_{cutoff}<f2+f_{IF}-f1=f2-f1+f_{IF} \quad \text{Expression 17}$$

Thus, f1, f2, and $f_{IF}$ may satisfy Expression 16 and Expression 17. Actually, $f_{cutoff}>f_{IF}$ is satisfied, and thus only Expression 16 becomes a restriction condition.

When Expression 16 is modified, the following expression is obtained.

$$f_{cutoff}+f_{IF}<f2-f1 \quad \text{Expression 18}$$

In other words, a difference between frequencies f2 and f1 that are adjacent to each other being constantly larger than a sum of $f_{cutoff}$ and $f_{IF}$ becomes a condition for performing measuring using frequency division.

When there is no restriction on a magnitude relation between f1 and f2, the condition of f1>f2 can be eliminated, and, from Expression 18, a condition according to the following expression may be satisfied for the frequencies f1 and f2 that are adjacent to each other.

$$f_{cutoff}+f_{IF}<|f2-f1| \quad \text{Expression 19}$$

FIG. 207 is an example of a timing diagram of frequency division driving in the sixth modification example of the first embodiment of the present technology. a in this diagram represents a frequency sweep of a first antenna (the transmission antenna 221, the reception antenna 231, and the like). b in this diagram represents a frequency sweep of a second antenna (the transmission antenna 222, the reception antenna 232, and the like). c in this diagram represents a frequency sweep of a third antenna (the transmission antenna 223, the reception antenna 233, and the like).

FIG. 208 is an example of a timing diagram representing operations of each unit disposed inside a sensor device according to the sixth modification example of the first embodiment of the present technology.

In FIGS. 207 and 208, the first antenna sweeps frequencies a1 to a2, during that period, the second antenna sweeps frequencies a3 to a4, and the third antenna sweeps frequencies a5 to a6.

Then, the first antenna sweeps frequencies a3 to a4, during that period, the second antenna sweeps frequencies a5 to a6, and the third antenna sweeps frequencies a1 to a2. Next, the first antenna sweeps frequencies a5 to a6, during that period, the second antenna sweeps frequencies a1 to a2, and the third antenna sweeps frequencies a3 to a4.

Any method may be used as a frequency sweeping method as long as a frequency for each antenna is independent and does not need to be an up-chirp as illustrated in FIG. 207. For all antennas, all the transmission bands are swept. In this control, all the frequency bands can be used, and the resolution of the moisture sensor is improved.

FIG. 209 is an example of a timing diagram of frequency division driving acquired when a sweeping period according to the sixth modification example of the first embodiment of the present technology is shortened.

FIG. 210 is an example of a timing diagram of operations of each unit disposed inside the sensor device acquired when a sweeping period according to the sixth modification example of the first embodiment of the present technology is shortened.

In FIGS. 209 and 210, the first antenna sweeps frequencies a1 to a2, during that period, the second antenna sweeps frequencies a3 to a4, and the third antenna sweeps frequencies a5 to a6. By narrowing a frequency band to be swept, the sweeping period can be shortened.

The control illustrated in FIGS. 207 to 210 can be applied to the sensor devices 200 illustrated in FIGS. 200 to 203.

FIG. 211 is an example of a timing diagram of frequency division driving in which frequencies of two antennas are the same in the sixth modification example of the first embodiment of the present technology. a in this diagram illustrates sweeping of frequencies of the first and third antennas. b in this diagram illustrates sweeping of frequencies of the second antenna.

FIG. 212 is an example of a timing diagram illustrating operations of each unit disposed inside a sensor device in which frequencies of two antennas are the same in the sixth modification example of the first embodiment of the present technology.

In FIGS. 211 and 212, the first and third antennas sweep frequencies a1 to a2, and, during that period, the second antenna sweeps frequencies a4 to a6. Then, the first and third antennas sweep frequencies a4 to a6, and, during that period, the second antenna sweeps frequencies a1 to a2. By narrowing a frequency band to be swept, the sweeping period can be shortened. This control is applied to the sensor device 201 illustrated in FIG. 204.

In this way, according to the sixth modification example of the first embodiment of the present technology, a transmitter supplies transmission signals of mutually-different frequencies to a plurality of transmission antennas, and thus the transmission switch 216 and the reception switch 217 are unnecessary.

Seventh Modification Example

In the first embodiment described above, an independent transmission line is connected to each of a plurality of antennas, and it cannot be avoided to increase the size of the probe in accordance with the number of antennas. In a sensor device 200 according to a seventh modification example of the first embodiment, a plurality of antennas are connected to one transmission line including a delay line, which is different from the first embodiment.

FIG. 213 is a diagram illustrating an example of a cross-sectional view of an in-probe substrate 321 according to a seventh modification example of the first embodiment of the present technology. a in this diagram represents a cross-sectional view of the in-probe substrate 321 acquired when it is seen in the Z-axis direction. b in this diagram represents a cross-sectional view of the in-probe substrate 321 acquired when it is seen in the Y-axis direction.

As illustrated in this diagram, in the in-probe substrate 321, a plurality of transmission antennas such as transmission antennas 221, 222, and 223 and the like are formed. Such transmission antennas are connected using a transmission line such as a strip line or the like. The transmission lines for respective transmission antennas are not independent from each other, and this corresponds to a state in which a plurality of transmission antennas are commonly electrically connected to one transmission line as an equivalent circuit. The configuration of the in-probe substrate 322 on the reception side has horizontal symmetry with respect to that on the transmission side.

FIG. 214 is a diagram illustrating a transmission path of a signal for each antenna in the seventh modification example of the first embodiment of the present technology. A transmission source is denoted by TX, and positions of transmission antennas 221, 222, and 223 are denoted by A, B, and C. A reception destination is denoted by RX, and positions of reception antennas 231, 232, and 233 are respectively denoted by P, Q, and R. An arrow represents a transmission direction of a signal. A solid line represents a signal that is a transmission/reception target. A dotted line represents an interference signal or a disturbance signal.

In a case in which moisture measurement of three positions is desired to be performed by simultaneously transmitting electromagnetic waves from three transmission antennas, as illustrated in this diagram, mainly, a propagation delay time of each of paths TX-A-P-RX, TX-B-Q-RX, and TX-C-R-RX needs to be measured.

However, as described above, in the sensor device 200, a plurality of antennas are commonly electrically connected to one transmission line on the transmission side and the reception side.

For this reason, as a reception signal, all the signals that have passed through the reception antennas P, Q, and R from the transmission antennas A, B, and C are superimposed and measured. In addition, signals of paths passing through TX-A-Q-RX, TX-A-R-RX, TX-B-P-RX, TX-B-R-RX, TX-C-P-RX, and TX-C-Q-RX other than the three paths described above are included as well.

In addition, in a case in which matching of a transmission antenna is not sufficiently taken, reflection occurs inside a transmission probe. For this reason, a path in which a signal radiated from the transmission antenna after the signal is reflected inside the transmission probe is also superimposed on the reception signal. In other words, signals of a path passing through TX-C-B-Q-RX, TX-B-A-P-RX, and the like other than nine paths described above are also included. It is apparent that an event of reflection occurring due to no matching of an antenna connected to a transmission line is an event of an electromagnetic wave reflecting on a boundary face between a transmission line and an antenna due to no impedance matching between the transmission line and the antenna. Similarly, in a case in which matching of a reception antenna is not sufficiently taken, reflection occurs inside a reception probe. For this reason, a path in which a signal received from a transmission antenna is reflected inside the reception probe is also superimposed in a reception signal. In other words, signals of paths passing through TX-B-Q-R-RX, TX-A-P-Q-RX, and the like other than the paths described above are also included.

FIG. 215 is a diagram illustrating transmission path of signals of two systems in the seventh modification example of the first embodiment of the present technology. As illustrated in this diagram, two systems of TX-C-B-Q-RX and TX-C-R-RX will be focused.

For example, in a case in which main transmission lines to antennas of the transmission probe and the reception probe have the same structure, two paths illustrated in this diagram are almost the same and thus cannot be separated, and a propagation delay between C-R cannot be correctly acquired.

FIG. 216 is a diagram illustrating an example of a sensor device 200 in which a delay line is disposed in the seventh modification example of the first embodiment of the present technology. A delay line is inserted into a main transmission line to an antenna of one of the transmission probe or the reception probe.

For example, as illustrated in this diagram, delay lines 265 and 266 are respectively inserted between P-Q and Q-R of the reception probe. In accordance with such delay lines, there is a path difference between two paths TX-C-B-Q-RX and TX-C-R-RX that cannot be separated in FIG. 215. For this reason, reception signals of the paths can be separated.

As described above, by appropriately disposing delay lines inside the in-probe substrates 321 and 322, signals of paths TX-A-P-RX, TX-B-Q-RX, and TX-C-R-RX that are measurement targets can be configured not to overlap with other paths. For this reason, the amount of moisture can be measured with high accuracy.

FIG. 217 is a diagram illustrating an example of a shape of a delay line 265 in the seventh modification example of the first embodiment of the present technology. The shape of the delay line 265 may be a meandering shape as illustrated in a in this diagram or may be a zigzag shape as illustrated in b in this diagram. As illustrated in c in this diagram, the shape may be a spiral shape. The shape is not limited to the shapes illustrated in this diagram as long as the transmission line can be wired longer than in a case in which the delay line is not disposed.

As illustrated in d, e, and f in this diagram, vias may be formed along the delay line 265. In accordance with this, jump of an electromagnetic wave due to electromagnetic coupling between lines adjacent to each other can be prevented, and thus the delay effect can be improved more than in a case in which no via is formed.

FIG. 218 is a diagram illustrating another example of the shape of the delay line 265 in the seventh modification example of the first embodiment of the present technology. When the shape is configured to be the meandering shape or the zigzag shape as illustrated in a and b in this diagram, a direction of an amplitude of the delay line may be set to a wiring direction of the transmission line. At this time as illustrated in c and d in this diagram, vias can be formed.

FIG. 219 is a diagram for describing a method of setting an amount of delay of the delay line in the seventh modification example of the first embodiment of the present technology. Until now, although the structure for separating two paths has been described, it will be reviewed that occurrence of a propagation delay difference of a certain degree is actually desirable. When a frequency response is transformed into an impulse response using an inverse Fourier transform thereof, in a case in which there is a propagation delay difference between two paths that is equal to or larger than the resolution, both paths can be separated, and thus an amount of moisture can be measured with high accuracy. More specifically, when a frequency band is denoted by df, it is preferable that the propagation delay difference is equal to or larger than 1/dF.

A case in which there are two paths including path A and path B from TX to RX as illustrated in a in this diagram, and the numbers of through points of the paths are the same will be considered. A propagation delay $T_A$ from TX to RX in path A is acquired by integrating propagation delays between respective points and is represented using the following expression.

[Math. 1]

$$T_A = \sum_{n=1}^{N} T_{An} \quad \text{Expression 20}$$

Similarly, a propagation delay $T_B$ from TX to RX in path B is represented using the following expression.

[Math. 2]

$$T_B = \sum_{n=1}^{N} T_{Bn} \quad \text{Expression 21}$$

Thus, it is preferable to determine positions of antennas and amounts of delays of delay lines such that a propagation delay difference dT satisfies the following expression.

$$dT=|TB-TA|\geq 1/df \quad \text{Expression 22}$$

A case in which there are two paths including path A and path B from TX to RX as illustrated in b in this diagram, and the numbers of through points of the paths are different from each other will be considered. Here, the number of through points of the path A will be denoted by N, and the number of through points of the path B will be denoted by M. Similar to the case of a in this diagram, propagation delays $T_B$ from TX to RX in the path A and the path B are represented using the following expression. A propagation delay $T_A$ is as represented in Expression 20.

[Math. 3]

$$T_B = \sum_{m=1}^{M} T_{Bm} \quad \text{Expression 23}$$

Thus, it is preferable to determine positions of antennas and amounts of delays of delay lines such that a propagation delay difference dT satisfies Expression 22. For example, in a case in which a range of frequencies to be measured is 1 GHz to 9 GHz, it is preferable that a propagation delay difference between the two paths is equal to or longer than 125 ps.

In this way, according to the seventh modification example of the first embodiment of the present technology, the delay line 265 and the like are inserted into the transmission line, and thus signals of different paths can be separated.

2. Second Embodiment

In the first embodiment described above, although the in-probe substrates 321 and 322 are connected to be orthogonal to the measurement unit substrate 311, in this configuration, connectors and cables need to be wired between substrates, and the structure becomes complicated. In this second embodiment, the number of such substrates is reduced, and connectors and cables connecting the substrates are reduced, which is different from the first embodiment. In accordance with this, according to the second embodiment, compared to the first embodiment, an effect of being able to reduce the number of components such as substrates, connectors, cables, and the like included in a sensor device 200 is acquired.

FIG. 220 is a diagram illustrating an example of a sensor device 200 according to the second embodiment of the present technology. Inside this sensor device 200 according to the second embodiment, only an electronic substrate 311-1 is disposed inside a sensor casing 305 in place of the measurement unit substrate 311, the in-probe substrate 321 and the in-probe substrate 322. A part of the electronic substrate 311-1 has a rectangular shape, one pair of substrate protrusion parts (a transmission substrate protrusion part and a reception substrate protrusion part) are connected to the substrate rectangular part, and they are integrated together. Thus, the substrate rectangular part and a direction in which the transmission substrate protrusion part and the reception substrate protrusion part extend (in other words, plane directions of such substrates) are parallel to each other, and, described in more detail, such substrates are formed on the same plane. Circuits on the measurement unit substrate 311 are disposed in the substrate rectangular part. In the substrate protrusion parts, circuits on the in-probe substrates 321 and 322 such as the transmission antennas 221 to 223 and the like are formed. In accordance with this configuration, Constituent elements (4) and (7) are unnecessary.

In addition, FIG. 220 illustrates that the sensor device 200 according to the second embodiment of the present technology can include planar antennas illustrated in FIGS. 19 to 47 as all the antennas (transmission antennas 221 to 223 and reception antennas 231 to 233) included in the sensor device 200 as an example. Similarly, the sensor device 200 according to the second embodiment of the present technology also can use the antennas of the planar shape and the slot shape illustrated in FIGS. 48 to 74 as all the antennas (the transmission antennas 221 to 223 and the reception antennas 231 to 233) included in the sensor device 200 as an example.

Similar to the sensor device 200 (FIG. 4) according to the first embodiment of the present technology in which the measurement unit substrate 311 is housed in the measurement unit casing 310, the transmission in-probe substrate 321 is housed in the transmission probe casing 320*a*, and the reception in-probe substrate 322 is housed in the reception probe casing 320*b*, in the sensor device 200 (FIG. 220) according to the second embodiment of the present technology, the substrate rectangular part of the electronic substrate 311-1 is housed in a measurement unit casing 310, the transmission substrate protrusion part of the electronic substrate 311-1 is housed in a transmission probe casing 320*a*, and the reception substrate protrusion part of the electronic substrate 311-1 is housed in a reception probe casing 320*b*.

Here, when the sensor device 200 according to the first embodiment of the present technology and the sensor device 200 according to the second embodiment of the present technology are compared with each other, there are different points in the cross-sectional shapes of the transmission probe casing 320*a* and the reception probe casing 320*b*. This will be described with reference to FIGS. 189 and 221, and an effect brought by the cross-sectional shapes of the transmission probe casing 320*a* and the reception probe casing 320*b* according to the second embodiment of the present technology will be described with reference to FIG. 221.

FIG. 221 is an example of a cross-sectional view in which structural characteristics of the sensor devices 200 according to the second embodiment of the present technology and a comparative example acquired when seen from above are superimposed. a in this diagram is an example of a cross-sectional view of the sensor device 200 according to the second embodiment of the present technology acquired when seen from above. b in this diagram is an example of the cross-sectional view of the sensor device 200 of the comparative example. Two ovals illustrated in a of this diagram represent a transmission probe casing and a reception probe casing. Similarly, two perfect circles illustrated in b of this diagram represents a transmission probe casing and a reception probe casing.

In a and b of this diagram, areas, to which a color is applied, that are on the outer side of the transmission probe casing and the reception probe casing represent soil. Soil positioned between the transmission probe casing and the reception probe casing is soil that is a target of which the amount of moisture is measured. In addition, rectangles represented using broken lines in a and b in this diagram represent outer shapes of the measurement unit casing 310.

As illustrated in a in FIG. 221, the sensor device 200 according to the second embodiment of the present technology includes the following configuration in place of Constituent element (9). A length (a width) of the substrate protrusion part of the electronic substrate 311-1 in the X-axis direction is larger than a thickness (a size in the Z-axis direction) thereof. In addition, as illustrated in a in this diagram, a distance dz from the center of the substrate protrusion part to a casing end of the probe casing 320 in a direction (the Z-axis direction) perpendicular to the electronic substrate 311-1 is smaller than a distance dx from the center of the substrate protrusion part to a casing end of the probe casing 320 in a direction (the X-axis direction) parallel to the electronic substrate 311-1. This configuration will be referred to as Constituent element (9'). As illustrated in b in this diagram, dz is the same as dx in the comparative example. When the probe casing of the sensor device 200 according to the second embodiment of the present technology illustrated in a of FIG. 221 and the probe casing of the sensor device 200 according to the first embodiment of the present technology illustrated in a of FIG. 189 are compared with each other, the structures (Configuration (9) and Configuration (9')) in which a distance from the center of the substrate to the end of the probe casing in a direction perpendicular to the substrate is shorter than a distance from the center of the substrate to an end of the probe casing in a direction parallel to the substrate are the same. However, in a of FIG. 221 and a of FIG. 189, directions of the substrates housed in the probe casings are different from each other (rotated by 90°). For this reason, in such diagrams, directions of the cross-sections of the probe casings are also different from each other (rotated by 90°).

In a and b of FIG. 221, rainfall from above the sensor device 200 of two probe casings (the transmission probe casing and the reception probe casing) illustrated in each of the diagrams falls into an area on the outer side of the measurement unit casing 310 denoted by broken lines in the diagram. Rain that has fallen into the area on the outer side of the measurement unit casing 310 penetrates (in other words, diffuses) into a soil that is a target of which an amount of moisture is to be measured and is positioned between the two probe casings.

Here, when the thicknesses of the probe casings of Constituent element (9') and the comparative example (in other words, the sizes of the probe casings in a diffusion direction in which rainfall diffuses from the measurement unit casing 310 to the measurement target area) are compared with each other, the size of the probe casing is smaller in Constituent element (9') than in the comparative example.

In the case of the comparative example, moisture necessarily linearly diffuses from limited soil that is on the outer side of the measurement unit casing 310 and is a sheet surface upward direction and a sheet surface downward direction of the measurement target area to the soil of the measurement target area. In this case, in accordance with diffusion of moisture from the outer side of the measurement unit casing 310 to the measurement target area, a moisture density of the soil decreases, and the moisture is not complemented from the outside of a diffusion path in the middle of the diffusion path.

In contrast to this, in the case of Constituent element (9'), in a wide area that is on an outer side of the measurement unit casing 310 and is from one probe casing and reaches the other probe casing, moisture diffuses in a planar shape from soil of the upward direction and the downward direction of the sheet surface to the probe casing. Then, when a part of moisture that has diffused into the probe casing in a planar shape diffuses to the moisture measurement target area between the probe casings, it diffuses while moisture is complemented from soil of the upward direction and downward direction of the sheet surface of the probe casing.

For this reason, in Constituent element (9') illustrated in a of FIG. 221, a moisture density of soil of a moisture measurement target area is closer to an amount of original moisture of the soil (an amount of soil moisture of an area in which the sensor device 200 is not disposed) than a moisture density of the soil of the moisture measurement target area in the comparative example illustrated in b of FIG. 221. In accordance with this, the sensor device 200 according to the second embodiment of the present technology can measure moisture of soil more accurately than the comparative example.

FIG. 222 is a diagram illustrating an example of coating positions of electric wave absorbing units at the time of two-sides radiation in an example, in which one transmission antenna and one reception antenna are included, according to the second embodiment of the present technology. In this diagram, as illustrated in FIG. 4 and the like, the electric wave absorbing units 341 and 344 are represented using rectangles of dotted lines. As illustrated in a in this diagram, it is the most preferable that the whole probe other than antennas be coated with the electric wave absorbing units. In a case in which a part of the probe other than antennas is coated, as illustrated in b in this diagram, a lower end of the electric wave absorbing unit be an upper end of the antenna. As illustrated in c in this diagram, the lower end of the electric wave absorbing unit can be separated from the upper end of the antenna.

FIGS. 353*a* to 353*d* are top views (projected views) of a sensor device 200 in a case in which the electric wave absorbing units 341 illustrated in FIGS. 153*a* to 153*d* are respectively applied to the electric wave absorbing units 341 and 344 included in the sensor device 200 illustrated in FIG. 222*a* as an example in which the electric wave absorbing units are applied to a sensor device 200. In addition, positional relations of the electronic substrate 311-1, the transmission antenna 221, the reception antenna 231, and the electric wave absorbing units 341 and 344 in the Y direction are illustrated in a front view and a side view of FIG. 222*a*. A front view and a side view of the sensor device 200 acquired in a case in which the electric wave absorbing units 341 illustrated in FIG. 153*a* to 153*d* are respectively applied to the electric wave absorbing units 341 and 344 included in the sensor device 200 illustrated in FIG. 222*a* are the same as the front view and the side view of the sensor device 200 illustrated in FIG. 222*a*.

a in FIG. 353 illustrates a top view of the sensor device 200 including an electric wave absorbing unit 341 of which an outer side and an inner side have oval shapes. b in this diagram illustrates a top view of the sensor device 200 including an electric wave absorbing unit 341 of which an outer side has an oval shape and an inner side has a rectangular shape. c in this diagram illustrates a top view of the sensor device 200 including an electric wave absorbing unit 341 of which an outer side has a rectangular shape and an inner side has an oval shape. d in this diagram illustrates a top view of the sensor device 200 including an electric wave absorbing unit 341 of which an outer side and an inner side have rectangular shapes.

As positional relations of the transmission substrate protrusion part of the electronic substrate 311-1, the transmission antenna 221, the reception substrate protrusion part of the electronic substrate 311-1, and the reception antenna 231 and the electric wave absorbing units 341 and 344 on a top view (a top view that is a projected view), positions at which the electric wave absorbing units 341 and 344 are disposed are on an outer side and on a whole periphery of positions at which the transmission substrate protrusion part of the electronic substrate 311-1, the transmission antenna 221, the reception substrate protrusion part of the electronic substrate 311-1, and the reception antenna 231 are disposed, which are illustrated in FIGS. 353*a* to 353*d*.

From the top view (a projected view) illustrated in FIG. 353, it can be understood that the electric wave absorbing unit 341 is disposed on the whole periphery of an outer side of the transmission substrate protrusion part of the electronic substrate 311-1, and the electric wave absorbing unit 344 is disposed on the whole periphery of an outer side of the reception substrate protrusion part of the electronic substrate 311-1, and it can be understood from the front view and the side view of FIG. 222 that areas in which the electric wave absorbing units 341 and 344 are disposed on the whole periphery of the outer side of the transmission substrate protrusion part and the reception substrate protrusion part of the electronic substrate 311-1 are areas in which a transmission antenna (221 in the example illustrated in FIG. 222) and a reception antenna (231 in the example illustrated in FIG. 222) are not disposed in the Y-axis direction of the sensor device 200.

In addition, forms of the electric wave absorbing units illustrated in FIGS. 153 and 353 are not limited to that of the sensor device 200 illustrated in FIG. 222*a* and can be applied to various sensor devices 200 described in this specification.

FIG. 223 is a diagram illustrating an example in which coating with the electric wave absorbing unit is not performed at the time of two-sides radiation in an example, in which one transmission antenna and one reception antenna are included, according to the second embodiment of the present technology. As illustrated in this diagram, coating with the electric wave absorbing unit may not be performed.

FIG. 224 is a diagram illustrating an example of a coating portion of the electric wave absorbing unit at the time of one-side radiation according to the second embodiment of the present technology. This diagram is similar to FIG. 222 except that the antenna is configured for one-side radiation.

FIG. 225 is a diagram illustrating an example in which coating with the electric wave absorbing unit is not performed at the time of one-side radiation according to the second embodiment of the present technology. This diagram is similar to FIG. 223 except that the antenna is configured for one-side radiation.

FIG. 226 is a diagram illustrating an example in which one side is coated at the time of one-side radiation according to the second embodiment of the present technology. As illustrated in this diagram, a face on a side on which the antenna of the electronic substrate 311-1 is not formed may be further coated with the electric wave absorbing unit.

FIG. 227 is a diagram illustrating an example in which a transmission line and a tip end are coated at the time of two-sides radiation according to the second embodiment of the present technology. As illustrated in this diagram, the tip end of the probe may be further coated with the electric wave absorbing units 349 and 350.

FIG. 228 is a diagram illustrating an example in which only a tip end is coated at the time of two-sides radiation according to the second embodiment of the present technology. As illustrated in this diagram, only the tip end of the probe can be further coated with the electric wave absorbing units 349 and 350.

FIG. 229 is a diagram illustrating an example in which a transmission line and a tip end are coated at the time of one-side radiation according to the second embodiment of the present technology. This diagram is similar to FIG. 227 except that the antenna is configured for one-side radiation.

FIG. 230 is a diagram illustrating an example in which only a tip end is coated at the time of one-side radiation according to the second embodiment of the present technology. This diagram is similar to FIG. 228 except that the antenna is configured for one-side radiation.

FIG. 231 is a diagram illustrating an example in which a transmission line, one face, and a tip end are coated at the time of one-side radiation according to the second embodiment of the present technology. As illustrated in this diagram, at the time of one-side radiation, in addition to the transmission line and the tip end, a face of the electronic substrate 311-1 in which an antenna is not formed may be further coated with an electric wave absorbing unit.

FIG. 232 is a diagram illustrating an example of coating portions of an electric wave absorbing unit at the time of disposing a plurality of antenna pairs of two-sides radiation according to the second embodiment of the present technology. As illustrated in this diagram, when two or more pairs of antennas are formed, electric wave absorbing units 341, 342, 344, and 345 are disposed between such antennas.

FIG. 233 is a diagram illustrating another example of coating portions of an electric wave absorbing unit at the time of disposing a plurality of antenna pairs of two-sides radiation according to the second embodiment of the present technology. As illustrated in this diagram, a part of the probe other than the antenna may be coated.

FIG. 234 is a diagram illustrating an example in which an electric wave absorbing unit is formed in a sensor casing according to the second embodiment of the present technology. a in this diagram illustrates a comparative example in which an electric wave absorbing unit is not formed in a sensor casing 305. b and c in this diagram illustrate examples in which an electric wave absorbing unit is formed in a sensor casing 305. A black part in this diagram illustrates an electric wave absorbent material.

As illustrated in b in this diagram, at the time for forming an exterior, an electric wave absorbent material such as a ferrite may be buried in the sensor casing 305. A black part in this diagram illustrates an electric wave absorbent material. This electric wave absorbent material functions as an electric wave absorbing unit. In addition, as illustrated in c in this diagram, after an exterior casing is formed, a layer of an electric wave absorbent material may be disposed on the inner side thereof.

In this way, according to the second embodiment of the present technology, antennas are formed in one electronic substrate 311-1, and thus the number of substrates can be decreased to be smaller than that of the first embodiment in which the measurement unit substrate 311 and the in-probe substrates 321 and 322 are connected.

First Modification Example

FIG. 237 is a diagram illustrating an example of a sensor device 200 in which antennas of a planar shape and a slot shape that are antennas of a horizontal-direction radiation type to be described below are disposed as a first modification example of the second embodiment of the present technology. In this diagram, there is such a feature that the sensor device 200 according to the second embodiment of the present technology uses antennas of a planar shape and a slot shape and a horizontal direction radiation type illustrated in FIGS. 238 to 240 to be described below as all the antennas (the transmission antennas 221 to 223 and the reception antennas 231 to 233) included in the sensor device 200 as an example.

FIGS. 238 to 240 are diagrams illustrating a structure of an antenna of a planar shape and a slot shape and the horizontal-direction radiation type. In the antenna of the horizontal-direction radiation type illustrated in FIGS. 238 to 240, shapes of slots included in the antenna of the planar shape and the slot shape illustrated in FIGS. 69 to 71 are changed.

In addition, the antenna of the planar shape and the slot shape illustrated in FIGS. 69 to 71 is appropriate for being used in the sensor devices 200 according to the first embodiment of the present technology and the modification examples, and the antenna of the planar shape and the slot shape and the horizontal-direction radiation type illustrated in FIGS. 238 to 240 is appropriate for being used in the sensor device 200 according to the first modification example of the second embodiment of the present technology.

Here, in the sensor device 200 (for example, in FIG. 4) according to the first embodiment of the present technology, the transmission probe substrate 321 including a transmission antenna and the reception probe substrate 322 including a reception antenna and the transmission substrate protrusion part including a transmission antenna and the reception substrate protrusion part including a reception antenna in the sensor device 200 (FIG. 237) according to the first modification example of the second embodiment of the present technology have different directions of a substrate plane in which antennas are formed (rotated by 90°). For this reason, the antennas illustrated in FIGS. 69 to 71 and the antennas illustrated in FIGS. 238 to 240 have different directions of coordinate axes in the drawing. More specifically, for example, in FIG. 239, a thickness direction of the substrate is the Z-axis direction, a direction in which the signal line 255 extends (for example, a direction in which the probe casing and the substrate protrusion parts extend) is the Y-axis direction, and a direction in which a slot intersecting with the signal line 255 extends is the X-axis direction.

The antenna of the planar shape and the slot shape and the horizontal-direction radiation type illustrated in FIGS. 238 to 240 has a structure in which, among slots included in shield layers (shield layers 256 and 254) exposed from the electromagnetic wave absorbent material 251 and is exposed to the space, a slot with which the signal line 255 intersects extends up to an outer edge of the shield layers 254 and 256 (in other words, an outer edge of the substrate protrusion part in which antennas are formed) in the extending direction (the X-axis direction) of this slot.

In the antenna of the planar shape and the slot shape and the horizontal-direction radiation type illustrated in FIGS. 238 to 240, in accordance with a structure in which slots included in the shield layers 254 and 256 that are radiation elements in the transmission antenna (reception elements in the reception antenna) extend up to an outer edge of the shield layers (in other words, an outer edge of the substrate protrusion part in which the antenna is formed), electromagnetic waves are radiated from an opening part of the slot formed in the outer edge of the shield layers (an outer edge of the substrate protrusion part) to the outside of the substrate. The electromagnetic waves are mainly radiated to a front side in the direction in which the slots extend up to the opening part. In other words, a direction (the X-axis direction) in which the slot intersecting with the signal line 255 extends to the opening part becomes a direction of main radiation of electromagnetic waves in this antenna. In FIG. 239, electromagnetic waves are mainly radiated in the X-axis direction, in other words, a direction that is parallel to a substrate plane in which the antenna is formed and is orthogonal to the extending direction of the signal line 255 (in other words, the extending direction of the probe), and thus, in this specification, the antenna illustrated in FIGS. 238 to 240 will be conveniently referred to as an antenna of a planar shape and a slot shape and the horizontal direction radiation type or an antenna of the horizontal direction radiation type.

In the antenna of the planar shape and the slot shape and the horizontal-direction radiation type illustrated in FIGS. 238 to 240, electromagnetic waves are mainly radiated in a direction that is a direction parallel to the substrate plane in which the antenna is formed and is a direction orthogonal to the extending direction of the probe, and thus this antenna is appropriate for being used in the sensor device 200 according to the second embodiment of the present technology in which the transmission substrate protrusion part in which a transmission antenna is formed and the reception substrate protrusion part in which a reception antenna is formed are formed in the same plane.

In addition, in the antenna of the planar shape and the slot shape and the horizontal-direction radiation type illustrated in FIG. 237 and FIGS. 238 to 240, some electromagnetic waves are radiated in a direction orthogonal to the shield layers 254 and 256 in which slots are disposed.

In the antenna of the planar shape and the slot shape and the horizontal-direction radiation type illustrated in FIG. 237 and FIGS. 238 to 240, a ratio between electromagnetic waves radiated in a main radiation direction (a direction parallel to the substrate in which the antenna is formed) and electromagnetic wave radiated in a direction orthogonal to the main radiation (a direction orthogonal to the substrate in which the antenna is formed) changes in accordance with (1) a width of the substrate in which the antenna is formed (more specifically, a size of the substrate that is a size of the substrate in a direction orthogonal to the extending direction of the signal line 255 intersecting with the slot) and (2) a frequency of the electromagnetic waves radiated from the antenna.

In order to sufficiently increase the ratio of electromagnetic waves radiated in the main radiation direction among electromagnetic waves radiated from the antenna described above, it is preferable that (1) the above-described width of the substrate in which the antenna is formed is approximately equal to or smaller than ⅕ of a wavelength of electromagnetic waves at (2) the above-described center frequency of electromagnetic waves radiated from the antenna.

As an example, in a case in which a frequency band of electromagnetic waves radiated from the antenna described above is 1 gigahertz (GHz) to 9 gigahertz (GHz), it is preferable that (1) the width W of the substrate in which the antenna is formed is equal to or smaller than 12 millimeters (mm).

FIG. 241 is a diagram illustrating one configuration example of the electronic substrate 311-1 according to the first modification example of the second embodiment of the present technology. There are three sets of antennas, and the antennas are antennas of the planar shape and the slot shape and the horizontal-direction radiation type illustrated in FIGS. 238 to 240. a in this diagram is a top view of the electronic substrate 311-1 acquired when it is seen from above, and b in this diagram is a front view of the electronic substrate 311-1 acquired when it is seen in the Z-axis direction. c in this diagram is a side view of the electronic substrate 311-1 acquire when it is seen in the X-axis direction.

FIGS. 242 to 250 illustrate a planar shape and a cross-sectional shape of a transmission substrate protrusion part in the electronic substrate 311-1 according to the first modification example of the second embodiment of the present technology.

In FIGS. 242 to 250, the planar shape of the in-probe substrate 321 according to the first embodiment of the present technology illustrated in FIGS. 105 to 113 is changed to be adapted to the transmission substrate protrusion part according to the second embodiment of the present technology. The changed portion is a part connected to the measurement unit illustrated on an upper side of the sheet surface (a negative direction of the Y axis) (when described for the in-probe substrate 321 according to the first embodiment of the present technology, a portion connected to the transmission line connecting unit; when described for the transmission substrate protrusion part according to the second embodiment of the present technology, a portion connected to the substrate rectangular part). The other shapes are the same, and thus detailed description thereof will be omitted.

FIGS. 242 and 243 illustrate a planar shape and a cross-sectional shape in a case in which the electronic substrate 311-1 according to the first modification example of the second embodiment of the present technology is formed as an electronic substrate having three wiring layers. FIGS. 242 and 243 respectively correspond to FIGS. 105 and 106.

FIGS. 244 to 246 illustrate a planar shape and a cross-sectional shape in a case in which the electronic substrate 311-1 according to the first modification example of the second embodiment of the present technology is formed as an electronic substrate having five wiring layers. FIGS. 244 to 246 respectively correspond to FIGS. 107 to 109.

FIGS. 247 to 250 illustrate a planar shape and a cross-sectional shape in a case in which the electronic substrate 311-1 according to the first modification example of the second embodiment of the present technology is formed as an electronic substrate having seven wiring layers. FIGS. 247 to 250 respectively correspond to FIGS. 110 to 113.

By using a column of vias for shielding as a structure for shielding a lateral side of a signal line included in the substrate, the transmission in-probe substrate according to the first embodiment of the present technology illustrated in FIGS. 105 and 106 has an effect of configuring the width of the substrate to be smaller than that of the transmission in-probe substrate not having this structure illustrated in FIGS. 103 and 104.

By using a column of vias for shielding as a structure for shielding a lateral side of a signal line included in the substrate, also the substrate protrusion part according to the second embodiment of the present technology illustrated in FIGS. 242 and 243 has an effect of configuring the width of the substrate to be smaller than that of a substrate not having this structure.

On the other hand, the transmission in-probe substrate according to the first embodiment of the present technology illustrated in FIGS. 107 to 109 and FIGS. 110 to 113, compared to the transmission in-probe substrate illustrated in FIGS. 105 and 106, by using more signal line layers, decreases the number of signal lines disposed in one signal line layer and acquires an effect of configuring the width of the substrate to be small in accordance with this.

Also the substrate protrusion part according to the second embodiment of the present technology illustrated in FIGS. 244 to 246 and FIGS. 247 to 250, compared to the transmission in-probe substrate illustrated in FIGS. 242 and 243, by using more signal line layers, decreases the number of signal lines disposed in one signal line layer and acquires an effect of configuring the width of the substrate to be small in accordance with this.

FIG. 251 is a diagram illustrating an influence of the width of the substrate protrusion part and a cross-sectional area of the probe casing housing this on measurement of the amount of moisture in the sensor device 200 according to the first modification example of the second embodiment of the present technology illustrated in FIG. 237.

a, b, and c in FIG. 251 are cross-sectional views of the transmission probe casing 320*a* and the reception probe casing 320*b* acquired when the sensor device 200 according to the first modification example of the second embodiment of the present technology is seen in a positive direction of the Y axis from above. In each of a, b, and c in this diagram, a rectangle on the left side represents the transmission substrate protrusion part, and a line of a thin oval disposed on the outer circumference thereof represents the transmission probe casing 320*a*. A rectangle on the right side represents the reception substrate protrusion part, and a line of an oval disposed on the outer circumference thereof represents the reception probe casing 320*b*. A white part of the inner side of the probe casing represents a space inside the probe casing. A part to which a thin color is applied on the outer side of the probe casing represents soil similar to that before insertion of the probe casing. On the other hand, a part to which a thick color is applied near the outer side of the probe casing represents an area into which soil pushed as a result of insertion of the probe casing has moved and of which a density of soil becomes higher than the density of the soil before insertion of the probe in accordance with this.

In addition, in a, b, and c in this diagram, (1) transmission substrate protrusion parts and reception substrate protrusion parts of three types having different widths are housed in a transmission probe casing 320*a* and a reception probe casing 320*b* of an oval shape in which a ratio of the length of a major axis to the length of a minor axis is 2:1, and (2), in these three types, the transmission substrate protrusion parts and the reception substrate protrusion parts are disposed such that distances therebetween are the same. Here, the sensor device 200 illustrated in FIGS. 237 and 251 includes antennas of the planar shape and the slot shape and the horizontal-direction radiation type described with reference to FIGS. 238 to 240. For this reason, in a, b, and c in this diagram, the antennas are disposed such that distances between a radiation end portion of a transmission antenna and a reception end portion of a reception antenna are the same, in other words, distances between a transmission antenna and a reception antenna are the same.

When areas into which soil pushed in accordance with insertion of the probe casing into soil has moved and of which a density of soil becomes high are compared between a, b, and c in this diagram, the larger the width of the substrate protrusion part housed inside the probe casing, the larger the width of the area. As a result, the larger the width of the substrate protrusion part, the higher the ratio of the area of which the density of soil has increased in an area between the transmission antenna and the reception antenna. When the density of soil becomes high, easiness in penetration of moisture and the surface area of a grain boundary of soil change, and the amount of moisture held by the soil changes. For this reason, the higher the ratio of the area of which the density of soil has increased, a result of measurement of the amount of moisture of the soil deviates more greatly from the amount of original moisture of the soil that is a target for measurement.

To the contrary, the smaller the width of the substrate protrusion part housed inside the probe casing, the smaller the width of the area of which the density of soil has increased. As a result, the smaller the width of the substrate protrusion part, the lower a ratio of the area of which the density of soil has increased in an area between the transmission antenna and the reception antenna. In accordance with this, a result of measurement of the amount of moisture of soil becomes closer to the amount of original moisture of the soil. In other words, an amount of moisture of soil can be accurately measured.

From the point of view described above, the smaller the width of the substrate protrusion part, the more accurately a sensor device including this inside the probe casing can measure the amount of moisture of soil.

The sensor device 200 according to the second embodiment of the present technology (1), by using a column of vias for shielding as a structure for shielding a lateral side of a signal line in the substrate protrusion part housed inside the probe casing, can configure the width of the substrate protrusion part to be small.

Then, in accordance with this, an effect of accurately measuring an amount of moisture of soil can be acquired.

(2) In a case in which a plurality of antennas are included in the substrate protrusion part housed inside the probe casing, and a plurality of signal lines are included for connection to the plurality of antennas, by using a plurality of wiring layers and forming at least one or more of the plurality of signal lines in different wiring layers, the width of the substrate protrusion part can be configured to be small. In accordance with this, an effect of accurately measuring the amount of moisture of soil can be acquired.

Second Modification Example

The sensor devices 200 according to the second embodiment (FIG. 220) of the present technology and the first modification example (FIG. 237) thereof, as a structure for fixing a direction and a position of the substrate protrusion part (and the electronic substrate 311-1) in which an antenna is formed, similar to the first embodiment (FIG. 4) of the present technology, include the positioning part.

On the other hand, a second modification example of the second embodiment of the present technology, as another example of the structure for fixing a direction and a position of the substrate protrusion part (the electronic substrate 311-1), includes a structure for butting the substrate against a sensor casing (more specifically, the probe casing 320).

FIG. 252 is a diagram illustrating an example of a sensor device 200 according to a second modification example of the second embodiment of the present technology.

FIG. 253 is an example of a cross-sectional view of a sensor casing 305 and an electronic substrate 311-1 thereof in the second modification example of the second embodiment of the present technology illustrated in FIG. 252. a in FIG. 253 illustrates a cross-sectional view of the sensor casing 305 taken along line A-A' illustrated in FIG. 252. b in FIG. 253 illustrates a cross-sectional view of the sensor casing 305 taken along line B-B' illustrated in FIG. 252.

In the structure for butting the electronic substrate 311-1 against the probe casing 320, a substrate protrusion part included in the electronic substrate 311-1 is brought into contact with the probe casing 320 at least two points among a total of four points that are a product of two points in the width direction (the X-axis direction) of the substrate illustrated in a of FIG. 252 and two points in the thickness direction (the Z-axis direction) of the substrate illustrated in b of FIG. 253, whereby positions of the substrate protrusion part disposed inside the probe casing 320 and antennas included therein are fixed.

Third Modification Example

FIG. 254 is a diagram illustrating another example of the structure for fixing directions and positions of a transmission antenna and a reception antenna as yet another example of the second embodiment of the present technology. A sensor device 200 illustrated in FIG. 254 does not include the sensor casing 305 included in the second embodiment (FIG. 220) of the present technology. Instead of not including the sensor casing 305, the sensor device 200 illustrated in FIG. 254 includes at least (1) a transmission probe formed using a structure in which the periphery of a transmission substrate protrusion part (the same as the transmission probe substrate 321 in the sensor device 200 illustrated in FIG. 4) including a transmission antenna and a transmission line for transmission connected thereto is hardened using a resin and (2) a reception probe formed using a structure in which the periphery of a reception substrate protrusion part (the same as the reception probe substrate 322 in the sensor device 200 illustrated in FIG. 4) including a reception antenna and a transmission line for reception connected thereto is hardened using a resin and has a structure in which the transmission probe of (1) described above and the reception probe of (2) are fixed with respect to each other.

The sensor device 200 illustrated in FIG. 254 includes the transmission probe of (1) described above and the reception probe of (2) described above and may have a structure in which the transmission probe of (1) described above and the reception probe of (2) are fixed with respect to each other by (3) further including a third structure part different from (1) and (2) described above. The sensor device 200 illustrated in FIG. 254 includes the transmission probe of (1) described above, the reception probe of (2) described above, and a structure part in which the periphery of a substrate rectangular part included in the electronic substrate 311-1 is hardened using a resin as (3) the third structure part described above and has a structure in which structures of (1) to (3) described above are integrated and fixed.

Here, regarding the transmission probe of (1) described above and the reception probe of (2) described above, in order to prevent "such probes being deformed when such probes are inserted into soil, electronic substrates disposed inside the probes being deformed, as a result, a distance between a transmission antenna and a reception antenna formed in the electronic substrate being changed from a predetermined value, and error occurring in a result of measurement of an amount of moisture", in the transmission probe formed using the structure in which the periphery of the transmission substrate protrusion part of (1) described above is hardened using a resin described above, it is preferable that a strength of a resin part included in this probe is higher than the strength of the single transmission substrate protrusion part included in this probe. In other words, it is preferable that the strength of the transmission probe in which the periphery of the transmission substrate protrusion part is hardened using a resin be twice the strength of the single transmission substrate protrusion part included in this probe or more. Furthermore, in other words, in a case in which an amount of deformation of the transmission probe in which the periphery of the transmission substrate protrusion part is hardened using a resin using the method illustrated in FIG. 135 and the amount of deformation of the single transmission substrate protrusion part included in this probe are compared with each other, it is preferable that the amount of deformation of the transmission probe in which the periphery of the transmission substrate protrusion part is hardened using a resin be ½ of the amount of deformation of the single transmission substrate protrusion part included in this probe or less.

Similarly, regarding the reception probe formed using the structure in which the periphery of the reception substrate protrusion part of (1) described above is hardened using a resin, it is preferable that a strength of a resin part included in this probe be higher than the strength of the single reception substrate protrusion part included in this probe. In other words, it is preferable that the strength of the reception probe in which the periphery of the reception substrate protrusion part is hardened using a resin be twice the strength of the single reception substrate protrusion part included in this probe or more. Furthermore, in other words, in a case in which an amount of deformation of the reception probe in which the periphery of the reception substrate protrusion part is hardened using a resin using the method illustrated in FIG. 135 and the amount of deformation of the single reception substrate protrusion part included in this probe are compared with each other, it is preferable that the amount of deformation of the reception probe in which the periphery of the reception substrate protrusion part is hardened using a resin be ½ of the amount of deformation of the single reception substrate protrusion part included in this probe or less.

Fourth Modification Example

As described with reference to FIGS. 191 to 199, the fifth modification example of the first embodiment of the present technology, as a structure used for preventing deformation at the time of inserting the probe casing 320 into soil even in a case in which the hardness of the soil in which the sensor device 200 is used is markedly high, has the structure for improving the strength of the probe casing 320 without having a concern for degrading the accuracy of measurement of the amount of moisture.

A fourth modification example of the second embodiment of the present technology illustrated in FIGS. 255 to 264 is an example in which the structure for improving the strength of the probe casing 320 without having a concern for degrading the accuracy of measurement of the amount of moisture described above is adapted to the second embodiment of the present technology. In the probe casing 320 illustrated in FIGS. 255 to 264, similar to the probe casing 320 illustrated in FIGS. 191 to 199, areas in which electromagnetic waves that are transmitted and received are mainly transmitted are avoided, and the thickness of the probe casing 320 is enlarged in the other areas so as not to degrade the accuracy of measurement of the amount of moisture.

In addition, when the cross-sectional shape of the casing illustrated in FIGS. 255 to 264 is described, as a comparative example not including a thick casing, the shape of the casing of a of FIG. 221 will be referred to.

FIG. 255 is a diagram illustrating fourth modification example 1 of the second embodiment of the present technology.

In the probe casing 320 illustrated in this diagram, the thickness thereof is enlarged in a sheet surface outer direction by avoiding a sheet surface inner direction in which electromagnetic waves are mainly transmitted through the casing.

In FIG. 255, as a shape for enlarging a thickness of the casing, as illustrated in a in FIG. 255, the thickness of the casing may be enlarged in a form in which a discontinuous point and an inflexion point are not present on both the outer circumference and the inner circumference of the casing. As illustrated in b in FIG. 255, the thickness may be enlarged in the inner direction of the casing. In this case, compared with the comparative example, the number of discontinuous points and inflexion points increases on the inner circumference of the casing. As illustrated in c in FIG. 255, the thickness may be enlarged in the outer direction of the casing. In this case, when compared with the comparative example, the number of discontinuous points or inflexion points increases on the outer circumference of the casing. As illustrated in d of FIG. 255, the thickness may be enlarged in both the inner direction and the outer direction of the casing. In this case, when compared with the comparative example, the number of discontinuous points or inflexion points increases on both the inner circumference and the outer circumference of the casing.

FIG. 256 is a diagram illustrating fourth modification example 2 of the second embodiment of the present technology.

In the probe casing 320 illustrated in this diagram, the thickness is enlarged at one portion in one of a sheet surface upward direction and a downward direction by avoiding the sheet surface inner direction in which electromagnetic waves are mainly transmitted through the casing.

In FIG. 256, as a shape for enlarging a thickness of the casing, as illustrated in a in FIG. 256, the thickness of the casing may be enlarged in a form in which a discontinuous point and an inflexion point are not present on both the outer circumference and the inner circumference of the casing. As illustrated of b of FIG. 256, the thickness may be enlarged in the inner direction of the casing. In this case, compared with the comparative example, the number of discontinuous points and inflexion points increases on the inner circumference of the casing. As illustrated of c of FIG. 256, the thickness may be enlarged in the outer direction of the casing. In this case, when compared with the comparative example, the number of discontinuous points or inflexion points increases on the outer circumference of the casing. As illustrated in d of FIG. 256, the thickness may be enlarged in both the inner direction and the outer direction of the casing. In this case, when compared with the comparative example, the number of discontinuous points or inflexion points increases on both the inner circumference and the outer circumference of the casing.

FIG. 257 is a diagram illustrating fourth modification example 3 of the second embodiment of the present technology.

In the probe casing 320 illustrated in this diagram, the thickness is enlarged at two portions in a sheet surface upward direction and a downward direction by avoiding a sheet surface inner direction in which electromagnetic waves are mainly transmitted through the casing.

In FIG. 257, as a shape for enlarging a thickness of the casing, as illustrated in a of FIG. 257, in a shape in which a discontinuous point and an inflexion point are not present on both the outer circumference and the inner circumference of the casing, the thickness of the casing may be enlarged. As illustrated in b of FIG. 257, the thickness may be enlarged in the inner direction of the casing. In such a case, when compared with the comparative example, the number of discontinuous points or inflexion points increases on the inner circumference of the casing. As illustrated in c of FIG. 257, the thickness may be enlarged in the outer direction of the casing. In such case, when compared with the comparative example, the number of discontinuous points or inflexion points increases on the outer circumference of the casing. As illustrated in d of FIG. 257, the thickness may be enlarged in both the inner direction and the outer direction of the casing. In such a case, when compared with the comparative example, the number of discontinuous points or inflexion points increase on both the inner circumference and the outer circumference of the casing.

FIG. 258 is a diagram illustrating exceptional cases of the fourth modification example of the second embodiment of the present technology. In the probe casing 320 illustrated in this diagram, exceptionally, and the thickness is enlarged at two portions in the sheet surface horizontal direction also including a sheet surface inner direction in which electromagnetic waves are mainly transmitted through the casing. In this case, although there is a concern for degradation of the accuracy of measurement of the amount of moisture, an effect of improving the strength of the probe casing 320 can be acquired.

In FIG. 258, as a shape for enlarging a thickness of the casing, as illustrated in a of FIG. 258, in a shape in which a discontinuous point and an inflexion point are not present on both the outer circumference and the inner circumference of the casing, the thickness of the casing may be enlarged. As illustrated in b of FIG. 258, the thickness may be enlarged in the inner direction of the casing. In this case, when compared with the comparative example, the number of discontinuous points or inflexion points increases on the inner circumference of the casing.

As illustrated in c of FIG. 258, the thickness may be enlarged in the outer direction of the casing. In this case, when compared with the comparative example, the number of discontinuous points or inflexion points increases on the outer circumference of the casing. As illustrated in d of FIG. 258, the thickness may be enlarged in both the inner direction and the outer direction of the casing. In such a case, when compared with the comparative example, the number of discontinuous points or inflexion points increases on both the inner circumference and the outer circumference of the casing.

FIG. 259 is a diagram illustrating fourth modification example 4 of the second embodiment of the present technology.

In the probe casing 320 illustrated in this diagram, the thickness is enlarged at three portions excluding the sheet surface inner direction by avoiding the sheet surface inner direction in which electromagnetic waves are mainly transmitted through the casing.

In FIG. 259, as a shape for enlarging a thickness of the casing, as illustrated in a of FIG. 259, in a shape in which a discontinuous point and an inflexion point are not present on both the outer circumference and the inner circumference of the casing, the thickness of the casing may be enlarged. As illustrated in b of FIG. 259, the thickness may be enlarged in the inner direction of the casing. In such a case, when compared with the comparative example, the number of discontinuous points or inflexion points increases on the inner circumference of the casing. As illustrated in c of FIG. 259, the thickness may be enlarged in the outer direction of the casing. In such case, when compared with the comparative example, the number of discontinuous points or inflexion points increases on the outer circumference of the casing. As illustrated in d of FIG. 259, the thickness may be enlarged in both the inner direction and the outer direction of the casing. In such a case, when compared with the comparative example, the number of discontinuous points or inflexion points increase on both the inner circumference and the outer circumference of the casing.

FIG. 260 is a diagram illustrating fourth modification example 5 of the second embodiment of the present technology. In a structure illustrated in this diagram, only antennas of the structure illustrated in FIG. 255 are changed into one-side radiation, and the shape of the casing is the same.

FIG. 261 is a diagram illustrating fourth modification example 6 of the second embodiment of the present technology. In a structure illustrated in this diagram, only antennas of the structure illustrated in FIG. 256 are changed into one-side radiation, and the shape of the casing is the same.

FIG. 262 is a diagram illustrating fourth modification example 7 of the second embodiment of the present technology.

In a structure illustrated in this diagram, only antennas of the structure illustrated in FIG. 257 are changed into one-side radiation, and the shape of the casing is the same.

FIG. 263 is a diagram illustrating exceptional cases of the fourth modification example of the second embodiment of the present technology. In a structure illustrated in this diagram, only antennas of the structure illustrated in FIG. 258 are changed into one-side radiation, and the shape of the casing is the same.

FIG. 264 is a diagram illustrating fourth modification example 8 of the second embodiment of the present technology.

In a structure illustrated in this diagram, only antennas of the structure illustrated in FIG. 259 are changed into one-side radiation, and the shape of the casing is the same.

In the fourth modification example of the second embodiment of the present technology illustrated in FIGS. 255 to 264, the structure in which a part of the probe casing is thickened represented in the fifth modification example of the first embodiment of the present technology illustrated in FIGS. 191 to 199 is applied to the probe casing according to the second embodiment of the present technology illustrated in a of FIG. 221.

Here, although the probe casing illustrated in a of FIG. 221 illustrates Constituent element (9') according to the second embodiment of the present technology, the probe casing illustrated in this diagram is acquired by rotating the probe casing that is Constituent element (9) according to the first embodiment of the present technology illustrated in a of FIG. 190 by 90°.

As examples of Constituent element (9) according to the first embodiment of the present technology, in addition to a of FIG. 190, there are b to d of FIG. 190. Similar to a case in which the structure acquired by rotating the casing of a of FIG. 190 by 90° is Constituent element (9') according to the second embodiment, structures acquired by rotating the casings of b to d of FIG. 190 by 90° can also be used as Constituent element (9') according to the second embodiment in the second embodiment.

As the fourth modification example of the second embodiment of the present technology, the structures illustrated in FIGS. 255 to 264 can also be applied to each of the structures acquired by rotating the casings of b to d of FIG. 190 described above by 90°.

In this way, according to the fourth modification example of the second embodiment of the present technology, an area in which electromagnetic waves transmitted and received are mainly transmitted is avoided such that the accuracy of measurement of the amount of moisture is not degraded, and the thickness of the probe casing 320 is enlarged in the other areas, and, in accordance with this, even in a case in which a degree of hardness of soil is markedly high, deformation of the probe casing 320 and substrates of the inside thereof at the time of inserting the probe into the soil can be reduced, and, as a result, moisture can be measured more accurately.

Fifth Modification Example

In the second embodiment described above, although the sensor device 200 measures moisture at one predetermined point in an X-Z plane parallel to the ground surface, in this configuration, a plurality of sensor device 200 are necessary when a plurality of points are measured. A sensor device 200 according to a fifth modification example of the second embodiment measures a plurality of points in the X-Z plane, which is different from the first embodiment.

FIG. 265 is a diagram illustrating one configuration example of the sensor device 200 according to the fifth modification example of the second embodiment of the present technology. This sensor device 200 according to the second embodiment includes an electronic substrate 311-1 in which two or more (for example, three) protrusion parts are formed, which is different from the second embodiment. Each protrusion part has an antenna formed therein and functions as a probe. a in this diagram illustrates an example in which a measurement circuit is disposed for each probe pair, and b in this diagram illustrates an example in which one measurement circuit is shared.

As illustrated in a in this diagram, in probes (protrusion parts) of the first pair, a transmission antenna 221-1 and a reception antenna 231-1 are formed. Such antennas are connected to a measurement circuit 210-1. In probes of the second pair, a transmission antenna 221-2 and a reception antenna 231-2 are formed. Such antennas are connected to a measurement circuit 210-2. In probes of the third pair, a transmission antenna 221-3 and a reception antenna 231-3 are formed. Such antennas are connected to a measurement circuit 210-3. The electronic substrate 311-1 may be inserted into soil with being stored in a casing, or the electronic substrate 311-1 may be directly inserted into soil without being stored in a casing.

The electronic substrate 311-1 includes two or more probes, and thus amounts of moisture of a plurality of points can be measured using one sensor device 200.

In addition, as illustrated in b in this diagram, three probes may share one measurement circuit 210.

FIG. 266 is a diagram illustrating an example of a sensor device 200 before and after connection of an electronic substrate in the fifth modification example of the second embodiment of the present technology. a in this diagram illustrates the electronic substrate before connection, and b in this diagram illustrates the electronic substrate after connection.

As illustrated in a in this diagram, electronic substrates 311-1, 311-2, and 311-3 are prepared, and, as illustrated in b in this diagram, those may be connected using connection parts 370 and 371.

FIG. 267 is a diagram illustrating one configuration example of a sensor device 200, in which a plurality of pairs of antennas are disposed for each probe, according to the fifth modification example of the second embodiment of the present technology. a in this diagram illustrates an example in which a measurement circuit is disposed for each probe pair, and b in this diagram illustrates an example in which one measurement circuit is shared. As illustrated in this diagram, a plurality of pairs of antennas may be disposed for each probe pair.

FIG. 268 is a diagram illustrating one configuration example of a sensor device 200, in which lengths of probe pairs are different from each other, according to the fifth modification example of the second embodiment of the present technology. a in this diagram illustrates an example in which the number of antennas is different for each probe pair. b in this diagram illustrates an example in which the number of antennas for each probe pair is the same.

As illustrated in a in this diagram, by changing the length for each probe pair, three antennas may be disposed in probes of the first pair, two antennas may be disposed in probes of the second pair, and one antenna may be disposed in probes of the third pair. As illustrated in b in this diagram, by changing the length for each probe pair, one pair of antennas may be disposed for each probe pair. In accordance with the configuration illustrated in this diagram, the sensor device 200 can measure amounts of moisture of different depths for each point.

FIG. 269 is a diagram illustrating one configuration example of a sensor device 200, in which a transmission antenna is shared by a plurality of reception antennas, according to the fifth modification example of the second embodiment of the present technology. a in this diagram illustrates an example in which two reception antennas share one transmission antenna. b in this diagram illustrates an example in which four reception antennas share one transmission antenna.

As illustrated in a in this diagram, the number of probes may be three, a transmission antenna 221-1 may be formed in a probe disposed at the center, a reception antenna 231-1 may be formed in one of the remaining two probes, and a reception antenna 231-2 may be formed in the other probe. In addition, as illustrated in b in this diagram, the number of probes may be three, a transmission antenna 221-1 may be formed in a probe disposed at the center, reception antennas 231-1 and 232-1 may be formed in one of the remaining two probes, and reception antennas 231-2 and 232-2 may be formed in the other probe. By sharing the transmission antenna, the number of probes can be reduced.

FIG. 270 is a diagram illustrating one configuration example of a sensor device 200, in which substrate faces of electronic substrates face each other, according to the fifth modification example of the second embodiment of the present technology. a in this diagram illustrates a perspective view acquired when end portions of the electronic substrates are connected. b in this diagram illustrates a top view acquired when end portions of electronic substrates are connected. c in this diagram illustrates a perspective view acquired when portions of the electronic substrates other than the end portions are connected. d in this diagram illustrates a top view acquired when portions of electronic substrates other than end portions are connected.

As illustrated in a and b in this diagram, end portions of electronic substrates 311-1, 311-2, and 311-3 may be connected and fixed using a connection part 370 such that substrate planes thereof are parallel to each other. As illustrated in c and d in this diagram, portions (center portions or the like) of the electronic substrates 311-1, 311-2, and 311-3 other than end portions may be connected using connection parts 370 and 371 such that substrate planes thereof are parallel to each other.

FIG. 271 is a diagram illustrating one configuration example of a sensor device 200, which measures a plurality of points arranged in a two-dimensional lattice shape, according to the fifth modification example of the second embodiment of the present technology. As illustrated in this diagram, electronic substrates 311-1, 311-2, and 311-3 each including three probes disposed in the X-axis direction may be connected using connection parts 370 to 375 such that substrate planes thereof face each other. In accordance with this, the sensor device 200 can measure amounts of moisture at 3×3 points arranged in a two-dimensional lattice shape in an X-Z plane parallel to the ground surface.

FIG. 272 is a diagram illustrating one configuration example of a sensor device 200, in which a level is added, according to the fifth modification example of the second embodiment of the present technology. As illustrated in a in this diagram, a level 376 may be disposed in an electronic substrate 311-1 in which three probes are disposed. In addition, as illustrated in b in this diagram, levels 376 and 377 may be disposed. The level 376 detects a slope in a direction (the X-axis direction) in which probes are arranged. The level 377 detects a slope in a direction (the Z-axis direction) perpendicular to the direction in which the probes are arranged.

As illustrated in c in this diagram, levels 376 and 377 may be disposed in a sensor device 200 measuring a plurality of points arranged in a two-dimensional lattice shape.

FIG. 273 is a diagram illustrating one configuration example of a sensor device 200, in which transmission/reception directions of electromagnetic waves intersect with each other, according to the fifth modification example of the second embodiment of the present technology. As illustrated in a in this diagram, the electronic substrates 311-1 and 311-2 may be connected using a connection part 370, and a transmission signal of a transmission antenna 221-1 may be received by a reception antenna 232-1 of which a position in the Y-axis direction is different from that of the antenna. In addition, a transmission signal of a transmission antenna 222-1 may be received by a reception antenna 231-1 of which a position in the Y-axis direction is different from that of the antenna. In accordance with this, the sensor device 200 can measure amounts of moisture at intermediate depths of the transmission antennas 221-1 and 222-1.

In addition, as illustrated in b in this diagram, three probes are disposed, and electromagnetic waves may be transmitted and received such that transmission/reception directions of the electromagnetic waves intersect with each other.

In this way, according to the fifth modification example of the second embodiment of the present technology, since three or more probes are disposed in the electronic substrates, the sensor device 200 can measure amounts of moisture of a plurality of points.

Sixth Modification Example

In the second embodiment described above, although positions of antennas of the transmission probe and the reception probe are symmetrical to each other, it is difficult to further decrease the size of the sensor device 200 in this configuration. In this sixth modification example of the second embodiment, positions of antennas of the transmission probe and the reception probe are configured to be asymmetrical to each other, which is different from the second embodiment.

FIG. 274 is a diagram for describing an effect acquired when positions of antennas are configured to be asymmetrical to each other in the sixth modification example of the second embodiment of the present technology. An electronic substrate 311-1 disposed inside a sensor device 200 includes a quadrangle part of a quadrangle shape (a rectangle or the like) and one pair of protrusion parts. A transmission antenna 221 is formed in one of the one pair of protrusion parts, and a reception antenna 231 is formed in the other protrusion part. Such protrusion parts function as a transmission probe and a reception probe.

As illustrated in a in this diagram, a configuration in which positions of antennas in a depth (the Y-axis direction) are the same in the transmission probe and the reception probe will be assumed as a comparative example. In contrast to this, in the sixth modification example of the second embodiment, as illustrated in b and c in this diagram, antennas are disposed at different positions in the Y-axis direction in the transmission probe and the reception probe.

In a, b, and c in this diagram, a distance d between the antennas are the same. A distance between the probes (in other words, a width) will be denoted by w. An angle formed between a direction from the transmission antenna to the reception antenna and the X axis will be denoted by θ. In b in this diagram, θ is 45 degrees, and x in this diagram θ is 60 degrees.

In this case, the following expression is satisfied between the width w and the distance d.

$$w = d \times \cos(\theta) \quad \text{Expression 24}$$

In the expression represented above, cos( ) is a cosine function.

In a in this diagram, θ is 0 degrees, and thus, from Expression 24, the width w is the same as the distance d. In b in this diagram, θ is 45 degrees, and thus, from Expression 24, the width w is $d/2^{1/2}$. In c in this diagram, θ is 60 degrees, and thus, from Expression 24, the width w is d/2. In this way, by configuring the positions of the antennas to be asymmetrical between the transmission side and the reception side, the width w can be configured to be small without changing the distance between the antennas. Since the distance between the antennas are the same, the accuracy of measurement can be maintained. For this reason, the size of the sensor device 200 can be configured to be small while the accuracy of measurement is maintained.

FIG. 275 is a diagram illustrating one configuration example of a sensor device according to the sixth modification example of the second embodiment of the present technology. As illustrated in a in this diagram, the length of the probe may be changed on the reception side and the transmission side, and antennas may be formed at tip ends thereof. As illustrated in b and c in this diagram, the length of the probe may be configured to be the same on the reception side and the transmission side, and positions of the transmission antenna and the reception antenna in the depth direction (the Y-axis direction) may be changed.

FIG. 276 is a diagram illustrating one configuration example of a sensor device 200 in which the quadrangle part is configured to be a parallelogram shape in the sixth modification example of the second embodiment of the present technology. In order to configure a length of a transmission line from the transmission antenna 221 to the measurement circuit 210 and a length of a transmission line from the reception antenna 231 to the measurement circuit 210 to be the same, the quadrangle part can be configured to have a trapezoidal shape. a in this diagram is an example in which the transmission side is configured to be deeper than the reception side, b in this diagram is an example in which the reception side is configured to be deeper than the transmission side. c and d in this diagram are examples in which the lengths of the probes are the same on the transmission side and the reception side.

By configuring the length of the transmission line to be the same on the reception side and the transmission side, a correction value of one of the transmission side and the reception side can be applied to the other.

FIG. 277 is a diagram illustrating one configuration example of the sensor device 200 in which a quadrangle part is configured to be a rectangular shape, and the lengths of the transmission lines on the transmission side and the reception side coincide with each other in the sixth modification example of the second embodiment of the present technology. The quadrangle part can be configured to be a rectangular shape, and lengths of transmission lines on the transmission side and the reception side can be configured to coincide with each other. a in this diagram is an example in which the transmission side is deeper than the reception side, and b in this diagram is an example in which the reception side is deeper than the transmission side. c and d in this diagram are examples in which the length of the probe is configured to be the same on the transmission side and the reception side.

FIG. 278 is a diagram illustrating one configuration example of a sensor device 200 measuring a plurality of points in the sixth modification example of the second embodiment of the present technology. By forming a plurality of antennas for each probe, a plurality of points can be measured in the Y-axis direction.

a in this diagram is an example in which the transmission side is configured to be deeper than the reception side, and b in this diagram is an example in which the reception side is configured to be deeper than the transmission side. c and d in this diagram are examples in which the length of the probe is configured to be the same on the transmission side and the reception side. e and f in this diagram are examples in which the quadrangle part is configured to have a parallelogram shape. g and h in this diagram are examples in which the quadrangle part is configured to have a parallelogram shape, and the length of the probe is configured to be the same on the transmission side and the reception side.

FIG. 279 is a diagram illustrating one configuration example of a sensor device 200 measuring two points by sharing antennas in the sixth modification example of the second embodiment of the present technology. As illustrated in a in this diagram, transmission antennas 221 and 222 and a reception antenna 231 can be shared as well. As illustrated in b in this diagram, reception antennas 231 and 232 and a transmission antenna 221 can be shared as well.

c and d in this diagram are examples in which the length of the probe is configured to be the same on the transmission side and the reception side. e and f in this diagram are examples in which the quadrangle part is configured to have a parallelogram. g and h in this diagram are examples in which the quadrangle part is configured to have a parallelogram shape, and the length of the probe is configured to be the same on the transmission side and the reception side.

FIG. 280 is a diagram illustrating one configuration example of a sensor device 200 that measures three or more points by sharing antennas in the sixth modification example of the second embodiment of the present technology. By configuring two antennas and sharing the antennas, three or more points can be measured as well.

For example, as illustrated in a in this diagram, by forming transmission antennas 221 and 222 and reception antennas 231 and 232, the transmission antennas 221 and 222 and the reception antenna 232 can be shared. As illustrated in b in this diagram, by forming transmission antennas 221 and 222 and reception antennas 231 and 232, one transmission antenna can be configured to be shared by a plurality of reception antennas.

c and d in this diagram are examples in which the length of the probe is configured to be the same on the transmission side and the reception side. e and f in this diagram are examples in which the quadrangle part is configured to have a parallelogram shape. g and h in this diagram are examples in which the quadrangle part is configured to have a parallelogram shape, and the length of the probe is configured to be the same on the transmission side and the reception side.

FIG. 281 is a diagram illustrating another example of a sensor device 200 measuring two points by sharing antennas in the sixth modification example of the second embodiment of the present technology. As illustrated in a in this diagram, when the reception antenna 231 is shared by the transmission antennas 221 and 222, the positions of the transmission antenna 221 and the reception antenna 231 in the Y-axis direction can be configured to be the same. As illustrated in b in this diagram, when the transmission antenna is shared by two reception antennas, the positions of one of such reception antennas and the transmission antenna in the Y-axis direction can be configured to be the same.

c and d in this diagram are examples in which the length of the probe is configured to be the same on the transmission side and the reception side. e and f in this diagram are examples in which the quadrangle part is configured to have a parallelogram shape. g and h in this diagram are examples in which the quadrangle part is configured to have a parallelogram shape, and the length of the probe is configured to be the same on the transmission side and the reception side.

FIG. 282 is a diagram illustrating another example of a sensor device 200 that measures three or more points by sharing antennas in the sixth modification example of the second embodiment of the present technology. As illustrated in a in this diagram, when two antennas are formed, and the reception antenna 232 is shared by the transmission antennas 221 and 222, the positions of the transmission antenna 221 and the reception antenna 232 in the Y-axis direction can be configured to be the same. As illustrated in b in this diagram, when two antennas are formed, and transmission antennas are shared by two reception antennas, the positions of one of such reception antennas and one of the transmission antennas in the Y-axis direction can be configured to be the same.

c and d in this diagram are examples in which the length of the probe is configured to be the same on the transmission side and the reception side. e and f in this diagram are examples in which the quadrangle part is configured to have a parallelogram shape. g and h in this diagram are examples in which the quadrangle part is configured to have a parallelogram shape, and the length of the probe is configured to be the same on the transmission side and the reception side.

FIG. 283 is a diagram illustrating one configuration example of a sensor device in which the number of probes is increased in the sixth modification example of the second embodiment of the present technology. As illustrated in a in this diagram, by configuring the number of probes to be three, a transmission antenna 221 disposed at the center can be configured to be shared by reception antennas 231-1 and 231-2 of both sides. As illustrated in b in this diagram, by configuring the number of probes to be three, a reception antenna 231 disposed at the center can be configured to be shared by transmission antennas 221-1 and 222-2 of both sides. c and d in this diagram are examples in which lengths of the three probes are configured to be the same.

FIG. 284 is a diagram illustrating one configuration example of a sensor device in which the number of probes and the number of antennas are increased in the sixth modification example of the second embodiment of the present technology. As illustrated in a in this diagram, by configuring the number of probes to be three, a transmission antenna 221 disposed at the center can be configured to be shared by reception antennas 231-1, 232-1, 231-2, and 232-2 of both sides. As illustrated in b in this diagram, by configuring the number of probes to be three, a reception antenna 231 disposed at the center can be configured to be shared by transmission antennas 221-1, 222-1, 221-2, and 222-2 of both sides. c and d in this diagram are examples in which lengths of the three probes are configured to be the same.

In this way, according to the sixth modification example of the second embodiment of the present technology, the positions of antennas other on the transmission side and the reception side are configured to be asymmetrical to each, and thus the size of the sensor device 200 can be further decreased.

3. Third Embodiment

In the first embodiment described above, although planar antennas are formed in the in-probe substrates 321 and 322, the shape of the antennas is not limited to the planar shape. A sensor device 200 according to this third embodiment includes antennas of a cylindrical shape, which is different from the first embodiment.

FIG. 285 is a diagram illustrating an example of the sensor device 200 according to the third embodiment of the present technology. The sensor device 200 according to the third embodiment does not include the in-probe substrates 321 and 322 and includes coaxial cables 281 to 286, which is different from the first embodiment. Transmission antennas 221 to 223 are formed at one ends of the coaxial cables 281 to 283, and reception antennas 231 to 233 are formed at one ends of the coaxial cables 284 to 286. The other ends of the coaxial cables 281 to 286 are connected to the measurement unit substrate 311.

FIG. 286 is an example of a cross-sectional view and a side view of an antenna in the third embodiment of the present technology. a in this diagram is a cross-sectional view of the antenna acquired when seen from above. b in this diagram is a side view of the antenna when seen from a front face (the Z-axis direction) of the sensor device 200, and c in this diagram is a side view of the antenna seen in a side face (the X axis) direction of the sensor device 200.

The coaxial cable 281 and the like are composed of a signal line 281-3 having a linear shape, a shield layer 281-2 coating the signal line 281-3, and a coating layer 281-1 coating the shield layer 281-2. A part of the shield layer 281-2 is exposed at one end of the coaxial cable 281 and the like, and a part of the signal line 281-3 is exposed at a front of this exposed shield layer 281-2. This exposed signal line 281-3 and the exposed shield layer 281-2 configures antennas (a transmission antenna and a reception antenna). The exposed signal line 281-3 in the antennas functions as a transmission element of the transmission antenna and a reception element of the reception antenna. In this way, a transmission line (the coaxial cable 281) between the measurement unit substrate 311 and the antenna, and the antenna are continuously formed using the same material.

FIG. 287 is a diagram illustrating an example of a cross-sectional view of a coaxial cable in the third embodiment of the present technology. As illustrated in a in this diagram, a cavity is formed inside the probe casing 320 for each coaxial cable, and the coaxial cable can be disposed inside the cavity.

As illustrated in b in this diagram, a plurality of coaxial cables can be fixed using a fixture 380 and can be disposed in the cavity disposed inside the probe casing 320. As the fixture 380, a cable tie, an adhesive agency, or the like are used. By fixing the plurality of coaxial cables using the fixture 380, the strength in the cable extending direction is improved more than one coaxial cable.

As illustrated in c in this diagram, a plurality of coaxial cables can be fixed using a fixture 381 and can be disposed in the cavity formed inside the probe casing 320. As the fixture 381, a guide structure, a casing, or the like is used. As illustrated in d in this diagram, in the structure of c in the diagram, a thick portion of the casing of a side on which electromagnetic waves are mainly transmitted may be formed to be the smallest in one cross-section of the probe casing.

FIG. 288 is a diagram illustrating an example of a sensor device in which the number of antennas is decreased in the third embodiment of the present technology. As illustrated in this diagram, one antenna pair may be configured.

FIG. 289 is a diagram illustrating an example a cross-sectional view and a side view of an antenna acquired when the number of antennas is decreased in the third embodiment of the present technology.

FIG. 290 is a diagram illustrating an example of a cross-sectional view of coaxial cables acquired when the number of antennas is decreased in the third embodiment of the present technology. As illustrated in a in this diagram, the coaxial cables can be disposed in cavities of the inside of a probe casing 320. As illustrated in b in this diagram, the coaxial cables may be disposed in the cavities of the inside of the probe casing 320 by fixing them using a fixture 381. As illustrated in c in this diagram, for the structure of b in this diagram, a thick portion of the casing of a side through which electromagnetic waves are mainly transmitted can be configured to be the smallest in one cross-section of the probe casing.

In this way, according to the third embodiment of the present technology, since an antenna of a cylindrical shape is formed at the tip end of the coaxial cable, the in-probe substrate becomes unnecessary.

4. Fourth Embodiment

In the first embodiment described above, when a watering nozzle is added to the moisture measuring system 100, the sensor device 200 is separately disposed, and, it is difficult to dispose them at appropriate positions in this configuration. The moisture measuring system 100 according to this fourth embodiment fixes a watering nozzle at an appropriate position, which is different from the first embodiment. In addition, in the sensor device included in the moisture measuring system 100 according to the fourth embodiment, various sensor devices described in this specification (for example, the sensor devices according to the first to third embodiments and modification examples thereof) can be used.

FIG. 291 is a diagram illustrating an example of moisture measuring systems 100 according to the fourth embodiment of the present technology and a comparative example. a in this diagram is a diagram illustrating an example of a moisture measuring system according to a comparative example in which a sensor device 200 and a watering nozzle 530 are not connected. b in this diagram is a diagram illustrating an example of the moisture measuring system 100 according to the fourth embodiment.

As illustrated in a in this diagram, when the sensor device 200 and the watering nozzle 530 are separately disposed, a user needs to install depending on his or her intuition. However, in this case, when watering control is performed using the sensor device 200, in a case in which a distance between the sensor device 200 and the watering nozzle 530 is not constant, there is a concern that a variation may occur in a time delay until a change of the amount of moisture is detected. As a result, watering control does not appropriately function, and there is a problem in that excessive water stress may be given to a plant.

Thus, in the fourth embodiment, as illustrated in b in this diagram, the sensor device 200 and a watering nozzle holder 520 are connected using a connection part 370. A watering nozzle 530 is held in the watering nozzle holder 520. The watering nozzle 530 is mounted at one end of a watering tube 510. In accordance with the configuration of b in this diagram, a distance between the sensor device 200 and the watering nozzle holder 520 can be configured to be constant without any variation.

However, in a configuration in which the watering nozzle holder 520 is connected to one sensor device 200, it is easy for the position of the sensor device 200 to deviate due to the weight of the watering tube 510, and a gap occurs between soil and a moisture sensor, the amount of moisture cannot be measured with high accuracy. For this reason, by disposing the watering nozzle holder 520 between a plurality of sensor devices 200, a stronger support structure may be formed.

FIG. 292 is a diagram illustrating an example of a moisture measuring system 100, in which a plurality of sensor devices are connected, according to the fourth embodiment of the present technology. As illustrated in a in this diagram, a sensor device 200, a sensor device 201, and a watering nozzle holder 520 can be connected using a connection part 370. In addition, the number of sensor devices to be connected is not limited to two.

As illustrated in b in this diagram, lengths of probe casings 320 of the sensor device 200 and the sensor device 201 in a depth direction (the Y-axis direction) may be different from each other.

FIG. 293 is an example of a top view of the moisture measuring system 100, in which a plurality of sensor devices are connected, according to the fourth embodiment of the present technology. This diagram illustrates a top view acquired when seen from above (the Y-axis direction).

As illustrated in a in this drawing, the shape of the connection part 370 when seen from above may be a linear shape, or as illustrated in b in this drawing, may be a shape acquired by bending a segment at a predetermined angle. As illustrated in c in this drawing, the shape of the connection part 370 may be an arc shape.

FIG. 294 is a diagram illustrating an example of a moisture measuring system 100 in which a support member is disposed in the fourth embodiment of the present technology. Similar to the connection part 370, the support member 540 connects the sensor device 200 and the sensor device 201 and the watering nozzle holder 520.

In a in this diagram, an upper half part is a top view of the moisture measuring system 100, and a lower half part is a side view. In the moisture measuring system 100 illustrated in FIG. 294*a*, similar to FIG. 292*b*, a side face has a shape including two sensor devices 200 and 201 of which lengths of probe casings 320 in the depth direction (the Y-axis direction) are different from each other. Similar to FIG. 293*c*, the above-described system illustrated in FIG. 294*a* has a shape in which an upper face includes a support member 540 of an arc shape. The top view illustrated in the upper half part of FIG. 294*a* illustrates a state in which the moisture sensor system 100 including the support member 540 of the arc shape described above is disposed to surround a plant that is a watering target.

Also in b in this diagram, an upper half part is a top view of the moisture measuring system 100, and a lower half part is a side view. Similar to FIG. 292*b*, the moisture measuring system 100 illustrated in FIG. 294*b* has a shape in which a side face includes two sensor devices 200 and 201 of which lengths of probe casings 320 in the depth direction (the Y-axis direction) are different from each other. In the above-described system illustrated in FIG. 294*b*, similar to FIG. 293*b*, an upper face has a shape acquired by bending a support member 540 of a linear shape. The top view illustrated in the upper half part of FIG. 294*b* illustrates a state in which the moisture sensor system 100 including the bent support member 540 described above is disposed to surround a plant that is a watering target.

In the moisture measuring system 100 illustrated in FIG. 294, a plurality of sensor devices having different shapes can be disposed at positions having an equal distance from a plant that is a watering target and also having an equal distance from the watering nozzle and surrounding the periphery of the plant. In accordance with this, at a place near a plant that is a watering target at which conditions of distances from both the plant described above and the watering nozzle are the same condition, a plurality of pieces of information can be measured using sensor devices having different shape.

FIG. 295 is a diagram illustrating an example of a moisture measuring system 100 in which a plurality of sensor devices and a plurality of watering nozzle holders are connected in the fourth embodiment of the present technology. As illustrated in this diagram, sensor devices 200 and 201 and watering nozzle holders 520 to 522 can be connected using a connection part 370. The number of the watering nozzle holders and the number of the sensor devices are not respective limited to three and two in this diagram.

FIG. 296 is a diagram illustrating an example of a moisture measuring system 100 in which a watering tube holder is connected in the fourth embodiment of the present technology. As illustrated in a in this diagram, a watering tube holder 550 may be used in place of the watering nozzle holder 520. The watering tube holder 550 is mounted at a predetermined position of the sensor device 200. In this case, the connection part 370 and the watering nozzle 530 become unnecessary, and the cost can be reduced. b in this diagram illustrates a top view of the moisture measuring system 100 illustrated in a of this diagram.

In addition, as illustrated in c in this diagram, the watering tube holder 550 can be mounted at a predetermined position of a connection part 370 connecting a plurality of sensor devices. d in this diagram illustrates a top view of a moisture measuring system 100 illustrated in c in this diagram.

In addition, as illustrated in e in this diagram, sensor devices 200 and 201 can be connected using a connection part 370, and watering tube holders 550 and 551 can be mounted in the sensor devices 200 and 201. f in this diagram illustrates a top view of the moisture measuring system 100 illustrated in e in this diagram.

FIG. 297 is a diagram illustrating an example of a moisture measuring system 100 that performs watering through a watering nozzle in the fourth embodiment of the present technology. As illustrated in a in this diagram, a configuration in which a watering tube 510 causes water to flow into the inside of the watering nozzle 530 may be employed. In this configuration, water flows in soil through the watering nozzle 530. In this case, as illustrated in b in this diagram, a plurality of sensor devices can be connected also using a connection part 370. In addition, as illustrated in c in this diagram, lengths of probe casings 320 of sensor devices 200 and 201 in the depth direction (the Y-axis direction) may be different from each other.

FIG. 298 is a diagram illustrating an example of a moisture measuring system 100 in which an arrangement direction of the probe and a segment parallel to a connection part are orthogonal to each other in the fourth embodiment of the present technology. This diagram represents a top view of the moisture measuring system 100. As illustrated in the drawing, sensor devices can be connected such that the arrangement direction of each of probes of the sensor devices 200 and 201 and a segment parallel to a connection part 370 having a linear shape are orthogonal to each other. In this case, a shape of letter H is formed when seen above.

As illustrated in a in this diagram, a watering tube holder 550 may be mounted in the connection part 370. As illustrated in b in this diagram, a watering nozzle holder 520 may be mounted in the connection part 370.

In this way, according to the fourth embodiment of the present technology, the sensor device 200 and the watering nozzle 530 are fixed to appropriate positions, and thus a distance therebetween can be maintained to be constant.

5. Fifth Embodiment

In the first embodiment described above, when a transmission antenna and a reception antenna included in the sensor device 200 are installed in soil, in order to avoid a situation in which directions of antennas and a distance between the antennas deviate from a predetermined direction and a predetermined distance in accordance with application of stress to such antennas, the transmission antenna and the reception antenna and the transmission line connected thereto are housed inside the strong casing probe.

However, for example, in a case in which a degree of hardness of soil that is a measurement target such as a well-cultivated field is low, there is a likelihood of the sensor device 200 of a structure in which a strong casing is not included being able to be used. Thus, the sensor device 200 according to the fifth embodiment of the present technology does not include the sensor casing 305 and has a structure for realizing high durability without including a sensor casing. In accordance with this, the sensor device 200 according to the fifth embodiment of the present technology, compared to the sensor device 200 of the present technology including the sensor casing 305, acquires an effect of decreasing the number of components, reducing an external size, decreasing a weight, simplifying a manufacturing method, and reducing a manufacturing cost.

FIGS. 299 and 300 are diagrams illustrating an example of a front view and a side view of the sensor device 200 according to a fifth embodiment of the present technology. The sensor device 200 according to the fifth embodiment of the present technology illustrated in FIGS. 299 and 300 is acquired by changing the second embodiment of the present technology and the modification examples thereof into a form not including the probe casing 305. a in FIG. 299 illustrates a front view of the sensor device 200, and b in this diagram illustrates a side view of the sensor device 200. a in FIG. 300 is an example of a rear view of the sensor device 200. b in this diagram is an example of a cross-sectional view acquired when the sensor device 200 is cut along line C-C' illustrated in a in this drawing. c in this drawing is an example of a cross-sectional view acquired when the sensor device 200 is cut along line D-D' illustrated in a in this drawing. d in this drawing is an example of a cross-sectional view acquired when the sensor device 200 is cut along line E-E' illustrated in a in this drawing. As illustrated in FIGS. 299 and 300, the sensor device 200 according to the fifth embodiment of the present technology includes one electronic substrate 311-1. The configuration of this electronic substrate 311-1 is similar to that of the second embodiment. On a rear face of the electronic substrate 311-1, a battery 313, and the like are disposed.

As illustrated in FIGS. 299 and 300, in the sensor device 200 according to the fifth embodiment of the present technology, an electronic substrate 311-1 is coated using a coating resin. This coating resin is illustrated using a black thick line disposed on the outer side of the electronic substrate 311-1 in FIGS. 299 and 300. This coating resin has an electromagnetic wave transmissivity and water resistance and more preferably has chemical resistance and is preferably has flexibility higher than the electronic substrate 311-1. The sensor device 200 according to the present technology requires a predetermined mechanical strength such that, when antennas included therein and transmission lines connected to the antennas are inserted into a predetermined soil, the antennas and the transmission lines are not deformed. In the sensor device 200 according to the fifth embodiment of the present technology, the electronic substrate 311-1 has a role for securing the predetermined mechanical strength described above. On the other hand, the coating resin described above has a role for protecting the electronic substrate 311-1 from water and agricultural chemicals. Here, when a cavity is generated between the coating resin and the electronic substrate 311-1 (in other words, when the coating resin floats from the front face of the electronic substrate 311-1), when the sensor device 200 is inserted into soil, stress is applied to this floating coating resin, and there is a concern that the coating resin may be broken. Thus, in the sensor device 200 according to the fifth embodiment of the present technology, in order to coat the electronic substrate 311-1 without incurring a cavity between the electronic substrate 311-1 and the coating resin, a resin having flexibility is used for the coating resin. In addition, the sensor device 200 according to the fifth embodiment of the present technology measures an amount of moisture in a medium between two antennas by transmitting electromagnetic waves from a transmission antenna covered with the coating resin and receiving the electromagnetic waves using a reception antenna covered with the coating resin. Thus, in the sensor device 200 according to the fifth embodiment of the present technology, as the coating resin, a resin having electromagnetic wave transmissivity is used.

FIGS. 301 and 302 are diagrams illustrating an example of a front view and a side view of a sensor device 200 according to another example 1 of the fifth embodiment of the present technology.

a in FIG. 301 illustrates a front view of the sensor device 200, and b in this diagram illustrates a side view of the sensor device 200. a in FIG. 302 is an example of a rear view of the sensor device 200. b in this diagram is an example of a cross-sectional view acquired when the sensor device 200 is cut along line C-C' illustrated a in this diagram. c in this diagram is an example of a cross-sectional view acquired when the sensor device 200 is cut along line D-D' in a in this diagram. d in this diagram is an example of a cross-sectional view acquired when the sensor device 200 is cut along line E-E' illustrated in a in this diagram.

In addition, in FIGS. 299 and 300, black thick lines on outer sides of the measurement unit substrate 311 and the in-probe substrates 321 and 322 represent coating resins.

A user of the sensor device 200 according to the fifth embodiment of the present technology inserts an antenna part of the sensor device 200 into soil with a part including a measurement unit of the sensor device 200 being held. For this reason, in order to realize the sensor device 200 not including the probe casing 305 as in the fifth embodiment of the present technology on the basis of the sensor device 200 of a form in which the measurement unit substrate 311 and the in-probe substrates 321 and 322 are configured as different substrates as in the first embodiment of the present technology, it is preferable that the in-probe substrates 321 and 322 be fixed to the measurement unit substrate 311 not through the probe casing 305 such that directions and positions are not changed when the in-probe substrates 321 and 322 are inserted into soil.

Thus, the sensor device 200 according to another example 1 of the fifth embodiment of the present technology illustrated in FIGS. 301 and 302, similar to the sensor device 200 illustrated in FIGS. 180 and 181, includes frames 291 to 294. Such frames integrate and fix the measurement unit substrate 311 and the in-probe substrates 321 and 322 in the state of being orthogonal to each other, and in accordance with this, this structure formed through fixation has the predetermined mechanical strength described above.

In the sensor device 200 according to another example 1 of the fifth embodiment of the present technology illustrated in FIGS. 301 and 302, the outer side of the structure formed through fixation is coated with a coating resin that has flexibility higher than that of the measurement unit substrate 311 and the in-probe substrates 321 and 322, has electromagnetic wave transmissivity and water resistance, and more preferably, has chemical resistance.

FIGS. 303 and 304 are diagrams illustrating an example of a front view and a side view of a sensor device 200 according to another example 2 of the fifth embodiment of the present technology.

a in FIG. 303 illustrates a front view of the sensor device 200, and b in this diagram illustrates a side view of the sensor device 200. a in FIG. 304 is an example of a rear view of the sensor device 200. b in this diagram is an example of a cross-sectional view acquired when the sensor device 200 is cut along line C-C' illustrated in a in this drawing. c in this drawing is an example of a cross-sectional view acquired when the sensor device 200 is cut along line D-D' illustrated in a in this drawing. d in this drawing is an example of a cross-sectional view acquired when the sensor device 200 is cut along line E-E' illustrated in a in this drawing. In addition, in FIGS. 303 and 304, black thick lines on outer sides of the measurement unit substrate 311 and the in-probe substrates 321 and 322 represent coating resins.

The sensor device 200 according to another example 2 of the fifth embodiment of the present technology illustrated in FIGS. 303 and 304, similar to the sensor device 200 illustrated in FIGS. 182 and 183, has a structure in which a notch is formed in any one of the measurement unit substrate and the in-probe substrate, and two substrates are fitted to each other using these. According to this fitting, the measurement unit substrate 311 and the in-probe substrates 321 and 322 are integrated and fixed in the state of being orthogonal to each other, and, in accordance with this, the structure formed through the fixation has the predetermined mechanical strength described above.

In the sensor device 200 according to another example 2 of the fifth embodiment of the present technology illustrated in FIGS. 303 and 304, the outer side of the structure formed through fixation is coated with a coating resin that has flexibility higher than that of the measurement unit substrate 311 and the in-probe substrates 321 and 322, has electromagnetic wave transmissivity and water resistance, and more preferably, has chemical resistance.

FIGS. 305 and 306 are diagrams illustrating an example of a front view and a side view of a sensor device 200 according to another example 3 of the fifth embodiment of the present technology.

a in FIG. 305 illustrates a front view of the sensor device 200, and b in this diagram illustrates a side view of the sensor device 200. a in FIG. 306 is an example of a rear view of the sensor device 200. b in this diagram is an example of a cross-sectional view acquired when the sensor device 200 is cut along line C-C' illustrated in a in this drawing. c in this drawing is an example of a cross-sectional view acquired when the sensor device 200 is cut along line D-D' illustrated in a in this drawing. d in this drawing is an example of a cross-sectional view acquired when the sensor device 200 is cut along line E-E' illustrated in a in this drawing. In addition, in FIGS. 303 and 304, black thick lines on outer sides of the measurement unit substrate 311 and the in-probe substrates 321 and 322 represent coating resins.

The sensor device 200 according to another example 3 of the fifth embodiment of the present technology illustrated in FIGS. 305 and 306, similar to the sensor device 200 illustrated in FIGS. 184 and 185, includes jigs fixing a measurement unit substrate and in-probe substrates. In accordance with these jigs, the measurement unit substrate 311 and the in-probe substrates 321 and 322 are integrated and fixed in the state of being orthogonal to each other, and in accordance with this, this structure formed through fixation has the predetermined mechanical strength described above.

In the sensor device 200 according to another example 3 of the fifth embodiment of the present technology illustrated in FIGS. 305 and 306, the outer side of the structure formed through fixation is coated with a coating resin that has flexibility higher than that of the measurement unit substrate 311 and the in-probe substrates 321 and 322, has electromagnetic wave transmissivity and water resistance, and more preferably, has chemical resistance.

In this way, according to the fifth embodiment of the present technology, the substrates included in the sensor device 200 are coated with a resin, and, in accordance with this, the sensor device 200 not using the sensor casing 305 is realized. As a result, the sensor device 200 according to the fifth embodiment of the present technology, compared to the sensor device 200 of the present technology including the sensor casing 305, acquires an effect of decreasing the number of components, reducing an external size, decreasing a weight, simplifying a manufacturing method, and reducing a manufacturing cost.

6. Sixth Embodiment

In the first embodiment described above, substrates are stored inside the sensor casing 305 in which one pair of protrusion parts (probes) are disposed. In a sensor device 200 according to a sixth embodiment, a stem is connected to a probe, which is different from the first embodiment. In other words, the sensor device according to the sixth embodiment has a structure in which a stem is added to various kinds of sensor devices described in this specification (for example, the sensor devices according to the first to third embodiments and the modification examples thereof).

FIG. 307 is a diagram illustrating an example of the sensor device 200 according to the sixth embodiment of the present technology. a in this diagram is a diagram illustrating an example of an internal structure of the sensor device 200. b in this diagram is an example of an external view of the sensor device 200.

A sensor casing 305 according to the fifth embodiment is composed of a main body part 305-3 of a rectangular shape, a stem 305-4 of a pipe shape, and a protrusion part 305-5 of which a part is further divided into two parts and protrudes. A measurement unit substrate 311 is stored in the main body part 305-3, and a level 376 is mounted in an upper part. A transmission antenna 221 and a reception antenna 231 are stored inside the protrusion part 305-5. This protrusion part 305-5 functions as a probe. The stem 305-4 connects the main body part 305-3 and the protrusion part 305-5 (the probe), and coaxial cables 281 and 282 are wired on the inside thereof. By using such cables, the transmission antenna 221 and the reception antenna 231 are connected to the measurement unit substrate 311. In addition, the level 376 is disposed as necessary.

In addition, as illustrated in b in this diagram, scales indicating depths are written on the front face of the sensor casing 305, and a temperature sensor 390 is mounted as necessary. Furthermore, a pH sensor, an EC (Electro Conductivity) sensor, and the like can be additionally mounted. However, such sensors need to be disposed at positions at which electromagnetic waves radiated from the probe are not reflected by various sensor. For this reason, it is preferable that the temperature sensor 390 and the like be disposed on a ferrite of the probe (an electric wave absorbing unit) or at a position further away from that.

By connecting the main body part 305-3 and the probe using the stem 305-4, the probe can be easily inserted into a deep position in the ground surface. By using the scales of the surface of the stem 305-4, a depth of a measurement point of the sensor device 200 can be accurately acquired. The stem 305-4 can be inserted vertically with respect to the ground surface using the level 376. By using various sensors, the state of soil can be measured multilaterally.

FIG. 308 is a diagram illustrating an example of a sensor device in which a position of the main body part is changed in the sixth embodiment of the present technology. a in this diagram is a diagram illustrating an example of an internal structure of the sensor device 200. b in this diagram is an example of an external view of the sensor device 200.

As illustrated in this diagram, by adding an antenna part 305-6 of a rectangular shape, the antenna part 305-6 and the main body part 305-3 can be connected also using the stem 305-4. An antenna 213 is stored inside the antenna part 305-6. The protrusion part 305-5 (the probe) is connected to a lower part of the main body part 305-3.

In this way, according to the sixth embodiment of the present technology, the stem 305-4 is connected to the probe, and thus the probe can be easily inserted into a deep position in soil.

7. Seventh Embodiment

In the first embodiment described above, although one pair of probes used for insertion into soil are disposed in the sensor device 200, in this configuration, there are cases in which a distance between the probes changes due to degradation of the probes, deformation of members according to stones and solid soil. Although deformation can be prevented by thickening the probes to improve the strength, there is a concern that the size and the weight of the sensor device 200 become large, and it may be difficult to insert the probes into soil. In a sensor device 200 according to the seventh embodiment, the strength of the sensor device 200 is improved by adding pillars, which is different from the first embodiment.

FIG. 309 is a diagram illustrating an example of sensor devices 200 according to the seventh embodiment of the present technology and a comparative example. a in this diagram illustrates a first comparative example. b, c, and d in this diagram illustrate cross-sectional views respectively cut along line A-A', line B-B', and line C-C' illustrated in a in this drawing.

As illustrated in a in this drawing, the first comparative example in which a spacer 600 is disposed between probe casings 320-3 and 320-4 having a pillar shape will be considered. In the probe casing 320-3, transmission antennas 221 to 223 are formed and function as a transmission probe. In the probe casing 320-4, reception antennas 231 to 233 are formed and function as a reception probe.

As in the first comparative example, when the spacer 600 is disposed between antennas, soil is not inserted between the antennas, and an amount of moisture cannot be measured.

e in this diagram illustrates a second comparative example. f, g, and h in this diagram illustrate cross-sectional views cut along line A-A', line B-B', and line C-C' illustrated in e in this diagram. In the second comparative example, a spacer is separated into a plurality of spacers such as spacers 600 to 603 and the like, and a space is formed between antennas. In this second comparative example, although soil is inserted between antennas, there is a concern that the soil is not sufficiently inserted between the antennas due to interruption of the spacer 600.

i in this diagram is a perspective view of the sensor device 200 according to the seventh embodiment. In the sensor device 200 according to the seventh embodiment, three pillars 610 are added. Between the probe casings 320-3 and 320-4, a spacer is not disposed. The pillar 610 and the probe casings 320-3 and 320-4 are connected using reinforcing parts 620 and 621. In accordance with this shape, a spacer is not disposed between the antennas, and thus soil is not interrupted by a spacer and is inserted between the antennas.

In addition, water is sufficiently transferred to soil, and the amount of water transferred to the probe becomes small. In addition, since a gap between the probes is large, there is a little concern that growth of a root of a plant is interrupted by the gap.

FIG. 310 is a diagram illustrating an example of a cutout face of the sensor device 200 according to the seventh embodiment of the present technology. In this diagram, a pillar 610 behind the sensor device 200 is omitted. Cross-sectional views taken along line B-B' (an area in which the transmission antenna 221, the transmission in-probe substrate 321, the reception antenna 231 and the reception in-probe substrate 322 are disposed) illustrated in this diagram and line C-C' (an area in which the transmission antenna 221 and the reception antenna 231 are not disposed, and the transmission in-probe substrate 321 and the reception in-probe substrate 322 are disposed) will be represented in FIG. 311 and subsequent diagrams.

Similar to FIG. 310, FIGS. 354 and 355 are diagrams illustrating an example of a cutout face of the sensor device 200 according to the seventh embodiment of the present technology. In FIGS. 354 and 355, the pillar 610 and the reinforcing parts 620 and 621 included on the rear side of the sensor device 200, which are omitted in FIG. 310, are illustrated. FIG. 354 illustrates a form in which the sensor device 200 includes a pillar 610 of a cylindrical shape, and FIG. 355 illustrates a form in which the sensor device 200 includes a pillar 610 having a square column shape. In the Y-axis direction of the sensor device 200, in an area in which antennas (transmission antennas 221 to 223 and reception antennas 231 to 233) included in the sensor device 200 are not disposed, a pillar 610 included on the rear side of the sensor device 200 is connected to the transmission probe casing 320-3 through the reinforcing part 620 and is connected to the reception probe casing 320-4 through the reinforcing part 621.

FIG. 311 is a diagram illustrating an example of a cross-sectional view of the sensor device 200 according to the seventh embodiment of the present technology. a and b in this diagram are examples of cross-sections taken along line B-B'. c in this diagram is an example of a cross-sectional view taken along line C-C'. Any one of a and b in this diagram can be applied to c in this diagram. In other words, the sensor device 200 can be configured by combining any one of structures illustrated in a and b in this diagram as a structure of a cross-section in line B-B' and a structure illustrated in c in this diagram as a structure of a cross-section in line C-C'.

A structure of the sensor device 200 acquired in a case in which a and c in FIG. 311 are combined is illustrated in FIG. 356. In the sensor device 200 illustrated in FIG. 356, a form in which (1), in the Y-axis direction, the reinforcing parts 620 and 610 extend from an area in which the transmission antennas 221 to 223 and the reception antennas 231 to 233 are disposed across an area in which such antennas are not disposed and (2), in both an area in which the transmission antennas 221 to 223 and the reception antennas 231 to 233 are disposed in the Y-axis direction and an area in which such antennas are not disposed in the Y-axis direction, the probe casing 320-3 and the probe casing 320-4 are connected using the reinforcing parts 620 and 621 with an area of a linear shape joining the probe casing 320-3 and the probe casing 320-4 avoided is formed.

A structure of the sensor device 200 acquired in a case in which b and c in FIG. 311 are combined is illustrated in FIG. 357. In the sensor device 200 illustrated in FIG. 357, a form in which (1), in the Y-axis direction, in an area in which the transmission antennas 221 to 223 and the reception antennas 231 to 233 are not disposed, the probe casing 320-3 and the probe casing 320-4 are connected using the reinforcing parts 620 and 621 with an area of a linear shape joining the probe casing 320-3 and the probe casing 320-4 avoided, (2) in an area in which the transmission antennas 221 to 223 and the reception antennas 231 to 233 are disposed, the pillar 610 is disposed on a lateral side of the probe casing 320-3 and the probe casing 320-4, and (3), in a boundary part between the area of (1) described above and thee area of (2) described above, the reinforcing parts 620 and 621 of (1) described above and the pillar 610 of (2) described above are connected is formed.

In addition, different from the example illustrated in FIG. 310*d, e*, and *f* to be described below, in the example illustrated in FIGS. 310*a, b*, and *c*, an antenna and a sensor are not disposed inside the pillar 610.

d and e in FIG. 311 are an example of a cross-sectional view taken along line B-B'. f in this drawing is an example of a cross-sectional view taken along line C-C'. Any one of d and e in this diagram can be applied to f in this diagram. In other words, the sensor device 200 can be configured by combining any one of structures illustrated in d and e in this diagram as a structure of a cross-section in line B-B' and a structure illustrated in f in this diagram as a structure of a cross-section in line C-C'.

A structure of the sensor device 200 acquired in a case in which d and f in FIG. 311 are combined is illustrated in FIG. 358. In the sensor device 200 illustrated in FIG. 358, a form in which (1) the pillar 610 extends from an area in which, in the Y-axis direction, the transmission antennas 221 to 223 and the reception antennas 231 to 233 are disposed across an area in which such antennas are not disposed, (2), in both an area in which the transmission antennas 221 to 223 and the reception antennas 231 to 233 are disposed in the Y-axis direction and an area in which such antennas are not disposed in the Y-axis direction, the probe casing 320-3 and the probe casing 320-4 are connected using the reinforcing parts 620 and 621 and the pillar 610 with an area of a linear shape joining the probe casing 320-3 and the probe casing 320-4 avoided is formed.

A structure of the sensor device 200 acquired in a case in which e and f in FIG. 311 are combined is illustrated in FIG. 359. In the sensor device 200 illustrated in FIG. 359, a form in which (1) the pillar 610 extends from an area in which the transmission antennas 221 to 223 and the reception antennas 231 to 233 are disposed in the Y-axis direction across an area in which such antennas are not disposed, (2), in an area in which the transmission antennas 221 to 223 and the reception antennas 231 to 233 are not disposed in the Y-axis direction, the probe casing 320-3 and the probe casing 320-4 are connected using the reinforcing parts 620 and 621 and the pillar 610 with an area of a linear shape joining the probe casing 320-3 and the probe casing 320-4 avoided, and (3) in an area in which the transmission antennas 221 to 223 and the reception antennas 231 to 233 are disposed, the pillar 610 is disposed on a lateral side of the probe casing 320-3 and the probe casing 320-4 in the Y-axis direction is formed.

As illustrated in d, e, and f in FIG. 311, in any one, some or all of such areas, by disposing a sensor such as an antenna, a temperature sensor, a PH sensor (a hydrogen ion concentration sensor), an EC sensor (an electroconductivity sensor), or the like inside the pillar 610, it can be also used as a third probe.

g in FIG. 311 is an example of a cross-sectional view taken along line B-B'. h in this diagram is an example of a cross-sectional view taken along line C-C'. A structure of the sensor device 200 acquired in a case in which g and h in FIG. 311 are combined is illustrated in FIG. 360. As illustrated in g and h in FIG. 311, the structure may be reinforced using the reinforcing parts 620 and 621 without disposing the pillar 610.

i in this diagram is an example of a cross-sectional view taken along line B-B'. j in this diagram is an example of a cross-sectional view taken along line C-C'. A structure of the sensor device 200 acquired in a case in which i and j in FIG. 311 are combined is illustrated in FIG. 361. As illustrated in i and j in FIG. 311, in a case in which the pillar 610 is not disposed, the cross-section may be configured to be in a circle shape or an oval shape. In other words, in such a cross-section, a form in which the probe casing 320-3 and the probe casing 320-4 are connected at a plurality of points using the reinforcing parts 620 and 621 with an area of a linear shape joining the probe casing 320-3 and the probe casing 320-4 avoided may be used. Then, in such a cross-section, the probe casing 320-3 and the probe-casing 320-4 that are connected, the reinforcing part 620, and the reinforcing part 621 may be configured to form a closed curve such as a circle, an oval, or the like.

FIG. 312 is a diagram illustrating an example of a cross-section of a rectangular shape of the sensor device 200 according to the seventh embodiment of the present technology. In other words, FIG. 312 is a diagram illustrating an example in which the probe casing 320-3 and the probe casing 320-4 and the reinforcing part 620 and the reinforcing part 621 connected to these are arranged in a rectangular shape.

a and b in this diagram are examples of a cross-sectional view taken along line B-B'. c in this diagram is an example of a cross-sectional view taken along line C-C'. Any one of a and b in this diagram can be applied to c in this diagram. In other words, the sensor device 200 can be configured by combining any one of the structures illustrated in a and b in this diagram and the structure illustrated in c in this diagram. d in this diagram is an example of a cross-sectional view taken along line B-B'. i in this diagram is an example of a cross-sectional view taken along line C-C'. d in this diagram can be applied to f in this diagram. In other words, the sensor device 200 can be configured to be applied by combining the structure illustrated in d in this diagram and the structure illustrated in f in this diagram. As illustrated in a to c in this diagram, the cross-sectional shape can be configured in a rectangular shape, and two pillars 610 can be disposed.

g and e in this diagram are examples of a cross-sectional view taken along line B-B'. i in this diagram is an example of a cross-sectional view taken along line C-C'. Any one of g and e in this diagram can be applied to i in this diagram. In other words, the sensor device 200 can be configured by combining any one of the structures illustrated in g and e in this diagram and the structure illustrated in i in this diagram. As illustrated in e in this diagram, the cross-sectional shape can be configured to be a rectangular shape, and two pillars 610 can be disposed.

j and h in this diagram are examples of a cross-sectional view taken along line B-B'. k in this diagram is an example of a cross-sectional view taken along line C-C'. The sensor device 200 can be configured by combining any one of the structures illustrated in j and h in this diagram and the structure illustrated in k in this diagram. As illustrated in a combination of h and k in this diagram, the cross-sectional shape can be configured to be a rectangular shape, and four pillars 610 can be disposed. In addition, as illustrated in j and k in this diagram, the structure may be reinforced using the reinforcing parts without disposing inside the pillar 610.

FIG. 313 is a diagram illustrating an example of a cross-sectional view of a sensor device 200 in which the number of probes is three in the seventh embodiment of the present technology.

a and b in this diagram are examples of a cross-sectional view taken along line B-B'. c in this diagram is an example of a cross-sectional view taken along line C-C'. Any one of a and b in this diagram can be applied to c in this diagram.

In other words, the sensor device 200 can be configured by combining any one of the structures illustrated in a and b in this diagram and the structure illustrated in c in this diagram.

d and e in this diagram are examples of a cross-sectional view taken along line B-B'. f in this diagram is an example of a cross-sectional view taken along line C-C'. Any one of d and e in this diagram can be applied to f in this diagram. In other words, the sensor device 200 can be configured by combining any one of the structures illustrated in d and e in this diagram and the structure illustrated in f in this diagram.

g and h in this diagram are examples of a cross-sectional view taken along line B-B'. i in this diagram is an example of a cross-sectional view taken along line C-C'. Any one of g and h in this diagram can be applied to i in this diagram. In other words, the sensor device 200 can be configured by combining any one of the structures illustrated in g and h in this diagram and the structure illustrated in i in this diagram.

FIG. 314 is a diagram illustrating another example of a cross-sectional view of a sensor device 200 in which the number of probes is three in the seventh embodiment of the present technology. a, c, and e in this diagram are examples of a cross-sectional view taken along line B-B'. b. d. and f in this diagram are examples of a cross-sectional view taken along line C-C'. The sensor device 200 can be configured by combining any one of the structures illustrated in a and e in this diagram and the structure illustrated in b in this diagram. In addition, the sensor device 200 can be configured by combining the structure illustrated in c in this diagram and the structure illustrated in d in this diagram.

As illustrated in FIGS. 313 and 314, by disposing an antenna and a sensor inside the pillar 610, it can be used as a third probe.

FIG. 315 is a diagram illustrating an example of a cross-sectional view of a sensor device 200 in which the number of probes is four in the seventh embodiment of the present technology. a, c, and e in this diagram are examples of a cross-sectional view taken along line B-B'. b, d, and f in this diagram are examples of a cross-sectional view taken along line C-C'. As illustrated in this diagram, by storing an antenna and a sensor of each of the pillars 610 and 611, they can be used as third and fourth probes.

FIG. 316 is another example of a perspective view of the sensor device 200 according to the seventh embodiment of the present technology. This diagram is a diagram of the sensor device 200 seen from a Y+ direction (a tip end side of the probe casings 320-3 and 320-4) to a Y-direction (a measurement unit casing 310 side). The measurement unit casing 310 that is a base is disposed between the probe casings 320-3 and 320-4. This measurement unit casing 310 functions as a reinforcing part. It is preferable that the size of this reinforcing part be larger than that of the reinforcing part 360 of the tip end or the like.

FIG. 317 is an example of a sensor device 200 in which a groove is formed in a spacer in the seventh embodiment of the present technology. As illustrated in this diagram, a wavelike grove can be formed in the spacer 601 and the like. This groove prevents water that has been released from being transferred to the sensor device 200 and forming a gap. In addition, a gap that can be formed in accordance with the sensor device 200 in a case in which the sensor device 200 is inserted can be inhibited.

FIG. 318 is a diagram illustrating an example of a groove of a spacer in the seventh embodiment of the present technology. As illustrated in a, b, and c in this diagram, a hole of a mesh shape can be formed in the spacer. In accordance with formation of a hole, moisture in peripheral soil can be easily transferred, and it becomes difficult to block the growth of a root.

In addition, in the seventh embodiment described with reference to FIGS. 309 to 318 and FIGS. 354 to 361, as an internal configuration of the sensor casing 305 (for example, the configuration of substrates, antennas, a transmission line, an electric wave absorbent material, and the like), the configurations described in the first to third embodiments and the modification examples thereof can be used.

In this way, according to the seventh embodiment of the present technology, the probes are reinforced using pillars or reinforcing parts, and thus, the strength of the sensor device 200 can be improved.

8. Eighth Embodiment

In the first embodiment described above, although the measurement unit casing 310 and the probe casing 320 are integrated together, in this configuration, when the probe casing 320 is inserted into soil, the casing is deformed, and there is a concern that a distance between antennas may change. In accordance with variations in the distance between the antennas, error occurs in a measured value of the amount of moisture. In a sensor device 200 according to this eighth embodiment, a probe casing is divided, which is different from the first embodiment.

FIG. 319 is a diagram illustrating a comparative example and an example of a sensor device 200 according to the eighth embodiment of the present technology. a in this diagram is a diagram illustrating an example of a sensor device 200 of the comparative example in which a measurement unit casing 310 and probe casings 320-3 and 320-4 are integrated. b in this diagram illustrates a state in which the probe casings 320-3 and 320-4 of the comparative example are inserted into soil. c in this diagram is a diagram illustrating an example of a sensor device 200 according to the eighth embodiment of the present technology in which a measurement unit casing 310 and probe casings 320-3 and 320-4 are separated. d in this diagram illustrates a state in which the probe casings 320-3 and 320-4 according to the eighth embodiment of the present technology are inserted into soil.

As illustrated in a in this diagram, the comparative example in which the measurement unit casing 310 and the probe casings 320-3 and 320-4 are integrated will be considered. The probe casings 320-3 and 320-4 include a transmission antenna 221 and a reception antenna 231, and these function as one pair of probes. When such probes are inserted into soil, as illustrated in b in this diagram, connection portions between the measurement unit casing 310 and the probes may be deformed. When the rigidity of the casing is configured to be sufficiently high, deformation can be prevented, but there are problems due to costs, convenience, and the like.

Thus, in the eighth embodiment of the present technology, as illustrated in c in this diagram, the measurement unit casing 310 and the probe casings 320-3 and 320-4 (probes) are separated. The measurement unit casing 310 and the probe casings 320-3 and 320-4 are electrically connected using coaxial cables 281 and 284, and the like.

In addition, in the probe casing 320-3, for example, transmission antennas 221 to 223 are formed, and, in the probe casing 320-4, for example, reception antennas 231 to 233 are formed.

By separating the measurement unit casing 310 and one pair of probes from each other, as illustrated in d in this diagram, connection portions between the measurement unit casing 310 and the probes can be prevented from being deformed when the probes are inserted into soil.

FIG. 320 is a diagram illustrating an example of a sensor device 200 in which scales and a stopper are disposed in the eighth embodiment of the present technology. As illustrated in a in this diagram, in each of the probe casings 320-3 and 320-4, scales indicating a distance (that is, a depth) from a tip end can be also provided. In accordance with this, a user can visually recognize an inserted depth.

In addition, as illustrated in b in this diagram, in upper parts of the probe casings 320-3 and 320-4, stoppers 630 and 631 preventing insertion for a depth exceeding a predetermined distance can be mounted as well. Both the scales and the stoppers can be disposed.

FIG. 321 is a diagram illustrating an example of the numbers of antennas on a transmission side and a reception side in the eighth embodiment of the present technology. When a user separates one pair of probes and inserts them at arbitrary positions, a distance between antennas has a different value in accordance with insertion positions. For this reason, the moisture measuring system 100 needs to measure a distance between the antennas. In this measurement of a distance between antennas, the number of antennas needs to be three or more on at least one of a transmission side and a reception side. The reason for this and a measurement method will be described below.

For example, as illustrated in a in this diagram, the number of antennas of the transmission side can be configured to be one, and the number of antennas of the reception side can be configured to be three. In addition, as illustrated in b in this diagram, the number of antennas of the transmission side can be configured to be three, and the number of antennas of the reception side can be configured to be one. As illustrated in c in this diagram, the number of antennas of each of the transmission side and the reception side can be also configured to be three.

FIG. 322 is a block diagram illustrating one configuration example of a signal processing unit 154 disposed inside a central processing device in the eighth embodiment of the present technology. This signal processing unit 154 further includes a memory 166 and a distance calculation unit 167.

A reciprocating delay time calculation unit 162 supplies a calculated reciprocating delay time to a moisture amount measurement unit 164 and a memory 166. In addition, a propagation transmission time calculation unit 163 supplies a calculated propagation transmission time to the moisture amount measurement unit 164 and the memory 166. The memory 166 stores values of such parameters.

A distance calculation unit 167 reads values stored in the memory 166 and calculates a distance between antennas using them. A calculation method will be described below. The distance calculation unit 167 supplies the calculated inter-antenna distance to the moisture amount measurement unit 164.

The moisture amount measurement unit 164 measures an amount of moisture on the basis of the reciprocating delay time and the propagation transmission time and the inter-antenna distance calculated by the distance calculation unit 167. When the inter-antenna distance changes, coefficient a and coefficient b represented in Expression 6 change. For this reason, the moisture amount measurement unit 164 corrects the coefficient a and the coefficient b in accordance with a measured inter-antenna distance and calculates an amount of moisture using Expression 6.

FIG. 323 is a diagram illustrating an example including a plate-shaped member according to the eighth embodiment of the present technology and an example of the sensor device 200 in which scales and stopper are provided. a in this diagram is a diagram illustrating an example of the plate-shaped member 632. In this plate-shaped member 632, one pair of holes used for inserting one pair of probes thereinto are emptied. For a user to use the sensor device 200 according to this embodiment (1) first, the user disposes the plate-shaped member 632 on the surface of soil that is a measurement target, (2) next, the user inserts two probes into the soil through one pair of holes included in the plate-shaped member 632, and (3) the sensor device 200 measures moisture of the soil using two probes inserted into the soil. More specifically, a propagation transmission time between antennas included in the two probes and a reciprocating delay time for each antenna are measured, the coefficients a and b represented in Expression 6 are corrected in accordance with a distance between antennas included in the two probes inserted into the soil, an amount of moisture is calculated using the coefficients after correction, and the calculated amount of moisture is output.

b in this diagram is a diagram illustrating an example of the sensor device 200 of which probes are inserted into holes of the plate-shaped member 632. Scales are assumed to be formed in the probes. In addition, as illustrated in c in this diagram, probes in which stoppers 630 and 631 are disposed can be also inserted into the holes of the plate-shaped member 632.

As illustrated in b and c in this diagram, by using the plate-shaped member 632, a distance between the probes can be fixed. Then, as a result of insertion of the probes into the ground surface through the holes included in the plate-shaped member 632, even when the probes are inserted obliquely with respect to the ground surface, the amount of moisture is corrected in accordance with a distance between antennas included in the inserted probes, and the corrected amount of moisture is output. In addition, in a case in which the probes are able to be inserted vertically with respect to the ground surface, a distance between the antennas is a designed value, and thus measurement of a distance between the antennas becomes unnecessary.

FIG. 324 is a diagram illustrating an example in which a parallelepiped member is included in the eighth embodiment of the present technology and an example of a sensor device in which scales and stopper are provided. a in this diagram is a diagram illustrating an example of the parallelepiped member 633. In this parallelepiped member 633, one pair of holes for inserting one pair of probes are emptied. A method of measuring an amount of moisture using the parallelepiped member 633 is similar to the method of measuring an amount of moisture using the plate-shaped member 632.

b in this diagram is a diagram illustrating an example of a sensor device 200 in which probes are inserted into the holes of the parallelepiped member 633. Scales are provided in the probes. In addition, as illustrated in c in this diagram, probes in which stoppers 630 and 631 are provided can be also inserted into the holes of the parallelepiped member 633.

In addition, as illustrated in d in this diagram, levels 376 and 377 can be mounted in the parallelepiped member 633, and the probes also can be inserted into the holes of the member.

FIG. 325 is a diagram illustrating an example of a sensor device in which a probe casing is not separated in the eighth embodiment of the present technology. a in this diagram is a diagram illustrating an example of a sensor device 200 in which a measurement unit casing 310 and probe casings 320-3 and 320-4 are not separated but integrated. b in this diagram illustrates an example of a state in which the sensor device 200 illustrated in a in this diagram is inserted into soil.

As illustrated in b in this diagram, also in a case in which the probes are not separated, a connection portion between the measurement unit casing 310 and the probe is deformed, and a distance between antennas may change. Alternatively, deformation may occur due to degradation over time. For this reason, the signal processing unit 154 illustrated in FIG. 320 also can be applied to a moisture measuring system 100 including a sensor device 200 in which a measurement unit casing 310 and probe casings 320-3 and 320-4 are integrated. In accordance with this, a changed inter-antenna distance can be accurately calculated, and the accuracy of measurement of an amount of moisture can be improved on the basis of the calculated value.

FIG. 326 is a diagram illustrating a method of measuring an inter-antenna distance in the eighth embodiment of the present technology. As illustrated in a in this diagram, the sensor device 200 transmits electromagnetic waves from the transmission antenna 221, and each of the reception antennas 231 to 233 receives the electromagnetic waves.

The distance calculation unit 167 described above calculates a propagation delay time between the transmission antenna 221 and the reception antennas 231 as $\tau_{d1}$ using Expression 5. Similarly, the distance calculation unit 167 calculates a propagation delay time between the transmission antenna 221 and the reception antennas 232 as $\tau_{d2}$ and calculates a propagation delay time between the transmission antenna 221 and the reception antennas 233 as $\tau_{d3}$.

Here, the following relation equation is satisfied between the propagation delay time $\tau_d$ and the inter-antenna distance d.

$$\tau_d=\{(\varepsilon_b)^{1/2}/C\}d \qquad \text{Expression 25}$$

In the expression represented above, $\varepsilon_b$ represents a dielectric constant of a medium, and C is the speed of light.

When the dielectric constant is uniform over the whole medium, from Expression 25, the inter-antenna distance d is in proportion to the propagation delay time $\tau_d$, and $\tau_{d1}$, $\tau_{d2}$, and $\tau_{d3}$ can be replaced with d1, d2, and d3. d1 is a distance between the transmission antenna 221 and the reception antenna 231, and d2 is a distance between the transmission antenna 221 and the reception antenna 232. d3 is a distance between the transmission antenna 221 and the reception antenna 233.

b in this diagram represents a circle in which a ratio of distances from arbitrary two points is constant. Such a circle is called an Apollonius's circle.

It is assumed that the transmission antenna 221 and the reception antennas 231 to 233 are positioned on a predetermined x-y plane. A direction in which the reception probe grows is an x-axis direction, and positions of the reception antennas 231 to 233 on this x axis will be denoted by x1, x2, and x3. The distance calculation unit 167 acquires a circle (an Apollonius's circle) in which distances from x1 and x2 are at the ratio of d1:d2 on the x-y plane. This circle corresponds to a circle of a dashed line illustrated in this diagram. In addition, the distance calculation unit 167 acquires a circle in which distances from x2 and x3 are at the ratio of d2:d3. This circle corresponds to a circle of a dotted line illustrated in a in this diagram.

The distance calculation unit 167 calculates coordinates of intersections of the acquired two circles. These coordinates correspond to a position of the transmission antenna 221. The distance calculation unit 167 calculates a distance between the calculated coordinates of the transmission antenna 221 and any one of x1 to x3 (x2 or the like) and supplies the calculated distance to the moisture amount measurement unit 164.

In addition, in this diagram, although a two-dimensional coordinate system has been considered, calculation can be also performed in a three-dimensional coordinate system. In such a case, when calculation is performed with a circle being replaced with a sphere, the distance calculation unit 167 can acquire a distance.

When an amount of moisture between the transmission antenna 221 and the reception antenna 232 is measured, the distance calculation unit 167 uses not only a propagation delay time $\tau_{d2}$ but also a propagation delay time rai between the transmission antenna 221 and the reception antenna 231 and the like. In accordance with this, an amount of moisture can be measured more accurately.

In addition, in the eighth embodiment described with reference to FIGS. 319 to 326, other than the probe casings being separated, the configurations described in the first to third embodiments and the modification examples thereof can be used.

In this way, according to the eighth embodiment of the present technology, one pair of probe casings are separated from the measurement unit casing 310, and thus, it can be prevented that a distance between antennas changes due to deformation of the casings when the probe casings are inserted into soil In accordance with this, the amount of moisture can be measured more accurately.

9. Ninth Embodiment

In the first embodiment described above, although one pair of probes of the sensor device 200 are inserted into soil, in this configuration, in a case in which the soil is hard, there is concern that the probes may be deformed. In this moisture measuring system 100 according to the ninth embodiment, by inserting a guide into soil before insertion of probes, the deformation of the probes is prevented, which is different from the first embodiment.

FIG. 327 is a diagram illustrating an example of a method of inserting a sensor device 200 in the ninth embodiment of the present technology. This moisture measuring system according to the ninth embodiment further includes a guide 640, which is different from the first embodiment. In addition, the outer shape of the sensor device 200 according to the ninth embodiment, for example, is similar to that according to the sixth embodiment including a stem. A sensor device 200 having an outer shape different from that according to the sixth embodiment can be also used.

The guide 640 is made of metal and has one pair of protrusion parts formed at a tip end thereof. The shape of such protrusion parts is approximately the same as that of the probes. It is preferable that the outer shape of the guide 640 be smaller than the outer shape of the sensor device 200. Particularly, it is more preferable that an outer shape of a protrusion part of the guide 640 be smaller than the outer shape of the probe of the sensor device 200. By configuring the outer shape of the guide 640 to be much smaller than the sensor device 200, it can respond to various sensor devices 200 of shapes not including a stem.

As illustrated in a in this diagram, a user inserts the guide 640 into soil. A dashed line in this diagram represents a position of a ground surface. As illustrated in b in this diagram, the user extracts the guide 640. As a result, a hole of the same shape as that of the guide 640 is formed on the ground surface.

Then, as illustrated in c in this diagram, the user inserts the sensor device 200 into a hole and, as illustrated in d in this drawing, starts measurement of an amount of moisture.

FIG. 328 is a diagram illustrating another example of a method of inserting the sensor device 200 according to the ninth embodiment of the present technology. After the sensor device 200 is inserted into the inside of the guide 640, the guide 640 may be extracted. In such a case, a hollow member having a tip end at which a hole can be formed for which the inserted sensor device 200 can be extracted from the hole is used as the guide 640.

As illustrated in a in this diagram, the user inserts the guide 640 into the soil. Then, as illustrated in b and c in this diagram, the user inserts the sensor device 200 into the inside of the guide 640. Subsequently, as illustrated in d in this drawing, the user extracts the guide 640. Then, the sensor device 200 starts measurement of an amount of moisture.

In this way, according to the ninth embodiment of the present technology, the guide 640 is inserted before insertion of the sensor device 200, and thus the deformation of the probe at the time of inserting the sensor device 200 can be prevented. In accordance with this, the accuracy of measurement of an amount of moisture can be improved.

10. Tenth Embodiment

In the first embodiment described above, although one pair of probes of the sensor device 200 are inserted into soil, in this configuration, in a case in which the soil is hard, it may be difficult to insert the probes. In this sensor device 200 according to the tenth embodiment, insertion can be easily performed using a spiral shaped member or a shovel-type casing, which is different from the first embodiment.

FIG. 329 is a diagram illustrating an example of a sensor device 200 according to the tenth embodiment of the present technology. a in this diagram illustrates an example of a sensor device 200 in which an antenna is formed in a spiral shaped member, and b in this diagram illustrates an example of a sensor device 200 in which an antenna is formed in a sensor casing 305.

As illustrated in a and b in this diagram, the sensor device 200 according to the tenth embodiment includes a spiral shaped member 650. The spiral shaped member 650 is a casing of a cylindrical shape growing in a helix shape formed using a resin or ceramics.

As illustrated in a in this diagram, an antenna such as a transmission antenna 221, a reception antenna 231, or the like can be formed in the spiral shaped member 650. The spiral shaped member 650 is connected to a measurement unit casing 310 of a rectangular shape. When the antenna is formed, the spiral shaped member 650 functions as a probe.

In addition, as illustrated in b in this diagram, a sensor casing 305 in which one pair of protrusion parts are formed may be provided, and the spiral shaped member 650 may be connected to the casing. In such a case, antennas are formed in the protrusion parts of the sensor casing 305, and the protrusion parts function as probes. A rotation movable part 661 is mounted in the spiral shaped member 650, and the spiral shaped member 650 is connected to the sensor casing 305 through the rotation movable part 661. The rotation movable part 661 is member that can rotate around the Y axis along a protruding direction of the probe.

Insertion can be performed using torque by using the spiral shaped member 650, and thus insertion can be performed more easily than in the first embodiment having only branches. In addition, compared to a form in which both a transmission antenna and a reception antenna are disposed in one screw or on the surface of a casing of a post shape (prior art document: WO 2018/0224382, FIG. 3), in the sensor device 200 illustrated in FIGS. 329*a* and 329*b*, much soil is present between antennas and on the periphery of the antennas, and thus an amount of moisture can be measured with high accuracy.

In addition, a tip end of the spiral shaped member 650 may has a needle-shaped pointed shape. In accordance with this, insertion into soil can be performed more easily. In addition, the tip end part of the spiral shaped member 650 may be formed using metal. In accordance with this, the strength of the tip end part is improved, and thus insertion into soil can be performed further more easily.

When the tip end part of the spiral shaped member 650 is metal, the transmission antenna 221 and the reception antenna 231 are disposed at positions away from the tip end part by a predetermined distance or more. In accordance with this, insertion into soil can be easily performed without degrading the accuracy of measurement of moisture.

FIG. 330 is a diagram illustrating an example of a spiral shaped member and a sensor casing in the tenth embodiment of the present technology. a in this diagram illustrates an example of the spiral shaped member 650, and b in this diagram illustrates an example of the sensor casing 305.

In a case in which a rotation movable part 661 is disposed, as illustrated in a in this diagram, the rotation movable part 661 is fixed to the spiral shaped member 650. A lower end of this rotation movable part 661 protrudes, and, as illustrated b in this diagram, a fitting part 662 for fitting to the lower end of the rotation movable part 661 is mounted in an upper part of the sensor casing 305.

In addition, as illustrated in b in this diagram, a tip end of a protrusion part (a probe) of the sensor casing 305 is sharpened. In accordance with this, insertion into soil can be easily performed. The tip end part of the probe and the rotation movable part 661 may be formed using metal. In accordance with this, the strength of the tip end part and the rotation movable part 661 is improved, and insertion into soil can be performed more easily.

In addition, the rotation movable part 661 and the sensor casing 305 can be detached using the fitting part 662. In addition, in this case, the spiral shaped member 650 may be formed using metal. In accordance with this, after the probe is inserted into soil using the spiral shaped member 650, the spiral shaped member 650 can be removed from the soil. For this reason, both easy insertion and measurement of moisture with high accuracy can be achieved together.

FIG. 331 is a diagram illustrating another example of a spiral shaped member and a sensor casing in the tenth embodiment of the present technology. a in this diagram illustrates an example of the spiral shaped member 650, and b in this diagram illustrates an example of the sensor casing 305. As illustrated in this diagram, a rotation movable part 661 may be fixed to the sensor casing 305, and a fitting part 662 may be disposed in the spiral shaped member 650.

FIG. 332 is a diagram illustrating an example of a sensor device, in which a double spiral-shaped probe is disposed, according to the tenth embodiment of the present technology. As illustrated in this drawing, the spiral shaped member 650 may be formed in a double spiral shape, and antennas such as the transmission antenna 221 and the like may be formed in the spiral shaped member 650. When the form illustrated in FIG. 329*a* and the form illustrated in FIG. 332 are compared with each other, in the former form, while both a transmission antenna and a reception antenna cannot be disposed at the same position in the Y direction, in the latter form, both a transmission antenna and a reception antenna can be disposed at the same position in the Y direction.

FIG. 333 is a diagram illustrating an example of a sensor device, in which a spiral shaped member having a double spiral shape is disposed, according to the tenth embodiment of the present technology. As illustrated in this diagram, a sensor casing 305 in which one pair of protrusion parts are formed is disposed, and the spiral shaped member 650 having the double spiral shape may be connected to the casing.

FIG. 334 is a diagram illustrating an example of a spiral shaped member having a double spiral shape and a sensor casing in the tenth embodiment of the present technology. As illustrated in a in this diagram, a rotation movable part 661 is fixed to the spiral shaped member 650, and, as illustrated in b in this diagram, a fitting part 662 may be mounted in an upper part of the sensor casing 305. As illustrated in c in this diagram, a fitting part 662 is disposed in the spiral shaped member 650, and, as illustrated in d in this drawing, a rotation movable part 661 may be fixed to the sensor casing 305.

Figure 335:
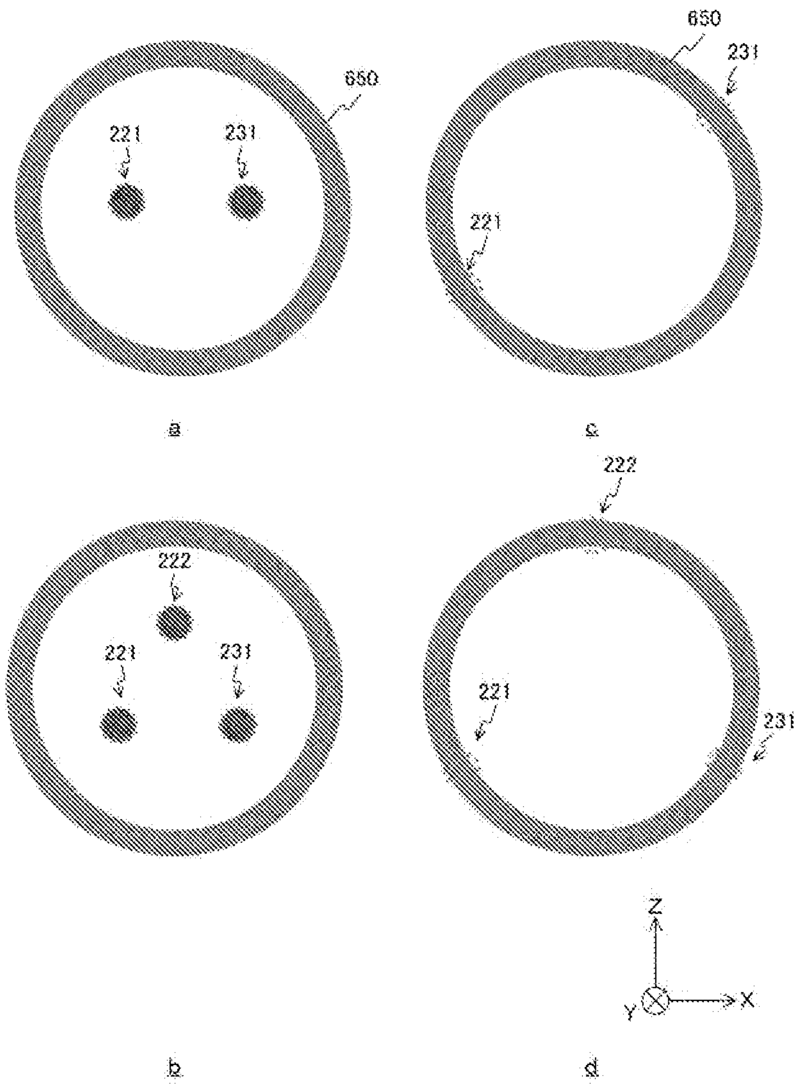

FIG. 335 is a diagram illustrating an example of a positional relation between the spiral shaped member and antennas in the tenth embodiment of the present technology. This diagram illustrates a positional relation when seen from above. In a case in which no antenna is formed in the spiral shaped member 650 (for example, the case illustrated in FIG. 329*b*), as illustrated in a of FIG. 335, a transmission antenna 221 and a reception antenna 231 are disposed inside of the spiral shaped member 650 when seen from above. Alternatively, as illustrated in b in this diagram, three antennas may be disposed inside the spiral shaped member 650. In this case, for example, as in FIGS. 311*d* and 358, the sensor casing 305 includes three probes, and three antennas are formed in each probe.

In addition, as illustrated in c in FIG. 335, two antennas may be formed in the spiral shaped member 650 (for example, in the case illustrated in FIG. 329*a*). Alternatively, as illustrated in d in FIG. 335, three antennas may be formed in the spiral shaped member 650.

As illustrated in this diagram, the number of transmission antennas and the number of reception antennas may not be the same. In other words, not only a measurement method corresponding to a 1:1 ratio of transmission antennas and reception antennas, but measurement according to paths corresponding 1 to many and many to 1 may be performed.

FIG. 336 is a diagram illustrating an example of a cross-sectional view of a spiral shaped member in the tenth embodiment of the present technology. As illustrated in a in this diagram, in the spiral shaped member 650, a coaxial cable 653 is stored inside of a cylindrical shaped casing 651, and an electric wave absorbent material 652 is filled between the coaxial cable 653 and the cylindrical shaped casing 651. As illustrated in b in this diagram, two or more coaxial cables 653 may be wired inside a circular space, and an electric wave absorbent material 652 may be filled between the space and the cylindrical shaped casing 651.

In addition, as illustrated in c in this diagram, an electric wave absorbent material 652 may be filled between two or more coaxial cables 653 and a cylindrical shaped casing 651. As illustrated in d in this diagram, each of coaxial cables 653 may be coated with an electric wave absorbent material 652, and the coated coaxial cables may be stored inside a cylindrical shaped casing 651. As illustrated in e in this diagram, a flexible substrate 654 may be coated with an electric wave absorbent material 652 and be stored inside of a cylindrical shaped casing 651.

FIG. 337 is a diagram illustrating an example of a sensor device including a shovel-type casing in the tenth embodiment of the present technology. A sensor casing 305 may be built inside of a shovel-type casing 670 without using a spiral shaped member 650.

The shovel-type casing 670 includes a handle 671 and a flat plate part 672. A blade 673 is formed at a tip end of the flat plate part 672. In addition, a space is formed inside of the flat plate part 672, and a protrusion part (a probe) of the sensor casing 305 protrudes to the inside of the space. Insertion into soil can be easily performed using the handle 671 and the blade 673, a space is open on the periphery of the probe, thus, soil can be present on the periphery of the probe, and thus degradation of the accuracy of measurement of moisture can be prevented.

The flat plate part 672 is formed using a resin or ceramics. It is preferable that the handle 671 and the blade 673 be formed using a resin, ceramics, or metal. Here, the flat plate part 662 reflects electromagnetic waves radiated from the probe and thus is a part that may have an adverse influence on measurement of moisture of soil. For this reason, it is preferable that the flat plate part be formed using not metal that strongly reflects electromagnetic waves but a resin or ceramics that transmit electromagnetic waves well. On the other hand, the handle 671 and the blade 673 positioned far from the probe may be formed using metal for improving the strength.

b in this diagram is an example of a cross-sectional view taken along line A-A' in a in this diagram. As illustrated in b in this diagram, it is preferable that one pair of probes be positioned on a center line of the flat plate part 662. In addition, as illustrated in c in this diagram, the size (thickness) of the flat plate part 662 in the Z-axis direction may be smaller than the diameter of the probe.

In addition, as illustrated in d in this diagram, the handle 671 and the blade 673 and the flat plate part 672 may be separate members. As illustrated in e in this diagram, the flat plate part 672 and the handle 671 may be configured as separate members. In addition, in the form illustrated in a in this diagram, a material composing the flat plate part 672 is disposed only in an outer edge portion of the flat plate part 672, and an inner side of the outer edge portion is hollowed in the flat plate part 672. On the other hand, as illustrated in e in this diagram, a form in which a material composing the flat plate part 672 is disposed in both an outer edge of the flat plate part 672 and a partition part positioned on the inner side of the outer edge portion, and a hollow area disposed on the inner side of the outer edge portion is arranged with being divided into a plurality of parts by the partition part may be employed. A structure in which a probe is built in this partition part may be used. As illustrated in f in this diagram, a structure in which the blade 673 and the flat plate part 672 are configured as separate members, and two or more hollow areas are included on the inner side of the outer edge portion included in the flat plate part 672 may be used. As illustrated in g in this diagram, a structure in which a probe is built in the outer edge portion of the flat plate part 672, a one hollow area is arranged on the inner side of the outer edge portion may be used.

FIG. 338 is a diagram illustrating an example of a shovel-type casing in the tenth embodiment of the present technology. This diagram illustrates only the part of the shovel-type casing 670 illustrated in FIG. 337.

FIG. 339 is a diagram illustrating an example of the shape of a handle in the tenth embodiment of the present technology. As illustrated in a in this diagram, a handle 671 having a columnar shape is vertically mounted at a center position of the flat plate part 672. As illustrated in b in this diagram, a handle 671 may be mounted on an outer side of the center of the flat plate part 672.

As illustrated in c in this diagram, a handle 671 may have a shape having a bending part. As illustrated in d and e in this diagram, a plurality of bending parts may be disposed. In e in this diagram, a hollow rectangle is formed.

As illustrated in f in this diagram, a handle 671 and a flat plate part 672 may be connected using a shaft 675. At that time, as illustrated in g in this diagram, the handle 671 may have a hollow rectangular shape, and, as illustrated in h in this diagram, may have a hollow triangle shape.

Such a structure is determined in consideration of a type of soil into which the probe is inserted, an insertion depth, situations at the time of installation, and environments after installation.

FIG. 340 is a diagram illustrating examples of the shape of a blade in the tenth embodiment of the present technology. The blade 673 may be a single blade as illustrated in a in this diagram or may be multiple blades as illustrated in b in this diagram. Although the single blade is easy to insert, the strength thereof is lower than that of multiple blades and thus is appropriate for relatively soft soil, and the multiple blades have superior strength and are appropriate for hard soil. a and b in this drawing illustrate cross-sectional shapes of the blades, and c and subsequent diagrams illustrate shapes of the blades seen from a front face.

In the case of multiple blades, the blades may have an isosceles triangle shape as illustrated in c in this diagram or may have a right-angled triangle shape as illustrated in d in this diagram. As illustrated in e in this diagram, the blades may have a triangle shape other than these. In addition, as illustrated in f, g, and h in this diagram, the side may be bent. Such a structure is determined in consideration of a type of soil into which the probe is inserted, an insertion depth, situations at the time of installation, and environments after installation.

FIG. 341 is a diagram illustrating examples of a sensor device 200 in which a scaffold member is added in the tenth embodiment of the present technology. a in this diagram is an example of a front view of the sensor device 200 in which the scaffold member 675 is added. b in this diagram is an example of a top view of the sensor device 200 in a in this diagram.

The scaffold member 675 is a member of which an area is larger than the flat plate member 672 when seen from above (in a depth direction). By mounting the scaffold member 675 to an end face of the flat plate member 672, a user can place his or her legs in a corresponding position. By the user applying his or her weight to this scaffold member 675, it becomes further easer to insert the probe into soil.

In this way, according to the tenth embodiment of the present technology, the spiral member and the shovel-type casing are disposed, and thus, it becomes easy to insert the probe into soil.

11. Eleventh Embodiment

In the first embodiment described above, the sensor device 200 performs measurement using differences of dielectric constants of air, soil, and water in the soil. However, there are cases in which electric waves are absorbed by a medium, a SN (Signal-Noise) ratio of an impulse response is lowered, and error occurs in calculation of a propagation delay time that is a peak of the impulse response.

FIG. 342 is a block diagram illustrating an example of a sensor device 200 according to an eleventh embodiment of the present technology. Components other than a sensor control unit 211, a transmitter 214, a receiver 215, a transmission antenna 221, and a reception antenna 231 inside the sensor device 200 are omitted in this diagram.

As illustrated in a in this diagram, the sensor device 200 according to the eleventh embodiment includes a variable attenuator 720 in addition to a signal source 710 inside the transmitter 214, which is different from the first embodiment. The signal source 710 generates a transmission signal of predetermined power and supplies the generated transmission signal to the variable attenuator 720. The variable attenuator 720 attenuates a transmission signal (a transmission wave) in accordance with a control signal supplied from the sensor control unit 211 and supplies a resultant signal to the transmission antenna 221. In other words, the variable attenuator decreases the amplitude of the transmission signal (transmission wave) and supplies a resultant transmission signal to the transmission antenna 221.

The sensor control unit 211 adjusts an attenuation amount of the variable attenuator 720 on the basis of electric power of a reception signal (reception wave) received by the receiver 215 such that an attenuation amount of electromagnetic waves in soil, that is, an amount attenuated in the soil until electromagnetic waves transmitted from the transmission antenna 221 are received by the reception antenna 231 is supplemented. For example, (1) in a stage in which transmission of electromagnetic waves from the transmission antenna 221 starts or in a stage before output of "results of measurement of a propagation delay amount of electromagnetic waves in soil that is used for calculation of an amount of moisture of the soil", the variable attenuator 720 attenuates electric power of a transmission signal generated by the signal source 710 (or an amplitude of the generated transmission signal) with a first attenuation rate and transmits this as first electromagnetic waves from the transmission antenna 221. (2) By receiving the first electromagnetic waves described above using the reception antenna 231, an amount of attenuation during propagation of the electromagnetic waves from the transmission antenna 221 to the reception antenna 231 through soil is acquired. Then, the variable attenuator 720 adjusts an amount of electromagnetic waves to be attenuated in the variable attenuator 720 such that the amount of electromagnetic waves attenuated in the soil described above is supplemented. In other words, the variable attenuator 720 attenuates electric power of a transmission signal generated by the signal source 710 (or an amplitude of the generated transmission signal) with a second attenuation rate that is lower than the first attenuation rate described above (in other words, configures the electric power or the amplitude of the transmission signal to be larger than that of the case of (1) described above such that an amount of electromagnetic waves attenuated in the soil described above is supplemented in advance) and transmits this as second electromagnetic waves from the transmission antenna. Alternatively, (2)' by receiving the first electromagnetic waves described above using the reception antenna 231, electric power (or amplitude) of electromagnetic waves (a reception signal) received by the reception antenna 231 is acquired. Then, the variable attenuator 720 adjusts an amount of electromagnetic waves to be attenuated in the variable attenuator 720 such that the electric power (or the amplitude) of electromagnetic waves (a reception signal) received by the reception antenna 231 described above is a value set in advance (a target value). In other words, the variable attenuator 720 attenuates the electric power of a transmission signal generated by the signal source 710 (or the amplitude of the generated transmission signal) with a second attenuation rate that is lower than the first attenuation rate described above (in other words, configures the power or the amplitude of the transmission signal to be larger than that of the case of (1) described above such that the electric power or the amplitude of a reception signal is a value set in advance (a target value)) and transmits this as second electromagnetic waves from the transmission antenna.

In addition, as illustrated in b in this diagram, in place of the variable attenuator 720, a variable amplifier 721 is disposed inside the transmitter 214, and the sensor control unit 211 may adjust an amplification amount of a transmission signal (transmission waves).

In the form including the variable amplifier 721 illustrated in b in this diagram, the sensor control unit 211, on the basis of electric power of a reception signal (reception waves) received by the receiver 215, adjusts an amplification amount of the variable amplifier 721 such that an attenuation amount of electromagnetic waves in the soil, in other words, an amount of attenuation in the soil until electromagnetic waves transmitted from the transmission antenna 221 are received by the reception antenna 231 is supplemented. For example, (1) in a stage in which transmission of electromagnetic waves from the transmission antenna 221 starts or a stage before output of "results of measurement of a propagation delay amount of electromagnetic waves in soil that is used for calculation of a moisture amount of the soil", the variable amplifier 721 amplifies the electric power of a transmission signal generated by the signal source 710 (or the amplitude of the generated transmission signal) with a first amplification rate and transmits this as first electromagnetic waves from the transmission antenna 221. (2) By receiving the first electromagnetic waves described above using the reception antenna 231, an amount of attenuation during propagation of the electromagnetic waves from the transmission antenna 221 to the reception antenna 231 through soil is acquired. Then, the variable amplifier 721 adjusts an amount of electromagnetic waves to be amplified in the variable amplifier 721 such that the amount of electromagnetic waves attenuated in the soil described above is supplemented. In other words, the variable amplifier 721 amplifies electric power of a transmission signal generated by the signal source 710 (or an amplitude of the generated transmission signal) with a second amplification rate that is higher than the first amplification rate described above (in other words, configures the electric power or the amplitude of the transmission signal to be larger than that of the case of (1) described above such that an amount of electromagnetic waves attenuated in the soil described above is supplemented in advance) and transmits this as second electromagnetic waves from the transmission antenna. Alternatively, (2)' by receiving the first electromagnetic waves described above using the reception antenna 231, electric power (or amplitude) of electromagnetic waves (a reception signal) received by the reception antenna 231 is acquired. Then, the variable amplifier 721 adjusts an amount of electromagnetic waves to be amplified in the variable amplifier 721 such that the electric power (or the amplitude) of electromagnetic waves (a reception signal) received by the reception antenna 231 described above is a value set in advance (a target value). In other words, the variable amplifier 721 amplifies the electric power of a transmission signal generated by the signal source 710 (or the amplitude of the generated transmission signal) with a second amplification rate that is higher than the first attenuation rate described above (in other words, configures the power or the amplitude of the transmission signal to be larger than that of the case of (1) described above such that the electric power or the amplitude of a reception signal is a value set in advance (a target value)) and transmits this as second electromagnetic waves from the transmission antenna.

In this way, the sensor device 200 according to the eleventh embodiment of the present technology includes the variable attenuator 720 or the variable amplifier 721 between the signal source 710 of a transmission signal and the transmission antenna 221. Then, when an amount of moisture included in soil is measured by receiving a transmission signal (electromagnetic waves) transmitted from the transmission antenna 221 as a reception signal (electromagnetic waves) using the reception antenna 231, an amount of electromagnetic waves attenuated when the electromagnetic waves propagate from the transmission antenna to the reception antenna though soil is acquired, and adjustment of configuring the electric power or the amplitude of a transmission signal transmitted from the transmission antenna 221 to be large is performed such that this attenuation amount is complemented. Then, by receiving the transmission signal after the adjustment described above transmitted from the transmission antenna 221 using the reception antenna 231, an amount of moisture included in the soil between the transmission antenna 221 and the reception antenna 231 is measured. In accordance with this, an SN ratio of a transmission signal transmitted from the transmission antenna 221 and a reception signal received by the reception antenna 231 is improved, and the accuracy of measurement of the amount of moisture is improved.

FIG. 343 is an example of a timing diagram illustrating operations of respective units disposed inside the sensor device 200 according to the eleventh embodiment of the present technology and is an example of a timing diagram acquired in a case in which the configuration illustrated in FIG. 342*a* is used.

(1) At the beginning of the timing diagram illustrated in FIG. 343, first, the sensor control unit 211 starts the operation of the sensor device 200 ("operation start setting" illustrated in FIG. 343).

(2) Next, the sensor control unit 211 sets the first attenuation rate described above in the variable attenuator 720 as an attenuation rate thereof. In accordance with this, electric power of a transmission signal generated by the signal source 710 (or the amplitude of the generated transmission signal) is set to be attenuated with the first attenuation rate described above using the variable attenuator 720 ("attenuation amount setting" illustrated in FIG. 343).

(3) Next, the transmission signal attenuated with the first attenuation rate is transmitted from the transmission antenna 221, and this is received as a reception signal by the reception antenna 231 ("transmission" "reception" illustrated in FIG. 343).

(4) Next, an amount of electromagnetic waves attenuated in soil until the electromagnetic waves (a transmission signal) transmitted from the transmission antenna 221 are received by the reception antenna 231 is acquired ("difference calculation" illustrated in FIG. 343).

(5) The sensor control unit 211 sets the second attenuation rate described above in the variable attenuator 720 as an attenuation rate thereof such that the acquired attenuation amount in the soil acquired in (4) described above is supplemented. In accordance with this, it is set for the variable attenuator 720 to attenuate electric power of a transmission signal generated by the signal source 710 (or an amplitude of the generated transmission signal) with the second attenuation rate described above such that the attenuation amount in the soil described above is supplemented ("attenuation amount setting" illustrated in FIG. 343).

(6) The variable attenuator 720 attenuates a transmission signal generated by the signal source 710 with the second attenuation rate described above and transmits the attenuated signal from the transmission antenna, whereby formal measurement of the amount of moisture of soil starts ("measurement start" illustrated in FIG. 343).

(7) As described in the item of time-divisional scanning measurement, in order to improve reproducibility of measurement results, the sensor device 200 of the present technology repeats an operation of transmitting, receiving, and detecting electromagnetic waves (a transmission, reception, and wave detecting operation) in one measurement frequency of one transmission/reception antenna pair a plurality of number of times. When the execution ends by repeating the operation of transmitting, receiving, and detecting electromagnetic waves a plurality of number of times. Measurement of one time is completed ("measurement completion" illustrated in FIG. 343).

Here, as illustrated in FIG. 343, a period of (1) to (5) described above is a period in which the electric power or the amplitude of a transmission signal is adjusted ("output adjustment period" illustrated in FIG. 343), and a period of (6) to (7) described above is a measurement period in which an amount of moisture of soil is formally measured ("measurement period" illustrated in FIG. 343).

Although FIG. 343 is an example of a timing diagram of a case in which the configuration illustrated in FIG. 342*a* is used, a timing diagram of a case in which the configuration illustrated in FIG. 342*b* is used is the same as FIG. 343 except that "attenuation amount setting" illustrated in FIG. 343, in other words, a setting of an attenuation amount in the variable attenuator 720 becomes a setting of an amplification amount in the variable amplifier 721.

FIG. 344 is a diagram illustrating an example of a transmission waveform in the eleventh embodiment of the present technology. As illustrated in this diagram, the sensor device 200 starts transmission of first electromagnetic waves of which an amplitude is a first amplitude at a timing TO. Then, during the output adjustment period described with reference to FIG. 343, first electromagnetic waves of which an amplitude is the first amplitude are transmitted. In the output adjustment period, a second amplitude that is an amplitude of a transmission signal at the time of performing formal measurement of an amount of moisture of soil is determined. From a timing T1, second electromagnetic waves of which an amplitude is a second amplitude are transmitted and becomes a formal measurement period for an amount of moisture of soil. After second electromagnetic waves of which an amplitude is the second amplitude are transmitted for a predetermined measurement period, at a timing T2, transmission of electromagnetic waves ends, and the sensor device 200 outputs measurement results. When the measurement results are output at the timing T2, the sensor device 200 may transition to a sleep state.

FIG. 345 is a diagram illustrating an example of a transmission waveform acquired when transmission power is adjusted in accordance with an amount of moisture in the eleventh embodiment of the present technology. More specifically, waveforms of a transmission signal transmitted by the sensor device 200 in first and second states acquired in a case in which (1), first, in the first state in which the amount of moisture of soil is a first amount of moisture, the sensor device 200 performs first moisture measurement (2) thereafter, in the second state in which the amount of moisture of soil changes to a second amount of moisture larger than the first amount of moisture, the sensor device 200 performs second moisture measurement are illustrated.

(1) First, in the first state in which the amount of moisture of soil is a first amount of moisture, the sensor device 200 (1-1) starts to operate at a timing TO.

(1-2) Between the timing T0 and a timing T1, first electromagnetic waves (a transmission signal) of a first amplitude generated in accordance with the variable attenuator 720 performing attenuation with the first attenuation rate or the variable amplifier 721 performing amplification with the first amplification rate are transmitted, and in accordance with this, output adjustment in first measurement is performed.

(1-3) Between the timing T1 and a timing T2, second electromagnetic waves (a transmission signal) of a second amplitude generated in accordance with the variable attenuator 720 performing attenuation with the second attenuation rate or the variable amplifier 721 performing amplification with the second amplification rate are transmitted, and in accordance with this, formal measurement of an amount of moisture in the first measurement is performed.

(1-4) At the timing T2, measurement results are output, and then the process transitions to a sleep state.

(2) Thereafter, in a second state in which the amount of moisture of soil has been changed to a second amount of moisture larger than the first amount of moisture, the sensor device 200 (2-1) starts to operate at a timing T3.

(2-2) Between the timing T3 and a timing T4, first electromagnetic waves (a transmission signal) of the first amplitude generated in accordance with the variable attenuator 720 performing attenuation with the first attenuation rate or the variable amplifier 721 performing amplification with the first amplification rate are transmitted, and in accordance with this, output adjustment in second measurement is performed.

(2-3) Between the timing T4 and a timing T5, third electromagnetic waves (a transmission signal) of a third amplitude larger than the second amplitude generated in accordance with the variable attenuator 720 performing attenuation with a third attenuation rate lower than the second attenuation rate or the variable amplifier 721 performing amplification with a third amplification rate higher than the second amplification rate are transmitted, and in accordance with this, formal measurement of an amount of moisture in the second measurement is performed.

(2-4) At the timing T2, measurement results are output, and then the process transitions to a sleep state.

As described first with reference to FIG. 140, the moisture measuring system 100 of the present technology and the central processing device 150 included therein acquire an amount of moisture included in soil using that a propagation delay time $\tau d$ of electromagnetic waves propagating through soil is in a linear relation (Expression 6) with the amount x of moisture of soil. However, the propagation delay time $\tau d$ also changes in accordance with a relative dielectric constant $\varepsilon$ of the medium. For this reason, in a case in which the sensor device 200 (more specifically, the transmission antenna 221 and the reception antenna 231 included in the sensor device 200) is disposed in a second medium (for example, air) of which a dielectric constant $\varepsilon$ is greatly different from that of a first medium (for example, soil) that is assumed to be a target for measuring an amount of moisture, and the sensor device 200 is caused to perform a measurement operation, the amount of moisture included in the medium (in this case, the air) cannot be correctly measured. For example, when the amount x of moisture is calculated from the propagation delay time τd of electromagnetic waves using the linear relation (Expression 6) represented above in a state in which the sensor device 200 is operated with being exposed to the air, a calculated value of the amount of moisture may have a negative value.

In such a case, the sensor device 200 may not perform the operation of increasing the electric power of the transmission signal (or the amplitude of the transmission signal) using the variable attenuator 720 or the variable amplifier 721 described above. Then, a message indicating that the measurement has not been correctly performed may be output from the output unit 156. For example, an error message, a message indicating that the amount of moisture of the measurement target is out of a measurable range of an amount of moisture, or a negative value as an amount of moisture may be displayed in the output unit 156.

FIG. 346 is a diagram illustrating another example of a transmission waveform acquired when transmission power is adjusted in accordance with an amount of moisture in the eleventh embodiment of the present technology and illustrates an example of a transmission waveform transmitted by the sensor device 200 also including a case in which the sensor device 200 is disposed in a medium for which the amount of moisture cannot be correctly measured. More specifically, (1) first, as illustrated in FIG. 345, between a timing T0 to a timing T2, the sensor device 200 (more specifically, the transmission antenna 221 and the reception antenna 231 included in the sensor device 200) is disposed in a first medium (that is, soil) of which a dielectric constant is within a range set in advance as a measurement target, and the sensor device 200 performs first moisture measurement in a first state in which the amount of moisture included in the medium described above is a first amount of moisture.

(2) Thereafter, similar to FIG. 345, between timings T3 to T5, the sensor device 200 (more specifically, the transmission antenna 221 and the reception antenna 231 included in the sensor device 200) is disposed in the first medium (that is, soil) of which a dielectric constant of the medium is within a range set in advance as a measurement target, and the sensor device 200 performs second moisture measurement in a second state in which the amount of moisture included in the first medium described above has been changed to a second amount of moisture larger than the first amount of moisture.

(3) Thereafter, an example of waveforms of a transmission signal transmitted by the sensor device 200 in the first to third states described above is illustrated in a case in which the sensor device 200 performs third moisture measurement in a third state that is a state in which the sensor device 200 (more specifically, the transmission antenna 221 and the reception antenna 231 included in the sensor device 200) is disposed in a second medium (for example, air) of which a dielectric constant of the medium is outside the range set in advance as a measurement target.

Here, between (1) described above (in other words, between timings T0 to T2) and between (2) described above (in other words, between timings T3 to T5), a waveform of a transmission signal transmitted by the sensor device 200 is the same as the waveform illustrated in FIG. 345, and description here will be omitted.

Then, (3) in a third state in which the sensor device 200 is disposed in a second medium of which a dielectric constant of the medium is outside the range of a dielectric constant of the first medium set in advance as a measurement target, the sensor device 200 (3-1) starts to operate at a timing T6.

(3-2) Between timings T6 to T7, first electromagnetic waves (transmission signal) of a first amplitude generated in accordance with the variable attenuator 720 performing attenuation with the first attenuation rate or the variable amplifier 721 performing amplification with the first amplification rate are transmitted, and these are received, and wave detection may be performed. Then, as a result thereof, a dielectric constant of a medium through which electromagnetic waves have propagated between the transmission antenna 221 and the reception antenna 231 is determined to be outside the range set in advance as a target for measuring an amount of moisture.

(3-3) At a timing T7, a message indicating that an amount of moisture of the medium cannot be correctly measured, an error message, or a negative value as an amount of moisture is output to the output unit 156. Then, the sensor device 200 transitions to a sleep state.

FIG. 347 is a diagram illustrating an example of a waveform of a transmission/reception signal in the eleventh embodiment of the present technology. In this diagram, a solid line represents a waveform of a transmission signal transmitted from the transmission antenna 221, a broken line represents a waveform of a reception signal received by the reception antenna 231, and a two-dot chain line represents the magnitude of an amplitude that is a target value of reception power. In this diagram, first waves of the transmission waveform and the reception waveform correspond to electromagnetic waves in the output adjustment period illustrated in FIG. 344, and second waves of the transmission waveform and the reception waveform correspond to electromagnetic waves in the measurement period illustrated in FIG. 344. a in this diagram illustrates a case in which the amplitude of the first electromagnetic wave received by the reception antenna 231 during the output adjustment period has the same magnitude as that of the amplitude that is a target value of reception power. In this case, the second electromagnetic waves during a measurement period are represented to be transmitted with the same amplitude as that of the first electromagnetic waves from the transmission antenna and be received with the same amplitude as that of the first electromagnetic waves by the reception antenna. b in this diagram illustrates a case in which an amplitude of the first electromagnetic waves received by the reception antenna 231 during the output adjustment period is smaller than the amplitude that is a target value of reception power. In this case, the second electromagnetic waves during the measurement period are illustrated to be transmitted from the transmission antenna with the amplitude to be larger than that of the first electromagnetic waves such that the amplitude of the reception waveform received by the reception antenna has the same magnitude as that of the amplitude that is a target value of reception power.

As illustrated in b in this diagram, the sensor device 200 increases transmission power in accordance with reception power.

In this way, according to the eleventh embodiment of the present technology, the sensor device 200 can improve an SN ratio by adjusting the magnitude of transmission power in accordance with the magnitude of reception power.

In addition, in a case in which the magnitude of transmission power of electromagnetic waves is restricted by laws and regulations in a county in which the sensor device 200 is used, the sensor device 200 may adjust the transmission power to observe the magnitude of transmission power restricted by the laws and regulations.

12. Twelfth Embodiment

In the first embodiment described above, although the measurement unit substrate 311 is disposed at a position at which a direction (the Y-axis direction) in which the probe grows and the substrate plane are parallel to each other, the measurement unit substrate 311 may be disposed at a position at which the Y-axis direction and the substrate plane are parallel to each other. In a sensor device 200 according to this twelfth embodiment, a measurement unit substrate 311 is disposed at a position at which the Y-axis direction and a substrate plane are perpendicular to each other, which is different from the first embodiment.

FIG. 348 is a diagram illustrating the twelfth embodiment of the present technology. An effect of accurately measuring moisture by arranging a transmission antenna and a reception antenna of a planar shape to face each other in a predetermined direction and be disposed at positions having a predetermined distance therebetween, and fixing the directions and positions of the transmission antenna and the reception antenna can be acquired not only in a form illustrated in FIG. 4, FIG. 75, and the like in which the measurement unit substrate extends in parallel with one plane set by the X axis and the Y axis but also in a form illustrated in FIG. 348 in which the measurement unit substrate extends in parallel with one plane set by the X axis and the Z axis.

The sensor device 200 according to the twelfth embodiment of the present technology takes a form in which a measurement unit substrate extends in parallel with one plane set by the X axis and the Z axis.

In addition, in the twelfth embodiment of the present technology described above, as configurations other than the extending direction of the measurement unit substrate described above, the configurations included in the first embodiment of the present technology and the modification examples thereof can be applied. As an example, a form in which the measurement unit substrate extending in parallel with the XZ plane described above, the transmission probe substrate, and the reception probe substrate are housed in one sensor casing 305 may be also employed.

It should be noted that the above-described embodiments show examples for embodying the present technique, and matters in the embodiments and matters specifying the invention in the claims have a corresponding relationship with each other. Similarly, the matters specifying the invention in the claims and the matters in the embodiments of the present technology having the same name have a corresponding relationship with each other. However, the present technology is not limited to the embodiments and can be embodied by applying various modifications to the embodiments without departing from the gist thereof.

The effects described in this specification are merely examples and are not intended as limiting, and other effects may be obtained.

In addition, the configuration included in the sensor device 200 according to the first embodiment of the present technology, for example, can be represented as below. A sensor device including: a transmission antenna (for example, the transmission antenna 221) configured to transmit a signal (an electrical signal, an AC signal, and a transmission signal) as electromagnetic waves; a reception antenna (for example, the reception antenna 231) configured to receive the electromagnetic waves transmitted from the transmission antenna and transmitted through a medium (M); a measurement unit (for example, the measurement circuit 210 or a part of the measurement circuit 210, for example, a circuit acquired by excluding the antenna 213 from the measurement circuit 210) configured to measure the electromagnetic waves propagating to the reception antenna; and a sensor casing (the sensor casing 305), further including a transmission substrate (the transmission in-probe substrate 321) that is an electronic substrate including a plurality of wiring layers (for example, a conductor: the first wiring layer in which the shield layer 254 is wired and a conductor: the second wiring layer in which the signal line 255 is wired) and a reception substrate (the reception in-probe substrate 322) that is an electronic substrate including a plurality of wiring layers (for example, the first wiring layer in which the conductor: the shield layer 254 is wired and a conductor: the second wiring layer in which the signal line 255 is wired), the sensor device alternatively further including a first coating layer that, in a part of the transmission substrate, coats an outer circumference of the substrate and is formed from an electromagnetic wave absorbent material (for example, the electromagnetic wave absorbent material 251 or the electric wave absorbing unit 341, and the like) and a second coating layer that, in a part of the reception substrate, coats an outer circumference of the substrate and is formed from an electromagnetic wave absorbent material (for example, the electromagnetic wave absorbent material 251 or the electric wave absorbing unit 344, and the like), the sensor casing includes a transmission probe casing that is a part of the sensor casing and houses the transmission substrate and a reception probe casing that is another part of the sensor casing and houses the reception substrate, the transmission substrate includes a transmission line for transmission (for example, the signal line 255 and the shield layers 254 and 256 illustrated in FIGS. 87 and 88) and a transmission exposure part (for example, the radiation element 330 illustrated in FIG. 4, the radiation element illustrated in FIG. 19: the signal line 255, the conductors 258, 259 illustrated in FIG. 37, and the like) that configures a part of the transmission antenna, the transmission line for transmission is formed using a wiring layer included in the transmission substrate, includes a first shield layer and a first signal line overlapping each other, and is electrically connected to the measurement unit, the transmission exposure part is a conductor that is formed using a wiring layer included in the transmission substrate, is electrically connected to the first signal line, and is exposed from the first shield layer or the first coating layer, the reception substrate includes a transmission line for reception (for example, the same as the signal line 255 and the shield layers 254 and 256 included in the transmission substrate illustrated in FIGS. 86 and 87) and a reception exposure part (for example, the same as the radiation element 330 illustrated in FIG. 4, the radiation element 255 illustrated in FIG. 19, the conductors 258 and 259 illustrated in FIG. 37, and the like) configuring a part of the reception antenna, the transmission line for reception is formed using a wiring layer included in the reception substrate, includes a second shield layer and a second signal line overlapping each other, and is electrically connected to the measurement unit, the reception exposure part is a conductor that is formed using a wiring layer included in the reception substrate, is electrically connected to the second signal line, and is exposed from the second shield layer or the second coating layer, each of the transmission exposure part and the reception exposure part has both a size of a second direction (a length direction of the substrate, for example, the Y-axis direction illustrated in FIGS. 4, 35, and 88) that is a direction orthogonal to a first direction and is parallel to an extending direction of the transmission line and a size of a third direction (a width direction of the substrate, for example, the Z-axis direction illustrated in FIGS. 4, 37, and 88) that is orthogonal to the first and second directions to be larger than a size of the first direction (a thickness direction of the substrate, for example, the X-axis direction illustrated in FIGS. 4, 37, and 88) that is a direction of the overlapping and extends in parallel with a plane set by the second direction and the third direction, and the transmission line for transmission and the transmission exposure part formed using a wiring layer included in the transmission substrate and the transmission line for reception and the reception exposure part formed using a wiring layer included in the reception substrate are arranged such that the plane of the radiation element and the plane of the reception element are on the same plane, are arranged at positions separate away from each other by a predetermined distance, and have the extending directions and the positions fixed inside the sensor casing.

In addition, the configuration included in the sensor device 200 according to the first modification example of the second form of the present technology, for example, can be represented as below.

A sensor device including: a transmission antenna (for example, the transmission antenna 221 illustrated in FIG. 237) configured to transmit a signal (an electrical signal, an AC signal, and a transmission signal) as electromagnetic waves; a reception antenna (for example, the reception antenna 231 illustrated in FIG. 237) configured to receive the electromagnetic waves transmitted from the transmission antenna and transmitted through a medium (M); a measurement unit (for example, the measurement circuit 210 or a part of the measurement circuit 210, for example, a circuit acquired by excluding the antenna 213 from the measurement circuit 210) configured to measure the electromagnetic waves propagating to the reception antenna; and a sensor casing (the sensor casing 305), further including a transmission substrate (the transmission substrate protrusion part) that is an electronic substrate including a plurality of wiring layers (for example, a conductor: the first wiring layer in which the shield layer 254 is wired and a conductor: the second wiring layer in which the signal line 255 is wired illustrated in FIGS. 242 and 243), a reception substrate (the reception substrate protrusion part) that is an electronic substrate including a plurality of wiring layers (for example, the same as a conductor: the first wiring layer in which the shield layer 254 is wired and a conductor: the second wiring layer in which the signal line 255 is wired in FIGS. 242 and 243), and a measurement unit substrate (the substrate rectangular part of the electronic substrate 311-1) that is an electronic substrate including a plurality of wiring layers and includes the measurement unit, the sensor device alternatively further including a first coating layer that, in a part of the transmission substrate, coats an outer circumference of the substrate and is formed from an electromagnetic wave absorbent material (for example, the electromagnetic wave absorbent material 251 or the electric wave absorbing unit 341, and the like) and a second coating layer that, in a part of the reception substrate, coats an outer circumference of the substrate and is formed from an electromagnetic wave absorbent material (for example, the electromagnetic wave absorbent material 251 or the electric wave absorbing unit 344, and the like), the sensor casing includes a transmission probe casing that is a part of the sensor casing and houses the transmission substrate and a reception probe casing that is another part of the sensor casing and houses the reception substrate, the transmission substrate includes a transmission line for transmission (for example, in b to d illustrated in FIG. 49, a part positioned outside of rectangles denoted by reference signs Dy and Dz and superimposing the signal line 255 and the shield layer 254 and 256 or, in FIGS. 242 and 243, a part positioned outside a rectangular area circumscribed about a slot and superimposing the signal line 255 and the shield layers 254 and 256) and a transmission slot antenna (for example, in FIGS. 48 to 50 or FIGS. 238 to 240, particularly, in b to d of FIG. 49, an area positioned inside the rectangles denoted by reference signs Dy and Dz), the transmission line for transmission is formed using a wiring layer included in the transmission substrate, includes a first shield layer and a first signal line overlapping each other, and is electrically connected to the measurement unit, the transmission slot antenna includes a radiation element having a slot (for example, in d of FIG. 49, a conductor: a part of the shield layer 254 and is inside rectangles denoted by reference signs Dy and Dz) and a transmission slot signal line part (for example, in d of FIG. 49, the signal line 255 intersecting with the slot) that is electrically connected to the first signal line and intersects with the slot described above, the radiation element described above is a conductor electrically connected to the first shield layer (for example, in d of FIG. 49, a conductor: a part of the shield layer 254 and is outside the rectangles denoted by reference signs Dy and Dz), the transmission slot antenna described above is connected to the transmission line for transmission described above, the reception substrate includes a transmission line for reception (for example, in b to d of FIG. 49, the same as a part positioned outside the rectangles denoted by reference signs Dy and Dz and superimposing the signal line 255 and the shield layers 254 and 256 or, in FIGS. 242 and 243, the same as a part positioned outside a rectangular area circumscribed about the slot and superimposing the signal line 255 and the shield layers 254 and 256) and a reception slot antenna (for example, in FIGS. 48 to 50 or FIGS. 238 to 240, particularly, b to d of FIG. 49, the same as an area positioned inside rectangles denoted by reference signs Dy and Dz), the transmission line for reception is formed using a wiring layer included in the reception substrate, includes a second shield layer and a second signal line overlapping each other, and is electrically connected to the measurement unit, the reception slot antenna includes a reception element (for example, in d of FIG. 48, the same as a part of the conductor 254 and is inside rectangles denoted by reference signs Dy and Dz) including a slot and a reception slot signal line part (for example, in d of FIG. 49, the same as the signal line 255 intersecting with the slot) that is electrically connected to the second signal line and intersects with the slot described above, the reception element described above is a conductor electrically connected to the second shield layer described above (for example, in d of FIG. 49, a conductor: that is a part of the shield layer 254 and is outside the rectangles denoted by reference signs Dy and Dz), the reception slot antenna described above is connected to the transmission line for reception, each of the radiation element including the transmission slot and the reception element including the reception slot has both a size of a second direction (a length direction of the substrate, for example, the Y-axis direction illustrated in FIG. 237, FIGS. 238 to 240, and FIGS. 242 to 246) that is a direction orthogonal to the first direction and is parallel to an extending direction of the transmission line and a size of a third direction (a width direction of the substrate, for example, the X-axis direction illustrated in FIGS. 237, 238 to 240, and 242 to 246) that is orthogonal to the first and second directions to be larger than a size of the first direction (a thickness direction of the substrate, for example, the Z-axis direction illustrated in FIGS. 237, 238 to 240 and 244 to 246) that is a direction of the overlapping and extends in parallel with a plane set by the second direction and the third direction, and the transmission line for transmission and the radiation element formed using a wiring layer included in the transmission substrate and the transmission line for reception and the reception element formed using a wiring layer included in the reception substrate are arranged such that the plane of the radiation element and the plane of the reception element are on the same plane, are arranged at positions separate away from each other by a predetermined distance, and have the extending directions and the positions fixed inside the sensor casing.

13. Thirteenth Embodiment

In the first embodiment described above, although antennas of a planar shape or a planar shape and a slot shape (in other words, slot antennas) are used as the transmission antennas 221 to 223, it is preferable that performances such as reflectance, transmittance, radiation capability, and the like be further improved. In this sensor device 200 according to a thirteenth embodiment, the performance of antennas is improved by thickening some of signals lines inside a split line, which is different from the first embodiment.

FIG. 362 is an example of a cross-sectional view and a plan view illustrating one configuration example of a transmission antenna 221 according to the thirteenth embodiment of the present technology. a in this diagram, for example, similar to FIG. 19, is an example of a cross-sectional view of a transmission antenna 221 and a transmission probe substrate 321 forming this seen in the Z-axis direction. b to d in this diagram, for example, similar to FIG. 20, is a diagram of the transmission antenna 221 and the transmission probe substrate 321 forming this seen in the X-axis direction (a diagram of a substrate plane direction). b in this diagram is an example of a plan view of layer L1. c in this diagram is an example of a plan view of layer L2. d in this diagram is an example of a plan view of layer L3. In FIG. 362, a direction in which a transmission signal is transmitted is the Y-axis direction. An arrow extending in the Y-axis direction illustrated near the center of a in this diagram represents a direction in which a transmission signal is to be transmitted.

Here, the layers L1 to L3 are layers (wiring layers) formed using conductors in a transmission in-probe substrate 321 (an in-probe substrate forming the transmission antenna 221). The layer L1 is a layer in which a shield layer 254 close to a reception antenna 231 out of shield layers 254 and 256 is formed. In addition, the layer L2 is a layer in which at least some of signal lines 255 are wired. The layer L3 is a layer in which the shield layer 256 far from the reception antenna 231 is formed. In a in this diagram, segments L1A to L1B are segments of the layer L1, and segments L2A to L2B are segments of the layer L2. Segments L3A to L3B are segments of the layer L3.

In this diagram, for the convenience of description, although the number of layers formed inside a transmission in-probe substrate 321 is three, four or more layers may be formed. In addition, the structure of transmission antennas 222 and 223 and reception antennas 231 to 233 is the same as that of the transmission antenna 221. In addition, in a case in which the antennas illustrated in this diagram are used as the transmission antennas 221 to 223 and the reception antennas 231 to 233, a direction in which such antennas are disposed in the sensor device 200, for example, similar to a direction in which the antennas illustrated in FIGS. 19 and 20 and the antennas illustrated in FIGS. 31 and 32 are disposed in the sensor device 200 according to the first embodiment illustrated in FIG. 4. In addition, in a case in which the antenna illustrated in FIG. 362 is used as the transmission antennas 221 to 223, a direction in which a transmission signal is transmitted is a Y+ direction (a direction of an arrow illustrated near the center of a in this diagram), and, in a case in which the antenna illustrated in FIG. 362 is used as the reception antennas 231 to 233, a direction in which a reception signal is transmitted is a Y− direction (a direction opposite to the arrow illustrated near the center of a in this diagram)

As illustrated in a in this diagram, inside the in-probe substrate 321, a signal line 255 is wired along the Y-axis direction. Here, a part of the signal line 255 is exposed to the surface of the in-probe substrate 321 in an area corresponding to the transmission antennas 221 to 223. In other words, at least a part of the signal line 255 is exposed from a shield layer 254 and an electric wave absorbent material 251 to be described below in an area of coordinates Y1 to Y2 corresponding to the transmission antennas 221 to 223, and the part that is a part of the signal line 255 and is exposed from the shield layer 254 and the electric wave absorbent material 251 is disposed on a side closer to the substrate surface described above (in more detail, a side close to the reception antenna 231) than a part that is a part of the signal line 255 and is coated with the shield layer 254 and the electric wave absorbent material 251 (or a part at which the shield layer 254 and the electric wave absorbent material 251 overlap each other) by using a conductor disposed on a side close to the substrate surface of the in-probe substrate 321. A part of the signal line 255 that is not exposed from the shield layer 254 and the electric wave absorbent material 251 (a part at which the shield layer 254 and the electric wave absorbent material 251 are coated or overlap each other) will be referred to as a signal line part 255-5, and a part exposed from the shield layer 254 and the electric wave absorbent material 251 will be referred to as an exposed pattern part 255-6.

In a case in which the antenna illustrated in a in this diagram is used as the transmission antennas 221 to 223, for example, similar to the radiation element (the conductor 258) of the antenna illustrated in FIGS. 19 and 31, electromagnetic waves are radiated from the exposed pattern part 255-6.

On the other hand, in a case in which the antenna illustrated in FIG. 362 is used as the reception antennas 231 to 233, similar to the reception element represented in a paragraph describing FIGS. 19 and 31, electromagnetic waves (transmission waves radiated from the transmission antennas 221 to 223) are received in the exposed pattern part 255-6.

On one of both faces of the in-probe substrate 321, a shield layer 254 is formed, and on the other face, a shield layer 256 is formed. The shield layers 254 and 256 are connected to the ground. In the in-probe substrates 321 in which the shield layers 254 and 256 are formed, an area other than a predetermined area corresponding to the transmission antennas 221 to 223 is coated with an electric wave absorbent material 251 (ferrite or the like). More specifically, as illustrated in FIGS. 4 and 350, except for a predetermined area corresponding to the transmission antennas 221 to 223, the whole periphery of the in-probe substrate 321 may be coated with the electric wave absorbent material

251. For example, an area from coordinates Y1 to coordinates Y2 in this diagram functions as the transmission antenna 221, and the layers L1 and L3 of this area are disposed to be exposed from the shield layer 254 and the electric wave absorbent material 251.

As illustrated in a to c in this diagram, the exposed pattern part 255-6 is formed in the layer L1 and is connected to the signal line part 255-5 of the layer L2 using a via. In this diagram, a black part represent a via. In addition, a width (a width in a direction going through with the transmission direction of the transmission signal; the width in the Z direction in this diagram) of the exposed pattern part 255-6 is larger (in other words, thicker) than a width in the direction of the signal line part 255-5 described above. In addition, the exposed pattern part 255-6 is separated from the shield layer 254 and thus is not connected to the ground.

As illustrated d in this diagram, in the shield layer 256, a pattern of a predetermined area (coordinates Y1 to Y2 and the like) corresponding to the transmission antennas 221 to 223 has a shape different from the shape of the part not exposed from the electromagnetic wave absorbent material 251, and this part will be referred to as a shield-side pattern part 256-5. In other words, the shield layer 256 that is a part of the shield layer 256 and is disposed in an area that is exposed from the electromagnetic wave absorbent material 251 and forms the transmission antennas 221 to 223 (in other words, an area of coordinates Y1 to Y2 or an area in which the exposed pattern part 255-6 is disposed) will be particularly referred to as a shield-side pattern part 256-5. A width (a width in a direction going through with the transmission direction of a transmission signal; a width in the Z direction in this diagram) of this shield-side pattern part 256-5 is smaller than the width of the exposed pattern part 255-6 in the direction described above. In addition, a width (a width in a direction going through with the transmission direction of a transmission signal; a width in the Z direction in this diagram) of the shield-side pattern part 256-5 is smaller than a width of the shield layer 256 that is a part of the shield layer 256 and is disposed in an area coated with the electromagnetic wave absorbent material 251 (or an area in which the electromagnetic wave absorbent material 251 is superimposed) in the direction described above.

As illustrated in a to d in this diagram, in an area excluding the transmission antennas 221 to 223 (an area excluding coordinates Y1 to Y2), in accordance with a structure in which a shield layer 254 is disposed on one surface side of the substrate of a part (a signal line part 255-5) of the signal line 255, a shield layer 256 is disposed on the other surface side of the substrate of the part of the signal line 255 described above, and a part of the signal line 255 (a signal line part 255-5) is disposed between the shield layer 254 described above and the shield layer 256 described above, a strip line is formed. Then, the strip line described above, in the Y-axis direction (a direction in which a signal is transmitted) in this diagram, is disposed in each of (1) a near side (a side that is a transmission source of a signal) of a predetermined area (coordinates Y1 to Y2 and the like) corresponding to the transmission antennas 221 to 223 and (2) a front side (a side that is a transmission destination of a signal) of the predetermined area (coordinates Y1 to Y2 and the like) corresponding to the transmission antennas 221 to 223. In an area in which such a strip line is disposed, the electric wave absorbent material 251 coats an outer side of the strip line or is disposed to be superimposed on the strip line.

In addition, in the example of a to d in this diagram, by using a substrate having three wiring layers L1 to L3 (layers of conductors), although the exposed pattern part 255-6 is formed in the same wiring layer as the shield layer 254, a structure used as this embodiment is an exception. The exposed pattern part 255-6 may be disposed on a substrate surface side of the shield layer 254 using a wiring layer disposed on the substrate surface side of the shield layer 254. As one example, by using a substrate having four wiring layer L1 to L4, an exposed pattern part 255-6 may be formed in the layer L1, a shield layer 254 may be formed in the layer L2, a part of a signal line 255 (a signal line part 255-5) configuring a strip line may be formed in the layer L3, and a shield layer 256 may be formed in the layer L4. Alternatively, by using a wiring layer disposed on a substrate inner side of the shield layer 254, the exposed pattern part 255-6 may be disposed on a substrate inner side of the shield layer 254. As one example, by using a substrate having four wiring layers L1 to L4, a shield layer 254 may be formed in the layer L1, an exposed pattern part 255-6 may be formed in the layer L2, a part of the signal line 255 configuring a strip line (a signal line part 255-5) may be formed in the layer L3, and a shield layer 256 may be formed in the layer L4.

(13-1)

To sum up, the sensor device 200 includes:

- a signal line 255 of which at least a part is wired inside a predetermined substrate (the in-probe substrate 321) and which has a width in a predetermined area (coordinates Y1 to coordinates Y2 and the like) larger than a width in an area other than the predetermined area;
- a first shield layer (254) formed on one of two faces of the substrate;
- a second shield layer (256) formed on the other of the two faces of the substrate; and an electric wave absorbent material 251 coating a part of the substrate other than the predetermined area in which the first and second shield layers are formed.

In accordance with this, low reflectance, high transmittance, and high radiation capability can be achieved altogether.

(13-2)

In addition, in (13-1) described above, the signal line 255 described above includes a first exposed pattern part (255-6) exposed to the predetermined area of the one face, the first shield layer (254) is formed in an area other than the predetermined area of the one face, the second shield layer (256) includes a second shield-side pattern part (256-5) formed in the predetermined area, and a width of the second shield-side pattern part is smaller than that of the first exposed pattern part.

Referring to FIG. 363, the principle of improvement of performances such as reflectance, transmittance, radiation capability, and the like will be described. Generally, as an antenna having good transmittance while matching a transmission line, a slot antenna in which a slit is formed in an external conductor or the ground is used. However, when a slot antenna is formed in a small structure, radiation efficiency becomes markedly low due to transmission of most of signals, or, to the contrary, although the radiation efficiency is high, the matching may easily deteriorate.

In this diagram, inductance per unit length of a signal line will be denoted by Ls, and inductance per unit length of a return line will be denoted by Lr. The smaller the width of the line. The higher such inductance. The balancing h of a transmission line including the signal line and a return line is represented using the following Expression.

$$h=Lr/(Ls+Lr) \qquad \text{Expression 26}$$

As illustrated in a in this drawing, in a case in which the width of the signal line is configured to be smaller than that of the return line, from Expression 26, 0<h<<0.5. On the other hand, as illustrated in b in this diagram, in a case in which the width of the signal line is configured to be larger than that of the return line, from Expression 20, 0.5<<h<1.

Generally, a current flowing through a signal line and a current flowing through a return line have the same magnitude and opposite directions. When transmission lines having different balances are connected, even in a case in which impedance of a plurality of transmission lines to be connected is the same, propagation of a signal of a common mode occurs. This common mode is a propagation mode in which currents flowing through the signal line and the return line have the same direction.

As illustrated in c in this diagram, when transmission lines having different balances are simply connected, mismatching of balances occurs, and switching to a propagation mode of an electromagnetic field is not smoothly performed, but switching to a common mode in which a part of electric power swings in the signal line and the return line with the same phase is performed. The larger a difference between balances, the higher a ratio of switching to the common mode, and the common mode allows easy radiation at a structure discontinuous point and thus can be used as an antenna.

In the case of being used as an antenna, two types of transmission lines having different balances can be divided into a signal transmission part for the purpose of transmission of signals and an antenna part for the purpose of radiation. In order to transmit a signal to an antenna and the like of a later stage, a signal transmission part is included also in the later stage of the antenna part. In other words, it is preferable that an antenna part have a configuration in which the antenna part is interposed between two signal transmission parts.

According to the principle as described above, a common mode occurs also in the signal transmission part. Thus, as illustrated in FIG. 362, it is preferable that an outer face of the signal transmission part be covered with an electric wave absorbent material 251 such as a ferrite or the like, and a common mode occurring in the signal transmission part be eliminated. In addition, as illustrated in this diagram, in order not to attenuate a signal desired to be transmitted in accordance with an electric wave absorbent material, a structure in which the signal transmission part has an inner-layer line such as a strip line or the like is preferable.

In accordance with this, low reflectivity, high transmittance, and high radiation capability in a broad band can be achieved altogether. In this diagram, the antenna part corresponds to an antenna such as the transmission antenna 221. The signal line corresponds to the signal line 255, and the return line corresponds to the shield layers 254 and 256.

FIG. 364 is an example of a cross-sectional view and a plan view illustrating one configuration example of transmission antennas 221 of different types in the thirteenth embodiment of the present technology. a in this diagram is an example of a cross-sectional view of the transmission antenna 221 seen in the Z-axis direction. b in this diagram is an example of a plan view of a layer L1. c in this diagram is an example of a plan view of a layer L2. d in this diagram is an example of a plan view of a layer L3.

As illustrated in a to c in this diagram, the shape of a pattern of a predetermined area (coordinates Y1 to Y2 and the like) corresponding to the transmission antennas 221 to 223 in the signal line 255 is different from the shape of a part not exposed from the electromagnetic wave absorbent material 251. In the signal line 255, a part corresponding to the transmission antenna 221 is set as an inner-layer pattern part 255-7, and the remaining part is set as a signal line part 255-5. As illustrated in c in this diagram, a width of the inner-layer pattern part 255-7 is larger than that of the signal line part 255-5. In the transmission antenna 221, the inner-layer pattern part 255-7 achieves a function similar to that of the exposed pattern part 255-6 illustrated in FIG. 362.

In addition, as illustrated in d in FIG. 364, a shield-side pattern part 256-5 is formed in the layer L3, and a width thereof is smaller than that of the inner-layer pattern part 255-7.

(13-3)

To sum up, in (13-1) described above, the signal line 255 described above includes the inner-layer pattern part (255-7) formed inside the substrate, the first shield layer (254) is formed in an area other than the predetermined area described above in the one face described above, the second shield layer (256) includes the second shield-side pattern part (256-5) formed in the predetermined area described above, and a width of the second shield-side pattern part is smaller than that of the inner-layer pattern part described above.

FIG. 365 is an example of a cross-sectional view and a plan view illustrating one configuration example of transmission antennas 221 of different types in the thirteenth embodiment of the present technology. a in this diagram is an example of a cross-sectional view of the transmission antenna 221 seen in the Z-axis direction. b in this diagram is an example of a plan view of a layer L1. c in this diagram is an example of a plan view of a layer L2. d in this diagram is an example of a plan view of a layer L3.

As illustrated in b in this diagram, the shape of a pattern of a predetermined area (coordinates Y1 to Y2 and the like) corresponding to the transmission antennas 221 to 223 in the shield layer 254 is different from the shape of the shield layer 254 of an area in which the electric wave absorbent material 251 coats the shield layer 254 or overlaps the shield layer 254. This part will be referred to as a shield-side pattern part 254-5. A width of this shield-side pattern part 254-5 is smaller than that of the inner-layer pattern part 255-7.

As illustrated in c in this diagram, the width of the inner-layer pattern part 255-7 is larger than that of the signal line part 255-5. As illustrated in d in this diagram, a shield-side pattern part 256-5 is formed in the layer L3, and a width thereof is smaller than that of the inner-layer pattern part 255-7.

(13-4)

To sum up, in (13-1) described above, the signal line 255 includes the inner-layer pattern part 255-7 formed inside the substrate described above.

The first shield layer (254) described above includes the first shield-side pattern (254-5) part formed in the predetermined area described above.

The second shield layer (256) includes the second shield-side pattern part (256-5) formed in the predetermined area described above.

A width of the first and second shield-side pattern part is smaller than that of the inner-layer pattern part 255-7.

FIG. 366 is an example of a cross-sectional view and a plan view illustrating one configuration example of transmission antennas 221 of different types in the thirteenth embodiment of the present technology. a in this diagram is an example of a cross-sectional view of the transmission antenna 221 seen in the Z-axis direction. b in this diagram is an example of a plan view of a layer L1. c in this diagram is an example of a plan view of a layer L2. d in this diagram is an example of a plan view of a layer L3.

As illustrated in c in this diagram, in the layer L2, an inner-layer pattern part 255-7 is formed in a part corresponding to the transmission antenna 221, a signal line part 255-5 is formed in a part corresponding to the signal transmission line part, and a width of the inner-layer pattern part 255-7 is larger than that of the signal line part 255-5. As illustrated in d in this diagram, in the layer L3, a shield-side pattern part 256-5 is formed, and a width thereof is smaller than that of the inner-layer pattern part 255-7.

In addition, as illustrated in d in this diagram, in the layer L3, exposed pattern parts 255-8*a* and 255-8*b* connected to the inner-layer pattern part 255-7 through a via are formed.

(13-5)

To sum up, in (13-1) described above, the signal line 255 described above includes the inner-layer pattern part (255-7) formed inside the substrate described above and the second exposed pattern parts (255-8*a* and 255-8*b*) exposed to the other face described above.

The first shield layer (254) described above is formed in an area other than the predetermined area described above in the one face described above.

The second shield layer (256) includes the second shield-side pattern part (256-5) formed in the predetermined area described above.

A width of the second shield-side pattern part described above is smaller than that of the inner-layer pattern part described above.

FIG. 367 is an example of a cross-sectional view and a plan view illustrating one configuration example of transmission antennas 221 of different types in the thirteenth embodiment of the present technology. a in this diagram is an example of a cross-sectional view of the transmission antenna 221 seen in the Z-axis direction. b in this diagram is an example of a plan view of a layer L1. c in this diagram is an example of a plan view of a layer L2. d in this diagram is an example of a plan view of a layer L3.

As illustrated in b in this diagram, in the layer L1, an exposed pattern part 255-6 connected to a signal line part 255-5 through a via is formed. As illustrated in c in this diagram, the signal line part 255-5 is formed in the layer L2. As illustrated in d in this diagram, a shield-side pattern part 256-5 is formed in the layer L3, and a width thereof is smaller than that of the exposed pattern part 255-6.

In addition, as illustrated in d in this diagram, in the layer L3, exposed pattern parts 255-8*a* and 255-8*b* connected to the exposed pattern part 255-6 through a via are formed.

(13-6)

To sum up, in (13-1) described above, the signal line 255 described above includes a first exposed pattern part (255-5) exposed to the one face described above, and second exposed pattern parts (255-8*a* and 255-8*b*) exposed to the other face described above.

The first shield layer (254) is formed in an area other than the predetermined area described above in the one face described above.

The second shield layer (256) includes a second shield-side pattern part (256-5) formed in the predetermined area described above.

A width of the second shield-side pattern part described above is smaller than that of the first exposed pattern part described above.

FIG. 368 is an example of a cross-sectional view and a plan view illustrating one configuration example of transmission antennas 221 of different types in the thirteenth embodiment of the present technology. a in this diagram is an example of a cross-sectional view of the transmission antenna 221 seen in the Z-axis direction. b in this diagram is an example of a plan view of a layer L1. c in this diagram is an example of a plan view of a layer L2. d in this diagram is an example of a plan view of a layer L3.

As illustrated in b in this diagram, in the layer L1, an exposed pattern part 255-6 connected to a signal line part 255-5 through a via and a shield layer 254 are formed. As illustrated in c in this diagram, in the layer L2, an inner-layer line 255-9 and a signal line part 255-5 are formed. The inner-layer line 255-9 is connected to the shield layer 254 and the shield layer 256 through vias and, in accordance with this, is connected to the ground. A width of the inner-layer line 255-9 is in the same level as that of the signal line part 255-5.

In addition, as illustrated in d in this diagram, in the layer L3, the exposed pattern part 255-6 connected to the ground is not formed, and an exposed pattern part 255-8*c* connected to the signal line part 255-5 through a via is formed. A width of the exposed pattern parts 255-6 and 255-8*c* is larger than that of the signal line part 255-5.

(13-7)

To sum up, in (13-1) described above, an inner-layer line 255-9 connected to the ground is further formed inside the substrate described above.

The signal line 255 described above includes the first exposed pattern part (255-6) exposed to the one face described above and a second exposed pattern part (255-8*c*) exposed to the other face described above.

The first shield layer (254) is formed in an area other than the predetermined area described above in the one face described above.

The second shield layer (256) described above is formed in an area other than the predetermined area described above in the other face described above.

(13-8)

In addition, in the transmission antenna 221 illustrated in each of FIG. 362 and FIGS. 364 to 368, as illustrated in FIG. 51, a predetermined terminating resistor (the resistor 260 or the like) may be connected to one end of the signal line 255.

(13-9)

In addition, in the transmission antenna 221 of each of FIG. 362 and FIGS. 364 to 368, as illustrated in FIG. 54, another antenna 261 may be connected to one end of the signal line 255.

In this way, according to the thirteenth embodiment of the present technology, a part of the signal line 255 is thickened, and thus the performance of the slot antenna can be improved.

The present technology can also have the following configurations.

(1) A sensor device including: a transmission antenna configured to transmit a signal as electromagnetic waves; a reception antenna configured to receive the electromagnetic waves transmitted from the transmission antenna and transmitted through a medium; a measurement unit configured to measure the electromagnetic waves propagating to the reception antenna; and a sensor casing, further including a transmission substrate that is an electronic substrate including a plurality of wiring layers, a reception substrate that is an electronic substrate including a plurality of wiring layers, and a measurement unit substrate that is an electronic substrate including a plurality of wiring layers and includes the measurement unit or alternatively further including a first coating layer coating an outer circumference of the substrate in a part of the transmission substrate and formed using an electromagnetic absorbent material and a second coating layer coating an outer circumference of the substrate in a part of the reception substrate and formed using an electromagnetic absorbent material, the sensor casing includes a transmission probe casing that is a part of the sensor casing and houses the transmission substrate and a reception probe casing that is another part of the sensor casing and houses the reception substrate, the transmission substrate includes a transmission line for transmission and a transmission slot antenna, the transmission line for transmission is formed using a wiring layer included in the transmission substrate, includes a first shield layer and a first signal line with being superimposed together, and is electrically connected to the measurement unit, the transmission slot antenna includes a radiation element having a slot and a transmission slot signal line part that is electrically connected to the first signal line and intersects with the slot, the radiation element is a conductor electrically connected to the first shield layer, the transmission slot antenna is connected to the transmission line for transmission, the reception substrate includes a transmission line for reception and a reception slot antenna, the transmission line of reception is formed using a wiring layer included in the reception substrate, includes a second shield layer and a second signal line with being superimposed together, and is electrically connected to the measurement unit, the reception slot antenna includes a reception element having a slot and a reception slot signal line part that is electrically connected to the second signal line and intersects with the slot, the reception element is a conductor electrically connected to the second shield layer, the reception slot antenna is connected to the transmission line for reception, each of the radiation element having the transmission slot and the reception element having the reception slot has both a size of a second direction that is a direction orthogonal to the first direction and is parallel to an extending direction of the transmission line and a size of a third direction that is orthogonal to first and second directions to be larger than a size of the first direction that is a superimposition direction, the transmission line for transmission and the radiation element that are formed using a wiring layer extending in parallel with a plane set by the second direction and the third direction and included in the transmission substrate and the transmission line for reception and the reception element that are formed using a wiring layer included in the reception substrate are arranged such that the plane of the radiation element and the plane of the reception element are on the same plane, and are disposed at positions separate away from each other by a predetermined distance, and have fixed extending directions and positions inside the sensor casing.

(2) The sensor device described in (1), the slot included in the transmission slot antenna extends to an outer edge of the transmission substrate and includes an opening part on the outer edge of the transmission substrate, and the slot included in the reception slot antenna extends to an outer edge of the reception substrate and includes an opening part on the outer edge of the reception substrate.

(3) The sensor device described in (2), a width of the transmission substrate in a direction orthogonal to an extending direction of the substrate is equal to or smaller than ⅕ of a wavelength of the electromagnetic waves transmitted from the transmission antenna, and a width of the reception substrate in a direction orthogonal to the extending direction of the substrate is equal to or smaller than ⅕ of the wavelength of the electromagnetic waves transmitted from the transmission antenna.

(4) The sensor device described in (2), the measurement unit performs control of transmitting electromagnetic waves of different frequencies at different times from the transmission antenna, a width of the transmission substrate in a direction orthogonal to an extending direction of the substrate is equal to or smaller than ⅕ of a wavelength of an electromagnetic wave having a center frequency among the electromagnetic waves transmitted from the transmission antenna, and a width of the reception substrate in a direction orthogonal to the extending direction of the substrate is equal to or smaller than ⅕ of a wavelength of an electromagnetic wave having a center frequency among the electromagnetic waves transmitted from the transmission antenna.

(5) The sensor device described in any one of (1) to (4), further including a positioning part used for fixing the extending direction and the position for each of the transmission substrate and the reception substrate.

(6) The sensor device described in (5), the positioning part is fixed to the sensor casing and is integrated with the sensor casing.

(7) The sensor device described in (5), the sensor casing has a structure including the positioning part.

(8) The sensor device described in any one of (1) to (4), the extending direction and the position for each of the transmission substrate and the reception substrate are fixed by butting each of the transmission substrate and the reception substrate against the sensor casing at least at two or more points.

(9) The sensor device described in any one of (1) to (8), a structure acquired by hardening a periphery of each of the transmission substrate and the reception substrate using a resin is included, and a strength of the structure acquired by hardening the periphery of the transmission substrate using the resin is twice that of the transmission substrate or more, and a strength of the structure acquired by hardening the periphery of the reception substrate using the resin is twice that of the reception substrate or more.

(10) The sensor device described in any one of (1) to (9), the transmission probe casing is formed using an electromagnetic wave transmissive material such that a strength of the casing is higher than a strength of the transmission substrate, and the reception probe casing is formed using an electromagnetic wave transmissive material such that a strength of the casing is higher than a strength of the reception substrate.

(11) The sensor device described in any one of (1) to (10), a thickness of a part of the transmission probe casing is larger than a thickness of the other part in a cross-section orthogonal to an extending direction of the casing, and a thickness of a part of the reception probe casing is larger than a thickness of the other part in a cross-section orthogonal to an extending direction of the casing.

(12) The sensor device described in (11), in a cross-section orthogonal to the extending direction of the transmission probe casing, a thickness of the transmission probe casing that is positioned in a direction parallel to the substrate from a center of the transmission substrate is larger than a thickness of the transmission probe casing that is positioned in a direction orthogonal to the substrate from the center of the transmission substrate, and, in a cross-section orthogonal to the extending direction of the reception probe casing, a thickness of the reception probe casing that is positioned in a direction parallel to the substrate from a center of the reception substrate is larger than a thickness of the reception probe casing that is positioned in a direction orthogonal to the substrate from the center of the reception substrate.

(13) The sensor device described in (11), in a cross-section orthogonal to the extending direction of the transmission probe casing, in a thickness of the transmission probe casing that is positioned in a direction orthogonal to the substrate from a center of the transmission substrate, the thickness of the casing that is positioned on a side far from the reception substrate is larger than the thickness of the casing that is positioned on a side close to the reception substrate, and, in a cross-section orthogonal to the extending direction of the reception probe casing, in a thickness of the reception probe casing that is positioned in a direction orthogonal to the substrate from a center of the reception substrate, the thickness of the casing that is positioned on a side far from the transmission substrate is larger than the thickness of the casing that is positioned on a side close to the transmission substrate.

(14) The sensor device described in any one of (1) to (13), in the transmission substrate, a plurality of vias connected to the first shield layer are included, and a shield structure according to a column of the plurality of vias is included on a lateral side of the first signal line, and, in the reception substrate, a plurality of vias connected to the second shield layer are included, and a shield structure according to a column of the plurality of vias is included on a lateral side of the second signal line.

(15) The sensor device described in any one of (1) to (14), the transmission substrate includes a plurality of transmission antennas, and the reception substrate includes a plurality of reception antennas.

(16) The sensor device described in (15), in the transmission substrate, the transmission line for transmission connected to the plurality of transmission antennas is disposed independently for each of the plurality of antennas, and, in the reception substrate, the transmission line for reception connected to the plurality of reception antennas is disposed independently for each of the plurality of antennas.

(17) The sensor device described in (16), the measurement unit performs control of selecting the transmission antenna one at each time among the plurality of transmission antennas in an order set in advance and transmitting the electromagnetic waves.

REFERENCE SIGNS LIST

100 Moisture measuring system
110 Communication path
150 Central processing device
151 Central control unit
152 Antenna
153 Central communication unit
154 Signal processing unit
155 Storage unit
156 Output unit
162 Reciprocating delay time calculation unit
163 Propagation transmission time calculation unit
164 Moisture amount measurement unit
165 Coefficient storing unit
166 Memory
167 Distance calculation unit
200, 201 Sensor device
210, 210-1 to 210-3 Measurement circuit
211 Sensor control unit
212 Sensor communication unit
213 Antenna
214, 214-1, 214-2, 214-3, 420 Transmitter
214-4 Transceiver
215, 215-1, 216-2, 215-3 Receiver
216 Transmission switch
216-1, 445 Switch
217 Reception switch
218-1 to 218-3, 219-1 to 219-3 Transmission line
220 Transmission probe unit
221 to 223, 221-1 to 221-3, 222-1 to 222-3, 223-1 Transmission antenna
230 Reception probe unit
231 to 233, 231-1 to 231-3, 232-1 to 232-3, 233-1 Reception antenna
241-1, 241-2, 241-3, 431, 441, 453 Mixer
242-1, 242-2, 242-3 Local oscillator
243-1, 243-2, 243-3 Low pass filter
244-1, 244-2, 244-3, 433, 443, 455 ADC
254-5, 256-5 Shield-side pattern part
251, 652 Electric wave absorbent material
252, 253 Solder resist
254, 256 Shield layer
255 Signal line
255-5 Signal line part
255-6, **255-8*a*, 255-8*b*, 255-8*c*** Exposed pattern part
255-7 Inner layer pattern part
255-9 Inner layer line
257 to 259, 254-1, 254-2, 255-1, 255-2, 255-3, 256-1, 256-2 Conductor
260 Resistor
261 Antenna
262 Can-shield
265, 266 Delay line
271 to 274, 654 Flexible substrate
275 to 279 Rigid substrate
281 to 286, 653 Coaxial cable
281-1 Coating layer
281-2 Shield layer
281-3 Signal line
291 to 294 Frame
305 Sensor casing
305-1 Front casing
305-2 Rear casing
305-3 Main body part
305-4 Stem
305-5 Protrusion part
305-6 Antenna unit
310 Measurement unit casing
311 Measurement unit substrate
311-1 to 311-3 Electronic substrate
312 Measurement unit semiconductor device
313, 340 Battery
314, 315, 323, 324 Connector
320, 320-1 to 320-4 Probe casing
321, 322 In-probe substrate
325 Shield layer
330 to 332 Radiation element
333 to 335 Reception element
341 to 350 Electric wave absorbing unit

351 to 358 Positioning part
359-1, 359-2 Jig
360, 361, 620, 621 Reinforcing part
362 to 364 Rain gutter
370 to 375 Connection part
376, 377 Level
380, 381 Fixture
390 Temperature sensor
410 Directional coupler
411 to 413 Transmission line
414, 415 Terminating resistor
421 Driver
422 Transmission signal oscillator
430 Incident wave receiver
432, 442, 454 Band pass filter
440 Reflected wave receiver
450 Transmitted wave receiver
455 Second receiver
451 Receiver
452 Local signal oscillator
460 Sensor signal processing unit
470 Sensor control unit
471 Transmission control unit
472 Reflection coefficient calculation unit
473 Transmission coefficient calculation unit
510 Watering tube
520 to 522 Watering nozzle holder
530 Watering nozzle
540 Support member
550, 551 Watering tube holder
600 to 603 Spacer
610, 611 Pillar
620, 621 Reinforcing part
630, 631 Stopper
632 Plate-shaped member
633 Parallelepiped member
640 Guide
650 Spiral shaped member
651 Cylindrical casing
661 Rotation movable part
662 Fitting part
670 Shovel-type casing
671 Handle
672 Flat plate part
673 Blade
674 Shaft
675 Scaffold member
710 Signal source
720 Variable attenuator
721 Variable amplifier

What is claimed is:

1. A sensor device, comprising:

a transmission antenna configured to transmit a signal as electromagnetic waves;

a reception antenna configured to receive the electromagnetic waves transmitted from the transmission antenna and transmitted through a medium;

a measurement unit configured to measure the electromagnetic waves propagating to the reception antenna; and a sensor casing, further comprising an electronic substrate including a plurality of wiring layers, wherein the electronic substrate includes a transmission substrate part, a reception substrate part, and a substrate part including the measurement unit, the sensor device alternatively further comprising a first coating layer that, in a part of the transmission substrate part, coats an outer circumference of the substrate and is formed from an electromagnetic wave absorbent material and a second coating layer that, in a part of the reception substrate part, coats an outer circumference of the substrate and is formed from an electromagnetic wave absorbent material, wherein the sensor casing includes a transmission probe casing that is a part of the sensor casing and houses the transmission substrate part and a reception probe casing that is another part of the sensor casing and houses the reception substrate part, wherein the transmission substrate part includes a transmission line for transmission and a transmission slot antenna, wherein the transmission line for transmission is formed using a wiring layer included in the transmission substrate part, includes a first shield layer and a first signal line overlapping each other, and is electrically connected to the measurement unit, wherein the transmission slot antenna includes a radiation element including a slot and a transmission slot signal line part that is electrically connected to the first signal line and intersects with the slot, the radiation element being a conductor electrically connected to the first shield layer, wherein the transmission slot antenna is connected to the transmission line for transmission, wherein the reception substrate part includes a transmission line for reception and a reception slot antenna, wherein the transmission line for reception is formed using a wiring layer included in the reception substrate part, includes a second shield layer and a second signal line overlapping each other, and is electrically connected to the measurement unit, wherein the reception slot antenna includes a reception element including a slot and a reception slot signal line part that is electrically connected to the second signal line and intersects with the slot, the reception element being a conductor electrically connected to the second shield layer, wherein the reception slot antenna is connected to the transmission line for reception, wherein each of the radiation element including the transmission slot and the reception element including the reception slot has both a size of a second direction that is a direction orthogonal to a first direction and is parallel to an extending direction of the transmission line and a size of a third direction that is orthogonal to the first and second directions to be larger than a size of the first direction that is a direction of the overlapping and extends in parallel with a plane set by the second direction and the third direction, and wherein the transmission line for transmission and the radiation element formed using a wiring layer included in the transmission substrate part and the transmission line for reception and the reception element formed using a wiring layer included in the reception substrate are arranged such that the plane of the radiation element and the plane of the reception element are on the same plane, are arranged at positions separate away from each other by a predetermined distance, and have the extending directions and the positions fixed inside the sensor casing.

2. The sensor device according to claim 1, wherein the slot included in the transmission slot antenna extends to an outer edge of the transmission substrate part and includes an opening part on the outer edge of the transmission substrate part, and wherein the slot included in the reception slot antenna extends to an outer edge of the reception substrate part and includes an opening part on the outer edge of the reception substrate part.

3. The sensor device according to claim 2, wherein a width of the transmission substrate part in a direction orthogonal to an extending direction of the substrate is equal to or smaller than 1/5 of a wavelength of the electromagnetic waves transmitted from the transmission antenna, and wherein a width of the reception substrate part in a direction orthogonal to the extending direction of the substrate is equal to or smaller than 1/5 of the wavelength of the electromagnetic waves transmitted from the transmission antenna.

4. The sensor device according to claim 2, wherein the measurement unit performs control of transmitting electromagnetic waves of different frequencies at different times from the transmission antenna, wherein a width of the transmission substrate part in a direction orthogonal to an extending direction of the substrate is equal to or smaller than 1/5 of a wavelength of an electromagnetic wave having a center frequency among the electromagnetic waves transmitted from the transmission antenna, and wherein a width of the reception substrate part in a direction orthogonal to the extending direction of the substrate is equal to or smaller than 1/5 of a wavelength of an electromagnetic wave having a center frequency among the electromagnetic waves transmitted from the transmission antenna.

5. The sensor device according to claim 1, further comprising a positioning part used for fixing the extending direction and the position for each of the transmission substrate part and the reception substrate part.

6. The sensor device according to claim 5, wherein the positioning part is fixed to the sensor casing and is integrated with the sensor casing.

7. The sensor device according to claim 5, wherein the sensor casing has a structure including the positioning part.

8. The sensor device according to claim 1, wherein the extending direction and the position for each of the transmission substrate part and the reception substrate part are fixed by butting each of the transmission substrate part and the reception substrate part against the sensor casing at least at two or more points.

9. The sensor device according to claim 1, wherein a structure acquired by hardening a periphery of each of the transmission substrate part and the reception substrate part using a resin is included, and wherein a strength of the structure acquired by hardening the periphery of the transmission substrate part using the resin is twice that of the transmission substrate part or more, and a strength of the structure acquired by hardening the periphery of the reception substrate part using the resin is twice that of the reception substrate part or more.

10. The sensor device according to claim 1, wherein the transmission probe casing is formed using an electromagnetic wave transmissive material such that a strength of the casing is higher than a strength of the transmission substrate part, and wherein the reception probe casing is formed using an electromagnetic wave transmissive material such that a strength of the casing is higher than a strength of the reception substrate part.

11. The sensor device according to claim 1, wherein a thickness of a part of the transmission probe casing is larger than a thickness of the other part in a cross-section orthogonal to an extending direction of the casing, and wherein, a thickness of a part of the reception probe casing is larger than a thickness of the other part in a cross-section orthogonal to an extending direction of the casing.

12. The sensor device according to claim 11, wherein, in a cross-section orthogonal to the extending direction of the transmission probe casing, a thickness of the transmission probe casing that is positioned in a direction parallel to the substrate from a center of the transmission substrate part is larger than a thickness of the transmission probe casing that is positioned in a direction orthogonal to the substrate from the center of the transmission substrate part, and wherein, in a cross-section orthogonal to the extending direction of the reception probe casing, a thickness of the reception probe casing that is positioned in a direction parallel to the substrate from a center of the reception substrate part is larger than a thickness of the reception probe casing that is positioned in a direction orthogonal to the substrate from the center of the reception substrate part.

13. The sensor device according to claim 11, wherein, in a cross-section orthogonal to the extending direction of the transmission probe casing, in a thickness of the transmission probe casing that is positioned in a direction orthogonal to the substrate from a center of the transmission substrate part, the thickness of the casing that is positioned on a side far from the reception substrate part is larger than the thickness of the casing that is positioned on a side close to the reception substrate part, and wherein, in a cross-section orthogonal to the extending direction of the reception probe casing, in a thickness of the reception probe casing that is positioned in a direction orthogonal to the substrate from a center of the reception substrate part, the thickness of the casing that is positioned on a side far from the transmission substrate part is larger than the thickness of the casing that is positioned on a side close to the transmission substrate part.

14. The sensor device according to claim 1, wherein, in the transmission substrate part, a plurality of vias connected to the first shield layer are included, and a shield structure according to a column of the plurality of vias is included on a lateral side of the first signal line, and wherein, in the reception substrate part, a plurality of vias connected to the second shield layer are included, and a shield structure according to a column of the plurality of vias is included on a lateral side of the second signal line.

15. The sensor device according to claim 1, wherein the transmission substrate part includes a plurality of transmission antennas, and wherein the reception substrate part includes a plurality of reception antennas.

16. The sensor device according to claim 15, wherein, in the transmission substrate part, the transmission line for transmission connected to the plurality of transmission antennas is disposed independently for each of the plurality of antennas, and wherein, in the reception substrate part, the transmission line for reception connected to the plurality of reception antennas is disposed independently for each of the plurality of antennas.

17. The sensor device according to claim 16, wherein the measurement unit performs control of selecting the transmission antenna one at each time among the plurality of transmission antennas in an order set in advance and transmitting the electromagnetic waves.

* * * * *